US010329539B1

(12) United States Patent
McBrine et al.

(10) Patent No.: US 10,329,539 B1
(45) Date of Patent: Jun. 25, 2019

(54) RECOMBINANT B11 BACTERIOPHAGES AND USES THEREOF

(71) Applicant: Charles Stark Draper Laboratory, Inc., Cambridge, MA (US)

(72) Inventors: Connor McBrine, Somerville, MA (US); Georgiana Kourepenos, Acton, MA (US); Parker Dow, Boston, MA (US); Jason Holder, Swampscott, MA (US)

(73) Assignee: THE CHARLES STARK DRAPER LABORATORY INC., Cambridge, MA (US)

( * ) Notice: Subject to any disclaimer, the term of this patent is extended or adjusted under 35 U.S.C. 154(b) by 0 days.

(21) Appl. No.: 15/908,197

(22) Filed: Feb. 28, 2018

(51) Int. Cl.

| | |
|---|---|
| ***C12N 7/00*** | (2006.01) |
| ***C12N 15/74*** | (2006.01) |
| ***C12Q 1/02*** | (2006.01) |
| ***C12Q 1/04*** | (2006.01) |
| *C12N 15/82* | (2006.01) |

(52) U.S. Cl.
CPC ............... *C12N 7/00* (2013.01); *C12N 15/74* (2013.01); *C12Q 1/025* (2013.01); *C12Q 1/04* (2013.01); *C12N 15/82* (2013.01); *C12N 2795/00021* (2013.01); *C12N 2795/00043* (2013.01)

(58) Field of Classification Search
CPC .......... C07K 14/14; C12N 2720/12323; C12N 2770/32122; A61K 2039/5258
See application file for complete search history.

(56) References Cited

U.S. PATENT DOCUMENTS 6,461,608 B1 * 10/2002 Averback .............. A23L 3/3463 424/93.6

* cited by examiner

*Primary Examiner* — Bao Q Li
(74) *Attorney, Agent, or Firm* — Christopher J. McKenna; Foley & Lardner LLP

(57) ABSTRACT

The present disclosure provides compositions including recombinant B11 bacteriophages, methods for making the same, and uses thereof. The recombinant B11 bacteriophages disclosed herein are useful for the identification and/or antibiotic susceptibility profiling of specific bacterial strains/species present in a sample.

21 Claims, 32 Drawing Sheets

Specification includes a Sequence Listing.

Figure 1

B11 site 6 donor (SEQ ID NO: 2):

TTAATTGATGAACGTTATCCAGATATTGTAACGGATTAAAATACTTACAGCTATCTAGTATGTAACTAGGCGGATTG
CCATTTGTAAATTATCTATTTAATCGAACTGAGGAAATACTAATGAAACAATTCTTTCAACTACTTCTAAGCCTACT
TTTCAAACTACCGGTTCTATCATATTTTGCTGAGAAGAAACGATTAGAGAAAGAGAAAAAGGAAGAAGAAAAGCGTC
AGCAAGAACAACGTCAAAAAGAACTACTTGATGAACAACGTCGCGAACAAGAAGATCATTATCGAAAAACCGCTTAC
GATCGCCTAGCAAAACTTATTCATACTCGGTGGTATGATGAGTTTAATGCATACGAAAAGAAACTAGTTGATCTTGC
TGTATCGAGTGGTAAAGCAGTTAGTGTTAAGTATGGTAAAGTTACTAAGATGCAGCACCCTCATCAATTTAAACTAC
TTAATGATTGGCTGGATGATATTCCAGTAGAAGATTATTCTAAGTGAAGAGGAGATATACAATGGTCTTCACACTCG
AAGATTTCGTTGGGGACTGGCGACAGACAGCCGGCTACAACCTGGACCAAGTCCTTGAACAGGGAGGTGTGTCCAGT
TTGTTTCAGAATCTCGGGGTGTCCGTAACTCCGATCCAAAGGATTGTCCTGAGCGGTGAAAATGGGCTGAAGATCGA
CATCCATGTCATCATCCCGTATGAAGGTCTGAGCGGCGACCAAATGGGCCAGATCGAAAAAATTTTTAAGGTGGTGT
ACCCTGTGGATGATCATCACTTTAAGGTGATCCTGCACTATGGCACACTGGTAATCGACGGGGTTACGCCGAACATG
ATCGACTATTTCGGACGGCCGTATGAAGGCATCGCCGTGTTCGACGGCAAAAAGATCACTGTAACAGGGACCCTGTG
GAACGGCAACAAAATTATCGACGAGCGCCTGATCAACCCCGACGGCTCCCTGCTGTTCCGAGTAACCATCAACGGAG
TGACCGGCTGGCGGCTGTGCGAACGCATTCTGGCGTAAGTTTAAATAAAAGAAAATAAAGACGAAGTTTTTCTTTAC
ATGGAGAGGGGTTTATGCCGTAATTATACACTTACTTTGATAAGATTTTTAATATCAGTAAAATGGGTATATGTTGC
CTTTTTATCTTTGTGAACCAGTAAGCAACAGGTTCCTTCATTTACGGTATTGGTTTGTTTTAATGGGATATTTAAAG
CATATTCAAACAGATCATCCATCCAGTTAAATGCCATGAACTTATTGATAAGGACATGATCGAAATCAATTAATTCA
ATAAACGAATCGATCTCAGATTGATAATACTCTACAACCATTTTAGACCATTCTTTGTTTATCGC

Figure 7(A)

>B11 contig 6, no Nanoluc insertion (SEQ ID NO: 1)

CGATTTGCTTAGTACATTCATTACATTTACTATTCATCCTTATTTACCTTTAATAAATTTGCTTATCAAAAGAGCAATTAATTGGGATAGTGATAAC
TTCATTAGTAACTACATGTTTGCCTGTCTTTTTAAAGAATTGGGCAAATTTTGAAGTAGCTGGAATTACAAAGGTATCATCCCGATCATTATTTGAC
ATATTGTANAAAGTAAANTTACCGTCTANNTNAAACCTAATNNNCCANTNAATATNNCGTANTTTGAAATCTATACCAAATCTTAANTGANCATCAA
TNAATTCAGAACCACCGTANTCATAAGCTCCGGTGAAATTCCAATTAATTTCTGCGAATTGGAAAGTTACAGGATGTTCGCCATGTTCATCTTGTAT
GTAGTAACCATCATGAGCTTTCCAATAGATNACTAAATCATGCATGCTACCAGCCTCAAAGAAATAATAGGGGAGTCTAGACTCCCCTATTAATTTA
TTTTGCTTTTAGCCANTCTTCTANTGGNGGTAAATANTTCTCATGNGCCCANTTAATNATTGTTTCTACAACAGGACCNTGTANNTCAAGGTTNCCT
GAGATTTCATGNGGTTCATCAATAGATAGAACCCACGTNTGTGGCGCAATGCGTTCAGTTGCTTTNGTTAGATACACATCAGGCATTAACGTAAGAT
TCAATTGATCGCCGTCAAAATCAGCCGTATTGTTCAGTATCAGTCGTTAATTGATACCCGCACCATTACGTGCAGCTCTAGCTTTCACTAGAAGACC
AGACTATATCTTCACCCTTCCTTTCGGAGTGGGGTGTCTCCCATTTCGAGTCACTTGACCCTACATCCTATTTCTAGGACCGGTGCACCTGATACCG
TGATAGTCGTTGAACCTTCTCCTATTCCTAAATGGAATGTTACGGAGCTTGGCTGCTGATTGACCCTACCTAATCTTTTTCAAACCTTGGCTTTGTC
TTTCGACTCGCAGTGGTAGATTAGTTTAACAGGATATCCCAGCAATTAGAGAGAACTCAACCCAACGATTACTCATTGGGGGAACTAGATTTGATTA
ACTTAATAAGGTATTTATCAAGCACCCCATTCTTTTCAAAGATTGCTCTTCGAACAGTATTCGGATGCTTAATACCGACATCTCTTGCAAAGTGTGG
AATACTCGGATACACTTTGGTAGTGTTCAAGATGGTGTCAGTTACTTCAATTGGAGTACCTTTTCCATTACTAGGTTTTCCAAATGAGGCTTCAATT
TCTTTTTGAGTGTATTTAGGGAAATCTTCAGGATTAGCGGTATATGAGAATACCAAACCATCCATGATTTCCTTACTACCTCTAACTAGATGGTAAT
AGGCTTTATTACGTTTAGTACCTAGTGCAAGTTCCATTTCTGCTAAGTTATGAAACACATGTAATGTCTTAGTCTTATAGTCTAAAACATAAACTGT
CTTGGTACTATCTCGATCAGCAATCTTAGTCTCACCGGTAATAAATTCAAATGTGAATCTATTTCTATACGGCTTAGTCTTATGATCACGTATAATA
ACCCAAACCGTATTTTTATTAACTCCTAATGCCCGAGCAAGTTCATTCATCGAGTAATAAGTAGTCTTTTCACCAGTGGTAACGTCAGTTGCAATTA
CCCGTCTATTTTCTTTTCTTAATCCATTTTTGTAAGCATGCTCAATGTTTTCACCACGAGTCATCCACTCCAAATTAGATGGTAAGTTATTATGTTT
GTTGCCGTCTTTATGATTGACTTCATAATCTGGTCCAGGTGATGGACCATGGAAAGCTAAACAGATTAATATATGAACTCCCTTACTCTTAGATGTT
TTTTCATCATTTTTTGCACCAATATTGAGATATGTCCCAATCGATGTTTTAGTAAGGAAGAAATTACATATTCTATTTAACCGCTTATGACGAATTG
TTCCTAAGTTACTAGCTTCATATGCTGAGTATCCAGGAATATCCCGCCATTCAATTTTAAATGAAGCCGGATCAAAGACGGACACTACTCCGTTTTG
TTCCATTGTTTTTACCCTTATTTAGTTATTCAATTGTCCATTAGGCGCTTTAAGGCATAAAACTGACATGCTGATAGAATTATCATTAATGTCATCT
TTTACTTTAGTAATAAAGAACTGCTGCGTAGATCCACGTTGAAGCGTTGGCAATATCTTCAGATAGTTCGTTAGGCTATCCCGCACCATTACGTGCA
GCTCTAGTTCTCACTAGATGTTGAGACTATATCTTCACCTTTGGCTTTATCCAGTAAGGTGCTTCCCACTTCGATTTAAGGGATTCTATACCCACCC
ACTTGGGCCCTACTCTACTCCCTCTACCTTACGGCATGGTTTCGATAGTCGTTGAGGATTCCTCATACTCCTTTTAATTAAGAAGGTTAGAGGCTTT
CCTGCTGATTGACTCTATTCAATACTTTTCGAACTTTTCCGTATTAGCTTTCGCTATCCGTTTCAGTGTATTGACCTAGCGAGTTATCCCAGCATTT
CAAGAAGTTTTGTCGAGTATCATTTCTGATACAAGGAAACCATTATTAAGTTGATCCACTACACTAAGATTACTTAGGTGGTATGTAGCTTCTCTTT
ACGCGCTTTGTATCGGTTATATTCGTCAATGGATTTATTAACCATCTCTTGAGTTAATTTAGAAACGTATTCGAATAGCCGTTCCTTATCTTCAACT
CTACAGATGACATATCCATTAAATAATCTCAGTTCTGGTTTCTTCAAGATGTCTTGCACTGACCCCTTGATTAATCCAGTCCTAAGTTGCAATTGTG
TTAAGTTCTCATACCTGCCAAAGGTGTTAGTTTTGAAGTCTATGCAATAAACTTCAATAGCGTTCTTCCGCTTCTGTGGATGATAATCCCCAGTTAC
TTCAAACACGTACTTACCATTGTAAGGTTTAGTTAGATGCGCCATGACTACATGCAGCCCTTTACCATGACCTAGCTCTAAGAACTCTGCAACTTCT
TTCATCGAGATGAAGTTATACACCTCACCCGTGGTTACATCAGTGCATTTAACAGCTAATGCGTGTTTGTTTGCACCGGTTATAAATGCATGTTTTA
CATTACCACTGCGAGTTTCCCACTCTAGGTTAAGGTAATGGTTATGATGCTTATTGGTGTCTTTATGGTTAACGTCCAAGGATACATAATTCTCAGG
TAATCCATGGAAAGCCATACATACGAAACGATGCACGTATCGTATTTTGCGAACACCTTCATCATTGTGGATATTAACCGTCAGGTAAGTACCCTTA
GATGTTTTGTTCTCATGTTGAGAAATCAACTCACCTTTAAGGTTCCTTACTTGACCATGGTCACTGACTTCATAGTTACTGAAACCAGGTATACTTC
GCCATCTTATTTCTTCATTCATATTTCCTCATTAGAGATTCTTGGTTACCACACCCAGAATCTGTAGCGCTACGACTTAATAAATTAATTTCGGTGA
AAAGTACAACCCATCCCTTTATAAGGGGCTGCTTCTGCAATTAGCTCTTTAAATAGATCTGCAATGATTTGGTTATATTGAAGTACATTCTCATATA
CAAATGAGAATGCTTCACGAGTTGTCATGTTAAACTTNGCTTTTAGNTTNTTNGTTAGATGATACTTTAATAATTGACAACCTACNCCCCANGGNAT
ATGTANTTCATCATAATCATGCGGGTCACTAATAGAAGTGATTACTGCACGTGCCGTAGCGTTGAGACGAGCACCAAACATGTGACGCCGAGCAAGA
CCAGGCTTTTGAGCAATTCGTGATTTTGCGTAGATCTCGTAGAACTGGCCATATAGTCTTAGTCCTCGCATAGTCCTATTCTGAGCTTTAATTGGAC
TAAGTGGTACAGATGATGCATCAATACTAGCGAAGGTTAAGGTAGCATCAATTGCTGCTTCAATTGGTTTATCTAAGTAAGTACCAGATGTGGTTGA
TTCTGCTACGAAACAGAGTTTAGAAGGAACTGGTAAATATTTAGGGAATAACTTATCTTTATTCTGAGCAACGAATTGAGCGAATTCGGATTTATTA
TTAGANATAATATTTGCATCTAGTAGGAATTGGAAGATCTCATTGAAATTATCAATGAAGTGATTTAATCCTCTTTCAAATCCTCGATGCAGTAGCC
TATCTACTTTNCTGCGTGTTTCTTTAGAACCAATAGATTCNACATCGTATCGATAAGAAGTATCAGTTAGATATGCTAAGAAATCGAATTCTTTAGT
TACTAGATATCCGGTTAGCATAATGATTAAACGTGGGTTAATTAGNCTACGTACNTGTTTTGGTGTACGAACCCACATTGATGGTTCGATAGGACGG
CTAGAAGTATTGACAACTGGAGTATTACAAATATCACAGATTACTCCGAGTTTATGTGCGTCTTCGATTGCTCGACAATCACAGCTTACACTACTTT
CAATTGCTTCTGAATCTTGGAAATGAGAATAGAAATGCCTATCAAATTCTTCTTTCTCATCTGAGTTACTCGTATTGTAATCATTGGCATAAATTCG
TTTACCCGTAAATTGATCATGAACTTCATTATGATCAACAACTTTGGCATAAAGACCCATACCAAACTCCTATTTATCGATTAACAAAAAAGGAGAT
ATAAGCGGCCCCCGAAGGAGCCGCTATATCAGTTTTTACAATGGACCACCAACGGAGCCTGGCCCGATCCTAGCGTCATCTACAAAGCTTAACCTCC
GCTCTTCTCTGTAGCATACCGGCACTAGTATCATTTACCATCCATTGTAGTTTTTGATCACACGTCACCTTTTGAGTAACTCCTTTCGGTTAAGTGA
TCTATCATCCTCGTGTAGTGATAGGTCGACCTAGACTAAGTCCACTAGTCGATTACTTCACGGAACCTACTCCTAACCGTTATCACCGAAGTGAACC
AGGGTCGCAGTATTAGAATCGGGATGTTACTTATTTAACATCCCTATCTACCGAGGTATTTCCTATTAGTACCAGGTACCCGGTGCATTATAGGAAG
GAGCGCCGTAAGTTTGACCCATGCTGCCAGCCATNCCAACTTGTGCACTACCAGAAACAGCCATGTTACCCATACCGGTGTAACCAGCGAAGCGCTG
TTGACCGAAGTTGGTAATTAGGTTTTCCATGGTTACAGTTACACCAGCNGCTGCTGCTGCGGCATCCATTGCGGTGATGAATTTCGGGTTAAAGGTT
AGACGACGAGCACGACCAGTATAGGTAACGTTACCTAGGTACATCTTGTCGAAGCCTTTACTGTTATTCATACGACGCACAATGTGGTCATTACCTA
CCTGAGTAGCATACCAGGTCTTCCACTCTTGGTCATTACCTTCAGACATGTTCATGGCACCTAGAACGTCGAGATCACGACGGTCGCTTAGTTCACC
ATGCTCATCAGTGTAGTGACCGAGGTCTACTTCATGATGGTTGTCAAAGATAATCGGACCAGCTTCAGCTAGATTATAGAACTGACGGAAATCAGTG
CCGTATAGGTTAGTTAGAGCTTGGAAGATCAGACTAACTGCACGAGCTTGGTTTACGCCACCAGCTGCATCTAGGACGACTTGCTCAATAGCTGAGT
TGTCTCCCATTGGATCGACATCGATCTGGAATGCAGGGTTCTGGTTAACCATCTTGTTCATTAGCATTACGAAGTTGCTGTCGTCTGCCATGAATGC
TTCGGTGCGAGTTTCAATCGCTTTACCTAGCTCTGAGTAATAACCAAGTGCACCAATATCACGCATCTTACTAGTAGCGATCTTCGGCATTAGAGTA
CGAGCCCATGCCTGAGATGCAGTTGCACGATACGCGTTACCAAGCGCGAACAGCCACATTTCTAGAGTCCATGCTTGGATCCAGGACGCCTTACGAA
CGTCAGTAATAACGATGTAAGGAGTGAACTGCGGAGGTAGAACTGCACCAGGTAGAGTTACGCCAAACATGCCTTGTTGCTGGCCAGTGGTCGGAGT
CCAATGTAGATCTACGAATAGACTAACTTGGTTTAGCTGGCTATCGGTATCATAGAACTCGTTCTCAGGTACGTTGGTTTTCTTACCACGGCTAGTG
GAGATGACCAGGTCAGAACGGATCGGATTACCACAGCTATCTTTAACCGGAATACCATTGTAGTCTAGNTTGCAGGTAAGCTGTTCGTTTTCTGCTT
TGATGTGGGTCGCAATAGAGAACGGAGTCTCATTGTTACGACGNGCAATAGCATCTTCACAGATNTTAACNGATTCAACTAGTAGGTTCTTAACAGC
TAGTTCATCTTTGAAGTCGAAGTCAGCATACACTGCACGTGGACCGGCAGATAGTACTTCTAGACCAGGGATGTTGTAACGGTTCCGTAGGAACTCG
CCGATCTTGCTCCAGTATTGAGCAGTGAATACATCACGCGGTAGTACCTTCTCTTCAATGATGTCATCAGTTAGACCATTGTTGATTTTGTGGGTAC

Figure 7(B)

GGGGACGGATGCGAGTACCAGGTAGGTTATCGAGTACTAGAGTACGAACGAATGCCTTCATGGAACCATTGATATCTTTAGCTAGTTTAACAATGAG
TAGACCAGCCATACCNACTTGTTGNGCATCNCGATCGAAACGATGGATATCGAAGTCATCAGGTAGGTCCTGATGGCGGATTGCTTCTTCTTTTACT
TTAGTGAATACTTGTAGGGCATCTGCTGAACGAGCATCAGAGCCATCTAGCCGACCAGAGCGACGCATTAGATGGTTAATGCCAGTAGTNGACCCAG
GNGCGCCAGNNGGACGTTGAGCTTGACGNTGTGCAGTGGGTTGCGGAGCNGGAGCNGTAGCTTGAGTTTGAACGGTGCCGATTTCGTTTTCGTTAAC
AGCCATTTTAAATACCTTTACGATTATGGTTTCTTGATCAAGAAGAACCTAAGTACTNAGTATACTAGATTCAATTTAGTAATATAAATCTCAAATT
TTTTTCATTACAACATAGACGCTATAATCTGCTATCAGCAGATCGTAACGAACACTATGTTCACTACATATTATTACAATCTGAGTATTATTTATTT
TTCATCTTACAATTTCCATATCTTCTTTTTTGAGTTTATGGGTATAAAGTTTGAATCCAGAAACTAATTTACGTCAGTCCTGTATTAAATAATAACT
ATCAGTATTTTTATAAAATGCAGTTATCATTTACTTCGCATATACTTACGAACTGTTCCAAAAAGAGAATGATACAGTTTGTATAGTTTACTAACTG
GATCAACTTTATTATTATCAGTTGTATCAAATTTAGCAATAAATGGTGAATGTGCCGAAGCAGATGTTTCATTTACTTTAACTACACTACCAAATCG
ATATGCGACTAATACCTTTATTAATTCCTCATGGAGTTTAGTAGCAGTTGCTAATGGATTGGGATCATTAGGATCTATCTTAATCCTACGCTCGACA
TTGAAAAAGTTTACTACAATTTCTTTGCTAGTCATGTATACAGTAAGATCTTTGTTATTACCTAAATATAGTGGCGGATCTTCAACATTATTTTTAG
CCATTGTATATTCCTATTTGTAATTACTACTGTTGTTACCAAACTATGATATAGATCTCAATTAATTTTTAATCGGATAATAACCATGTATAATTTA
TTTAAGAATGCTCCGTCACGTAAATTGGGGCAGGTGGTTGATCCTAACATCCATTATATCCGACGAATCTACGCTGAGCAAATTAGGGACGTTAAAA
GTTATTATAGACGGGCACCGAAGTATGTTGAATCTAAAAACATATTAGCACAAATGATTCGACATTTTAACGTAGAGTTACTAAGTGATGATGCTAC
TTTTATAAAGAACGTGGACGATCGTTCACGTGCTATTATTCGTTCATTTGGTATTACATCATCTTTAAATAAAGGTAAGGTTCATGTAGGTGGTGTT
ACACTTGGTCCTCAAACTGAAGAAGTTCTAGTATCCACATCAGAGAGCTTTGATCTAAAAGATCTAAATAAAACATGGTATAAACTTTCCCCTGTTA
CGTATCTGTATCATACACGTACTGATACTAATTTACCTATCATGAACAATACCACACAGGGTAGAGGCTATGGTGTAACTCTAGTAAATATACCAAT
GCTTCTTGTGATGTACCGTTACTGGTATCGATGGCAAGTTGAGAAGAATCCTGATGAAGTAGAAGACACTTATAGGTTTATAGGATCATTTGTATTG
CCAAATATGGTTGACTCTTATTTAGATATTTCTTTCTTTAATAGGTTAGCAAGGAATGCTTTAGATATTAAAAATCCAACATTCCCTATACCGCATC
CATTTTACATCACTGATATGAATCCACGTATTGATAAACTATGTACAACTATCAATAGAGAATCCATATTAAAAGGTGTAGACATGGAAGGTTTATC
ATGGATAACACCAGCTATCGTACAATCTAATTTGTTCGATATGATGCGGCTCCCACGAGAACCTATTAACAGGAATAATGAATGGGCTTATGTATTG
GCTCGCACACCCTTCATTAAGTATCTTGTAGGGCAGCTTTTAAAGAATACTGGTTATGATCAATCTTCTGTTAACACTGTATTAATTGATCTTATAG
AAGCATCTAATGATCAAGCATTTAAGCAACAAGCAAATAGTGAGTTTGTAAAAGCTCAACAGGCACAAGTTGATTGGATGATAGATGCACTTAAAAG
AAAAGAAATGTGACATAAACCCCCTCCTAAATTGGAGGGGGTTATATGCCGTTTTATTAGAAATTACCTTTCTTCATTTTAGAAAGTAATTTTCTAC
GTTCAGCTCGGTTAATTCCTGGGATAGCTGGTAATAGCATTTTATTACTAAACTTACCTGGCTTGCGGTCATGATTTAGTAATTGATCAACTACAGC
TTGGTCACTGCTTTTAACTCCATTATCCATTTCATCTAATGGGTCCATAATAGCTTTAGCAGTCAATCTTAGATGAGTAACTAGTTCATCAAATGAA
CTATCGGTATTAATAAGTTGTTTATCAACACCTTCTTTAAGAGCTTGTTTAATAGTTACGTCTTTTACCAGGATATTATCACATTCCCAAAGAGTTG
TATGATGGGTATTTAACATTAATTCAAGTGAGACATTATTGTAATCGTTGTCAGCACTTGAGTGCCAATTGAATTCATCAATATAGTCATTTAGACT
CATTAACTTTGGTGGTTCGTTACTAGAGGTAATTAAACCAATTGGTTGAACATCATCTAGTGAACTTTTATCACTAGTAATTGCAGTTGTTTCAGTA
GTAACATCAACTTCTTTTAATTCGTTGGTATAAGTTACATATACTAATTCTTCACTACCGTCATCCAAAAGAACATAGGCTGTTGCTTTGGTGGAAT
CATCAGGTGCTAATCCATGGATCCTAATACGATTATCATTTACTAATTTACTATAATCATTCCAGTGATTACACGAACTTCATTAGTCTTTTCCATT
ATCATCTACCTCTTTTAATTTATCTTTAATATATTTCGGATAAAGCTCGTTTTCTTCACGAGTTAANCCNGNTGGNNCGGTTGGTAATGTGATAGTN
CCNCTNTTAATTGCCTTCTTCATCCGATCTAAGTCAAAATTAAATTCGGTATGATTTNTCATTATATTGAACCATATTAAGTTAGTAATTGGCAATC
AGACTATATAAATCTTAATTATTTTTTAGTATATAAGCCTCCCACTAGGGGAGGCTATATTTCTTAATAGAAGTCAGAGATGAGTCGATCGTTATTT
TTATCAATAAGGAAAATACCTAGGGACTCTAAGGTTAGATAGAATACACCCATAGTNTTTCCAATGATAGTTCTAACGTCAGCAACACGCGTAATAA
CTTCTGGAATACGACCAGTTTCTACTACTGTACTCGGGATATGGAAATCACCAATACTGGTTTTATTTTCTTCAGTAACCCATGCTTGAATACGAGC
AGCTAATTTCTTATCTTCGATACCATCAATCCATTCTTTGATCGCAGTTTTATTATTAAGAGTAACTGAGATCTTTACATGTGAATAAGGTGGATCA
CCAGCGTCACCAAATGATGGAGCAAATACAGTCTTCCACACTAATCCCTTTTTATGGGTTGAGTTATCTTCAGATTTATAAGACTCAGGTCGTTTAG
TTTGACCACTTGTCAGATACTCAGCTTTACCACTTCTAACAGACTCAATAATTTCTCTTTCGATATCACCAACTTCTTTTAGAATTGAAGCCAAGTC
GATTTTCTCTTCAGTCTTTACAGTTTTAATGATATCTTCCATGAGTGTTTTAGCACGACTATTAATCTTCTTAGGTACTTTACTATCCCTTAGTCCN
ACNCCNTTNATCTCCATNCGNGANTCATTAAACATNACCCCTTCTTGGGCATCCTGTGATGCAAAGTAATGTTTAGAACGAGTAGTTAAGGCCAGTA
CTGCGAAATAANATTCGTTCTTCATTGCAAATAGACGAAGCTTATCTTTAGATACACCCATATTAGCGGATTGAATCGCNAAGATATGCATAACTAC
TTCAGANACTAGAAACACTAGTGCNAATACTAGTCGNTTAGCTTCATTGCTAAAAGTTACTTTACCAAAGAATTCCTCAACCCACCATTGTAATGTA
AACATAGTGGAGTCAGTATCTGAAATAACAGCAGCTCGTCTATACACAGTTGGAAAAGCATGAATGCTTGATGGTACACATTTAGTCAAGAAGAAAG
CTTCAATCAATAGACGATATTCATTAAGAGTTTCAGCGATATTTCGACCAGTGGCATAAACTTGGTTNANTGTATCTGGATCNGANTCTTTTAGTTT
AGCTTTAGATCGACCTTTAACAGTATCAAAGCAAATAAAGCTAGCCAANAGATCCATATCACCATCATAAGTTGAATATTCTTCTTCAGTGATGATT
TGTTCTTTTGTTCCAACCTGGCTTAATTTAATTAGAAAGCTCTTGATTAATTCTTTATTGTATTTATATAAGTGATATAGATCACCTACNTACATAA
CTGCTGCTCGTTCGACTGGTGTCATCCCAGTAGCTAGTTTTAAAATCTGNGCCGTGTANTACTTATTTTGCCAATAGTGTTTAGTTGAATAAAGAAC
CATATCAACTACTTCTTCTGGCGTTGGGCAATGTAGATTAAAATTAGTTACTGCTTTTTGAATTAACTCCATATCAGCTACATTAATANTNTTTACT
AAATTAGCTTTTGTGATTTCTGGAGTATAATAATGCCTATTACCCATAATGAATTTTTCATTATTTGAGTTAGCATAAGAGGTACCAGTTCTACAGG
TAGATGTTAAACTAGAGTGTGTGGACTTATAATAAAGAATAGTGGCAGCAGATACAGTACCGCCTGAATATGAGTTATTGTTAATTTTGAAGTTTTC
TTGNTCNCCTTTACGTACTTGTGCAAGTTCTGTTTTAATTTGTGAATTCTCTTTATCGCCGGCCTGTAGGAAAGCAGCTGCTTCACGTTCAGCCTGC
ATCTGNTCACCTTTAACACGCTTACGGTTTTTCACACCTTCNGCAATATAGATGGAGTGCGTNGACTGTCTAACAGACTCTGGTAAATATGCGGTCA
TTGATGGAGATAATAATAGATTCTGTTTCTTAACACGGTTAAGAAAAGCCATAAATGAAACCGTCTTTAATTCCCTATCACCAAACTTATTTTTATC
TAGAATAGTTGCTAATGGATTACGAAGTGCATATTCGCCATTTTGACGTAATTGTTCTTTAACAAATTCTTTACATTCTTCTAAACTAATATTTAAT
TCATCTTTTGTCATTAATTGAAGATATTTGGCATTATCATCAAGACATGCATTAATGATATCAATATCACGATGGTAATCATTGACATCTTTTAAAA
ACGGATTTGGTTGGGCAAATGCGGTCATTTCACATATCTCTCAGTATACTTATTTTTTAATTATAGTGAATGATTTCTCTCTNTTTAACTAAAAAAG
AAAAGGAAAGAATGGGTACCCTATACGGGNACCCTAAATTGAGAGGTAGCACATCAACTTACATTCACATTAGATGATGTAAGNAAGTAAAAATAAN
ACAACATAAAAGGAGCCATNATGGCTCCTTTATAGTTATTCATATGTCACTGAAGTTGGTGGTGCATTATTTTGNCGCACTGCCAATAGAATGCGAT
CATACATTTTATTATCGACATCATCCCATACTAATGTCANACGNTTACCATCTACACGTTCTAATGTATTCGCAACAATCCAAGGNATNCCAATAAA
CATCACACTTTCATTATTGGCCATTCGTACACGAATNTAATTGTATTGTGTTGGATCAACTGGAGCTGANCCTGCTGGTAAACTTGGATATACTTGC
TGCCCNGCAGCAGCTACATCAAAACCCATTGCAGATGCTACAGACGCAGTAACAATACCTTCGACTGTAACGTTCTTAAAATTAGTACCTAGGATAG
CATATGGATAGACCTCGAATGAGATCCTATCACCTGCTTGAATGTCTCGAATATTAACAGCCATGGTAATACCCTAAAATAGTTGGTTACATAGGGT
ATTACTCATCTAGTAATACNACTACACCAAACAGACCTTTCGTATCCATTGGNACTGTAATGANTACATGTCCATNTGGATANTTTTCTTTAAAGCT
ATTGATAAAGTCGGTNCAATATTCAATAACATATCCTTTAGTAGAATAATTCTCTAACTCAATATCTTCNTCAGGATCATCAAATGAGTCATGTCCA
TACATCAGCATATGGATNTATATGTCATTATTAAGCGTATCCATATAACTTAACTTACGTGATTCTTCAAATAAATCAAGTGGTGTTGGACAATCTG
GATATATCATTCGTTTTGTATATTCACGAAGCAAATGTTGCGAATATACTTCTGACTCTTTAGATTTAAATACGATAAATACTCGTTTTTCCATATC
GGTTCCTAGTAGGAAGCCTATGTGAACCGATAGGCTTTCCTATTTGCGTCAATTGTTAATATGTGTCACTTAATCCACATCATTGTAACAGTCCATA
CCAAAGTCTTCACCTTCTAGAATATAACCCTGATTATGTTGATCAACTGCTATTGATTGGATTCTTTCTACACCATATCCATTCTGATAGAGATGTG
CTATTTCAGATTGTAGTTTGCTAGCCAATGTTTTACACACGGTCGCAAACCACATATTAAGAATACTCAATGCATATTTATCTTGCATAATCACAGG
TGCTACCGATGGAAAGTATTCTTGTAAATAATAGTCAACCCCTATAATTGGTTGAGTAGGCTGTTGCGCTAGAAATTCAATATATGAATTAATTGCC

Figure 7(C)

TGATACCATAATTGTTCTATAGACTGGTGTTCAGTATATGGGTAAGGGTATTGTAAGACTTATTGACAACTACATCAGCCATTTTATTAACAATGGG
CCAGATATCACTGATGTTAATAACTACGAAACTCGTCATTCCTTGTTGACCTGGAGTTATGTTATTAGCATCATTTATCCGCTGCATTTCTTGTTGT
CTATAAAGAAGTGGATGCATCATGTTTGAGACCTCATAACTAATTTAGTTACCATCTTATATTTATCTACTTCTATACATTTAAGACTAGTAATAAG
ATTACCTGCTTGAATAACTTGTTTTTGGATTATCTCTAGGAAATCAGTTCCAAATAAATCCAATACCCTTTCGATAATCTCAGCAGATCTTAAGTGC
CAATTGATGGTATTAGGATTTCCCTGATGATCAAATACCATCATACTCGTCGGTCTATCCGGTTCTATATAGGTATCGCTTAAGTAATCTTCTAACC
ATTGCTCTAAAAGGTAGGCCAATCTAATCTCTGCCAGTGGTTAAAATATTCACATATGCTGCTAGAAGTCTATTGATACACCACAGTACAAAGTCA
GTCGGTTCATCTACACCTAGCTCTTCCGTAAAAGAACGCGGTTTCAAAATTAGCAACAATTGCATATTGACTCCACTCTTTACCAGTGACTATAGTT
AATAGAACAACTTTGTTATCTATTACACTAATGAACTTATAGTCTATTAAATTCTTCGGTGTTCTATGTAGTAATTGGATTCCAGTTGTATAGAACA
AATTAATGAACTCATCCCAATCTGGACCATTTCCTAGTTGTATTGATATATCCACAAAAGGAATAACCGTATTATCCTGTTGTAATTTAGACATCAT
CTTAACAACCCATTGAGTTAATAAGACGATGACTGTAGCTTCATCTTTATTTGTTAGGTAAGTAAATTTCTTTATCAATGTGATTAATTGTGGGAAT
ACCACTTCGATTGGCAATACATATACCAGACGTTGTACTTCCTCCGATGTACAATCCATCTCGTGCTTCTGTTTCATACCACAGTTCCTTAGTATTT
GTTGGAATGAGGTGCATGATCTGCTCAGCACCCTCATCGAGAAGTTCTATTAGTTTATGCATGAAATGAATGTCTTTAGCATATTCATAGAACATTT
CTTCTTTAACGACCATTTGCATAAGCTTCTGTTCTGCCAATGCAACAAGCAAATGCATTGCTTCGATATAACTAATATCTAAAAGTCCAATACAAA
TCTTAGATAGTTATCATCTTTAATAAGTTTACTTTTAGTCGCTCTTAGTAAAAAACGAGGTTGTNGTGTGGGTAATGGTGACGTATAGATCTTCTGG
TTTCTCAGTATCATAAATAACCCTATTTAACTGGATGTTACCAGCTGATGGTAGAACTACCCGGTTAGAACAATTATACAGATAAGTTGTTAAATCA
ATATCACAAATATCCCTATAACCCAGCATCTGATTAATTAGTTCTATGACATCATTAGATGTNCNACCNGATGCNCTCTCAGACGCTGCTGCCAATA
CAATTGTTAATGCATATTCTGCACCAATACTATTTTTTATAGATTTCCAAATATCAGAATGTTGNTCTTGTACAAAAGATCTTACTTCCATTCTGAT
ACACATTGATGTGTCTTTATCATTAGATATGTTCATTATAAAAACCTTATAANCGNTATAAAGCCCNCCNTANGGAGGGCTTTATTTAGTATAGATT
ATTTTCTAAAATGTATCGCTCAGCTTGCGCTCGCTGATCATCAGGTANATAATCACCACGTTGATATTCAAATACTAATTTCTCAATAGGATAAGTT
GCATTCTTATTCTTGTATACAGAAATTACATAGCTATGATACTCTAGTTCATACTTAACATCATGCTCAATTCTGGTTGAAAAATAAGCCATGTTAA
TAGAACTAACTAGAGGGCTAATATATTTCTCTTCAAATAGTAATAAATTATCAAGTCCTAAACTTGCAAAGAAATCATGGTTAACCTTAGGTATTAG
GTAAGATACTTTAATATTACTATATTGTTTAACAATTACGCCAATAAGTAATGCAGTTAACTGTTCTTGAATATATTCTACTGCGATGTTGTATGCA
TGGTTAGTGGTGATGTGGTCTTTATTTAAAGTATAGCTACCGCCATTGGTAATAGATGGCTGAGTTTTACGTCTAGATTCGTAGATACTATAACCTA
GTGTTTGTAAATTAATTTTGTCAAAGCCATGGAAGAAAGTCCGTAGAAATTCACTAAATAAATAGTTTAATGGGTTCAGTAGGTTAAGTGATACCAC
TGCATGATCATCACCATTATCAATCCCATGGACACGATCATATTCTGCGATTCGATAATCTTTACCACTGATTAAAGTTATAACTGAACCAGCTTTA
ACTACATCCCATTGGATCCATGTACCGCTATCGATATATTTTGCTACTTGCTTATAGATATCTAGATAGATAGTTTCTAGATAAGGTAGTTTCATTA
GATTTTCTACCCAAGCAACTTTATTACTATCTACGTCAGTTACAGCACAATTAAAAATAGCTGCGGCCATCTTAAGATTGGTGTACTGGTCTTTGGC
TGTTTTATATGAAACTAAACTCTCTACTATATTTTCAACCATTAGATGTAAAAACTGTTGAGCCACATCTTTACTCAATTTCACCCCAATCGCTTCA
TCAATTGAAGCTGAAGCTGTAAGCTGACCTAGTAAATCGTATATTGCTTTTTCTTGGTGGCGCGTATCAAGTACAATGAGCTTATTCGACATTATAT
TTCTCCAATTAATTTTTTGGAATAGCGATCCAAACTGTGTTCTTTAACCGATAGAATATTACAAACTTACCTGCATTTACTCTAGGTATAATTTTTA
ATATATCCCAAAGATCAGATGCGGCCTCATGATTATCATGAAACCATTGGATTTCTTGAGGGGTGTTATTTATTGGATTATATCCAGTAGTATACAT
GAATTCAAAAGAGTCAATAGAGTATTTAAAGAAGTCATCAATTAAGCTGTCCTCTACTGATTTAAATATATGCTCTAATGTACCATAGTCATCTGGA
TGTATTCCAAAGCTTTGGCACCTAATCGCTAAACGCGTATTTATTAACTCTTTTGGCGATCTTGGTACTAACTTGGCTATCACCCTCGTTACATCTA
TTACATACAGGTCAGCCACTTGGGGAGTAGTCACAGTACAATCTCTCGTTAAATGTTCAGGAACATGATATAGATCTAAAAATATTTTTAGTCAAAT
CTGTTCGTGGTAAGCCGATGTATATTATACCTTAGTTGGGTATTATCTCCATCGAAAAAACGCGTACAGCGCATTATAGGACGTTTTTATGAATCCA
ATTACTAAGGCTTTACGTGATATTTCTTTTAAGATCCCAAAACAGATATTAAATACTGTTTTCNTATCTANCGAAATGTCAGGCTGTGGTGCAGCTA
TCTCACTAGAAACCAGGATACGCGAAGCTGTTATTGAACCACGTGTTATGTTAGATATTGATTTAGTCGGTGGTTCAAAAGTATTCATTCCACTAGA
TTTTCCAGTGCAAGCAGAATATGTTGACCCTTATACAGTGGTTTATTACATTCCAGACGAATACACTCAGCAACGCCCAATTATCCAATGTTACAGT
ATCCATTTTGGAGTATTAGGATTCCATACTGCTGGCTATGCTATGCACTATAATGAATCAAGTATGGGTGCATTAACACGACGTGTACTAGATTCAG
CTAGACAGTTACCAGTCGCCCAAACAGCATATATCAACTTAATTAACCCACACACTGTCATGGTCAGGTATATCAATATCCCTAACTACTCATCATT
CCTTGCCTGTCGCGTAGGTAATGATGANGAGCTAAATACCATACGACCTACAGCCATACCTGCATTTTCAAAACTCATTGAGTATGCTGTTAAGTCA
TACATCTACAATGAGTTATTTGTATCTATGGGTGANGCACAGTTATCAGGTGGTGCTGAGTTAGGTGTATTCCGTGATAAGGTTTATGAATATGCCG
ATGCTGAAGAACTATATCAGGAACAATTAATGCGTTGGATGAAAATATCCAGGCAGTTCAATGATCCTGAAGGTAAGCGACATCATATTCGGACAAT
CACAGCCGCTCAATAAAAAAATAAAAAAAAGACATATTGCCCTCCCATTGCGGGAGGGCTTATGCCATTAAGGTAATATCTAAATAACACNATATTT
AAAAACATACTGGTATAANNCATCATCAATTAACACTGTTGAGAATCTTTTTGATGAGATCACCAGGTGCGATACCAATGCCTGAACAATACCGTCT
AAAGTTATTACACGGTTGACATGCTTTCTTTTCAACGATATTTAATTCAAAGCAAATATTGCCACGTGAATCTAGAATGGATATAAATGCTTTGTTA
CCTGTTACGCGATATGTCTTACCGAATACAACAGTTGTTTTATATGCAAGGCTATTCATGATTATTCCTTTAACATGGATTATTATCATGTTTGTAA
TATAGCCTTTAAATGTATTTAAATATTTATTAAACCNNATAGCGATGNGCTATATATGTTTTNAATACCTCATANGCCTTATCNGTTGCCATGGANC
TATTGACAAAATCAGAATGATCAATCTTAATAATCTTACCGAATGAATCATAATCGATAGTTGTAACNNCTATTCGATCACTATCACGGATCAATAG
TTTATTTTATTTAAAACAAAAATATTCCATTTCTCGCCATCGGCTAAAATAACATCCTCATCTTTAAGATTAAGACGAACAAACTGTTTTACATAAA
TACTTAACTGAGCAACTGTTGACATAATGATTTCTCGATATCTGTTAATGAACTAATCATATCTCGGACATTNATGGTAATAACATTTTTATAAGTT
AAATAAGTTGGATATGAACCCATAAATGTAATAGTCCCACAGATATGATTTTTATATCTAATATCAANACANCCGTCATATCTCCAGATAAAATCAA
ATGATCCTTTAGTGTGGTGNTCAAGTGNAAGAATAGAACCACTAACTAATTTAGGATATTGTTCAAATTCAGACATTACATAATCTGCCAGTTCCTT
AACCTCAGGATAATCAATCAATAATAGCATATACGTAAATCTCAATNAGTTAATATAACACCCCATCCAGGGTGGACTCTTTCGAAAAATGGTAATG
TATTATTTCGTATACTNTCTGCATCAATATTTGGAATGTGGATGGTACAACAGTGGGGGTTACTGTCAATCTTGAAATAGAAATTATCTTTTAAATC
TTCAACCTTGGATGTTTGNAATGGATATAAAATACCATTCCCCCAAACATACCAACGNCTATACAGCTTATCGTTTAACCGCTTCTCAATAACCGAA
TGCGATTTGAAACGAGGAACTCGCAAACGCATCCCGTTTACTTCAGCCCATTTGTCTACCCGNTCATAGCTAATAATTCCATCCTTAACCATTACAA
AGATAAATCCCTCAACTATGTTGGGGAGACGAACTACGTGTTTCAGAACCATAGTAAACGGAGATAACGTCAGATCAAGTTCAGCTGCCATTTGCTC
GTCGAGCTTTTTAGCAGTGTTCTTTGCCATCGGTTATCTCCTAATATACAGATTATTAATTATCGCTAGTTATTTAATATCTGCAAAATTCTGATTT
ACTTTACCCATAAAAATACCATCGGCTCTATCGTCATAATAAAGCTTCCCTGCTTTAGCATTACATANAACTCCATAAATGTGACCATTGTAACCAT
CAAAATTAAATAAAGATGGATTATGCGGTACATGAATGAATCCCATTTTATCGCACAGAAACTTAGCTACAGCAGCCGATCGGCTAATACCTGCCTC
ACAGTGTACGAATAGGTGTTGANCCTTACCAAGAGCTTCACAGAANGAAATAATACGTTGTGCATGNCGATGATCAAATAGATCATAAGAAGAATCA
ACATAATCCTCAATGTCATCAACATTGATACGTAAATAATTAAGATGTTTTGCTGAATAAAGTGGGACTCTACCTTTCTCCAGTAGACAGATCATAT
TTCTAGGGGAATAAAATGATTCAGCCACATGCAAAGGAATATAAGTAACTGTATTTACTGGCTTCATATTACACCTCGTTACAAAAAAATAAAAGGA
GCCCCGAAGGGCTCCAGTATANGTTAATCGAATACAAGACCACTACTAGTTGCTTGGTCATCCACATCTAGAGTAGACTGACGCTTACGCATATTAG
CTTTGGCTCGATTCATCATTTCACGACGTTCTTCTAATCGNTTACGAATATCTTCAANAGATAGNCNANTGATCACAAAATGCATTTGATCGAAATC
ATATTTCTCGGGATCAGCATAACCAGTGGTACGAGTTAAAACAGTGTTAATGGATACTTCGCGATCAGGGTCAGTGTATAGCGAAGCAATAGAAATT
GGGTCCAGAATAGCCTGGGCTTCTTGACGATCAAAACACACGTGTAATTGGACAGTCTGTACAGGTACATCATGGTGTTTATGGAAGTGTGCCCAGT
TAGTGATATCCATTAGATCAAGACTTTGGTGTTCTTGATTAAATAGAGTTACTAGTGCATNTAGTACTTCNAGAATGTTTTGGTTCACCATTGACTG
CGGTANACCTTCAACATTCTCATGATAGTTAATAATCATCGGAACTTTACTAACAGAGGAAACCCCTTCAAANGTCTTAAGGCTACCACTNCTATTN
CGAAGACTAATATCACTGTCGTAAGATCCAATGACCACACTTACAACTACTTCACCTTGTTGTTGTAGATGACTNACAAGNGAAGGACCAATNGTTG

Figure 7(D)

AACCAGAAGCACCACCCATTGANTANACNACNATGTTAGNATCCCCTGCTGGGAAATGATGGGCAATGGCAGGAATATGTGCAGAGATTAGTTCTGC
GGCTGCCTTACGATCTTTACCCATACCGATAGCACGTTTACGTGCNGTCTGGTCAGCTAGCTTAGTATCCGCTTCAATAATGATCGTATTATCGTCA
GTATTGTGTTTGTGTTTATTNTGTACACTGGTATCAATGTAGCAAACATCCTCATGATAACCATGGAATAGTTCACCAATACGGAAACCAGCACCAC
CACAAAAGTAAATTCGAGTTTTACTTTAGACATCATTACACCTCATTGTGATTAATATAATTCATATACCAACTTGTAAATGGTATCAGTGCTTAAA
AGTAACGATCTCTTCATGAGTTCGTTCTTGATGAACATTAATTCATTAACCACTTTACCAGTATCAGATTTAAATTCGATTACCATCTTATCTCGAC
ACATGTATGTTTGCCAAGTACCACCAGACTTAACACAATCAATAATCATGTTAAGTACATTCTTAACTTCAATCTTACTAACTTTATAACGATAAAC
GTTTAGAAGTTCAGTAAGCCATTTCGTTTTTGGGATTTTGGCATTTTTACGTTCTTTTGAAATATCAAAAGGAATTAGTGCAATGATCTCACCATCT
TTGTTGGTGAATTCAAATACCATTCCTTTTGAGTTAGCTAAAGGACGAATGTTNTAATTNCCTTTANCACTNCATACTTCTTCAGATAACTTAACTA
ACCTATCTAGTTGAACATCAGATGCATGAATGTTATCTTCTTTAAATGCTTTCTTTAGTTCATCATGAGTTAGTGGAGTACGTACTAGAGTGTAATC
TTTCTGTTCAGTCATTTTTCATTTTTNCNATTTTCNANTTCAAATTAAACGGTATTGGCTTTTATAGCCAATCCCTTATTACTAAAAGTAATAGATT
CTCGAACTAAGGATGGTTATACCCCTTCTCTAATAATAAGGAATATTATATGGGACCCCCCAAAGGGTCCCCCCACATAATATACTATTTATATAAT
TTCTTTTAGAAGAAAAGAGATAAATAAGAGAAATACAGTCTATTAAAGTAATGAATTTCTCAAAAATTAAATAGTACACCGCNCNNNNNTTNCGNCG
GANGGTCCTGCCGGACNANNGTCCGGATGTGCGNNANTAGNGGGTTTTTCAAAAATACNTGCATCGCGGTTGAATTGAGNGGTTGATTATAACGTNN
GATCTTAATNGTAAATAGAACTTCNTCAACATCTGNATGNCATCCTTCNAAACTAAAATATACTTCAGTCCGATCAATAAACTGATACATTTCTACA
GCTGGTTCAGCTGGATCTTTAAAGGCCANCTTATTAGCGAAATAATCAGTATNGGCTAGAATTAATTCTTTTACATTANTTGCATTCTTCTTATCAA
CAAGGAATTCAAACTCTTCAAGGTTATCTGTTTTGAAAATACCTTGATANGATGACGACTNGATTAGTTNATCACTGATATCATCAACATGAACNCC
TGGCATAAATTCAATGACTGGTAGAATAAGCTTGTTACCTCCTACGCCNTNAGCNATATGAATNCCAANCACATTACCATCACTAATGTATTCGTCA
TTACCGCAAATAACGGCACCAGCCGCTAGATATAAATTATCAACATATTTCAGATTATCGGCAATAATGCGAGATAGTACATATTCTCGCACCATGG
CATCATCTGGACTTGACTGCGGTTTAAAAGTATAGTGGGTGTTATGACTACTCATGGTCGCACATGTAACAAAAACTGAAATATCTACTGGATTAAA
TACCCAATGAACGGAGATATCCTCTAATTTATGTGGATGATGTAAACCATCTAGCTTAGATAGGGCTTGGAGTTGTTCTTCCCAGGTGATGTTAAAT
TGAGTCATTTTTCTAACCTCTTCATTTATTAAAAATAATACACTTATTTTACTTTAGCAGTTGATACTTCACATACATTAACTAATTGTTCAAATAA
CGGTTCATTATCTGGATCATTAACTAATTTGATGTATTAATAATAATACCAGAATACAGCATATCAGCTGCATCTCGATCACTTGTTTTAATTCTGG
TTACACCTTCCCACTTCCATCCATAGTAAATTAAATCAAATGATGAACCAATGTTAAAGGTTGATTGAATAAATTTGCATGTACCATTTTCTTTTAA
CCAATCAGGCCTATATGGTTCATTTTTATAAAATTCATGCATGAGTACTTTAAAATCAGTTTTAATGTTTTCATGAATAATGCAATCAATAGAATTA
AGAGCTTCATCAAGAGCTGATTTAGACTCAATAATGATTTCTAATACATTGGCAGATTTAGTGTAATCATACCTAGTTCATCTGAGTGTGCTCTTC
CGATTTGAAATACATTGAGCTTACCAATTGGTAAGGTGGCTTTTAATGGCAGATTAGTATAGTGAGATACATCGCTTTTATAACTGTCTTCATATGA
CTCAATTAAATTAAGCCATGCTCTTTCAATACGTGTATTCTCAAAATGNTGTTCTTCTTCTAGTAGTCTAGAAATTAGATGATTAATGTATTGAACA
TTATGGCCAGTACCNGTAATTNAATTATATTTCGTATTACCGGTAATTCCCCATTTATTATTTTCTTTATTTATCCAACCGTAGATTACACTGTTTT
TAGGATATTTATTTTTAAAATTATCGTATATTTCTTTTAGATGTGGATTAGGGGTAAAACTAAAAGTAGTTGATTCAGTCATTATAGATACCTATTT
GAATATTGTTTATTATTGCAAATTAGTAATATAGATCTTAAACTTTTTAACTCAGCATAAAGCCTCCCCTAGGGGAGGCNATATGTTCATTTATCT
ATTTCAGCGTTTGGATCATACCAAGGTAATAAACTTAGTAGTGCCGGTTGTGTTTCTTCATATCCTCTAAGATTGTTGCTTCACTTGCACCTTCTA
ACATAGTGGTGAAAGTAATCATGTTCTTAGAGTTATATATCGGACGTAGACCATTACCAAAGAATTTNACNTGTTGAACCATTATTTTGAAATCAGG
GTTATCGACTACATCTGGGATATAGATANCAGGTGGCGCACTGAAATAACGTTTAATTAACTCAATAGCCCAATACGTTGGTAAATCACCAAACTGT
GATTTCACTGTAGCTAGGTTTAATTGGAATGCTTTAGGTTCTTCAGGCGGCGGTTCCACCGGATCAATTGGATCAGTGGGTTCTTCAGGGCCAGTAG
GTTCAGTAGGCTCTTCAGGATCCTCTGGATCGCCTTCTGTTGGCTTTTCTTCAGATGTGCCACCATCAGGGTCACNTGAACCATCATCATCTTCAAC
GGGCTCCTCAGGCGTTTCTATAGGCTCCTTCGGATCTTCCTGATTCTCCGATAGATCGGGCTCTTCTGATTCCCCATCTCCATTTGCTTCAGTAGAA
GACGTGTCTTCTGATTCTTCATCTGTTGTCGAGTCAGTTGNGGCTGTGTTTTCTGAATCGGCAGTGGTATTTCATTTTCACTTGATTCAGTAGAAAC
AATTTCAGTAGGAGTGGTTTCAAGTTCATTGACACTATCCTCTGCATTAGTTACTTCATTAGGGATTTCACTAATTTCTGATAATGTTACTGGTGCA
CTTACTGCGCGAGCTTTTCGTTTAGCCATGGTTGTACCTTAGATAGAATAGTATTATGGTAAGTGACTAATTCAGGATCAGTTAAATTGATACTTTG
AATAGTCATATTCAGAATTACATAGGAGTCCATTGTTCTCCGGGTATATCCAGTTAATTCCATCTTGTTATATTTCTGTACATGATCTGGAACCCAA
TCACCAAAGATAACACCCAGTTTATGAAAACGATACACCAATCTGGATAATGCACGTTGGGTTTCAGTTGGGAATATATCGGGAACATTTTCGGGAA
CAGTACATTTATCACTAAATGGAGTAATAATAGGACCACGATGAATGGTGTAGCTAAGCTTAAAGATAACAGCACCAAGTTCGTCATTAATACGCCT
AAGTATACGATAACCATAATCGGTACGCTCAAGTTTATATACATTACTAGGATCAGCATCTGCTAACCTTCTAGCATGTCGTCTAGTGCACGTTTGA
TACCACGGTTATAGATGAGTTCACGTTCTATGTAATCTCTCTCAAAAGCGGCCTGAGGGCTTTCTTTCTCAAATTCCTTAGTTACTGACCAAGAAAT
TGTTTCACCAGTTAATTCATCAGTTAAAACATACAGATATGTCATAGAGTCAACGTATGAATACTGGATAGAGTANCGTGATAAATCACATGGCTTA
GCATTTAATCGTTCTTCTTTTAAATAGAAAAACATATCTTGTAAATGATTATAAGTTTGGCAGCCACCACCAAGATGATCAATATCAATAGACGTAT
CTGGCTTGACTGGAGCTTTGCAGCAACTCATTACACACCTCTACAATTATATTTGAGTTATTGTACTACAGATGATAAAGAGAAAATACATCATAAG
CCCTCTCCTTATGGAGAGGGNATTATATTTACATAGTGTTAAAACACGCATTAAATTTAGATAATGAGCAGCCAGTATAAATTAATGATTGCTCTAG
TTGTATGATGACATCGCCATTACTATCAAAATCAGCAGCAATAAAAGTAGATTCAGTTATCTTAAAAGTAGATGGCAGCATTTCTAAATAATTAAAT
ATTGCTTGATTATCGATGTCATGAGGATTTAAATCCATATGTTACCTATACATNGATAGTTATGGACCAAATATTAACAGGNCTGCATAAGACAATT
GTGATTAAATCTCCATGAGTTCTCTGATAATGGTTGAAACACATAACTTTGATTAACTTTAATTTTTTAGTTTCTTTATTTTGAATTTCTTTGATAA
GTGATTCAATAAGATCAGTAGTAATAAGTGAATGACCATCAATAAATGGTTTTATACTTACTAGCGAATCTTTGTTAAATAGAATTGCATCATCATA
TTCACATGTAGATGCGGTCTTGTATATGGATGCAACTTTATTAACTTTGTCATNAGTGACTATAGAAAAATTAAATTCANTCTTAGTTTTACTNAAC
GATGTTTCAAATAATTTATATTTATCAATAATAGTTTTATTATCAATAAATGATTTCATTCCAATATTTAAATCTATGTCCAGGGTATAAGANTTAT
GTATTAATCCAACTGATAGTTGAGTTTCATTACCACTATTGTTAAACTTAATATTATTAACTGAACATATCTGATTATTAATAAACGATAATAATAG
TTTAGAAATAGTTTTAATAACATTAACTTCATAATCATTATTAGTACAAGCAAGTGCAGTTGTCATGTATCGACTAACTTGACNAACATCTAGTTTC
TGATAGNNACTANCACTATCTANCCATGGGTCAATANTTAAAAAAATCCTTAGACTAGCTAGAATATCNGAAGATGTTTCAGAATAAATGAAAAACA
CATTATTATTAAGATCATCTTTTAGCCAACCACTAGTTCTAAGATTTTCTAGATCTTTTTCATTAGATACCGATTGACTTAATTGCTGAATTAAACT
AGGGTTAGCTAGGTTTAATAAACTAATCATTTTATAAACCATTTTATTATCCTCTAATTTATGTAATTACATGGAATAAATAACATAAGTACTTTTA
TGACTTATGATTTGATTCTCCAGGAGGTTTTCCCAATGGCAACTATTAAAGAAGTCCTTGATAGAAATTTTAAGGATGTTCAATTTGATCGCGATTT
ATGTAAAAGAATTATTGACTTTACTATCAGTTTTATGAATAGGAATGCTGATCACTCTGCTTTCTTTGGTGGTGTATTACTAGGTGTACAACAAGTT
AAATTCTTCGATACGGATCGTGAGATTTGGTATGATGATGTTTTACGAATTGATGAAGCGCTGTTAGTCCAAGATTTTAAGTCAGTTGAATTCATTG
ACCCTAACCATCGTGTAATGTCAGATGTATTCAATCATCTTCCTGCCTATATTTGTTCTAGGCTTTTAAAAACAACTAATGTTCCTTTGAATATTAG
ACATGAAGCAATGGTTAGTTGTTTCATGGTGTTGCATTTTAAATATCTAACATCTTTACTTGTACCACGCTTTAAATATCCTGCACGTAAAGAAGTA
GCCGAAGCTGCATTCGCCGCACTCAATTATCGATTTGACATTAAGACAATTGGGTCATGGGAGAAACTATTTAGGCAACGGGCTGAAGGTATCATTG
CACCTGATTCTATTTATGCACCTTTCTTAACTGGTAAAACACAAGAACTGGATTATTGGTCTGGTCGTGTGGTATCTGATACTCAAACACGTCTACG
TGAATTAATCAACAAGTACTATGATGTTTATATCAGAACACTGCAATCAGGTGGTAAATTAGTTATTTCATCGGATATGGCTGTTAATTCTGATGGT
GAGCAGATTCTACGCGATAAGTCTACTGGGTATCGCTCATATCTTACTTATATCCATCAAGTTGCGCAACAAGAACAAAATTTCATTAGACCTGAGT
TAGTCGGTATTATTGAAAAGATAATGCCCACAATGCCACCAGAAATGTTCATGGCGACACTTAGACACCTTTCCCGTAACATCGGTCAACCTAGGGC
ACAAAAGCTTGAGAAACTCGTAGATGAGTGCTTATTGTATGCTTTCGATTATATGCAATCACTCCGTACAATGGTTGCTAGAAATAATGATCTACAA
ACATTGCTTGTAAAAATACGAGCAAAGATAATGGCATCTAAAACAGAAAATGCTCAAGTTATTTTCATGCGTGAAGAAGGTGAGAAGTTAGTTAGGG

Figure 7(E)

ATGCGACTAATTCTAGGGTACCTGCATATATCGCAGCAACTAGGACTGGGTTGATGTTGTATTTAATTCTACGTGCTATGACTAAGAATTACTATAC
AAAACAAAATAAACATAATGCCCTCCCGCAATGGGAGGGCTTATGCTGTTAAGTAACATTAGCTAGATTGATCATTACATAAATTTTTCAGAGCATC
GTAAATAGCCACATAAGTAAAATAGTTAAACTATCTTTAATTTCCTTACGTGGGGTGCCACTGAATCCACCCCATGATACATTTGTATTACTAACNC
ATACAGTGCTAATAGCTGGCTCATGATAGCCACCATCTACTTTACGCTTTGCATAAACCTTAGCCGTAATTTCTCCACGTAACTTTTTGAAGAAAAC
TAGAGCACCCGGAACGACTATACGTTTATTACCAATCTTCGTAATAAATTCTTTACGATTAGTAAAGTGCTCTTTTAATAAATCATTAATAATTTTA
GTTAAACTATCAATTTCATTCTTCATCGACACGTTGTTAGTTCCTTACAAATAAACTTGATAACGTGATCACTTACAAATTTCAATGGACCAGAACA
ATTAGATTTCTCAATAGCGGTTTCAGTGTATGAAATTATTTGATTTCCACTTAAGGATAATGAATCAAATAATTCATAAGAGTTATTATTTTATTCT
TAAAGGATACTGCATATTGACTATTTCACTATTGATGCAAAATAGGTTAATAGCTGGGATAGATACAGAGTTATCTGAAGTATGGCTATTTTCCGTA
ATATTCCAATTACTGTATACAGTGAAAATATTTGCAGCTAGTAAAAGGTTGGCATTAACCGTTTCTAAACTAACATACTCCACAGAAGTACCTTTAT
GCCAATATAGTTCAATTGGATTAACCCAAGTATACCCAATGGTTTTATAGAAGGCATGCATTACATATTCTCGCCAACGTGTGGGTTTCTTATTATC
AGTTAAAACACACGTAATATTGCCTGACGGATAAATGTGGTGGATGCTACATGCATTAATTTCATCTCTAACATTAGTTGTTTCAGTAATATTAGAA
TGATCCTGTTTGAATAGCCATTTTAAATGACTATTAGTTGTGTCATCACCTTCCCCATTTGCAATGTCATTTTCTAACCACTTTTCAAATGTAGCTT
GTCTATCAGGTGTTGGCATTCCCCAATAGGTAGCTAAATGAAACGATAATAGTATCGAATAATATCATCATCGTTAAGAATATTTTATCCAGTTTCC
AGTGATGTTGATACTCGTATACTTCGCTTGGAATATTATTTACTTGATACCATGTATTAATTAATACTTGAATTGTTAATTGCCGAATACTCTCACT
TGTTAGAGTGTAATATTCCCTGCTATGCGGCTCTTCAATTGTCACTTCTTGATCAGTATAACCAATGTATTTAGGTTTACCATCGATGAGTGCAAAA
TTAACATTCCATGATGTATCATTACTAAAAGTGATATTAATAAAACCTTGTTCAAAGCTAGGCTTCACTACGAAACTGACATCATCCTTCTGATATG
TCATTTGCGTTAGAATACCAAAATTAATTTTAGATGTAAATTCTTTATCGAAGTTATGTTTATAAAGTAATCCTAGTAAACAATCAATTTTATTAAT
AGTGTGGTTTTCTAATAATAAATCAGTATTTGTAAGTTCATTAATTTTCATTTTAACCTCTCTAAAATTTACAATCTAGTTTTACTTATTGAATAAG
CAAACATGTAATATATATCTTAATTATTTTTAGCATAGTTTTTAACAACATAAAGCCTCCCCGAAGGGAGGCGTATATGCTTTAGCTTTTTGGTTAGT
ACCGACAGTCTGCTCATTCTTTTCAGTTTGAGCATTTCGCCGAAGTTGACTAACCAGACCATTGCCAGCCGCAACTACATCGGGAGAAAAGAATGCA
TTGATATCAAAGTTCTGATCTTGGTTGCGAGTCTTCCCAGGTGGGACCATCGGATATACTTTTGCCATTAGCTTAATCCTACACCGTCGTAAGTTAC
CCGATTACCAACTGCACGTTCAATCTGGTCTTGAATACCATTACGTGCACGTAGTACGTCAGCAGATAAACCACCCCAGTCTAATTTCTGGTTATTG
GGGTTCATACCGCGAATGTTTAGTTTACGGAACATTTGACGAGCGTATTCTTGTACACCTTCAGAAACATCAGTCAGTGCAGAGAACTCAACGTTTA
GATCAAGGTTCTGACCAATCTGTGATGCATCTTTACGGTTTTCCCAAGGACCAGTAGTTAATGGGAACATGTTGGTGCAAAGATAAGCNTTAACGCA
ATCCTGGAAGGTAGGATCNGGTTCTACGAATAGAACAGTCATACCGTAGAAGGTAGCGTCGTATTTCTCAACCGGTACAATGCCATCTGATACAATA
CGCGGTACTTTGGTATTCTCATCTGCAATACCATAGTTGATCCACCATTGTAAGAAACGTTGGATAGCGCGGTTTTGTAATTCCCAGCAACCAAAGT
TTGGGTTAGACCGGGCACGGGTTACGTTAGTAGCCGTTTGGATAACTTCACCAGAACCACCCCAGGGTGCTTCAGCGTTATCTACAGTAAGCGTACG
TTGTAAACCATCGATGGTACGAGTATGCGTTTCAACGAAAGCCTTAAGACATGCAACTAACCAGTTAGTATTACTAGCATACTTAAAGAATCGTGGA
GCATCTAGTAGGAACGGCACTAAGTTACGTGCCACATATGGCGTGTTAGTAGCCAGGTTAGCTAAGTCAGGCCGAAATACGTTAGTACCAGCCTGAG
CAAGGTTTACAGTGTTACGGGCACCACCAGCACCATAACCAGTCTCGGGTGCCATCGGATCATTATAGCGAGCCATTTAACTTTTCCTCATTCTGAA
AGCCACCCACTCATTGCTGAGCAGGTGGGGTTTCAATACGAACAGTTTCCAGATTGAAGTTCAACGTGGTCCGCGGGTTATTAGCCTCAACAGTTAC
GTTGCAAGTCCAGCTGGTGCCGTTATTTGCGTCAATCGGAGTGATCTCTGTACGCGGGATAATGTTGACACGAGTACCGAACATATCACGTACTAGA
TCGAGAATATACTCGTCACAACGCTCAACTAATTGTTCAGGTGTTAGTGTAGCATTACCGCTAAATTGAGCGTGTACTTTATGGATCAGTCGGATTA
ATACACAGCAAATATTAACAGTAATCGGTGATAGAAGTACAGATGTATCATCTAGCATTACTGAACGTAGGCACGGATAATAGGAGCTACGATGGTC
ATATGACTGACTCCAAGTAGCACCATTCGCCCAAGCTTGTGCCCGTACACGATCATCAAAGAATTTAACATTTAGATCTTTAACAAAAGTAACACGG
TTATTAGGACTTACATCCATTTCCATACCTGGAACTAGATTACCAGTTCCAGCACCTGCATAGCGTGCCCATGACATAGCTACGTCTAAAAGCTGCG
GTACATATTTACGATAGGTACCATCCATTAGTTTGCCAGATTGCATTACAATCATAGCGCGACAAACACCAGTTCCGTATAGAGTGGATTCTGGGAA
AGCTTTTAGGCGAGTGATAATCTGTTGAACACGACTTAGCTCAGTAGCTTCATCAGGTAGACGACTATCAGTTTCTACGAATGTAGTGAAGAAATAT
TGTAGATCACGCCGCGCACTTAGTACGCGCATTGCCCGATATTTTGATTCCATCGGAAGGCCAGTGTCATAAAGAACACCGAACTGATATTCTGCAA
TGTTATTATAGCGATCATTTAATTTGCCAAAGTTAATATTTTCAATATCAACTAATTTGGCATATTCTTCTAGATCAGTTGTACCGTCAGTACCACC
ACTAGCATAGATGTTACCATCTTTACCTAACGTAATGCCGCCATCTAGTGGACCGAGTACNTGAATACCCTGGTAAGGATCACCATCAACAGCTAAG
AAGGTTAGGAAGTCAATTTCACCAGGTGCAGTAGTATGCGCAGCAGCGGCTGGGTTAACTCGCATCTCAGTGTCATAAATCATCTGACGAACAAGAT
CAATGTTCTCATGATAGACGTAGAACTGAGAGAACGGTGAATAAAGTGGACTTAGGCCAGAGACTACACCATCATCTGAGTAAGAATCAACTAATAC
ATCACCAACATAAAGGTCAGCGTTATACATATCGCTGTAAACACCTTTATCAAATGTAATGTTTAGATAATCTTGCTGGTCAGCAGTTTTGACAATA
ACTGGACTAGTGCCTACTTCAGGCTTCTCAATTAACTGAATACGGAATTGACGAGTTTTAAACTTCGCCATAGCTGCTTCATCGAACTCTTCGATAT
CAGCAGTTGTAGTACTCCATACACGCATACCGTTAGAATCACCTAATTTACCAAAGAAGGAAACCGGTGCTTCAAATAACGGATATACTAGTGATTG
AGATCCATCTTTATCTGATACTAAAGTACCTGGTAGTACACGTTGTGTACCTACTTCAGAGGTATTATCTTCAATAAGAATAATACGTGCCTTTAGA
CCATCAACTTTATCAGCAGTCGGGACTGGTGCATTACCAATGTCACGAACACTGTTTGGATAGTTGAAACCACTAAGACGACGAATCGTAAGTGGGA
TTTCATCTTCCACAATTTCAATAGCAACAATTAACCGAGATGGATTAGCTGCATCTTCAGGACGTAGACGTTTAACATAAAACCATTACCACGGCCA
AGAAGGTTAAGTGCTAATAGTGATTGTGTATTGAAAAACTTACTACGTGGATCAAGCGATGCTTGACCATAGATGGATGCAAAACCATCATCAGAAT
CACCGACATAAGTGGTTTCAGTCGGTCCTGTCTCAGTGAAGAGACGTAATAGCGGACAGTGTTGTGCGAACGTGATGTCCGGACGGATCAGGGGCCG
GCGGCTACGATCCCGGATACCATTAAACACAACCCTAGGGACAGCGTTGTAATATGCCATCTTTTTGATTCTCCCAAGTTGGAGCTTTGAACTCGAT
GTTATGAGTGTTAACTAACAGTCAATCATAGATATTAATCATAGTTGACCATACTAGTTATTTTTTACTATCCATTTAAGGAGTAGCGGTAATGTTT
TTGCTACCGTATGAAACTACAGTTTGTAAAACTCTATACAATCCCACCGGCGGTGGAAAATTATATCCTAAACAATATGTTGATCAAATTGAAAATG
CGATCAAGAAAGCCAATGTGTATCTACCCATTCCACCTGTTGATGCACGTAATGGTGAAACGCTAGAGCATAGTGGACAGATTACCCCAGTTGATGA
TTTTGAGGATATTAAGAAATTTACTCAAATTGTCAATATCGGTGATCGTGATAATCCTAAGCTAGTNGTTGATGCTCGTCTATATAAAAAGATTGAA
CAGCGTACTGGTATTCCTAGGATTATTCAGCAGAATGAGTGGCAATTCCAATATATTCGGATGGCACTTAATATCAAACTATTACGTGAAGGCCCGG
ACTTCCTCCATCGCTTAGGTGATATCCCAGTTAAAGTTTTCTATAATTGGATCTCAGGCATCCTAACACAAAAATACAGCCTACCACCTGAATCAAC
CCAAGCTATTTGGGTAATCTGTGCTGTTTATTACTTTGCTATGCAAGATGATGNTCTAACAGAACCAGNTCAGGAACGNGATCGGTTAATACCAATT
ATTTCCCGTCTTACATATATTCCAGCTGGTTTTATTGCNGATGTTATTGATACATTAGGTCCACTTCATAATGCCGGTGATCTAGCTTATGAGATTT
CAACTAANGGNCGTTCGATCAGGATGGGTAAACTAAAATTCAGTGATCTACAATTATTAGTATCACCGAGTTGGTTTGGTACCGCTTCCCGTGAAAA
CGTAGGTGTGGCACTAGAACACATGCCAACTTACATCACACTGATCTACATGGCATTAGCTGATCGCTCATACCGTAAAACAGTTTTAAGTCAGAAA
GTTGAAATGATTTCACGTTCTGATGATGCAAGTCGTTTTATTAATCTAGTGAATGAAGCTGTAAGTAGCCAATTCGTTAAGTAAATATAGGGGTGAA
TCAATGAACGCATATCTATTGCGNCATGCGATTGATAACGTTTGGTGTAACCCAGCCCAGGACCGACAGTTTGTTTATGAACTGAAACAGCTNACCC
CACGCTACGGCGTGAGGGTAAACTGGGTGGTTGATTACACCCGGTATAAGCTACCAGTCCAAAGTACACGTGATTATTGGCATCTTTATCAAATTGG
TAAAATGATTCCTAAACACCTGGGCTTGCCTAAGGTTTACAATAAGTGGATGAGCCTAAATGAGTTGGCTCAAAACCATTTAAATTTAGCAGACGTT
TATGTAAATAGTGGTATTAATTATTCACGTAATGATACATACGTTTTAATAACCAGTTCGCAAAATCTTTTAATTGCTGTTAAGATAGATCCATTAT
TCCCTGATCTCGATGAAAATCAACCCTATCTTCATGTTTATAACAATGCTTACTTTCAATCAAATAGATCGGATGTAGCTGGACATAGATGGTTAGT
TTCTGAATCGTATCGAGTTAAAACAATATCTGAATTAACTCAATTTCAGATTAAGATAATGGATACCATAGCATCTAAAGGTGGTGTTCCTAAATAC
TTTGTAAATGGTAGATATGTTAATGAGATATCTCCTGTTACAGCAACAGTCGGTGATGTTTGTGATTTCATTCTAGATCCATCCATTAAAAGGATGG
TAGATTTTGATCTACGTACATTACCTGTTTTCATGTCAGAAATAGATAGTGAAAGAAATATATTTTACACTACACTGATAAGACTGTGCAAACAATT

Figure 7(F)

GAGTTCTTTGATGATGTTGAAGCATATATCTATCAGCCATTAGGTAATAATCGTTATACTGGTGTTAATTACCATCATAACGAGAGCCGTTGGATGC
GGATGCTTACACATAAAGATTATTCTATACCAACTGCACGAATTGATCAGTTTAAAGCACTTCATCCAGAAGATCCTCGACGTGGTGCTGATCCTAC
TCGTTGGCCAAGTCAAAACTGGAAAGCATTAGATAATCTAGTATTTAGAATCTACATACATCATTCTGGTTATGATCGCCCATTAGTTGCTGATTCA
CATCGTATTCAAATTCTGTATCGTTTAAAATCAGAAGATATCATAAGGGCTATGACTGGTGCAGATTCTGGTAATCCTTTATGGCGAGCTGAAAATC
TAGAGCAATCACCATATTGCTGGTTCATGTCAGCACCATCTAGTTTCGTATACCCATTAACATTCAATCTACCTGAAGAAACATCGCCTAGTAAGGT
AGAAGCGCAGAATATGGCTGGTGATGTTTTTGGTTATTATGAAGCAGCTAATATTCAAGGTTATAATCCAGCTTGGGTTTATAATGATGCTGGTCTA
AAGACCGCTGATTTACGATACAACTACTGGCTAGATGCAACTGTATTTGAGTATGATGAGAAAGGTATCTTATTAGGTTATAATTATCATACAGCAG
GTCGCAAATATTTCCCTAAAGATAGTCGTTGTGCATATGTTGAATGCATTAATGGTAAAGGAAGTGTAGATCTACATGAAGCATATGGGAATGATCC
CGTGCCTTTACGTGATGGTGACAACTGGCGAGTTTATGTTAGTCCTGTTTGGGCTGGCGTACCAACTGGCGAATGGCAAGATATAACAGACCATCCA
GATCGAAACAACTGGGGTTTTTATGATGATACCACTGATGATAAACGTTGGGTTTGGATAGCTAAGTCAAATGAGTGGTATGGCCTAGTAAGAACCG
ATGAGTACTTCTATCTAAAAGAATTAAAGTTTAATAAAACTGATGGTATCATTAAATGGAGTATACGTAATACTGAAACTCATAATGGTGTAAAAGT
CGATAAATTGATGGAGATACCATTTGGTCAGTATGATGTGTTTGTAAATGGTCGGCCTATCATTGAAGGTCTTGATTACACGCGTGAATGGCCTCAA
ACTGTATTATGTAATCTGGAATATTTAAATGCAGATCCAAATGCAGTTAATACGATTCTTCTACGTGGAACAGGTTTCCCAACACCAGATTTAAAAC
CATACGAACCTGGCGAGATTGGTTTCATTGAGTATGGCGTATTGTCTAATGATGGTATTTATAAAGTACATTCAAATAAACAATCACGCATAATCAT
TGATGGTCATTATCGTGACCCTGCTGATCTTGAATTCCAAGAAGATCAAGGCACTACTGTTATCACTGATGAACGCAATGGTGCACCATTCCAAATA
CAAACACCACAGGCNCGCTTCCGNGATGTTTATAATGATGATTACCAAGCTAGGATTAAGGATGATGCACGGGATAAACAAGTCACTGATTTTATGA
CTGAATATTTCCCAATGAAACCTCAACCTAATCCGGACAAGATCGATTATAGATACCAGGTGCTTTCAGCGTTTTCATGTAAGATCATTCATGATAT
CGTAAAAGAATATATCAAACCNCCATATCAAAATGGACGGTATAGTGACGATGATATTGTTAAGCAGCTAAAAGATTACGAGTGGTTAGCAGCTTAT
GACATTATCAATAAAGGCTACAACAAAAATAAAGTTGTAGTTTATCCACATTGGTATACTGAACCTGTAGAACTAGATATTTCCAATGGGAATATTT
AAATCGTATTCTATCGATATATCTACGTGAAGTACCGCCACTATCCTTGTTCGTTAAGATTAAAAGGAATCAACCATGACAACGTCATATGAAAGTA
GCCAGTACCAACCACCACAGCATAAAAACCATTTCTGGTTTAGAGGTGATATTGTCTCATATGCTGGTGANACTGGNAAAGCAATCCCTGCTAAAGG
AGATTTAGTATTTGACGCAGCACAAGGTTGGTTTATTGTTCGTGAAGTTGATGAAACAACTGGGGTATCTATCTTAGATCCATGGTACATGCCCCAA
AAACCAGGCAATGAAAATGAACAAAACCTACTAGTTGCTGTAGGTCCAGGATATAGCTCAGAATCTTATCGGTTATTCCTAGATCAGTCTGTAACAC
CATTTAATATTTGCCCAGACCGGCGATTACATTTTTATGGATCAATGGTGCATGGCTATAAAGTTTTCCTAGGTTCAGATATATCAGAAATACATGG
TAAAGTGATTTCCCTGTTCTATGATAATGCTGGTAATTATCTAGGGCCAACTATACCAGTTGAATCAGTACCCGATCCATTGACTCAACAGAATGTT
GTTAAAGCGTTAATGAATGGTAGGACTGCTGAGAAAATGCAAAATGGTGAACGTGTAACTCTAGTAGCTTATGATGACGTGGGTGGGCCTGTTTCGA
TTGCTCAACTCGTTGTAATGAATACTGAAGTTATAGCNCAAGAGGATACCTCNAAGAAATATGTAGGTGGTATCACTATTGAATCACCATTCATCTC
NCCAGCTGATCCNAAAGTTATTGAGTTCCCATTAAACGTACCAGTTGAATCATTACCGATGATGGGTGCTGTTCATTACCGTGATGGTAAGAAGCAT
GTGATGAATATTGATGGTACGGCAATGGCAATTTATGGTTTACGTAACTATATTGCCACTGAGGAAGGACAAGAGTTTAAATTAACTCTATCTTACC
AATTAGCACAAGATGAGTTATCATACTTATCGACTCCTTCGGCTAACCGTCGTATTCAGGAGACATATACAGCGCGTACCACGCCTGTACAGGGTGC
TTACAGTTGTCGTATGTTTGTTTATCCNGCTTGGGTTAATGAGGCAGTNGGTTACAGATTAGAATTCTGGTTAGCCAATATTGATCGTCAACAAATT
TGGAATATTACCCCATATGTTGAATTAGGTGCAAACTCAGCACCCTTTAACCCACGTGGTTATGGTACTATCCAAACACTAACATATGCGGTTAACC
TAAACCAAGTTGATGGACGATTCCTACCAGTTCGATTTGCATCTACTTTCCAAGTAGCACTATTGAGCGCTGGTAATAATCGGAATGCTAACTGGGA
NATCTATTCACGCCCTGANCAAGGTGAAGCATATGGTCGTGATCTTAAAGCCGATATNGAATTTATCAATGGTAATCTTTGGGATCTCCGGTTAGCT
AATGGNGCACAGTCACAAGCTGCCTGGCTTAAGAAAATGTACTTTGCTGCTGAGCCATTAACTGGTCCAATGGAAGCTACTCCNCCNACACCTACGC
ATTTCCGGGTGCGTACAGTGCATAACGAGTATGAGTATACGGTAAGTCAATGGAATACTGCNTTNCGNATTAATGCTCAAGATATGGCCGATGGTGC
TTTACTACAANTCACCTGGATTCGTCGTGAGTATGATACNGACCTACAGTTAGCCATTACCGCATTACCTTGTTTACAACGTTAAATATANNGCCCC
CTAGGNNNNNCCTAGGGGGCTTTATAACGTCTTTTAACACATTATCCATATGAGACTATACTTTACAATTGCCGTTCAATACGGCTTTATTATGGCA
CATTAAAATAAGTACCTTAAAGGGCAGTGTATGGACGTTATACTTTTCAATAGTGATTGGGATAAATACTACAGCGCTAGTGTTGATCTTACTACTA
AAAATAAATCNTTTATAAAGTTAGCNTTNACTTATAAAAAGATGGGTATTAAAAATTACAAATTTATACTAGCTATATTGGACCAAGGTTTAATTGG
GGTGGATCCATATGACCCTAATCTTAGCGAAGAAATGAAGTTNCGTATTAACATGGAATGCAAATATAATCCTTGGTATTTTTTTAGGGAAGTGGCA
AGAATCCCCCCTAACTCGGGTAATAANCCAATTCCATTCCAAGCTAACCGTGGTAATATTGCTTTATTCTGGTGTTATTTCAATCACGTAGATTTTG
GTTTATTACAGCCTCGTCAGACAGGTAAGTCCGTATCAACTGACGTGCTCAATACAGGCATGATGTATATCTGGGGNGAGAACACTAAGATTAANCT
TATTACTAAAGATAACAAACTACGNAATGCTAACATCGAGCGTCTAAAAGTAATGCGTGATTTGTTACCAGAGTATATCCACTATACNGATCCATTA
GATGCGGATAACTCCGAATTGATGACATGTATTAGATTAGGTAATAGGTATNTAACAGCTGTTGGTCGAAATGATGTTAACGCAGCTGATAAATTAG
GTCGTGGTCTTACTGTACCAAATATGCACTTTGACGAACTTGCCTATATTAACTTAATTGGTGTTTCACTACCTGTTGCACTTGCNTCAGGTTCAGC
AGCTCGTGATGAAGCTCGCCGTGAGAACCAGCCTTATGGTAACATCTATACAACTACAGCTGGTAACATCACTACCCGTGATGGTGAATTTGCATAT
CACTTCTTAACAGGTGGNTGCCCATGGTCAGAGGAATTCTTTGATCTACCAGATCAGAAAACTCTACATCGTGTTGTAGAAAAAGGCACTACTGGAA
AGAAACCTCTAGTTTATGGTGCATTTAACCACCGTCAATTAGGACGTACCGATGAGTGGTTATATAACACACTTCGTGAATCAGGTTCATTCGGTGA
AATTGCCGATAGGGACTTCTTCAATATCTGGACAGTTGGTGGTGAAGGTTCACCCTTATCATCAGATGAGAAAGATAAACTTAAAAACAATATGCGT
GAGCCAAGCTGGACAGAAATCACNGATGATGGTTANACACTTCGTTGGTATATACCAAAAGANGAAGTAGCCTCACGGATGATGAAGGGTAGGTTCG
TTATGGGTACCGACCCATCTGAACTTCTTGGTGAAGATAATGACGCCACTGGCACAGTTGTAGTTGACGTAGAAACACATGAGGTTATGTGTGTTGG
NAGATACAATGAATCATCAGTNCCATCAATGGGTAATTTCTTTGCAACAATGCTATTNANATATCCTAATATTCTTTGGATACCAGAACGTAAATCA
ATAGGTATATCGTTAATTGACCATGTTATCTTGATTCTNCATACTAAAGGANTAGATCCATTCCGGCGTATCTTTAACAGAATTGTCAATGAATCAT
CAGAAAGAGAAAATGATTTCAGAGACATTCAAACTCCGNTATCAGCAAGACAACCATCGTTNTATGATAGGTTTAAACGTTATTTTGGCTATGCAAC
GTCAGGTACTGGCGAGTATTCTCGTGATAATCTATTTAAGGTGGCATTACCATCAGCAATGCATTATGGGGTAAGGACCATCTATGATAAACCACTT
AGCACGGAGTTATTAGCACTTACTATCCGTAATGGTAGAATTGACCATGCTAAGGGGAACCATGANGACTTAGTGGTATCATTATTATTAGCCCANT
GGTTATTAATACAAGGTAAGAATTTATCTTATTATGGTATCAATGTTCCCATCTTAGGTAAATCAAAATTACGTGATAAAGAACCAAGNCAACTTGA
AAAATATCATGAAGAGAAAGAACAGCAAGGTCGNAAAGAATTTGAAGAGATAATTGANCAGCTTCGCGGTGAAAAGAACCCGATGATTGCAGCTAAA
TTAGAAATGCGNTTGAAACAATTGTCTAAACGTGTTAATATTGATGATANCAGTGGTGTAGGTATTGATGCCATGTTAAATCAAGCTCGTGCAGAGC
GTACACGTAGAGTGCGTATTAACAGATATTCTAGAAATAGTTGGTATTAAACAAAAAAAATAATAATACGTTACCCTCTTCGCAATGAAGAGGGTAT
TTGAAGTTAAGNAACTCTAGCGAACAAAAGATTACTGGAGTTAGAATTAATATGATAGTTAGACGATCCGTCAATCCATTTAGCATCGGAAATCTTG
TTTACAAGCTGACCATTGCCAATGTAACCTAGGAAAGTTTTATTATCATATACAGCAATTTTGATTAGCTCATTTCGTCCGTAGACTAGTGGCTTAC
CATTGAATGCTGTTACTTCTAAACCAGACATGTATCCATAAATTGGATCAGGTCTGGAACTTGTTTCAAAGACTTTCATTCGAAGTCTCATCTGCAA
GAAAGCCCATTTTGGGCAAAAAATGTCAAGCTTAAACTTGACGACATATAGCCCTCCTGGTGCGACAGGAGGGCTAATCTTTTCAGAACGTACGGTG
TTGTTATAATACTGCTAGCGAAAATACCCATGATAGGTAAGTAGCTAATCCGCAGTTCTCTTGGATGATACCTACTGACAGTGTAGTTGCAAATGTG
CTGTTTGGAACCCCACTGGTTTAGCGGCCAGTGGAATTCCTTTTATGCCGCTTTTTCTTTCTTTACTGGATATTTCTTATATTTACAAACCCACGT
TCTTACGCTGGTAGGTATCTTCCTTCTTATTATATTCGTAGTTCTCGATGAGGCACTTGTTGCTGAACTCGACCATCGAACACATCTTGTCCATGAT
GACTTCAGATATTTACCATGTTCATAAATTCGGCGTAGTTGTAGCCGGTATTCATGTCGAGATAGTCTTGTTCGACCATATCGTCATTCAGGTACTT
GACGTAAGCCTCGGCGTGAGCAGTGGCTACCGACTTGGTGAAGAAGTAACGAGCGTGCTGACGGTTCTGTTCGAACTGACGCAGATTAGTAGTGGCC
TGACCGCCGAAACCATTGACCTCCATTACCCCGTAAACAGTACGATCATCCAGAGTAGTGATCTGTGCAATCACTACACGAGAAGCATTTTCCGAAT

Figure 7(G)

GGTCGATGAACGTCATACTGTAAATCTCGATTTCTTTGAAGTCTTCCATTAGAATTTCCTGTTAAAAAAATGAATAGACAACCCCTACCTTCGGGTA
GGGGCTTTATGCCGTCAACCGACAATAAGGTCCCGAATCGTTACGATCTAGGTATCAGATGCAGGTTTAGTCAAACGAGTTACACGAATATAAACCA
TGTAGTCACTCAGAGATAGAACTTTTTCACTTATACATCTTCCAGCGTCATGATTACGACATGATAAGGACTATCAGCATTGTGACCCATGCACGTC
TCGCATTTGAAGATCCGCCACATGCCATACGAAGGCAGCTCGCGGTTTTTCACATAAACGTAGTCGTGCGCTGCCACGAGGTATTTTTGTTGAATCG
AGAATTCACAAGTGATGTAACCTTTTTCACGGATGAATTCTTGAGTCATCTGATCAAAAGTCTGTTTGAGTTCATCAGTAAGAGCGACTTGGGTTTC
GAACATTGAAATATTCCTTTTGATATATTAAATAGTTTTGATTATTTCGGAGTTATTGAATATTTAGGTTACCATCTGCTCTATATAGACTCGGCTG
ATTTCATTTAAGTAAGCGAGTGCCAATAGAATACCAGCCCAAATAACAATTTTTCGAGTAGTCTGTTTTTCTATTACACCTGGGTGTGATTCACGAA
TACTACGGTGACAAAATACATAAAACAGACACAGACTCATTGTAACAAAGATAATGGTAAACCATCCTAGATAGATCATTTTCTTCACCTATTTTTA
TAAATAGAGTTTATAGTTTAGTCAGGCGGATGATTTCTTCTAAAGCTGCATCAACTTGATAATACGGCCATGAATCAACACGAGGTTCGTTATCAAA
GTATGTCCAAAGTTGAATACCTTGGAGTTTATTGTAGAATACATTGATTCTGATTCCTTCATGGCCAACAAGACCTTCAATGTAAGCTGCACCATGC
ACATACGTAACATGTAGTGCGTACTCGCTATCTTCACCAGCGTATTGCATAGGTCTGGAGTAGATGAAGGAATAAGGATTAAATGGATCAGCCTGAG
TGATATGTTCGAAGAATTCTTTCAAACTAGATTTTTTCATATTGGACATTATATTTTCCTCATGATTTATTAAGTCTATCTTCTAGGAGGTAGACTT
AATACTATTCGATGTTATTTTAAGACGCCTGCCTTGTAACCTTTAACAACAGTTCTAGCTTCTAATGCACTGATTTCGCCAATGTGTTTACGCAGTG
CTTTAATAGCGTTGATGGTAGGTTCATTATCCGCGATATGTCGCCAGTTTCCCTTACCCTTAATGAGTTCAACATCCTGGACATATAGACCATCTTT
AACTAGATCCATTGTTTCTACCAACTTTTCGACTTCTTTAGTTAGATGCGTATGAAGACTGGCGAGGGACATGTCAGTCATTTGATGCACATCATAG
AGAAATCCCTATTATCAGAAGACGATAAAATTTCTTTGGTGAGTTTATTTACAGTGTCAATGTTTGCTGCAATTGAAACTAGCAGTGCAGCATATTT
CTCTGCATTATAATTCATTAATACGTATTCCTATTTAAAATTGGATTTAGTGTAATGCGGTAATACTGCGAATATCTAATTCATGTAAATCATATTT
CTTTAGGAACTCATTCACCGCTTGCTGAATGGTGTACCCACTCGGAGATTCCCACTGAGTACCATTAAAAGCAATAATACGATAACCTACCATTTTT
TATTCCTCTAATCACAAAATAAATACCCTCCCGAAGGAGGGTATTTATATCGTTACCAATTGATTACAGCGACAAACTCAAATACCCGACACAATTC
TTTATCACGATGGGCATGATGAAAAGATTTACCTTCAATACCGCAATACGGATAAAACAATTTTCGGTGTTCCGTGTCGCCGAACCAGAAGGTGGTG
TTATTGGAATCAACCACACCATGGATAGCCACATCACGAATGTACTGAAATACATGAACTGCCTTATCAGTGATCACTCGAAGTTCTACACCGTGTT
CCTTCATCATAGCCAGGATGTCTTCCTTGGTGTAATCTGCTTGTTCAGCATTGGTCATGATCTTGTGAGTCAGAGAACGCTTTTCCTTGTCACCGAA
ACAGATACAGACCAATTGCACCAACTGACCTTCTACCTTGAGACCACTGGTCGGTTTTAGTAGAACGAACTCATCATATTTGTAATCATTGGTGACA
ATCAGTGCCGACTTATTGCGAGTGACAATGCCTAGGTTATACGACATAATTAATCTTCCTCATTTTAGAATATGTTGAACCTTGTGGATGTCTTCCA
GGCTATGACCAAGACCAGTGGCTTTGTAAGAATGTTCCTGATCAACACGCTTGTGATATGCAAGCAGTGCATCTACTGGATGTTCAGCGAAGAAGTA
TTCAGTGTTGTTGCAGTCCCAAGCGAACTCCCATTCACCATCACGAATCTCTATTTTGTTAGCACTGAGGTAAGTGATATTGATGGTATTTACAGTG
GCATTACCACCAATGAGGTAGTACGATCCTTCATTGCTACGAACATCGATCCTGCCGCCATCGATAGTATCCTGATAGTAGAAACCACGGTCGAAGA
ATAACTTCAGCATCGAAGTGAAGTAGCTGTTCAATACAGCTTGAGCATCTTTCTCTTCGACCACCCATTTTCCATCAACGATGTTATTCAGGTAATT
ACGATCATGATTGATCCCGACATTATCCACGATGTCAGCGTAGTTCTTATGGAACTTAGCAATCTCGTACAAACGTTCCAGAGCAGCAAAACGGAAA
GGGCTGGTGGATGCAGAGCCAGAATGATCCGACCTACGCTCCACAAACCGGTCCCGTTGACCTCGTAACTTTCTTCGAGGTAACCTTTGATACCAC
AGTTAACTTCAAGTTCATCTGCTGGGAAACCGGTGCGGAGCCGCCTACGGATAGCCAATAGTACCGATTCGGATTCTTCCGGATCGAACAGGTCTAT
GCCGAAAGTAATCCAGCTACCACGTACTTTGTGCTGGTATGCCAGGCGTACAGTATCACCGAATGGAGAAATGAACCAGCGTTCGTCTTCCGATACG
ACCAAATGGCAACCACATTGCCACAGGGTACTTAGAGGATCGTTAGAGGCGAGAATGCGCTTGGTGTCGTTCATATCCGACGAAGTAGCATCTGGAC
TGCCATGTAGGTGTGTCAGAATAAACAGAAGCGATGATTCTGTAGTTTGAGCACTCAACATTGCGCGAGTGATGGTTGCATTGATGATCATGAGATA
TCTTCCTTTTTACAGTTTATGAATATATTGCTAAATAAAAAAATATTACGATGTAGAAAATAAAAGGGAGTCCGAAGACTCCCATTATTGCGTGTAA
TCTATTTGATGATAACCGCTTTAGAAAGAGTTTCCATACTTCCAATAACTAATTTGGATTTCTCTTCTTCAGGGTTCNCCATTGCTTCACGCAGGAG
TTCACCAATAGTTTTGGGTTGAACATCATCACTGATTTCACGCGAGCATGCCGAGTCGTCGTACATATCAAACACATTCAGATCATCATCATCCAGG
GGCGTGCTGTCATTCCATGAATAGCTTGATTCATCCGAGGTATCATCAGACTCACCATACTGTTCACTGAGGTCACGGTCCAGTTCAGCCTCATACA
TCTCGCTAATTGCTTTATCGTCTTCTTCTTGCGCCTTACGACGAGAAGTCTTGTAGAACGGAAGCAGGCGTTGCAGGACTTTATGGAACTTCTTCTT
GCTGATCAACCAGCTAACAGAGTAGCGAGACAGCTTTACTTCAGCTGCTTTGATAGTCGGATCGGAGTACAGCGCCATGACTAGCTTGTCCAGTTTG
TGCAGATGATCTTTAAACGAGTTTGCATAAGCAGGATGTTCCCGAAGAGTGAACATCACAAACGAACGCATGTCAGTGATATAGTACTGACTGTGAT
GTTTGTTGATTTCGATGTATACCGGATCTACTGCGCGGTTATAATCGAATTCCTCTGCCCAGGTAAGGCTACGTACTTTAGTAGGACGAGGACCTTC
TGCCCAACGAACAGTCGGATGTTTCTCACGGATGTTCCAACCATGATTGCGATCATACTCGGTTGACTCTTCTTTGAACCAGGTGAAATTACCTTCA
CCGCGCGATACAATACCACGGCACCAACTGACGTTGATTGCCTTGTTACGGCTTTCAGTAAGATCACAGGGCATGTCCAGAATAGCGACATAACTGT
TATGACCATTGGCCACAACGCCGAGAACAGTAGCTTCGAATGTCTCGTAGCGCTGTCCAGGATACACACGTTCATTCTCATCCAGGTAACGAAGGGA
GCAGGATTCGAAGATAGCACGAGTACCGGCAGGGAAATGGGCACGACCGAAAGGTTGTTCGGCCTTTCTTTCTTTACGACGGCTGATAACCCATTCC
AGTTTTTCTTTGGTCAGACGGGTTACGGGTTCACGATACTGTTTCATGGTAATTTCCTTTTTACGATTGATTGGGTTGAGTACATCTCAATGCATCC
TTTTCAAGACGCATTGAGATGGGGTCTCCGAAGAGACCCATCTATTATTCTTGGGTCAGTTCCCCAAGACGACCTTCGGCTTTCATGCGACGGATTT
CCGAGATGGATTTACCGTACATTTTGGCCAGTTCTTTCACAGTACCTTCAGGCACAGGTTTGTTCATGTCGCGGAAGTTCTGCTTAGCGATATTGTA
ACGCTGATGTTGAAGAGTCTTCAGTTCCGAACGTACCAGAGCGTTACCGGCACATTGGGAGATGAATGTAACCATGAAGGTCTTCAGCTTGCCACGG
TAGACGTTGACCCAAGCACAGGACTCATCCACGTGGATGTTCTTGTACTCGGAAACCTTGGCGTATTCCAGCAGGCCGACGGCATCGGGACCGTTGT
CCTGATAAACCATCTTGTTGAACAGGCCCAGGGCGATATCGGAGGAACGCTCACCTTTTATGAAGGCGATGGCGTCTTCGATGATCTTGGTTTCCAG
GTCTTTGTACTTGACCGGGTCGTTCTTGATCAACAGTAGCATGGCGTCGACCTTGACAGTCAAACCCATGTCGGCACCGCGTCGATCGATCAACTCG
TTGTGCTGTTTCTGCGTGAACACGGGATCTATGTTCTTGAAAGCTTTCAGGAGACGCTGTTCCATTTACTTGTCCTCTTTGACGTTGAATGCATACA
TGGTACATTTCGGCTTAGCCGGGTGTTGGCACCACTCTTTAGATACCTTGCCCTCAGGTTTAGTGAGATCGTAATAGAACTCACCACCTGCGGCAGC
GATACCCATCAGTACTGCAATGAATCCCATTCCGATCTTTACTTTCATTTGGCAATGATCCGTTGTACGAAGTGTTGAAGGTTGGCTACCAGGCGTT
CGAATTCTTCTTCGGTTACCTGGTCACGATGCGATTCCAGAAGTACTTCTACTTCCGGCAGGACGTTCATGGCGATATCCAACTGGATACGGCTGAT
GAACTCTTCCGTTGTGATATTTCGATCACGACGAATACGACTTACCAGCTTGCGATGTTGTTCGCTGTTGCGGTAGGTNGAGATCTTATCGATAAGA
ATATCAGAGATACTGCTTTCGATCTGTTCGGCTACAGCCTGACCGTCTTCCTTTACGGTAGCTTTGACCGCGAGGATGGCAGCAACGGCTGTTGCGC
CAACTGCCAGTGCAATAAGACCAAGTGCGTTTTCTTTGATGAAGTTCATATTGATTATCCTTTCAAAGTTGCATCATCATTGAAGATATCAGGACCC
ACCGAGAGACTTCCCAGAAGATCCGGAGCAATGTAAACAGAGTTGAGGGTTTCGTATACACCGGTAACAGCATCTACGTTAACCAGGCTAGAACTGC
GCATGGGTACCCATTCACCGTTACGGAAGGCTTCACCGACCAGTACACGAACATCATCTACGTCAGTGCGGTTCGGCCATAGATCCTTACCTTCTAC
TATTTTTACATTACGAGCATGGTAGACCAGTTTACCATTCATGCGAGCAACGATATTCGGACGGCACATGTTGTCGATTACTTTAACTGCTACGGAC
TTTTCCATTTTTATTTCTCTATTTAGTTACGAGCATTTCTTGACCATTGGGACCGATACGATGACCGAGGATAACAGTTTCATTAGAAATAGTTTGC
TCTTCAAACTTAGCGTTTACAAACAGTCCACCAAAAGTCAAACCAATAACCACTAGTGCGAATGCTTTCATTTTTAAAGTCCCTTTTTACATTAATT
GAAGGTTAAATATCAAGTTAGTAATATACTGTTTAAATATGGTTTGAATAAGGGAGTAGTAGTTATTACATATCGTGCAGGTAGGTCTCATCAATGA
TGGCACGGGCTAGCTCAATGAGACTATCTTCATCAACAACAATGTTACCATCTTTCCAGGTAGCGCTATGGGATAACCAGTTACGGTAATCCTTACC
TCGTACAGGATTGATGCATACCTGACGAGTAGCTGCATCACGGTCACCACGGAAACCCATGATAGCACGTGCACGACGGATTGCTTCTTTCTCCAAG
TCTTCGTCAGATTTAAAAGTCAGGAAAGTTGTCATAGTTTGATTCCTTTTTACTGATTTAATAGGTTTAATTACACTGTTGTGATATACTGGTTAAA
ATGGTTTGAATGTATTATTTCATTTCCACAGACGACAATAGTCATCTACATGTCGAGTGATTTCTGCAACAGCCCTGAGTCGCCGGCGGCCAGTTAA
TTTAGAGCAGTGTTTATTAACTAATGTATCAACAGTTTTACGTAACCTAACACAGCGTTCTTCATTAGGTATATCTTGTTCGATAAACAGGCTAGTT

Figure 7(H)

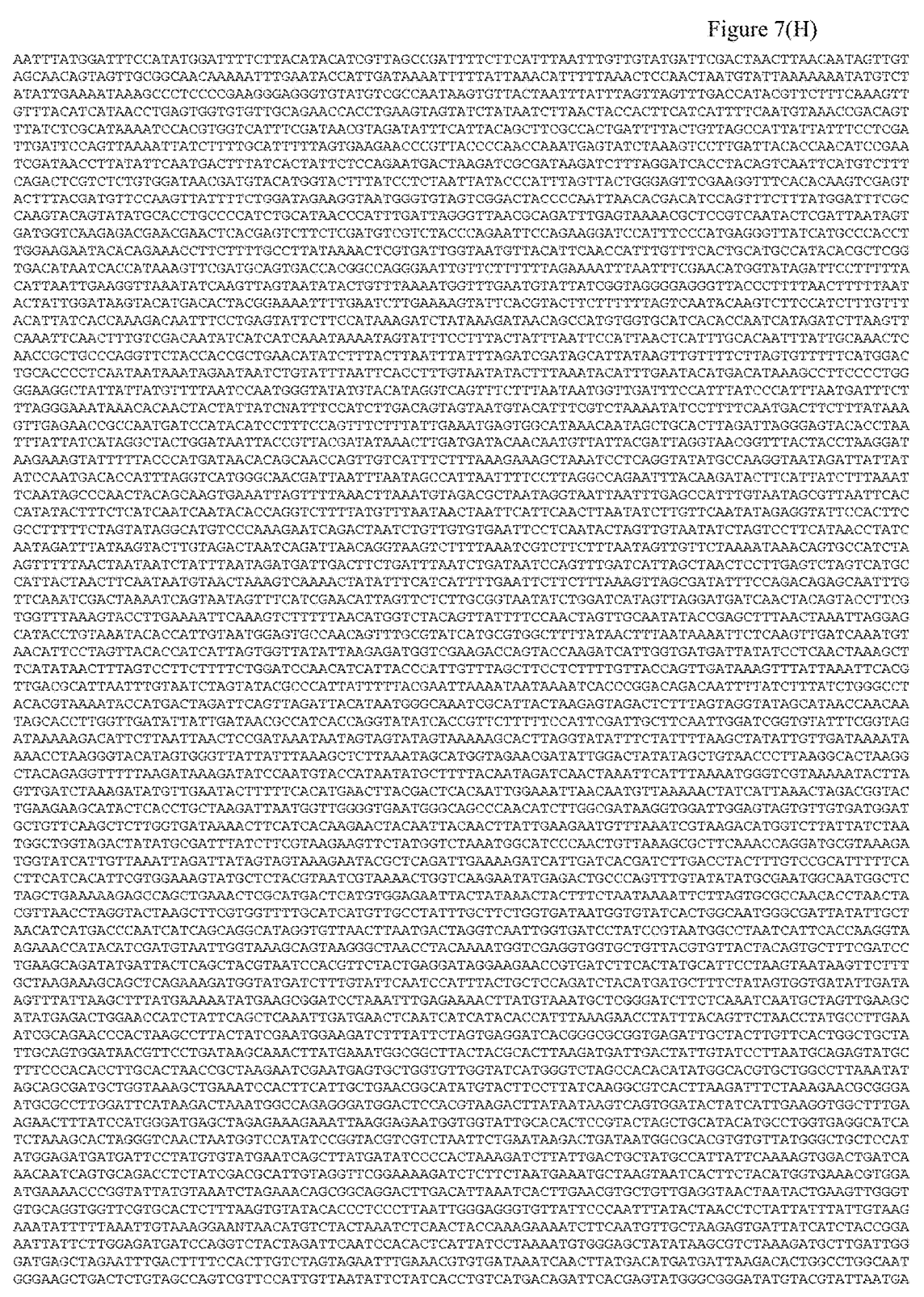

AATTTATGGATTTCCATATGGATTTTCTTACATACATCGTTAGCCGATTTTCTTCATTTAATTTGTTGTATGATTCGACTAACTTAACAATAGTTGT
AGCAACAGTAGTTGCGGCAACAAAAATTTGAATACCATTGATAAAATTTTTATTAAACATTTTTAAACTCCAACTAATGTATTAAAAAAATATGTCT
ATATTGAAAATAAAGCCCTCCCCGAAGGGAGGGTGTATGTCGCCAATAAGTGTTACTAATTTATTTAGTTAGTTTGACCATACGTTCTTTCAAAGTT
GTTTACATCATAACCTGAGTGGTGTGTTGCAGAACCACCTGAAGTAGTATCTATAATCTTAACTACCACTTCATCATTTTCAATGTAAACCGACAGT
TTATCTCGCATAAAATCCACGTGGTCATTTCGATAACGTAGATATTTCATTACAGCTTCGCCACTGATTTTACTGTTAGCCATTATTATTTCCTCGA
TTGATTCCAGTTAAAATTATCTTTTGCATTTTTAGTGAAGAACCCGTTACCCCAACCAAATGAGTATCTAAAGTCCTTGATTACACCAACATCCGAA
TCGATAACCTTATATTCAATGACTTTATCACTATTCTCCAGAATGACTAAGATCGCGATAAGATCTTTAGGATCACCTACAGTCAATTCATGTCTTT
CAGACTCGTCTCTGTGGATAACGATGTACATGGTACTTTATCCTCTAATTATACCCATTTAGTTACTGGGAGTTCGAAGGTTTCACACAAGTCGAGT
ACTTTACGATGTTCCAAGTTATTTTCTGGATAGAAGGTAATGGGTGTAGTCGGACTACCCCAATTAACACGACATCCAGTTTCTTTATGGATTTCGC
CAAGTACAGTATATGCACCTGCCCCATCTGCATAACCCATTTGATTAGGGTTAACGCAGATTTGAGTAAAACGCTCCGTCAATACTCGATTAATAGT
GATGGTCAAGAGACGAACGAACTCACGAGTCTTCTCGATGTCGTCTACCCAGAATTCCAGAAGGATCCATTTCCCATGAGGGTTATCATGCCCACCT
TGGAAGAATACACAGAAACCTTCTTTTGCCTTATAAAACTCGTGATTGGTAATGTTACATTCAACCATTTGTTTCACTGCATGCCATACACGCTCGG
TGACATAATCACCATAAAGTTCGATGCAGTGACCACGGCCAGGGAATTGTTCTTTTTTAGAAAATTTAATTTCGAACATGGTATAGATTCCTTTTTA
CATTAATTGAAGGTTAAATATCAAGTTAGTAATATACTGTTTAAAATGGTTTGAATGTATTATCGGTAGGGGAGGGTTACCCTTTTAACTTTTTAAT
ACTATTGGATAAGTACATGACACTACGGAAAATTTTGAATCTTGAAAAGTATTCACGTACTTCTTTTTTAGTCAATACAAGTCTTCCATCTTTGTTT
ACATTATCACCAAAGACAATTTCCTGAGTATTCTTCCATAAAGATCTATAAAGATAACAGCCATGTGGTGCATCACACCAATCATAGATCTTAAGTT
CAAATTCAACTTTGTCGACAATATCATCATCAAATAAAATAGTATTTCCTTTACTATTTAATTCCATTAACTCATTTGCACAATTTATTGCAAACTC
AACCGCTGCCCAGGTTCTACCACCGCTGAACATATCTTTACTTAATTTATTTAGATCGATAGCATTATAAGTTGTTTTCTTAGTGTTTTTCATGGAC
TGCACCCCTCAATAATAAATAGAATAATCTGTATTTAATTCACCTTTGTAATATACTTTAAATACATTTGAATACATGACATAAAGCCTTCCCCTGG
GGAAGGCTATTATTATGTTTTAATCCAATGGGTATATGTACATAGGTCAGTTTCTTTAATAATGGTTGATTTCCATTTATCCCATTTAATGATTTCT
TTAGGGAAATAAACACAACTACTATTATCNATTTCCATCTTGACAGTAGTAATGTACATTTCGTCTAAAATATCCTTTTCAATGACTTCTTTATAAA
GTTGAGAACCGCCAATGATCCATACATCCTTTCCAGTTTCTTTATTGAAATGAGTGGCATAAACAATAGCTGCACTTAGATTAGGGAGTACACCTAA
TTTATTATCATAGGCTACTGGATAATTACCGTTACGATATAAACTTGATGATACAACAATGTTATTACGATTAGGTAACGGTTTACTACCTAAGGAT
AAGAAAGTATTTTTACCCATGATAACACAGCAACCAGTTGTCATTTCTTTAAAGAAAGCTAAATCCTCAGGTATATGCCAAGGTAATAGATTATTAT
ATCCAATGACACCATTTAGGTCATGGGCAACGATTAATTTAATAGCCATTAATTTTCCTTAGGCCAGAATTTACAAGATACTTCATTATCTTTAAAT
TCAATAGCCCAACTACAGCAAGTGAAATTAGTTTTAAACTTAAATGTAGACGCTAATAGGTAATTAATTTGAGCCATTTGTAATAGCGTTAATTCAC
CATATACTTTCTCATCAATCAATACACCAGGTCTTTTATGTTTAATAACTAATTCATTCAACTTAATATCTTGTTCAATATAGAGGTATTCCACTTC
GCCTTTTTCTAGTATAGGCATGTCCCAAAGAATCAGACTAATCTGTTGTGTGAATTCCTCAATACTAGTTGTAATATCTAGTCCTTCATAACCTATC
AATAGATTTATAAGTACTTGTAGACTAATCAGATTAACAGGTAAGTCTTTTAAATCGTCTTCTTTAATAGTTGTTCTAAAATAAACAGTGCCATCTA
AGTTTTTAACTAATAATCTATTTAATAGATGATTGACTTCTGATTTAATCTGATAATCCAGTTTGATCATTAGCTAACTCCTTGAGTCTAGTCATGC
CATTACTAACTTCAATAATGTAACTAAAGTCAAAACTATATTTCATCATTTTGAATTCTTCTTTAAAGTTAGCGATATTTCCAGACAGAGCAATTTG
TTCAAATCGACTAAAATCAGTAATAGTTTCATCGAACATTAGTTCTCTTGCGGTAATATCTGGATCATAGTTAGGATGATCAACTACAGTACCTTCG
TGGTTTAAAGTACCTTGAAAATTCAAAGTCTTTTTAACATGGTCTACAGTTATTTTCCAACTAGTTGCAATATACCGAGCTTTAACTAAATTAGGAG
CATACCTGTAAATACACCATTGTAATGGAGTGCCAACAGTTTGCGTATCATGCGTGGCTTTTATAACTTTAATAAAATTCTCAAGTTGATCAAATGT
AACATTCCTAGTTACACCATCATTAGTGGTTATATTAAGAGATGGTCGAAGACCAGTACCAAGATCATTGGTGATGATTATATCCTCAACTAAAGCT
TCATATAACTTTAGTCCTTCTTTTCTGGATCCAACATCATTACCCATTGTTTAGCTTCCTCTTTTGTTACCAGTTGATAAAGTTTATTAAATTCACG
TTGACGCATTAATTTGTAATCTAGTATACGCCCATTATTTTTACGAATTAAAATAATAAAATCACCCGGACAGACAATTTTATCTTTATCTGGGCCT
ACACGTAAAATACCATGACTAGATTCAGTTAGATTACATAATGGGCAAATCGCATTACTAAGAGTAGACTCTTTAGTAGGTATAGCATAACCAACAA
TAGCACCTTGGTTGATATTATTGATAACGCCATCACCAGGTATATCACCGTTCTTTTTCCATTCGATTGCTTCAATTGGATCGGTGTATTTCGGTAG
ATAAAAAGACATTCTTAATTAACTCCGATAAATAATAGTAGTATAGTAAAAAGCACTTAGGTATATTTCTATTTTAAGCTATATTGTTGATAAAATA
AAACCTAAGGGTACATAGTGGGTTATTATTTAAAGCTCTTAAATAGCATGGTAGAACGATATTGGACTATATAGCTGTAACCCTTAAGGCACTAAGG
CTACAGAGGTTTTTAAGATAAAGATATCCAATGTACCATAATATGCTTTTACAATAGATCAACTAAATTCATTTAAAATGGGTCGTAAAAATACTTA
GTTGATCTAAAGATATGTTGAATACTTTTTCACATGAACTTACGACTCACAATTGGAAATTAACAATGTTAAAAACTATCATTAAACTAGACGGTAC
TGAAGAAGCATACTCACCTGCTAAGATTAATGGTTGGGGTGAATGGGCAGCCCAACATCTTGGCGATAAGGTGGATTGGAGTAGTGTTGTGATGGAT
GCTGTTCAAGCTCTTGGTGATAAAACTTCATCACAAGAACTACAATTACAACTTATTGAAGAATGTTTAAATCGTAAGACATGGTCTTATTATCTAA
TGGCTGGTAGACTATATGCGATTTATCTTCGTAAGAAGTTCTATGGTCTAAATGGCATCCCAACTGTTAAAGCGCTTCAAACCAGGATGCGTAAAGA
TGGTATCATTGTTAAATTAGATTATAGTAGTAAAGAATACGCTCAGATTGAAAAGATCATTGATCACGATCTTGACCTACTTTGTCCGCATTTTTCA
CTTCATCACATTCGTGGAAAGTATGCTCTACGTAATCGTAAAACTGGTCAAGAATATGAGACTGCCCAGTTTGTATATATGCGAATGGCAATGGCTC
TAGCTGAAAAAGAGCCAGCTGAAACTCGCATGACTCATGTGGAGAATTACTATAAACTACTTTCTAATAAAATTCTTAGTGCGCCAACACCTAACTA
CGTTAACCTAGGTACTAAGCTTCGTGGTTTTGCATCATGTTGCCTATTTGCTTCTGGTGATAATGGTGTATCACTGGCAATGGGCGATTATATTGCT
AACATCATGACCCAATCATCAGCAGGCATAGGTGTTAACTTAATGACTAGGTCAATTGGTGATCCTATCCGTAATGGCCTAATCATTCACCAAGGTA
AGAAACCATACATCGATGTAATTGGTAAAGCAGTAAGGGCTAACCTACAAAATGGTCGAGGTGGTGCTGTTACGTGTTACTACAGTGCTTTCGATCC
TGAAGCAGATATGATTACTCAGCTACGTAATCCACGTTCTACTGAGGATAGGAAGAACCGTGATCTTCACTATGCATTCCTAAGTAATAAGTTCTTT
GCTAAGAAAGCAGCTCAGAAAGATGGTATGATCTTTGTATTCAATCCATTTACTGCTCCAGATCTACATGATGCTTTCTATAGTGGTGATATTGATA
AGTTTATTAAGCTTTATGAAAAATATGAAGCGGATCCTAAATTTGAGAAAACTTATGTAAATGCTCGGGATCTTCTCAAATCAATGCTAGTTGAAGC
ATATGAGACTGGAACCATCTATTCAGCTCAAATTGATGAACTCAATCATCATACACCATTTAAAGAACCTATTTACAGTTCTAACCTATGCCTTGAA
ATCGCAGAACCCACTAAGCCTTACTATCGAATGGAAGATCTTTATTCTAGTGAGGATCACGGGCGCGGTGAGATTGCTACTTGTTCACTGGCTGCTA
TTGCAGTGGATAACGTTCCTGATAAGCAAACTTATGAAATGGCGGCTTACTACGCACTTAAGATGATTGACTATTGTATCCTTAATGCAGAGTATGC
TTTCCCACACCTTGCACTAACCGCTAAGAATCGAATGAGTGCTGGTGTTGGTATCATGGGTCTAGCCACACATATGGCACGTGCTGGCCTTAAATAT
AGCAGCGATGCTGGTAAAGCTGAAATCCACTTCATTGCTGAACGGCATATGTACTTCCTTATCAAGGCGTCACTTAAGATTTCTAAAGAACGCGGGA
ATGCGCCTTGGATTCATAAGACTAAATGGCCAGAGGGATGGACTCCACGTAAGACTTATAATAAGTCAGTGGATACTATCATTGAAGGTGGCTTTGA
AGAACTTTATCCATGGGATGAGCTAGAGAAAGAAATTAAGGAGAATGGTGGTATTGCACACTCCGTACTAGCTGCATACATGCCTGGTGAGGCATCA
TCTAAAGCACTAGGGTCAACTAATGGTCCATATCCGGTACGTCGTCTAATTCTGAATAAGACTGATAATGGCGCACGTGTGTTATGGGCTGCTCCAT
ATGGAGATGATGATTCCTATGTGTATGAATCAGCTTATGATATCCCCACTAAAGATCTTATTGACTGCTATGCCATTATTCAAAAGTGGACTGATCA
AACAATCAGTGCAGACCTCTATCGACGCATTGTAGGTTCGGAAAAGATCTCTTCTAATGAAATGCTAAGTAATCACTTCTACATGGTGAAACGTGGA
ATGAAAACCCGGTATTATGTAAATCTAGAAACAGCGGCAGGACTTGACATTAAATCACTTGAACGTGCTGTTGAGGTAACTAATACTGAAGTTGGGT
GTGCAGGTGGTTCGTGCACTCTTTAAGTGTATACACCCTCCCTTAATTGGGAGGGTGTTATTCCCAATTTATACTAACCTCTATTATTTATTGTAAG
AAATATTTTTAAATTGTAAAGGAANTAACATGTCTACTAAATCTCAACTACCAAAGAAAATCTTCAATGTTGCTAAGAGTGATTATCATCTACCGGA
AATTATTCTTGGAGATGATCCAGGTCTACTAGATTCAATCCACACTCATTATCCTAAAATGTGGGAGCTATATAAGCGTCTAAAGATGCTTGATTGG
GATGAGCTAGAATTTGACTTTTCCACTTGTCTAGTAGAATTTGAAACGTGTGATAAATCAACTTATGACATGATGATTAAGACACTGGCCTGGCAAT
GGGAAGCTGACTCTGTAGCCAGTCGTTCCATTGTTAATATTCTATCACCTGTCATGACAGATTCACGAGTATGGGCGGGATATGTACGTATTAATGA

Figure 7(I)

TAATGAAGACGTACATGCTTTAACTTATTCTGAAATTGTACGTAATAGCTTTAAAGATCCTAAAGTTATTCTAGACGAAATTCTTAGGGTAGAAGAA
GCACAAGAACGAATGGTTGCAGTAGCCCGCACTATGGGTGAAGCACATGACGCAGTTCATGCGTATGCTCTTAATCAGGTACCCAATGATCAAGAAC
TTTACAATAAAGTATTCATGTTCTTCATCGCTCTATATTTCCTAGAACGTATCCAGTTCATGGCATCCTTTGCAGTAACCTTTGCTATTGGTCGTAC
TGGTGCATTCCAGCAAATTGCAACCGCTGTTAAGAAAATTGCCCAAGACGAATTCGAAATCCATGCACAATATGGACAAGAAGTTATTCGTGCACTA
CTGGCAACTGAACGCGGTAAACTCGCTTACAGTCAATGTAAAGATAAAATCATTGAACTACTATGGGAAATTGTAAAGACTGAAGTTACCTGGATTA
ATTATCTATTCTCTGAAGGTCGTGAACTAACTGGTGTTAATGCGACTAAACTTATTAACTGGGTACTTTTCAATGCTAATGCCGCAGCAACATTCCT
AAGTATTGAAAATGATGTTGTAGAACAGTATCAAGTGGAGTTTAAAGAATCAGCTGGATTTGATTTTGTTTGGCCAGAGAAGAACCCACTTCTTTAT
ATGGAAGACTACCTAGATATTTCATCAACCCAAGCATCTCCTCAGGAAGAAGAGAAGCCTGATTACATGGTCAACGTTGTAAATGATGTTGGTGAAG
AAGAAGAATTTGAGGTTGACTTCTTATGATTAAGATTATCGCATTCGTAGTTTTAATGTGGTCCACTGTCCTATTTGCAGCAACTGAAGTAAAATCA
ACTACAGATGGTATTATTGCACATTCAGAATGTCAGCTAGTTGCTAAAGATAGTAGTGTTGTCGGCACTACTGTTGGAGGTGCGGTTGGAGCCACCG
CAGGCGCTGTATTAGGTCGAGCAATCTTTGGTAAATCTGGAGGTTGGGTAGGTGGTTTAATCGGTGGTGCCGCAGGCGGCGCAGTCGGTAATAATGT
TAGTGCTACTGAAACATTTCAATGTAAACTGATTGTTAATACAGATGGCAAGCAGTACATGGTTCAAACAGTTACCAATGAAAAACCAAAGGTTGGT
GATAAAGTCACTGTTGTTGAAATGAATGATGGTACACGAGATATAATGTAGACATAATGACCCTCCCTTAATTGGGAGGGTTTATGCTAACAATTCT
ATAGCACTCTTATTAACAGTCATCAACGAGAGAGTAGACATGAATAAAATGCTAAACTTCCTAAACCGTACGCTATATAGCGGTACTGAAAAAGTAT
CTTCAAAAGCTACACCAAGTCTAGAACACTTTAAAACAAATGTTGAACAAGTAGATAAAAAGATTCTACAACCCTTTAGTACTAAATTTAAAACCAT
TCTAAAAGAATGTTACAGTAATGAGGAGTGGGTTGAAGAACAATCATTTATTGAAGAACCTATTGATCTTGGTTCAGCTGCACGCGGTCTTACCGAG
CGCGGTATTATGCGTGGTGATTGGGGACGCTTAGCGCATTCCACTATTAAAGAAGCAGAAGGTATGATGCGTACTTATAGTGGTCGTCTAAATGAAG
ATATGGAGGCATCTGAAATTAATGAAGTAATTCAAGATATGCCTTATAACTTCACAGCTGGCTCAGCTAATACTAGCCGTTTAGAAGAAGATGACTC
TATTTTTGTTGAAGCAGATACAACTGTAGTTGAACCTCTGTCTAAGCAGACTCTGCCAAAAGTAGCAGAGCTTACTAATCAATTAGTGGAAGTCTAT
AACCGAATTACTGAAGAATTTACAGAAACTGGTATTGCTAAAGTTGAACAAGTTGAACAGCCAGCAGTTCTTGTAGCACTTGGTGAGATCATTAGTA
GTTTTAATAAACTAATTGATTTATCTTGCGGTGCTCTACCAGTGGAAGAAACTGTTATTGTAGAGGAGGATCCGTTACCTGCCATTGTTACTGGTCC
AACTACTGAACCCATTGATGGTGAAATTCTACCGGTTGATGCTATTAATAATTCTGCGGCATTAGAAGAATTCATTGAAGAAGTATTAAGTACTAAT
CCAGAATTCATTAAATATCAAAGTATGAATGATAGTAATATTGATTCATATCTAACTGGGGATGACTGGATTATACTGAAATTCAAAGATGGTTCTT
ATTATTTATACAATGCCCAAAGTGCCGGTGAAACGAATATAGAAATCATGAAAGATATGGCCGAAACTGGTAGTGGTCTTAATGGTTTTATAAATCG
GGTTATTCGTGGCGGGTATGTAGAGAAGTCCATCATTAATACTCCCGGTTTTATACAAGTCTCAAATGAAGGTCTTATCGATTCAATCAAAAAAGTT
CTTGGCATTTCTAATCGAGGTGATCAGAAACGTATCTGGCGTTCATCGTCCAGTGCAAGAGGATTTCTGGAACAACTAGAATCTACATTTGGCAATC
CACAATGGCTTAATAAGCAGGTATTCGTTACTGGCGATATCAATAGTAATGGTATAGCTAACGTACTGAGTATTAATGGTAAAGTCAGTATCGAGGA
TGCCATTCGTGCAGTAGAACCATTCTTCAAACTCGAAGAAAAGTCTAATCGCGAAATGGAGTCTTACAGGCAGAAGACTAAACCTGCATTGGATCTA
CTCATTAAGAATGCACATAACCTAGACGCTAACGTATACAAAGAAGCAAAGGCTATCGTAGACAAGGCACGTGCTGGATTCAAGACTAGTGTTAAAT
GGCCTGCCGGTACTATTACAGGTAAGGGTACCTATAATTCACCTCGCACCGTGGTCGCGAAATATCCATCTACTGATAGTAAACTCAAAGCTCTTAC
TGAAGAAGAAGCAGCTAAGGCCATGAACTTAATTATATCGGCATTGGAACGTCAGATAACTCTTAGCTTCAAGTTCCCTGATTTACCAGATCCACTG
GAAGGACTAATCTACGATATGTTGGATAACCCTAGTCCAATAGCTGGTATCGATTACTATGATTGGAATGATTTGTTATTCGCATGCTTTGGCCCTG
GGATTGATGATGATGTGATGGAAGTTAATAAAATGCGGCAATACCACTCATTCATTGATATCATGGAGGCCGCCGCAAAATGGGTAGATCGGTCTAT
AAAAGGTAGGTTAGCAATGGGTAATGAAAACTACCAGTAATGTATCTAATATTATGTAGAAATAATCCCTCCCCCTTGTTTCTACATTAGTCATAAT
AGATCGGAGCCAGTCCCCCTTCCAACTGGCTCCCAGAGAGTAAAACTCTTTGCTGGGCATTAATGACGATATATCGCCTCCCTTCGGGGAGGCTTTA
TATTTTGTTTTTACGTATGTATATTAAAATATGTATAAACAACATAGAGTAATTATAAAATGATCAAAAATGAACTTTTACCAGGGCTAATCTATGC
CCAAAAAGAATTTGATAAAATTGCAGCTAATGTAAAAGACTATGATAANTATAAAAGACGCGAAGCTGGTAGGGCAAGTGCCGTTTTAAGAAGTCTA
GTGAGCAATATTGTAAATCAGAATAAACCATCCTCACTTGAACATGAAGGCAAAGTTAGTACTACTAATACTAATGAATATTTAGAAGAAGTTAATA
ATTACTTCTTTAACATTAATAATATTAAATTAATTTCTCCTAAACTCATAAAAGAGAAATTAACAATTGATCTAATGAATATTTATGTTAAATGGAA
TATGATTGGAGTGGCTGGCCGAAATGATGTTCCAATTATTGAACACAGAATTAATGATTGGTGCGAAGTGACCGATGTCTACATTAATGGTAATAAG
ATAACTTCTTTACAATGGCCACGTTGAATTTAAAATAAGTTGTAATAAAATACCTAGCATTACATGTTATGTATTGAAGCACAATGCCCGAATGGTG
AAATTGGTAAACACAGAAGACTTAAAATCTTCCGGCTACGGTCTTGTCGGTTCGAATCCGACTTCGGGCACCAATTTAAATACGGAGTGTAGCGCAG
TTGGTAGCGCGCCTGCTTTGGGAGCAGGATGTCGGGAGTTCGAGTCTCCCCACTCCGACCATTTTAATAATAGGTAAATAGGATGGATAATAAATGG
ATATCATGGGAACATCAAATTATAGGAACAGCTCTTTACGCTATTCTTAGTGACCCTGAATTAACTAATATTCAATTAGCTCAAGGCTTACACTATC
TAACAGAAGCAAAGTCTTCTGTATTACATGTTTGTAATAACCATATTACATTCACTGTAACCTATCCACATGGCACATTTAGAACCAATGTAATTAG
AGAGTGCCCTGCTAGTGATACAAATACATTCAAATGGTCAGGTGTATTAGTCCGTCAAAAAGATGGAACATTCTTACCAGAATAAATAAAAAGGGCC
TATAGCTCAGTTGGTTAGAGCAGGCGACTCATAATCGCTTGGTCGCAGGTTCAAGTCCTGCTGGGCCCACCATATACTAGCCTCCCACTTGGGGGAG
GTTTTATACTGTCTCATTGAGGAAAACATGAATACAGTAATAATGTTGGTATTATCTATCAAAGTTGGATTATTTGGTTTCATTTCGACTAATGAAA
GTAATATCCTATTTGAAAATAGGGAACAGTGTATTTCTCATCTGGATATTCTGGAACATAAATACAAGTCTCTTGAAGTTATTCGAAATGAGAATAC
TCTAAAGATAACCGAAAGAGATAACCATTCTATTTATATTTTTAAATGTCTCTAGGAAAATACATGGAACATCAANAACAAAAAGAACTATTGAGAC
AACCATTACAAACACTTTATAATCTTACTTTTAGTCCCCGTTTACGTAATGGAGCGAAGGCTCCCGATTGGATTCACCTGACCGATGAAGTAACCCT
ATTCCCAAACGGATTAGATATTACAATCAACGCTGTTACACGTTGCATCAAATGGGAACTTATCGGCGAGGATGTAAGTAACATTACTTATGTTGAA
GCTATGTTCTTTAATAAAGGTCTTAAAGCAGTTAAAGCCTATCTCAAACATACGGAGTAAATATGGATCATCTAACCCCAACGCAGAGCGCTGTATA
TTTCACATTTATTAGCCCTGAGTTTATAAAGCTAACTCTTGTTGAATCTTTTGTAGCGATCCACAAGAAACATCCAGAAGTAAAGCATTGCGTTAAG
AAAAAGATTAGTGCTAATGAAACGCAGTTTATCTTTATCTTCAAAGATGGGACTGATAATTTAATCATTACACGTAAAACTGAACCTTGCCCTGAAC
TGGATAGCCCAGTAGGCGATAGTATTAAGTTGTCCGGCGAAGAACTTAAAAATATTCTTGCTAAGTACGATCGTCCCAAGGATGGTAACTATTTCAA
GCACTGGACTGATCGCCCGTAATAAAATATTACTGGTTATGTAATACTATGTAGGAAGTCATGTCCATACGTTTGCGCTCATAGTTCAGTTGGTTAG
AATACCCGCCTGTCACGCGGGTGGTCAGGGGTTCGAGTCCCCTTGGGCGCGCCATTTAATTCCGTGATAGCTCAGTCGGTAGAGCAAGTGACTGTTA
ATCACTGGGTCCCTGGTTCGAGTCCAGGTCACGGAGCCATATTCTAAAGAGTAGCTTCGGCTACTCTTTTATGTTGCCATGGGTTATCTTATGAATT
AAAATGATTTACTTGAGAGCACACTCATGTTTGAATTACTATTATCNCCAGATATAGGCGAAGAGTTACCCTTGGTTGGATTTAATGAAATTATTAA
ATTAGGTGATCTACCTGTAGCGTTAGCTGGTACAATGTCATATGTGGATGGAAATACACTGTATGTTGGATCTGGTCATCATACTGAAGGACAAACA
GCTGCAACTGTGTTCAGACGTTTTACCATATCGCCATTTGCCGATATAGGTGCAACTGCTTCTGGAACATTCTTACCAGGGGTATCTTTAGGATTTG
GGACATTACATAAGAATAACTTTATTGTTTATGGCGGTATTACTGGATGGAACTCGGCTGGTAATGGTGGTACGGGAACATCTAACTTTATACAACA
TTTTGATATAGCTACAGGCAATAGGGTTGAGCGATATAGTGGTCCCGTACCACTTTGGGGCACAGCCTCCGCATCAGATGGTAATGATCTTATTCTA
TGCGTTAACCCANTTGGNGTAANNGCAATGCGNTTAAAACCATCNNGTAAGNCNTGGCTTAGNGGNCAAGANTATTCAGGTGGTGCTCGTTCAGGTC
AACAGTTATTCTTTTATAATGGTTACTTTTACCATTTTGGTGGTTGGGATAATACAAAGAACATACCTAATCTTGAAGTTTATCGATATAATGCAAC
TACCTTAATATGGGAGCAAACACCTTGGATGATTATACCTGCTGATAAAGGAACAATCTGGCAAGGTAANGGTTATGTAGATGGNGACTATTTTAAT
TACCTTAACGCTGTTGATGTCGGCGGTGTAACTAAAATGTTTGCACAACGTTTTAATATTAGGCGCCGGAAATGGGCTGAACCATTTGAACTAGGTA
TCGGATTCCTNAATATTTCATCTATAGCTAAAGGTCCGGATAATAGCATGATCATTGTAGGTGGATCTAAAATGCCAGTTGGTGGTGGAGCANANAT
GTTGAAAAGCCAATTGTTATCAGGTNTCTATCAGGTAAAACTAGCACCATTAATCATTGATTAAAATAATAATATTTATAACTATTTAGATAATTAT
ACTGGCACGATGATATTATGTAAGAGTACTATANTAAAGTATTCTTAAATCTATCCACTAAACACACTCGGTGGTAGAACTTATTATAGAGTGTGTC

Figure 7(J)

TAAATGCCAGGGGTTTGCCACCCCTGGNTATATTCATTGTTACTATTATAAATTCATTTATAGATGAGAAAAGGTTTTATCACCTTTTCAAAATCGG
CATTTAATTCCAGTTAAAAAAACTGAATCTATGCTACATTGTAATAAAGGAGTCTATTATGACTAACTCTAATCCGTTTGTAAGAACTATTGTAAAG
TACCAAGATATCCTAGATGCTTTAATTCAAAAAACGAATGAGAACTGGGTTAATTATCGATCTAATTCTATTGGNCATATTGTTATTCGTGAATACA
GGACTGTTGGATTATTTGTAGGTCGGCAATGTGGTAGTACAACTGCATTGATTGAGTTTGCTAATCGTCANCCTGGCGAATGTCTAGCTGTATTTGT
AGAAGATAAAATTAAACAGGCTGTACTGGCTAAGTTCCAGAATGCTAAAGATAATATTGTTTCTTGTTTAATTACACACCAACTCCGNAAATATATT
CATCAACCTGAAGAATCATCTATTCAAAAAGATATTAAAGAAGAATTAATATCGTCTGTAAAATATATTCTTGTTGACAATGCCTCATTTAATCTGA
ACCTACGCGGTATCACTGATAAAGAATTTAACCAGTGGGTTGCAGATACTTTTGGTACAGAGGTAATGGTGGTTCGTTTTAGTTAGAATTAGTAACT
TTGATAGTTTCTAATAAGATTAACTACACGTTATTACATAATGTCATAACAAGAAATAAATAATACTCAGATTGTAATAATATGTAGTTATTACAT
ATCTATATTAGGTTGTCAGTAACTCATCTCTAATATAAAATCGCCATAATTCTTCCGTGATAGCTCAGTCGGTAGAGCAAGTGACTGTTACGATTTC
ATTGGTAAGTACCCGAGTGGCAGCAGGGAGCGGACTGTTAATCCGTTGGCGAAAGCCCACCGTAGGTTCGAATCCTACCTTACCAGCCAAATTCTAA
AGAGTAGCCAGCTGGCTACTTTTATCTTGTTCTATAGATCGAACTAGCTATCTATTTTTTAAACCCTAGGTTCGATATGAAAGAAAAAAATAATTAA
TGGTTATCGGGCTCTGTATTTACCTGAACATCGGCAGGCAAAAGCTAACCCCAAAATGTTTGGATGGGTATACGAACACCGTGTAGTCGGTGAAGAT
ACAATCGGAAGATCTCTTTACGATGACGAAGAGGTTCATCATTTGGATGAGAACAAACTCAATAACCATCCCGATAATCTTTTGATCCTCCCTCAAT
CACAGCATCTAAAACTACATGCATGGATGAAACGACTGGGCATTGATCCAAAGAACTATCCTACAAAACTTGTGGTGCTTGTGGTAGGGTAATGAA
TCATAAATTGATTAAATTCTGTAACCCTGAGTGTTCTGCCAAAGGTCGACGTAAGGTTGATCGACCATCTAAAGAACAACTCGTCCTTGACGTTACA
TTGTTATCTCTTGTGAAAATAGGAGAAAAGTATGGGGTATCGGATAATGCAATTCGTAAATGGTGTCGGTCATACAAAATCAATATTCCAGCTAGGT
TTATTAGGGTCAGCACTAATGGGGGTATTAGCACCTTGGCCCCCACACAATAAAAAATATACTCGATGTAGATTAATATACAAAAACATAATCACTGG
GTCCCTGGTTCNANNCCAGGTCACGGAGCCAATTCATAGTTTTAGATTTAGTTATATTTCACTACTATGTAAACTATAAAGGCAGCTAATGCTGCCT
TTATGTCGTCTTGTAAAAGTACCCAGTAGTTGAATCTTATAGCTGAATACAAATAGGGTAAAGACATGTCACTTAAAGCATTGCAAGATATAGTTAG
TAGTGTTCCTACAAATGAACAAAAGGAACGATTAGTTAAAGTTCGGAAAACGATGGAAGAGCTAAATGAGTCTATTAAGAATCAGATTCGTAATAAA
CGACCTAGTCAAGCTCTTCTCGACAAAACGATAAACTGGGGTACCAAGTATGGCTAAGACATTAGTTCGTGCAAAGCTGATTACTGAAGCTGGTCAA
TGGATGTCGTCTGACTGCGAATGTGGTTTCCGTGCATGTCGATTCGTGAAACTTGGTAATGATCATGTAAACATAAAAGACTTTGAGGCTATGATCA
CGGCATTCGAAGTTGGTGACATGTTAGTGATTTGGCCAAATGGGCTTAGAACTTCGTATAGTGTGGATAATTTCAATAAGTACTTTTCCCATATCAA
AGATGAATACCATGAGACTGATCTCCGTCCACTCTTTTACCCCAAGTAGTTGAGCTTATGATAACTATATTCGTGTATAAATACATTACATTCGTTA
TACCCTTTAATTGATTGAAATCAAGCTACATAAAAGTGATGAATACTTTAACCCAATGATGTATAAATTAAAAAGTATGCACACTAAAAATACAGAT
GGTGTTTATTTGATATTTTTACCAACGCCTACTATCGATGATCAAATTAACACCATGCAAGGGTATATTATCAATAAATCCGGTAATCTCATTAGGA
CTACTGTACAGTCATGGCGATTTGAGAAAATTGAATTCAAAGACTTAGCCAAACATGATAGACGTTGGTTATTTATTGAATATTACATTAATGTTAA
ACAAACGAAAAATAATATAATCAAAGAGCAACAAGATGAATTAACTAAATTTATTTATTATAGTACTCTAAGTTAAAACAAATAAAAAAATAAATAT
AAGAGCTAGCCCCTAATGGGCTAGCTTTATGTTATCTTACTCTGCTACATCTTTTACATCAGGTTTATTATTCCAACGTACTGCTCTCGCAATACCA
TACGTAAGAATAAGAGCACCCACGGTGCCAATAGTGGTGCTAATAATAATGCCAAGAGTTTTTGGNTCNATATTCATATTTAGTNTCCTATTTACAA
TTAATAGAAAATATTACTTTTAGTAATATCANNTTNNTNATATACNNTTTAAATANGTTTGAATATAACTTTATTTATTATATAATAAATTAAAATAAT
ACTTTCATATACACTATATGTAGAAGATTNCGCCGCTATAGCTCAGCTAGGTAGAGCAACGCACTTGTAATGCGTAGGTCCTCCGTTCGATTCGGAG
TGGCGGCACCAAATTTACTGAGGTTAAACTATTCTTAAATATATTAGGTATGGATTGAACGNGAAAGACTCAGTAAATCATATTGCCCCTCC
ATATGGAGGGGCTTATGTTTGTCATTAATCAGGAAAATATAAAATGAGNCATCTATTATTTATCATCCAAGAATACATTACTAATAAATTTGAGATA
ACACGAATTGATATGAAGCCAGGTAATAGAATGTTACGTGTATGTTTATACGGTCAACATAAGGGAAAAGGTTTCGTCCGTATAGATTTATGGTCAG
TTGGTTATCGCATTACAAAGAAATAATACTCCAGATTATTTAATATGTATTAATCAAAGGAGTTTATAATGAGTAATGAAACTAACTATCTAGGTTA
TGAATGGAAAACAGATATAACTACTTCAAATCTTAATAGAGTGGTTGATTTATATACACTTGAATTAACATGGTTAAAAGAAGATTTTAATGATACT
CTTTTTATAAAGTCTTATAAAGTGCTAGAGGGTCTATTAGAGGAACCGTCTAGGGCAATCCATGATGATACAGTANCCATTCAAGATCAATTAGATG
AATTAAATACTGTTTTTAAATTAGTATTTGGAAAAGATAATAACGTAGAGTTATCAATTAATAATGATTCAATTATTGTGATCGGTGCTACAGATGC
AACTAAAGAAAAGTTAGAAGCAGAGGTGCGTGAGTTTGCATATAGAAAATCATTAATTGATGAACGTTATCCAGANATTGTAACGGATTAAAATACT
TACAGCTATCTAGTATGTAACTAGGCGGATTGCCATTTGTAAATTATCTATTTAATCGAACTGAGGAAATACTAATGAAACAATTCTTTCAACTACT
TCTAAGCCTACTTTTCAAACTACCGGTTCTATCATATTTTGCTGAGAAGAAACGATTAGAGAAAGAGAAAAAGGAAGAAGAAAAGCGTCAGCAAGAA
CAACGTCAAAAAGAACTACTTGATGAACAACGTCGCGAACTAGAAGATCATTATCGAAAGACGGCTTACGATCGCCTAGCAAAACTTATTCATACTC
GGTGGTATGATGAGTTTAATGCATACGAAAAGAAACTAGTTGATCTTGCTGTATCGAGTGGTAAAGCAGTTAGTGTTAAGTATGGTAAAGTTACTAA
GATGCAGCACCCTCATCAATTTAAACTACTTAATGATTGGCTGGATGATATTCCAGTAGAAGATTATTCTAAGTGAGTTTAAATAAAAGAAAATAAA
GACATAGCCCCTCTCCANNTGGAGAGGGGTTTATGCCGTAATTATACACTTACTTTGATAAGATTTTTAATATCAGTNAAATGGGTATATGTTGCCT
TTTTATCTTTGTGAACCAGTANGCAACAGGTNCCTTCATTTACNGTATTGGTTTGTTTTAATGGGATATTTAAAGCATATTCAAANAGATCATCCAT
CCAGTTAAATNCCATGAACTTATTGATAAGGACATGATCGAAATCAATTAATNCAATAAACGAATCGATCTCANATTGATAATACTCTACAACCATT
TTAGACCATTCTTTGTTTATNGCCTCAATGACATTAGGATTATTTATTTTATTAAATAACTCANTNCGTTCCTNAGTAGGTAAACTGAGGTAATAAT
TAATATTACTCCTAACGATATCTGGATTAGTGATATCNATTTTTTCTGGTAAGTTATATTTACTATCTACATAATTCTTAGTTTCTGGTGTCATTCT
CCAGCAACCATAATCAGCAGTAGTACTTGATGGATCTATTTAGTCTCCACTACTTTAGAAAATACATCTACATATAAATTAACAGATTCGTATACA
TCAGGTCTGATTGGATTAAAGTTTAAACTTTTAATAAGACCCCTAACTGGCCGAGTACCAATTAGACAATGCAATTCAAGCTTAACATTTTCCTCTT
TAGCCATCTTAAATANATCAGCAAAACTGAGCTTTTCTGCCATTTAGAATATACCTTTTATTAATTGGACAAATAGATTAGATACACATAGCAATAG
AATAAACCATAAACCTAGTCTTTGTAATTTATCTATACGCTTAGCTTTTTGTTTCCTCTTTAATCTAACTAATAATGTATTTTTAATATCATTCATT
AAATTATCTCAGATTTTTAGACGGTGTATAAACCCTCAGTATTACATGTTGTTATGATATTGTAAAGACGATGCCAATAGCGATCATACGTATTTTT
ACGTTTGTAGCTATTGGTNCGGATGACTAGATTGGCGACCCAGTGATTCTGATCAATGGTCTCATGTAGATGCCCGAAATAAGCCCCCAGTTCAATT
TCGAATGGGATCTTACACTCACGCCCCTTACACATTGCTTCACGCAATAAACGCATTGCAGAATTCTCTGCATTGGTATCTTTAAATAAAAGACTAA
TGTATCCAGGGCTACCACCAGTTTCTTCATCAACATGGCCTGAACAGCAATAAATAGTTGCAACATTGATAAATTGATTAAACCATTTAATTAATGG
CCTACATGCTTCATCAATAAGATCTTCATATTCAGGTTTATACATTACTTTAACAGTATCATCTGCACGTTGTTTCACATGATGAAAATATTGCTCC
CAATTTACATTAGTGTAATATAGCATATCCATATTAGAATTACTCATACAAATCAACCCCATATGTTATTGGCATATTCGCGGTCATTGAAAATGCG
GGTAAGATCCATCCGCTTTTGAATGCGCGCTAGTATCCATTTTAGTTGTTTAGTTGATAGTTCTTGATTTTGCTTGTACTCACCTGTAGCATGGATG
TAATAATCAAATTTACGACTTACAGTAGTAGTATGTGCACATGCAATAGCAAATGCTTCAAGTGCAGTTAGTTTGGTTGATCCATTATCATTACAAT
TAGGGATAAACTCAAGTACACTATTAACTGCATCTACACCACTACCCAAATGAGCCCAATCTTTCTTGGTGATGTTGATACCCATGTCTTTAAGAAT
AACTGTATATATGTCACCATTCTCCATAGTGAACATCATAGAAGTATTACCATTAAACAACCTGCGTTCTATGACTGGCAAGATATTTACTTCAACT
TTAAACCAATCAGCTAAATCAACACCTGCGGTAAGGGCATTCAATAGATCATAAACATTATCTATAGTTCCAGCAAAAGCCATAGTTTTAACACGTT
TACCTTGCCAAGTAACTGTCGGATGAAAAATTATCTTGTGGCAATCATTGTAATATACATCTACACCTTCAGCTTTAGCAGTTAGATCAATATAACC
GTTATCTAATACTGGAAGTCGCCCAATGCTATCAGTTGCATTATTCCGCTCAATTAATAGGCAGTCTGCAATCATGACTTTACCATCATTTACGATA
TATGTCATTTTCACTCCTTATAATAAAATAAATAGGCTTAAGCGAAATAAAGCCCTCCCCGAAGGGAGGGCATTATCAATAGGTGGGATCTCGGCGG
CACCTTCATTTGCGGACGGGAACGCTGAAGGGAGATAGTCCGGGAGATCCCGATTTGGGTATTCTTTACATATGGTATTACTGCAAGTATTTGTTCC
CCGCAGTATAATCACCATTGATCCAATTTTTGATTACAACACTGATCCCTTCATTTTCTTTAACGGTAACCCCCAACTCAAGATCGATTGATTGATA
AGCTACAGCCGCCAGTGTTAACCGAAGATAAACGGATCCATCTTTTTCGATATCGTAGGATACTACGAACCCGTCTTGTAGATTTGTAGCTGGAATG

Figure 7(K)

TATTAGCATGTTGTGGATGGAGACGATCCATATTGTACTCGACGACATCTAGTAGATATTGCCGAGCATCAGCAGCATTATCAAATCCGAGANCGCA
CAGACCGATCGGATAGCGAGCTTGCGTGCATGTAACTTTCATAGATACTACACGATGTTGTTTGCACATTATATTTTCCTCTTAGATGTCAAAACCC
TCCCGATCAGGGGAGGGTATCTCATTGGTACTTCTTCAGCAAAACTGAAACTAAGATAAAAGAGCAATCGTAAAGGAACTACATAGAATAGTGTATT
TCTTTTACTATTTTTACACAACCTCTTTAGATGGGGGTTCTTTATGAATCCAGTCTAAAGTTGTTGGTAAACTATTATCTGATCTGAAGGTACACAC
CGTCCGGAACCGAGAGTGATCAACTACAGATAATTGCCCGTTAATCGCAGCCTCATATTGCCTACACAACTTCACACACCTTTTCTCTAGATCAGTT
GGTTCGTAACCTTCTTCTCTTGGTTCAGTGTATGGTCCATCCCAAAAGAATATTAATCTAAGATCAATCCCAGATTTATACTCCGCTTGGTATGAAT
ATTGNTGAACATCAAAATCATCTAATTCTTCAACTAGATGTGATGTTATTGTTCTAGGNTGTTCATGAGTTAATTCACTGTATATATGTTTATTTCT
AGGGTTTTGTAAATCAACTACGATAAGTTGACTAGTCATTTTAACTTTTATCCAGATGTCTATTACGAGTGCGTTCCACTGCTGTAGGTTCGACAGT
GGCTCGCGGTAGATAAGTAATCTCCGGGAAAGTCTTATTAAGAGCATCTTCAATTAGCTCTTTAGCAATCTCTGCATCGATGTAATGGTTTAGAATA
ATACCACGATGATACAGGAAGAAGCTGTATTCATCATAACCATGGCGAAGACTTACTTTACCACGATACCCACCATAGGTTAGAGTATCTTCGTTAA
TTCATTCCGATAAATATCAAGTTGGATATTATTTTGAAGATGCATTTGAATGAAGTCATTACTATCACCGCCGAATAGGGTTGGTCGTTTCCGACCA
GTAACAACATCTTGGATGGAATCCATTAGTCGGTTAATGTCTGTTTCTAATCGTTGGATATCACATTGAGAATTCATTGCTTCATGGAAACGAGTTA
CAACTGCATTGAATTCTTCTTCAGTCCAACCACTGGTACGTTTTCATAATCAACAATGATAATACCGAACCAGGCATAACCGTTAGAATGTTTACTT
TAACACATAGATGAGGTACATTATCAGCACCTGACTGATGGTTAACAGTGTAATTATTATTACGGCTGATTACTAGTTTGATAAAAGGTAGACTAAT
GATTGACGCCATGGAAATATTCCTTTTGTATTTTTTAAATTAAAGTAGGAGTTATTATTGAGTTTCAACTCAATACATCAATAACTCCAGTATGTTT
TCAAAATTAAATACATGTATTTACAGTTACATTGTAACCAGTTAGTTTTGCCAACAATACAAATTAGCGAACCTGTTCGATTTTTTCAGAAACAATG
AAAATATGTGCAATACGATCCTCATCAANATACCGATATCGAAATGAGGTATAACTAGATGACACATCCGTATCGTTTAAATAGGTGATATTAAAAT
CATCTACTTCCCTACCATTAGCAGCCGCAACGGTATTTAGAATGTTGAGTAGACTCATTTTACAGATTCCTTTTTAGTATATTAATATTTCAATAGA
CTATTGATAAAAGCATTAGGGTCATAACGGTTATTTGAAAAAGCCGCCATTACATCACACCCTGGCTGATCTTTAAATCTGATATCTTCAGGAATAT
CGAAGTCAGGGAACATTAGTTTAATATACTCCCTAACTTCTTGATCTCGTAGATATGGAATCTCCACCATGTAATCAACGCGACCTTTCCTTAGAAG
TGCTTTATCAATATTCTCAGGATGGTTTGTAGTTAGAATGGTCATAGTCTCATCTAGTGGAACAATGCCATCTAGCCCATTTAATAGAGCTGACAAA
GTTAATCCGCTAGCTGGTTGTTCATACGTGATTCCATTCTTCATGCATTTCTTTAATTTCCACCATCGGCGAATTGTGGTAAATAATGGATCTTTTT
CATCGGCCCATTTGAAACACCCAGTTCAGCCATAGCATAAGCACTTATCCCAAAACCTTGATCATCGCTATTTTCATCAAAGATATAGATGGTGTCA
TTAACCCAACTACAGAGTATCCTTCATAGTCATCTTTAAGATCAACCCATGCAGACGGATATTTTTCAATTAAATCAATAAAAGAATATTTCCTCTC
TAATTCCTTTATCTCTTTATCTAGTTTTACAGGATCATTTAAAACACGATCTTTAACTGCCGGGGTATCATCGAAATCTTCAATTAGAAGAATATTA
CCTTTAGGTAGTGTAGTAAATGCCCGCCTAAGACTATCATTGGTCATAGAGGCTAATGACAGTGCACTAACATTTTTATTAAAATGTGAGGCAATCG
CTTTACTGATTGAGGTTTACCAGTACCAGGAGGACCTGTTAGAACACAAGTGAATTTATAGGGTAGTCCACGATCATCGTACCATTTCCGATCAGAA
TAGAATTCTTCAATCTTATTAAGGAATTCTTCTTTGATCTCTTTACGCAAAATCACCGTGTTGATATCGCGTTTAGTAACTTCAATCTCATTGCCCC
AACGGTTACCATCCCAATGTGAAATAGTCAGACCCCTTTCATTTGGGCGCCAATGGTAAGCATCTACTAAATCAATAATTAGTTTACTACTCCTAGA
TAATCCACGGATAGTAATATCCATTTGATCTCGACTGGCATTTTGACTATCCCGGCGTGCTTTTACAAACCAGAATAACCTACCTTTAAACAGAAAG
AAATGTAAGCCAAAACCAACACCAATTTTCTGTTTAGTTGCACTATAACTTTGCTCATCAACATTAGTTGAAAAACGTCGATTAAATCCAGCTAATG
GCTGCTTAATATACCATTCCATGAAACAATCAAAGTTCTTCTCGTTCAGCCCATTACCCATGTTGGTAATATGTAGACTAACTGTAAACTGATTTAA
TGCGAACCTAGCTAGTTTACTTGGTAAGCCTCTTAGAGTGGTCCAGAATAAACCACCAATTGCCATTCCGATAGCTCCACCCATAACCATATTCTTC
TGAGAGATATCGATGAACATGGCGTAATATTGCAATAAGGTTTCTATAATCATACTAGCATCCCTCTGGATAGCTTAGGAAATATTGTCCACAGATC
ATGTATTCACGTTCTAGAAATCTAGAGTATGACTTTCAAATATTTCACCTACATCTTTACCATAGATTTCCGTATACCCATTTTTGAATACGGCCAT
TACATAAACATCAGACATAGTCATGCCGTAGTTATAAATTTGATTGTCTCTGTATTTTGGATGAAATAGGTCATATAAAAAACGAGTCATTGAACTA
TTGGCAACAGTTGTCACCCCTTTCTGCTTTAAGGCATAACGTACTTGTTTAACCACATAGTTAACTTTAGAGCGCTCGCCAAATACCGTCAGTTTAT
CTACATTGCAATTACGATATCCCATAACACCAGGATTAGCTATCACGGTGTGTTTTGGAACACGTACATCAAAGATAATGCCATTAGGGGATAGAAT
AATCTTTTCATGGTTAAATAGAACATGAAATAAATGTCGTTCTGGTTTAGTGATTTTGATACTTAACCCAATCACCCCACTAATCTTTCTTTCTAGA
TCTTCTAGTGACTGCATCACCATGTGATATTGATTGAAGAAAGCATTGTTCTTATATTGATCTAATTCAAAGTATTTCCAACTTCCACGAAATGAAT
AGCATGGCTTTGGTATAACCTTTAGTTAATCGACACTTGAGTTTGTCAAACCAGCTTTCAAGATAACTCTCGACTGTAAACCAAGTGGGTTATTATA
TAAGTTTATTGGAATATGATAAGCTAAATCTGTACATAGTTCGACGATGCATTTATATTCCTGCCAAATAAAGAAAAATAAAGGGCTCCGAAGAGCC
CTTTATGTATTAGATTTTTACAGACCAACTTTGCTCCGAATTCCTGATATAGGAAATTGTCTGACGCATTATCCCAATTTTCTCGATCAGTTACACCA
TAATAATGGAATTCTAGTTCAGTAGGTCCACCAACAAAACCATTCTTAGCATAGCTATAAACTTGCCATTGGTTAGCTTAATCAGTGTATCCACATA
GAAACTATTACGGTTCCATATTTCATTGTGGATGTACTTAAATACCACACTGTNGATATACTTAAATTGCGCACTTGGTTTTCCGAGTACACTCCAA
TAGAATTTACGGATACCTATTTCGGTCTTGAAATTAAACTCTCCGTTGCGAATGTTGTTAGAAACAATACGTGCCAGTTTATTAACCCGATTTCTTC
ACCGATTAGATAGATCCCGGAAACACTACATCCATCTCCTATTGATCCATTATTAACTAGTGGATCAACACCATATTCATCAGTGAAAATGGTTTTG
ATAACCTCTTTACCTTCTCGACGCACTAACATATTCAGGTGACCATCTTCGATATATGACATATGGCTAGGCTGAATATATTCACTTGTATCGACGA
TAACATCATTCGCCATTACATTAAACTGTAGATGGTTTACCAGATCACTAATACCTTTAAAACGAATGGCTTGGTTCGCTGTATTTAGATCGACATA
CACCACGACATCAATAATGCCTTGTTTTAGTGATTTGTCATCTTTGTCAGTAGTTGTATCAATTTTACGTAATTTTGATATAGTTCACTAAAACAAG
ATATGATGTCATCATGTAGTTTAATTACATCAGATCCATTTCGTTCAAGCGCTTTAAGCGATACGTTAAACCAATACGAATTTTATTAGAACGACGT
GCCATGGTTATATCACCTATGTTAAATTAATGAATTATTTATTCAATTACCGTACTACATCTGTGATTAGAATAAGTTCACCATCACTATTGATAAC
ACTATAGCTTTTACAATTTCGATGCGCTTACTAATAATCTTATTCTCTAGATCTACTTTTACGATATTAACACGAATTACCTTATTCGATTGATCAT
GCATTTCTTTAAAATGCATTCGATATTTTACCAATGACAGCTTTTAATTTTCAATGCTGTCAATGGATGAATATTTAAAACTATATGCTTCTGCCAG
GGTTTTGCATTACCCACAACCGTAGTTAGGGTACCCCAATAATCATAAACATACAACGCAGTATCACTATTGGGATTATCGATAATTTCAATTATAA
ATCCACTTGTATCACTCCTATTAGTTTATTGATAGTACACTTGTAATATAGATCTTAAATAAATTATGATCTAACCATTTAAAATAGATAAAGCCTC
TATATGCCAATGGTGTATTAGTTCTTCTTTACTAATAATATTATTGAAGTAGTTTAACCGATGTGATACCATTAATTTAGAATGCATATCGACTTCA
CTACTTACCTTAATCACCCCAGTCTCTAATAATTGCAGAGATCCAACATACGCAAATAAAGTTGGTTTTAAATACCAGTGTTCCCTATATTGTTTTT
GATCAGGTACATTTCCTATAATGTAGTCAGTAGAATTACTTCGGTATGCGTAAATAGTTGATTTAGAACCAAGTAAATTAAGATCGATATCATAACT
CCCGCTTTTAGCTGCAATACATTCAATAACTGATGGGGCCACACATATACGGTTGGTTACACTGTCTTCGCCATCAGCTCTATTACTTGGAATATAT
GGCCTTAATAAACATAATCCCCAAGGTATACTGTCGATATGTGATACATAATTAACCTATTTAATTAAAACAGATAACGCTCTGTTACTGAACGATA
TTGTGACATGATGTTTAATGGATCAACATCCACTGGTGCTTTAGTGACAGTTAAGCGAGCACCTTTTAAAAATCACCAATATCTAATTTCCTTACAG
TAACATCATGGATAGTGTTTTTCGTAATCCACTCAGTATCAATGCTATTGTGAGGATATTATTCTTAATCCATTTGTCAGAGTCCCTAAATGGAATG
GTATAAACATACACAACCATTTTAAAATATCACTTTTATCGATATTATTTGACAATAGATTGTAATATCCCTATCAACAGTAGCATATCTATCACTA
TCAAATAACTTTTCGATAGCGCTACCAATACCTAAATAAGATGCATCTTTTTCAGATGACGTTGCATATAGGTATTGGTTAGACTCAATACCATCCC
ACATAACAAGTTCACCAGATCTTTTAAATCCTGGCATTAATTCATCTTGTTTATAAAGAGAACCATGGTAAGTAATTCTGGTTTATTCATAATAAAA
TCCACTATGCTTTATAAGAGTTATGGTTATCAATTAACTTCAAGGTAGTAGTGTGGCAGTATTGAAGTGATTGGTTACTGCTTCGATCAGCATTTGC
TCGATGTTGATTTTGTAGTATTCTGGTTCTTCGTTCAATTCCCAATAATAGTCGCACGTAATAGTGCAGGTGCTATGAATCTAACTACCTTACCATG
TGTGTCAAACTCTACATGAACATTGCATATTGTTCAGTAGTATGATTTTATAGAAATGAATTACCAGCGTAACTGCGACCTCTATTTCACCATGAAT
ACTGGAGTAGGTTTCCTGGTGGAATACTTTACCTTTAAGGCGTGTATTCTCTTCAATGATATTACCAATTCTTTCAATTTGTCTTATCTAGTTGCAT
TTGTAGGTTCCTATTAATAAATGTATACGATGGATATCTTTTACGATTTCCGGTGCTTATCCATATCTAGTTTTATATCAGTATATATCTTGAATCT

Figure 7(L)

ATTAGATAGGCTATCCATATCTACGTGCAATGCCCGAATATGCATATCAGTATCTTTTGGTTTACCTTCAGACTCCCATACGGCCTTTGCGATATCA
AATGCTACATTGTTCAAATAGTATTCGACTTCATGTTCATCAAGCAAAAGAGCATCATGGAAACCAATACGTGATAGAATGGCGTAATCACGCTGAT
TAACATCTCTCCAATCTTTACGCACTAAGTAACTTTTACCAATTCCATCTTTTTTACAACTTTTACTAATAATTTCTATAATGAACTTATCATGCCA
TTTATAATCCATAATCATTACTCCTTTATTTAATCAGCTTCATTACTAGAGGAACAGATAGACTTATGCCATTAGCCATTTTAGCTAGAATATGATA
GACATCGTCTGCTTCTTGATTATTGTACAAGGTATAGAAATGGCATCACCATAGTAAGGACTGTAGTTAATACGGTCGCCATACACACCACTCACAA
AACTATAATCTAATCCATCCGTGGTAGTCATAATAACTACAACATGATCATCCCCAACTATACCGGATTCTAAATCCTCACATAGTTCTAGTTTTGT
TGCACACCTCGTTGACAGATCCATACTTCACGGTATTGATGATGAGGATATGGATTACATGCTACATCATTTTCACTAACGAAGTACATAGTCCCCC
AGTTGTAAGACTGGAATTGGGTTGTTGTTTGTGGGCTTCCCATACCTCTTCCATACAAAGGTATGTTGTTAACCCATAGACCATCGTTATTAAGACT
ATCAACGATCCATCACGGACACGTACTACACGGAGTGTTTTTGCCATTTTTAATTATCCTAAATACATAAAGGAATCACTTAGTAAACACCATTGAC
AATAGCATCGCGGAAACGAGACCATTCCGTTTGACCAACTACGAATACTCGTTCTTTAGGACGCCATAGATGATCACCGCAGTCAAGACCCAAGTAA
AGCATATTGGTTTTCCATGATTGCGATGAACACGTAGTTTAGCTGATACACTGAACTCACACATTACTTCATTTACATCAAGATGTGTAGTGTATCA
CTATCATACCTGACATACTGATACCAATTGATTTACGAACTCGGATTAGATCCTCAGTCATCACCCGCCAAGTTACCAGATGCTCGTAATACTCATC
TGGTGTCATGTTGTTTTTATAATTCAGTGCACCTGGAGTCATTGACATCAGTTAGTGAACTGGAAGTCATGTAATACATCCAATCACTATTATGACG
GAGTTCTTTAAGCTTCTCTGTATTACGATATTAGTAGTTGCTTTAGTCATCTACGTACCCTCATCAGATACATAAGTACGTTCAGGCTGAACACATA
TTTGATGTTATTAATTACAGCTGTGATATAAACCTGATATTCTTTTGAAATAGATTCCATCAGTTCAATAGATACGGAATTGAACTCTGAATAAGTT
ATTTACTTTCTTAGTTCATCAATTCTACCGACCGTAATTACACCAACATCTCTGAAACTGATAACTGGATAGTGTTTCCAATATAACAATTCAGTTT
ACCAAGATGAATTACTTGAATTGTTTCATCGCACCATTGTTTCTTTTCTATTGTAGTATTCAACACGACGTTCGATGAAGACGCGAGTACCAGAAAC
AGAGGTGTACGCATTCAGTCATAACCATACTTATGGTACGTTATTTGGATCTTGGCGCCATTTTGGATGAATGCTTTCATTTGTATTTTCCTTTTAC
GAAATAGAAGCCCTCCCGAAGGAGGGCAATTACCATTATTAAATTACGAGTCTATTACTTCTTTTAATTTTCACCAGGGGTAGCTAGATAATCTACA
TTATATTTAATAGCAATTACACCACAAGTTCTTTTTCATAGCTGTTCTACCTGATCGCATATTTATCAATAGCTCCATCTTCTACATCCTCGTATAA
TGGATATTGACTATAATATTATCAGGTGTAAGTACAGACAGTTTCAATCCCATCTTTACCAATGACTGGGTGATATGTCTGTTTAAGACCTTTACAA
TGATAGTGATAGGTATGCGCTGTGTTTAGGTGGTCATGTAAAGATACCTCATAAACCGTTGGGTAGTCCGTCTTTAAGACAGTTAGTTGATTAACAT
CTTTCAATGATTATCTGCAATATTCTTAGCCAATAACAGTAGATCATTGGTGATATGTTTTAATGAGAACTTAAGCCTCTCCCTTTGTTTATATCGG
AACCTTATTATCACAGTAACTCCATCCGGTTATTTTTATAATTCAGTACAGTGATTGGTGTATTCGGTACAAAGACGGCTAGTTCGTCATCGAATAC
AATGTAAACCATCACTTTATAATTATTAACCGATTCTTGGAATTGTTGTGTGATTACATTATAGTCTTTTGTGCGATGGCTAAGAAACAGCTCACTA
TTAGCTCGGCAGAAACTATGTCGCGCTTTTTATCAGCACTCATAACAGCGATACCACGGATAATGAATTTATTATCTAAGGTATATTTTCTTTGAGA
CATCGCATAGTCGACTACATCAACATCGCCGCCAAATAGCACGGCATTTTCACCGTATCCACAAATAAGAGCCATTTATAATTACCTGTTTAAAAAT
TATATTCAATAAATTGAGAGTGAATAGTTCACTACATTCCCATGTACGACTTGCTAATTTATATTTACCTTTAACAGGTAAGTCAAATAACGTAATG
CTTTTCTACTGAACCAGCCTCATGATTAACCAATAGAACATTCCTAGCCTTCAGAATATTTGAACAATTTACAAGTTCATAATCATCTCGCTTAGGT
GTCAATAGCTACATTAGTGCCTGGTTTCTAGCATACCAGAGCACCTCATGACCCTCTGGATTAATAATAGAGATATAGCTGACGTTCAGCGGGTAAC
CACAAGTTACGTGGATCATANTCTCCATTAACATCAAAGAATTTAAATATCATAGAGTTGGAACCGGTTTTGATGGATCAGCAATTANTGCAGATTC
NTCTACATAAACCATTGCNAAGTTTTCACCTTCTTTACGAATACCAGTAGAAGGTGTTTTCGATGGATCATAACGATAATTGGCACTGCTGTCCAGC
TGTTAAATAAGTTGGGCCAGTTAATGCATTGGGTTTTGGATGAGGAATATCAATTTTAGTAATACAATATTGACCAGTACGAAACTCACGCATTATA
TTAACCTCTTAATGAATAACTGTTGCAGAAGGACGACATTTCATAGTTTTAAAAATGTCAGTAGGATAGATATTACCAGCTTGTCCGAAAGGTTTAT
CGGCTAGAAGAAACTGCGGACAAACTGTTTGTAGATAACCACTATCAGTGGGTAGGAATCCTTCAATATCACTGATGAGAATTTGCCAGATGGGCAA
TTGGTTATAATAGTCATCCATATTGTAGTATGCGTGGAGTTTACCACCGAACCCATATACAAACTGATGAGTATCAATTAGACGAATACCAAATTTA
GGTTGTCGTCCCATCCTT

Figure 8(A)

>B11 contig 6, Nanoluc insertion (SEQ ID NO: 12)

CGATTTGCTTAGTACATTCATTACATTTACTATTCATCCTTATTTACCTTTAATAAATTTGCTTATCAAAAGAGCAATTAATTGGGATAGTGATAAC
TTCATTAGTAACTACATGTTTGCCTGTCTTTTTAAAGAATTGGGCAAATTTTGAAGTAGCTGGAATTACAAAGGTATCATCCCGATCATTATTTGAC
ATATTGTANAAAGTAAANTTACCGTCTANNTNAAACCTAATNNNCCANTNAATATNNCGTANTTTGAAATCTATACCAAATCTTAANTGANCATCAA
TNAATTCAGAACCACCGTANTCATAAGCTCCGGTGAAATTCCAATTAATTTCTGCGAATTGGAAAGTTACAGGATGTTCGCCATGTTCATCTTGTAT
GTAGTAACCATCATGAGCTTTCCAATAGATNACTAAATCATGCATGCTACCAGCCTCAAAGAAATAATAGGGGAGTCTAGACTCCCCTATTAATTTA
TTTTGCTTTTAGCCANTCTTCTANTGGNGGTAAATANTTCTCATGNGCCCANTTAATNATTGTTTCTACAACAGGACCNTGTANNTCAAGGTTNCCT
GAGATTTCATGNGGTTCATCAATAGATAGAACCCACGTNTGTGGCGCAATGCGTTCAGTTGCTTNGTTAGATACACATCAGGCATTAACGTAAGAT
TCAATTGATCGCCGTCAAAATCAGCCGTATTGTTCAGTATCAGTCGTTAATTGATACCCGCACCATTACGTGCAGCTCTAGCTTTCACTAGAAGACC
AGACTATATCTTCACCCTTCCTTTCGGAGTGGGGTGTCTCCCATTTCGAGTCACTTGACCCTACATCCTATTTCTAGGACCGGTGCACCTGATACCG
TGATAGTCGTTGAACCTTCTCCTATTCCTAAATGGAATGTTACGGAGCTTGGCTGCTGATTGACCCTACCTAATCTTTTTCAAACCTTGGCTTTGTC
TTTCGACTCGCAGTGGTAGATTAGTTTAACAGGATATCCCAGCAATTAGAGAGAACTCAACCCAACGATTACTCATTGGGGAACTAGATTTGATTA
ACTTAATAAGGTATTTATCAAGCACCCCATTCTTTTCAAAGATTGCTCTTCGAACAGTATTCGGATGCTTAATACCGACATCTCTTGCAAAGTGTGG
AATACTCGGATACACTTTGGTAGTGTTCAAGATGGTGTCAGTTACTTCAATTGGAGTACCTTTTCCATTACTAGGTTTTCCAAATGAGGCTTCAATT
TCTTTTTGAGTGTATTTAGGGAAATCTTCAGGATTAGCGGTATATGAGAATACCAAACCATCCATGATTTCCTTACTACCTCTAACTAGATGGTAAT
AGGCTTTATTACGTTTAGTACCTAGTGCAAGTTCCATTTCTGCTAAGTTATGAAACACATGTAATGTCTTAGTCTTATAGTCTAAAACATAAACTGT
CTTGGTACTATCTCGATCAGCAATCTTAGTCTCACCGGTAATAAATTCAAATGTGAATCTATTTCTATACGGCTTAGTCTTATGATCACGTATAATA
ACCCAAACCGTATTTTTATTAACTCCTAATGCCCGAGCAAGTTCATTCATCGAGTAATAAGTAGTCTTTTCACCAGTGGTAACGTCAGTTGCAATTA
CCCGTCTATTTTCTTTTCTTAATCCATTTTTGTAAGCATGCTCAATGTTTTCACCACGAGTCATCCACTCCAAATTAGATGGTAAGTTATTATGTTT
GTTGCCGTCTTTATGATTGACTTCATAATCTGGTCCAGGTGATGGACCATGGAAAGCTAAACAGATTAATATATGAACTCCCTTACTCTTAGATGTT
TTTTCATCATTTTTTGCACCAATATTGAGATATGTCCCAATCGATGTTTTAGTAAGGAAGAAATTACATATTCTATTTAACCGCTTATGACGAATTG
TTCCTAAGTTACTAGCTTCATATGCTGAGTATCCAGGAATATCCCGCCATTCAATTTTAAATGAAGCCGGATCAAAGACGGACACTACTCCGTTTTG
TTCCATTGTTTTTACCCTTATTTAGTTATTCAATTGTCCATTAGGCGCTTTAAGGCATAAAACTGACATGCTGATAGAATTATCATTAATGTCATCT
TTTACTTTAGTAATAAAGAACTGCTGCGTAGATCCACGTTGAAGCGTTGGCAATATCTTCAGATAGTTCGTTAGGCTATCCCGCACCATTACGTGCA
GCTCTAGTTCTCACTAGATGTTGAGACTATATCTTCACCTTTGGCTTTATCCAGTAAGGTGCTTCCCACTTCGATTTAAGGGATTCTATACCCACCC
ACTTGGGCCCTACTCTACTCCCTCTACCTTACGGCATGGTTTCGATAGTCGTTGAGGATTCCTCATACTCCTTTTAATTAAGAAGGTTAGAGGCTTT
CCTGCTGATTGACTCTATTCAATACTTTTCGAACTTTTCCGTATTAGCTTTCGCTATCCGTTTCAGTGTATTGACCTAGCGAGTTATCCCAGCATTT
CAAGAAGTTTTGTCGAGTATCATTTCTGATACAAGGAAACCATTATTAAGTTGATCCACTACACTAAGATTACTTAGGTGGTATGTAGCTTCTCTTT
ACGCGCTTTGTATCGGTTATATTCGTCAATGGATTTATTAACCATCTCTTGAGTTAATTTAGAAACGTATTCGAATAGCCGTTCCTTATCTTCAACT
CTACAGATGACATATCCATTAAATAATCTCAGTTCTGGTTTCTTCAAGATGTCTTGCACTGACCCCTTGATTAATCCAGTCCTAAGTTGCAATTGTG
TTAAGTTCTCATACCTGCCAAAGGTGTTAGTTTTGAAGTCTATGCAATAAACTTCAATAGCGTTCTTCCGCTTCTGTGGATGATAATCCCCAGTTAC
TTCAAACACGTACTTACCATTGTAAGGTTTAGTTAGATGCGCCATGACTACATGCAGCCCTTTACCATGACCTAGCTCTAAGAACTCTGCAACTTCT
TTCATCGAGATGAAGTTATACACCTCACCCGTGGTTACATCAGTGCATTTAACAGCTAATGCGTGTTTGTTTGCACCGGTTATAAATGCATGTTTTA
CATTACCACTGCGAGTTTCCCACTCTAGGTTAAGGTAATGGTTATGATGCTTATTGGTGTCTTTATGGTTAACGTCCAAGGATACATAATTCTCAGG
TAATCCATGGAAAGCCATACATACGAAACGATGCACGTATCGTATTTTGCGAACACCTTCATCATTGTGGATATTAACCGTCAGGTAAGTACCCTTA
GATGTTTTGTTCTCATGTTGAGAAATCAACTCACCTTTAAGGTTCCTTACTTGACCATGGTCACTGACTTCATAGTTACTGAAACCAGGTATACTTC
GCCATCTTATTTCTTCATTCATATTTCCTCATTAGAGATTCTTGGTTACCACACCCAGAATCTGTAGCGCTACGACTTAATAAATTAATTTCGGTGA
AAAGTACAACCCATCCCTTTATAAGGGGCTGCTTCTGCAATTAGCTCTTTAAATAGATCTGCAATGATTTGGTTATATTGAAGTACATTCTCATATA
CAAATGAGAATGCTTCACGAGTTGTCATGTTAAACTTNGCTTTTAGNTTNTTNGTTAGATGATACTTTAATAATTGACAACCTACNCCCCANGGNAT
ATGTANTTCATCATAATCATGCGGGTCACTAATAGAAGTGATTACTGCACGTGCCGTAGCGTTGAGACGAGCACCAAACATGTGACGCCGAGCAAGA
CCAGGCTTTTGAGCAATTCGTGATTTTGCGTAGATCTCGTAGAACTGGCCATATAGTCTTAGTCCTCGCATAGTCCTATTCTGAGCTTTAATTGGAC
TAAGTGGTACAGATGATGCATCAATACTAGCGAAGGTTAAGGTAGCATCAATTGCTGCTTCAATTGGTTTATCTAAGTAAGTACCAGATGTGGTTGA
TTCTGCTACGAAACAGAGTTTAGAAGGAACTGGTAAATATTTAGGGAATAACTTATCTTTATTCTGAGCAACGAATTGAGCGAATTCGGATTTATTA
TTAGANATAATATTTGCATCTAGTAGGAATTGGAAGATCTCATTGAAATTATCAATGAAGTGATTTAATCCTCTTTCAAATCCTCGATGCAGTAGCC
TATCTACTTTNCTGCGTGTTTCTTTAGAACCAATAGATTCNACATCGTATCGATAAGAAGTATCAGTTAGATATGCTAAGAAATCGAATTCTTTAGT
TACTAGATATCCGGTTAGCATAATGATTAAACGTGGGTTAATTAGNCTACGTACNTGTTTTGGTGTACGAACCCACATTGATGGTTCGATAGGACGG
CTAGAAGTATTGACAACTGGAGTATTACAAATATCACAGATTACTCCGAGTTTATGTGCGTCTTCGATTGCTCGACAATCACAGCTTACACTACTTT
CAATTGCTTCTGAATCTTGGAAATGAGAATAGAAATGCCTATCAAATTCTTCTTTCTCATCTGAGTTACTCGTATTGTAATCATTGGCATAAATTCG
TTTACCCGTAAATTGATCATGAACTTCATTATGATCAACAACTTTGGCATAAAGACCCATACCAAACTCCTATTTATCGATTAACAAAAAAGGAGAT
ATAAGCGGCCCCCGAAGGAGCCGCTATATCAGTTTTTACAATGGACCACCAACGGAGCCTGGCCCGATCCTAGCGTCATCTACAAAGCTTAACCTCC
GCTCTTCTCTGTAGCATACCGGCACTAGTATCATTTACCATCCATTGTAGTTTTTGATCACACGTCACCTTTTGAGTAACTCCTTTCGGTTAAGTGA
TCTATCATCCTCGTGTAGTGATAGGTCGACCTAGACTAAGTCCACTAGTCGATTACTTCACGGAACCTACTCCTAACCGTTATCACCGAAGTGAACC
AGGGTCGCAGTATTAGAATCGGGATGTTACTTATTTAACATCCCTATCTACCGAGGTATTTCCTATTAGTACCAGGTACCCGGTGCATTATAGGAAG
GAGCGCCGTAAGTTTGACCCATGCTGCCAGCCATNCCAACTTGTGCACTACCAGAAACAGCCATGTTACCCATACCGGTGTAACCAGCGAAGCGCTG
TTGACCGAAGTTGGTAATTAGGTTTTCCATGGTTACAGTTACACCAGCNGCTGCTGCTGCGGCATCCATTGCGGTGATGAATTTCGGGTTAAAGGTT
AGACGACGAGCACGACCAGTATAGGTAACGTTACCTAGGTACATCTTGTCGAAGCCTTTACTGTTATTCATACGACGCACAATGTGGTCATTACCTA
CCTGAGTAGCATACCAGGTCTTCCACTCTTGGTCATTACCTTCAGACATGTTCATGGCACCTAGAACGTCGAGATCACGACGGTCGCTTAGTTCACC
ATGCTCATCAGTGTAGTGACCGAGGTCTACTTCATGATGGTTGTCAAAGATAATCGGACCAGCTTCAGCTAGATTATAGAACTGACGGAAATCAGTG
CCGTATAGGTTAGTTAGAGCTTGGAAGATCAGACTAACTGCACGAGCTTGGTTTACGCCACCAGCTGCATCTAGGACGACTTGCTCAATAGCTGAGT
TGTCTCCCATTGGATCGACATCGATCTGGAATGCAGGGTTCTGGTTAACCATCTTGTTCATTAGCATTACGAAGTTGCTGTCGTCTGCCATGAATGC
TTCGGTGCGAGTTTCAATCGCTTTACCTAGCTCTGAGTAATAACCAAGTGCACCAATATCACGCATCTTACTAGTAGCGATCTTCGGCATTAGAGTA
CGAGCCCATGCCTGAGATGCAGTTGCACGATACGCGTTACCAAGCGCGAACAGCCACATTTCTAGAGTCCATGCTTGGATCCAGGACGCCTTACGAA
CGTCAGTAATAACGATGTAAGGAGTGAACTGCGGAGGTAGAACTGCACCAGGTAGAGTTACGCCAAACATGCCTTGTTGCTGGCCAGTGGTCGGAGT
CCAATGTAGATCTACGAATAGACTAACTTGGTTTAGCTGGCTATCGGTATCATAGAACTCGTTCTCAGGTACGTTGGTTTTCTTACCACGGCTAGTG
GAGATGACCAGGTCAGAACGGATCGGATTACCACAGCTATCTTTAACCGGAATACCATTGTAGTCTAGNTTGCAGGTAAGCTGTTCGTTTTCTGCTT
TGATGTGGGTCGCAATAGAGAACGGAGTCTCATTGTTACGACGNGCAATAGCATCTTCACAGATNTTAACNGATTCAACTAGTAGGTTCTTAACAGC
TAGTTCATCTTTGAAGTCGAAGTCAGCATACACTGCACGTGGACCGGCAGATAGTACTTCTAGACCAGGGATGTTGTAACGGTTCCGTAGGAACTCG
CCGATCTTGCTCCAGTATTGAGCAGTGAATACATCACGCGGTAGTACCTTCTCTTCAATGATGTCATCAGTTAGACCATTGTTGATTTTGTGGGTAC

Figure 8(B)

GGGGACGGATGCGAGTACCAGGTAGGTTATCGAGTACTAGAGTACGAACGAATGCCTTCATGGAACCATTGATATCTTTAGCTAGTTTAACAATGAG
TAGACCAGCCATACCNACTTGTTGNGCATCNCGATCGAAACGATGGATATCGAAGTCATCAGGTAGGTCCTGATGGCGGATTGCTTCTTCTTTTACT
TTAGTGAATACTTGTAGGGCATCTGCTGAACGAGCATCAGAGCCATCTAGCCGACCAGAGCGACGCATTAGATGGTTAATGCCAGTAGTNGACCCAG
GNGCGCCAGNNGGACGTTGAGCTTGACGNTGTGCAGTGGGTTGCGGAGCNGGAGCNGTAGCTTGAGTTTGAACGGTGCCGATTTCGTTTTCGTTAAC
AGCCATTTTAAATACCTTTACGATTATGGTTTCTTGATCAAGAAGAACCTAAGTACTNAGTATACTAGATTCAATTTAGTAATATAAATCTCAAATT
TTTTTCATTACAACATAGACGCTATAATCTGCTATCAGCAGATCGTAACGAACACTATGTTCACTACATATTATTACAATCTGAGTATTATTTATTT
TTCATCTTACAATTTCCATATCTTCTTTTTTGAGTTTATGGGTATAAAGTTTGAATCCAGAAACTAATTTACGTCAGTCCTGTATTAAATAATAACT
ATCAGTATTTTTATAAAATGCAGTTATCATTTACTTCGCATATACTTACGAACTGTTCCAAAAAGAGAATGATACAGTTTGTATAGTTTACTAACTG
GATCAACTTTATTATTATCAGTTGTATCAAATTTAGCAATAAATGGTGAATGTGCCGAAGCAGATGTTTCATTTACTTTAACTACACTACCAAATCG
ATATGCGACTAATACCTTTATTAATTCCTCATGGAGTTTAGTAGCAGTTGCTAATGGATTGGGATCATTAGGATCTATCTTAATCCTACGCTCGACA
TTGAAAAAGTTTACTACAATTTCTTTGCTAGTCATGTATACAGTAAGATCTTTGTTATTACCTAAATATAGTGGCGGATCTTCAACATTATTTTTAG
CCATTGTATATTCCTATTTGTAATTACTACTGTTGTTACCAAACTATGATATAGATCTCAATTAATTTTTAATCGGATAATAACCATGTATAATTTA
TTTAAGAATGCTCCGTCACGTAAATTGGGGCAGGTGGTTGATCCTAACATCCATTATATCCGACGAATCTACGCTGAGCAAATTAGGGACGTTAAAA
GTTATTATAGACGGGCACCGAAGTATGTTGAATCTAAAAACATATTAGCACAAATGATTCGACATTTTAACGTAGAGTTACTAAGTGATGATGCTAC
TTTTATAAAGAACGTGGACGATCGTTCACGTGCTATTATTCGTTCATTTGGTATTACATCATCTTTAAATAAAGGTAAGGTTCATGTAGGTGGTGTT
ACACTTGGTCCTCAAACTGAAGAAGTTCTAGTATCCACATCAGAGAGCTTTGATCTAAAAGATCTAAATAAAACATGGTATAAACTTTCCCCTGTTA
CGTATCTGTATCATACACGTACTGATACTAATTTACCTATCATGAACAATACCACACAGGGTAGAGGCTATGGTGTAACTCTAGTAAATATACCAAT
GCTTCTTGTGATGTACCGTTACTGGTATCGATGGCAAGTTGAGAAGAATCCTGATGAAGTAGAAGACACTTATAGGTTTATAGGATCATTTGTATTG
CCAAATATGGTTGACTCTTATTTAGATATTTCTTTCTTTAATAGGTTAGCAAGGAATGCTTTAGATATTAAAAATCCAACATTCCCTATACCGCATC
CATTTTACATCACTGATATGAATCCACGTATTGATAAACTATGTACAACTATCAATAGAGAATCCATATTAAAAGGTGTAGACATGGAAGGTTTATC
ATGGATAACACCAGCTATCGTACAATCTAATTTGTTCGATATGATGCGGCTCCCACGAGAACCTATTAACAGGAATAATGAATGGGCTTATGTATTG
GCTCGCACACCCTTCATTAAGTATCTTGTAGGGCAGCTTTTAAAGAATACTGGTTATGATCAATCTTCTGTTAACACTGTATTAATTGATCTTATAG
AAGCATCTAATGATCAAGCATTTAAGCAACAAGCAAATAGTGAGTTTGTAAAAGCTCAACAGGCACAAGTTGATTGGATGATAGATGCACTTAAAAG
AAAAGAAATGTGACATAAACCCCCTCCTAAATTGGAGGGGGTTATATGCCGTTTTATTAGAAATTACCTTTCTTCATTTTAGAAAGTAATTTTCTAC
GTTCAGCTCGGTTAATTCCTGGGATAGCTGGTAATAGCATTTTATTACTAAACTTACCTGGCTTGCGGTCATGATTTAGTAATTGATCAACTACAGC
TTGGTCACTGCTTTTAACTCCATTATCCATTTCATCTAATGGGTCCATAATAGCTTTAGCAGTCAATCTTAGATGAGTAACTAGTTCATCAAATGAA
CTATCGGTATTAATAAGTTGTTTATCAACACCTTCTTTAAGAGCTTGTTTAATAGTTACGTCTTTTACCAGGATATTATCACATTCCCAAAGAGTTG
TATGATGGGTATTTAACATTAATTCAAGTGAGACATTATTGTAATCGTTGTCAGCACTTGAGTGCCAATTGAATTCATCAATATAGTCATTTAGACT
CATTAACTTTGGTGGTTCGTTACTAGAGGTAATTAAACCAATTGGTTGAACATCATCTAGTGAACTTTTATCACTAGTAATTGCAGTTGTTTCAGTA
GTAACATCAACTTCTTTTAATTCGTTGGTATAAGTTACATATACTAATTCTTCACTACCGTCATCCAAAAGAACATAGGCTGTTGCTTTGGTGGAAT
CATCAGGTGCTAATCCATGGATCCTAATACGATTATCATTTACTAATTTACTATAATCATTCCAGTGATTACACGAACTTCATTAGTCTTTTCCATT
ATCATCTACCTCTTTTAATTTATCTTTAATATATTTCGGATAAAGCTCGTTTTCTTCACGAGTTAANCCNGNTGGNNCGGTTGGTAATGTGATAGTN
CCNCTNTTAATTGCCTTCTTCATCCGATCTAAGTCAAAATTAAATTCGGTATGATTTNTCATTATATTGAACCATATTAAGTTAGTAATTGGCAATC
AGACTATATAAATCTTAATTATTTTTTAGTATATAAGCCTCCCACTAGGGGAGGCTATATTTCTTAATAGAAGTCAGAGATGAGTCGATCGTTATTT
TTATCAATAAGGAAAATACCTAGGGACTCTAAGGTTAGATAGAATACACCCATAGTNTTTCCAATGATAGTTCTAACGTCAGCAACACGCGTAATAA
CTTCTGGAATACGACCAGTTTCTACTACTGTACTCGGGATATGGAAATCACCAATACTGGTTTTATTTTCTTCAGTAACCCATGCTTGAATACGAGC
AGCTAATTTCTTATCTTCGATACCATCAATCCATTCTTTGATCGCAGTTTTATTATTAAGAGTAACTGAGATCTTTACATGTGAATAAGGTGGATCA
CCAGCGTCACCAAATGATGGAGCAAATACAGTCTTCCACACTAATCCCTTTTTATGGGTTGAGTTATCTTCAGATTTATAAGACTCAGGTCGTTTAG
TTTGACCACTTGTCAGATACTCAGCTTTACCACTTCTAACAGACTCAATAATTTCTCTTTCGATATCACCAACTTCTTTTAGAATTGAAGCCAAGTC
GATTTTCTCTTCAGTCTTTACAGTTTTAATGATATCTTCCATGAGTGTTTTAGCACGACTATTAATCTTCTTAGGTACTTTACTATCCCTTAGTCCN
ACNCCNTTNATCTCCATNCGNGANTCATTAAACATNACCCCTTCTTGGGCATCCTGTGATGCAAAGTAATGTTTAGAACGAGTAGTTAAGGCCAGTA
CTGCGAAATAANATTCGTTCTTCATTGCAAATAGACGAAGCTTATCTTTAGATACACCCATATTAGCGGATTGAATCGCNAAGATATGCATAACTAC
TTCAGANACTAGAAACACTAGTGCNAATACTAGTCGNTTAGCTTCATTGCTAAAAGTTACTTTACCAAAGAATTCCTCAACCCACCATTGTAATGTA
AACATAGTGGAGTCAGTATCTGAAATAACAGCAGCTCGTCTATACACAGTTGGAAAAGCATGAATGCTTGATGGTACACATTTAGTCAAGAAGAAAG
CTTCAATCAATAGACGATATTCATTAAGAGTTTCAGCGATATTTCGACCAGTGGCATAAACTTGGTTNANTGTATCTGGATCNGANTCTTTTAGTTT
AGCTTTAGATCGACCTTTAACAGTATCAAAGCAAATAAAGCTAGCCAANAGATCCATATCACCATCATAAGTTGAATATTCTTCTTCAGTGATGATT
TGTTCTTTTGTTCCAACCTGGCTTAATTTAATTAGAAAGCTCTTGATTAATTCTTTATTGTATTTATATAAGTGATATAGATCACCTACNTACATAA
CTGCTGCTCGTTCGACTGGTGTCATCCCAGTAGCTAGTTTTAAAATCTGNGCCGTGTANTACTTATTTTGCCAATAGTGTTTAGTTGAATAAAGAAC
CATATCAACTACTTCTTCTGGCGTTGGGCAATGTAGATTAAAATTAGTTACTGCTTTTTGAATTAACTCCATATCAGCTACATTAATANTNTTTACT
AAATTAGCTTTTGTGATTTCTGGAGTATAATAATGCCTATTACCCATAATGAATTTTTCATTATTTGAGTTAGCATAAGAGGTACCAGTTCTACAGG
TAGATGTTAAACTAGAGTGTGTGGACTTATAATAAAGAATAGTGGCAGCAGATACAGTACCGCCTGAATATGAGTTATTGTTAATTTTGAAGTTTTC
TTGNTCNCCTTTACGTACTTGTGCAAGTTCTGTTTTAATTTGTGAATTCTCTTTATCGCCGGCCTGTAGGAAAGCAGCTGCTTCACGTTCAGCCTGC
ATCTGNTCACCTTTAACACGCTTACGGTTTTTCACACCTTCNGCAATATAGATGGAGTGCGTNGACTGTCTAACAGACTCTGGTAAATATGCGGTCA
TTGATGGAGATAATAATAGATTCTGTTTCTTAACACGGTTAAGAAAAGCCATAAATGAAACCGTCTTTAATTCCCTATCACCAAACTTATTTTTATC
TAGAATAGTTGCTAATGGATTACGAAGTGCATATTCGCCATTTTGACGTAATTGTTCTTTAACAAATTCTTTACATTCTTCTAAACTAATATTTAAT
TCATCTTTTGTCATTAATTGAAGATATTTGGCATTATCATCAAGACATGCATTAATGATATCAATATCACGATGGTAATCATTGACATCTTTTAAAA
ACGGATTTGGTTGGGCAAATGCGGTCATTTCACATATCTCTCAGTATACTTATTTTTTAATTATAGTGAATGATTTCTCTCTNTTTAACTAAAAAAG
AAAAGGAAAGAATGGGTACCCTATACGGGNACCCTAAATTGAGAGGTAGCACATCAACTTACATTCACATTAGATGATGTAAGNAAGTAAAAATAAN
ACAACATAAAAGGAGCCATNATGGCTCCTTTATAGTTATTCATATGTCACTGAAGTTGGTGGTGCATTATTTTGNCGCACTGCCAATAGAATGCGAT
CATACATTTTATTATCGACATCATCCCATACTAATGTCANACGNTTACCATCTACACGTTCTAATGTATTCGCAACAATCCAAGGNATNCCAATAAA
CATCACACTTTCATTATTGGCCATTCGTACACGAATNTAATTGTATTGTGTTGGATCAACTGGAGCTGANCCTGCTGGTAAACTTGGATATACTTGC
TGCCCNGCAGCAGCTACATCAAAACCCATTGCAGATGCTACAGACGCAGTAACAATACCTTCGACTGTAACGTTCTTAAAATTAGTACCTAGGATAG
CATATGGATAGACCTCGAATGAGATCCTATCACCTGCTTGAATGTCTCGAATATTAACAGCCATGGTAATACCCTAAAATAGTTGGTTACATAGGGT
ATTACTCATCTAGTAATACNACTACACCAAACAGACCTTTCGTATCCATTGGNACTGTAATGANTACATGTCCATNTGGATANTTTTCTTTAAAGCT
ATTGATAAAGTCGGTNCAATATTCAATAACATATCCTTTAGTAGAATAATTCTCTAACTCAATATCTTCNTCAGGATCATCAAATGAGTCATGTCCA
TACATCAGCATATGGATNTATATGTCATTATTAAGCGTATCCATATAACTTAACTTACGTGATTCTTCAAATAAATCAAGTGGTGTTGGACAATCTG
GATATATCATTCGTTTTGTATATTCACGAAGCAAATGTTGCGAATATACTTCTGACTCTTTAGATTTAAATACGATAAATACTCGTTTTTCCATATC
GGTTCCTAGTAGGAAGCCTATGTGAACCGATAGGCTTTCCTATTTGCGTCAATTGTTAATATGTGTCACTTAATCCACATCATTGTAACAGTCCATA
CCAAAGTCTTCACCTTCTAGAATATAACCCTGATTATGTTGATCAACTGCTATTGATTGGATTCTTTCTACACCATATCCATTCTGATAGAGATGTG
CTATTTCAGATTGTAGTTTGCTAGCCAATGTTTTACACACGGTCGCAAACCACATATTAAGAATACTCAATGCATATTTATCTTGCATAATCACAGG
TGCTACCGATGGAAAGTATTCTTGTAAATAATAGTCAACCCCTATAATTGGTTGAGTAGGCTGTTGCGCTAGAAATTCAATATATGAATTAATTGCC

Figure 8(C)

TGATACCATAATTGTTCTATAGACTGGTGTTCAGTATATGGGTAAGGGTATTGTAAGACTTATTGACAACTACATCAGCCATTTTATTAACAATGGG
CCAGATATCACTGATGTTAATAACTACGAAACTCGTCATTCCTTGTTGACCTGGAGTTATGTTATTAGCATCATTTATCCGCTGCATTTCTTGTTGT
CTATAAAGAAGTGGATGCATCATGTTTGAGACCTCATAACTAATTTAGTTACCATCTTATATTTATCTACTTCTATACATTTAAGACTAGTAATAAG
ATTACCTGCTTGAATAACTTGTTTTTGGATTATCTCTAGGAAATCAGTTCCAAATAAATCCAATACCCTTTCGATAATCTCAGCAGATCTTAAGTGC
CAATTGATGGTATTAGGATTTCCCTGATGATCAAATACCATCATACTCGTCGGTCTATCCGGTTCTATATAGGTATCGCTTAAGTAATCTTCTAACC
ATTGCTCTAAAAAGGTAGGCCAATCTAATCTCTGCCAGTGGTTAAAATATTCACATATGCTGCTAGAAGTCTATTGATACACCACAGTACAAAGTCA
GTCGGTTCATCTACACCTAGCTCTTCCGTAAAAGAACGCGGTTTCAAAATTAGCAACAATTGCATATTGACTCCACTCTTTACCAGTGACTATAGTT
AATAGAACAACTTTGTTATCTATTACACTAATGAACTTATAGTCTATTAAATTCTTCGGTGTTCTATGTAGTAATTGGATTCCAGTTGTATAGAACA
AATTAATGAACTCATCCCAATCTGGACCATTTCCTAGTTGTATTGATATATCCACAAAAGGAATAACCGTATTATCCTGTTGTAATTTAGACATCAT
CTTAACAACCCATTGAGTTAATAAGACGATGACTGTAGCTTCATCTTTATTTGTTAGGTAAGTAAATTTCTTTATCAATGTGATTAATTGTGGGAAT
ACCACTTCGATTGGCAATACATATACCAGACGTTGTACTTCCTCCGATGTACAATCCATCTCGTGCTTCTGTTTCATACCACAGTTCCTTAGTATTT
GTTGGAATGAGGTGCATGATCTGCTCAGCACCCTCATCGAGAAGTTCTATTAGTTTATGCATGAAATGAATGTCTTTAGCATATTCATAGAACATTT
CTTCTTTAACGACCATTTGCATAAGCTTCTGTTCTGCCAATGCAACAAGCAAATGCATTGCTTCGATATAACTAATATCTAAAAAGTCCAATACAAA
TCTTAGATAGTTATCATCTTTAATAAGTTTACTTTTAGTCGCTCTTAGTAAAAAACGAGGTTGTNGTGTGGGTAATGGTGACGTATAGATCTTCTGG
TTTCTCAGTATCATAAATAACCCTATTTAACTGGATGTTACCAGCTGATGGTAGAACTACCCGGTTAGAACAATTATACAGATAAGTTGTTAAATCA
ATATCACAAATATCCCTATAACCCAGCATCTGATTAATTAGTTCTATGACATCATTAGATGTNCNACCNGATGCNCTCTCAGACGCTGCTGCCAATA
CAATTGTTAATGCATATTCTGCACCAATACTATTTTTTATAGATTTCCAAATATCAGAATGTTGNTCTTGTACAAAAGATCTTACTTCCATTCTGAT
ACACATTGATGTGTCTTTATCATTAGATATGTTCATTATAAAAACCTTATAANCGNTATAAAGCCCNCCNTANGGAGGGCTTTATTTAGTATAGATT
ATTTTCTAAAATGTATCGCTCAGCTTGCGCTCGCTGATCATCAGGTANATAATCACCACGTTGATATTCAAATACTAATTTCTCAATAGGATAAGTT
GCATTCTTATTCTTGTATACAGAAATTACATAGCTATGATACTCTAGTTCATACTTAACATCATGCTCAATTCTGGTTGAAAAATAAGCCATGTTAA
TAGAACTAACTAGAGGGCTAATATATTTCTCTTCAAATAGTAATAAATTATCAAGTCCTAAACTTGCAAAGAAATCATGGTTAACCTTAGGTATTAG
GTAAGATACTTTAATATTACTATATTGTTTAACAATTACGCCAATAAGTAATGCAGTTAACTGTTCTTGAATATATTCTACTGCGATGTTGTATGCA
TGGTTAGTGGTGATGTGGTCTTTATTTAAAGTATAGCTACCGCCATTGGTAATAGATGGCTGAGTTTTACGTCTAGATTCGTAGATACTATAACCTA
GTGTTTGTAAATTAATTTTGTCAAAGCCATGGAAGAAAGTCCGTAGAAATTCACTAAATAAATAGTTTAATGGGTTCAGTAGGTTAAGTGATACCAC
TGCATGATCATCACCATTATCAATCCCATGGACACGATCATATTCTGCGATTCGATAATCTTTACCACTGATTAAAGTTATAACTGAACCAGCTTTA
ACTACATCCCATTGGATCCATGTACCGCTATCGATATATTTTGCTACTTGCTTATAGATATCTAGATAGATAGTTTCTAGATAAGGTAGTTTCATTA
GATTTTCTACCCAAGCAACTTTATTACTATCTACGTCAGTTACAGCACAATTAAAAATAGCTGCGGCCATCTTAAGATTGGTGTACTGGTCTTTGGC
TGTTTTATATGAAACTAAACTCTCTACTATATTTTCAACCATTAGATGTAAAAACTGTTGAGCCACATCTTTACTCAATTTCACCCCAATCGCTTCA
TCAATTGAAGCTGAAGCTGTAAGCTGACCTAGTAAATCGTATATTGCTTTTTCTTGGTGGCGCGTATCAAGTACAATGAGCTTATTCGACATTATAT
TTCTCCAATTAATTTTTTGGAATAGCGATCCAAACTGTGTTCTTTAACCGATAGAATATTACAAACTTACCTGCATTTACTCTAGGTATAATTTTTA
ATATATCCCAAAGATCAGATGCGGCCTCATGATTATCATGAAACCATTGGATTTCTTGAGGGGTGTTATTTATTGGATTATATCCAGTAGTATACAT
GAATTCAAAAGAGTCAATAGAGTATTTAAAGAAGTCATCAATTAAGCTGTCCTCTACTGATTTAAATATATGCTCTAATGTACCATAGTCATCTGGA
TGTATTCCAAAGCTTTGGCACCTAATCGCTAAACGCGTATTTATTAACTCTTTTGGCGATCTTGGTACTAACTTGGCTATCACCCTCGTTACATCTA
TTACATACAGGTCAGCCACTTGGGGAGTAGTCACAGTACAATCTCTCGTTAAATGTTCAGGAACATGATATAGATCTAAAAATATTTTTAGTCAAAT
CTGTTCGTGGTAAGCCGATGTATATTATACCTTAGTTGGGTATTATCTCCATCGAAAAAACGCGTACAGCGCATTATAGGACGTTTTTATGAATCCA
ATTACTAAGGCTTTACGTGATATTTCTTTTAAGATCCCAAAACAGATATTAAATACTGTTTTCNTATCTANCGAAATGTCAGGCTGTGGTGCAGCTA
TCTCACTAGAAACCAGGATACGCGAAGCTGTTATTGAACCACGTGTTATGTTAGATATTGATTTAGTCGGTGGTTCAAAAGTATTCATTCCACTAGA
TTTTCCAGTGCAAGCAGAATATGTTGACCCTTATACAGTGGTTTATTACATTCCAGACGAATACACTCAGCAACGCCCAATTATCCAATGTTACAGT
ATCCATTTTGGAGTATTAGGATTCCATACTGCTGGCTATGCTATGCACTATAATGAATCAAGTATGGGTGCATTAACACGACGTGTACTAGATTCAG
CTAGACAGTTACCAGTCGCCCAAACAGCATATATCAACTTAATTAACCCACACACTGTCATGGTCAGGTATATCAATATCCCTAACTACTCATCATT
CCTTGCCTGTCGCGTAGGTAATGATGANGAGCTAAATACCATACGACCTACAGCCATACCTGCATTTTCAAAACTCATTGAGTATGCTGTTAAGTCA
TACATCTACAATGAGTTATTTGTATCTATGGGTGANGCACAGTTATCAGGTGGTGCTGAGTTAGGTGTATTCCGTGATAAGGTTTATGAATATGCCG
ATGCTGAAGAACTATATCAGGAACAATTAATGCGTTGGATGAAAATATCCAGGCAGTTCAATGATCCTGAAGGTAAGCGACATCATATTCGGACAAT
CACAGCCGCTCAATAAAAAAATAAAAAAAAGACATATTGCCCTCCCATTGCGGGAGGGCTTATGCCATTAAGGTAATATCTAAATAACACNATATTT
AAAAACATACTGGTATAANNCATCATCAATTAACACTGTTGAGAATCTTTTTGATGAGATCACCAGGTGCGATACCAATGCCTGAACAATACCGTCT
AAAGTTATTACACGGTTGACATGCTTTCTTTTCAACGATATTTAATTCAAAGCAAATATTGCCACGTGAATCTAGAATGGATATAAATGCTTTGTTA
CCTGTTACGCGATATGTCTTACCGAATACAACAGTTGTTTTATATGCAAGGCTATTCATGATTATTCCTTTAACATGGATTATTATCATGTTTGTAA
TATAGCCTTTAAATGTATTTAAATATTTATTAAACCNNATAGCGATGNGCTATATATGTTTTNAATACCTCATANGCCTTATCNGTTGCCATGGANC
TATTGACAAAATCAGAATGATCAATCTTAATAATCTTACCGAATGAATCATAATCGATAGTTGTAACNNCTATTCGATCACTATCACGGATCAATAG
TTTATTTTATTTAAAACAAAAATATTCCATTTCTCGCCATCGGCTAAAATAACATCCTCATCTTTAAGATTAAGACGAACAAACTGTTTTACATAAA
TACTTAACTGAGCAACTGTTGACATAATGATTTCTCGATATCTGTTAATGAACTAATCATATCTCGGACATTNATGGTAATAACATTTTTATAAGTT
AAATAAGTTGGATATGAACCCATAAATGTAATAGTCCCACAGATATGATTTTTATATCTAATATCAANACANCCGTCATATCTCCAGATAAAATCAA
ATGATCCTTTAGTGTGGTGNTCAAGTGNAAGAATAGAACCACTAACTAATTTAGGATATTGTTCAAATTCAGACATTACATAATCTGCCAGTTCCTT
AACCTCAGGATAATCAATCAATAATAGCATATACGTAAATCTCAATNAGTTAATATAACACCCCATCCAGGGTGGACTCTTTCGAAAAATGGTAATG
TATTATTTCGTATACTNTCTGCATCAATATTTGGAATGTGGATGGTACAACAGTGGGGGTTACTGTCAATCTTGAAATAGAAATTATCTTTTAAATC
TTCAACCTTGGATGTTTGNAATGGATATAAAATACCATTCCCCCAAACATACCAACGNCTATACAGCTTATCGTTTAACCGCTTCTCAATAACCGAA
TGCGATTTGAAACGAGGAACTCGCAAACGCATCCCGTTTACTTCAGCCCATTTGTCTACCCGNTCATAGCTAATAATTCCATCCTTAACCATTACAA
AGATAAATCCCTCAACTATGTTGGGGAGACGAACTACGTGTTTCAGAACCATAGTAAACGGAGATAACGTCAGATCAAGTTCAGCTGCCATTTGCTC
GTCGAGCTTTTTAGCAGTGTTCTTTGCCATCGGTTATCTCCTAATATACAGATTATTAATTATCGCTAGTTATTTAATATCTGCAAAATTCTGATTT
ACTTTACCCATAAAAATACCATCGGCTCTATCGTCATAATAAAGCTTCCCTGCTTTAGCATTACATANAACTCCATAAATGTGACCATTGTAACCAT
CAAAATTAAATAAAGATGGATTATGCGGTACATGAATGAATCCCATTTTATCGCACAGAAACTTAGCTACAGCAGCCGATCGGCTAATACCTGCCTC
ACAGTGTACGAATAGGTGTTGANCCTTACCAAGAGCTTCACAGAANGAAATAATACGTTGTGCATGNCGATGATCAAATAGATCATAAGAAGAATCA
ACATAATCCTCAATGTCATCAACATTGATACGTAAATAATTAAGATGTTTTGCTGAATAAAGTGGGACTCTACCTTTCTCCAGTAGACAGATCATAT
TTCTAGGGGAATAAAATGATTCAGCCACATGCAAAGGAATATAAGTAACTGTATTTACTGGCTTCATATTACACCTCGTTACAAAAAAATAAAAGGA
GCCCCGAAGGGCTCCAGTATANGTTAATCGAATACAAGACCACTACTAGTTGCTTGGTCATCCACATCTAGAGTAGACTGACGCTTACGCATATTAG
CTTTGGCTCGATTCATCATTTCACGACGTTCTTCTAATCGNTTACGAATATCTTCAANAGATAGNCNANTGATCACAAAATGCATTTGATCGAAATC
ATATTTCTCGGGATCAGCATAACCAGTGGTACGAGTTAAAACAGTGTTAATGGATACTTCGCGATCAGGGTCAGTGTATAGCGAAGCAATAGAAATT
GGGTCCAGAATAGCCTGGGCTTCTTGACGATCAAAACACACGTGTAATTGGACAGTCTGTACAGGTACATCATGGTGTTTATGGAAGTGTGCCCAGT
TAGTGATATCCATTAGATCAAGACTTTGGTGTTCTTGATTAAATAGAGTTACTAGTGCATNTAGTACTTCNAGAATGTTTTGGTTCACCATTGACTG
CGGTANACCTTCAACATTCTCATGATAGTTAATAATCATCGGAACTTTACTAACAGAGGAAACCCCTTCAAANGTCTTAAGGCTACCACTNCTATTN
CGAAGACTAATATCACTGTCGTAAGATCCAATGACCACACTTACAACTACTTCACCTTGTTGTTGTAGATGACTNACAAGNGAAGGACCAATNGTTG

Figure 8(D)

AACCAGAAGCACCACCCATTGANTANACNACNATGTTAGNATCCCCTGCTGGGAAATGATGGGCAATGGCAGGAATATGTGCAGAGATTAGTTCTGC
GGCTGCCTTACGATCTTTACCCATACCGATAGCACGTTTACGTGCNGTCTGGTCAGCTAGCTTAGTATCCGCTTCAATAATGATCGTATTATCGTCA
GTATTGTGTTTGTGTTTATTNTGTACACTGGTATCAATGTAGCAAACATCCTCATGATAACCATGGAATAGTTCACCAATACGGAAACCAGCACCAC
CACAAAAGTAAATTCGAGTTTTACTTTAGACATCATTACACCTCATTGTGATTAATATAATTCATATACCAACTTGTAAATGGTATCAGTGCTTAAA
AGTAACGATCTCTTCATGAGTTCGTTCTTGATGAACATTAATTCATTAACCACTTTACCAGTATCAGATTTAAATTCGATTACCATCTTATCTCGAC
ACATGTATGTTTGCCAAGTACCACCAGACTTAACACAATCAATAATCATGTTAAGTACATTCTTAACTTCAATCTTACTAACTTTATAACGATAAAC
GTTTAGAAGTTCAGTAAGCCATTTCGTTTTTGGGATTTTGGCATTTTTACGTTCTTTTGAAATATCAAAAGGAATTAGTGCAATGATCTCACCATCT
TTGTTGGTGAATTCAAATACCATTCCTTTTGAGTTAGCTAAAGGACGAATGTTNTAATTNCCTTTANCACTNCATACTTCTTCAGATAACTTAACTA
ACCTATCTAGTTGAACATCAGATGCATGAATGTTATCTTCTTTAAATGCTTTCTTTAGTTCATCATGAGTTAGTGGAGTACGTACTAGAGTGTAATC
TTTCTGTTCAGTCATTTTTCATTTTTNCNATTTTCNANTTCAAATTAAACGGTATTGGCTTTTATAGCCAATCCCTTATTACTAAAAGTAATAGATT
CTCGAACTAAGGATGGTTATACCCCTTCTCTAATAATAAGGAATATTATATGGGACCCCCCAAAGGGTCCCCCCACATAATATACTATTTATATAAT
TTCTTTTAGAAGAAAAGAGATAAATAAGAGAAATACAGTCTATTAAAGTAATGAATTTCTCAAAAATTAAATAGTACACCGCNCNNNNNTTNCGNCG
GANGGTCCTGCCGGACNANNGTCCGGATGTGCGNNANTAGNGGGTTTTTCAAAAATACNTGCATCGCGGTTGAATTGAGNGGTTGATTATAACGTNN
GATCTTAATNGTAAATAGAACTTCNTCAACATCTGNATGNCATCCTTCNAAACTAAAATATACTTCAGTCCGATCAATAAACTGATACATTTCTACA
GCTGGTTCAGCTGGATCTTTAAAGGCCANCTTATTAGCGAAATAATCAGTATNGGCTAGAATTAATTCTTTTACATTANTTGCATTCTTCTTATCAA
CAAGGAATTCAAACTCTTCAAGGTTATCTGTTTTGAAAATACCTTGATANGATGACGACTNGATTAGTTNATCACTGATATCATCAACATGAACNCC
TGGCATAAATTCAATGACTGGTAGAATAAGCTTGTTACCTCCTACGCCNTNAGCNATATGAATNCCAANCACATTACCATCACTAATGTATTCGTCA
TTACCGCAAATAACGGCACCAGCCGCTAGATATAAATTATCAACATATTTCAGATTATCGGCAATAATGCGAGATAGTACATATTCTCGCACCATGG
CATCATCTGGACTTGACTGCGGTTTAAAAGTATAGTGGGTGTTATGACTACTCATGGTCGCACATGTAACAAAAACTGAAATATCTACTGGATTAAA
TACCCAATGAACGGAGATATCCTCTAATTTATGTGGATGATGTAAACCATCTAGCTTAGATAGGGCTTGGAGTTGTTCTTCCCAGGTGATGTTAAAT
TGAGTCATTTTTCTAACCTCTTCATTTATTAAAAATAATACACTTATTTTACTTTAGCAGTTGATACTTCACATACATTAACTAATTGTTCAAATAA
CGGTTCATTATCTGGATCATTAACTAATTTGATGTATTAATAATAATACCAGAATACAGCATATCAGCTGCATCTCGATCACTTGTTTTAATTCTGG
TTACACCTTCCCACTTCCATCCATAGTAAATTAAATCAAATGATGAACCAATGTTAAAGGTTGATTGAATAAATTTGCATGTACCATTTTCTTTTAA
CCAATCAGGCCTATATGGTTCATTTTTATAAAATTCATGCATGAGTACTTTAAAATCAGTTTTAATGTTTTCATGAATAATGCAATCAATAGAATTA
AGAGCTTCATCAAGAGCTGATTTAGACTCAATAATGATTTCTAATACATTGGCAGATTTTAGTGTAATCATACCTAGTTCATCTGAGTGTGCTCTTC
CGATTTGAAATACATTGAGCTTACCAATTGGTAAGGTGGCTTTTAATGGCAGATTAGTATAGTGAGATACATCGCTTTTATAACTGTCTTCATATGA
CTCAATTAAATTAAGCCATGCTCTTTCAATACGTGTATTCTCAAAATGNTGTTCTTCTTCTAGTAGTCTAGAAATTAGATGATTAATGTATTGAACA
TTATGGCCAGTACCNGTAATTNAATTATATTTCGTATTACCGGTAATTCCCCATTTATTATTTTCTTTATTTATCCAACCGTAGATTACACTGTTTT
TAGGATATTTATTTTTAAAATTATCGTATATTTCTTTTAGATGTGGATTAGGGGTAAAACTAAAAGTAGTTGATTCAGTCATTATAGATACCTATTT
GAATATTGTTTATTATTGCAAATTAGTAATATAGATCTTAAACTTTTTTAACTCAGCATAAAGCCTCCCCTAGGGGAGGCNATATGTTCATTTATCT
ATTTCAGCGTTTGGATCATACCAAGGTAATAAACTTAGTAGTGCCGGTTGTTGTTTCTTCATATCCTCTAAGATTGTTGCTTCACTTGCACCTTCTA
ACATAGTGGTGAAAGTAATCATGTTCTTAGAGTTATATATCGGACGTAGACCATTACCAAAGAATTTNACNTGTTGAACCATTATTTTGAAATCAGG
GTTATCGACTACATCTGGATATAGATANCAGGTGGCGCACTGAAATAACGTTTAATTAACTCAATAGCCCAATACGTTGGTAAATCACCAAACTGT
GATTTCACTGTAGCTAGGTTTAATTGGAATGCTTTAGGTTCTTCAGGCGGCGGTTCCACCGGATCAATTGGATCAGTGGGTTCTTCAGGGCCAGTAG
GTTCAGTAGGCTCTTCAGGATCCTCTGGATCGCCTTCTGTTGGCTTTTCTTCAGATGTGCCACCATCAGGGTCACNTGAACCATCATCATCTTCAAC
GGGCTCCTCAGGCGTTTCTATAGGCTCCTTCGGATCTTCCTGATTCTCCGATAGATCGGGCTCTTCTGATTCCCCATCTCCATTTGCTTCAGTAGAA
GACGTGTCTTCTGATTCTTCATCTGTTGTCGAGTCAGTTGNGGCTGTGTTTTCTGAATCGGCAGTGGTATTTCATTTTCACTTGATTCAGTAGAAAC
AATTTCAGTAGGAGTGGTTTCAAGTTCATTGACACTATCCTCTGCATTAGTTACTTCATTAGGGATTTCACTAATTTCTGATAATGTTACTGGTGCA
CTTACTGCGCGAGCTTTTCGTTTAGCCATGGTTGTACCTTAGATAGAATAGTATTATGGTAAGTGACTAATTCAGGATCAGTTAAATTGATACTTTG
AATAGTCATATTCAGAATTACATAGGAGTCCATTGTTCTCCGGGTATATCCAGTTAATTCCATCTTGTTATATTTCTGTACATGATCTGGAACCCAA
TCACCAAAGATAACACCCAGTTTATGAAAACGATACACCAATCTGGATAATGCACGTTGGGTTTCAGTTGGGAATATATCGGGAACATTTTCGGGAA
CAGTACATTTATCACTAAATGGAGTAATAATAGGACCACGATGAATGGTGTAGCTAAGCTTAAAGATAACAGCACCAAGTTCGTCATTAATACGCCT
AAGTATACGATAACCATAATCGGTACGCTCAAGTTTATATACATTACTAGGATCAGCATCTGCTAACCTTCTAGCATGTCGTCTAGTGCACGTTTGA
TACCACGGTTATAGATGAGTTCACGTTCTATGTAATCTCTCTCAAAAGCGGCCTGAGGGCTTTCTTTCTCAAATTCCTTAGTTACTGACCAAGAAAT
TGTTTCACCAGTTAATTCATCAGTTAAAACATACAGATATGTCATAGAGTCAACGTATGAATACTGGATAGAGTANCGTGATAAATCACATGGCTTA
GCATTTAATCGTTCTTCTTTTAAATAGAAAAACATATCTTGTAAATGATTATAAGTTTGGCAGCCACCACCAAGATGATCAATATCAATAGACGTAT
CTGGCTTGACTGGAGCTTTGCAGCAACTCATTACACACCTCTACAATTATATTTGAGTTATTGTACTACAGATGATAAAGAGAAAATACATCATAAG
CCCTCTCCTTATGGAGAGGGNATTATATTTACATAGTGTTAAAACACGCATTAAATTTAGATAATGAGCAGCCAGTATAAATTAATGATTGCTCTAG
TTGTATGATGACATCGCCATTACTATCAAAATCAGCAGCAATAAAAGTAGATTCAGTTATCTTAAAAGTAGATGGCAGCATTTCTAAATAATTAAAT
ATTGCTTGATTATCGATGTCATGAGGATTTAAATCCATATGTTACCTATACATNGATAGTTATGGACCAAATATTAACAGGNCTGCATAAGACAATT
GTGATTAAATCTCCATGAGTTCTCTGATAATGGTTGAAACACATAACTTTGATTAACTTTAATTTTTTAGTTTCTTTATTTTGAATTTCTTTGATAA
GTGATTCAATAAGATCAGTAGTAATAAGTGAATGACCATCAATAAATGGTTTTATACTTACTAGCGAATCTTTGTTAAATAGAATTGCATCATCATA
TTCACATGTAGATGCGGTCTTGTATATGGATGCAACTTTATTAACTTTGTCATNAGTGACTATAGAAAAATTAAATTCANTCTTAGTTTTACTNAAC
GATGTTTCAAATAATTTATATTTATCAATAATAGTTTTATTATCAATAAATGATTTCATTCCAATATTTAAATCTATGTCCAGGGTATAAGANTTAT
GTATTAATCCAACTGATAGTTGAGTTTCATTACCACTATTGTTAAACTTAATATTATTAACTGAACATATCTGATTATTAATAAACGATAATAATAG
TTTAGAAATAGTTTTAATAACATTAACTTCATAATCATTATTAGTACAAGCAAGTGCAGTTGTCATGTATCGACTAACTTGACNAACATCTAGTTTC
TGATAGNNACTANCACTATCTANCCATGGGTCAATANTTAAAAAAATCCTTAGACTAGCTAGAATATCNGAAGATGTTTCAGAATAAATGAAAAACA
CATTATTATTAAGATCATCTTTTAGCCAACCACTAGTTCTAAGATTTTCTAGATCTTTTTCATTAGATACCGATTGACTTAATTGCTGAATTAAACT
AGGGTTAGCTAGGTTTAATAAACTAATCATTTTATAAACCATTTTATTATCCTCTAATTTATGTAATTACATGGAATAAATAACATAAGTACTTTTA
TGACTTATGATTTGATTCTCCAGGAGGTTTTCCCAATGGCAACTATTAAAGAAGTCCTTGATAGAAATTTTAAGGATGTTCAATTTGATCGCGATTT
ATGTAAAAGAATTATTGACTTTACTATCAGTTTTATGAATAGGAATGCTGATCACTCTGCTTTCTTTGGTGGTGTATTACTAGGTGTACAACAAGTT
AAATTCTTCGATACGGATCGTGAGATTTGGTATGATGATGTTTTACGAATTGATGAAGCGCTGTTAGTCCAAGATTTTAAGTCAGTTGAATTCATTG
ACCCTAACCATCGTGTAATGTCAGATGTATTCAATCATCTTCCTGCCTATATTTGTTCTAGGCTTTTAAAAACAACTAATGTTCCTTTGAATATTAG
ACATGAAGCAATGGTTAGTTGTTTCATGGTGTTGCATTTTAAATATCTAACATCTTTACTTGTACCACGCTTTAAATATCCTGCACGTAAAGAAGTA
GCCGAAGCTGCATTCGCCGCACTCAATTATCGATTTGACATTAAGACAATTGGGTCATGGGAGAAACTATTTAGGCAACGGGCTGAAGGTATCATTG
CACCTGATTCTATTTATGCACCTTTCTTAACTGGTAAAACACAAGAACTGGATTATTGGTCTGGTCGTGTGGTATCTGATACTCAAACACGTCTACG
TGAATTAATCAACAAGTACTATGATGTTTATATCAGAACACTGCAATCAGGTGGTAAATTAGTTATTTCATCGGATATGGCTGTTAATTCTGATGGT
GAGCAGATTCTACGCGATAAGTCTACTGGGTATCGCTCATATCTTACTTATATCCATCAAGTTGCGCAACAAGAACAAAATTTCATTAGACCTGAGT
TAGTCGGTATTATTGAAAAGATAATGCCCACAATGCCACCAGAAATGTTCATGGCGACACTTAGACACCTTTCCCGTAACATCGGTCAACCTAGGGC
ACAAAAGCTTGAGAAACTCGTAGATGAGTGCTTATTGTATGCTTTCGATTATATGCAATCACTCCGTACAATGGTTGCTAGAAATAATGATCTACAA
ACATTGCTTGTAAAAATACGAGCAAAGATAATGGCATCTAAAACAGAAAATGCTCAAGTTATTTCATGCGTGAAGAAGGTGAGAAGTTAGTTAGGG

Figure 8(E)

ATGCGACTAATTCTAGGGTACCTGCATATATCGCAGCAACTAGGACTGGGTTGATGTTGTATTTAATTCTACGTGCTATGACTAAGAATTACTATAC
AAAACAAAATAAACATAATGCCCTCCCGCAATGGGAGGGCTTATGCTGTTAAGTAACATTAGCTAGATTGATCATTACATAAATTTTTCAGAGCATC
GTAAATAGCCACATAAGTAAAATAGTTAAACTATCTTTAATTTCCTTACGTGGGGTGCCACTGAATCCACCCCATGATACATTTGTATTACTAACNC
ATACAGTGCTAATAGCTGGCTCATGATAGCCACCATCTACTTTACGCTTTGCATAAACCTTAGCCGTAATTTCTCCACGTAACTTTTTGAAGAAAAC
TAGAGCACCCGGAACGACTATACGTTTATTACCAATCTTCGTAATAAATTCTTTACGATTAGTAAAGTGCTCTTTTAATAAATCATTAATAATTTTA
GTTAAACTATCAATTTCATTCTTCATCGACACGTTGTTAGTTCCTTACAAATAAACTTGATAACGTGATCACTTACAAATTTCAATGGACCAGAACA
ATTAGATTTCTCAATAGCGGTTTCAGTGTATGAAATTATTTGATTTCCACTTAAGGATAATGAATCAAATAATTCATAAGAGTTATTATTTTATTCT
TAAAGGATACTGCATATTGACTATTTCACTATTGATGCAAAATAGGTTAATAGCTGGGATAGATACAGAGTTATCTGAAGTATGGCTATTTTCCGTA
ATATTCCAATTACTGTATACAGTGAAAATATTTGCAGCTAGTAAAAGGTTGGCATTAACCGTTTCTAAACTAACATACTCCACAGAAGTACCTTTAT
GCCAATATAGTTCAATTGGATTAACCCAAGTATACCCAATGGTTTTATAGAAGGCATGCATTACATATTCTCGCCAACGTGTGGGTTTCTTATTATC
AGTTAAAACACACGTAATATTGCCTGACGGATAAATGTGGTGGATGCTACATGCATTAATTTCATCTCTAACATTAGTTGTTTCAGTAATATTAGAA
TGATCCTGTTTGAATAGCCATTTTAAATGACTATTAGTTGTGTCATCACCTTCCCCATTTGCAATGTCATTTTCTAACCACTTTTCAAATGTAGCTT
GTCTATCAGGTGTTGGCATTCCCCAATAGGTAGCTAAATGAAACGATAATAGTATCGAATAATATCATCATCGTTAAGAATATTTTATCCAGTTTCC
AGTGATGTTGATACTCGTATACTTCGCTTGGAATATTATTTACTTGATACCATGTATTAATTAATACTTGAATTGTTAATTGCCGAATACTCTCACT
TGTTAGAGTGTAATATTCCCTGCTATGCGGCTCTTCAATTGTCACTTCTTGATCAGTATAACCAATGTATTTAGGTTTACCATCGATGAGTGCAAAA
TTAACATTCCATGATGTATCATTACTAAAAGTGATATTAATAAAACCTTGTTCAAAGCTAGGCTTCACTACGAAACTGACATCATCCTTCTGATATG
TCATTTGCGTTAGAATACCAAAATTAATTTTAGATGTAAATTCTTTATCGAAGTTATGTTTATAAAGTAATCCTAGTAAACAATCAATTTTTATTAAT
AGTGTGGTTTTCTAATAATAAATCAGTATTTGTAAGTTCATTAATTTTCATTTTAACCTCTCTAAAATTTACAATCTAGTTTTACTTATTGAATAAG
CAAACATGTAATATATATCTTAATTATTTTTAGCATAGTTTTTAACAACATAAAGCCTCCCCGAAGGGAGGCGATATGCTTTAGCTTTTTGGTTAGT
ACCGACAGTCTGCTCATTCTTTTCAGTTTGAGCATTTCGCCGAAGTTGACTAACCAGACCATTGCCAGCCGCAACTACATCGGGAGAAAAGAATGCA
TTGATATCAAAGTTCTGATCTTGGTTGCGAGTCTTCCCAGGTGGGACCATCGGATATACTTTTGCCATTAGCTTAATCCTACACCGTCGTAAGTTAC
CCGATTACCAACTGCACGTTCAATCTGGTCTTGAATACCATTACGTGCACGTAGTACGTCAGCAGATAAACCACCCCAGTCTAATTTCTGGTTATTG
GGGTTCATACCGCGAATGTTTAGTTTACGGAACATTTGACGAGCGTATTCTTGTACACCTTCAGAAACATCAGTCAGTGCAGAGAACTCAACGTTTA
GATCAAGGTTCTGACCAATCTGTGATGCATCTTTACGGTTTTCCCAAGGACCAGTAGTTAATGGGAACATGTTGGTGCAAAGATAAGCNTTAACGCA
ATCCTGGAAGGTAGGATCNGGTTCTACGAATAGAACAGTCATACCGTAGAAGGTAGCGTCGTATTTCTCAACCGGTACAATGCCATCTGATACAATA
CGCGGTACTTTGGTATTCTCATCTGCAATACCATAGTTGATCCACCATTGTAAGAAACGTTGGATAGCGCGGTTTTGTAATTCCCAGCAACCAAAGT
TTGGGTTAGACCGGGCACGGGTTACGTTAGTAGCCGTTTGGATAACTTCACCAGAACCACCCCAGGGTGCTTCAGCGTTATCTACAGTAAGCGTACG
TTGTAAACCATCGATGGTACGAGTATGCGTTTCAACGAAAGCCTTAAGACATGCAACTAACCAGTTAGTATTACTAGCATACTTAAAGAATCGTGGA
GCATCTAGTAGGAACGGCACTAAGTTACGTGCCACATATGGCGTGTTAGTAGCCAGGTTAGCTAAGTCAGGCCGAAATACGTTAGTACCAGCCTGAG
CAAGGTTTACAGTGTTACGGGCACCACCAGCACCATAACCAGTCTCGGGTGCCATCGGATCATTATAGCGAGCCATTTAACTTTTCCTCATTCTGAA
AGCCACCCACTCATTGCTGAGCAGGTGGGGTTTCAATACGAACAGTTTCCAGATTGAAGTTCAACGTGGTCCGCGGGTTATTAGCCTCAACAGTTAC
GTTGCAAGTCCAGCTGGTGCCGTTATTTGCGTCAATCGGAGTGATCTCTGTACGCGGGATAATGTTGACACGAGTACCGAACATATCACGTACTAGA
TCGAGAATATACTCGTCACAACGCTCAACTAATTGTTCAGGTGTTAGTGTAGCATTACCGCTAAATTGAGCGTGTACTTTATGGATCAGTCGGATTA
ATACACAGCAAATATTAACAGTAATCGGTGATAGAAGTACAGATGTATCATCTAGCATTACTGAACGTAGGCACGGATAATAGGAGCTACGATGGTC
ATATGACTGACTCCAAGTAGCACCATTCGCCCAAGCTTGTGCCCGTACACGATCATCAAAGAATTTAACATTTAGATCTTTAACAAAAGTAACACGG
TTATTAGGACTTACATCCATTTCCATACCTGGAACTAGATTACCAGTTCCAGCACCTGCATAGCGTGCCCATGACATAGCTACGTCTAAAAGCTGCG
GTACATATTTACGATAGGTACCATCCATTAGTTTGCCAGATTGCATTACAATCATAGCGCGACAAACACCAGTTCCGTATAGAGTGGATTCTGGGAA
AGCTTTTAGGCGAGTGATAATCTGTTGAACACGACTTAGCTCAGTAGCTTCATCAGGTAGACGACTATCAGTTTCTACGAATGTAGTGAAGAAATAT
TGTAGATCACGCCGCGCACTTAGTACGCGCATTGCCCGATATTTTGATTCCATCGGAAGGCCAGTGTCATAAAGAACACCGAACTGATATTCTGCAA
TGTTATTATAGCGATCATTTAATTTGCCAAAGTTAATATTTTCAATATCAACTAATTTGGCATATTCTTCTAGATCAGTTGTACCGTCAGTACCACC
ACTAGCATAGATGTTACCATCTTTACCTAACGTAATGCCGCCATCTAGTGGACCGAGTACNTGAATACCCTGGTAAGGATCACCATCAACAGCTAAG
AAGGTTAGGAAGTCAATTTCACCAGGTGCAGTAGTATGCGCAGCAGCGGCTGGGTTAACTCGCATCTCAGTGTCATAAATCATCTGACGAACAAGAT
CAATGTTCTCATGATAGACGTAGAACTGAGAGAACGGTGAATAAAGTGGACTTAGGCCAGAGACTACACCATCATCTGAGTAAGAATCAACTAATAC
ATCACCAACATAAAGGTCAGCGTTATACATATCGCTGTAAACACCTTTATCAAATGTAATGTTTAGATAATCTTGCTGGTCAGCAGTTTTGACAATA
ACTGGACTAGTGCCTACTTCAGGCTTCTCAATTAACTGAATACGGAATTGACGAGTTTTAAACTTCGCCATAGCTGCTTCATCGAACTCTTCGATAT
CAGCAGTTGTAGTACTCCATACACGCATACCGTTAGAATCACCTAATTTACCAAAGAAGGAAACCGGTGCTTCAAATAACGGATATACTAGTGATTG
AGATCCATCTTTATCTGATACTAAAGTACCTGGTAGTACACGTTGTGTACCTACTTCAGAGGTATTATCTTCAATAAGAATAATACGTGCCTTTAGA
CCATCAACTTTATCAGCAGTCGGGACTGGTGCATTACCAATGTCACGAACACTGTTTGGATAGTTGAAACCACTAAGACGACGAATCGTAAGTGGGA
TTTCATCTTCCACAATTTCAATAGCAACAATTAACCGAGATGGATTAGCTGCATCTTCAGGACGTAGACGTTTAACATAAAACCATTACCACGGCCA
AGAAGGTTAAGTGCTAATAGTGATTGTGTATTGAAAAACTTACTACGTGGATCAAGCGATGCTTGACCATAGATGGATGCAAAACCATCATCAGAAT
CACCGACATAAGTGGTTTCAGTCGGTCCTGTCTCAGTGAAGAGACGTAATAGCGGACAGTGTTGTGCGAACGTGATGTCCGGACGGATCAGGGGCCG
GCGGCTACGATCCCGGATACCATTAAACACAACCCTAGGGACAGCGTTGTAATATGCCATCTTTTTGATTCTCCCAAGTTGGAGCTTTGAACTCGAT
GTTATGAGTGTTAACTAACAGTCAATCATAGATATTAATCATAGTTGACCATACTAGTTATTTTTTACTATCCATTTAAGGAGTAGCGGTAATGTTT
TTGCTACCGTATGAAACTACAGTTTGTAAAACTCTATACAATCCCACCGGCGGTGGAAAATTATATCCTAAACAATATGTTGATCAAATTGAAAATG
CGATCAAGAAAGCCAATGTGTATCTACCCATTCCACCTGTTGATGCACGTAATGGTGAAACGCTAGAGCATAGTGGACAGATTACCCCAGTTGATGA
TTTTGAGGATATTAAGAAATTTACTCAAATTGTCAATATCGGTGATCGTGATAATCCTAAGCTAGTNGTTGATGCTCGTCTATATAAAAGATTGAA
CAGCGTACTGGTATTCCTAGGATTATTCAGCAGAATGAGTGGCAATTCCAATATATTCGGATGGCACTTAATATCAAACTATTACGTGAAGGCCCGG
ACTTCCTCCATCGCTTAGGTGATATCCCAGTTAAAGTTTTCTATAATTGGATCTCAGGCATCCTAACACAAAAATACAGCCTACCACCTGAATCAAC
CCAAGCTATTTGGGTAATCTGTGCTGTTTATTACTTTGCTATGCAAGATGATGNTCTAACAGAACCAGNTCAGGAACGNGATCGGTTAATACCAATT
ATTTCCCGTCTTACATATATTCCAGCTGGTTTTATTGCNGATGTTATTGATACATTAGGTCCACTTCATAATGCCGGTGATCTAGCTTATGAGATTT
CAACTAANGGNCGTTCGATCAGGATGGGTAAACTAAAATTCAGTGATCTACAATTATTAGTATCACCGAGTTGGTTTGGTACCGCTTCCCGTGAAAA
CGTAGGTGTGGCACTAGAACACATGCCAACTTACATCACACTGATCTACATGGCATTAGCTGATCGCTCATACCGTAAAACAGTTTTAAGTCAGAAA
GTTGAAATGATTTCACGTTCTGATGATGCAAGTCGTTTTATTAATCTAGTGAATGAAGCTGTAAGTAGCCAATTCGTTAAGTAAATATAGGGGTGAA
TCAATGAACGCATATCTATTGCGNCATGCGATTGATAACGTTTGGTGTAACCCAGCCCAGGACCGACAGTTTGTTTATGAACTGAAACAGCTNACCC
CACGCTACGGCGTGAGGGTAAACTGGGTGGTTGATTACACCCGGTATAAGCTACCAGTCCAAAGTACACGTGATTATTGGCATCTTTATCAAATTGG
TAAAATGATTCCTAAACACCTGGGCTTGCCTAAGGTTTACAATAAGTGGATGAGCCTAAATGAGTTGGCTCAAAACCATTTAAATTTAGCAGACGTT
TATGTAAATAGTGGTATTAATTATTCACGTAATGATACATACGTTTTAATAACCAGTTCGCAAAATCTTTTAATTGCTGTTAAGATAGATCCATTAT
TCCCTGATCTCGATGAAAATCAACCCTATCTTCATGTTTATAACAATGCTTACTTTCAATCAAATAGATCGGATGTAGCTGGACATAGATGGTTAGT
TTCTGAATCGTATCGAGTTAAAACAATATCTGAATTAACTCAATTTCAGATTAAGATAATGGATACCATAGCATCTAAAGGTGGTGTTCCTAAATAC
TTTGTAAATGGTAGATATGTTAATGAGATATCTCCTGTTACAGCAACAGTCGGTGATGTTTGTGATTTCATTCTAGATCCATCCATTAAAAGGATGG
TAGATTTTGATCTACGTACATTACCTGTTTTCATGTCAGAAATAGATAGTGAAAGAAATATATTTTACACTACACTGATAAGACTGTGCAAACAATT

Figure 8(F)

GAGTTCTTTGATGATGTTGAAGCATATATCTATCAGCCATTAGGTAATAATCGTTATACTGGTGTTAATTACCATCATAACGAGAGCCGTTGGATGC
GGATGCTTACACATAAAGATTATTCTATACCAACTGCACGAATTGATCAGTTTAAAGCACTTCATCCAGAAGATCCTCGACGTGGTGCTGATCCTAC
TCGTTGGCCAAGTCAAAACTGGAAAGCATTAGATAATCTAGTATTTAGAATCTACATACATCATTCTGGTTATGATCGCCCATTAGTTGCTGATTCA
CATCGTATTCAAATTCTGTATCGTTTAAAATCAGAAGATATCATAAGGGCTATGACTGGTGCAGATTCTGGTAATCCTTTATGGCGAGCTGAAAATC
TAGAGCAATCACCATATTGCTGGTTCATGTCAGCACCATCTAGTTTCGTATACCCATTAACATTCAATCTACCTGAAGAAACATCGCCTAGTAAGGT
AGAAGCGCAGAATATGGCTGGTGATGTTTTTGGTTATTATGAAGCAGCTAATATTCAAGGTTATAATCCAGCTTGGGTTTATAATGATGCTGGTCTA
AAGACCGCTGATTTACGATACAACTACTGGCTAGATGCAACTGTATTTGAGTATGATGAGAAAGGTATCTTATTAGGTTATAATTATCATACAGCAG
GTCGCAAATATTTCCCTAAAGATAGTCGTTGTGCATATGTTGAATGCATTAATGGTAAAGGAAGTGTAGATCTACATGAAGCATATGGGAATGATCC
CGTGCCTTTACGTGATGGTGACAACTGGCGAGTTTATGTTAGTCCTGTTTGGGCTGGCGTACCAACTGGCGAATGGCAAGATATAACAGACCATCCA
GATCGAAACAACTGGGGTTTTTATGATGATACCACTGATGATAAACGTTGGGTTTGGATAGCTAAGTCAAATGAGTGGTATGGCCTAGTAAGAACCG
ATGAGTACTTCTATCTAAAAGAATTAAAGTTTAATAAAACTGATGGTATCATTAAATGGAGTATACGTAATACTGAAACTCATAATGGTGTAAAAGT
CGATAAATTGATGGAGATACCATTTGGTCAGTATGATGTGTTTGTAAATGGTCGGCCTATCATTGAAGGTCTTGATTACACGCGTGAATGGCCTCAA
ACTGTATTATGTAATCTGGAATATTTAAATGCAGATCCAAATGCAGTTAATACGATTCTTCTACGTGGAACAGGTTTCCCAACACCAGATTTAAAAC
CATACGAACCTGGCGAGATTGGTTTCATTGAGTATGGCGTATTGTCTAATGATGGTATTTATAAAGTACATTCAAATAAACAATCACGCATAATCAT
TGATGGTCATTATCGTGACCCTGCTGATCTTGAATTCCAAGAAGATCAAGGCACTACTGTTATCACTGATGAACGCAATGGTGCACCATTCCAAATA
CAAACACCACAGGCNCGCTTCCGNGATGTTTATAATGATGATTACCAAGCTAGGATTAAGGATGATGCACGGGATAAACAAGTCACTGATTTTATGA
CTGAATATTTCCCAATGAAACCTCAACCTAATCCGGACAAGATCGATTATAGATACCAGGTGCTTTCAGCGTTTTCATGTAAGATCATTCATGATAT
CGTAAAAGAATATATCAAACCNCCATATCAAAATGGACGGTATAGTGACGATGATATTGTTAAGCAGCTAAAAGATTACGAGTGGTTAGCAGCTTAT
GACATTATCAATAAAGGCTACAACAAAAATAAAGTTGTAGTTTATCCACATTGGTATACTGAACCTGTAGAACTAGATATTTCCAATGGGAATATTT
AAATCGTATTCTATCGATATATCTACGTGAAGTACCGCCACTATCCTTGTTCGTTAAGATTAAAAGGAATCAACCATGACAACGTCATATGAAAGTA
GCCAGTACCAACCACCACAGCATAAAAACCATTTCTGGTTTAGAGGTGATATTGTCTCATATGCTGGTGANACTGGNAAAGCAATCCCTGCTAAAGG
AGATTTAGTATTTGACGCAGCACAAGGTTGGTTTATTGTTCGTGAAGTTGATGAAACAACTGGGGTATCTATCTTAGATCCATGGTACATGCCCCAA
AAACCAGGCAATGAAAATGAACAAAACCTACTAGTTGCTGTAGGTCCAGGATATAGCTCAGAATCTTATCGGTTATTCCTAGATCAGTCTGTAACAC
CATTTAATATTTGCCCAGACCGGCGATTACATTTTTATGGATCAATGGTGCATGGCTATAAAGTTTTCCTAGGTTCAGATATATCAGAAATACATGG
TAAAGTGATTTCCCTGTTCTATGATAATGCTGGTAATTATCTAGGGGCCAACTATACCAGTTGAATCAGTACCCGATCCATTGACTCAACAGAATGTT
GTTAAAGCGTTAATGAATGGTAGGACTGCTGAGAAAATGCAAAATGGTGAACGTGTAACTCTAGTAGCTTATGATGACGTGGGTGGGCCTGTTTCGA
TTGCTCAACTCGTTGTAATGAATACTGAAGTTATAGCNCAAGAGGATACCTCNAAGAAATATGTAGGTGGTATCACTATTGAATCACCATTCATCTC
NCCAGCTGATCCNAAAGTTATTGAGTTCCCATTAAACGTACCAGTTGAATCATTACCGATGATGGGTGCTGTTCATTACCGTGATGGTAAGAAGCAT
GTGATGAATATTGATGGTACGGCAATGGCAATTTATGGTTTACGTAACTATATTGCCACTGAGGAAGGACAAGAGTTTAAATTAACTCTATCTTACC
AATTAGCACAAGATGAGTTATCATACTTATCGACTCCTTCGGCTAACCGTCGTATTCAGGAGACATATACAGCGCGTACCACGCCTGTACAGGGTGC
TTACAGTTGTCGTATGTTTGTTTATCCNGCTTGGGTTAATGAGGCAGTNGGTTACAGATTAGAATTCTGGTTAGCCAATATTGATCGTCAACAAATT
TGGAATATTACCCCATATGTTGAATTAGGTGCAAACTCAGCACCCTTTAACCCACGTGGTTATGGTACTATCCAAACACTAACATATGCGGTTAACC
TAAACCAAGTTGATGGACGATTCCTACCAGTTCGATTTGCATCTACTTTCCAAGTAGCACTATTGAGCGCTGGTAATAATCGGAATGCTAACTGGGA
NATCTATTCACGCCCTGANCAAGGTGAAGCATATGGTCGTGATCTTAAAGCCGATATNGAATTTATCAATGGTAATCTTTGGGATCTCCGGTTAGCT
AATGGNGCACAGTCACAAGCTGCCTGGCTTAAGAAAATGTACTTTGCTGCTGAGCCATTAACTGGTCCAATGGAAGCTACTCCNCCNACACCTACGC
ATTTCCGGGTGCGTACAGTGCATAACGAGTATGAGTATACGGTAAGTCAATGGAATACTGCNTTNCGNATTAATGCTCAAGATATGGCCGATGGTGC
TTTACTACAANTCACCTGGATTCGTCGTGAGTATGATACNGACCTACAGTTAGCCATTACCGCATTACCTTGTTTACAACGTTAAATATANNGCCCC
CTAGGNNNNNCCTAGGGGGCTTTATAACGTCTTTTAACACATTATCCATATGAGACTATACTTTACAATTGCCGTTCAATACGGCTTTATTATGGCA
CATTAAAATAAGTACCTTAAAGGGCAGTGTATGGACGTTATACTTTTCAATAGTGATTGGGATAAATACTACAGCGCTAGTGTTGATCTTACTACTA
AAAATAAATCNTTTATAAAGTTAGCNTTNACTTATAAAAAGATGGGTATTAAAAATTACAAATTTATACTAGCTATATTGGACCAAGGTTTAATTGG
GGTGGATCCATATGACCCTAATCTTAGCGAAGAAATGAAGTTNCGTATTAACATGGAATGCAAATATAATCCTTGGTATTTTTTTAGGGAAGTGGCA
AGAATCCCCCCTAACTCGGGTAATAANCCAATTCCATTCCAAGCTAACCGTGGTAATATTGCTTTATTCTGGTGTTATTTCAATCACGTAGATTTTG
GTTTATTACAGCCTCGTCAGACAGGTAAGTCCGTATCAACTGACGTGCTCAATACAGGCATGATGTATATCTGGGGNGAGAACACTAAGATTAANCT
TATTACTAAAGATAACAAACTACGNAATGCTAACATCGAGCGTCTAAAAGTAATGCGTGATTTGTTACCAGAGTATATCCACTATACNGATCCATTA
GATGCGGATAACTCCGAATTGATGACATGTATTAGATTAGGTAATAGGTATNTAACAGCTGTTGGTCGAAATGATGTTAACGCAGCTGATAAATTAG
GTCGTGGTCTTACTGTACCAAATATGCACTTTGACGAACTTGCCTATATTAACTTAATTGGTGTTTCACTACCTGTTGCACTTGCNTCAGGTTCAGC
AGCTCGTGATGAAGCTCGCCGTGAGAACCAGCCTTATGGTAACATCTATACAACTACAGCTGGTAACATCACTACCCGTGATGGTGAATTTGCATAT
CACTTCTTAACAGGTGGNTGCCCATGGTCAGAGGAATTCTTTGATCTACCAGATCAGAAAACTCTACATCGTGTTGTAGAAAAAGGCACTACTGGAA
AGAAACCTCTAGTTTATGGTGCATTTAACCACCGTCAATTAGGACGTACCGATGAGTGGTTATATAACACACTTCGTGAATCAGGTTCATTCGGTGA
AATTGCCGATAGGGACTTCTTCAATATCTGGACAGTTGGTGGTGAAGGTTCACCCTTATCATCAGATGAGAAAGATAAACTTAAAAACAATATGCGT
GAGCCAAGCTGGACAGAAATCACNGATGATGGTTANACACTTCGTTGGTATATACCAAAAGANGAAGTAGCCTCACGGATGATGAAGGGTAGGTTCG
TTATGGGTACCGACCCATCTGAACTTCTTGGTGAAGATAATGACGCCACTGGCACAGTTGTAGTTGACGTAGAAACACATGAGGTTATGTGTGTTGG
NAGATACAATGAATCATCAGTNCCATCAATGGGTAATTTCTTTGCAACAATGCTATTNANATATCCTAATATTCTTTGGATACCAGAACGTAAATCA
ATAGGTATATCGTTAATTGACCATGTTATCTTGATTCTNCATACTAAAGGANTAGATCCATTCCGGCGTATCTTTAACAGAATTGTCAATGAATCAT
CAGAAAGAGAAAATGATTTCAGAGACATTCAAACTCCGNTATCAGCAAGACAACCATCGTTNTATGATAGGTTTAAACGTTATTTTGGCTATGCAAC
GTCAGGTACTGGCGAGTATTCTCGTGATAATCTATTTAAGGTGGCATTACCATCAGCAATGCATTATGGGGTAAGGACCATCTATGATAAACCACTT
AGCACGGAGTTATTAGCACTTACTATCCGTAATGGTAGAATTGACCATGCTAAGGGGAACCATGANGACTTAGTGGTATCATTATTATTAGCCCANT
GGTTATTAATACAAGGTAAGAATTTATCTTATTATGGTATCAATGTTCCCATCTTAGGTAAATCAAAATTACGTGATAAAGAACCAAGNCAACTTGA
AAAATATCATGAAGAGAAAGAACAGCAAGGTCGNAAAGAATTTGAAGAGATAATTGANCAGCTTCGCGGTGAAAAGAACCCGATGATTGCAGCTAAA
TTAGAAATGCGNTTGAAACAATTGTCTAAACGTGTTAATATTGATGATANCAGTGGTGTAGGTATTGATGCCATGTTAAATCAAGCTCGTGCAGAGC
GTACACGTAGAGTGCGTATTAACAGATATTCTAGAAATAGTTGGTATTAAACAAAAAAAATAATAATACGTTACCCTCTTCGCAATGAAGAGGGTAT
TTGAAGTTAAGNAACTCTAGCGAACAAAAGATTACTGGAGTTAGAATTAATATGATAGTTAGACGATCCGTCAATCCATTTAGCATCGGAAATCTTG
TTTACAAGCTGACCATTGCCAATGTAACCTAGGAAAGTTTTATTATCATATACAGCAATTTTGATTAGCTCATTTCGTCCGTAGACTAGTGGCTTAC
CATTGAATGCTGTTACTTCTAAACCAGACATGTATCCATAAATTGGATCAGGTCTGGAACTTGTTTCAAAGACTTTCATTCGAAGTCTCATCTGCAA
GAAAGCCCATTTTGGGCAAAAAATGTCAAGCTTAAACTTGACGACATATAGCCCTCCTGGTGCGACAGGAGGGCTAATCTTTTCAGAACGTACGGTG
TTGTTATAATACTGCTAGCGAAAATACCCATGATAGGTAAGTAGCTAATCCGCAGTTCTCTTGGATGATACCTACTGACAGTGTAGTTGCAAATGTG
CTGTTTGGAACCCCACTGGTTTAGCGGCCAGTGGGAATTCCTTTTATGCCGCTTTTTCTTTCTTTACTGGATATTTCTTATATTTACAAACCCACGT
TCTTACGCTGGTAGGTATCTTCCTTCTTATTATATTCGTAGTTCTCGATGAGGCACTTGTTGCTGAACTCGACCATCGAACACATCTTGTCCATGAT
GACTTCAGATATTTACCATGTTCATAAATTCGGCGTAGTTGTAGCCGGTATTCATGTCGAGATAGTCTTGTTCGACCATATCGTCATTCAGGTACTT
GACGTAAGCCTCGGCGTGAGCAGTGGCTACCGACTTGGTGAAGAAGTAACGAGCGTGCTGACGGTTCTGTTCGACTGACGCAGATTAGTAGTGGCC
TGACCGCCGAAACCATTGACCTCCATTACCCCGTAAACAGTACGATCATCCAGAGTAGTGATCTGTGCAATCACTACACGAGAAGCATTTTCCGAAT

Figure 8(G)

GGTCGATGAACGTCATACTGTAAATCTCGATTTCTTTGAAGTCTTCCATTAGAATTTCCTGTTAAAAAAATGAATAGACAACCCCTACCTTCGGGTA
GGGGCTTTATGCCGTCAACCGACAATAAGGTCCCGAATCGTTACGATCTAGGTATCAGATGCAGGTTTAGTCAAACGAGTTACACGAATATAAACCA
TGTAGTCACTCAGAGATAGAACTTTTTCACTTATACATCTTCCAGCGTCATGATTACGACATGATAAGGACTATCAGCATTGTGACCCATGCACGTC
TCGCATTTGAAGATCCGCCACATGCCATACGAAGGCAGCTCGCGGTTTTTCACATAAACGTAGTCGTGCGCTGCCACGAGGTATTTTTGTTGAATCG
AGAATTCACAAGTGATGTAACCTTTTTCACGGATGAATTCTTGAGTCATCTGATCAAAAGTCTGTTTGAGTTCATCAGTAAGAGCGACTTGGGTTTC
GAACATTGAAATATTCCTTTTGATATATTAAATAGTTTTGATTATTTCGGAGTTATTGAATATTTAGGTTACCATCTGCTCTATATAGACTCGGCTG
ATTTCATTTAAGTAAGCGAGTGCCAATAGAATACCAGCCCAAATAACAATTTTTCGAGTAGTCTGTTTTTCTATTACACCTGGGTGTGATTCACGAA
TACTACGGTGACAAAATACATAAAACAGACACAGACTCATTGTAACAAAGATAATGGTAAACCATCCTAGATAGATCATTTTCTTCACCTATTTTTA
TAAATAGAGTTTATAGTTTAGTCAGGCGGATGATTTCTTCTAAAGCTGCATCAACTTGATAATACGGCCATGAATCAACACGAGGTTCGTTATCAAA
GTATGTCCAAAGTTGAATACCTTGGAGTTTATTGTAGAATACATTGATTCTGATTCCTTCATGGCCAACAAGACCTTCAATGTAAGCTGCACCATGC
ACATACGTAACATGTAGTGCGTACTCGCTATCTTCACCAGCGTATTGCATAGGTCTGGAGTAGATGAAGGAATAAGGATTAAATGGATCAGCCTGAG
TGATATGTTCGAAGAATTCTTTCAAACTAGATTTTTTCATATTGGACATTATATTTTCCTCATGATTTATTAAGTCTATCTTCTAGGAGGTAGACTT
AATACTATTCGATGTTATTTTAAGACGCCTGCCTTGTAACCTTTAACAACAGTTCTAGCTTCTAATGCACTGATTTCGCCAATGTGTTTACGCAGTG
CTTTAATAGCGTTGATGGTAGGTTCATTATCCGCGATATGTCGCCAGTTTCCCTTACCCTTAATGAGTTCAACATCCTGGACATATAGACCATCTTT
AACTAGATCCATTGTTTCTACCAACTTTTCGACTTCTTTAGTTAGATGCGTATGAAGACTGGCGAGGGACATGTCAGTCATTTGATGCACATCATAG
AGAAATCCCTATTATCAGAAGACGATAAAATTTCTTTGGTGAGTTTATTTACAGTGTCAATGTTTGCTGCAATTGAAACTAGCAGTGCAGCATATTT
CTCTGCATTATAATTCATTAATACGTATTCCTATTTAAAATTGGATTTAGTGTAATGCGGTAATACTGCGAATATCTAATTCATGTAAATCATATTT
CTTTAGGAACTCATTCACCGCTTGCTGAATGGTGTACCCACTCGGAGATTCCCACTGAGTACCATTAAAAGCAATAATACGATAACCTACCATTTTT
TATTCCTCTAATCACAAAATAAATACCCTCCCGAAGGAGGGTATTTATATCGTTACCAATTGATTACAGCGACAAACTCAAATACCCGACACAATTC
TTTATCACGATGGGCATGATGAAAAGATTTACCTTCAATACCGCAATACGGATAAAACAATTTTCGGTGTTCCGTGTCGCCGAACCAGAAGGTGGTG
TTATTGGAATCAACCACACCATGGATAGCCACATCACGAATGTACTGAAATACATGAACTGCCTTATCAGTGATCACTCGAAGTTCTACACCGTGTT
CCTTCATCATAGCCAGGATGTCTTCCTTGGTGTAATCTGCTTGTTCAGCATTGGTCATGATCTTGTGAGTCAGAGAACGCTTTTCCTTGTCACCGAA
ACAGATACAGACCAATTGCACCAACTGACCTTCTACCTTGAGACCACTGGTCGGTTTTAGTAGAACGAACTCATCATATTTGTAATCATTGGTGACA
ATCAGTGCCGACTTATTGCGAGTGACAATGCCTAGGTTATACGACATAATTAATCTTCCTCATTTTAGAATATGTTGAACCTTGTGGATGTCTTCCA
GGCTATGACCAAGACCAGTGGCTTTGTAAGAATGTTCCTGATCAACACGCTTGTGATATGCAAGCAGTGCATCTACTGGATGTTCAGCGAAGAAGTA
TTCAGTGTTGTTGCAGTCCCAAGCGAACTCCCATTCACCATCACGAATCTCTATTTTGTTAGCACTGAGGTAAGTGATATTGATGGTATTTACAGTG
GCATTACCACCAATGAGGTAGTACGATCCTTCATTGCTACGAACATCGATCCTGCCGCCATCGATAGTATCCTGATAGTAGAAACCACGGTCGAAGA
ATAACTTCAGCATCGAAGTGAAGTAGCTGTTCAATACAGCTTGAGCATCTTTCTCTTCGACCACCCATTTTCCATCAACGATGTTATTCAGGTAATT
ACGATCATGATTGATCCCGACATTATCCACGATGTCAGCGTAGTTCTTATGGAACTTAGCAATCTCGTACAAACGTTCCAGAGCAGCAAAACGGAAA
GGGCTGGTGGGATGCAGAGCCAGAATGATCCGACCTACGCTCCACAAACCGGTCCCGTTGACCTCGTAACTTTCTTCGAGGTAACCTTTGATACCAC
AGTTAACTTCAAGTTCATCTGCTGGGAAACCGGTGCGGAGCCGCCTACGGATAGCCAATAGTACCGATTCGGATTCTTCCGGATCGAACAGGTCTAT
GCCGAAAGTAATCCAGCTACCACGTACTTTGTGCTGGTATGCCAGGCGTACAGTATCACCGAATGGAGAAATGAACCAGCGTTCGTCTTCCGATACG
ACCAAATGGCAACCACATTGCCACAGGGTACTTAGAGGATCGTTAGAGGCGAGAATGCGCTTGGTGTCGTTCATATCCGACGAAGTAGCATCTGGAC
TGCCATGTAGGTGTGTCAGAATAAACAGAAGCGATGATTCTGTAGTTTGAGCACTCAACATTGCGCGAGTGATGGTTGCATTGATGATCATGAGATA
TCTTCCTTTTTACAGTTTATGAATATATTGCTAAATAAAAAAATATTACGATGTAGAAAATAAAAGGGAGTCCGAAGACTCCCATTATTGCGTGTAA
TCTATTTGATGATAACCGCTTTAGAAAGAGTTTCCATACTTCCAATAACTAATTTGGATTTCTCTTCTTCAGGGTTCNCCATTGCTTCACGCAGGAG
TTCACCAATAGTTTTGGGTTGAACATCATCACTGATTTCACGCGAGCATGCCGAGTCGTCGTACATATCAAACACATTCAGATCATCATCATCCAGG
GGCGTGCTGTCATTCCATGAATAGCTTGATTCATCCGAGGTATCATCAGACTCACCATACTGTTCACTGAGGTCACGGTCCAGTTCAGCCTCATACA
TCTCGCTAATTGCTTTATCGTCTTCTTCTTGCGCCTTACGACGAGAAGTCTTGTAGAACGGAAGCAGGCGTTGCAGGACTTTATGGAACTTCTTCTT
GCTGATCAACCAGCTAACAGAGTAGCGAGACAGCTTTACTTCAGCTGCTTTGATAGTCGGATCGGAGTACAGCGCCATGACTAGCTTGTCCAGTTTG
TGCAGATGATCTTTAAACGAGTTTGCATAAGCAGGATGTTCCCGAAGAGTGAACATCACAAACGAACGCATGTCAGTGATATAGTACTGACTGTGAT
GTTTGTTGATTTCGATGTATACCGGATCTACTGCGCGGTTATAATCGAATTCCTCTGCCCAGGTAAGGCTACGTACTTTAGTAGGACGAGGACCTTC
TGCCCAACGAACAGTCGGATGTTTCTCACGGATGTTCCAACCATGATTGCGATCATACTCGGTTGACTCTTCTTTGAACCAGGTGAAATTACCTTCA
CCGCGCGATACAATACCACGGCACCAACTGACGTTGATTGCCTTGTTACGGCTTTCAGTAAGATCACAGGGCATGTCCAGAATAGCGACATAACTGT
TATGACCATTGGCCACAACGCCGAGAACAGTAGCTTCGAATGTCTCGTAGCGCTGTCCAGGATACACACGTTCATTCTCATCCAGGTAACGAAGGGA
GCAGGATTCGAAGATAGCACGAGTACCGGCAGGGAAATGGGCACGACCGAAAGGTTGTTCGGCCTTTCTTTCTTTACGACGGCTGATAACCCATTCC
AGTTTTTCTTTGGTCAGACGGGTTACGGGTTCACGATACTGTTTCATGGTAATTTCCTTTTTACGATTGATTGGGTTGAGTACATCTCAATGCATCC
TTTTCAAGACGCATTGAGATGGGGTCTCCGAAGAGACCCATCTATTATTCTTGGGTCAGTTCCCCAAGACGACCTTCGGCTTTCATGCGACGGATTT
CCGAGATGGATTTACCGTACATTTTGGCCAGTTCTTTCACAGTACCTTCAGGCACAGGTTTGTTCATGTCGCGGAAGTTCTGCTTAGCGATATTGTA
ACGCTGATGTTGAAGAGTCTTCAGTTCCGAACGTACCAGAGCGTTACCGGCACATTGGGAGATGAATGTAACCATGAAGGTCTTCAGCTTGCCACGG
TAGACGTTGACCCAAGCACAGGACTCATCCACGTGGATGTTCTTGTACTCGGAAACCTTGGCGTATTCCAGCAGGCCGACGGCATCGGGACCGTTGT
CCTGATAAACCATCTTGTTGAACAGGCCCAGGGCGATATCGGAGGAACGCTCACCTTTTATGAAGGCGATGGCGTCTTCGATGATCTTGGTTTCCAG
GTCTTTGTACTTGACCGGGTCGTTCTTGATCAACAGTAGCATGGCGTCGACCTTGACAGTCAAACCCATGTCGGCACCGCGTCGATCGATCAACTCG
TTGTGCTGTTTCTGCGTGAACACGGGATCTATGTTCTTGAAAGCTTTCAGGAGACGCTGTTCCATTTACTTGTCCTCTTTGACGTTGAATGCATACA
TGGTACATTTCGGCTTAGCCGGGTGTTGGCACCACTCTTTAGATACCTTGCCCTCAGGTTTAGTGAGATCGTAATAGAACTCACCACCTGCGGCAGC
GATACCCATCAGTACTGCAATGAATCCCATTCCGATCTTTACTTTCATTTGGCAATGATCCGTTGTACGAAGTGTTGAAGGTTGGCTACCAGGCGTT
CGAATTCTTCTTCGGTTACCTGGTCACGATGCGATTCCAGAAGTACTTCTACTTCCGGCAGGACGTTCATGGCGATATCCAACTGGATACGGCTGAT
GAACTCTTCCGTTGTGATATTTCGATCACGACGAATACGACTTACCAGCTTGCGATGTTGTTCGCTGTTGCGGTAGGTNGAGATCTTATCGATAAGA
ATATCAGAGATACTGCTTTCGATCTGTTCGGCTACAGCCTGACCGTCTTCCTTTACGGTAGCTTTGACCGCGAGGATGGCAGCAACGGCTGTTGCGC
CAACTGCCAGTGCAATAAGACCAAGTGCGTTTTCTTTGATGAAGTTCATATTGATTATCCTTTCAAAGTTGCATCATCATTGAAGATATCAGGACCC
ACCGAGAGACTTCCCAGAAGATCCGGAGCAATGTAAACAGAGTTGAGGGTTTCGTATACACCGGTAACAGCATCTACGTTAACCAGGCTAGAACTGC
GCATGGGTACCCATTCACCGTTACGGAAGGCTTCACCGACCAGTACACGAACATCATCTACGTCAGTGCGGTTCGGCCATAGATCCTTACCTTCTAC
TATTTTTACATTACGAGCATGGTAGACCAGTTTACCATTCATGCGAGCAACGATATTCGGACGGCACATGTTGTCGATTACTTTAACTGCTACGGAC
TTTTCCATTTTTATTTCTCTATTTAGTTACGAGCATTTCTTGACCATTGGGACCGATACGATGACCGAGGATAACAGTTTCATTAGAAATAGTTTGC
TCTTCAAACTTAGCGTTTACAAACAGTCCACCAAAAGTCAAACCAATAACCACTAGTGCGAATGCTTTCATTTTTAAAGTCCCTTTTTACATTAATT
GAAGGTTAAATATCAAGTTAGTAATATACTGTTTAAATATGGTTTGAATAAGGGAGTAGTAGTTATTACATATCGTGCAGGTAGGTCTCATCAATGA
TGGCACGGGCTAGCTCAATGAGACTATCTTCATCAACAACAATGTTACCATCTTTCCAGGTAGCGCTATGGGATAACCAGTTACGGTAATCCTTACC
TCGTACAGGATTGATGCATACCTGACGAGTAGCTGCATCACGGTCACCACGGAAACCCATGATAGCACGTGCACGACGGATTGCTTCTTTCTCCAAG
TCTTCGTCAGATTTAAAAGTCAGGAAAGTTGTCATAGTTTGATTCCTTTTTACTGATTTAATAGGTTTAATTACACTGTTGTGATATACTGGTTAAA
ATGGTTTGAATGTATTATTTCATTTCCACAGACGACAATAGTCATCTACATGTCGAGTGATTTCTGCAACAGCCCTGAGTCGCCGGCGGCCAGTTAA
TTTAGAGCAGTGTTTATTAACTAATGTATCAACAGTTTTACGTAACCTAACACAGCGTTCTTCATTAGGTATATCTTGTTCGATAAACAGGCTAGTT

Figure 8(H)

AATTTATGGATTTCCATATGGATTTTCTTACATACATCGTTAGCCGATTTTCTTCATTTAATTTGTTGTATGATTCGACTAACTTAACAATAGTTGT
AGCAACAGTAGTTGCGGCAACAAAAATTTGAATACCATTGATAAAATTTTTATTAAACATTTTTAAACTCCAACTAATGTATTAAAAAAATATGTCT
ATATTGAAAATAAAGCCCTCCCCGAAGGGAGGGTGTATGTCGCCAATAAGTGTTACTAATTTATTTAGTTAGTTTGACCATACGTTCTTTCAAAGTT
GTTTACATCATAACCTGAGTGGTGTGTTGCAGAACCACCTGAAGTAGTATCTATAATCTTAACTACCACTTCATCATTTTCAATGTAAACCGACAGT
TTATCTCGCATAAAATCCACGTGGTCATTTCGATAACGTAGATATTTCATTACAGCTTCGCCACTGATTTTACTGTTAGCCATTATTATTTCCTCGA
TTGATTCCAGTTAAAATTATCTTTTGCATTTTTAGTGAAGAACCCGTTACCCCAACCAAATGAGTATCTAAAGTCCTTGATTACACCAACATCCGAA
TCGATAACCTTATATTCAATGACTTTATCACTATTCTCCAGAATGACTAAGATCGCGATAAGATCTTTAGGATCACCTACAGTCAATTCATGTCTTT
CAGACTCGTCTCTGTGGATAACGATGTACATGGTACTTTATCCTCTAATTATACCCATTTAGTTACTGGGAGTTCGAAGGTTTCACACAAGTCGAGT
ACTTTACGATGTTCCAAGTTATTTTCTGGATAGAAGGTAATGGGTGTAGTCGGACTACCCCAATTAACACGACATCCAGTTTCTTTATGGATTTCGC
CAAGTACAGTATATGCACCTGCCCCATCTGCATAACCCATTTGATTAGGGTTAACGCAGATTTGAGTAAAACGCTCCGTCAATACTCGATTAATAGT
GATGGTCAAGAGACGAACGAACTCACGAGTCTTCTCGATGTCGTCTACCCAGAATTCCAGAAGGATCCATTTCCCATGAGGGTTATCATGCCCACCT
TGGAAGAATACACAGAAACCTTCTTTTGCCTTATAAAACTCGTGATTGGTAATGTTACATTCAACCATTTGTTTCACTGCATGCCATACACGCTCGG
TGACATAATCACCATAAAGTTCGATGCAGTGACCACGGCCAGGGAATTGTTCTTTTTTAGAAAATTTAATTTCGAACATGGTATAGATTCCTTTTTA
CATTAATTGAAGGTTAAATATCAAGTTAGTAATATACTGTTTAAAATGGTTTGAATGTATTATCGGTAGGGGAGGGTTACCCTTTTAACTTTTTAAT
ACTATTGGATAAGTACATGACACTACGGAAAATTTTGAATCTTGAAAAGTATTCACGTACTTCTTTTTTAGTCAATACAAGTCTTCCATCTTTGTTT
ACATTATCACCAAAGACAATTTCCTGAGTATTCTTCCATAAAGATCTATAAAGATAACAGCCATGTGGTGCATCACACCAATCATAGATCTTAAGTT
CAAATTCAACTTTGTCGACAATATCATCATCAAATAAAATAGTATTTCCTTTACTATTTAATTCCATTAACTCATTTGCACAATTTATTGCAAACTC
AACCGCTGCCCAGGTTCTACCACCGCTGAACATATCTTTACTTAATTTATTTAGATCGATAGCATTATAAGTTGTTTTCTTAGTGTTTTTCATGGAC
TGCACCCCTCAATAATAAATAGAATAATCTGTATTTAATTCACCTTTGTAATATACTTTAAATACATTTGAATACATGACATAAAGCCTTCCCCTGG
GGAAGGCTATTATTATGTTTTAATCCAATGGGTATATGTACATAGGTCAGTTTCTTTAATAATGGTTGATTTCCATTTATCCCATTTAATGATTTCT
TTAGGGAAATAAACACAACTACTATTATCNATTTCCATCTTGACAGTAGTAATGTACATTTCGTCTAAAATATCCTTTTCAATGACTTCTTTATAAA
GTTGAGAACCGCCAATGATCCATACATCCTTTCCAGTTTCTTTATTGAAATGAGTGGCATAAACAATAGCTGCACTTAGATTAGGGAGTACACCTAA
TTTATTATCATAGGCTACTGGATAATTACCGTTACGATATAAACTTGATGATACAACAATGTTATTACGATTAGGTAACGGTTTACTACCTAAGGAT
AAGAAAGTATTTTTACCCATGATAACACAGCAACCAGTTGTCATTTCTTTAAAGAAAGCTAAATCCTCAGGTATATGCCAAGGTAATAGATTATTAT
ATCCAATGACACCATTTAGGTCATGGGCAACGATTAATTTAATAGCCATTAATTTTCCTTAGGCCAGAATTTACAAGATACTTCATTATCTTTAAAT
TCAATAGCCCAACTACAGCAAGTGAAATTAGTTTTAAACTTAAATGTAGACGCTAATAGGTAATTAATTTGAGCCATTTGTAATAGCGTTAATTCAC
CATATACTTTCTCATCAATCAATACACCAGGTCTTTTATGTTTAATAACTAATTCATTCAACTTAATATCTTGTTCAATATAGAGGTATTCCACTTC
GCCTTTTTCTAGTATAGGCATGTCCCAAAGAATCAGACTAATCTGTTGTGTGAATTCCTCAATACTAGTTGTAATATCTAGTCCTTCATAACCTATC
AATAGATTTATAAGTACTTGTAGACTAATCAGATTAACAGGTAAGTCTTTTAAATCGTCTTCTTTAATAGTTGTTCTAAAATAAACAGTGCCATCTA
AGTTTTTAACTAATAATCTATTTAATAGATGATTGACTTCTGATTTAATCTGATAATCCAGTTTGATCATTAGCTAACTCCTTGAGTCTAGTCATGC
CATTACTAACTTCAATAATGTAACTAAAGTCAAAACTATATTTCATCATTTTGAATTCTTCTTTAAAGTTAGCGATATTTCCAGACAGAGCAATTTG
TTCAAATCGACTAAAATCAGTAATAGTTTCATCGAACATTAGTTCTCTTGCGGTAATATCTGGATCATAGTTAGGATGATCAACTACAGTACCTTCG
TGGTTTAAAGTACCTTGAAAATTCAAAGTCTTTTTAACATGGTCTACAGTTATTTTCCAACTAGTTGCAATATACCGAGCTTTAACTAAATTAGGAG
CATACCTGTAAATACACCATTGTAATGGAGTGCCAACAGTTTGCGTATCATGCGTGGCTTTTATAACTTTAATAAAATTCTCAAGTTGATCAAATGT
AACATTCCTAGTTACACCATCATTAGTGGTTATATTAAGAGATGGTCGAAGACCAGTACCAAGATCATTGGTGATGATTATATCCTCAACTAAAGCT
TCATATAACTTTAGTCCTTCTTTTCTGGATCCAACATCATTACCCATTGTTTAGCTTCCTCTTTTGTTACCAGTTGATAAAGTTTATTAAATTCACG
TTGACGCATTAATTTGTAATCTAGTATACGCCCATTATTTTTACGAATTAAAATAATAAAATCACCCGGACAGACAATTTTATCTTTATCTGGGCCT
ACACGTAAAATACCATGACTAGATTCAGTTAGATTACATAATGGGCAAATCGCATTACTAAGAGTAGACTCTTTAGTAGGTATAGCATAACCAACAA
TAGCACCTTGGTTGATATTATTGATAACGCCATCACCAGGTATATCACCGTTCTTTTTCCATTCGATTGCTTCAATTGGATCGGTGTATTTCGGTAG
ATAAAAAGACATTCTTAATTAACTCCGATAAATAATAGTAGTATAGTAAAAAGCACTTAGGTATATTTCTATTTTAAGCTATATTGTTGATAAAATA
AAACCTAAGGGTACATAGTGGGTTATTATTTAAAGCTCTTAAATAGCATGGTAGAACGATATTGGACTATATAGCTGTAACCCTTAAGGCACTAAGG
CTACAGAGGTTTTTAAGATAAAGATATCCAATGTACCATAATATGCTTTTACAATAGATCAACTAAATTCATTTAAAATGGGTCGTAAAAATACTTA
GTTGATCTAAAGATATGTTGAATACTTTTTCACATGAACTTACGACTCACAATTGGAAATTAACAATGTTAAAAACTATCATTAAACTAGACGGTAC
TGAAGAAGCATACTCACCTGCTAAGATTAATGGTTGGGGTGAATGGGCAGCCCAACATCTTGGCGATAAGGTGGATTGGAGTAGTGTTGTGATGGAT
GCTGTTCAAGCTCTTGGTGATAAAACTTCATCACAAGAACTACAATTACAACTTATTGAAGAATGTTTAAATCGTAAGACATGGTCTTATTATCTAA
TGGCTGGTAGACTATATGCGATTTATCTTCGTAAGAAGTTCTATGGTCTAAATGGCATCCCAACTGTTAAAGCGCTTCAAACCAGGATGCGTAAAGA
TGGTATCATTGTTAAATTAGATTATAGTAGTAAAGAATACGCTCAGATTGAAAAGATCATTGATCACGATCTTGACCTACTTTGTCCGCATTTTTCA
CTTCATCACATTCGTGGAAAGTATGCTCTACGTAATCGTAAAACTGGTCAAGAATATGAGACTGCCCAGTTTGTATATATGCGAATGGCAATGGCTC
TAGCTGAAAAAGAGCCAGCTGAAACTCGCATGACTCATGTGGAGAATTACTATAAACTACTTTCTAATAAAATTCTTAGTGCGCCAACACCTAACTA
CGTTAACCTAGGTACTAAGCTTCGTGGTTTTGCATCATGTTGCCTATTTGCTTCTGGTGATAATGGTGTATCACTGGCAATGGGCGATTATATTGCT
AACATCATGACCCAATCATCAGCAGGCATAGGTGTTAACTTAATGACTAGGTCAATTGGTGATCCTATCCGTAATGGCCTAATCATTCACCAAGGTA
AGAAACCATACATCGATGTAATTGGTAAAGCAGTAAGGGCTAACCTACAAAATGGTCGAGGTGGTGCTGTTACGTGTTACTACAGTGCTTTCGATCC
TGAAGCAGATATGATTACTCAGCTACGTAATCCACGTTCTACTGAGGATAGGAAGAACCGTGATCTTCACTATGCATTCCTAAGTAATAAGTTCTTT
GCTAAGAAAGCAGCTCAGAAAGATGGTATGATCTTTGTATTCAATCCATTTACTGCTCCAGATCTACATGATGCTTTCTATAGTGGTGATATTGATA
AGTTTATTAAGCTTTATGAAAAATATGAAGCGGATCCTAAATTTGAGAAAACTTATGTAAATGCTCGGGATCTTCTCAAATCAATGCTAGTTGAAGC
ATATGAGACTGGAACCATCTATTCAGCTCAAATTGATGAACTCAATCATCATACACCATTTAAAGAACCTATTTACAGTTCTAACCTATGCCTTGAA
ATCGCAGAACCCACTAAGCCTTACTATCGAATGGAAGATCTTTATTCTAGTGAGGATCACGGGCGCGGTGAGATTGCTACTTGTTCACTGGCTGCTA
TTGCAGTGGATAACGTTCCTGATAAGCAAACTTATGAAATGGCGGCTTACTACGCACTTAAGATGATTGACTATTGTATCCTTAATGCAGAGTATGC
TTTCCCACACCTTGCACTAACCGCTAAGAATCGAATGAGTGCTGGTGTTGGTATCATGGGTCTAGCCACACATATGGCACGTGCTGGCCTTAAATAT
AGCAGCGATGCTGGTAAAGCTGAAATCCACTTCATTGCTGAACGGCATATGTACTTCCTTATCAAGGCGTCACTTAAGATTTCTAAAGAACGCGGGA
ATGCGCCTTGGATTCATAAGACTAAATGGCCAGAGGGATGGACTCCACGTAAGACTTATAATAAGTCAGTGGATACTATCATTGAAGGTGGCTTTGA
AGAACTTTATCCATGGGATGAGCTAGAGAAAGAAATTAAGGAGAATGGTGGTATTGCACACTCCGTACTAGCTGCATACATGCCTGGTGAGGCATCA
TCTAAAGCACTAGGGTCAACTAATGGTCCATATCCGGTACGTCGTCTAATTCTGAATAAGACTGATAATGGCGCACGTGTGTTATGGGCTGCTCCAT
ATGGAGATGATGATTCCTATGTGTATGAATCAGCTTATGATATCCCCACTAAAGATCTTATTGACTGCTATGCCATTATTCAAAAGTGGACTGATCA
AACAATCAGTGCAGACCTCTATCGACGCATTGTAGGTTCGGAAAAGATCTCTTCTAATGAAATGCTAAGTAATCACTTCTACATGGTGAAACGTGGA
ATGAAAACCCGGTATTATGTAAATCTAGAAACAGCGGCAGGACTTGACATTAAATCACTTGAACGTGCTGTTGAGGTAACTAATACTGAAGTTGGGT
GTGCAGGTGGTTCGTGCACTCTTTAAGTGTATACACCCTCCCTTAATTGGGAGGGTGTTATTCCCAATTTATACTAACCTCTATTATTTATTGTAAG
AAATATTTTTAAATTGTAAAGGAANTAACATGTCTACTAAATCTCAACTACCAAAGAAAATCTTCAATGTTGCTAAGAGTGATTATCATCTACCGGA
AATTATTCTTGGAGATGATCCAGGTCTACTAGATTCAATCCACACTCATTATCCTAAAATGTGGGAGCTATATAAGCGTCTAAAGATGCTTGATTGG
GATGAGCTAGAATTTGACTTTTCCACTTGTCTAGTAGAATTTGAAACGTGTGATAAATCAACTTATGACATGATGATTAAGACACTGGCCTGGCAAT
GGGAAGCTGACTCTGTAGCCAGTCGTTCCATTGTTAATATTCTATCACCTGTCATGACAGATTCACGAGTATGGGCGGATATGTACGTATTAATGA

Figure 8(I)

TAATGAAGACGTACATGCTTTAACTTATTCTGAAATTGTACGTAATAGCTTTAAAGATCCTAAAGTTATTCTAGACGAAATTCTTAGGGTAGAAGAA
GCACAAGAACGAATGGTTGCAGTAGCCCGCACTATGGGTGAAGCACATGACGCAGTTCATGCGTATGCTCTTAATCAGGTACCCAATGATCAAGAAC
TTTACAATAAAGTATTCATGTTCTTCATCGCTCTATATTTCCTAGAACGTATCCAGTTCATGGCATCCTTTGCAGTAACCTTTGCTATTGGTCGTAC
TGGTGCATTCCAGCAAATTGCAACCGCTGTTAAGAAAATTGCCCAAGACGAATTCGAAATCCATGCACAATATGGACAAGAAGTTATTCGTGCACTA
CTGGCAACTGAACGCGGTAAACTCGCTTACAGTCAATGTAAAGATAAAATCATTGAACTACTATGGGAAATTGTAAAGACTGAAGTTACCTGGATTA
ATTATCTATTCTCTGAAGGTCGTGAACTAACTGGTGTTAATGCGACTAAACTTATTAACTGGGTACTTTTCAATGCTAATGCCGCAGCAACATTCCT
AAGTATTGAAAATGATGTTGTAGAACAGTATCAAGTGGAGTTTAAAGAATCAGCTGGATTTGATTTTGTTTGGCCAGAGAAGAACCCACTTCTTTAT
ATGGAAGACTACCTAGATATTTCATCAACCCAAGCATCTCCTCAGGAAGAAGAGAAGCCTGATTACATGGTCAACGTTGTAAATGATGTTGGTGAAG
AAGAAGAATTTGAGGTTGACTTCTTATGATTAAGATTATCGCATTCGTAGTTTTAATGTGGTCCACTGTCCTATTTGCAGCAACTGAAGTAAAATCA
ACTACAGATGGTATTATTGCACATTCAGAATGTCAGCTAGTTGCTAAAGATAGTAGTGTTGTCGGCACTACTGTTGGAGGTGCGGTTGGAGCCACCG
CAGGCGCTGTATTAGGTCGAGCAATCTTTGGTAAATCTGGAGGTTGGGTAGGTGGTTTAATCGGTGGTGCCGCAGGCGGCGCAGTCGGTAATAATGT
TAGTGCTACTGAAACATTTCAATGTAAACTGATTGTTAATACAGATGGCAAGCAGTACATGGTTCAAACAGTTACCAATGAAAAACCAAAGGTTGGT
GATAAAGTCACTGTTGTTGAAATGAATGATGGTACACGAGATATAATGTAGACATAATGACCCTCCCTTAATTGGGAGGGTTTATGCTAACAATTCT
ATAGCACTCTTATTAACAGTCATCAACGAGAGAGTAGACATGAATAAAATGCTAAACTTCCTAAACCGTACGCTATATAGCGGTACTGAAAAAGTAT
CTTCAAAAGCTACACCAAGTCTAGAACACTTTAAAACAAATGTTGAACAAGTAGATAAAAAGATTCTACAACCCTTTAGTACTAAATTTAAAACCAT
TCTAAAAGAATGTTACAGTAATGAGGAGTGGGTTGAAGAACAATCATTTATTGAAGAACCTATTGATCTTGGTTCAGCTGCACGCGGTCTTACCGAG
CGCGGTATTATGCGTGGTGATTGGGGACGCTTAGCGCATTCCACTATTAAAGAAGCAGAAGGTATGATGCGTACTTATAGTGGTCGTCTAAATGAAG
ATATGGAGGCATCTGAAATTAATGAAGTAATTCAAGATATGCCTTATAACTTCACAGCTGGCTCAGCTAATACTAGCCGTTTAGAAGAAGATGACTC
TATTTTTGTTGAAGCAGATACAACTGTAGTTGAACCTCTGTCTAAGCAGACTCTGCCAAAAGTAGCAGAGCTTACTAATCAATTAGTGGAAGTCTAT
AACCGAATTACTGAAGAATTTACAGAAACTGGTATTGCTAAAGTTGAACAAGTTGAACAGCCAGCAGTTCTTGTAGCACTTGGTGAGATCATTAGTA
GTTTTAATAAACTAATTGATTTATCTTGCGGTGCTCTACCAGTGGAAGAAACTGTTATTGTAGAGGAGGATCCGTTACCTGCCATTGTTACTGGTCC
AACTACTGAACCCATTGATGGTGAAATTCTACCGGTTGATGCTATTAATAATTCTGCGGCATTAGAAGAATTCATTGAAGAAGTATTAAGTACTAAT
CCAGAATTCATTAAATATCAAAGTATGAATGATAGTAATATTGATTCATATCTAACTGGGGATGACTGGATTATACTGAAATTCAAAGATGGTTCTT
ATTATTTATACAATGCCCAAAGTGCCGGTGAAACGAATATAGAAATCATGAAAGATATGGCCGAAACTGGTAGTGGTCTTAATGGTTTTATAAATCG
GGTTATTCGTGGCGGGTATGTAGAGAAGTCCATCATTAATACTCCCGGTTTTATACAAGTCTCAAATGAAGGTCTTATCGATTCAATCAAAAAAGTT
CTTGGCATTTCTAATCGAGGTGATCAGAAACGTATCTGGCGTTCATCGTCCAGTGCAAGAGGATTTCTGGAACAACTAGAATCTACATTTGGCAATC
CACAATGGCTTAATAAGCAGGTATTCGTTACTGGCGATATCAATAGTAATGGTATAGCTAACGTACTGAGTATTAATGGTAAAGTCAGTATCGAGGA
TGCCATTCGTGCAGTAGAACCATTCTTCAAACTCGAAGAAAAGTCTAATCGCGAAATGGAGTCTTACAGGCAGAAGACTAAACCTGCATTGGATCTA
CTCATTAAGAATGCACATAACCTAGACGCTAACGTATACAAAGAAGCAAAGGCTATCGTAGACAAGGCACGTGCTGGATTCAAGACTAGTGTTAAAT
GGCCTGCCGGTACTATTACAGGTAAGGGTACCTATAATTCACCTCGCACCGTGGTCGCGAAATATCCATCTACTGATAGTAAACTCAAAGCTCTTAC
TGAAGAAGAAGCAGCTAAGGCCATGAACTTAATTATATCGGCATTGGAACGTCAGATAACTCTTAGCTTCAAGTTCCCTGATTTACCAGATCCACTG
GAAGGACTAATCTACGATATGTTGGATAACCCTAGTCCAATAGCTGGTATCGATTACTATGATTGGAATGATTTGTTATTCGCATGCTTTGGCCCTG
GGATTGATGATGATGTGATGGAAGTTAATAAAATGCGGCAATACCACTCATTCATTGATATCATGGAGGCCGCCGCAAAATGGGTAGATCGGTCTAT
AAAAGGTAGGTTAGCAATGGGTAATGAAAACTACCAGTAATGTATCTAATATTATGTAGAAATAATCCCTCCCCCTTGTTTCTACATTAGTCATAAT
AGATCGGAGCCAGTCCCCCTTCCAACTGGCTCCCAGAGAGTAAAACTCTTTGCTGGGCATTAATGACGATATATCGCCTCCCTTCGGGGAGGCTTTA
TATTTTGTTTTTACGTATGTATATTAAAATATGTATAAACAACATAGAGTAATTATAAAATGATCAAAAATGAACTTTTACCAGGGCTAATCTATGC
CCAAAAAGAATTTGATAAAATTGCAGCTAATGTAAAAGACTATGATAANTATAAAAGACGCGAAGCTGGTAGGGCAAGTGCCGTTTTAAGAAGTCTA
GTGAGCAATATTGTAAATCAGAATAAACCATCCTCACTTGAACATGAAGGCAAAGTTAGTACTACTAATACTAATGAATATTTAGAAGAAGTTAATA
ATTACTTCTTTAACATTAATAATATTAAATTAATTTCTCCTAAACTCATAAAAGAGAAATTAACAATTGATCTAATGAATATTTATGTTAAATGGAA
TATGATTGGAGTGGCTGGCCGAAATGATGTTCCAATTATTGAACACAGAATTAATGATTGGTGCGAAGTGACCGATGTCTACATTAATGGTAATAAG
ATAACTTCTTTACAATGGCCACGTTGAATTTAAAATAAGTTGTAATAAAATACCTAGCATTACATGTTATGTATTGAAGCACAATGCCCGAATGGTG
AAATTGGTAAACACAGAAGACTTAAAATCTTCCGGCTACGGTCTTGTCGGTTCGAATCCGACTTCGGGCACCAATTTAAATACGGAGTGTAGCGCAG
TTGGTAGCGCGCCTGCTTTGGGAGCAGGATGTCGGGAGTTCGAGTCTCCCCACTCCGACCATTTTAATAATAGGTAAATAGGATGGATAATAAATGG
ATATCATGGGAACATCAAATTATAGGAACAGCTCTTTACGCTATTCTTAGTGACCCTGAATTAACTAATATTCAATTAGCTCAAGGCTTACACTATC
TAACAGAAGCAAAGTCTTCTGTATTACATGTTTGTAATAACCATATTACATTCACTGTAACCTATCCACATGGCACATTTAGAACCAATGTAATTAG
AGAGTGCCCTGCTAGTGATACAAATACATTCAAATGGTCAGGTGTATTAGTCCGTCAAAAAGATGGAACATTCTTACCAGAATAAATAAAAAGGGCC
TATAGCTCAGTTGGTTAGAGCAGGCGACTCATAATCGCTTGGTCGCAGGTTCAAGTCCTGCTGGGCCCACCATATACTAGCCTCCCACTTGGGGGAG
GTTTTATACTGTCTCATTGAGGAAAACATGAATACAGTAATAATGTTGGTATTATCTATCAAAGTTGGATTATTTGGTTTCATTTCGACTAATGAAA
GTAATATCCTATTTGAAAATAGGGAACAGTGTATTTCTCATCTGGATATTCTGGAACATAAATACAAGTCTCTTGAAGTTATTCGAAATGAGAATAC
TCTAAAGATAACCGAAAGAGATAACCATTCTATTTATATTTTTAAATGTCTCTAGGAAAATACATGGAACATCAANAACAAAAAGAACTATTGAGAC
AACCATTACAAACACTTTATAATCTTACTTTTAGTCCCCGTTTACGTAATGGAGCGAAGGCTCCCGATTGGATTCACCTGACCGATGAAGTAACCCT
ATTCCCAAACGGATTAGATATTACAATCAACGCTGTTACACGTTGCATCAAATGGGAACTTATCGGCGAGGATGTAAGTAACATTACTTATGTTGAA
GCTATGTTCTTTAATAAAGGTCTTAAAGCAGTTAAAGCCTATCTCAAACATACGGAGTAAATATGGATCATCTAACCCCAACGCAGAGCGCTGTATA
TTTCACATTTATTAGCCCTGAGTTTATAAAGCTAACTCTTGTTGAATCTTTTGTAGCGATCCACAAGAAACATCCAGAAGTAAAGCATTGCGTTAAG
AAAAAGATTAGTGCTAATGAAACGCAGTTTATCTTTATCTTCAAAGATGGGACTGATAATTTAATCATTACACGTAAAACTGAACCTTGCCCTGAAC
TGGATAGCCCAGTAGGCGATAGTATTAAGTTGTCCGGCGAAGAACTTAAAAATATTCTTGCTAAGTACGATCGTCCCAAGGATGGTAACTATTTCAA
GCACTGGACTGATCGCCCGTAATAAAATATTACTGGTTATGTAATACTATGTAGGAAGTCATGTCCATACGTTTGCGCTCATAGTTCAGTTGGTTAG
AATACCCGCCTGTCACGCGGGTGGTCAGGGGTTCGAGTCCCCTTGGGCGCGCCATTTAATTCCGTGATAGCTCAGTCGGTAGAGCAAGTGACTGTTA
ATCACTGGGTCCCTGGTTCGAGTCCAGGTCACGGAGCCATATTCTAAAGAGTAGCTTCGGCTACTCTTTTATGTTGCCATGGGTTATCTTATGAATT
AAAATGATTTACTTGAGAGCACACTCATGTTTGAATTACTATTATCNCCAGATATAGGCGAAGAGTTACCCTTGGTTGGATTTAATGAAATTATTAA
ATTAGGTGATCTACCTGTAGCGTTAGCTGGTACAATGTCATATGTGGATGGAAATACACTGTATGTTGGATCTGGTCATCATACTGAAGGACAAACA
GCTGCAACTGTGTTCAGACGTTTTACCATATCGCCATTTGCCGATATAGGTGCAACTGCTTCTGGAACATTCTTACCAGGGGTATCTTTAGGATTTG
GGACATTACATAAGAATAACTTTATTGTTTATGGCGGTATTACTGGATGGAACTCGGCTGGTAATGGTGGTACGGGAACATCTAACTTTATACAACA
TTTTGATATAGCTACAGGCAATAGGGTTGAGCGATATAGTGGTCCCGTACCACTTTGGGGCACAGCCTCCGCATCAGATGGTAATGATCTTATTCTA
TGCGTTAACCCANTTGGNGTAANNGCAATGCGNTTAAAACCATCNNGTAAGNCNTGGCTTAGNGGNCAAGANTATTCAGGTGGTGCTCGTTCAGGTC
AACAGTTATTCTTTTATAATGGTTACTTTTACCATTTTGGTGGTTGGGATAATACAAAGAACATACCTAATCTTGAAGTTTATCGATATAATGCAAC
TACCTTAATATGGGAGCAAACACCTTGGATGATTATACCTGCTGATAAAGGAACAATCTGGCAAGGTAANGGTTATGTAGATGGNGACTATTTTAAT
TACCTTAACGCTGTTGATGTCGGCGGTGTAACTAAAATGTTTGCACAACGTTTTAATATTAGGCGCCGGAAATGGGCTGAACCATTTGAACTAGGTA
TCGGATTCCTNAATATTTCATCTATAGCTAAAGGTCCGGATAATAGCATGATCATTGTAGGTGGATCTAAAATGCCAGTTGGTGGTGGAGCANANAT
GTTGAAAAGCCAATTGTTATCAGGTNTCTATCAGGTAAAACTAGCACCATTAATCATTGATTAAAATAATAATATTTATAACTATTTAGATAATTAT
ACTGGCACGATGATATTATGTAAGAGTACTATANTAAAGTATTCTTAAATCTATCCACTAAACACACTCGGTGGTAGAACTTATTATAGAGTGTGTC

Figure 8(J)

TAAATGCCAGGGGTTTGCCACCCCTGGNTATATTCATTGTTACTATTATAAATTCATTTATAGATGAGAAAAGGTTTTATCACCTTTTCAAAATCGG
CATTTAATTCCAGTTAAAAAAACTGAATCTATGCTACATTGTAATAAAGGAGTCTATTATGACTAACTCTAATCCGTTTGTAAGAACTATTGTAAAG
TACCAAGATATCCTAGATGCTTTAATTCAAAAAACGAATGAGAACTGGGTTAATTATCGATCTAATTCTATTGGNCATATTGTTATTCGTGAATACA
GGACTGTTGGATTATTTGTAGGTCGGCAATGTGGTAGTACAACTGCATTGATTGAGTTTGCTAATCGTCANCCTGGCGAATGTCTAGCTGTATTTGT
AGAAGATAAAATTAAACAGGCTGTACTGGCTAAGTTCCAGAATGCTAAAGATAATATTGTTTCTTGTTTAATTACACACCAACTCCGNAAATATATT
CATCAACCTGAAGAATCATCTATTCAAAAAGATATTAAAGAAGAATTAATATCGTCTGTAAAATATATTCTTGTTGACAATGCCTCATTTAATCTGA
ACCTACGCGGTATCACTGATAAAGAATTTAACCAGTGGGTTGCAGATACTTTTGGTACAGAGGTAATGGTGGTTCGTTTTAGTTAGAATTAGTAACT
TTGATAGTTTCTAATAAGATTAACTACACGTTATTTACATAATGTCATAACAAGAAATAAATAATACTCAGATTGTAATAATATGTAGTTATTACAT
ATCTATATTAGGTTGTCAGTAACTCATCTCTAATATAAAATCGCCATAATTCTTCCGTGATAGCTCAGTCGGTAGAGCAAGTGACTGTTACGATTTC
ATTGGTAAGTACCCGAGTGGCAGCAGGGAGCGGACTGTTAATCCGTTGGCGAAAGCCCACCGTAGGTTCGAATCCTACCTTACCAGCCAAATTCTAA
AGAGTAGCCAGCTGGCTACTTTTATCTTGTTCTATAGATCGAACTAGCTATCTATTTTTTAAACCCTAGGTTCGATATGAAAGAAAAAAATAATTAA
TGGTTATCGGGCTCTGTATTTACCTGAACATCGGCAGGCAAAAGCTAACCCCAAAATGTTTGGATGGGTATACGAACACCGTGTAGTCGGTGAAGAT
ACAATCGGAAGATCTCTTTACGATGACGAAGAGGTTCATCATTTGGATGAGAACAAACTCAATAACCATCCCGATAATCTTTTGATCCTCCCTCAAT
CACAGCATCTAAAACTACATGCATGGATGAAACGACTGGGCATTGATCCAAAGAACTATCCTACAAAACTTTGTGGTGCTTGTGGTAGGGTAATGAA
TCATAAATTGATTAAATTCTGTAACCCTGAGTGTTCTGCCAAAGGTCGACGTAAGGTTGATCGACCATCTAAAGAACAACTCGTCCTTGACGTTACA
TTGTTATCTCTTGTGAAAATAGGAGAAAAGTATGGGGTATCGGATAATGCAATTCGTAAATGGTGTCGGTCATACAAAATCAATATTCCAGCTAGGT
TTATTAGGGTCAGCACTAATGGGGGTATTAGCACCTTGGCCCCCACACAATAAAAATATACTCGATGTAGATTAATATACAAAAACATAATCACTGG
GTCCCTGGTTCNANNCCAGGTCACGGAGCCAATTCATAGTTTTAGATTTAGTTATATTTCACTACTATGTAAACTATAAAGGCAGCTAATGCTGCCT
TTATGTCGTCTTGTAAAAGTACCCAGTAGTTGAATCTTATAGCTGAATACAAATAGGGTAAAGACATGTCACTTAAAGCATTGCAAGATATAGTTAG
TAGTGTTCCTACAAATGAACAAAAGGAACGATTAGTTAAAGTTCGGAAAACGATGGAAGAGCTAAATGAGTCTATTAAGAATCAGATTCGTAATAAA
CGACCTAGTCAAGCTCTTCTCGACAAAACGATAAACTGGGGTACCAAGTATGGCTAAGACATTAGTTCGTGCAAAGCTGATTACTGAAGCTGGTCAA
TGGATGTCGTCTGACTGGGAATGTGGTTTCCGTGCATGTCGATTCGTGAAACTTGGTAATGATCATGTAAACATAAAAGACTTTGAGGCTATGATCA
CGGCATTCGAAGTTGGTGACATGTTAGTGATTTGGCCAAATGGGCTTAGAACTTCGTATAGTGTGGATAATTTCAATAAGTACTTTTCCCATATCAA
AGATGAATACCATGAGACTGATCTCCGTCCACTCTTTTACCCCAAGTAGTTGAGCTTATGATAACTATATTCGTGTATAAATACATTACATTCGTTA
TACCCTTTAATTGATTGAAATCAAGCTACATAAAAGTGATGAATACTTTAACCCAATGATGTATAAATTAAAAAGTATGCACACTAAAAATACAGAT
GGTGTTTATTTGATATTTTTACCAACGCCTACTATCGATGATCAAATTAACACCATGCAAGGGTATATTATCAATAAATCCGGTAATCTCATTAGGA
CTACTGTACAGTCATGGCGATTTGAGAAAATTGAATTCAAAGACTTAGCCAAACATGATAGACGTTGGTTATTTATTGAATATTACATTAATGTTAA
ACAAACGAAAAATAATATAATCAAAGAGCAACAAGATGAATTAACTAAATTTATTTATTATAGTACTCTAAGTTAAAACAAATAAAAAAATAAATAT
AAGAGCTAGCCCCTAATGGGCTAGCTTTATGTTATCTTACTCTGCTACATCTTTTACATCAGGTTTATTATTCCAACGTACTGCTCTCGCAATACCA
TACGTAAGAATAAGAGCACCCACGGTGCCAATAGTGGTGCTAATAATAATGCCAAGAGTTTTTGGNTCNATATTCATATTTAGTNTCCTATTTACAA
TTAATAGAAAATATTACTTTTAGTAATATCANNTTNNTNATATACNNTTTAAATANGTTTGAATATAACTTTATTTATTATATAATAAATTAAAATAAT
ACTTTCATATACACTATATGTAGAAGATTNCGCCGCTATAGCTCAGCTAGGTAGAGCAACGCACTTGTAATGCGTAGGTCCTCCGTTCGATTCGGAG
TGGCGGCACCAAATTTACTGAGGTTTAAACTATTCTTAAATATATTAGTTAGGATGGGATTGAACGNGAAAGACTCAGTAAATCATATTGCCCCTCC
ATATGGAGGGGCTTATGTTTGTCATTAATCAGGAAAATATAAAATGAGNCATCTATTATTTATCATCCAAGAATACATTACTAATAAATTTGAGATA
ACACGAATTGATATGAAGCCAGGTAATAGAATGTTACGTGTATGTTTATACGGTCAACATAAGGGAAAAGGTTTCGTCCGTATAGATTTATGGTCAG
TTGGTTATCGCATTACAAAGAAATAATACTCCAGATTATTTAATATGTATTAATCAAAGGAGTTTATAATGAGTAATGAAACTAACTATCTAGGTTA
TGAATGGAAAACAGATATAACTACTTCAAATCTTAATAGAGTGGTTGATTTATATACACTTGAATTAACATGGTTAAAAGAAGATTTTAATGATACT
CTTTTTATAAAGTCTTATAAAGTGCTAGAGGGTCTATTAGAGGAACCGTCTAGGGCAATCCATGATGATACAGTANCCATTCAAGATCAATTAGATG
AATTAAATACTGTTTTTAAATTAGTATTTGGAAAAGATAATAACGTAGAGTTATCAATTAATAATGATTCAATTATTGTGATCGGTGCTACAGATGC
AACTAAAGAAAAGTTAGAAGCAGAGGTGCGTGAGTTTGCATATAGAAAATCATTAATTGATGAACGTTATCCAGATATTGTAACGGATTAAAATACT
TACAGCTATCTAGTATGTAACTAGGCGGATTGCCATTTGTAAATTATCTATTTAATCGAACTGAGGAAATACTAATGAAACAATTCTTTCAACTACT
TCTAAGCCTACTTTTCAAACTACCGGTTCTATCATATTTTGCTGAGAAGAAACGATTAGAGAAAGAGAAAAAGGAAGAAGAAAAGCGTCAGCAAGAA
CAACGTCAAAAAGAACTACTTGATGAACAACGTCGCGAACAAGAAGATCATTATCGAAAAACCGCTTACGATCGCCTAGCAAAACTTATTCATACTC
GGTGGTATGATGAGTTTAATGCATACGAAAAGAAACTAGTTGATCTTGCTGTATCGAGTGGTAAAGCAGTTAGTGTTAAGTATGGTAAAGTTACTAA
GATGCAGCACCCTCATCAATTTAAACTACTTAATGATTGGCTGGATGATATTCCAGTAGAAGATTATTCTAAGTGAAGAGGAGATATACAATGGTCT
TCACACTCGAAGATTTCGTTGGGGACTGGCGACAGACAGCCGGCTACAACCTGGACCAAGTCCTTGAACAGGGAGGTGTGTCCAGTTTGTTTCAGAA
TCTCGGGGTGTCCGTAACTCCGATCCAAAGGATTGTCCTGAGCGGTGAAAATGGGCTGAAGATCGACATCCATGTCATCATCCCGTATGAAGGTCTG
AGCGGCGACCAAATGGGCCAGATCGAAAAAATTTTTAAGGTGGTGTACCCTGTGGATGATCATCACTTTAAGGTGATCCTGCACTATGGCACACTGG
TAATCGACGGGGTTACGCCGAACATGATCGACTATTTCGGACGGCCGTATGAAGGCATCGCCGTGTTCGACGGCAAAAAGATCACTGTAACAGGGAC
CCTGTGGAACGGCAACAAAATTATCGACGAGCGCCTGATCAACCCCGACGGCTCCCTGCTGTTCCGAGTAACCATCAACGGAGTGACCGGCTGGCGG
CTGTGCGAACGCATTCTGGCGTAAGTTTAAATAAAAGAAAATAAAGACGAAGTTTTTCTTTACATGGAGAGGGGTTTATGCCGTAATTATACACTTA
CTTTGATAAGATTTTTAATATCAGTAAAATGGGTATATGTTGCCTTTTTATCTTTGTGAACCAGTAAGCAACAGGTACCTTCATTTACTGTATTGGT
TTGTTTTAATGGGATATTTAAAGCATATTCAAACAGATCATCCATCCAGTTAAATACCATGAACTTATTGATAAGGACATGATCGAAATCAATTAAT
CCAATAAACGAATCGATCTCAGATTGATAATACTCTACAACCATTTTAGACCATTCTTTGTTTATCGCCTCAATGACATTAGGATTATTTATTTTAT
TAAATAACTCANTNCGTTCCTNAGTAGGTAAACTGAGGTAATAATTAATATTACTCCTAACGATATCTGGATTAGTGATATCNATTTTTTCTGGTAA
GTTATATTTACTATCTACATAATTCTTAGTTTCTGGTGTCATTCTCCAGCAACCATAATCAGCAGTAGTACTTGATGGATCTATTTTAGTCTCCACT
ACTTTAGAAAATACATCTACATATAAATTAACAGATTCGTATACATCAGGTCTGATTGGATTAAAGTTTAAACTTTTAATAAGACCCCTAACTGGCC
GAGTACCAATTAGACAATGCAATTCAAGCTTAACATTTTCCTCTTTAGCCATCTTAAATANATCAGCAAAACTGAGCTTTTCTGCCATTTAGAATAT
ACCTTTTATTAATTGGACAAATAGATTAGATACACATAGCAATAGAATAAACCATAAACCTAGTCTTTGTAATTTATCTATACGCTTAGCTTTTTGT
TTCCTCTTTAATCTAACTAATAATGTATTTTTAATATCATTCATTAAATTATCTCAGATTTTTAGACGGTGTATAAACCCTCAGTATTACATGTTGT
TATGATATTGTAAAGACGATGCCAATAGCGATCATACGTATTTTTACGTTTGTAGCTATTGGTNCGGATGACTAGATTGGCGACCCAGTGATTCTGA
TCAATGGTCTCATGTAGATGCCCGAAATAAGCCCCCAGTTCAATTTCGAATGGGATCTTACACTCACGCCCCTTACACATTGCTTCACGCAATAAAC
GCATTGCAGAATTCTCTGCATTGGTATCTTTAAATAAAAGACTAATGTATCCAGGGCTACCACCAGTTTCTTCATCAACATGGCCTGAACAGCAATA
AATAGTTGCAACATTGATAAATTGATTAAACCATTTAATTAATGGCCTACATGCTTCATCAATAAGATCTTCATATTCAGGTTTATACATTACTTTA
ACAGTATCATCTGCACGTTGTTTCACATGATGAAAATATTGCTCCCAATTTACATTAGTGTAATATAGCATATCCATATTAGAATTACTCATACAAA
TCAACCCCATATGTTATTGGCATATTCGCGGTCATTGAAAATGCGGGTAAGATCCATCCGCTTTTGAATGCGCGCTAGTATCCATTTTAGTTGTTTA
GTTGATAGTTCTTGATTTTGCTTGTACTCACCTGTAGCATGGATGTAATAATCAAATTTACGACTTACAGTAGTAGTATGTGCACATGCAATAGCAA
ATGCTTCAAGTGCAGTTAGTTTGGTTGATCCATTATCATTACAATTAGGGATAAACTCAAGTACACTATTAACTGCATCTACACCACTACCCAAATG
AGCCCAATCTTTCTTGGTGATGTTGATACCCATGTCTTTAAGAATAACTGTATATATGTCACCATTCTCCATAGTGAACATCATAGAAGTATTACCA
TTAAACAACCTGCGTTCTATGACTGGCAAGATATTTACTTCAACTTTAAACCAATCAGCTAAATCAACACCTGCGGTAAGGGCATTCAATAGATCAT
AAACATTATCTATAGTTCCAGCAAAAGCCATAGTTTTAACACGTTTACCTTGCCAAGTAACTGTCGGATGAAAAATTATCTTGTGGCAATCATTGTA

Figure 8(K)

ATATACATCTACACCTTCAGCTTTAGCAGTTAGATCAATATAACCGTTATCTAATACTGGAAGTCGCCCAATGCTATCAGTTGCATTATTCCGCTCA
ATTAATAGGCAGTCTGCAATCATGACTTTACCATCATTTACGATATATGTCATTTTCACTCCTTATATAATAAAATAAATAGGCTTAAGCGAAATAAAG
CCCTCCCCGAAGGGAGGGCATTATCAATAGGTGGGATCTCGGCGGCACCTTCATTTGCGGACGGGAACGCTGAAGGGAGATAGTCCGGGAGATCCCG
ATTTGGGTATTCTTTACATATGGTATTACTGCAAGTATTTGTTCCCCGCAGTATAATCACCATTGATCCAATTTTTGATTACAACACTGATCCCTTC
ATTTTCTTTAACGGTAACCCCCAACTCAAGATCGATTGATTGATAAGCTACAGCCGCCAGTGTTAACCGAAGATAAACGGATCCATCTTTTTCGATA
TCGTAGGATACTACGAACCCGTCTTGTAGATTTGTAGCTGGAATGTATTAGCATGTTGTGGATGGAGACGATCCATATTGTACTCGACGACATCTAG
TAGATATTGCCGAGCATCAGCAGCATTATCAAATCCGAGANCGCACAGACCGATCGGATAGCGAGCTTGCGTGCATGTAACTTTCATAGATACTACA
CGATGTTGTTTGCACATTATATTTTCCTCTTAGATGTCAAAACCCTCCCGATCAGGGGAGGGTATCTCATTGGTACTTCTTCAGCAAAACTGAAACT
AAGATAAAAGAGCAATCGTAAAGGAACTACATAGAATAGTGTATTTCTTTTACTATTTTTACACAACCTCTTTAGATGGGGGTTCTTTATGAATCCA
GTCTAAAGTTGTTGGTAAACTATTATCTGATCTGAAGGTACACACCGTCCGGAACCGAGAGTGATCAACTACAGATAATTGCCCGTTAATCGCAGCC
TCATATTGCCTACACAACTTCACACACCTTTTCTCTAGATCAGTTGGTTCGTAACCTTCTTCTCTTGGTTCAGTGTATGGTCCATCCCAAAAGAATA
TTAATCTAAGATCAATCCCAGATTTATACTCCGCTTGGTATGAATATTGNTGAACATCAAAATCATCTAATTCTTCAACTAGATGTGATGTTATTGT
TCTAGGNTGTTCATGAGTTAATTCACTGTATATATGTTTATTTCTAGGGTTTTGTAAATCAACTACGATAAGTTGACTAGTCATTTTAACTTTTATC
CAGATGTCTATTACGAGTGCGTTCCACTGCTGTAGGTTCGACAGTGGCTCGCGGTAGATAAGTAATCTCCGGGAAAGTCTTATTAAGAGCATCTTCA
ATTAGCTCTTTAGCAATCTCTGCATCGATGTAATGGTTTAGAATAATACCACGATGATACAGGAAGAAGCTGTATTCATCATAACCATGGCGAAGAC
TTACTTTACCACGATACCCACCATAGGTTAGAGTATCTTCGTTAATTCATTCCGATAAATATCAAGTTGGATATTATTTTGAAGATGCATTTGAATG
AAGTCATTACTATCACCGCCGAATAGGGTTGGTCGTTTCCGACCAGTAACAACATCTTGGATGGAATCCATTAGTCGGTTAATGTCTGTTTCTAATC
GTTGGATATCACATTGAGAATTCATTGCTTCATGGAAACGAGTTACAACTGCATTGAATTCTTCTTCAGTCCAACCACTGGTACGTTTTCATAATCA
ACAATGATAATACCGAACCAGGCATAACCGTTAGAATGTTTACTTTAACACATAGATGAGGTACATTATCAGCACCTGACTGATGGTTAACAGTGTA
ATTATTATTACGGCTGATTACTAGTTTGATAAAAGGTAGACTAATGATTGACGCCATGGAAATATTCCTTTTGTATTTTTTAAATTAAAGTAGGAGT
TATTATTGAGTTTCAACTCAATACATCAATAACTCCAGTATGTTTTCAAAATTAAATACATGTATTTACAGTTACATTGTAACCAGTTAGTTTTGCC
AACAATACAAATTAGCGAACCTGTTCGATTTTTTCAGAAACAATGAAAATATGTGCAATACGATCCTCATCAANATACCGATATCGAAATGAGGTAT
AACTAGATGACACATCCGTATCGTTTAAATAGGTGATATTAAAATCATCTACTTCCCTACCATTAGCAGCCGCAACGGTATTTAGAATGTTGAGTAG
ACTCATTTTACAGATTCCTTTTTAGTATATTAATATTTCAATAGACTATTGATAAAAGCATTAGGGTCATAACGGTTATTTGAAAAAGCCGCCATTA
CATCACACCCTGGCTGATCTTTAAATCTGATATCTTCAGGAATATCGAAGTCAGGGAACATTAGTTTAATATACTCCCTAACTTCTTGATCTCGTAG
ATATGGAATCTCCACCATGTAATCAACGCGACCTTTCCTTAGAAGTGCTTTATCAATATTCTCAGGATGGTTTGTAGTTAGAATGGTCATAGTCTCA
TCTAGTGGAACAATGCCATCTAGCCCATTTAATAGAGCTGACAAAGTTAATCCGCTAGCTGGTTGTTCATACGTGATTCCATTCTTCATGCATTTCT
TTAATTTCCACCATCGGCGAATTGTGGTAAATAATGGATCTTTTTCATCGGCCCATTTGAAACACCCAGTTCAGCCATAGCATAAGCACTTATCCCA
AAACCTTGATCATCGCTATTTTCATCAAAGATATAGATGGTGTCATTAACCCAACTACAGAGTATCCTTCATAGTCATCTTTAAGATCAACCCATGC
AGACGGATATTTTTCAATTAAATCAATAAAAGAATATTTCCTCTCTAATTCCTTTATCTCTTTATCTAGTTTTACAGGATCATTTAAAACACGATCT
TTAACTGCCGGGGTATCATCGAAATCTTCAATTAGAAGAATATTACCTTTAGGTAGTGTAGTAAATGCCCGCCTAAGACTATCATTGGTCATAGAGG
CTAATGACAGTGCACTAACATTTTTATTAAAATGTGAGGCAATCGCTTTACTGATTGAGGTTTACCAGTACCAGGAGGACCTGTTAGAACACAAGTG
AATTTATAGGGTAGTCCACGATCATCGTACCATTTCCGATCAGAATAGAATTCTTCAATCTTATTAAGGAATTCTTCTTTGATCTCTTTACGCAAAA
TCACCGTGTTGATATCGCGTTTAGTAACTTCAATCTCATTGCCCCAACGGTTACCATCCCAATGTGAAATAGTCAGACCCCTTTCATTTGGGCGCCA
ATGGTAAGCATCTACTAAATCAATAATTAGTTTACTACTCCTAGATAATCCACGGATAGTAATATCCATTTGATCTCGACTGGCATTTTGACTATCC
CGGCGTGCTTTTACAAACCAGAATAACCTACCTTTAAACAGAAAGAAATGTAAGCCAAAACCAACACCAATTTTCTGTTTAGTTGCACTATAACTTT
GCTCATCAACATTAGTTGAAAAACGTCGATTAAATCCAGCTAATGGCTGCTTAATATACCATTCCATGAAACAATCAAAGTTCTTCTCGTTCAGCCC
ATTACCCATGTTGGTAATATGTAGACTAACTGTAAACTGATTTAATGCGAACCTAGCTAGTTTACTTGGTAAGCCTCTTAGAGTGGTCCAGAATAAA
CCACCAATTGCCATTCCGATAGCTCCACCCATAACCATATTCTTCTGAGAGATATCGATGAACATGGCGTAATATTGCAATAAGGTTTCTATAATCA
TACTAGCATCCCTCTGGATAGCTTAGGAAATATTGTCCACAGATCATGTATTCACGTTCTAGAAATCTAGAGTATGACTTTCAAATATTTCACCTAC
ATCTTTACCATAGATTTCCGTATACCCATTTTTGAATACGGCCATTACATAAACATCAGACATAGTCATGCCGTAGTTATAAATTTGATTGTCTCTG
TATTTTGGATGAAATAGGTCATATAAAAAACGAGTCATTGAACTATTGGCAACAGTTGTCACCCCTTTCTGCTTTAAGGCATAACGTACTTGTTTAA
CCACATAGTTAACTTTAGAGCGCTCGCCAAATACCGTCAGTTTATCTACATTGCAATTACGATATCCCATAACACCAGGATTAGCTATCACGGTGTG
TTTTGGAACACGTACATCAAAGATAATGCCATTAGGGGATAGAATAATCTTTTCATGGTTAAATAGAACATGAAATAAATGTCGTTCTGGTTTAGTG
ATTTTGATACTTAACCCAATCACCCCACTAATCTTTCTTTCTAGATCTTCTAGTGACTGCATCACCATGTGATATTGATTGAAGAAAGCATTGTTCT
TATATTGATCTAATTCAAAGTATTTCCAACTTCCACGAAATGAATAGCATGGCTTTGGTATAACCTTTAGTTAATCGACACTTGAGTTTGTCAAACC
AGCTTTCAAGATAACTCTCGACTGTAAACCAAGTGGGTTATTATATAAGTTTATTGGAATATGATAAGCTAAATCTGTACATAGTTCGACGATGCAT
TTATATTCCTGCCAAATAAAGAAAAATAAAGGGCTCCGAAGAGCCCTTTATGTATTAGATTTTTACAGACCAACTTTGCTCGAATTCCTGATATAGG
AAATTGTCTGACGCATTATCCCAATTTTCTCGATCAGTTACACCATAATAATGGAATTCTAGTTCAGTAGGTCCACCAACAAAACCATTCTTAGCAT
AGCTATAAACTTGCCATTGGTTAGCTTAATCAGTGTATCCACATAGAAACTATTACGGTTCCATATTTCATTGTGGATGTACTTAAATACCACACTG
TNGATATACTTAAATTGCGCACTTGGTTTTCCGAGTACACTCCAATAGAATTTACGGATACCTATTTCGGTCTTGAAATTAAACTCTCCGTTGCGAA
TGTTGTTAGAAACAATACGTGCCAGTTTATTAACCCGATTTCTTCACCGATTAGATAGATCCCGGAAACACTACATCCATCTCCTATTGATCCATTA
TTAACTAGTGGATCAACACCATATTCATCAGTGAAAATGGTTTTGATAACCTCTTTACCTTCTCGACGCACTAACATATTCAGGTGACCATCTTCGA
TATATGACATATGGCTAGGCTGAATATATTCACTTGTATCGACGATAACATCATTCGCCATTACATTAAACTGTAGATGGTTTACCAGATCACTAAT
ACCTTTAAAACGAATGGCTTGGTTCGCTGTATTTAGATCGACATACACCACGACATCAATAATGCCTTGTTTTAGTGATTTGTCATCTTTGTCAGTA
GTTGTATCAATTTTACGTAATTTTGATATAGTTCACTAAAACAAGATATGATGTCATCATGTAGTTTAATTACATCAGATCCATTTCGTTCAAGCGC
TTTAAGCGATACGTTAAACCAATACGAATTTTATTAGAACGACGTGCCATGGTTATATCACCTATGTTAAATTAATGAATTATTTATTCAATTACCG
TACTACATCTGTGATTAGAATAAGTTCACCATCACTATTGATAACACTATAGCTTTTACAATTTCGATGCGCTTACTAATAATCTTATTCTCTAGAT
CTACTTTTACGATATTAACACGAATTACCTTATTCGATTGATCATGCATTTCTTTAAAATGCATTCGATATTTTACCAATGACAGCTTTTAATTTTC
AATGCTGTCAATGGATGAATATTTAAAACTATATGCTTCTGCCAGGGTTTTGCATTACCCACAACCGTAGTTAGGGTACCCCAATAATCATAAACAT
ACAACGCAGTATCACTATTGGGATTATCGATAATTTCAATTATAAATCCACTTGTATCACTCCTATTAGTTTATTGATAGTACACTTGTAATATAGA
TCTTAAATAAATTATGATCTAACCATTTAAAATAGATAAAGCCTCTATATGCCAATGGTGTATTAGTTCTTCTTTACTAATAATATTATTGAAGTAG
TTTAACCGATGTGATACCATTAATTTAGAATGCATATCGACTTCACTACTTACCTTAATCACCCCAGTCTCTAATAATTGCAGAGATCCAACATACG
CAAATAAAGTTGGTTTTAAATACCAGTGTTCCCTATATTGTTTTTGATCAGGTACATTTCCTATAATGTAGTCAGTAGAATTACTTCGGTATGCGTA
AATAGTTGATTTAGAACCAAGTAAATTAAGATCGATATCATAACTCCCGCTTTTAGCTGCAATACATTCAATAACTGATGGGGCCACACATATACGG
TTGGTTACACTGTCTTCGCCATCAGCTCTATTACTTGGAATATATGGCCTTAATAAACATAATCCCCAAGGTATACTGTCGATATGTGATACATAAT
TAACCTATTTAATTAAAACAGATAACGCTCTGTTACTGAACGATATTGTGACATGATGTTTAATGGATCAACATCCACTGGTGCTTTAGTGACAGTT
AAGCGAGCACCTTTTAAAAATCACCAATATCTAATTTCCTTACAGTAACATCATGGATAGTGTTTTTCGTAATCCACTCAGTATCAATGCTATTGTG
AGGATATTATTCTTAATCCATTTGTCAGAGTCCCTAAATGGAATGGTATAAACATACACAACCATTTTAAAATATCACTTTTATCGATATTATTTGA
CAATAGATTGTAATATCCCTATCAACAGTAGCATATCTATCACTATCAAATAACTTTTCGATAGCGCTACCAATACCTAAATAAGATGCATCTTTTT
CAGATGACGTTGCATATAGGTATTGGTTAGACTCAATACCATCCCACATAACAAGTTCACCAGATCTTTTAAATCCTGGCATTAATTCATCTTGTTT

Figure 8(L)

ATAAAGAGAACCATGGTAAGTAATTCTGGTTTATTCATAATAAAATCCACTATGCTTTATAAGAGTTATGGTTATCAATTAACTTCAAGGTAGTAGT
GTGGCAGTATTGAAGTGATTGGTTACTGCTTCGATCAGCATTTGCTCGATGTTGATTTTGTAGTATTCTGGTTCTTCGTTCAATTCCCAATAATAGT
CGCACGTAATAGTGCAGGTGCTATGAATCTAACTACCTTACCATGTGTGTCAAACTCTACATGAACATTGCATATTGTTCAGTAGTATGATTTTATA
GAAATGAATTACCAGCGTAACTGCGACCTCTATTTCACCATGAATACTGGAGTAGGTTTCCTGGTGGAATACTTTACCTTTAAGGCGTGTATTCTCT
TCAATGATATTACCAATTCTTTCAATTTGTCTTATCTAGTTGCATTTGTAGGTTCCTATTAATAAATGTATACGATGGATATCTTTTACGATTTCCG
GTGCTTATCCATATCTAGTTTTATATCAGTATATATCTTGAATCTATTAGATAGGCTATCCATATCTACGTGCAATGCCCGAATATGCATATCAGTA
TCTTTTGGTTTACCTTCAGACTCCCATACGGCCTTTGCGATATCAAATGCTACATTGTTCAAATAGTATTCGACTTCATGTTCATCAAGCAAAAGAG
CATCATGGAAACCAATACGTGATAGAATGGCGTAATCACGCTGATTAACATCTCTCCAATCTTTACGCACTAAGTAACTTTTACCAATTCCATCTTT
TTTACAACTTTTACTAATAATTTCTATAATGAACTTATCATGCCATTTATAATCCATAATCATTACTCCTTTATTTAATCAGCTTCATTACTAGAGG
AACAGATAGACTTATGCCATTAGCCATTTTAGCTAGAATATGATAGACATCGTCTGCTTCTTGATTATTGTACAAGGTATAGAAATGGCATCACCAT
AGTAAGGACTGTAGTTAATACGGTCGCCATACACACCACTCACAAAACTATAATCTAATCCATCCGTGGTAGTCATAATAACTACAACATGATCATC
CCCAACTATACCGGATTCTAAATCCTCACATAGTTCTAGTTTTGTTGCACACCTCGTTGACAGATCCATACTTCACGGTATTGATGATGAGGATATG
GATTACATGCTACATCATTTTCACTAACGAAGTACATAGTCCCCCAGTTGTAAGACTGGAATTGGGTTGTTGTTTGTGGGCTTCCCATACCTCTTCC
ATACAAAGGTATGTTGTTAACCCATAGACCATCGTTATTAAGACTATCAACGATCCATCACGGACACGTACTACACGGAGTGTTTTTGCCATTTTTA
ATTATCCTAAATACATAAAGGAATCACTTAGTAAACACCATTGACAATAGCATCGCGGAAACGAGACCATTCCGTTTGACCAACTACGAATACTCGT
TCTTTAGGACGCCATAGATGATCACCGCAGTCAAGACCCAAGTAAAGCATATTGGTTTTCCATGATTGCGATGAACACGTAGTTTAGCTGATACACT
GAACTCACACATTACTTCATTTACATCAAGATGTGTAGTGTATCACTATCATACCTGACATACTGATACCAATTGATTTACGAACTCGGATTAGATC
CTCAGTCATCACCCGCCAAGTTACCAGATGCTCGTAATACTCATCTGGTGTCATGTTGTTTTTATAATTCAGTGCACCTGGAGTCATTGACATCAGT
TAGTGAACTGGAAGTCATGTAATACATCCAATCACTATTATGACGGAGTTCTTTAAGCTTCTCTGTATTACGATATTAGTAGTTGCTTTAGTCATCT
ACGTACCCTCATCAGATACATAAGTACGTTCAGGCTGAACACATATTTGATGTTATTAATTACAGCTGTGATATAAACCTGATATTCTTTTGAAATA
GATTCCATCAGTTCAATAGATACGGAATTGAACTCTGAATAAGTTATTTACTTTCTTAGTTCATCAATTCTACCGACCGTAATTACACCAACATCTC
TGAAACTGATAACTGGATAGTGTTTCCAATATAACAATTCAGTTTACCAAGATGAATTACTTGAATTGTTTCATCGCACCATTGTTTCTTTTCTATT
GTAGTATTCAACACGACGTTCGATGAAGACGCGAGTACCAGAAACAGAGGTGTACGCATTCAGTCATAACCATACTTATGGTACGTTATTTGGATCT
TGGCGCCATTTTGGATGAATGCTTTCATTTGTATTTTCCTTTTACGAAATAGAAGCCCTCCCGAAGGAGGGCAATTACCATTATTAAATTACGAGTC
TATTACTTCTTTTAATTTTCACCAGGGGTAGCTAGATAATCTACATTATATTTAATAGCAATTACACCACAAGTTCTTTTTCATAGCTGTTCTACCT
GATCGCATATTTATCAATAGCTCCATCTTCTACATCCTCGTATAATGGATATTGACTATAATATTATCAGGTGTAAGTACAGACAGTTTCAATCCCA
TCTTTACCAATGACTGGGTGATATGTCTGTTTAAGACCTTTACAATGATAGTGATAGGTATGCGCTGTGTTTAGGTGGTCATGTAAAGATACCTCAT
AAACCGTTGGGTAGTCCGTCTTTAAGACAGTTAGTTGATTAACATCTTTCAATGATTATCTGCAATATTCTTAGCCAATAACAGTAGATCATTGGTG
ATATGTTTTAATGAGAACTTAAGCCTCTCCCTTTGTTTATATCGGAACCTTATTATCACAGTAACTCCATCCGGTTATTTTTATAATTCAGTACAGT
GATTGGTGTATTCGGTACAAAGACGGCTAGTTCGTCATCGAATACAATGTAAACCATCACTTTATAATTATTAACCGATTCTTGGAATTGTTGTGTG
ATTACATTATAGTCTTTTGTGCGATGGCTAAGAAACAGCTCACTATTAGCTCGGCAGAAACTATGTCGCGCTTTTTATCAGCACTCATAACAGCGAT
ACCACGGATAATGAATTTATTATCTAAGGTATATTTTCTTTGAGACATCGCATAGTCGACTACATCAACATCGCCGCCAAATAGCACGGCATTTTCA
CCGTATCCACAAATAAGAGCCATTTATAATTACCTGTTTAAAAATTATATTCAATAAATTGAGAGTGAATAGTTCACTACATTCCCATGTACGACTT
GCTAATTTATATTTACCTTTAACAGGTAAGTCAAATAACGTAATGCTTTTCTACTGAACCAGCCTCATGATTAACCAATAGAACATTCCTAGCCTTC
AGAATATTTGAACAATTTACAAGTTCATAATCATCTCGCTTAGGTGTCAATAGCTACATTAGTGCCTGGTTTCTAGCATACCAGAGCACCTCATGAC
CCTCTGGATTAATAATAGAGATATAGCTGACGTTCAGCGGGTAACCACAAGTTACGTGGATCATANTCTCCATTAACATCAAAGAATTTAAATATCA
TAGAGTTGGAACCGGTTTTGATGGATCAGCAATTANTGCAGATTCNTCTACATAAACCATTGCNAAGTTTTCACCTTCTTTACGAATACCAGTAGAA
GGTGTTTTCGATGGATCATAACGATAATTGGCACTGCTGTCCAGCTGTTAAATAAGTTGGGCCAGTTAATGCATTGGGTTTTGGATGAGGAATATCA
ATTTAGTAATACAATATTGACCAGTACGAAACTCACGCATTATATTAACCTCTTAATGAATAACTGTTGCAGAAGGACGACATTTCATAGTTTTAA
AAATGTCAGTAGGATAGATATTACCAGCTTGTCCGAAAGGTTTATCGGCTAGAAGAAACTGCGGACAAACTGTTTGTAGATAACCACTATCAGTGGG
TAGGAATCCTTCAATATCACTGATGAGAATTTGCCAGATGGGCAATTGGTTATAATAGTCATCCATATTGTAGTATGCGTGGAGTTTACCACCGAAC
CCATATACAAACTGATGAGTATCAATTAGACGAATACCAAATTTAGGTTGTCGTCCCATCCTT

RECOMBINANT B11 BACTERIOPHAGES AND USES THEREOF

SEQUENCE LISTING

The instant application contains a Sequence Listing which has been submitted electronically in ASCII format and is hereby incorporated by reference in its entirety. Said ASCII copy, created on Feb. 27, 2018, is named 102590-0610_SL.txt and is 277,834 bytes in size.

TECHNICAL FIELD

The present technology relates generally to compositions including recombinant B11 bacteriophages, methods for making the same, and uses thereof. The recombinant B11 bacteriophages disclosed herein are useful for the identification and/or antibiotic susceptibility profiling of specific bacterial strains/species present in a sample.

BACKGROUND

The following description of the background of the present technology is provided simply as an aid in understanding the present technology and is not admitted to describe or constitute prior art to the present technology.

Bacterial infections may complicate a patient's existing medical condition, and in some cases, may lead to death. Patients suffering from various bacterial infections often present with similar symptoms, thus making it difficult to accurately identify and characterize the bacterial species or strain responsible for the infection. Accurate identification of the bacteria through conventional lab tests can be challenging and may require incubation periods of up to several days. Additionally, some bacterial strains are not amenable to culturing and in vitro analysis in light of their fastidious nature. In other situations, the observable behavior of some bacterial strains is not readily distinguishable from others. Moreover, individual strains of a particular bacterial species may exhibit resistance to otherwise effective antibiotics.

Early and accurate identification of the bacterial strain(s) responsible for a patient's illness and determining its susceptibility to various antibiotics is an important aspect of the treatment selection decision process.

SUMMARY OF THE PRESENT TECHNOLOGY

In one aspect, the present disclosure provides a recombinant B11 bacteriophage nucleic acid sequence, wherein the nucleic acid sequence between (a) position 65,939 and position 65,940 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof. In certain embodiments, the open reading frame of the heterologous nucleic acid sequence is operably linked to an expression control sequence that is capable of directing expression of the reporter protein. The expression control sequence may be an inducible promoter or a constitutive promoter. Additionally or alternatively, in some embodiments, the recombinant B11 bacteriophage nucleic acid sequence comprises a sequence selected from the group consisting of SEQ ID NO: 2, SEQ ID NO: 3, SEQ ID NO: 4, and SEQ ID NO: 12.

Examples of fluorescent protein include, but are not limited to, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOκ, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa. Examples of chemiluminescent protein include, but are not limited to, β-galactosidase, horseradish peroxidase (HRP), or alkaline phosphatase. Examples of bioluminescent protein include, but are not limited to, Aequorin, firefly luciferase, *Renilla* luciferase, red luciferase, luxAB, or nanoluciferase. In some embodiments, the bioluminescent protein is nanoluciferase.

In one aspect, the present disclosure provides a vector comprising any of the recombinant B11 bacteriophage nucleic acid sequences disclosed herein, as well as bacterial host cells comprising the vectors of the present technology. The bacterial host cell may be a natural or non-natural host for B11 bacteriophage.

In another aspect, the present disclosure provides a recombinant B11 bacteriophage comprising any of the recombinant B11 bacteriophage nucleic acid sequences of the present technology. Also provided herein are recombinant B11 bacteriophages comprising a nucleic acid sequence selected from the group consisting of SEQ ID NO: 2, SEQ ID NO: 3, SEQ ID NO: 4, and SEQ ID NO: 12.

In one aspect, the present disclosure provides a bacterial host cell comprising a recombinant B11 bacteriophage disclosed herein. The bacterial host cell may be a natural or non-natural host for B11 bacteriophage.

In one aspect, the present disclosure provides a method for identifying at least one bacterial strain or species in a test sample obtained from a subject comprising (a) contacting the test sample comprising bacterial cells with a recombinant B11 bacteriophage of the present technology; and (b) detecting the expression of the reporter protein of the recombinant B11 bacteriophage, wherein detection of the reporter protein indicates the presence of at least one bacterial strain or species in the test sample. In some embodiments of the method, the expression of the reporter protein is measured in about 5, 10, 15, 20, 25, 30, 35, 40, 45, 50, 55, 60, 65, 70, 75, 80, 85, 90 or 120 minutes after contacting the test sample comprising bacterial cells with the recombinant B11 bacteriophage.

In another aspect, the present disclosure provides a method for determining the antibiotic susceptibility of a bacterial strain or species in a test sample obtained from a subject comprising (a) infecting a plurality of test samples comprising bacterial cells with a recombinant B11 bacteriophage of the present technology and an antibiotic, wherein the plurality of test samples is derived from the subject; (b) detecting the expression of the reporter protein of the recombinant B11 bacteriophage in the plurality of test samples; and (c) determining that the antibiotic is effective in inhibiting the bacterial strain or species in a test sample when the reporter protein expression levels of the recombinant B11 phage infected bacterial cells in the test sample are reduced relative to that observed in an untreated control sample comprising bacterial cells, wherein the untreated control sample is derived from the subject and is infected with the recombinant B11 bacteriophage of the present technology. The expression of the reporter protein may be measured in about 5, 10, 15, 20, 25, 30, 35, 40, 45, 50, 55, 60, 65, 70, 75, 80, 85, 90 or 120 minutes after infecting the plurality of test samples comprising bacterial cells with the recombinant B11 bacteriophage.

Additionally or alternatively, in some embodiments of the methods disclosed herein, the test sample is blood, sputum, mucus, lavage, saliva, or a swab obtained from the subject. In some embodiments, the subject is human.

In certain embodiments of the method, the antibiotic is selected from the group consisting of rifampicin, tetracycline, levofloxacin, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

In one aspect, the present disclosure provides methods for making a recombinant B11 bacteriophage of the present technology in a bacterial host cell. In some embodiments, the method comprises (a) contacting a first B11 bacteriophage genome with a first sgRNA-CRISPR enzyme complex and a second sgRNA-CRISPR enzyme complex in vivo under conditions where (i) the first sgRNA-CRISPR enzyme complex cleaves a first protospacer sequence 5' AGAAGATCATTATCGAAAGA 3' (SEQ ID NO: 5) within the first B11 bacteriophage genome; and (ii) the second sgRNA-CRISPR enzyme complex cleaves a second protospacer sequence 5' AGACATAGCCCCTCTCCACA 3' (SEQ ID NO: 6) within the first B11 bacteriophage genome to produce a cleaved first B11 bacteriophage genome; and (b) recombining in vivo the cleaved first B11 bacteriophage genome with a heterologous nucleic acid sequence in the presence of a recombination system under conditions to produce the recombinant B11 bacteriophage genome, wherein the bacterial host cell is infected with the first B11 bacteriophage genome, and wherein the heterologous nucleic acid sequence comprises an open reading frame that encodes a bioluminescent protein, a fluorescent protein, a chemiluminescent protein, or any combination thereof. In some embodiments, the first sgRNA-CRISPR enzyme complex comprises Cas9 and a first sgRNA having the sequence of 5' AGAAGAUCAUUAUCGAAAGAGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO: 7). Additionally or alternatively, in certain embodiments, the second sgRNA-CRISPR enzyme complex comprises Cas9 and a second sgRNA having the sequence 5' AGACAUAGCCCCUCUCCACAGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO: 8). The recombination system may be endogenous or non-endogenous. The first B11 bacteriophage genome may be recombinant or non-recombinant.

Additionally or alternatively, in some embodiments of the methods disclosed herein, the cleaved first B11 bacteriophage genome comprises a first cleaved bacteriophage genomic fragment and a second cleaved bacteriophage genomic fragment. In certain embodiments of the methods disclosed herein, the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment.

Additionally or alternatively, in some embodiments of the methods disclosed herein, the recombination system is a non-endogenous recombination system that is induced in the bacterial host cell. The non-endogenous recombination system may comprise lambda Red proteins Gam, Exo, and Beta operably linked to an inducible promoter. In some embodiments of the methods disclosed herein, the inducible promoter is araB and the non-endogenous recombination system is induced by the addition of arabinose.

Additionally or alternatively, in some embodiments of the methods disclosed herein, the bacterial host cell comprises a non-endogenous CRISPR expression vector comprising a nucleic acid sequence that encodes a first sgRNA, a second sgRNA, and a CRISPR enzyme. In some embodiments, the first sgRNA and the second sgRNA are operably linked to a constitutive promoter. In certain embodiments, the CRISPR enzyme is a Cas protein selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. The CRISPR enzyme may be operably linked to an inducible promoter, such as a tetracycline-inducible promoter.

In another aspect, the present disclosure provides sgRNAs that are useful for making the recombinant B11 bacteriophages disclosed herein. In some embodiments, the sgRNA sequence is selected from the group consisting of SEQ ID NO: 7 and SEQ ID NO: 8.

Also disclosed herein are kits comprising one or more coded/labeled vials that contain the recombinant B11 bacteriophage of the present technology, instructions for use, and optionally at least one antibiotic.

BRIEF DESCRIPTION OF THE DRAWINGS

FIG. 1 shows the heterologous nucleic acid sequence that was inserted into B11 phage genomic DNA between position 65,939 and position 65,940 of SEQ ID NO: 1 using single guide RNAs (sgRNAs) sgRNA 6.3A and sgRNA 6.3B (SEQ ID NO: 2). The underlined sequences represent the homologous 5' and 3' flanking regions of the heterologous nucleic acid sequence.

FIGS. 7(A)-7(L) show the B11 contig-6 genome sequence of non-recombinant B11 phage (SEQ ID NO: 1).

FIGS. 8(A)-8(L) show the B11 contig-6 genome sequence of the recombinant NanoLuc® B11 phage that was cleaved with sgRNA 6.3A and sgRNA 6.3B (SEQ ID NO: 12).

DETAILED DESCRIPTION

Figure 2A:
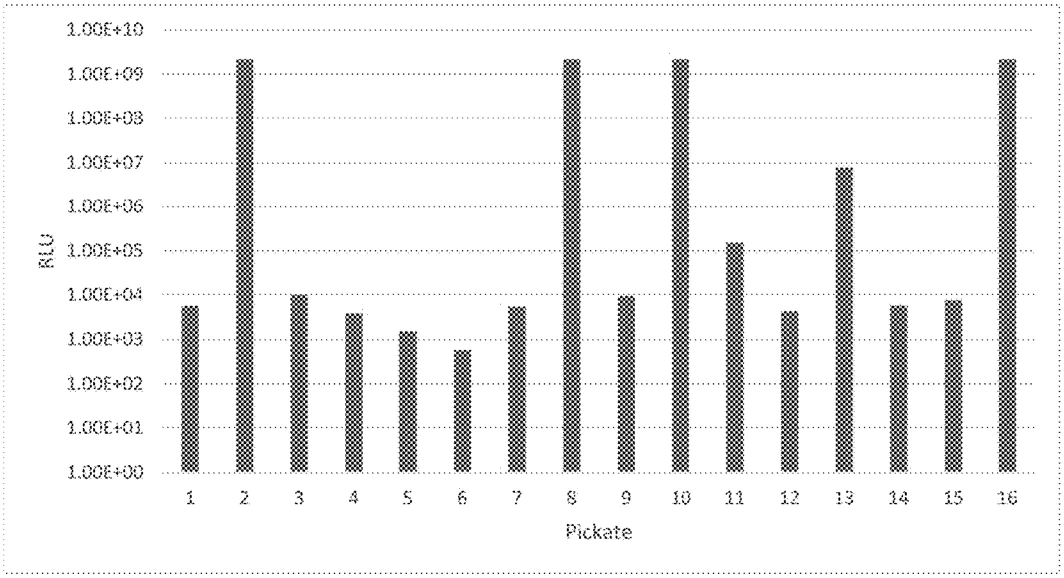
FIG. 2(A) shows the luminescence activity profile of individual plaques that were generated from the recombination experiments in *P. aeruginosa* PAO1 strain harboring crR-B11 6 (site 6.3 cutting plasmid) and pBBR1-B11 6 (site 6.3 donor plasmid).

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR* 1: *A Practical Approach* (IRL Press at Oxford University Press); MacPherson et al. (1995) PCR 2: A Practical Approach; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

Definitions

Unless defined otherwise, all technical and scientific terms used herein generally have the same meaning as commonly understood by one of ordinary skill in the art to which this technology belongs. As used in this specification and the appended claims, the singular forms “a”, “an” and “the” include plural referents unless the content clearly dictates otherwise. For example, reference to “a cell” includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term “about” in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, “bacteriophage” or “phage” refers to a virus that infects bacteria. Bacteriophages are obligate intracellular parasites that multiply inside bacteria by co-opting some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid can be either DNA or RNA (but not both).

Figure 5A:
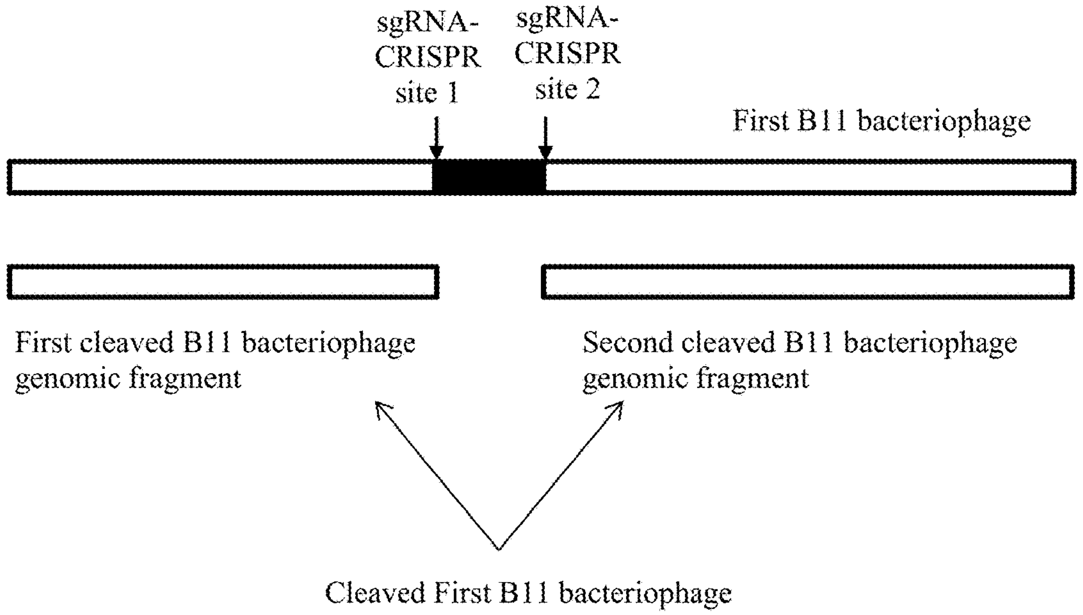
FIG. 5(A) shows a general schematic of a first B11 bacteriophage genome (i.e., intact B11 bacteriophage genome) and a cleaved first B11 bacteriophage genome. The cleaved first B11 bacteriophage genome comprises a first cleaved bacteriophage genomic fragment and a second cleaved bacteriophage genomic fragment.
Figure 5B:
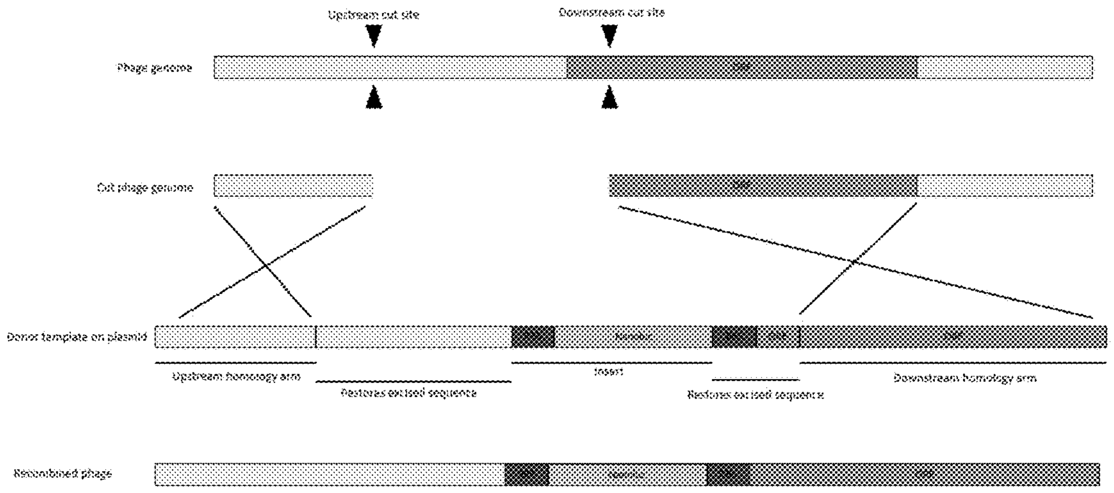
FIG. 5(B) shows a general schematic of the donor template design and recombination between a cleaved phage genome and the donor template. Two double-stranded breaks are generated by Cas9 at sites specified by the two sgRNAs. In some instances, Cas9 cleavage excises a phage DNA sequence that is important for phage viability. The donor template contains any exogenous reporter gene inserts like nanoluciferase, but must also restore the function of excised phage sequences. The 5' and 3' flanking regions of the donor template are homologous to the DNA sequences immediately adjacent to the two cleavage sites in the phage genome, and are necessary for repairing double-stranded breaks via homologous recombination.

As used herein, a “cleaved first B11 bacteriophage genome” refers to the B11 bacteriophage genome fragments that are formed after a first B11 bacteriophage genome has undergone enzymatic cleavage with one or two sgRNA-CRISPR enzyme complexes. When a first B11 bacteriophage genome is cleaved with two sgRNA-CRISPR enzyme complexes, the “cleaved first B11 bacteriophage genome” excludes the shortest nucleic acid sequence that lies between the cleavage site of the first sgRNA-CRISPR enzyme complex and the second sgRNA-CRISPR enzyme complex. See FIGS. 5(A)-5(B).

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, an "expression control sequence" refers to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences.

As used herein, a "heterologous nucleic acid sequence" is any sequence placed at a location in the genome where it does not normally occur. A heterologous nucleic acid sequence may comprise a sequence that does not naturally occur in a bacteriophage, or it may comprise only sequences naturally found in the bacteriophage, but placed at a non-normally occurring location in the genome. In some embodiments, the heterologous nucleic acid sequence is not a natural phage sequence. In certain embodiments, the heterologous nucleic acid sequence is a natural phage sequence that is derived from a different phage. In other embodiments, the heterologous nucleic acid sequence is a sequence that occurs naturally in the genome of a wild-type phage but is then relocated to another site where it does not naturally occur, rendering it a heterologous sequence at that new site.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, a "host cell" is a bacterial cell that can be infected by a phage to yield progeny phage particles. A host cell can form phage particles from a particular type of phage genomic DNA. In some embodiments, the phage genomic DNA is introduced into the host cell by infecting the host cell with a phage. In some embodiments, the phage genomic DNA is introduced into the host cell using transformation, electroporation, or any other suitable technique. In some embodiments, the phage genomic DNA is substantially pure when introduced into the host cell. In some embodiments, the phage genomic DNA is present in a vector when introduced into the host cell. The definition of host cell can vary from one phage to another. For example, *E. coli* may be the natural host cell for a particular type of phage, but *Klebsiella pneumoniae* is not.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/or entities are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, "operably linked" means that expression control sequences are positioned relative to a nucleic acid of interest to initiate, regulate or otherwise control transcription of the nucleic acid of interest.

As used herein, a "phage genome" or "bacteriophage genome" includes naturally occurring phage genomes and derivatives thereof. Generally, the derivatives possess the ability to propagate in the same hosts as the naturally occurring phage. In some embodiments, the only difference between a naturally occurring phage genome and a derivative phage genome is at least one of a deletion or an addition of nucleotides from at least one end of the phage genome (if the genome is linear) or at least one point in the genome (if the genome is circular).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous to the organism (originating from the same organism or progeny thereof) or exogenous (originating from a different organism or progeny thereof). By way of example, a promoter sequence can be substituted (e.g., by homologous recombination) for the native promoter of a gene in the genome of an organism, such that this gene has an altered expression pattern. This gene would be "recombinant" because it is separated from at least some of the sequences that naturally flank it. A nucleic acid is also considered "recombinant" if it contains any modifications that do not naturally occur in the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, a "recombinant bacteriophage genome" is a bacteriophage genome that has been genetically modified by the insertion of a heterologous nucleic acid sequence into the bacteriophage genome. A "recombinant bacteriophage" means a bacteriophage that comprises a recombinant bacteriophage genome. In some embodiments, the bacteriophage genome is modified by recombinant DNA technology to introduce a heterologous nucleic acid sequence into the genome at a defined site. In some embodiments, the heterologous nucleic acid sequence is introduced with no corresponding loss of endogenous phage genomic nucleotides. In other words, if bases N1 and N2 are adjacent in the wild-type bacteriophage genome, the heterologous nucleic acid sequence is inserted between N1 and N2. Thus, in the resulting recombinant bacteriophage genome, the heterologous nucleic acid sequence is flanked by nucleotides N1 and N2. In some embodiments, endogenous phage nucleotides are removed or replaced during the insertion of the heterologous nucleic acid sequence. For example, in some embodiments, the heterologous nucleic acid sequence is inserted in place of some or all of the endogenous phage sequence which is removed. In some embodiments, endogenous phage sequences are removed from a position in the phage genome distant from the site(s) of insertion of the heterologous nucleic acid sequences.

As used herein, a "recombinant B11 bacteriophage" or "recombinant B11 phage" means a B11 bacteriophage whose genomic DNA comprises a heterologous nucleic acid sequence that encodes a bioluminescent protein, a fluorescent protein, a chromogenic protein, or any combination thereof.

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

As used herein, "a sub-sample" refers to one or more samples containing bacterial cells that are derived from a test sample obtained from a subject. In some embodiments, the sub-sample is void of non-bacterial cells (e.g., human cells). In some embodiments, the sub-sample contains lysed human cells.

As used herein, "test sample" refers to a sample taken from a subject that is to be assayed for the presence of bacteria and/or for the antibiotic susceptibility of bacteria present in the sample. In some embodiments, the test sample is blood, sputum, mucus, lavage, or saliva. In certain embodiments, the test sample is a swab from a subject.

As used herein, the terms "subject," "individual," or "patient" are used interchangeably and refer to an individual organism, a vertebrate, a mammal, or a human. In certain embodiments, the individual, patient or subject is a human.

As used herein, a "vector" refers to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

Bacteriophage

Bacteriophage are obligate intracellular parasites that multiply inside bacteria by co-opting some or all of the host biosynthetic machinery. Phages contain nucleic acid and protein, and may be enveloped by a lipid membrane. Depending upon the phage, the nucleic acid genome can be either DNA or RNA but not both, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances no more than 500,000 bp. The number and amount of individual types of protein in phage particles will vary depending upon the phage. The proteins function in infection and to protect the nucleic acid genome from environmental nucleases.

Phage genomes come in a variety of sizes and shapes (e.g., linear or circular). Most phages range in size from 24-200 nm in diameter. The capsid is composed of many copies of one or more phage proteins, and acts as a protective envelope around the phage genome. Many phages have tails attached to the phage capsid. The tail is a hollow tube through which the phage nucleic acid passes during infection. The size of the tail can vary and some phages do not even have a tail structure. In the more complex phages, the tail is surrounded by a contractile sheath which contracts during infection of the bacterial host cell. At the end of the tail, phages have a base plate and one or more tail fibers attached to it. The base plate and tail fibers are involved in the binding of the phage to the host cell.

Lytic or virulent phages are phages which can only multiply in bacteria and lyse the bacterial host cell at the end of the life cycle of the phage. The lifecycle of a lytic phage begins with an eclipse period. During the eclipse phase, no infectious phage particles can be found either inside or outside the host cell. The phage nucleic acid takes over the host biosynthetic machinery and phage specific mRNAs and proteins are produced. Early phage mRNAs code for early proteins that are needed for phage DNA synthesis and for shutting off host DNA, RNA and protein biosynthesis. In some cases, the early proteins actually degrade the host chromosome. After phage DNA is made late mRNAs and late proteins are made. The late proteins are the structural proteins that comprise the phage as well as the proteins needed for lysis of the bacterial cell. In the next phase, the phage nucleic acid and structural proteins are assembled and infectious phage particles accumulate within the cell. The bacteria begin to lyse due to the accumulation of the phage lysis protein, leading to the release of intracellular phage particles. The number of particles released per infected cell can be as high as 1000 or more. Lytic phage may be enumerated by a plaque assay. The assay is performed at a low enough concentration of phage such that each plaque arises from a single infectious phage. The infectious particle that gives rise to a plaque is called a PFU (plaque forming unit).

Lysogenic phages are those that can either multiply via the lytic cycle or enter a quiescent state in the host cell. In the quiescent state, the phage genome exists as a prophage (i.e., it has the potential to produce phage). In most cases, the phage DNA actually integrates into the host chromosome and is replicated along with the host chromosome and passed on to the daughter cells. The host cell harboring a prophage is not adversely affected by the presence of the prophage and the lysogenic state may persist indefinitely. The lysogenic state can be terminated upon exposure to adverse conditions. Conditions which favor the termination of the lysogenic state include: desiccation, exposure to UV or ionizing radiation, exposure to mutagenic chemicals, etc. Adverse conditions lead to the production of proteases (rec A protein), the expression of the phage genes, reversal of the integration process, and lytic multiplication.

Recombinant B11 Phage Compositions of the Present Technology

In one aspect, the present disclosure provides a recombinant B11 bacteriophage nucleic acid sequence, wherein the nucleic acid sequence between position 65,939 and position 65,940 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof. In some embodiments, the heterologous nucleic acid sequence further comprises at least one segment that corresponds to at least part of the excised endogenous phage genome sequence between position 65,939 and position 65,940 of SEQ ID NO: 1.

The present disclosure also provides a recombinant B11 bacteriophage nucleic acid sequence, wherein the nucleic acid sequence (a) between position 65,469 and position 65,470 of SEQ ID NO: 1, or (b) between position 66,001 and 65,002 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof.

Also disclosed herein are recombinant B11 bacteriophages that comprise any recombinant B11 bacteriophage nucleic acid sequence disclosed herein. In some embodiments, the reporter protein(s) encoded by the heterologous nucleic acid sequence produces a detectable signal upon exposure to the appropriate stimuli, and the resulting signal permits detection of bacterial host cells infected by a recombinant B11 phage of the present technology.

In certain embodiments, the open reading frame encodes a reporter protein that serves as a marker that can be identified by screening bacterial host cells infected by a recombinant B11 phage of the present technology. Examples of such markers include by way of example and without limitation: a fluorescent label, a luminescent label, a chemiluminescence label, or an enzymatic label. In some embodiments, the heterologous nucleic acid sequence further comprises sequences naturally found in the bacteriophage, but placed at a non-normally occurring location in the genome.

In some embodiments, the length of the heterologous nucleic acid sequence is at least 100 bases, at least 200 bases, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In certain embodiments, the heterologous nucleic acid sequence comprises a length that is less than or equal to a length selected from the group consisting of 1 kb, 2 kb, 3 kb, 4 kb, 5 kb, 6 kb, 7 kb, 8 kb, 9 kb, and 10 kb. In some embodiments, the heterologous nucleic acid sequence comprises a length that is less than or equal to the maximum length of heterologous nucleic acid sequence that can be packaged into a phage particle comprising the phage genome.

In some embodiments, the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments, the heterologous nucleic acid sequence is inserted into the B11 phage genome with no loss of endogenous B11 phage genomic sequence. In some embodiments, the heterologous nucleic acid sequence replaces an endogenous B11 phage genomic sequence. In some embodiments, the heterologous nucleic acid sequence includes an endogenous B11 phage genomic sequence that was previously excised from the phage genome.

In certain embodiments, the heterologous nucleic acid sequence replaces an endogenous B11 phage genomic sequence that is less than the length of the heterologous nucleic acid sequence. Accordingly, in some embodiments, the length of the recombinant B11 phage genome is longer than the length of the wild-type B11 phage genome. In some embodiments, the heterologous nucleic acid sequence replaces an endogenous B11 phage genomic sequence that is greater than the length of the heterologous nucleic acid sequence. Thus, in some embodiments, the length of the recombinant B11 phage genome is shorter than the length of the wild-type B11 phage genome. In certain embodiments, the heterologous nucleic acid sequence replaces an endogenous B11 phage genomic sequence that is equal to the length of the heterologous nucleic acid sequence.

In certain embodiments, the open reading frame of the heterologous nucleic acid sequence encodes a reporter protein that confers a phenotype of interest on a host cell infected by a recombinant B11 phage of the present technology. In some embodiments, the phenotype of interest is the expression of the gene product encoded by the open reading frame of the heterologous nucleic acid sequence.

In certain embodiments, the open reading frame of the heterologous nucleic acid sequence is operably linked to an expression control sequence that is capable of directing expression of the open reading frame, wherein the open reading frame encodes a reporter protein (e.g., a bioluminescent protein, a fluorescent protein, a chemiluminescent protein, or any combination thereof). In some embodiments, the expression control sequence is located within the heterologous nucleic acid sequence. In other embodiments, the expression control sequence is located in the endogenous B11 phage genome sequence. For example, the open reading frame may be inserted into the B11 phage genome downstream of or in the place of an endogenous B11 phage open reading frame sequence. In some embodiments, the expression control sequence is an inducible promoter or a constitutive promoter (e.g., sarA promoter or lpp promoter). See e.g., Djordjevic & Klaenhammer, *Methods in Cell Science* 20(1):119-126 (1998). The inducible promoter or constitutive promoter may be an endogenous B11 phage promoter sequence, a phage promoter sequence that is non-endogenous to B11 phage, or a bacterial host promoter sequence. Additionally or alternatively, in some embodiments, the inducible promoter is a pH-sensitive promoter, or a temperature sensitive promoter.

In some embodiments, the heterologous nucleic acid sequence comprises a first open reading frame and at least one supplemental open reading frame. In certain embodiments, the first and the at least one supplemental open reading frames are operably linked to the same expression control sequences. In some embodiments, the first and the at least one supplemental open reading frames are operably linked to different expression control sequences.

Fluorescent proteins include, but are not limited to, blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOκ, mKO2, mOrange, and mOrange2), red fluorescent proteins (for example, mRaspberry, mCherry, dsRed, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), fluorescein, rhodamine, and photoswitchable fluorescent proteins (for example, Dronpa).

Examples of bioluminescent proteins are aequorin (derived from the jellyfish *Aequorea victoria*) and luciferases (including luciferases derived from firefly and *Renilla*, nanoluciferase, red luciferase, luxAB, and the like). These proteins have also been genetically separated into two distinct functional domains that will generate light only when the protein domains are closely co-localized. A variety of emission spectrum-shifted mutant derivatives of both of these proteins have been generated over the past decade and have been used for multi-color imaging and co-localization within a living cell.

Examples of chemiluminescent protein include β-galactosidase, horseradish peroxidase (HRP), and alkaline phosphatase. Peroxidases generate peroxide that oxidizes luminol in a reaction that generates light, whereas alkaline phosphatases remove a phosphate from a substrate molecule, destabilizing it and initiating a cascade that results in the emission of light.

In some embodiments, the open reading frame of the heterologous nucleic acid sequence comprises an epitope that can be detected with an antibody or other binding molecule. For example, an antibody that recognizes the epitope may be directly linked to a signal generating moiety (such as by covalent attachment of a chemiluminescent or fluorescent protein), or can be detected using at least one additional binding reagent such as a secondary antibody, directly linked to a signal generating moiety. In some embodiments, the epitope is absent in wild-type B11 bacteriophage and the bacterial host cell. Accordingly, detection of the epitope in a sample demonstrates the presence of a bacterial host cell infected by a recombinant B11 phage comprising a heterologous nucleic acid sequence, wherein the open reading frame of the heterologous nucleic acid sequence comprises the epitope. In other embodiments, the open reading frame of the heterologous nucleic acid sequence comprises a polypeptide tag sequence, such that the expression product of the open reading frame comprises the tag fused to a polypeptide or protein encoded by the open reading frame (e.g., poly-histidine, FLAG, Glutathione S-transferase (GST) etc.).

In some embodiments, the open reading frame of the heterologous nucleic acid sequence comprises a biotin binding protein such as avidin, streptavidin, or neutrAvidin that can be detected with a biotin molecule conjugated to an enzyme (e.g., β-galactosidase, horseradish peroxidase (HRP), and alkaline phosphatase) or an antibody. In some embodiments, an antibody conjugated to a biotin molecule may be directly linked to a signal generating moiety (such as by covalent attachment of a chemiluminescent or fluorescent protein), or can be detected using at least one additional binding reagent such as a secondary antibody, directly linked to a signal generating moiety.

Also disclosed herein are recombinant B11 bacteriophages comprising any of the recombinant B11 bacteriophage nucleic acid sequences disclosed herein. In some embodiments, the recombinant B11 bacteriophages comprise a nucleic acid sequence selected from the group consisting of SEQ ID NO: 2, SEQ ID NO: 3, SEQ ID NO: 4 and SEQ ID NO: 12.

In another aspect, the present disclosure provides a vector comprising any of the recombinant B11 bacteriophage nucleic acid sequences disclosed herein, as well as bacterial host cells comprising the vectors of the present technology. The bacterial host cell may be a natural or non-natural host for B11 bacteriophage.

The present disclosure also provides a bacterial host cell comprising a recombinant B11 bacteriophage disclosed herein. The bacterial host cell may be a natural or non-natural host for B11 bacteriophage.

Methods of Making Recombinant B11 Bacteriophage of the Present Technology

In one aspect, the present disclosure provides methods for making a recombinant B11 bacteriophage of the present technology in a bacterial host cell. The bacterial host cell may be a non-natural bacterial host cell or a natural bacterial host cell for B11 bacteriophage.

In some embodiments, the method comprises (a) contacting a first B11 bacteriophage genome with a first sgRNA-CRISPR enzyme complex and a second sgRNA-CRISPR enzyme complex in vivo under conditions where (i) the first sgRNA-CRISPR enzyme complex cleaves a first protospacer sequence 5' AGAAGATCATTATCGAAAGA 3' (SEQ ID NO: 5) within the first B11 bacteriophage genome; and (ii) the second sgRNA-CRISPR enzyme complex cleaves a second protospacer sequence 5' AGACATAGCCCCTCTCCACA 3' (SEQ ID NO: 6) within the first B11 bacteriophage genome to produce a cleaved first B11 bacteriophage genome; and (b) recombining in vivo the cleaved first B11 bacteriophage genome with a heterologous nucleic acid sequence in the presence of a recombination system under conditions to produce the recombinant B11 bacteriophage genome, wherein the bacterial host cell is infected with the first B11 bacteriophage genome, and wherein the heterologous nucleic acid sequence comprises an open reading frame that encodes a bioluminescent protein, a fluorescent protein, a chemiluminescent protein, or any combination thereof. In some embodiments, the first sgRNA-CRISPR enzyme complex comprises Cas9 and a first sgRNA having the sequence of 5' AGAAGAUCAUUAUCGAAAGAGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO: 7). Additionally or alternatively, in certain embodiments, the second sgRNA-CRISPR enzyme complex comprises Cas9 and a second sgRNA having the sequence of 5' AGACAUAGCCCCUCUCCACAGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO: 8). The recombination system may be endogenous or non-endogenous. The first B11 bacteriophage genome may be recombinant or non-recombinant.

The cleaved first B11 bacteriophage genome comprises a first cleaved bacteriophage genomic fragment and a second cleaved bacteriophage genomic fragment. In certain embodiments of the methods disclosed herein, the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment.

In some embodiments of the methods disclosed herein, the homologous 5' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the homologous 3' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the recombination system is a non-endogenous recombination system that is induced in the bacterial host cell. The non-endogenous recombination system may include a recombination expression vector that comprises lambda Red proteins Gam, Exo, and Beta operably linked to an inducible promoter. In some embodiments of the methods disclosed herein, the inducible promoter is araB and the non-endogenous recombination system is induced by the addition of arabinose. In some embodiments, the recombination expression vector further comprises the heterologous nucleic acid sequence. In other embodiments, the expression vector comprising the heterologous nucleic acid sequence is separate and distinct from the recombination expression vector comprising lambda Red proteins.

In other embodiments of the methods disclosed herein, the recombination system is a non-endogenous recombination system that includes a recombination expression vector comprising RecET (RecE, RecT) operons operably linked to an inducible promoter, and optionally the heterologous nucleic acid sequence. In some embodiments, the inducible promoter is araB and the non-endogenous recombination system is induced by the addition of arabinose. In other embodiments, the expression vector comprising the heterologous nucleic acid sequence is separate and distinct from the recombination expression vector comprising RecET.

In another embodiment of the methods disclosed herein, the recombination system is a non-endogenous recombination system that includes a recombination expression vector comprising RecA recombinase or a RecA gain-of-function variant operably linked to an inducible promoter and optionally the heterologous nucleic acid sequence. In some embodiments, the inducible promoter is araB and the non-endogenous recombination system is induced by the addition of arabinose. In other embodiments, the expression vector comprising the heterologous nucleic acid sequence is separate and distinct from the recombination expression vector comprising RecA recombinase or the RecA gain-of-function variant.

Additionally or alternatively, in some embodiments of the methods disclosed herein, the bacterial host cell comprises a non-endogenous CRISPR expression vector comprising a nucleic acid sequence that encodes a first sgRNA, a second sgRNA, and a CRISPR enzyme. In some embodiments, the first sgRNA and the second sgRNA are operably linked to a constitutive promoter. In some embodiments, the sequence of the first sgRNA and the second sgRNA is SEQ ID NO: 7 and SEQ ID NO: 8, respectively.

A variety of CRISPR enzymes are available for use in conjunction with the disclosed methods of the present disclosure. In some embodiments, the CRISPR enzyme is a Type II CRISPR enzyme. In some embodiments, the CRISPR enzyme catalyzes DNA cleavage. In some embodiments, the CRISPR enzyme catalyzes RNA cleavage. In some embodiments, the CRISPR enzyme is any Cas9 protein, for instance any naturally-occurring bacterial Cas9 as well as any variants, homologs or orthologs thereof. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or variants thereof. The CRISPR enzyme may be operably linked to an inducible promoter, such as a tetracycline-inducible promoter. In some embodiments, the CRISPR enzyme cleaves both strands of the target nucleic acid at the Protospacer Adjacent Motif (PAM) site.

In another aspect, the present disclosure provides sgRNAs that are useful for making the recombinant B11 bacteriophages disclosed herein. In some embodiments, the sgRNA sequence is selected from the group consisting of SEQ ID NO: 7 and SEQ ID NO: 8. The design of sgRNAs that are capable of cleaving at the other B11 genomic positions described herein, is within the scope of one of ordinary skill in the art.

Bacterial Identification and Antibiotic Susceptibility Profiling Methods of the Present Technology Accurate identification of bacterial species within a biological sample informs the selection of suitable therapies for treating bacterial infections. The recombinant B11 bacteriophages disclosed herein may be used to identify bacteria present within a biological sample (e.g., whole blood, plasma, serum). Such methods entail contacting the biological sample with a recombinant B11 bacteriophage disclosed herein, and detecting the presence of bacterial host cells infected by the recombinant B11 phage, wherein the recombinant B11 phage comprises a heterologous nucleic acid sequence that encodes a detectable gene product, thereby leading to the identification of bacteria present within the biological sample.

Additionally or alternatively, the recombinant B11 bacteriophages disclosed herein, may be used in methods for profiling antibiotic susceptibility of bacteria present within a biological sample (e.g., whole blood, plasma, serum). These methods include (a) infecting the biological sample with an antibiotic and a recombinant B11 bacteriophage disclosed herein, (b) detecting the presence of bacterial host cells infected by the recombinant B11 phage, wherein the recombinant B11 phage comprises a heterologous nucleic acid sequence that encodes a detectable gene product, and (c) determining that the antibiotic is effective in inhibiting the bacteria present in the biological sample when the levels of recombinant B11 phage infected bacterial host cells is reduced relative to that observed in an untreated control sample.

In one aspect, the present disclosure provides a method for identifying at least one bacterial strain or species in a test sample obtained from a subject comprising (a) separating bacterial cells isolated from the test sample into one or more sub-samples, (b) infecting each sub-sample with at least one recombinant B11 bacteriophage disclosed herein, wherein each recombinant B11 bacteriophage comprises a heterologous nucleic acid sequence encoding one or more reporter genes, and (c) identifying at least one bacterial strain or species in the test sample by detecting the expression of the one or more reporter genes of the at least one recombinant B11 bacteriophage. In certain embodiments, the at least one B11 bacteriophage comprises a nucleic acid sequence selected from the group consisting of SEQ ID NO: 2, SEQ ID NO: 3, SEQ ID NO: 4 and SEQ ID NO: 12. In certain embodiments, the method for identifying at least one bacterial strain or species in a test sample does not require the culturing of bacterial cells from the test sample or a sub-sample.

In some embodiments, identification of at least one bacterial strain or species includes detecting the expression of the one or more reporter genes of the at least one recombinant B11 bacteriophage, e.g., detectable expression of green fluorescence indicates the presence of bacterial species A in a test sample or sub-sample. In some embodiments, the absence of at least one bacterial strain or species is identified by the lack of detectable expression of the one or more reporter genes of the at least one recombinant B11 bacteriophage, e.g., undetectable expression of green fluorescence indicates the lack of bacterial species A in a test sample or sub-sample.

In some embodiments, the at least one recombinant B11 bacteriophage infects a single species of bacteria. In certain embodiments, the at least one recombinant B11 bacteriophage infects two or more species of bacteria.

In some embodiments, detection of the expression of the reporter gene is detection of the gene product itself, e.g., a fluorescent protein. In some embodiments, detection of the expression of the reporter gene is detection of an enzymatic reaction requiring the expression of the reporter gene, e.g., expression of luciferase to catalyze luciferin to produce light.

In some embodiments, the expression of the one or more reporter genes is detected in about 5, 10, 15, 20, 25, 30, 35, 40, 45, 50, 55, 60, 65, 70, 75, 80, 85, 90, 120 minutes or any time between any two of the preceding values after infecting a sub-sample with the at least one recombinant B11 bacteriophage disclosed herein.

The present disclosure also provides a method for identifying at least one bacterial strain or species in a test sample obtained from a subject comprising (a) infecting the test sample comprising bacterial cells with a recombinant B11 bacteriophage of the present technology; and (b) detecting the expression of the reporter protein of the recombinant B11 bacteriophage, wherein detection of the reporter protein indicates the presence of at least one bacterial strain or species in the test sample. In some embodiments of the method, the expression of the reporter protein is measured in about 5, 10, 15, 20, 25, 30, 35, 40, 45, 50, 55, 60, 65, 70, 75, 80, 85, 90 or 120 minutes after infecting the test sample comprising bacterial cells with the recombinant B11 bacteriophage.

Additionally or alternatively, in some embodiments of the methods disclosed herein, the test sample is blood, sputum, mucus, lavage, saliva, or a swab obtained from the subject. In some embodiments, the subject is human.

In another aspect, the present disclosure provides a method for determining the antibiotic susceptibility of a bacterial strain or species in a test sample obtained from a subject comprising (a) separating bacterial cells isolated from the test sample into a plurality of sub-samples, (b) infecting the plurality of sub-samples with a recombinant B11 bacteriophage disclosed herein and at least one antibiotic, wherein the recombinant B11 bacteriophage comprises a heterologous nucleic acid sequence encoding a reporter gene, and (c) detecting the expression of the reporter gene of the recombinant B11 bacteriophage in the presence of each antibiotic. In some embodiments, the method further comprises determining that the bacterial strain or species in the test sample is susceptible to an antibiotic if the reporter gene expression of the recombinant B11 bacteriophage in the antibiotic treated sub-sample is decreased relative to that observed in a control sub-sample that is not treated with the antibiotic. In other embodiments, the method further comprises determining that the bacterial strain or species in the test sample is resistant to an antibiotic if the reporter gene expression of the recombinant B11 bacteriophage in the antibiotic treated sub-sample is comparable to that observed in a control sub-sample that is not treated with the antibiotic. In certain embodiments, the method for determining the antibiotic susceptibility of a bacterial strain or species in a test sample does not require the culturing of bacterial cells from a test sample or a sub-sample.

Additionally or alternatively, in some embodiments of the recombinant B11 bacteriophages of the present technology, the reporter gene is nanoluciferase. In certain embodiments, recombinant B11 bacteriophage comprises a nucleic acid sequence selected from the group consisting of SEQ ID NO: 2, SEQ ID NO: 3, SEQ ID NO: 4 and SEQ ID NO: 12.

Examples of antibiotics include one or more of rifampicin, tetracycline, levofloxacin, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

In some embodiments of the method, the differences in the reporter gene expression of the recombinant B11 bacteriophage observed in the antibiotic treated sub-sample and the untreated control sub-sample is defined as μ.

Additionally or alternatively, in some embodiments of the method, the expression of the reporter gene is detected in about 5, 10, 15, 20, 25, 30, 35, 40, 45, 50, 55, 60, 65, 70, 75, 80, 85, 90, 120 minutes or any time between any two of the preceding values after infecting a sub-sample with a recombinant B11 bacteriophage disclosed herein.

In some embodiments, two or more sub-samples are tested for antibiotic susceptibility in series. In some embodiments, two or more sub-samples are tested for antibiotic susceptibility in parallel. In some embodiments, one or more sub-samples are tested for antibiotic susceptibility in a running assay (where resistance or sensitivity to one antibiotic is determined and the resistance or sensitivity to a second, third, fourth, fifth, etc., antibiotic is being assayed).

In some embodiments of the methods disclosed herein, isolating bacterial cells from a test sample includes incubating the test sample with distilled water to form a mixture, centrifuging the mixture to form a pellet that includes bacterial cells, and re-suspending the pellet to form a bacterial suspension comprising isolated bacterial cells after discarding the supernatant. The pellet may be re-suspended in a phosphate buffer. In some embodiments, the bacterial suspension is divided into one or more sub-samples.

In certain embodiments of the methods disclosed herein, mixing the test sample with distilled water will lead to the lysis of cells that lack cell walls (e.g., mammalian cells and red blood cells) while leaving cells with cell walls (e.g., bacteria) intact. Without wishing to be bound by theory, in some embodiments, the removal of cells that lack cell walls enhances the detection of reporter gene expression in bacterial cells infected with a recombinant B11 bacteriophage, as intact non-bacterial cells (e.g., red blood cells) may quench reporter gene expression. In some embodiments of the methods of the present technology, the mixture is about 90% distilled water and 10% test sample, about 80% distilled water and 20% test sample, about 70% distilled water and 30% test sample, about 60% distilled water and 40% test sample, about 50% distilled water and 50% test sample, about 40% distilled water and 60% test sample, about 30% distilled water and 70% test sample, about 20% distilled water and 80% sample, or about 10% distilled water and 90% test sample. In some embodiments of the methods disclosed herein, the mixture is incubated for 1, 2, 3, 4, 5, 6, 7, 8, 9, 10, 11, 12, 13, 14, or 15 minutes, or any time between two of the previously listed time points. Additionally or alternatively, in certain embodiments of the methods disclosed herein, the mixture is centrifuged for 1, 2, 3, 4, 5, 6, 7, 8, 9, 10, 11, 12, 13, 14, or 15 minutes, or any time between two of the previously listed time points.

Additionally or alternatively, in certain embodiments of the methods disclosed herein, each of the one or more sub-samples comprise between about 5 to 500, about 10 to 400, about 20 to 300, about 30 to 300, about 40 to 200 or about 50 to 100 bacterial cells. In some embodiments of the methods disclosed herein, each of the one or more sub-samples comprises between about 100 to 10,000, about 200 to 9,000, about 300 to 8,000, about 400 to 7,000, about 500 to 6,000, about 600 to 5,000, about 700 to 4,000, about 800 to 3,000, about 900 to 2,000, or about 1,000 to 1,500 bacterial cells.

In another aspect, the present disclosure provides a method for determining the antibiotic susceptibility of a bacterial strain or species in a test sample obtained from a subject comprising (a) infecting a plurality of test samples comprising bacterial cells with a recombinant B11 bacteriophage of the present technology and an antibiotic, wherein the plurality of test samples is derived from the subject; (b) detecting the expression of the reporter protein of the recombinant B11 bacteriophage in the plurality of test samples; and (c) determining that the antibiotic is effective in inhibiting the bacterial strain or species in a test sample when the reporter protein expression levels of the recombinant B11 phage infected bacterial cells in the test sample are reduced relative to that observed in an untreated control sample comprising bacterial cells, wherein the untreated control sample is derived from the subject and is infected with the recombinant B11 bacteriophage of the present technology. The expression of the reporter protein may be measured in about 5, 10, 15, 20, 25, 30, 35, 40, 45, 50, 55, 60, 65, 70, 75, 80, 85, 90 or 120 minutes after infecting the plurality of test samples comprising bacterial cells with the recombinant B11 bacteriophage. In other embodiments, the method further comprises determining that the bacterial strain or species in the test sample is resistant to the antibiotic when the reporter protein expression levels of the recombinant B11 bacteriophage infected bacterial cells in the test sample are comparable to that observed in an untreated control sample comprising recombinant B11 phage infected bacterial cells, wherein the untreated control sample is derived from the subject and is infected with the recombinant B11 bacteriophage of the present technology.

In any of the above embodiments of the methods of the present technology, the test sample is blood, sputum, mucus, lavage, saliva, or a swab obtained from the subject. In some embodiments of the methods disclosed herein, the test sample is obtained from a mammalian subject, including, for example, farm animals, such as sheep, pigs, cows, and horses; pet animals, such as dogs and cats; and laboratory animals, such as rats, mice and rabbits. In one embodiment, the mammal subject is a human.

Kits

The present technology provides kits including the recombinant B11 bacteriophages disclosed herein for bacteria identification and antibiotic susceptibility profiling.

In one aspect, the kits of the present technology comprise one or more coded/labeled vials that contain a plurality of the recombinant B11 bacteriophages disclosed herein, and instructions for use. In some embodiments, each coded/labeled vial corresponds to a different recombinant B11 bacteriophage. In other embodiments, each coded/labeled vial corresponds to the same recombinant B11 bacteriophage. In some embodiments, the kits of the present technology comprise one or more coded/labeled vials that contain at least one recombinant B11 bacteriophage comprising a nucleic acid sequence selected from the group consisting of SEQ ID NO: 2, SEQ ID NO: 3, SEQ ID NO: 4 and SEQ ID NO: 12.

In some embodiments, each phage vial is assigned a unique code that identifies the bacteriophage in the phage vial, or the types of bacteria that the bacteriophage strain infects. The unique code can be encoded by a machine discernible pattern, such as a bar code, a QR code, an alphanumeric string, or any other pattern that can be discerned by a reader. Each unique code may be shown as, for example, a bar code sticker on a vial or container storing a corresponding phage sample. In some embodiments, the kit is stored under conditions that permit the preservation of the bacteriophage genomes for extended periods, such as under bacteriophage-specific, controlled temperature, moisture, and pH conditions.

Additionally or alternatively, in some embodiments, the kits further comprise vials containing natural or non-natural bacterial host cells. In some embodiments, the bacterial host cells are *Pseudomonas aeruginosa*.

The kits may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular detection technique for which the kit is intended. Protocols for using these buffers and reagents for performing different steps of the procedure may also be included in the kit. Further optional components of the kits may include expression media for gene products encoded by the heterologous nucleic acids of the recombinant B11 bacteriophages disclosed herein, such as a medium containing nutrients and cofactors for bioluminescence, devices such as a lamp configured to illuminate at specific wavelengths of light to detect biofluorescence, and devices for measuring the extent of heterologous nucleic acid expression, such as a photometer or photodetector.

Additionally or alternatively, the kits disclosed herein may also include coded and labeled vials that contain a plurality of antibiotics. In some embodiments, the plurality of antibiotics comprises one or more of rifampicin, tetracycline, levofloxacin, and ampicillin. Other examples of antibiotics include penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

Additionally or alternatively, in some embodiments, the kits comprise one or more sgRNA sequences selected from the group consisting of SEQ ID NO: 7 and SEQ ID NO: 8.

EXAMPLES

Example 1: Design and Methods for Generating the Recombinant B11 Bacteriophages of the Present Technology This Example demonstrates that the methods of the present technology are useful for making the recombinant B11 bacteriophages disclosed herein in a bacterial host cell.

The recombinant *P. aeruginosa* B11 bacteriophage of the present technology were engineered using a 'break and recombine' (BAR) phage engineering method. The BAR method relies on (1) cleaving a phage genome in vivo at one or two locations using an RNA-guided endonuclease (e.g., Cas9)-sgRNA complex, and (2) providing a heterologous nucleic acid sequence comprising the nanoluciferase gene with an upstream ribosome binding site as well as 5' and 3' flanking regions that are homologous to a portion of the initial B11 phage genome (collectively, referred to as the donor template region). The donor template region also contains sequences that restore the function of any B11 phage DNA that was excised by the sgRNA-CRISPR enzyme complexes. The 5' and 3' flanking regions (about several hundred base pairs in length) are homologous to the DNA sequences immediately adjacent to the two cleavage sites in the phage genome (FIGS. 5(A)-5(B)), and are necessary for repairing double-stranded breaks via homologous recombination.

The desired insertion site (site 6.3) was immediately downstream of an open reading frame (ORF) of unknown function. The sequence of the initial B11 contig-6 genome is shown in FIGS. 7(A)-7(L) and is represented by SEQ ID NO: 1. The 20 bp protospacer site, along with the accompanying 3 bp protospacer adjacent motif (PAM) were identified near 'site 6.3.' The B11 protospacer sequences along with their adjacent PAM sites (PAM site underlined) are provided below:

| | |
|---|---|
| Protospacer 6.3A | 5' AGAAGATCATTATCGAA/AGACGG 3' (SEQ ID NO: 9) |
| Protospacer 6.3B | 5' AGACATAGCCCCTCTCC/ACATGG 3' (SEQ ID NO: 10) |

cleavage sites marked with a '/'

The complete sequences of sgRNA 6.3A, and sgRNA 6.3B are provided below:

sgRNA 6.3A RNA sequence: 5' AGAAGAUCAUUAUCGAAAGAGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO: 7)

sgRNA 6.3B RNA sequence: 5' AGACAUAGCCCCUCUCCACAGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO: 8).

The CRISPR expression vector (crR) was assembled for CRISPR-Cas9 mediated cleavage in *P. aeruginosa*. The crR plasmid is a shuttle vector containing a pUC origin of replication, a pRO1600 origin of replication, a kanamycin resistance cassette, and an *S. pyogenes* Cas9 gene (codon-optimized for expression in *P. aeruginosa*) operably linked to a pTet (tetracycline) promoter. The crR plasmid also contains a scaffold into which a segment of synthetic DNA can be inserted so as to permit the transcription of two sgRNAs (e.g., using a dual-guide cassette) by the lipoprotein (lpp) promoter. The nucleic acid sequences of the 'dual-guide cassettes' for sgRNAs 6.3A and 6.3B are provided below:

Dual-Guide Cassette (sgRNAs 6.3A and 6.3B):

(SEQ ID NO: 11)

AGCAGTGGTAAGGTCTCTTAACAGAAGATCATTATCGAAAGAGTTTTAGA

GCTAGAAATAGCAAGTTAAAATAAGGCTAGTCCGTTATCAACTTGAAAAA

GTGGCACCGAGTCGGTGCTTTTTTTGCTAACTGATACCGACTACGCCTGA

ACAGTCGAATCTTCACCTCGTCTGGTACCGACGCGGTCCCAAATATTGAC

AACATAAAAAACTTTGTGTTATACTTGTAACAGACATAGCCCCTCTCCAC

AGTTTTGAGACCAGCTCGTAGG

The 'dual-guide cassette' for sgRNAs 6.3A and 6.3B was PCR amplified, digested with the restriction enzyme BsaI, and ligated into a BsaI-digested crR plasmid to create the crR-B11 6' CRISPR expression vector.

The donor template vector was designed as follows. FIG. 1 shows the donor template sequence for B11 phage genomic DNA that was cleaved with sgRNA 6.3A and sgRNA 6.3B (SEQ ID NO: 2). The donor template sequences contain the nanoluciferase reporter gene with an upstream ribosome binding site (RBS), as well as the region of the B11 phage genome between the two CRISPR cleavage sites that is to be excised, such that the original sequence and function is restored. Specifically, the donor template sequences included 5' and 3' flanking regions (about 300 bp in length) that were perfectly homologous to the cleaved ends of the wild-type B11 phage genome so as to facilitate strand invasion and homologous recombination between the cleaved phage genome and the donor sequence, thereby repairing the double-stranded breaks and incorporating the nanoluciferase reporter gene. The protospacers/PAM sequences within the donor templates were modified such that the CRISPR system would not recognize and cleave the donor template, and would only target the wild-type phage genome. For example, the regions internal to the two cleavage sites (i.e., right of the upstream cut site and left of the downstream cut site) were either codon-reassigned or otherwise changed by single-base pair substitutions that were not expected to detrimentally affect phage function.

The recombination plasmid was assembled by PCR amplification of the plasmid 'pBBR1-Gent' with primers 5' CAGGTTCATCATGCCGTTTGTG 3' (SEQ ID NO: 13) and 5' TATTTGCCCATGGACGCACAC 3' (SEQ ID NO: 14) followed by a Gibson assembly reaction between the amplified plasmid and the donor template. The assembled recombination plasmid was designated as 'pBBR1-B11 6'.

The *P. aeruginosa* strain PAO1 was transformed with the crR-B11 6 and pBBR1-B11 6' plasmids. The strain was maintained in kanamycin at 250 µg/mL and gentamicin at 50 µg/mL. A 5 mL culture of this strain was grown to early-log phase and then treated with 1 µg/mL anhydrotetracycline (aTc) for two hours to induce Cas9 expression. The culture was then infected with wild-type B11 phage overnight. It was observed that aTc induction did not reduce phage titer/plaque formation.

Results.

PCR assays of the overnight lysate revealed that most transformants were wild-type non-recombinant B11 phage. To reduce contamination due to nanoluciferase protein and plasmid DNA, the lysate was purified by multiple rounds of size-exclusion filtration. The purified lysate was then subject to a large screen (automated brute force methodology) to enrich for recombinant B11 phage. Once determined to be reasonably pure, the sample was diluted and plated on a PAO1 overlay, such that single plaques could be recovered for genotypic and phenotypic analysis.

Figure 2B:
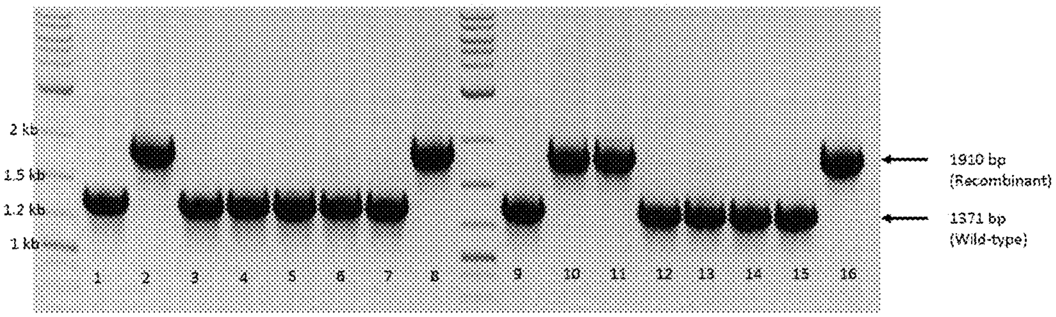
FIG. 2(B) shows flanking PCR assays that tested for the presence of recombinant NanoLuc® B11 bacteriophage using primer sets that flank site 6.3.
Figure 3A:
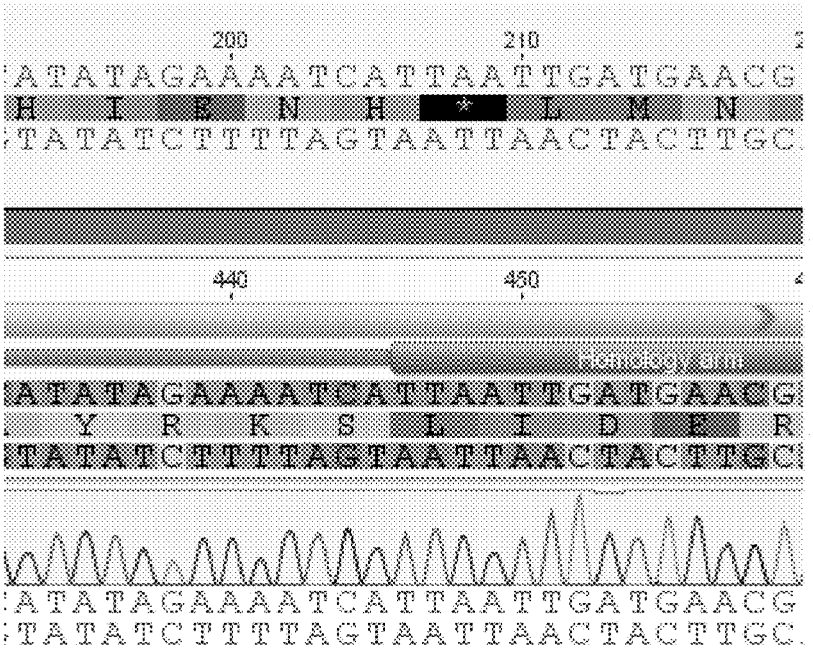
FIG. 3(A) shows the upstream junction sequence where the region of B11 phage genome intersects with the 5' homologous region of the donor plasmid. Figure discloses SEQ ID NOS 15, 16, 15, 17, and 15, respectively, in order of appearance.
Figure 3B:
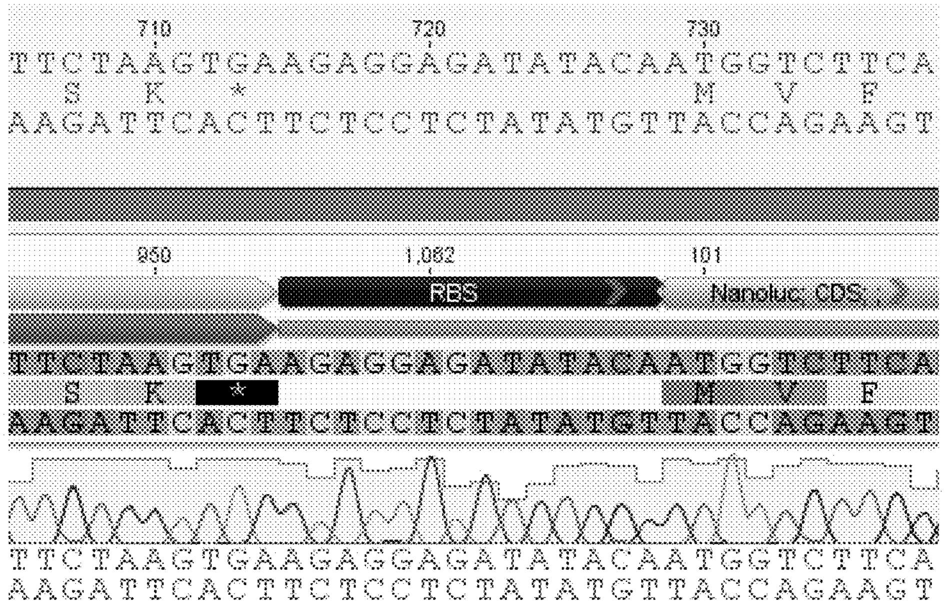
FIG. 3(B) shows the upstream junction sequence of the nanoluciferase insertion in the recombinant B11 phage genome cleaved by sgRNA 6.3A and sgRNA 6.3B: 5' TTCTAAGTGAAGAGGAGATATACAATGGTCTTCA 3' (SEQ ID NO: 3).
Figure 3C:
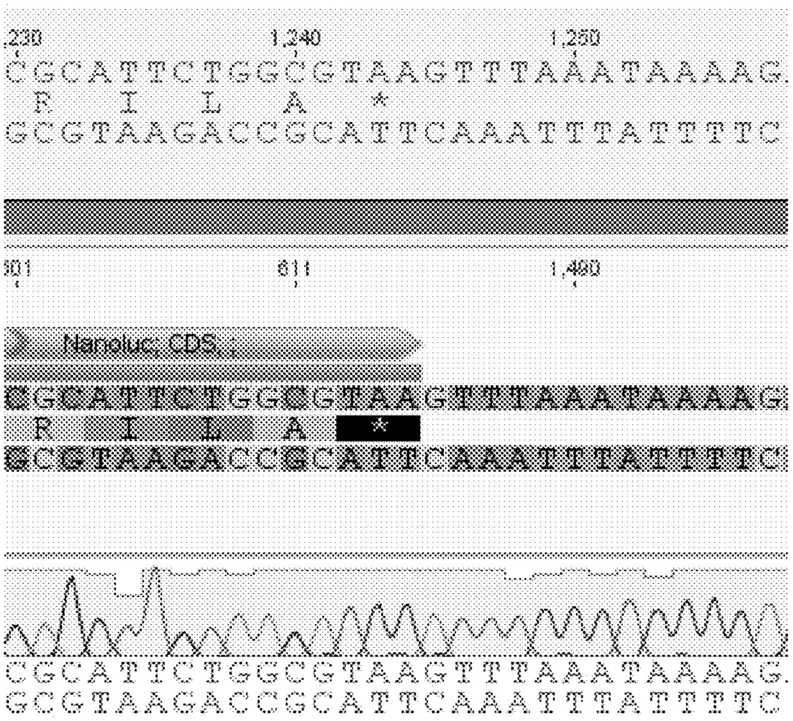
FIG. 3(C) shows the downstream junction sequence of the nanoluciferase insertion in the recombinant B11 phage genome cleaved by sgRNA 6.3A and sgRNA 6.3B: 5' CGCATTCTGGCGTAAGTTTAAATAAAAG 3' (SEQ ID NO: 4).). Figure discloses the protein sequence as SEQ ID NO: 18.
Figure 3D:
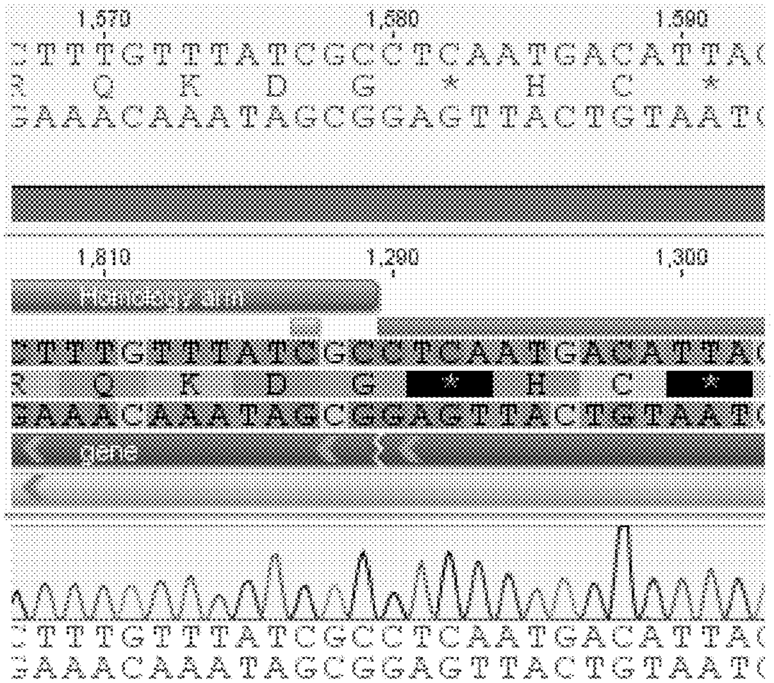
FIG. 3(D) shows the downstream junction sequence where the region of B11 phage genome intersects with the 3' homologous region of the donor plasmid. Figure discloses SEQ ID NOS 19, 20, 19, 20, and 19, respectively, in order of appearance.

16 single plaques were picked into 25 µl of Tris buffer, and 1 µl of each 'pickate' was used to infect 150 µl of mid-log PAO1 overnight. Relative luminescence units (RLU) readings were then recorded. The infections were also analyzed via PCR reaction using primers that flank the intended nanoluciferase insertion site. FIGS. 2(A)-2(B) demonstrate that pickates 2, 8, 10, and 16 were both genotypically and phenotypically positive for nanoluciferase insertion. The PCR product from pickate 2 was then sequenced. FIGS. 8(A)-8(L) show the B11 contig-6 genome sequence of the recombinant NanoLuc® B11 phage that was cleaved with sgRNA 6.3A and sgRNA 6.3B (SEQ ID NO: 12). FIGS. 3(B)-3(C) show the upstream and downstream junction sequences of the nanoluciferase insertions at site 6.3 within the recombinant B11 phage. FIG. 3(A) shows the upstream junction sequence where the region of B11 phage genome intersects with the 5' homologous region of the donor plasmid. FIG. 3(D) shows the downstream junction sequence where the region of B11 phage genome intersects with the 3' homologous region of the donor plasmid.

These results demonstrate that the methods of the present technology are useful for making the recombinant B11 bacteriophages disclosed herein in a bacterial host cell. Accordingly, the methods disclosed herein are useful for generating recombinant B11 bacteriophages that can be used in the identification and/or antibiotic susceptibility profiling of specific *P. aeruginosa* strains present in a sample.

Example 2: Functional Activity of the Recombinant B11 Bacteriophages of the Present Technology This Example demonstrates that the recombinant B11 bacteriophages of the present technology are useful for the identification and/or antibiotic susceptibility profiling of specific *P. aeruginosa* strains present in a sample.

Figure 4:
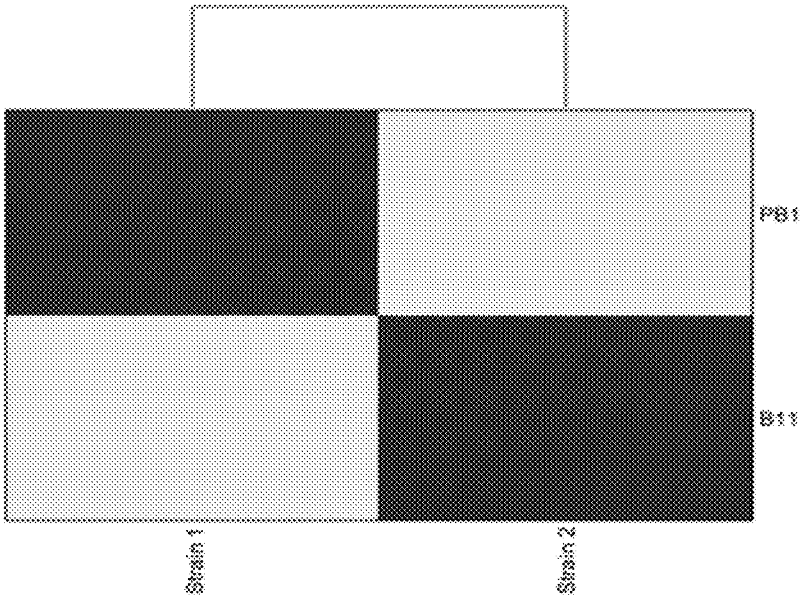
FIG. 4 shows a comparison of the host ranges of recombinant NanoLuc® B11 phage, and recombinant NanoLuc® PB1 phage. Grey means the given strain is infected by the indicated phage, whereas black means a given strain is not infected by the indicated phage.

*P. aeruginosa* clinical isolates (designated as strains 1-2) were infected with the recombinant NanoLuc® B11 phages disclosed herein and a recombinant NanoLuc® PB1 phage for 1 hour. FIG. 4 shows that the recombinant NanoLuc® B11 phages of the present technology successfully infected a *P. aeruginosa* clinical isolate (strain 1) that was incapable of being infected with a recombinant nanoluciferase expressing PB1 phage.

These results demonstrate that the methods of the present technology are useful for making the recombinant B11 bacteriophages disclosed herein in a bacterial host cell. Accordingly, the methods disclosed herein are useful for generating recombinant B11 bacteriophages that can be used in the identification and/or antibiotic susceptibility profiling of specific *P. aeruginosa* strains present in a sample.

Example 3: Antibiotic Susceptibility Profiling Using the Recombinant B11 Bacteriophages of the Present Technology Antibiotics were prepared by performing eleven 2-fold serial dilutions in Mueller Hinton Broth (Sigma, St. Louis, Mo.) in 96 well microtiter plates at a final volume of 100 µl. One column contained broth only and served as a no drug control.

Cells from an overnight growth blood culture in 25% human blood and 75% Tryptic Soy Broth TSB were diluted 1:10 in Mueller Hinton Broth. From this dilution, 5 µl of cells was added to each well of the antibiotic plate. Cells were pretreated with antibiotics (meropenem) for 120 minutes at 37° C. After the 120 minute pretreatment, 10 µl of phage suspension comprising the recombinant B11 phage of the present technology (1E6 pfu/reaction well) was added to each well and incubated at 37° C. for 45 minutes. After infection with the phage, 50 µl of the reaction was added to 50 µl Nano Glo Luciferase Substrate (Promega, Madison, Wis.) in a luminescent plate and read in a luminometer. The minimal inhibitory concentration (MIC) of each sample was determined using the ETEST® method (Biomerieux, St. Louis, Mo.) according to the manufacturer's instructions. The differences in the reporter gene expression of the recombinant B11 bacteriophage observed in the antibiotic treated samples and the untreated control samples is defined as µ.

Figure 6:
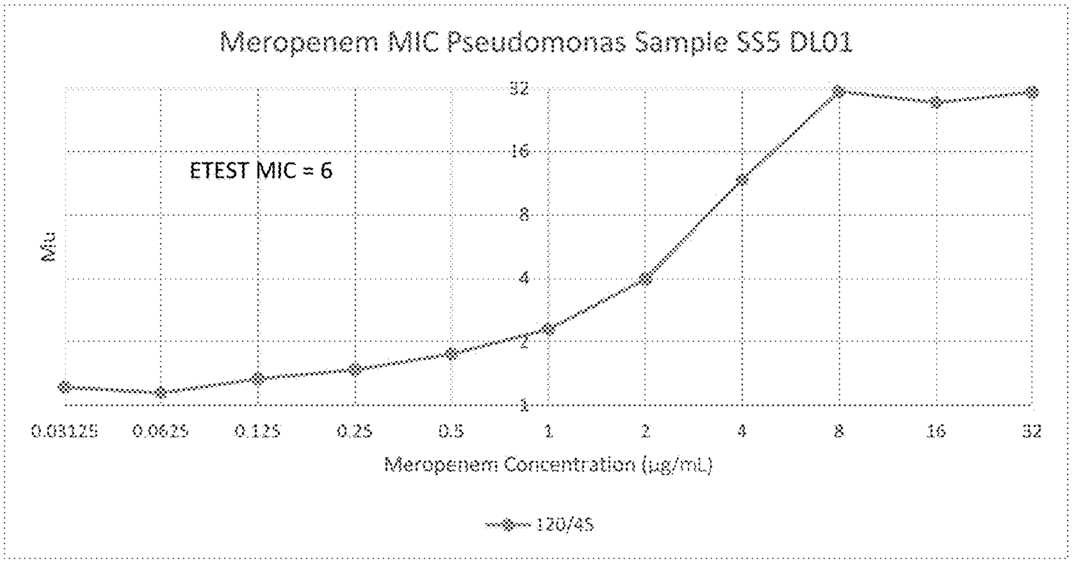
FIG. 6 shows the antibiotic susceptibility profile of a *P. aeruginosa* strain to meropenem using the recombinant B11 phages of the present technology.

FIG. 6 demonstrates that the recombinant B11 bacteriophages of the present technology were effective in determining the antibiotic susceptibility profile of *P. aeruginosa* strain SS5 DL01.

These results demonstrate that the recombinant B11 bacteriophages of the present technology are useful for determining the antibiotic susceptibility of a bacterial strain or species in a test sample. Accordingly, the recombinant B11 bacteriophages disclosed herein are useful for the identification and/or antibiotic susceptibility profiling of specific *P. aeruginosa* strains present in a sample.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A recombinant B11 bacteriophage nucleic acid sequence, wherein the nucleic acid sequence between position 65,939 and position 65,940 of SEQ ID NO: 1 is replaced with a heterologous nucleic acid sequence comprising an open reading frame that encodes a reporter protein, wherein the reporter protein is a bioluminescent protein, a fluorescent protein, or a chemiluminescent protein.

2. The recombinant B11 bacteriophage nucleic acid sequence of claim 1, wherein the open reading frame of the heterologous nucleic acid sequence is operably linked to an expression control sequence that is capable of directing expression of the reporter protein.

3. The recombinant B11 bacteriophage nucleic acid sequence of claim 2, wherein the expression control sequence is an inducible promoter or a constitutive promoter.

4. The recombinant B11 bacteriophage nucleic acid sequence of claim 1, wherein the fluorescent protein is selected from the group consisting of TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOκ, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa.

5. The recombinant B11 bacteriophage nucleic acid sequence of claim 1, wherein the chemiluminescent protein is β-galactosidase, horseradish peroxidase (HRP), or alkaline phosphatase.

6. The recombinant B11 bacteriophage nucleic acid sequence of claim 1, wherein the bioluminescent protein is Aequorin, firefly luciferase, *Renilla* luciferase, red luciferase, luxAB, or nanoluciferase.

7. The recombinant B11 bacteriophage nucleic acid sequence of claim 6, wherein the bioluminescent protein is nanoluciferase.

8. A recombinant B11 bacteriophage comprising the recombinant B11 bacteriophage nucleic acid sequence of claim 1.

9. A bacterial host cell comprising the recombinant B11 bacteriophage of claim 8.

10. A vector comprising the recombinant B11 bacteriophage nucleic acid sequence of claim 1.

11. A bacterial host cell comprising the vector of claim 10.

12. The bacterial host cell of claim 9, wherein the host cell is a natural or non-natural host for B11 bacteriophage.

13. The bacterial host cell of claim 11, wherein the host cell is a natural or non-natural host for B11 bacteriophage.

14. A kit comprising one or more coded/labeled vials that contain the recombinant B11 bacteriophage of claim 8, instructions for use, and optionally at least one antibiotic.

15. A method for identifying at least one bacterial strain or species in a test sample obtained from a subject comprising (a) infecting the test sample comprising bacterial cells with the recombinant B11 bacteriophage of claim 8; and (b) detecting the expression of the reporter protein of the recombinant B11 bacteriophage, wherein detection of the reporter protein indicates the presence of at least one bacterial strain or species in the test sample.

16. The method of claim 15, wherein the expression of the reporter protein is measured in about 5, 10, 15, 20, 25, 30, 35, 40, 45, 50, 55, 60, 65, 70, 75, 80, 85, 90 or 120 minutes after infecting the test sample comprising bacterial cells with the recombinant B11 bacteriophage.

17. A method for determining the antibiotic susceptibility of a bacterial strain or species in a test sample obtained from a subject comprising (a) infecting a plurality of test samples comprising bacterial cells with the recombinant B11 bacteriophage of claim 8 and an antibiotic, wherein the plurality of test samples is derived from the subject;

(b) detecting the expression of the reporter protein of the recombinant B11 bacteriophage in the plurality of test samples; and (c) determining that the antibiotic is effective in inhibiting the bacterial strain or species in a test sample when the reporter protein expression levels of the recombinant B11 phage infected bacterial cells in the test sample are reduced relative to that observed in an untreated control sample comprising bacterial cells, wherein the untreated control sample is derived from the subject and is infected with the recombinant B11 bacteriophage.

18. The method of claim 17, wherein the antibiotic is selected from the group consisting of rifampicin, tetracycline, levofloxacin, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

19. The method of claim 17, wherein the expression of the reporter protein is measured in about 5, 10, 15, 20, 25, 30, 35, 40, 45, 50, 55, 60, 65, 70, 75, 80, 85, 90 or 120 minutes after infecting the plurality of test samples comprising bacterial cells with the recombinant B11 bacteriophage.

20. The method of claim 15, wherein the test sample is blood, sputum, mucus, lavage, saliva, or a swab obtained from the subject.

21. The method of claim 20, wherein the subject is human.

* * * * *

SEQUENCE LISTING

<160> NUMBER OF SEQ ID NOS: 20

<210> SEQ ID NO 1
<211> LENGTH: 78879
<212> TYPE: DNA
<213> ORGANISM: Pseudomonas phage B11
<220> FEATURE:
<221> NAME/KEY: modified_base
<222> LOCATION: (203)..(203)
<223> OTHER INFORMATION: a, c, t, g, unknown or other
<220> FEATURE:
<221> NAME/KEY: modified_base
<222> LOCATION: (212)..(212)
<223> OTHER INFORMATION: a, c, t, g, unknown or other
<220> FEATURE:
<221> NAME/KEY: modified_base
<222> LOCATION: (223)..(224)
<223> OTHER INFORMATION: a, c, t, g, unknown or other
<220> FEATURE:
<221> NAME/KEY: modified_base
<222> LOCATION: (226)..(226)
<223> OTHER INFORMATION: a, c, t, g, unknown or other
<220> FEATURE:
<221> NAME/KEY: modified_base
<222> LOCATION: (236)..(238)
<223> OTHER INFORMATION: a, c, t, g, unknown or other
<220> FEATURE:
<221> NAME/KEY: modified_base
<222> LOCATION: (242)..(242)
<223> OTHER INFORMATION: a, c, t, g, unknown or other
<220> FEATURE:
<221> NAME/KEY: modified_base
<222> LOCATION: (244)..(244)
<223> OTHER INFORMATION: a, c, t, g, unknown or other
<220> FEATURE:
<221> NAME/KEY: modified_base
<222> LOCATION: (250)..(251)
<223> OTHER INFORMATION: a, c, t, g, unknown or other
<220> FEATURE:
<221> NAME/KEY: modified_base
<222> LOCATION: (256)..(256)
<223> OTHER INFORMATION: a, c, t, g, unknown or other
<220> FEATURE:
<221> NAME/KEY: modified_base
<222> LOCATION: (281)..(281)
<223> OTHER INFORMATION: a, c, t, g, unknown or other
<220> FEATURE:
<221> NAME/KEY: modified_base
<222> LOCATION: (285)..(285)
<223> OTHER INFORMATION: a, c, t, g, unknown or other
<220> FEATURE:
<221> NAME/KEY: modified_base -continued
<222> LOCATION: (293)..(293)
<223> OTHER INFORMATION: a, c, t, g, unknown or other
<220> FEATURE:
<221> NAME/KEY: modified_base
<222> LOCATION: (311)..(311)
<223> OTHER INFORMATION: a, c, t, g, unknown or other
<220> FEATURE:
<221> NAME/KEY: modified_base
<222> LOCATION: (419)..(419)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (509)..(509)
<223> OTHER INFORMATION: a, c, t, g, unknown or other
<220> FEATURE:
<221> NAME/KEY: modified_base
<222> LOCATION: (513)..(513)
<223> OTHER INFORMATION: a, c, t, g, unknown or other
<220> FEATURE:
<221> NAME/KEY: modified_base
<222> LOCATION: (522)..(522)
<223> OTHER INFORMATION: a, c, t, g, unknown or other
<220> FEATURE:
<221> NAME/KEY: modified_base
<222> LOCATION: (531)..(531)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (564)..(564)
<223> OTHER INFORMATION: a, c, t, g, unknown or other
<220> FEATURE:
<221> NAME/KEY: modified_base
<222> LOCATION: (569)..(570)
<223> OTHER INFORMATION: a, c, t, g, unknown or other
<220> FEATURE:
<221> NAME/KEY: modified_base
<222> LOCATION: (579)..(579)
<223> OTHER INFORMATION: a, c, t, g, unknown or other
<220> FEATURE:
<221> NAME/KEY: modified_base
<222> LOCATION: (594)..(594)
<223> OTHER INFORMATION: a, c, t, g, unknown or other
<220> FEATURE:
<221> NAME/KEY: modified_base
<222> LOCATION: (621)..(621)
<223> OTHER INFORMATION: a, c, t, g, unknown or other
<220> FEATURE:
<221> NAME/KEY: modified_base
<222> LOCATION: (648)..(648)
<223> OTHER INFORMATION: a, c, t, g, unknown or other
<220> FEATURE:
<221> NAME/KEY: modified_base
<222> LOCATION: (3627)..(3627)
<223> OTHER INFORMATION: a, c, t, g, unknown or other
<220> FEATURE:
<221> NAME/KEY: modified_base
<222> LOCATION: (3636)..(3636)
<223> OTHER INFORMATION: a, c, t, g, unknown or other
<220> FEATURE:
<221> NAME/KEY: modified_base
<222> LOCATION: (3639)..(3639)
<223> OTHER INFORMATION: a, c, t, g, unknown or other
<220> FEATURE:
<221> NAME/KEY: modified_base
<222> LOCATION: (3642)..(3642)
<223> OTHER INFORMATION: a, c, t, g, unknown or other
<220> FEATURE:

<221> NAME/KEY: modified_base
<222> LOCATION: (3675)..(3675)
<223> OTHER INFORMATION: a, c, t, g, unknown or other
<220> FEATURE:
<221> NAME/KEY: modified_base
<222> LOCATION: (3681)..(3681)
<223> OTHER INFORMATION: a, c, t, g, unknown or other
<220> FEATURE:
<221> NAME/KEY: modified_base
<222> LOCATION: (3684)..(3684)
<223> OTHER INFORMATION: a, c, t, g, unknown or other
<220> FEATURE:
<221> NAME/KEY: modified_base
<222> LOCATION: (3692)..(3692)
<223> OTHER INFORMATION: a, c, t, g, unknown or other
<220> FEATURE:
<221> NAME/KEY: modified_base
<222> LOCATION: (4080)..(4080)
<223> OTHER INFORMATION: a, c, t, g, unknown or other
<220> FEATURE:
<221> NAME/KEY: modified_base
<222> LOCATION: (4182)..(4182)
<223> OTHER INFORMATION: a, c, t, g, unknown or other
<220> FEATURE:
<221> NAME/KEY: modified_base
<222> LOCATION: (4212)..(4212)
<223> OTHER INFORMATION: a, c, t, g, unknown or other
<220> FEATURE:
<221> NAME/KEY: modified_base
<222> LOCATION: (4314)..(4314)
<223> OTHER INFORMATION: a, c, t, g, unknown or other
<220> FEATURE:
<221> NAME/KEY: modified_base
<222> LOCATION: (4323)..(4323)
<223> OTHER INFORMATION: a, c, t, g, unknown or other
<220> FEATURE:
<221> NAME/KEY: modified_base
<222> LOCATION: (5079)..(5079)
<223> OTHER INFORMATION: a, c, t, g, unknown or other
<220> FEATURE:
<221> NAME/KEY: modified_base
<222> LOCATION: (5190)..(5190)
<223> OTHER INFORMATION: a, c, t, g, unknown or other
<220> FEATURE:
<221> NAME/KEY: modified_base
<222> LOCATION: (6180)..(6180)
<223> OTHER INFORMATION: a, c, t, g, unknown or other
<220> FEATURE:
<221> NAME/KEY: modified_base
<222> LOCATION: (6252)..(6252)
<223> OTHER INFORMATION: a, c, t, g, unknown or other
<220> FEATURE:
<221> NAME/KEY: modified_base
<222> LOCATION: (6273)..(6273)
<223> OTHER INFORMATION: a, c, t, g, unknown or other
<220> FEATURE:
<221> NAME/KEY: modified_base
<222> LOCATION: (6279)..(6279)
<223> OTHER INFORMATION: a, c, t, g, unknown or other
<220> FEATURE:
<221> NAME/KEY: modified_base
<222> LOCATION: (6612)..(6612)
<223> OTHER INFORMATION: a, c, t, g, unknown or other
<220> FEATURE:
<221> NAME/KEY: modified_base
<222> LOCATION: (6621)..(6621)
<223> OTHER INFORMATION: a, c, t, g, unknown or other
<220> FEATURE:
<221> NAME/KEY: modified_base
<222> LOCATION: (6627)..(6627)
<223> OTHER INFORMATION: a, c, t, g, unknown or other
<220> FEATURE:
<221> NAME/KEY: modified_base
<222> LOCATION: (6783)..(6783)
<223> OTHER INFORMATION: a, c, t, g, unknown or other
<220> FEATURE:
<221> NAME/KEY: modified_base
<222> LOCATION: (6792)..(6792)
<223> OTHER INFORMATION: a, c, t, g, unknown or other
<220> FEATURE:
<221> NAME/KEY: modified_base
<222> LOCATION: (6800)..(6801)
<223> OTHER INFORMATION: a, c, t, g, unknown or other
<220> FEATURE:
<221> NAME/KEY: modified_base
<222> LOCATION: (6819)..(6819)
<223> OTHER INFORMATION: a, c, t, g, unknown or other
<220> FEATURE:
<221> NAME/KEY: modified_base
<222> LOCATION: (6840)..(6840)
<223> OTHER INFORMATION: a, c, t, g, unknown or other
<220> FEATURE:
<221> NAME/KEY: modified_base
<222> LOCATION: (6846)..(6846)
<223> OTHER INFORMATION: a, c, t, g, unknown or other
<220> FEATURE:
<221> NAME/KEY: modified_base
<222> LOCATION: (6945)..(6945)
<223> OTHER INFORMATION: a, c, t, g, unknown or other
<220> FEATURE:
<221> NAME/KEY: modified_base
<222> LOCATION: (9573)..(9573)
<223> OTHER INFORMATION: a, c, t, g, unknown or other
<220> FEATURE:
<221> NAME/KEY: modified_base
<222> LOCATION: (9576)..(9576)
<223> OTHER INFORMATION: a, c, t, g, unknown or other
<220> FEATURE:
<221> NAME/KEY: modified_base
<222> LOCATION: (9578)..(9578)
<223> OTHER INFORMATION: a, c, t, g, unknown or other
<220> FEATURE:
<221> NAME/KEY: modified_base
<222> LOCATION: (9582)..(9583)
<223> OTHER INFORMATION: a, c, t, g, unknown or other
<220> FEATURE:
<221> NAME/KEY: modified_base
<222> LOCATION: (9603)..(9603)
<223> OTHER INFORMATION: a, c, t, g, unknown or other
<220> FEATURE:
<221> NAME/KEY: modified_base
<222> LOCATION: (9606)..(9606)
<223> OTHER INFORMATION: a, c, t, g, unknown or other
<220> FEATURE:
<221> NAME/KEY: modified_base
<222> LOCATION: (9609)..(9609)
<223> OTHER INFORMATION: a, c, t, g, unknown or other
<220> FEATURE:
<221> NAME/KEY: modified_base
<222> LOCATION: (9661)..(9661)
<223> OTHER INFORMATION: a, c, t, g, unknown or other
<220> FEATURE:
<221> NAME/KEY: modified_base
<222> LOCATION: (9854)..(9854)
<223> OTHER INFORMATION: a, c, t, g, unknown or other
<220> FEATURE:
<221> NAME/KEY: modified_base
<222> LOCATION: (10379)..(10379)
<223> OTHER INFORMATION: a, c, t, g, unknown or other
<220> FEATURE:
<221> NAME/KEY: modified_base
<222> LOCATION: (10382)..(10382)
<223> OTHER INFORMATION: a, c, t, g, unknown or other
<220> FEATURE:
<221> NAME/KEY: modified_base
<222> LOCATION: (10385)..(10385)
<223> OTHER INFORMATION: a, c, t, g, unknown or other
<220> FEATURE:
<221> NAME/KEY: modified_base
<222> LOCATION: (10388)..(10388)
<223> OTHER INFORMATION: a, c, t, g, unknown or other
<220> FEATURE:
<221> NAME/KEY: modified_base
<222> LOCATION: (10397)..(10397)
<223> OTHER INFORMATION: a, c, t, g, unknown or other
<220> FEATURE:
<221> NAME/KEY: modified_base
<222> LOCATION: (10400)..(10400)

<223> OTHER INFORMATION: a, c, t, g, unknown or other
<220> FEATURE:
<221> NAME/KEY: modified_base
<222> LOCATION: (10403)..(10403)
<223> OTHER INFORMATION: a, c, t, g, unknown or other
<220> FEATURE:
<221> NAME/KEY: modified_base
<222> LOCATION: (10415)..(10415)
<223> OTHER INFORMATION: a, c, t, g, unknown or other
<220> FEATURE:
<221> NAME/KEY: modified_base
<222> LOCATION: (10488)..(10488)
<223> OTHER INFORMATION: a, c, t, g, unknown or other
<220> FEATURE:
<221> NAME/KEY: modified_base
<222> LOCATION: (10556)..(10556)
<223> OTHER INFORMATION: a, c, t, g, unknown or other
<220> FEATURE:
<221> NAME/KEY: modified_base
<222> LOCATION: (10580)..(10580)
<223> OTHER INFORMATION: a, c, t, g, unknown or other
<220> FEATURE:
<221> NAME/KEY: modified_base
<222> LOCATION: (10598)..(10598)
<223> OTHER INFORMATION: a, c, t, g, unknown or other
<220> FEATURE:
<221> NAME/KEY: modified_base
<222> LOCATION: (10610)..(10610)
<223> OTHER INFORMATION: a, c, t, g, unknown or other
<220> FEATURE:
<221> NAME/KEY: modified_base
<222> LOCATION: (10835)..(10835)
<223> OTHER INFORMATION: a, c, t, g, unknown or other
<220> FEATURE:
<221> NAME/KEY: modified_base
<222> LOCATION: (10837)..(10837)
<223> OTHER INFORMATION: a, c, t, g, unknown or other
<220> FEATURE:
<221> NAME/KEY: modified_base
<222> LOCATION: (10850)..(10850)
<223> OTHER INFORMATION: a, c, t, g, unknown or other
<220> FEATURE:
<221> NAME/KEY: modified_base
<222> LOCATION: (10853)..(10853)
<223> OTHER INFORMATION: a, c, t, g, unknown or other
<220> FEATURE:
<221> NAME/KEY: modified_base
<222> LOCATION: (10913)..(10913)
<223> OTHER INFORMATION: a, c, t, g, unknown or other
<220> FEATURE:
<221> NAME/KEY: modified_base
<222> LOCATION: (11051)..(11051)
<223> OTHER INFORMATION: a, c, t, g, unknown or other
<220> FEATURE:
<221> NAME/KEY: modified_base
<222> LOCATION: (11108)..(11108)
<223> OTHER INFORMATION: a, c, t, g, unknown or other
<220> FEATURE:
<221> NAME/KEY: modified_base
<222> LOCATION: (11117)..(11117)
<223> OTHER INFORMATION: a, c, t, g, unknown or other
<220> FEATURE:
<221> NAME/KEY: modified_base
<222> LOCATION: (11244)..(11244)
<223> OTHER INFORMATION: a, c, t, g, unknown or other
<220> FEATURE:
<221> NAME/KEY: modified_base
<222> LOCATION: (11246)..(11246)
<223> OTHER INFORMATION: a, c, t, g, unknown or other
<220> FEATURE:
<221> NAME/KEY: modified_base
<222> LOCATION: (11450)..(11450)
<223> OTHER INFORMATION: a, c, t, g, unknown or other
<220> FEATURE:
<221> NAME/KEY: modified_base
<222> LOCATION: (11453)..(11453)
<223> OTHER INFORMATION: a, c, t, g, unknown or other
<220> FEATURE:
<221> NAME/KEY: modified_base

```
<222> LOCATION: (11549)..(11549)
<223> OTHER INFORMATION: a, c, t, g, unknown or other
<220> FEATURE:
<221> NAME/KEY: modified_base
<222> LOCATION: (11585)..(11585)
<223> OTHER INFORMATION: a, c, t, g, unknown or other
<220> FEATURE:
<221> NAME/KEY: modified_base
<222> LOCATION: (11606)..(11606)
<223> OTHER INFORMATION: a, c, t, g, unknown or other
<220> FEATURE:
<221> NAME/KEY: modified_base
<222> LOCATION: (12014)..(12014)
<223> OTHER INFORMATION: a, c, t, g, unknown or other
<220> FEATURE:
<221> NAME/KEY: modified_base
<222> LOCATION: (12058)..(12058)
<223> OTHER INFORMATION: a, c, t, g, unknown or other
<220> FEATURE:
<221> NAME/KEY: modified_base
<222> LOCATION: (12112)..(12112)
<223> OTHER INFORMATION: a, c, t, g, unknown or other
<220> FEATURE:
<221> NAME/KEY: modified_base
<222> LOCATION: (12125)..(12125)
<223> OTHER INFORMATION: a, c, t, g, unknown or other
<220> FEATURE:
<221> NAME/KEY: modified_base
<222> LOCATION: (12145)..(12145)
<223> OTHER INFORMATION: a, c, t, g, unknown or other
<220> FEATURE:
<221> NAME/KEY: modified_base
<222> LOCATION: (12200)..(12200)
<223> OTHER INFORMATION: a, c, t, g, unknown or other
<220> FEATURE:
<221> NAME/KEY: modified_base
<222> LOCATION: (12262)..(12262)
<223> OTHER INFORMATION: a, c, t, g, unknown or other
<220> FEATURE:
<221> NAME/KEY: modified_base
<222> LOCATION: (12266)..(12266)
<223> OTHER INFORMATION: a, c, t, g, unknown or other
<220> FEATURE:
<221> NAME/KEY: modified_base
<222> LOCATION: (12308)..(12308)
<223> OTHER INFORMATION: a, c, t, g, unknown or other
<220> FEATURE:
<221> NAME/KEY: modified_base
<222> LOCATION: (12311)..(12311)
<223> OTHER INFORMATION: a, c, t, g, unknown or other
<220> FEATURE:
<221> NAME/KEY: modified_base
<222> LOCATION: (12356)..(12356)
<223> OTHER INFORMATION: a, c, t, g, unknown or other
<220> FEATURE:
<221> NAME/KEY: modified_base
<222> LOCATION: (12389)..(12389)
<223> OTHER INFORMATION: a, c, t, g, unknown or other
<220> FEATURE:
<221> NAME/KEY: modified_base
<222> LOCATION: (12422)..(12422)
<223> OTHER INFORMATION: a, c, t, g, unknown or other
<220> FEATURE:
<221> NAME/KEY: modified_base
<222> LOCATION: (12630)..(12630)
<223> OTHER INFORMATION: a, c, t, g, unknown or other
<220> FEATURE:
<221> NAME/KEY: modified_base
<222> LOCATION: (12663)..(12663)
<223> OTHER INFORMATION: a, c, t, g, unknown or other
<220> FEATURE:
<221> NAME/KEY: modified_base
<222> LOCATION: (12674)..(12674)
<223> OTHER INFORMATION: a, c, t, g, unknown or other
<220> FEATURE:
<221> NAME/KEY: modified_base
<222> LOCATION: (12686)..(12686)
<223> OTHER INFORMATION: a, c, t, g, unknown or other
<220> FEATURE:
```

<221> NAME/KEY: modified_base
<222> LOCATION: (12693)..(12693)
<223> OTHER INFORMATION: a, c, t, g, unknown or other
<220> FEATURE:
<221> NAME/KEY: modified_base
<222> LOCATION: (12723)..(12723)
<223> OTHER INFORMATION: a, c, t, g, unknown or other
<220> FEATURE:
<221> NAME/KEY: modified_base
<222> LOCATION: (12777)..(12777)
<223> OTHER INFORMATION: a, c, t, g, unknown or other
<220> FEATURE:
<221> NAME/KEY: modified_base
<222> LOCATION: (12822)..(12822)
<223> OTHER INFORMATION: a, c, t, g, unknown or other
<220> FEATURE:
<221> NAME/KEY: modified_base
<222> LOCATION: (14712)..(14712)
<223> OTHER INFORMATION: a, c, t, g, unknown or other
<220> FEATURE:
<221> NAME/KEY: modified_base
<222> LOCATION: (14904)..(14904)
<223> OTHER INFORMATION: a, c, t, g, unknown or other
<220> FEATURE:
<221> NAME/KEY: modified_base
<222> LOCATION: (14906)..(14906)
<223> OTHER INFORMATION: a, c, t, g, unknown or other
<220> FEATURE:
<221> NAME/KEY: modified_base
<222> LOCATION: (14910)..(14910)
<223> OTHER INFORMATION: a, c, t, g, unknown or other
<220> FEATURE:
<221> NAME/KEY: modified_base
<222> LOCATION: (14916)..(14916)
<223> OTHER INFORMATION: a, c, t, g, unknown or other
<220> FEATURE:
<221> NAME/KEY: modified_base
<222> LOCATION: (15003)..(15003)
<223> OTHER INFORMATION: a, c, t, g, unknown or other
<220> FEATURE:
<221> NAME/KEY: modified_base
<222> LOCATION: (15088)..(15088)
<223> OTHER INFORMATION: a, c, t, g, unknown or other
<220> FEATURE:
<221> NAME/KEY: modified_base
<222> LOCATION: (15091)..(15091)
<223> OTHER INFORMATION: a, c, t, g, unknown or other
<220> FEATURE:
<221> NAME/KEY: modified_base
<222> LOCATION: (15102)..(15102)
<223> OTHER INFORMATION: a, c, t, g, unknown or other
<220> FEATURE:
<221> NAME/KEY: modified_base
<222> LOCATION: (15105)..(15105)
<223> OTHER INFORMATION: a, c, t, g, unknown or other
<220> FEATURE:
<221> NAME/KEY: modified_base
<222> LOCATION: (15108)..(15108)
<223> OTHER INFORMATION: a, c, t, g, unknown or other
<220> FEATURE:
<221> NAME/KEY: modified_base
<222> LOCATION: (15180)..(15180)
<223> OTHER INFORMATION: a, c, t, g, unknown or other
<220> FEATURE:
<221> NAME/KEY: modified_base
<222> LOCATION: (16845)..(16845)
<223> OTHER INFORMATION: a, c, t, g, unknown or other
<220> FEATURE:
<221> NAME/KEY: modified_base
<222> LOCATION: (16852)..(16852)
<223> OTHER INFORMATION: a, c, t, g, unknown or other
<220> FEATURE:
<221> NAME/KEY: modified_base
<222> LOCATION: (17294)..(17294)
<223> OTHER INFORMATION: a, c, t, g, unknown or other
<220> FEATURE:
<221> NAME/KEY: modified_base
<222> LOCATION: (17399)..(17399)
<223> OTHER INFORMATION: a, c, t, g, unknown or other -continued
<220> FEATURE:
<221> NAME/KEY: modified_base
<222> LOCATION: (17648)..(17648)
<223> OTHER INFORMATION: a, c, t, g, unknown or other
<220> FEATURE:
<221> NAME/KEY: modified_base
<222> LOCATION: (17673)..(17674)
<223> OTHER INFORMATION: a, c, t, g, unknown or other
<220> FEATURE:
<221> NAME/KEY: modified_base
<222> LOCATION: (17982)..(17983)
<223> OTHER INFORMATION: a, c, t, g, unknown or other
<220> FEATURE:
<221> NAME/KEY: modified_base
<222> LOCATION: (17993)..(17993)
<223> OTHER INFORMATION: a, c, t, g, unknown or other
<220> FEATURE:
<221> NAME/KEY: modified_base
<222> LOCATION: (18008)..(18008)
<223> OTHER INFORMATION: a, c, t, g, unknown or other
<220> FEATURE:
<221> NAME/KEY: modified_base
<222> LOCATION: (18020)..(18020)
<223> OTHER INFORMATION: a, c, t, g, unknown or other
<220> FEATURE:
<221> NAME/KEY: modified_base
<222> LOCATION: (18029)..(18029)
<223> OTHER INFORMATION: a, c, t, g, unknown or other
<220> FEATURE:
<221> NAME/KEY: modified_base
<222> LOCATION: (18041)..(18041)
<223> OTHER INFORMATION: a, c, t, g, unknown or other
<220> FEATURE:
<221> NAME/KEY: modified_base
<222> LOCATION: (18110)..(18111)
<223> OTHER INFORMATION: a, c, t, g, unknown or other
<220> FEATURE:
<221> NAME/KEY: modified_base
<222> LOCATION: (18309)..(18309)
<223> OTHER INFORMATION: a, c, t, g, unknown or other
<220> FEATURE:
<221> NAME/KEY: modified_base
<222> LOCATION: (18401)..(18401)
<223> OTHER INFORMATION: a, c, t, g, unknown or other
<220> FEATURE:
<221> NAME/KEY: modified_base
<222> LOCATION: (18405)..(18405)
<223> OTHER INFORMATION: a, c, t, g, unknown or other
<220> FEATURE:
<221> NAME/KEY: modified_base
<222> LOCATION: (18450)..(18450)
<223> OTHER INFORMATION: a, c, t, g, unknown or other
<220> FEATURE:
<221> NAME/KEY: modified_base
<222> LOCATION: (18458)..(18458)
<223> OTHER INFORMATION: a, c, t, g, unknown or other
<220> FEATURE:
<221> NAME/KEY: modified_base
<222> LOCATION: (18574)..(18574)
<223> OTHER INFORMATION: a, c, t, g, unknown or other
<220> FEATURE:
<221> NAME/KEY: modified_base
<222> LOCATION: (18641)..(18641)
<223> OTHER INFORMATION: a, c, t, g, unknown or other
<220> FEATURE:
<221> NAME/KEY: modified_base
<222> LOCATION: (18740)..(18740)
<223> OTHER INFORMATION: a, c, t, g, unknown or other
<220> FEATURE:
<221> NAME/KEY: modified_base
<222> LOCATION: (18779)..(18779)
<223> OTHER INFORMATION: a, c, t, g, unknown or other
<220> FEATURE:
<221> NAME/KEY: modified_base
<222> LOCATION: (18881)..(18881)
<223> OTHER INFORMATION: a, c, t, g, unknown or other
<220> FEATURE:
<221> NAME/KEY: modified_base
<222> LOCATION: (19177)..(19177)

<223> OTHER INFORMATION: a, c, t, g, unknown or other
<220> FEATURE:
<221> NAME/KEY: modified_base
<222> LOCATION: (19326)..(19326)
<223> OTHER INFORMATION: a, c, t, g, unknown or other
<220> FEATURE:
<221> NAME/KEY: modified_base
<222> LOCATION: (19349)..(19349)
<223> OTHER INFORMATION: a, c, t, g, unknown or other
<220> FEATURE:
<221> NAME/KEY: modified_base
<222> LOCATION: (19370)..(19370)
<223> OTHER INFORMATION: a, c, t, g, unknown or other
<220> FEATURE:
<221> NAME/KEY: modified_base
<222> LOCATION: (19616)..(19616)
<223> OTHER INFORMATION: a, c, t, g, unknown or other
<220> FEATURE:
<221> NAME/KEY: modified_base
<222> LOCATION: (19732)..(19732)
<223> OTHER INFORMATION: a, c, t, g, unknown or other
<220> FEATURE:
<221> NAME/KEY: modified_base
<222> LOCATION: (19749)..(19749)
<223> OTHER INFORMATION: a, c, t, g, unknown or other
<220> FEATURE:
<221> NAME/KEY: modified_base
<222> LOCATION: (19756)..(19756)
<223> OTHER INFORMATION: a, c, t, g, unknown or other
<220> FEATURE:
<221> NAME/KEY: modified_base
<222> LOCATION: (19758)..(19758)
<223> OTHER INFORMATION: a, c, t, g, unknown or other
<220> FEATURE:
<221> NAME/KEY: modified_base
<222> LOCATION: (19760)..(19760)
<223> OTHER INFORMATION: a, c, t, g, unknown or other
<220> FEATURE:
<221> NAME/KEY: modified_base
<222> LOCATION: (20043)..(20043)
<223> OTHER INFORMATION: a, c, t, g, unknown or other
<220> FEATURE:
<221> NAME/KEY: modified_base
<222> LOCATION: (20053)..(20053)
<223> OTHER INFORMATION: a, c, t, g, unknown or other
<220> FEATURE:
<221> NAME/KEY: modified_base
<222> LOCATION: (20085)..(20085)
<223> OTHER INFORMATION: a, c, t, g, unknown or other
<220> FEATURE:
<221> NAME/KEY: modified_base
<222> LOCATION: (20152)..(20152)
<223> OTHER INFORMATION: a, c, t, g, unknown or other
<220> FEATURE:
<221> NAME/KEY: modified_base
<222> LOCATION: (20170)..(20170)
<223> OTHER INFORMATION: a, c, t, g, unknown or other
<220> FEATURE:
<221> NAME/KEY: modified_base
<222> LOCATION: (20176)..(20176)
<223> OTHER INFORMATION: a, c, t, g, unknown or other
<220> FEATURE:
<221> NAME/KEY: modified_base
<222> LOCATION: (20251)..(20251)
<223> OTHER INFORMATION: a, c, t, g, unknown or other
<220> FEATURE:
<221> NAME/KEY: modified_base
<222> LOCATION: (20257)..(20257)
<223> OTHER INFORMATION: a, c, t, g, unknown or other
<220> FEATURE:
<221> NAME/KEY: modified_base
<222> LOCATION: (20269)..(20269)
<223> OTHER INFORMATION: a, c, t, g, unknown or other
<220> FEATURE:
<221> NAME/KEY: modified_base
<222> LOCATION: (20296)..(20296)
<223> OTHER INFORMATION: a, c, t, g, unknown or other
<220> FEATURE:
<221> NAME/KEY: modified_base
<222> LOCATION: (20299)..(20299)
<223> OTHER INFORMATION: a, c, t, g, unknown or other
<220> FEATURE:
<221> NAME/KEY: modified_base
<222> LOCATION: (20302)..(20302)
<223> OTHER INFORMATION: a, c, t, g, unknown or other
<220> FEATURE:
<221> NAME/KEY: modified_base
<222> LOCATION: (20305)..(20305)
<223> OTHER INFORMATION: a, c, t, g, unknown or other
<220> FEATURE:
<221> NAME/KEY: modified_base
<222> LOCATION: (20313)..(20313)
<223> OTHER INFORMATION: a, c, t, g, unknown or other
<220> FEATURE:
<221> NAME/KEY: modified_base
<222> LOCATION: (20416)..(20416)
<223> OTHER INFORMATION: a, c, t, g, unknown or other
<220> FEATURE:
<221> NAME/KEY: modified_base
<222> LOCATION: (20488)..(20488)
<223> OTHER INFORMATION: a, c, t, g, unknown or other
<220> FEATURE:
<221> NAME/KEY: modified_base
<222> LOCATION: (21006)..(21006)
<223> OTHER INFORMATION: a, c, t, g, unknown or other
<220> FEATURE:
<221> NAME/KEY: modified_base
<222> LOCATION: (21012)..(21012)
<223> OTHER INFORMATION: a, c, t, g, unknown or other
<220> FEATURE:
<221> NAME/KEY: modified_base
<222> LOCATION: (21019)..(21019)
<223> OTHER INFORMATION: a, c, t, g, unknown or other
<220> FEATURE:
<221> NAME/KEY: modified_base
<222> LOCATION: (21024)..(21024)
<223> OTHER INFORMATION: a, c, t, g, unknown or other
<220> FEATURE:
<221> NAME/KEY: modified_base
<222> LOCATION: (21173)..(21173)
<223> OTHER INFORMATION: a, c, t, g, unknown or other
<220> FEATURE:
<221> NAME/KEY: modified_base
<222> LOCATION: (21175)..(21175)
<223> OTHER INFORMATION: a, c, t, g, unknown or other
<220> FEATURE:
<221> NAME/KEY: modified_base
<222> LOCATION: (21182)..(21182)
<223> OTHER INFORMATION: a, c, t, g, unknown or other
<220> FEATURE:
<221> NAME/KEY: modified_base
<222> LOCATION: (21184)..(21184)
<223> OTHER INFORMATION: a, c, t, g, unknown or other
<220> FEATURE:
<221> NAME/KEY: modified_base
<222> LOCATION: (21423)..(21423)
<223> OTHER INFORMATION: a, c, t, g, unknown or other
<220> FEATURE:
<221> NAME/KEY: modified_base
<222> LOCATION: (21425)..(21429)
<223> OTHER INFORMATION: a, c, t, g, unknown or other
<220> FEATURE:
<221> NAME/KEY: modified_base
<222> LOCATION: (21432)..(21432)
<223> OTHER INFORMATION: a, c, t, g, unknown or other
<220> FEATURE:
<221> NAME/KEY: modified_base
<222> LOCATION: (21435)..(21435)
<223> OTHER INFORMATION: a, c, t, g, unknown or other
<220> FEATURE:
<221> NAME/KEY: modified_base
<222> LOCATION: (21440)..(21440)
<223> OTHER INFORMATION: a, c, t, g, unknown or other
<220> FEATURE:
<221> NAME/KEY: modified_base
<222> LOCATION: (21454)..(21454)
<223> OTHER INFORMATION: a, c, t, g, unknown or other
<220> FEATURE:

<221> NAME/KEY: modified_base
<222> LOCATION: (21456)..(21457)
<223> OTHER INFORMATION: a, c, t, g, unknown or other
<220> FEATURE:
<221> NAME/KEY: modified_base
<222> LOCATION: (21471)..(21472)
<223> OTHER INFORMATION: a, c, t, g, unknown or other
<220> FEATURE:
<221> NAME/KEY: modified_base
<222> LOCATION: (21474)..(21474)
<223> OTHER INFORMATION: a, c, t, g, unknown or other
<220> FEATURE:
<221> NAME/KEY: modified_base
<222> LOCATION: (21478)..(21478)
<223> OTHER INFORMATION: a, c, t, g, unknown or other
<220> FEATURE:
<221> NAME/KEY: modified_base
<222> LOCATION: (21496)..(21496)
<223> OTHER INFORMATION: a, c, t, g, unknown or other
<220> FEATURE:
<221> NAME/KEY: modified_base
<222> LOCATION: (21517)..(21517)
<223> OTHER INFORMATION: a, c, t, g, unknown or other
<220> FEATURE:
<221> NAME/KEY: modified_base
<222> LOCATION: (21533)..(21534)
<223> OTHER INFORMATION: a, c, t, g, unknown or other
<220> FEATURE:
<221> NAME/KEY: modified_base
<222> LOCATION: (21544)..(21544)
<223> OTHER INFORMATION: a, c, t, g, unknown or other
<220> FEATURE:
<221> NAME/KEY: modified_base
<222> LOCATION: (21559)..(21559)
<223> OTHER INFORMATION: a, c, t, g, unknown or other
<220> FEATURE:
<221> NAME/KEY: modified_base
<222> LOCATION: (21570)..(21570)
<223> OTHER INFORMATION: a, c, t, g, unknown or other
<220> FEATURE:
<221> NAME/KEY: modified_base
<222> LOCATION: (21574)..(21574)
<223> OTHER INFORMATION: a, c, t, g, unknown or other
<220> FEATURE:
<221> NAME/KEY: modified_base
<222> LOCATION: (21583)..(21583)
<223> OTHER INFORMATION: a, c, t, g, unknown or other
<220> FEATURE:
<221> NAME/KEY: modified_base
<222> LOCATION: (21660)..(21660)
<223> OTHER INFORMATION: a, c, t, g, unknown or other
<220> FEATURE:
<221> NAME/KEY: modified_base
<222> LOCATION: (21684)..(21684)
<223> OTHER INFORMATION: a, c, t, g, unknown or other
<220> FEATURE:
<221> NAME/KEY: modified_base
<222> LOCATION: (21710)..(21710)
<223> OTHER INFORMATION: a, c, t, g, unknown or other
<220> FEATURE:
<221> NAME/KEY: modified_base
<222> LOCATION: (21778)..(21778)
<223> OTHER INFORMATION: a, c, t, g, unknown or other
<220> FEATURE:
<221> NAME/KEY: modified_base
<222> LOCATION: (21789)..(21789)
<223> OTHER INFORMATION: a, c, t, g, unknown or other
<220> FEATURE:
<221> NAME/KEY: modified_base
<222> LOCATION: (21798)..(21798)
<223> OTHER INFORMATION: a, c, t, g, unknown or other
<220> FEATURE:
<221> NAME/KEY: modified_base
<222> LOCATION: (21823)..(21823)
<223> OTHER INFORMATION: a, c, t, g, unknown or other
<220> FEATURE:
<221> NAME/KEY: modified_base
<222> LOCATION: (21874)..(21874)
<223> OTHER INFORMATION: a, c, t, g, unknown or other
<220> FEATURE:
<221> NAME/KEY: modified_base
<222> LOCATION: (21876)..(21876)
<223> OTHER INFORMATION: a, c, t, g, unknown or other
<220> FEATURE:
<221> NAME/KEY: modified_base
<222> LOCATION: (21880)..(21880)
<223> OTHER INFORMATION: a, c, t, g, unknown or other
<220> FEATURE:
<221> NAME/KEY: modified_base
<222> LOCATION: (21889)..(21889)
<223> OTHER INFORMATION: a, c, t, g, unknown or other
<220> FEATURE:
<221> NAME/KEY: modified_base
<222> LOCATION: (21894)..(21894)
<223> OTHER INFORMATION: a, c, t, g, unknown or other
<220> FEATURE:
<221> NAME/KEY: modified_base
<222> LOCATION: (22844)..(22844)
<223> OTHER INFORMATION: a, c, t, g, unknown or other
<220> FEATURE:
<221> NAME/KEY: modified_base
<222> LOCATION: (22907)..(22907)
<223> OTHER INFORMATION: a, c, t, g, unknown or other
<220> FEATURE:
<221> NAME/KEY: modified_base
<222> LOCATION: (22914)..(22914)
<223> OTHER INFORMATION: a, c, t, g, unknown or other
<220> FEATURE:
<221> NAME/KEY: modified_base
<222> LOCATION: (23167)..(23167)
<223> OTHER INFORMATION: a, c, t, g, unknown or other
<220> FEATURE:
<221> NAME/KEY: modified_base
<222> LOCATION: (23348)..(23348)
<223> OTHER INFORMATION: a, c, t, g, unknown or other
<220> FEATURE:
<221> NAME/KEY: modified_base
<222> LOCATION: (23351)..(23351)
<223> OTHER INFORMATION: a, c, t, g, unknown or other
<220> FEATURE:
<221> NAME/KEY: modified_base
<222> LOCATION: (23406)..(23406)
<223> OTHER INFORMATION: a, c, t, g, unknown or other
<220> FEATURE:
<221> NAME/KEY: modified_base
<222> LOCATION: (23647)..(23647)
<223> OTHER INFORMATION: a, c, t, g, unknown or other
<220> FEATURE:
<221> NAME/KEY: modified_base
<222> LOCATION: (23806)..(23806)
<223> OTHER INFORMATION: a, c, t, g, unknown or other
<220> FEATURE:
<221> NAME/KEY: modified_base
<222> LOCATION: (24617)..(24617)
<223> OTHER INFORMATION: a, c, t, g, unknown or other
<220> FEATURE:
<221> NAME/KEY: modified_base
<222> LOCATION: (24853)..(24853)
<223> OTHER INFORMATION: a, c, t, g, unknown or other
<220> FEATURE:
<221> NAME/KEY: modified_base
<222> LOCATION: (25080)..(25080)
<223> OTHER INFORMATION: a, c, t, g, unknown or other
<220> FEATURE:
<221> NAME/KEY: modified_base
<222> LOCATION: (25108)..(25108)
<223> OTHER INFORMATION: a, c, t, g, unknown or other
<220> FEATURE:
<221> NAME/KEY: modified_base
<222> LOCATION: (25371)..(25371)
<223> OTHER INFORMATION: a, c, t, g, unknown or other
<220> FEATURE:
<221> NAME/KEY: modified_base
<222> LOCATION: (25397)..(25397)
<223> OTHER INFORMATION: a, c, t, g, unknown or other
<220> FEATURE:
<221> NAME/KEY: modified_base
<222> LOCATION: (25411)..(25411)

<223> OTHER INFORMATION: a, c, t, g, unknown or other
<220> FEATURE:
<221> NAME/KEY: modified_base
<222> LOCATION: (25507)..(25507)
<223> OTHER INFORMATION: a, c, t, g, unknown or other
<220> FEATURE:
<221> NAME/KEY: modified_base
<222> LOCATION: (25692)..(25692)
<223> OTHER INFORMATION: a, c, t, g, unknown or other
<220> FEATURE:
<221> NAME/KEY: modified_base
<222> LOCATION: (25712)..(25713)
<223> OTHER INFORMATION: a, c, t, g, unknown or other
<220> FEATURE:
<221> NAME/KEY: modified_base
<222> LOCATION: (25718)..(25718)
<223> OTHER INFORMATION: a, c, t, g, unknown or other
<220> FEATURE:
<221> NAME/KEY: modified_base
<222> LOCATION: (25728)..(25728)
<223> OTHER INFORMATION: a, c, t, g, unknown or other
<220> FEATURE:
<221> NAME/KEY: modified_base
<222> LOCATION: (25742)..(25742)
<223> OTHER INFORMATION: a, c, t, g, unknown or other
<220> FEATURE:
<221> NAME/KEY: modified_base
<222> LOCATION: (25774)..(25774)
<223> OTHER INFORMATION: a, c, t, g, unknown or other
<220> FEATURE:
<221> NAME/KEY: modified_base
<222> LOCATION: (27450)..(27450)
<223> OTHER INFORMATION: a, c, t, g, unknown or other
<220> FEATURE:
<221> NAME/KEY: modified_base
<222> LOCATION: (29480)..(29480)
<223> OTHER INFORMATION: a, c, t, g, unknown or other
<220> FEATURE:
<221> NAME/KEY: modified_base
<222> LOCATION: (29507)..(29507)
<223> OTHER INFORMATION: a, c, t, g, unknown or other
<220> FEATURE:
<221> NAME/KEY: modified_base
<222> LOCATION: (31101)..(31101)
<223> OTHER INFORMATION: a, c, t, g, unknown or other
<220> FEATURE:
<221> NAME/KEY: modified_base
<222> LOCATION: (32562)..(32562)
<223> OTHER INFORMATION: a, c, t, g, unknown or other
<220> FEATURE:
<221> NAME/KEY: modified_base
<222> LOCATION: (32840)..(32840)
<223> OTHER INFORMATION: a, c, t, g, unknown or other
<220> FEATURE:
<221> NAME/KEY: modified_base
<222> LOCATION: (32855)..(32855)
<223> OTHER INFORMATION: a, c, t, g, unknown or other
<220> FEATURE:
<221> NAME/KEY: modified_base
<222> LOCATION: (32865)..(32865)
<223> OTHER INFORMATION: a, c, t, g, unknown or other
<220> FEATURE:
<221> NAME/KEY: modified_base
<222> LOCATION: (32922)..(32922)
<223> OTHER INFORMATION: a, c, t, g, unknown or other
<220> FEATURE:
<221> NAME/KEY: modified_base
<222> LOCATION: (32988)..(32988)
<223> OTHER INFORMATION: a, c, t, g, unknown or other
<220> FEATURE:
<221> NAME/KEY: modified_base
<222> LOCATION: (32991)..(32991)
<223> OTHER INFORMATION: a, c, t, g, unknown or other
<220> FEATURE:
<221> NAME/KEY: modified_base
<222> LOCATION: (33295)..(33295)
<223> OTHER INFORMATION: a, c, t, g, unknown or other
<220> FEATURE:
<221> NAME/KEY: modified_base
<222> LOCATION: (33364)..(33364)
<223> OTHER INFORMATION: a, c, t, g, unknown or other
<220> FEATURE:
<221> NAME/KEY: modified_base
<222> LOCATION: (35517)..(35517)
<223> OTHER INFORMATION: a, c, t, g, unknown or other
<220> FEATURE:
<221> NAME/KEY: modified_base
<222> LOCATION: (35526)..(35526)
<223> OTHER INFORMATION: a, c, t, g, unknown or other
<220> FEATURE:
<221> NAME/KEY: modified_base
<222> LOCATION: (35718)..(35718)
<223> OTHER INFORMATION: a, c, t, g, unknown or other
<220> FEATURE:
<221> NAME/KEY: modified_base
<222> LOCATION: (36058)..(36058)
<223> OTHER INFORMATION: a, c, t, g, unknown or other
<220> FEATURE:
<221> NAME/KEY: modified_base
<222> LOCATION: (36064)..(36064)
<223> OTHER INFORMATION: a, c, t, g, unknown or other
<220> FEATURE:
<221> NAME/KEY: modified_base
<222> LOCATION: (36607)..(36607)
<223> OTHER INFORMATION: a, c, t, g, unknown or other
<220> FEATURE:
<221> NAME/KEY: modified_base
<222> LOCATION: (36622)..(36622)
<223> OTHER INFORMATION: a, c, t, g, unknown or other
<220> FEATURE:
<221> NAME/KEY: modified_base
<222> LOCATION: (36667)..(36667)
<223> OTHER INFORMATION: a, c, t, g, unknown or other
<220> FEATURE:
<221> NAME/KEY: modified_base
<222> LOCATION: (36679)..(36679)
<223> OTHER INFORMATION: a, c, t, g, unknown or other
<220> FEATURE:
<221> NAME/KEY: modified_base
<222> LOCATION: (36985)..(36985)
<223> OTHER INFORMATION: a, c, t, g, unknown or other
<220> FEATURE:
<221> NAME/KEY: modified_base
<222> LOCATION: (37006)..(37006)
<223> OTHER INFORMATION: a, c, t, g, unknown or other
<220> FEATURE:
<221> NAME/KEY: modified_base
<222> LOCATION: (37249)..(37249)
<223> OTHER INFORMATION: a, c, t, g, unknown or other
<220> FEATURE:
<221> NAME/KEY: modified_base
<222> LOCATION: (37267)..(37267)
<223> OTHER INFORMATION: a, c, t, g, unknown or other
<220> FEATURE:
<221> NAME/KEY: modified_base
<222> LOCATION: (37306)..(37306)
<223> OTHER INFORMATION: a, c, t, g, unknown or other
<220> FEATURE:
<221> NAME/KEY: modified_base
<222> LOCATION: (37351)..(37351)
<223> OTHER INFORMATION: a, c, t, g, unknown or other
<220> FEATURE:
<221> NAME/KEY: modified_base
<222> LOCATION: (37429)..(37429)
<223> OTHER INFORMATION: a, c, t, g, unknown or other
<220> FEATURE:
<221> NAME/KEY: modified_base
<222> LOCATION: (37432)..(37432)
<223> OTHER INFORMATION: a, c, t, g, unknown or other
<220> FEATURE:
<221> NAME/KEY: modified_base
<222> LOCATION: (37504)..(37504)
<223> OTHER INFORMATION: a, c, t, g, unknown or other
<220> FEATURE:
<221> NAME/KEY: modified_base
<222> LOCATION: (37507)..(37507)
<223> OTHER INFORMATION: a, c, t, g, unknown or other
<220> FEATURE:

<221> NAME/KEY: modified_base
<222> LOCATION: (37510)..(37510)
<223> OTHER INFORMATION: a, c, t, g, unknown or other
<220> FEATURE:
<221> NAME/KEY: modified_base
<222> LOCATION: (37550)..(37550)
<223> OTHER INFORMATION: a, c, t, g, unknown or other
<220> FEATURE:
<221> NAME/KEY: modified_base
<222> LOCATION: (37579)..(37579)
<223> OTHER INFORMATION: a, c, t, g, unknown or other
<220> FEATURE:
<221> NAME/KEY: modified_base
<222> LOCATION: (37630)..(37631)
<223> OTHER INFORMATION: a, c, t, g, unknown or other
<220> FEATURE:
<221> NAME/KEY: modified_base
<222> LOCATION: (37642)..(37646)
<223> OTHER INFORMATION: a, c, t, g, unknown or other
<220> FEATURE:
<221> NAME/KEY: modified_base
<222> LOCATION: (37841)..(37841)
<223> OTHER INFORMATION: a, c, t, g, unknown or other
<220> FEATURE:
<221> NAME/KEY: modified_base
<222> LOCATION: (37856)..(37856)
<223> OTHER INFORMATION: a, c, t, g, unknown or other
<220> FEATURE:
<221> NAME/KEY: modified_base
<222> LOCATION: (37859)..(37859)
<223> OTHER INFORMATION: a, c, t, g, unknown or other
<220> FEATURE:
<221> NAME/KEY: modified_base
<222> LOCATION: (37970)..(37970)
<223> OTHER INFORMATION: a, c, t, g, unknown or other
<220> FEATURE:
<221> NAME/KEY: modified_base
<222> LOCATION: (38051)..(38051)
<223> OTHER INFORMATION: a, c, t, g, unknown or other
<220> FEATURE:
<221> NAME/KEY: modified_base
<222> LOCATION: (38198)..(38198)
<223> OTHER INFORMATION: a, c, t, g, unknown or other
<220> FEATURE:
<221> NAME/KEY: modified_base
<222> LOCATION: (38216)..(38216)
<223> OTHER INFORMATION: a, c, t, g, unknown or other
<220> FEATURE:
<221> NAME/KEY: modified_base
<222> LOCATION: (38243)..(38243)
<223> OTHER INFORMATION: a, c, t, g, unknown or other
<220> FEATURE:
<221> NAME/KEY: modified_base
<222> LOCATION: (38306)..(38306)
<223> OTHER INFORMATION: a, c, t, g, unknown or other
<220> FEATURE:
<221> NAME/KEY: modified_base
<222> LOCATION: (38367)..(38367)
<223> OTHER INFORMATION: a, c, t, g, unknown or other
<220> FEATURE:
<221> NAME/KEY: modified_base
<222> LOCATION: (38498)..(38498)
<223> OTHER INFORMATION: a, c, t, g, unknown or other
<220> FEATURE:
<221> NAME/KEY: modified_base
<222> LOCATION: (38624)..(38624)
<223> OTHER INFORMATION: a, c, t, g, unknown or other
<220> FEATURE:
<221> NAME/KEY: modified_base
<222> LOCATION: (38921)..(38921)
<223> OTHER INFORMATION: a, c, t, g, unknown or other
<220> FEATURE:
<221> NAME/KEY: modified_base
<222> LOCATION: (38933)..(38933)
<223> OTHER INFORMATION: a, c, t, g, unknown or other
<220> FEATURE:
<221> NAME/KEY: modified_base
<222> LOCATION: (38960)..(38960)
<223> OTHER INFORMATION: a, c, t, g, unknown or other
<220> FEATURE:
<221> NAME/KEY: modified_base
<222> LOCATION: (39092)..(39092)
<223> OTHER INFORMATION: a, c, t, g, unknown or other
<220> FEATURE:
<221> NAME/KEY: modified_base
<222> LOCATION: (39113)..(39113)
<223> OTHER INFORMATION: a, c, t, g, unknown or other
<220> FEATURE:
<221> NAME/KEY: modified_base
<222> LOCATION: (39149)..(39149)
<223> OTHER INFORMATION: a, c, t, g, unknown or other
<220> FEATURE:
<221> NAME/KEY: modified_base
<222> LOCATION: (39151)..(39151)
<223> OTHER INFORMATION: a, c, t, g, unknown or other
<220> FEATURE:
<221> NAME/KEY: modified_base
<222> LOCATION: (39227)..(39227)
<223> OTHER INFORMATION: a, c, t, g, unknown or other
<220> FEATURE:
<221> NAME/KEY: modified_base
<222> LOCATION: (39240)..(39240)
<223> OTHER INFORMATION: a, c, t, g, unknown or other
<220> FEATURE:
<221> NAME/KEY: modified_base
<222> LOCATION: (39324)..(39324)
<223> OTHER INFORMATION: a, c, t, g, unknown or other
<220> FEATURE:
<221> NAME/KEY: modified_base
<222> LOCATION: (39347)..(39347)
<223> OTHER INFORMATION: a, c, t, g, unknown or other
<220> FEATURE:
<221> NAME/KEY: modified_base
<222> LOCATION: (39545)..(39545)
<223> OTHER INFORMATION: a, c, t, g, unknown or other
<220> FEATURE:
<221> NAME/KEY: modified_base
<222> LOCATION: (39575)..(39575)
<223> OTHER INFORMATION: a, c, t, g, unknown or other
<220> FEATURE:
<221> NAME/KEY: modified_base
<222> LOCATION: (39665)..(39665)
<223> OTHER INFORMATION: a, c, t, g, unknown or other
<220> FEATURE:
<221> NAME/KEY: modified_base
<222> LOCATION: (39707)..(39707)
<223> OTHER INFORMATION: a, c, t, g, unknown or other
<220> FEATURE:
<221> NAME/KEY: modified_base
<222> LOCATION: (39731)..(39731)
<223> OTHER INFORMATION: a, c, t, g, unknown or other
<220> FEATURE:
<221> NAME/KEY: modified_base
<222> LOCATION: (39782)..(39782)
<223> OTHER INFORMATION: a, c, t, g, unknown or other
<220> FEATURE:
<221> NAME/KEY: modified_base
<222> LOCATION: (39820)..(39820)
<223> OTHER INFORMATION: a, c, t, g, unknown or other
<220> FEATURE:
<221> NAME/KEY: modified_base
<222> LOCATION: (39976)..(39976)
<223> OTHER INFORMATION: a, c, t, g, unknown or other
<220> FEATURE:
<221> NAME/KEY: modified_base
<222> LOCATION: (44407)..(44407)
<223> OTHER INFORMATION: a, c, t, g, unknown or other
<220> FEATURE:
<221> NAME/KEY: modified_base
<222> LOCATION: (46542)..(46542)
<223> OTHER INFORMATION: a, c, t, g, unknown or other
<220> FEATURE:
<221> NAME/KEY: modified_base
<222> LOCATION: (49791)..(49791)
<223> OTHER INFORMATION: a, c, t, g, unknown or other
<220> FEATURE:
<221> NAME/KEY: modified_base
<222> LOCATION: (54345)..(54345)

<223> OTHER INFORMATION: a, c, t, g, unknown or other
<220> FEATURE:
<221> NAME/KEY: modified_base
<222> LOCATION: (58249)..(58249)
<223> OTHER INFORMATION: a, c, t, g, unknown or other
<220> FEATURE:
<221> NAME/KEY: modified_base
<222> LOCATION: (59537)..(59537)
<223> OTHER INFORMATION: a, c, t, g, unknown or other
<220> FEATURE:
<221> NAME/KEY: modified_base
<222> LOCATION: (60478)..(60478)
<223> OTHER INFORMATION: a, c, t, g, unknown or other
<220> FEATURE:
<221> NAME/KEY: modified_base
<222> LOCATION: (60929)..(60929)
<223> OTHER INFORMATION: a, c, t, g, unknown or other
<220> FEATURE:
<221> NAME/KEY: modified_base
<222> LOCATION: (60934)..(60934)
<223> OTHER INFORMATION: a, c, t, g, unknown or other
<220> FEATURE:
<221> NAME/KEY: modified_base
<222> LOCATION: (60939)..(60940)
<223> OTHER INFORMATION: a, c, t, g, unknown or other
<220> FEATURE:
<221> NAME/KEY: modified_base
<222> LOCATION: (60949)..(60949)
<223> OTHER INFORMATION: a, c, t, g, unknown or other
<220> FEATURE:
<221> NAME/KEY: modified_base
<222> LOCATION: (60961)..(60962)
<223> OTHER INFORMATION: a, c, t, g, unknown or other
<220> FEATURE:
<221> NAME/KEY: modified_base
<222> LOCATION: (60968)..(60968)
<223> OTHER INFORMATION: a, c, t, g, unknown or other
<220> FEATURE:
<221> NAME/KEY: modified_base
<222> LOCATION: (60970)..(60970)
<223> OTHER INFORMATION: a, c, t, g, unknown or other
<220> FEATURE:
<221> NAME/KEY: modified_base
<222> LOCATION: (60979)..(60979)
<223> OTHER INFORMATION: a, c, t, g, unknown or other
<220> FEATURE:
<221> NAME/KEY: modified_base
<222> LOCATION: (60982)..(60982)
<223> OTHER INFORMATION: a, c, t, g, unknown or other
<220> FEATURE:
<221> NAME/KEY: modified_base
<222> LOCATION: (60988)..(60988)
<223> OTHER INFORMATION: a, c, t, g, unknown or other
<220> FEATURE:
<221> NAME/KEY: modified_base
<222> LOCATION: (61180)..(61180)
<223> OTHER INFORMATION: a, c, t, g, unknown or other
<220> FEATURE:
<221> NAME/KEY: modified_base
<222> LOCATION: (61195)..(61195)
<223> OTHER INFORMATION: a, c, t, g, unknown or other
<220> FEATURE:
<221> NAME/KEY: modified_base
<222> LOCATION: (61315)..(61315)
<223> OTHER INFORMATION: a, c, t, g, unknown or other
<220> FEATURE:
<221> NAME/KEY: modified_base
<222> LOCATION: (61397)..(61397)
<223> OTHER INFORMATION: a, c, t, g, unknown or other
<220> FEATURE:
<221> NAME/KEY: modified_base
<222> LOCATION: (61399)..(61399)
<223> OTHER INFORMATION: a, c, t, g, unknown or other
<220> FEATURE:
<221> NAME/KEY: modified_base
<222> LOCATION: (61427)..(61427)
<223> OTHER INFORMATION: a, c, t, g, unknown or other
<220> FEATURE:
<221> NAME/KEY: modified_base
<222> LOCATION: (61532)..(61532)
<223> OTHER INFORMATION: a, c, t, g, unknown or other
<220> FEATURE:
<221> NAME/KEY: modified_base
<222> LOCATION: (61623)..(61623)
<223> OTHER INFORMATION: a, c, t, g, unknown or other
<220> FEATURE:
<221> NAME/KEY: modified_base
<222> LOCATION: (61864)..(61864)
<223> OTHER INFORMATION: a, c, t, g, unknown or other
<220> FEATURE:
<221> NAME/KEY: modified_base
<222> LOCATION: (61957)..(61957)
<223> OTHER INFORMATION: a, c, t, g, unknown or other
<220> FEATURE:
<221> NAME/KEY: modified_base
<222> LOCATION: (62071)..(62071)
<223> OTHER INFORMATION: a, c, t, g, unknown or other
<220> FEATURE:
<221> NAME/KEY: modified_base
<222> LOCATION: (63256)..(63256)
<223> OTHER INFORMATION: a, c, t, g, unknown or other
<220> FEATURE:
<221> NAME/KEY: modified_base
<222> LOCATION: (63258)..(63259)
<223> OTHER INFORMATION: a, c, t, g, unknown or other
<220> FEATURE:
<221> NAME/KEY: modified_base
<222> LOCATION: (64474)..(64474)
<223> OTHER INFORMATION: a, c, t, g, unknown or other
<220> FEATURE:
<221> NAME/KEY: modified_base
<222> LOCATION: (64477)..(64477)
<223> OTHER INFORMATION: a, c, t, g, unknown or other
<220> FEATURE:
<221> NAME/KEY: modified_base
<222> LOCATION: (64493)..(64493)
<223> OTHER INFORMATION: a, c, t, g, unknown or other
<220> FEATURE:
<221> NAME/KEY: modified_base
<222> LOCATION: (64537)..(64538)
<223> OTHER INFORMATION: a, c, t, g, unknown or other
<220> FEATURE:
<221> NAME/KEY: modified_base
<222> LOCATION: (64541)..(64542)
<223> OTHER INFORMATION: a, c, t, g, unknown or other
<220> FEATURE:
<221> NAME/KEY: modified_base
<222> LOCATION: (64544)..(64544)
<223> OTHER INFORMATION: a, c, t, g, unknown or other
<220> FEATURE:
<221> NAME/KEY: modified_base
<222> LOCATION: (64551)..(64552)
<223> OTHER INFORMATION: a, c, t, g, unknown or other
<220> FEATURE:
<221> NAME/KEY: modified_base
<222> LOCATION: (64561)..(64561)
<223> OTHER INFORMATION: a, c, t, g, unknown or other
<220> FEATURE:
<221> NAME/KEY: modified_base
<222> LOCATION: (64632)..(64632)
<223> OTHER INFORMATION: a, c, t, g, unknown or other
<220> FEATURE:
<221> NAME/KEY: modified_base
<222> LOCATION: (64766)..(64766)
<223> OTHER INFORMATION: a, c, t, g, unknown or other
<220> FEATURE:
<221> NAME/KEY: modified_base
<222> LOCATION: (64845)..(64845)
<223> OTHER INFORMATION: a, c, t, g, unknown or other
<220> FEATURE:
<221> NAME/KEY: modified_base
<222> LOCATION: (65260)..(65260)
<223> OTHER INFORMATION: a, c, t, g, unknown or other
<220> FEATURE:
<221> NAME/KEY: modified_base
<222> LOCATION: (65454)..(65454)
<223> OTHER INFORMATION: a, c, t, g, unknown or other
<220> FEATURE:

<221> NAME/KEY: modified_base
<222> LOCATION: (65978)..(65979)
<223> OTHER INFORMATION: a, c, t, g, unknown or other
<220> FEATURE:
<221> NAME/KEY: modified_base
<222> LOCATION: (66038)..(66038)
<223> OTHER INFORMATION: a, c, t, g, unknown or other
<220> FEATURE:
<221> NAME/KEY: modified_base
<222> LOCATION: (66079)..(66079)
<223> OTHER INFORMATION: a, c, t, g, unknown or other
<220> FEATURE:
<221> NAME/KEY: modified_base
<222> LOCATION: (66089)..(66089)
<223> OTHER INFORMATION: a, c, t, g, unknown or other
<220> FEATURE:
<221> NAME/KEY: modified_base
<222> LOCATION: (66101)..(66101)
<223> OTHER INFORMATION: a, c, t, g, unknown or other
<220> FEATURE:
<221> NAME/KEY: modified_base
<222> LOCATION: (66143)..(66143)
<223> OTHER INFORMATION: a, c, t, g, unknown or other
<220> FEATURE:
<221> NAME/KEY: modified_base
<222> LOCATION: (66165)..(66165)
<223> OTHER INFORMATION: a, c, t, g, unknown or other
<220> FEATURE:
<221> NAME/KEY: modified_base
<222> LOCATION: (66207)..(66207)
<223> OTHER INFORMATION: a, c, t, g, unknown or other
<220> FEATURE:
<221> NAME/KEY: modified_base
<222> LOCATION: (66228)..(66228)
<223> OTHER INFORMATION: a, c, t, g, unknown or other
<220> FEATURE:
<221> NAME/KEY: modified_base
<222> LOCATION: (66272)..(66272)
<223> OTHER INFORMATION: a, c, t, g, unknown or other
<220> FEATURE:
<221> NAME/KEY: modified_base
<222> LOCATION: (66315)..(66315)
<223> OTHER INFORMATION: a, c, t, g, unknown or other
<220> FEATURE:
<221> NAME/KEY: modified_base
<222> LOCATION: (66317)..(66317)
<223> OTHER INFORMATION: a, c, t, g, unknown or other
<220> FEATURE:
<221> NAME/KEY: modified_base
<222> LOCATION: (66325)..(66325)
<223> OTHER INFORMATION: a, c, t, g, unknown or other
<220> FEATURE:
<221> NAME/KEY: modified_base
<222> LOCATION: (66386)..(66386)
<223> OTHER INFORMATION: a, c, t, g, unknown or other
<220> FEATURE:
<221> NAME/KEY: modified_base
<222> LOCATION: (66655)..(66655)
<223> OTHER INFORMATION: a, c, t, g, unknown or other
<220> FEATURE:
<221> NAME/KEY: modified_base
<222> LOCATION: (66949)..(66949)
<223> OTHER INFORMATION: a, c, t, g, unknown or other
<220> FEATURE:
<221> NAME/KEY: modified_base
<222> LOCATION: (68575)..(68575)
<223> OTHER INFORMATION: a, c, t, g, unknown or other
<220> FEATURE:
<221> NAME/KEY: modified_base
<222> LOCATION: (69069)..(69069)
<223> OTHER INFORMATION: a, c, t, g, unknown or other
<220> FEATURE:
<221> NAME/KEY: modified_base
<222> LOCATION: (69123)..(69123)
<223> OTHER INFORMATION: a, c, t, g, unknown or other
<220> FEATURE:
<221> NAME/KEY: modified_base
<222> LOCATION: (70063)..(70063)
<223> OTHER INFORMATION: a, c, t, g, unknown or other
<220> FEATURE:
<221> NAME/KEY: modified_base
<222> LOCATION: (72804)..(72804)
<223> OTHER INFORMATION: a, c, t, g, unknown or other
<220> FEATURE:
<221> NAME/KEY: modified_base
<222> LOCATION: (78300)..(78300)
<223> OTHER INFORMATION: a, c, t, g, unknown or other
<220> FEATURE:
<221> NAME/KEY: modified_base
<222> LOCATION: (78367)..(78367)
<223> OTHER INFORMATION: a, c, t, g, unknown or other
<220> FEATURE:
<221> NAME/KEY: modified_base
<222> LOCATION: (78377)..(78377)
<223> OTHER INFORMATION: a, c, t, g, unknown or other
<220> FEATURE:
<221> NAME/KEY: modified_base
<222> LOCATION: (78395)..(78395)
<223> OTHER INFORMATION: a, c, t, g, unknown or other

<400> SEQUENCE: 1
cgatttgctt agtacattca ttacatttac tattcatcct tatttacctt taataaattt 60
gcttatcaaa agagcaatta attgggatag tgataacttc attagtaact acatgtttgc 120
ctgtcttttt aaagaattgg gcaaattttg aagtagctgg aattacaaag gtatcatccc 180
gatcattatt tgacatattg tanaaagtaa anttaccgtc tanntnaaac ctaatnnncc 240
antnaatatn ncgtantttg aaatctatac caaatcttaa ntgancatca atnaattcag 300
aaccaccgta ntcataagct ccggtgaaat tccaattaat ttctgcgaat tggaaagtta 360
caggatgttc gccatgttca tcttgtatgt agtaaccatc atgagctttc caatagatna 420
ctaaatcatg catgctacca gcctcaaaga aataataggg gagtctagac tcccctatta 480
atttattttg cttttagcca ntcttctant ggnggtaaat anttctcatg ngcccantta 540
atnattgttt ctacaacagg accntgtann tcaaggttnc ctgagatttc atgnggttca 600
tcaatagata gaacccacgt ntgtggcgca atgcgttcag ttgctttngt tagatacaca 660
tcaggcatta acgtaagatt caattgatcg ccgtcaaaat cagccgtatt gttcagtatc 720
agtcgttaat tgatacccgc accattacgt gcagctctag ctttcactag aagaccagac 780
tatatcttca cccttccttt cggagtgggg tgtctcccat ttcgagtcac ttgaccctac 840
atcctatttc taggaccggt gcacctgata ccgtgatagt cgttgaacct tctcctattc 900
ctaaatggaa tgttacggag cttggctgct gattgaccct acctaatctt tttcaaacct 960
tggctttgtc tttcgactcg cagtggtaga ttagtttaac aggatatccc agcaattaga 1020
gagaactcaa cccaacgatt actcattggg ggaactagat ttgattaact taataaggta 1080
tttatcaagc accccattct tttcaaagat tgctcttcga acagtattcg gatgcttaat 1140
accgacatct cttgcaaagt gtggaatact cggatacact ttggtagtgt tcaagatggt 1200
gtcagttact tcaattggag taccttttcc attactaggt tttccaaatg aggcttcaat 1260
ttctttttga gtgtatttag ggaaatcttc aggattagcg gtatatgaga ataccaaacc 1320
atccatgatt tccttactac ctctaactag atggtaatag gctttattac gtttagtacc 1380
tagtgcaagt tccatttctg ctaagttatg aaacacatgt aatgtcttag tcttatagtc 1440
taaaacataa actgtcttgg tactatctcg atcagcaatc ttagtctcac cggtaataaa 1500
ttcaaatgtg aatctatttc tatacggctt agtcttatga tcacgtataa taacccaaac 1560
cgtattttta ttaactccta atgcccgagc aagttcattc atcgagtaat aagtagtctt 1620
ttcaccagtg gtaacgtcag ttgcaattac ccgtctattt tcttttctta atccattttt 1680

-continued

```
gtaagcatgc tcaatgtttt caccacgagt catccactcc aaattagatg gtaagttatt   1740
atgtttgttg ccgtctttat gattgacttc ataatctggt ccaggtgatg gaccatggaa   1800
agctaaacag attaatatat gaactccctt actcttagat gttttttcat catttttttgc   1860
accaatattg agatatgtcc caatcgatgt tttagtaagg aagaaattac atattctatt   1920
taaccgctta tgacgaattg ttcctaagtt actagcttca tatgctgagt atccaggaat   1980
atcccgccat tcaattttaa atgaagccgg atcaaagacg gacactactc cgttttgttc   2040
cattgttttt acccttattt agttattcaa ttgtccatta ggcgctttaa ggcataaaac   2100
tgacatgctg atagaattat cattaatgtc atcttttact ttagtaataa agaactgctg   2160
cgtagatcca cgttgaagcg ttggcaatat cttcagatag ttcgttaggc tatcccgcac   2220
cattacgtgc agctctagtt ctcactagat gttgagacta tatcttcacc tttggcttta   2280
tccagtaagg tgcttcccac ttcgatttaa gggattctat acccacccac ttgggcccta   2340
ctctactccc tctaccttac ggcatggttt cgatagtcgt tgaggattcc tcatactcct   2400
tttaattaag aaggttagag gctttcctgc tgattgactc tattcaatac ttttcgaact   2460
tttccgtatt agctttcgct atccgtttca gtgtattgac ctagcgagtt atcccagcat   2520
ttcaagaagt tttgtcgagt atcatttctg atacaaggaa accattatta agttgatcca   2580
ctacactaag attacttagg tggtatgtag cttctcttta cgcgctttgt atcggttata   2640
ttcgtcaatg gatttattaa ccatctcttg agttaattta gaaacgtatt cgaatagccg   2700
ttccttatct tcaactctac agatgacata tccattaaat aatctcagtt ctggtttctt   2760
caagatgtct tgcactgacc ccttgattaa tccagtccta agttgcaatt gtgttaagtt   2820
ctcatacctg ccaaaggtgt tagttttgaa gtctatgcaa taaacttcaa tagcgttctt   2880
ccgcttctgt ggatgataat ccccagttac ttcaaacacg tacttaccat tgtaaggttt   2940
agttagatgc gccatgacta catgcagccc tttaccatga cctagctcta agaactctgc   3000
aacttctttc atcgagatga agttatacac ctcacccgtg gttacatcag tgcatttaac   3060
agctaatgcg tgtttgtttg caccggttat aaatgcatgt tttacattac cactgcgagt   3120
ttcccactct aggttaaggt aatggttatg atgcttattg gtgtctttat ggttaacgtc   3180
caaggataca taattctcag gtaatccatg gaaagccata catacgaaac gatgcacgta   3240
tcgtattttg cgaacacctt catcattgtg gatattaacc gtcaggtaag tacccttaga   3300
tgttttgttc tcatgttgag aaatcaactc acctttaagg ttccttactt gaccatggtc   3360
actgacttca tagttactga aaccaggtat acttcgccat cttatttctt cattcatatt   3420
tcctcattag agattcttgg ttaccacacc cagaatctgt agcgctacga cttaataaat   3480
taatttcggt gaaaagtaca acccatccct ttataagggg ctgcttctgc aattagctct   3540
ttaaatagat ctgcaatgat ttggttatat tgaagtacat tctcatatac aaatgagaat   3600
gcttcacgag ttgtcatgtt aaacttngct tttagnttnt tngttagatg atactttaat   3660
aattgacaac ctacncccca nggnatatgt anttcatcat aatcatgcgg gtcactaata   3720
gaagtgatta ctgcacgtgc cgtagcgttg agacgagcac caaacatgtg acgccgagca   3780
agaccaggct tttgagcaat tcgtgatttt gcgtagatct cgtagaactg gccatatagt   3840
cttagtcctc gcatagtcct attctgagct ttaattggac taagtggtac agatgatgca   3900
tcaatactag cgaaggttaa ggtagcatca attgctgctt caattggttt atctaagtaa   3960
gtaccagatg tggttgattc tgctacgaaa cagagtttag aaggaactgg taaatattta   4020
gggaataact tatctttatt ctgagcaacg aattgagcga attcggattt attattagan   4080
```

ataatatttg catctagtag gaattggaag atctcattga aattatcaat gaagtgattt 4140
aatcctcttt caaatcctcg atgcagtagc ctatctactt tnctgcgtgt ttctttagaa 4200
ccaatagatt cnacatcgta tcgataagaa gtatcagtta gatatgctaa gaaatcgaat 4260
tctttagtta ctagatatcc ggttagcata atgattaaac gtgggttaat tagnctacgt 4320
acntgttttg gtgtacgaac ccacattgat ggttcgatag gacggctaga agtattgaca 4380
actggagtat tacaaatatc acagattact ccgagtttat gtgcgtcttc gattgctcga 4440
caatcacagc ttacactact ttcaattgct tctgaatctt ggaaatgaga atagaaatgc 4500
ctatcaaatt cttctttctc atctgagtta ctcgtattgt aatcattggc ataaattcgt 4560
ttacccgtaa attgatcatg aacttcatta tgatcaacaa ctttggcata aagacccata 4620
ccaaactcct atttatcgat taacaaaaaa ggagatataa gcggcccccg aaggagccgc 4680
tatatcagtt tttacaatgg accaccaacg gagcctggcc cgatcctagc gtcatctaca 4740
aagcttaacc tccgctcttc tctgtagcat accggcacta gtatcattta ccatccattg 4800
tagtttttga tcacacgtca ccttttgagt aactcctttc ggttaagtga tctatcatcc 4860
tcgtgtagtg ataggtcgac ctagactaag tccactagtc gattacttca cggaacctac 4920
tcctaaccgt tatcaccgaa gtgaaccagg gtcgcagtat tagaatcggg atgttactta 4980
tttaacatcc ctatctaccg aggtatttcc tattagtacc aggtacccgg tgcattatag 5040
gaaggagcgc cgtaagtttg acccatgctg ccagccatnc caacttgtgc actaccagaa 5100
acagccatgt tacccatacc ggtgtaacca gcgaagcgct gttgaccgaa gttggtaatt 5160
aggttttcca tggttacagt tacaccagcn gctgctgctg cggcatccat tgcggtgatg 5220
aatttcgggt taaaggttag acgacgagca cgaccagtat aggtaacgtt acctaggtac 5280
atcttgtcga agcctttact gttattcata cgacgcacaa tgtggtcatt acctacctga 5340
gtagcatacc aggtcttcca ctcttggtca ttaccttcag acatgttcat ggcacctaga 5400
acgtcgagat cacgacggtc gcttagttca ccatgctcat cagtgtagtg accgaggtct 5460
acttcatgat ggttgtcaaa gataatcgga ccagcttcag ctagattata gaactgacgg 5520
aaatcagtgc cgtataggtt agttagagct tggaagatca gactaactgc acgagcttgg 5580
tttacgccac cagctgcatc taggacgact tgctcaatag ctgagttgtc tcccattgga 5640
tcgacatcga tctggaatgc agggttctgg ttaaccatct tgttcattag cattacgaag 5700
ttgctgtcgt ctgccatgaa tgcttcggtg cgagtttcaa tcgctttacc tagctctgag 5760
taataaccaa gtgcaccaat atcacgcatc ttactagtag cgatcttcgg cattagagta 5820
cgagcccatg cctgagatgc agttgcacga tacgcgttac caagcgcgaa cagccacatt 5880
tctagagtcc atgcttggat ccaggacgcc ttacgaacgt cagtaataac gatgtaagga 5940
gtgaactgcg gaggtagaac tgcaccaggt agagttacgc caaacatgcc ttgttgctgg 6000
ccagtggtcg gagtccaatg tagatctacg aatagactaa cttggtttag ctggctatcg 6060
gtatcataga actcgttctc aggtacgttg gttttcttac cacggctagt ggagatgacc 6120
aggtcagaac ggatcggatt accacagcta tctttaaccg gaataccatt gtagtctagn 6180
ttgcaggtaa gctgttcgtt ttctgctttg atgtgggtcg caatagagaa cggagtctca 6240
ttgttacgac gngcaatagc atcttcacag atnttaacng attcaactag taggttctta 6300
acagctagtt catctttgaa gtcgaagtca gcatacactg cacgtggacc ggcagatagt 6360
acttctagac cagggatgtt gtaacggttc cgtaggaact cgccgatctt gctccagtat 6420

-continued

```
tgagcagtga atacatcacg cggtagtacc ttctcttcaa tgatgtcatc agttagacca   6480

ttgttgattt tgtgggtacg gggacggatg cgagtaccag gtaggttatc gagtactaga   6540

gtacgaacga atgccttcat ggaaccattg atatctttag ctagtttaac aatgagtaga   6600

ccagccatac cnacttgttg ngcatcncga tcgaaacgat ggatatcgaa gtcatcaggt   6660

aggtcctgat ggcggattgc ttcttctttt actttagtga atacttgtag ggcatctgct   6720

gaacgagcat cagagccatc tagccgacca gagcgacgca ttagatggtt aatgccagta   6780

gtngacccag gngcgccagn nggacgttga gcttgacgnt gtgcagtggg ttgcggagcn   6840

ggagcngtag cttgagtttg aacggtgccg atttcgtttt cgttaacagc cattttaaat   6900

acctttacga ttatggtttc ttgatcaaga agaacctaag tactnagtat actagattca   6960

atttagtaat ataaatctca aatttttttc attacaacat agacgctata atctgctatc   7020

agcagatcgt aacgaacact atgttcacta catattatta caatctgagt attatttatt   7080

tttcatctta caatttccat atcttctttt ttgagtttat gggtataaag tttgaatcca   7140

gaaactaatt tacgtcagtc ctgtattaaa taataactat cagtattttt ataaaatgca   7200

gttatcattt acttcgcata tacttacgaa ctgttccaaa aagagaatga tacagtttgt   7260

atagtttact aactggatca actttattat tatcagttgt atcaaattta gcaataaatg   7320

gtgaatgtgc cgaagcagat gtttcattta ctttaactac actaccaaat cgatatgcga   7380

ctaatacctt tattaattcc tcatggagtt tagtagcagt tgctaatgga ttgggatcat   7440

taggatctat cttaatccta cgctcgacat tgaaaaagtt tactacaatt tctttgctag   7500

tcatgtatac agtaagatct ttgttattac ctaaatatag tggcggatct tcaacattat   7560

ttttagccat tgtatattcc tatttgtaat tactactgtt gttaccaaac tatgatatag   7620

atctcaatta atttttaatc ggataataac catgtataat ttatttaaga atgctccgtc   7680

acgtaaattg gggcaggtgg ttgatcctaa catccattat atccgacgaa tctacgctga   7740

gcaaattagg gacgttaaaa gttattatag acgggcaccg aagtatgttg aatctaaaaa   7800

catattagca caaatgattc gacattttaa cgtagagtta ctaagtgatg atgctacttt   7860

tataaagaac gtggacgatc gttcacgtgc tattattcgt tcatttggta ttacatcatc   7920

tttaaataaa ggtaaggttc atgtaggtgg tgttacactt ggtcctcaaa ctgaagaagt   7980

tctagtatcc acatcagaga gctttgatct aaaagatcta aataaaacat ggtataaact   8040

ttcccctgtt acgtatctgt atcatacacg tactgatact aatttaccta tcatgaacaa   8100

taccacacag ggtagaggct atggtgtaac tctagtaaat ataccaatgc ttcttgtgat   8160

gtaccgttac tggtatcgat ggcaagttga gaagaatcct gatgaagtag aagacactta   8220

taggtttata ggatcatttg tattgccaaa tatggttgac tcttatttag atatttcttt   8280

ctttaatagg ttagcaagga atgctttaga tattaaaaat ccaacattcc ctataccgca   8340

tccattttac atcactgata tgaatccacg tattgataaa ctatgtacaa ctatcaatag   8400

agaatccata ttaaaaggtg tagacatgga aggtttatca tggataacac cagctatcgt   8460

acaatctaat ttgttcgata tgatgcggct cccacgagaa cctattaaca ggaataatga   8520

atgggcttat gtattggctc gcacaccctt cattaagtat cttgtagggc agcttttaaa   8580

gaatactggt tatgatcaat cttctgttaa cactgtatta attgatctta tagaagcatc   8640

taatgatcaa gcatttaagc aacaagcaaa tagtgagttt gtaaaagctc aacaggcaca   8700

agttgattgg atgatagatg cacttaaaag aaaagaaatg tgacataaac cccctcctaa   8760

attggagggg gttatatgcc gttttattag aaattacctt tcttcatttt agaaagtaat   8820
```

-continued

```
tttctacgtt cagctcggtt aattcctggg atagctggta atagcatttt attactaaac   8880
ttacctggct tgcggtcatg atttagtaat tgatcaacta cagcttggtc actgctttta   8940
actccattat ccatttcatc taatgggtcc ataatagctt tagcagtcaa tcttagatga   9000
gtaactagtt catcaaatga actatcggta ttaataagtt gtttatcaac accttcttta   9060
agagcttgtt taatagttac gtcttttacc aggatattat cacattccca aagagttgta   9120
tgatgggtat ttaacattaa ttcaagtgag acattattgt aatcgttgtc agcacttgag   9180
tgccaattga attcatcaat atagtcattt agactcatta actttggtgg ttcgttacta   9240
gaggtaatta aaccaattgg ttgaacatca tctagtgaac ttttatcact agtaattgca   9300
gttgtttcag tagtaacatc aacttctttt aattcgttgg tataagttac atatactaat   9360
tcttcactac cgtcatccaa aagaacatag gctgttgctt tggtggaatc atcaggtgct   9420
aatccatgga tcctaatacg attatcattt actaatttac tataatcatt ccagtgatta   9480
cacgaacttc attagtcttt tccattatca tctacctctt ttaatttatc tttaatatat   9540
ttcggataaa gctcgtttc ttcacgagtt aanccngntg gnncggttgg taatgtgata   9600
gtnccnctnt taattgcctt cttcatccga tctaagtcaa aattaaattc ggtatgattt   9660
ntcattatat tgaaccatat taagttagta attggcaatc agactatata aatcttaatt   9720
attttttagt atataagcct cccactaggg gaggctatat ttcttaatag aagtcagaga   9780
tgagtcgatc gttattttta tcaataagga aaatacctag ggactctaag gttagataga   9840
atacacccat agtntttcca atgatagttc taacgtcagc aacacgcgta ataacttctg   9900
gaatacgacc agtttctact actgtactcg ggatatggaa atcaccaata ctggttttat   9960
tttcttcagt aacccatgct tgaatacgag cagctaattt cttatcttcg ataccatcaa  10020
tccattcttt gatcgcagtt ttattattaa gagtaactga gatctttaca tgtgaataag  10080
gtggatcacc agcgtcacca aatgatggag caaatacagt cttccacact aatccctttt  10140
tatgggttga gttatcttca gatttataag actcaggtcg tttagtttga ccacttgtca  10200
gatactcagc tttaccactt ctaacagact caataatttc tctttcgata tcaccaactt  10260
cttttagaat tgaagccaag tcgattttct cttcagtctt tacagtttta atgatatctt  10320
ccatgagtgt tttagcacga ctattaatct tcttaggtac tttactatcc cttagtccna  10380
cnccnttnat ctccatncgn gantcattaa acatnacccc ttcttgggca tcctgtgatg  10440
caaagtaatg tttagaacga gtagttaagg ccagtactgc gaaataanat tcgttcttca  10500
ttgcaaatag acgaagctta tctttagata cacccatatt agcggattga atcgcnaaga  10560
tatgcataac tacttcagan actagaaaca ctagtgcnaa tactagtcgn ttagcttcat  10620
tgctaaaagt tactttacca aagaattcct caacccacca ttgtaatgta aacatagtgg  10680
agtcagtatc tgaaataaca gcagctcgtc tatacacagt tggaaaagca tgaatgcttg  10740
atggtacaca tttagtcaag aagaaagctt caatcaatag acgatattca ttaagagttt  10800
cagcgatatt tcgaccagtg gcataaactt ggttnantgt atctggatcn gantctttta  10860
gtttagcttt agatcgacct ttaacagtat caaagcaaat aaagctagcc aanagatcca  10920
tatcaccatc ataagttgaa tattcttctt cagtgatgat ttgttctttt gttccaacct  10980
ggcttaattt aattagaaag ctcttgatta attctttatt gtatttatat aagtgatata  11040
gatcacctac ntacataact gctgctcgtt cgactggtgt catcccagta gctagtttta  11100
aaatctgngc cgtgtantac ttattttgcc aatagtgttt agttgaataa agaaccatat  11160
```

-continued

```
caactacttc ttctggcgtt gggcaatgta gattaaaatt agttactgct ttttgaatta  11220
actccatatc agctacatta atantnttta ctaaattagc ttttgtgatt tctggagtat  11280
aataatgcct attacccata atgaattttt cattatttga gttagcataa gaggtaccag  11340
ttctacaggt agatgttaaa ctagagtgtg tggacttata ataaagaata gtggcagcag  11400
atacagtacc gcctgaatat gagttattgt taattttgaa gttttcttgn tcncctttac  11460
gtacttgtgc aagttctgtt ttaatttgtg aattctcttt atcgccggcc tgtaggaaag  11520
cagctgcttc acgttcagcc tgcatctgnt cacctttaac acgcttacgg tttttcacac  11580
cttcngcaat atagatggag tgcgtngact gtctaacaga ctctggtaaa tatgcggtca  11640
ttgatggaga taataataga ttctgtttct taacacggtt aagaaaagcc ataaatgaaa  11700
ccgtctttaa ttccctatca ccaaacttat ttttatctag aatagttgct aatggattac  11760
gaagtgcata ttcgccattt tgacgtaatt gttctttaac aaattcttta cattcttcta  11820
aactaatatt taattcatct tttgtcatta attgaagata tttggcatta tcatcaagac  11880
atgcattaat gatatcaata tcacgatggt aatcattgac atcttttaaa aacggatttg  11940
gttgggcaaa tgcggtcatt tcacatatct ctcagtatac ttattttta attatagtga  12000
atgatttctc tctntttaac taaaaaagaa aaggaaagaa tgggtaccct atacgggnac  12060
cctaaattga gaggtagcac atcaacttac attcacatta gatgatgtaa gnaagtaaaa  12120
ataanacaac ataaaaggag ccatnatggc tcctttatag ttattcatat gtcactgaag  12180
ttggtggtgc attattttgn cgcactgcca atagaatgcg atcatacatt ttattatcga  12240
catcatccca tactaatgtc anacgnttac catctacacg ttctaatgta ttcgcaacaa  12300
tccaaggnat nccaataaac atcacacttt cattattggc cattcgtaca cgaatntaat  12360
tgtattgtgt tggatcaact ggagctganc ctgctggtaa acttggatat acttgctgcc  12420
cngcagcagc tacatcaaaa cccattgcag atgctacaga cgcagtaaca ataccttcga  12480
ctgtaacgtt cttaaaatta gtacctagga tagcatatgg atagacctcg aatgagatcc  12540
tatcacctgc ttgaatgtct cgaatattaa cagccatggt aataccctaa aatagttggt  12600
tacatagggt attactcatc tagtaatacn actacaccaa acagaccttt cgtatccatt  12660
ggnactgtaa tgantacatg tccatntgga tanttttctt taaagctatt gataaagtcg  12720
gtncaatatt caataacata tcctttagta gaataattct ctaactcaat atcttcntca  12780
ggatcatcaa atgagtcatg tccatacatc agcatatgga tntatatgtc attattaagc  12840
gtatccatat aacttaactt acgtgattct tcaaataaat caagtggtgt tggacaatct  12900
ggatatatca ttcgttttgt atattcacga agcaaatgtt gcgaatatac ttctgactct  12960
ttagatttaa atacgataaa tactcgtttt tccatatcgg ttcctagtag gaagcctatg  13020
tgaaccgata ggctttccta tttgcgtcaa ttgttaatat gtgtcactta atccacatca  13080
ttgtaacagt ccataccaaa gtcttcacct tctagaatat aaccctgatt atgttgatca  13140
actgctattg attggattct ttctacacca tatccattct gatagagatg tgctatttca  13200
gattgtagtt tgctagccaa tgttttacac acggtcgcaa accacatatt aagaatactc  13260
aatgcatatt tatcttgcat aatcacaggt gctaccgatg gaaagtattc ttgtaaataa  13320
tagtcaaccc ctataattgg ttgagtaggc tgttgcgcta gaaattcaat atatgaatta  13380
attgcctgat accataattg ttctatagac tggtgttcag tatatgggta agggtattgt  13440
aagacttatt gacaactaca tcagccattt tattaacaat gggccagata tcactgatgt  13500
taataactac gaaactcgtc attccttgtt gacctggagt tatgttatta gcatcattta  13560
```

-continued

```
tccgctgcat ttcttgttgt ctataaagaa gtggatgcat catgtttgag acctcataac  13620
taatttagtt accatcttat atttatctac ttctatacat ttaagactag taataagatt  13680
acctgcttga ataacttgtt tttggattat ctctaggaaa tcagttccaa ataaatccaa  13740
taccctttcg ataatctcag cagatcttaa gtgccaattg atggtattag gatttccctg  13800
atgatcaaat accatcatac tcgtcggtct atccggttct atataggtat cgcttaagta  13860
atcttctaac cattgctcta aaaaggtagg ccaatctaat ctctgccagt ggttaaaata  13920
ttcacatatg ctgctagaag tctattgata caccacagta caaagtcagt cggttcatct  13980
acacctagct cttccgtaaa agaacgcggt ttcaaaatta gcaacaattg catattgact  14040
ccactcttta ccagtgacta tagttaatag aacaactttg ttatctatta cactaatgaa  14100
cttatagtct attaaattct tcggtgttct atgtagtaat tggattccag ttgtatagaa  14160
caaattaatg aactcatccc aatctggacc atttcctagt tgtattgata tatccacaaa  14220
aggaataacc gtattatcct gttgtaattt agacatcatc ttaacaaccc attgagttaa  14280
taagacgatg actgtagctt catctttatt tgttaggtaa gtaaatttct ttatcaatgt  14340
gattaattgt gggaatacca cttcgattgg caatacatat accagacgtt gtacttcctc  14400
cgatgtacaa tccatctcgt gcttctgttt cataccacag ttccttagta tttgttggaa  14460
tgaggtgcat gatctgctca gcaccctcat cgagaagttc tattagttta tgcatgaaat  14520
gaatgtcttt agcatattca tagaacattt cttctttaac gaccatttgc ataagcttct  14580
gttctgccaa tgcaacaagc aaatgcattg cttcgatata actaatatct aaaaagtcca  14640
atacaaatct tagatagtta tcatctttaa taagtttact tttagtcgct cttagtaaaa  14700
aacgaggttg tngtgtgggt aatggtgacg tatagatctt ctggtttctc agtatcataa  14760
ataaccctat ttaactggat gttaccagct gatggtagaa ctacccggtt agaacaatta  14820
tacagataag ttgttaaatc aatatcacaa atatccctat aacccagcat ctgattaatt  14880
agttctatga catcattaga tgtncnaccn gatgcnctct cagacgctgc tgccaataca  14940
attgttaatg catattctgc accaatacta tttttatag atttccaaat atcagaatgt  15000
tgntcttgta caaaagatct tacttccatt ctgatacaca ttgatgtgtc tttatcatta  15060
gatatgttca ttataaaaac cttataancg ntataaagcc cnccntangg agggctttat  15120
ttagtataga ttattttcta aaatgtatcg ctcagcttgc gctcgctgat catcaggtan  15180
ataatcacca cgttgatatt caaatactaa tttctcaata ggataagttg cattcttatt  15240
cttgtataca gaaattacat agctatgata ctctagttca tacttaacat catgctcaat  15300
tctggttgaa aaataagcca tgttaataga actaactaga gggctaatat atttctcttc  15360
aaatagtaat aaattatcaa gtcctaaact tgcaaagaaa tcatggttaa ccttaggtat  15420
taggtaagat actttaatat tactatattg tttaacaatt acgccaataa gtaatgcagt  15480
taactgttct tgaatatatt ctactgcgat gttgtatgca tggttagtgg tgatgtggtc  15540
tttatttaaa gtatagctac cgccattggt aatagatggc tgagttttac gtctagattc  15600
gtagatacta taacctagtg tttgtaaatt aattttgtca aagccatgga agaaagtccg  15660
tagaaattca ctaaataaat agtttaatgg gttcagtagg ttaagtgata ccactgcatg  15720
atcatcacca ttatcaatcc catggacacg atcatattct gcgattcgat aatctttacc  15780
actgattaaa gttataactg aaccagcttt aactacatcc cattggatcc atgtaccgct  15840
atcgatatat tttgctactt gcttatagat atctagatag atagtttcta gataaggtag  15900
```

-continued

```
tttcattaga ttttctaccc aagcaacttt attactatct acgtcagtta cagcacaatt  15960
aaaaatagct gcggccatct taagattggt gtactggtct ttggctgttt tatatgaaac  16020
taaactctct actatatttt caaccattag atgtaaaaac tgttgagcca catctttact  16080
caatttcacc ccaatcgctt catcaattga agctgaagct gtaagctgac ctagtaaatc  16140
gtatattgct ttttcttggt ggcgcgtatc aagtacaatg agcttattcg acattatatt  16200
tctccaatta attttttgga atagcgatcc aaactgtgtt ctttaaccga tagaatatta  16260
caaacttacc tgcatttact ctaggtataa tttttaatat atcccaaaga tcagatgcgg  16320
cctcatgatt atcatgaaac cattggattt cttgaggggt gttatttatt ggattatatc  16380
cagtagtata catgaattca aaagagtcaa tagagtattt aaagaagtca tcaattaagc  16440
tgtcctctac tgatttaaat atatgctcta atgtaccata gtcatctgga tgtattccaa  16500
agctttggca cctaatcgct aaacgcgtat ttattaactc ttttggcgat cttggtacta  16560
acttggctat caccctcgtt acatctatta catacaggtc agccacttgg ggagtagtca  16620
cagtacaatc tctcgttaaa tgttcaggaa catgatatag atctaaaaat atttttagtc  16680
aaatctgttc gtggtaagcc gatgtatatt ataccttagt tgggtattat ctccatcgaa  16740
aaaacgcgta cagcgcatta taggacgttt ttatgaatcc aattactaag gctttacgtg  16800
atatttcttt taagatccca aaacagatat taaatactgt tttcntatct ancgaaatgt  16860
caggctgtgg tgcagctatc tcactagaaa ccaggatacg cgaagctgtt attgaaccac  16920
gtgttatgtt agatattgat ttagtcggtg gttcaaaagt attcattcca ctagattttc  16980
cagtgcaagc agaatatgtt gacccttata cagtggttta ttacattcca gacgaataca  17040
ctcagcaacg cccaattatc caatgttaca gtatccattt tggagtatta ggattccata  17100
ctgctggcta tgctatgcac tataatgaat caagtatggg tgcattaaca cgacgtgtac  17160
tagattcagc tagacagtta ccagtcgccc aaacagcata tatcaactta attaacccac  17220
acactgtcat ggtcaggtat atcaatatcc ctaactactc atcattcctt gcctgtcgcg  17280
taggtaatga tgangagcta aataccatac gacctacagc catacctgca ttttcaaaac  17340
tcattgagta tgctgttaag tcatacatct acaatgagtt atttgtatct atgggtgang  17400
cacagttatc aggtggtgct gagttaggtg tattccgtga taaggtttat gaatatgccg  17460
atgctgaaga actatatcag gaacaattaa tgcgttggat gaaaatatcc aggcagttca  17520
atgatcctga aggtaagcga catcatattc ggacaatcac agccgctcaa taaaaaaata  17580
aaaaaaagac atattgccct cccattgcgg gagggcttat gccattaagg taatatctaa  17640
ataacacnat atttaaaaac atactggtat aanncatcat caattaacac tgttgagaat  17700
ctttttgatg agatcaccag gtgcgatacc aatgcctgaa caataccgtc taaagttatt  17760
acacggttga catgctttct tttcaacgat atttaattca aagcaaatat tgccacgtga  17820
atctagaatg gatataaatg ctttgttacc tgttacgcga tatgtcttac cgaatacaac  17880
agttgtttta tatgcaaggc tattcatgat tattccttta acatggatta ttatcatgtt  17940
tgtaatatag cctttaaatg tatttaaata tttattaaac cnnatagcga tgngctatat  18000
atgttttnaa tacctcatan gccttatcng ttgccatgga nctattgaca aaatcagaat  18060
gatcaatctt aataatctta ccgaatgaat cataatcgat agttgtaacn nctattcgat  18120
cactatcacg gatcaatagt ttattttatt taaaacaaaa atattccatt tctcgccatc  18180
ggctaaaata acatcctcat ctttaagatt aagacgaaca aactgtttta cataaatact  18240
taactgagca actgttgaca taatgatttc tcgatatctg ttaatgaact aatcatatct  18300
```

```
cggacattna tggtaataac atttttataa gttaaataag ttggatatga acccataaat  18360
gtaatagtcc cacagatatg atttttatat ctaatatcaa nacanccgtc atatctccag  18420
ataaaatcaa atgatccttt agtgtggtgn tcaagtgnaa gaatagaacc actaactaat  18480
ttaggatatt gttcaaattc agacattaca taatctgcca gttccttaac ctcaggataa  18540
tcaatcaata atagcatata cgtaaatctc aatnagttaa tataacaccc catccagggt  18600
ggactctttc gaaaaatggt aatgtattat ttcgtatact ntctgcatca atatttggaa  18660
tgtggatggt acaacagtgg gggttactgt caatcttgaa atagaaatta tcttttaaat  18720
cttcaacctt ggatgtttgn aatggatata aaataccatt cccccaaaca taccaacgnc  18780
tatacagctt atcgtttaac cgcttctcaa taaccgaatg cgatttgaaa cgaggaactc  18840
gcaaacgcat cccgtttact tcagcccatt tgtctacccg ntcatagcta ataattccat  18900
ccttaaccat tacaaagata aatccctcaa ctatgttggg gagacgaact acgtgtttca  18960
gaaccatagt aaacggagat aacgtcagat caagttcagc tgccatttgc tcgtcgagct  19020
ttttagcagt gttctttgcc atcggttatc tcctaatata cagattatta attatcgcta  19080
gttatttaat atctgcaaaa ttctgattta ctttacccat aaaaatacca tcggctctat  19140
cgtcataata aagcttccct gctttagcat tacatanaac tccataaatg tgaccattgt  19200
aaccatcaaa attaaataaa gatggattat gcggtacatg aatgaatccc attttatcgc  19260
acagaaactt agctacagca gccgatcggc taatacctgc ctcacagtgt acgaataggt  19320
gttgancctt accaagagct tcacagaang aaataatacg ttgtgcatgn cgatgatcaa  19380
atagatcata agaagaatca acataatcct caatgtcatc aacattgata cgtaaataat  19440
taagatgttt tgctgaataa agtgggactc tacctttctc cagtagacag atcatatttc  19500
taggggaata aaatgattca gccacatgca aaggaatata agtaactgta tttactggct  19560
tcatattaca cctcgttaca aaaaaataaa aggagccccg aagggctcca gtatangtta  19620
atcgaataca agaccactac tagttgcttg gtcatccaca tctagagtag actgacgctt  19680
acgcatatta gctttggctc gattcatcat ttcacgacgt tcttctaatc gnttacgaat  19740
atcttcaana gatagncnan tgatcacaaa atgcatttga tcgaaatcat atttctcggg  19800
atcagcataa ccagtggtac gagttaaaac agtgttaatg gatacttcgc gatcagggtc  19860
agtgtatagc gaagcaatag aaattgggtc cagaatagcc tgggcttctt gacgatcaaa  19920
acacacgtgt aattggacag tctgtacagg tacatcatgg tgtttatgga agtgtgccca  19980
gttagtgata tccattagat caagactttg gtgttcttga ttaaatagag ttactagtgc  20040
atntagtact tcnagaatgt tttggttcac cattgactgc ggtanacctt caacattctc  20100
atgatagtta ataatcatcg gaactttact aacagaggaa accccttcaa angtcttaag  20160
gctaccactn ctattncgaa gactaatatc actgtcgtaa gatccaatga ccacacttac  20220
aactacttca ccttgttgtt gtagatgact nacaagngaa ggaccaatng ttgaaccaga  20280
agcaccaccc attgantana cnacnatgtt agnatcccct gctgggaaat gatgggcaat  20340
ggcaggaata tgtgcagaga ttagttctgc ggctgcctta cgatctttac ccataccgat  20400
agcacgttta cgtgcngtct ggtcagctag cttagtatcc gcttcaataa tgatcgtatt  20460
atcgtcagta ttgtgtttgt gtttattntg tacactggta tcaatgtagc aaacatcctc  20520
atgataacca tggaatagtt caccaatacg gaaaccagca ccaccacaaa agtaaattcg  20580
agttttactt tagacatcat tacacctcat tgtgattaat ataattcata taccaacttg  20640
```

-continued

```
taaatggtat cagtgcttaa aagtaacgat ctcttcatga gttcgttctt gatgaacatt  20700
aattcattaa ccactttacc agtatcagat ttaaattcga ttaccatctt atctcgacac  20760
atgtatgttt gccaagtacc accagactta acacaatcaa taatcatgtt aagtacattc  20820
ttaacttcaa tcttactaac tttataacga taaacgttta gaagttcagt aagccatttc  20880
gtttttggga ttttggcatt tttacgttct tttgaaatat caaaaggaat tagtgcaatg  20940
atctcaccat ctttgttggt gaattcaaat accattcctt ttgagttagc taaaggacga  21000
atgttntaat tncctttanc actncatact tcttcagata acttaactaa cctatctagt  21060
tgaacatcag atgcatgaat gttatcttct ttaaatgctt tctttagttc atcatgagtt  21120
agtggagtac gtactagagt gtaatctttc tgttcagtca tttttcattt ttncnatttt  21180
cnanttcaaa ttaaacggta ttggctttta tagccaatcc cttattacta aaagtaatag  21240
attctcgaac taaggatggt tataccccctt ctctaataat aaggaatatt atatgggacc  21300
ccccaaaggg tccccccaca taatatacta tttatataat ttcttttaga agaaaagaga  21360
taaataagag aaatacagtc tattaaagta atgaatttct caaaaattaa atagtacacc  21420
gcncnnnnnt tncgncggan ggtcctgccg gacnanngtc cggatgtgcg nnantagngg  21480
gtttttcaaa aatacntgca tcgcggttga attgagnggt tgattataac gtnngatctt  21540
aatngtaaat agaacttcnt caacatctgn atgncatcct tcnaaactaa aatatacttc  21600
agtccgatca ataaactgat acatttctac agctggttca gctggatctt taaaggccan  21660
cttattagcg aaataatcag tatnggctag aattaattct tttacattan ttgcattctt  21720
cttatcaaca aggaattcaa actcttcaag gttatctgtt ttgaaaatac cttgatanga  21780
tgacgactng attagttnat cactgatatc atcaacatga acncctggca taaattcaat  21840
gactggtaga ataagcttgt tacctcctac gccntnagcn atatgaatnc caancacatt  21900
accatcacta atgtattcgt cattaccgca aataacggca ccagccgcta gatataaatt  21960
atcaacatat ttcagattat cggcaataat gcgagatagt acatattctc gcaccatggc  22020
atcatctgga cttgactgcg gtttaaaagt atagtgggtg ttatgactac tcatggtcgc  22080
acatgtaaca aaaactgaaa tatctactgg attaaatacc caatgaacgg agatatcctc  22140
taatttatgt ggatgatgta aaccatctag cttagatagg gcttggagtt gttcttccca  22200
ggtgatgtta aattgagtca tttttctaac ctcttcattt attaaaaata atacacttat  22260
tttactttag cagttgatac ttcacataca ttaactaatt gttcaaataa cggttcatta  22320
tctggatcat taactaattt gatgtattaa taataatacc agaatacagc atatcagctg  22380
catctcgatc acttgtttta attctggtta caccttccca cttccatcca tagtaaatta  22440
aatcaaatga tgaaccaatg ttaaaggttg attgaataaa tttgcatgta ccattttctt  22500
ttaaccaatc aggcctatat ggttcatttt tataaaattc atgcatgagt actttaaaat  22560
cagttttaat gttttcatga ataatgcaat caatagaatt aagagcttca tcaagagctg  22620
atttagactc aataatgatt tctaatacat tggcagattt tagtgtaatc atacctagtt  22680
catctgagtg tgctcttccg atttgaaata cattgagctt accaattggt aaggtggctt  22740
ttaatggcag attagtatag tgagatacat cgcttttata actgtcttca tatgactcaa  22800
ttaaattaag ccatgctctt tcaatacgtg tattctcaaa atgntgttct tcttctagta  22860
gtctagaaat tagatgatta atgtattgaa cattatggcc agtaccngta attnaattat  22920
atttcgtatt accggtaatt ccccatttat tattttcttt atttatccaa ccgtagatta  22980
cactgttttt aggatattta tttttaaaat tatcgtatat ttcttttaga tgtggattag  23040
```

```
gggtaaaact aaaagtagtt gattcagtca ttatagatac ctatttgaat attgtttatt  23100
attgcaaatt agtaatatag atcttaaact tttttaactc agcataaagc ctcccctagg  23160
ggaggcnata tgttcattta tctatttcag cgtttggatc ataccaaggt aataaactta  23220
gtagtgccgg ttgttgtttc ttcatatcct ctaagattgt tgcttcactt gcaccttcta  23280
acatagtggt gaaagtaatc atgttcttag agttatatat cggacgtaga ccattaccaa  23340
agaatttnac ntgttgaacc attattttga aatcagggtt atcgactaca tctgggatat  23400
agatancagg tggcgcactg aaataacgtt taattaactc aatagcccaa tacgttggta  23460
aatcaccaaa ctgtgatttc actgtagcta ggtttaattg gaatgcttta ggttcttcag  23520
gcggcggttc caccggatca attggatcag tgggttcttc agggccagta ggttcagtag  23580
gctcttcagg atcctctgga tcgccttctg ttggcttttc ttcagatgtg ccaccatcag  23640
ggtcacntga accatcatca tcttcaacgg gctcctcagg cgtttctata ggctccttcg  23700
gatcttcctg attctccgat agatcgggct cttctgattc cccatctcca tttgcttcag  23760
tagaagacgt gtcttctgat tcttcatctg ttgtcgagtc agttgnggct gtgttttctg  23820
aatcggcagt ggtatttcat tttcacttga ttcagtagaa acaatttcag taggagtggt  23880
ttcaagttca ttgacactat cctctgcatt agttacttca ttagggattt cactaatttc  23940
tgataatgtt actggtgcac ttactgcgcg agcttttcgt ttagccatgg ttgtacctta  24000
gatagaatag tattatggta agtgactaat tcaggatcag ttaaattgat actttgaata  24060
gtcatattca gaattacata ggagtccatt gttctccggg tatatccagt taattccatc  24120
ttgttatatt tctgtacatg atctggaacc caatcaccaa agataacacc cagtttatga  24180
aaacgataca ccaatctgga taatgcacgt tgggtttcag ttgggaatat atcgggaaca  24240
ttttcgggaa cagtacattt atcactaaat ggagtaataa taggaccacg atgaatggtg  24300
tagctaagct taaagataac agcaccaagt tcgtcattaa tacgcctaag tatacgataa  24360
ccataatcgg tacgctcaag tttatataca ttactaggat cagcatctgc taaccttcta  24420
gcatgtcgtc tagtgcacgt ttgataccac ggttatagat gagttcacgt tctatgtaat  24480
ctctctcaaa agcggcctga gggctttctt tctcaaattc cttagttact gaccaagaaa  24540
ttgtttcacc agttaattca tcagttaaaa catacagata tgtcatagag tcaacgtatg  24600
aatactggat agagtancgt gataaatcac atggcttagc atttaatcgt tcttctttta  24660
aatagaaaaa catatcttgt aaatgattat aagtttggca gccaccacca agatgatcaa  24720
tatcaataga cgtatctggc ttgactggag ctttgcagca actcattaca cacctctaca  24780
attatatttg agttattgta ctacagatga taaagagaaa atacatcata agccctctcc  24840
ttatggagag ggnattatat ttacatagtg ttaaaacacg cattaaattt agataatgag  24900
cagccagtat aaattaatga ttgctctagt tgtatgatga catcgccatt actatcaaaa  24960
tcagcagcaa taaaagtaga ttcagttatc ttaaaagtag atggcagcat ttctaaataa  25020
ttaaatattg cttgattatc gatgtcatga ggatttaaat ccatatgtta cctatacatn  25080
gatagttatg gaccaaatat taacaggnct gcataagaca attgtgatta aatctccatg  25140
agttctctga taatggttga aacacataac tttgattaac tttaattttt tagtttcttt  25200
attttgaatt tctttgataa gtgattcaat aagatcagta gtaataagtg aatgaccatc  25260
aataaatggt tttatactta ctagcgaatc tttgttaaat agaattgcat catcatattc  25320
acatgtagat gcggtcttgt atatggatgc aactttatta actttgtcat nagtgactat  25380
```

-continued

```
agaaaaatta aattcantct tagttttact naacgatgtt tcaaataatt tatatttatc  25440
aataatagtt ttattatcaa taaatgattt cattccaata tttaaatcta tgtccagggt  25500
ataagantta tgtattaatc caactgatag ttgagtttca ttaccactat tgttaaactt  25560
aatattatta actgaacata tctgattatt aataaacgat aataatagtt tagaaatagt  25620
tttaataaca ttaacttcat aatcattatt agtacaagca agtgcagttg tcatgtatcg  25680
actaacttga cnaacatcta gtttctgata gnnactanca ctatctancc atgggtcaat  25740
anttaaaaaa atccttagac tagctagaat atcngaagat gtttcagaat aaatgaaaaa  25800
cacattatta ttaagatcat cttttagcca accactagtt ctaagatttt ctagatcttt  25860
ttcattagat accgattgac ttaattgctg aattaaacta gggttagcta ggtttaataa  25920
actaatcatt ttataaacca ttttattatc ctctaattta tgtaattaca tggaataaat  25980
aacataagta cttttatgac ttatgatttg attctccagg aggttttccc aatggcaact  26040
attaaagaag tccttgatag aaattttaag gatgttcaat ttgatcgcga tttatgtaaa  26100
agaattattg actttactat cagttttatg aataggaatg ctgatcactc tgctttcttt  26160
ggtggtgtat tactaggtgt acaacaagtt aaattcttcg atacggatcg tgagatttgg  26220
tatgatgatg ttttacgaat tgatgaagcg ctgttagtcc aagattttaa gtcagttgaa  26280
ttcattgacc ctaaccatcg tgtaatgtca gatgtattca atcatcttcc tgcctatatt  26340
tgttctaggc ttttaaaaac aactaatgtt cctttgaata ttagacatga agcaatggtt  26400
agttgtttca tggtgttgca ttttaaatat ctaacatctt tacttgtacc acgctttaaa  26460
tatcctgcac gtaaagaagt agccgaagct gcattcgccg cactcaatta tcgatttgac  26520
attaagacaa ttgggtcatg ggagaaacta tttaggcaac gggctgaagg tatcattgca  26580
cctgattcta tttatgcacc tttcttaact ggtaaaacac aagaactgga ttattggtct  26640
ggtcgtgtgg tatctgatac tcaaacacgt ctacgtgaat taatcaacaa gtactatgat  26700
gtttatatca gaacactgca atcaggtggt aaattagtta tttcatcgga tatggctgtt  26760
aattctgatg gtgagcagat tctacgcgat aagtctactg ggtatcgctc atatcttact  26820
tatatccatc aagttgcgca acaagaacaa aatttcatta gacctgagtt agtcggtatt  26880
attgaaaaga taatgcccac aatgccacca gaaatgttca tggcgacact tagacacctt  26940
tcccgtaaca tcggtcaacc tagggcacaa aagcttgaga aactcgtaga tgagtgctta  27000
ttgtatgctt tcgattatat gcaatcactc cgtacaatgg ttgctagaaa taatgatcta  27060
caaacattgc ttgtaaaaat acgagcaaag ataatggcat ctaaaacaga aaatgctcaa  27120
gttattttca tgcgtgaaga aggtgagaag ttagttaggg atgcgactaa ttctagggta  27180
cctgcatata tcgcagcaac taggactggg ttgatgttgt atttaattct acgtgctatg  27240
actaagaatt actatacaaa acaaaataaa cataatgccc tcccgcaatg ggagggctta  27300
tgctgttaag taacattagc tagattgatc attacataaa tttttcagag catcgtaaat  27360
agccacataa gtaaaatagt taaactatct ttaatttcct tacgtggggt gccactgaat  27420
ccaccccatg atacatttgt attactaacn catacagtgc taatagctgg ctcatgatag  27480
ccaccatcta ctttacgctt tgcataaacc ttagccgtaa tttctccacg taactttttg  27540
aagaaaacta gagcacccgg aacgactata cgtttattac caatcttcgt aataaattct  27600
ttacgattag taaagtgctc ttttaataaa tcattaataa ttttagttaa actatcaatt  27660
tcattcttca tcgacacgtt gttagttcct tacaaataaa cttgataacg tgatcactta  27720
caaatttcaa tggaccagaa caattagatt tctcaatagc ggtttcagtg tatgaaatta  27780
```

-continued

```
tttgatttcc acttaaggat aatgaatcaa ataattcata agagttatta ttttattctt  27840
aaaggatact gcatattgac tatttcacta ttgatgcaaa ataggttaat agctgggata  27900
gatacagagt tatctgaagt atggctattt tccgtaatat tccaattact gtatacagtg  27960
aaaatatttg cagctagtaa aaggttggca ttaaccgttt ctaaactaac atactccaca  28020
gaagtacctt tatgccaata tagttcaatt ggattaaccc aagtataccc aatggtttta  28080
tagaaggcat gcattacata ttctcgccaa cgtgtgggtt tcttattatc agttaaaaca  28140
cacgtaatat tgcctgacgg ataaatgtgg tggatgctac atgcattaat ttcatctcta  28200
acattagttg tttcagtaat attagaatga tcctgtttga atagccattt taaatgacta  28260
ttagttgtgt catcaccttc cccatttgca atgtcatttt ctaaccactt ttcaaatgta  28320
gcttgtctat caggtgttgg cattccccaa taggtagcta aatgaaacga taatagtatc  28380
gaataatatc atcatcgtta agaatatttt atccagtttc cagtgatgtt gatactcgta  28440
tacttcgctt ggaatattat ttacttgata ccatgtatta attaatactt gaattgttaa  28500
ttgccgaata ctctcacttg ttagagtgta atattccctg ctatgcggct cttcaattgt  28560
cacttcttga tcagtataac caatgtattt aggtttacca tcgatgagtg caaaattaac  28620
attccatgat gtatcattac taaaagtgat attaataaaa ccttgttcaa agctaggctt  28680
cactacgaaa ctgacatcat ccttctgata tgtcatttgc gttagaatac caaaattaat  28740
tttagatgta aattctttat cgaagttatg tttataaagt aatcctagta aacaatcaat  28800
tttattaata gtgtggtttt ctaataataa atcagtattt gtaagttcat taattttcat  28860
tttaacctct ctaaaattta caatctagtt ttacttattg aataagcaaa catgtaatat  28920
atatcttaat tatttttagc atagttttta acaacataaa gcctccccga agggaggcga  28980
tatgctttag ctttttggtt agtaccgaca gtctgctcat tcttttcagt ttgagcattt  29040
cgccgaagtt gactaaccag accattgcca gccgcaacta catcgggaga aaagaatgca  29100
ttgatatcaa agttctgatc ttggttgcga gtcttcccag gtgggaccat cggatatact  29160
tttgccatta gcttaatcct acaccgtcgt aagttacccg attaccaact gcacgttcaa  29220
tctggtcttg aataccatta cgtgcacgta gtacgtcagc agataaacca ccccagtcta  29280
atttctggtt attggggttc ataccgcgaa tgtttagttt acggaacatt tgacgagcgt  29340
attcttgtac accttcagaa acatcagtca gtgcagagaa ctcaacgttt agatcaaggt  29400
tctgaccaat ctgtgatgca tctttacggt tttcccaagg accagtagtt aatgggaaca  29460
tgttggtgca aagataagcn ttaacgcaat cctggaaggt aggatcnggt tctacgaata  29520
gaacagtcat accgtagaag gtagcgtcgt atttctcaac cggtacaatg ccatctgata  29580
caatacgcgg tactttggta ttctcatctg caataccata gttgatccac cattgtaaga  29640
aacgttggat agcgcggttt tgtaattccc agcaaccaaa gtttgggtta gaccgggcac  29700
gggttacgtt agtagccgtt tggataactt caccagaacc accccagggt gcttcagcgt  29760
tatctacagt aagcgtacgt tgtaaaccat cgatggtacg agtatgcgtt tcaacgaaag  29820
ccttaagaca tgcaactaac cagttagtat tactagcata cttaaagaat cgtggagcat  29880
ctagtaggaa cggcactaag ttacgtgcca catatggcgt gttagtagcc aggttagcta  29940
agtcaggccg aaatacgtta gtaccagcct gagcaaggtt tacagtgtta cgggcaccac  30000
cagcaccata accagtctcg ggtgccatcg gatcattata gcgagccatt taacttttcc  30060
tcattctgaa agccacccac tcattgctga gcaggtgggg tttcaatacg aacagtttcc  30120
```

-continued

```
agattgaagt tcaacgtggt ccgcgggtta ttagcctcaa cagttacgtt gcaagtccag  30180
ctggtgccgt tatttgcgtc aatcggagtg atctctgtac gcgggataat gttgacacga  30240
gtaccgaaca tatcacgtac tagatcgaga atatactcgt cacaacgctc aactaattgt  30300
tcaggtgtta gtgtagcatt accgctaaat tgagcgtgta ctttatggat cagtcggatt  30360
aatacacagc aaatattaac agtaatcggt gatagaagta cagatgtatc atctagcatt  30420
actgaacgta ggcacggata ataggagcta cgatggtcat atgactgact ccaagtagca  30480
ccattcgccc aagcttgtgc ccgtacacga tcatcaaaga atttaacatt tagatcttta  30540
acaaaagtaa cacggttatt aggacttaca tccatttcca tacctggaac tagattacca  30600
gttccagcac ctgcatagcg tgcccatgac atagctacgt ctaaaagctg cggtacatat  30660
ttacgatagg taccatccat tagtttgcca gattgcatta caatcatagc gcgacaaaca  30720
ccagttccgt atagagtgga ttctgggaaa gcttttaggc gagtgataat ctgttgaaca  30780
cgacttagct cagtagcttc atcaggtaga cgactatcag tttctacgaa tgtagtgaag  30840
aaatattgta gatcacgccg cgcacttagt acgcgcattg cccgatattt tgattccatc  30900
ggaaggccag tgtcataaag aacaccgaac tgatattctg caatgttatt atagcgatca  30960
tttaatttgc caaagttaat attttcaata tcaactaatt tggcatattc ttctagatca  31020
gttgtaccgt cagtaccacc actagcatag atgttaccat ctttacctaa cgtaatgccg  31080
ccatctagtg gaccgagtac ntgaataccc tggtaaggat caccatcaac agctaagaag  31140
gttaggaagt caatttcacc aggtgcagta gtatgcgcag cagcggctgg gttaactcgc  31200
atctcagtgt cataaatcat ctgacgaaca agatcaatgt tctcatgata gacgtagaac  31260
tgagagaacg gtgaataaag tggacttagg ccagagacta caccatcatc tgagtaagaa  31320
tcaactaata catcaccaac ataaaggtca gcgttataca tatcgctgta aacaccttta  31380
tcaaatgtaa tgtttagata atcttgctgg tcagcagttt tgacaataac tggactagtg  31440
cctacttcag gcttctcaat taactgaata cggaattgac gagttttaaa cttcgccata  31500
gctgcttcat cgaactcttc gatatcagca gttgtagtac tccatacacg cataccgtta  31560
gaatcaccta atttaccaaa gaaggaaacc ggtgcttcaa ataacggata tactagtgat  31620
tgagatccat ctttatctga tactaaagta cctggtagta cacgttgtgt acctacttca  31680
gaggtattat cttcaataag aataatacgt gcctttagac catcaacttt atcagcagtc  31740
gggactggtg cattaccaat gtcacgaaca ctgtttggat agttgaaacc actaagacga  31800
cgaatcgtaa gtgggatttc atcttccaca atttcaatag caacaattaa ccgagatgga  31860
ttagctgcat cttcaggacg tagacgttta acataaaacc attaccacgg ccaagaaggt  31920
taagtgctaa tagtgattgt gtattgaaaa acttactacg tggatcaagc gatgcttgac  31980
catagatgga tgcaaaacca tcatcagaat caccgacata agtggtttca gtcggtcctg  32040
tctcagtgaa gagacgtaat agcggacagt gttgtgcgaa cgtgatgtcc ggacggatca  32100
ggggccggcg gctacgatcc cggataccat taaacacaac cctagggaca gcgttgtaat  32160
atgccatctt tttgattctc ccaagttgga gctttgaact cgatgttatg agtgttaact  32220
aacagtcaat catagatatt aatcatagtt gaccatacta gttatttttt actatccatt  32280
taaggagtag cggtaatgtt tttgctaccg tatgaaacta cagtttgtaa aactctatac  32340
aatcccaccg gcggtggaaa attatatcct aaacaatatg ttgatcaaat tgaaaatgcg  32400
atcaagaaag ccaatgtgta tctacccatt ccacctgttg atgcacgtaa tggtgaaacg  32460
ctagagcata gtggacagat taccccagtt gatgattttg aggatattaa gaaatttact  32520
```

```
caaattgtca atatcggtga tcgtgataat cctaagctag tngttgatgc tcgtctatat  32580
aaaaagattg aacagcgtac tggtattcct aggattattc agcagaatga gtggcaattc  32640
caatatattc ggatggcact taatatcaaa ctattacgtg aaggcccgga cttcctccat  32700
cgcttaggtg atatcccagt taaagttttc tataattgga tctcaggcat cctaacacaa  32760
aaatacagcc taccacctga atcaacccaa gctatttggg taatctgtgc tgtttattac  32820
tttgctatgc aagatgatgn tctaacagaa ccagntcagg aacgngatcg gttaatacca  32880
attatttccc gtcttacata tattccagct ggttttattg cngatgttat tgatacatta  32940
ggtccacttc ataatgccgg tgatctagct tatgagattt caactaangg ncgttcgatc  33000
aggatgggta aactaaaatt cagtgatcta caattattag tatcaccgag ttggtttggt  33060
accgcttccc gtgaaaacgt aggtgtggca ctagaacaca tgccaactta catcacactg  33120
atctacatgg cattagctga tcgctcatac cgtaaaacag ttttaagtca gaaagttgaa  33180
atgatttcac gttctgatga tgcaagtcgt tttattaatc tagtgaatga agctgtaagt  33240
agccaattcg ttaagtaaat ataggggtga atcaatgaac gcatatctat tgcgncatgc  33300
gattgataac gtttggtgta acccagccca ggaccgacag tttgtttatg aactgaaaca  33360
gctnacccca cgctacggcg tgagggtaaa ctgggtggtt gattacaccc ggtataagct  33420
accagtccaa agtacacgtg attattggca tctttatcaa attggtaaaa tgattcctaa  33480
acacctgggc ttgcctaagg tttacaataa gtggatgagc ctaaatgagt tggctcaaaa  33540
ccatttaaat ttagcagacg tttatgtaaa tagtggtatt aattattcac gtaatgatac  33600
atacgtttta ataaccagtt cgcaaaatct tttaattgct gttaagatag atccattatt  33660
ccctgatctc gatgaaaatc aaccctatct tcatgtttat aacaatgctt actttcaatc  33720
aaatagatcg gatgtagctg gacatagatg gttagtttct gaatcgtatc gagttaaaac  33780
aatatctgaa ttaactcaat ttcagattaa gataatggat accatagcat ctaaaggtgg  33840
tgttcctaaa tactttgtaa atggtagata tgttaatgag atatctcctg ttacagcaac  33900
agtcggtgat gtttgtgatt tcattctaga tccatccatt aaaaggatgg tagattttga  33960
tctacgtaca ttacctgttt tcatgtcaga aatagatagt gaaagaaata tattttacac  34020
tacactgata agactgtgca aacaattgag ttctttgatg atgttgaagc atatatctat  34080
cagccattag gtaataatcg ttatactggt gttaattacc atcataacga gagccgttgg  34140
atgcggatgc ttacacataa agattattct ataccaactg cacgaattga tcagtttaaa  34200
gcacttcatc cagaagatcc tcgacgtggt gctgatccta ctcgttggcc aagtcaaaac  34260
tggaaagcat tagataatct agtatttaga atctacatac atcattctgg ttatgatcgc  34320
ccattagttg ctgattcaca tcgtattcaa attctgtatc gtttaaaatc agaagatatc  34380
ataagggcta tgactggtgc agattctggt aatcctttat ggcgagctga aaatctagag  34440
caatcaccat attgctggtt catgtcagca ccatctagtt tcgtataccc attaacattc  34500
aatctacctg aagaaacatc gcctagtaag gtagaagcgc agaatatggc tggtgatgtt  34560
tttggttatt atgaagcagc taatattcaa ggttataatc cagcttgggt ttataatgat  34620
gctggtctaa agaccgctga tttacgatac aactactggc tagatgcaac tgtatttgag  34680
tatgatgaga aaggtatctt attaggttat aattatcata cagcaggtcg caaatatttc  34740
cctaaagata gtcgttgtgc atatgttgaa tgcattaatg gtaaaggaag tgtagatcta  34800
catgaagcat atgggaatga tcccgtgcct ttacgtgatg gtgacaactg gcgagtttat  34860
```

```
gttagtcctg tttgggctgg cgtaccaact ggcgaatggc aagatataac agaccatcca  34920
gatcgaaaca actggggttt ttatgatgat accactgatg ataaacgttg ggtttggata  34980
gctaagtcaa atgagtggta tggcctagta agaaccgatg agtacttcta tctaaaagaa  35040
ttaaagttta ataaaactga tggtatcatt aaatggagta tacgtaatac tgaaactcat  35100
aatggtgtaa aagtcgataa attgatggag ataccatttg gtcagtatga tgtgtttgta  35160
aatggtcggc ctatcattga aggtcttgat tacacgcgtg aatggcctca aactgtatta  35220
tgtaatctgg aatatttaaa tgcagatcca aatgcagtta atacgattct tctacgtgga  35280
acaggtttcc caacaccaga tttaaaacca tacgaacctg gcgagattgg tttcattgag  35340
tatggcgtat tgtctaatga tggtatttat aaagtacatt caaataaaca atcacgcata  35400
atcattgatg gtcattatcg tgaccctgct gatcttgaat tccaagaaga tcaaggcact  35460
actgttatca ctgatgaacg caatggtgca ccattccaaa tacaaacacc acaggcncgc  35520
ttccgngatg tttataatga tgattaccaa gctaggatta aggatgatgc acgggataaa  35580
caagtcactg attttatgac tgaatatttc ccaatgaaac ctcaacctaa tccggacaag  35640
atcgattata gataccaggt gctttcagcg ttttcatgta agatcattca tgatatcgta  35700
aaagaatata tcaaaccncc atatcaaaat ggacggtata gtgacgatga tattgttaag  35760
cagctaaaag attacgagtg gttagcagct tatgacatta tcaataaagg ctacaacaaa  35820
aataaagttg tagtttatcc acattggtat actgaacctg tagaactaga tatttccaat  35880
gggaatattt aaatcgtatt ctatcgatat atctacgtga agtaccgcca ctatccttgt  35940
tcgttaagat taaaaggaat caaccatgac aacgtcatat gaaagtagcc agtaccaacc  36000
accacagcat aaaaaccatt tctggtttag aggtgatatt gtctcatatg ctggtganac  36060
tggnaaagca atccctgcta aaggagattt agtatttgac gcagcacaag gttggtttat  36120
tgttcgtgaa gttgatgaaa caactggggt atctatctta gatccatggt acatgcccca  36180
aaaaccaggc aatgaaaatg aacaaaacct actagttgct gtaggtccag gatatagctc  36240
agaatcttat cggttattcc tagatcagtc tgtaacacca tttaatattt gcccagaccg  36300
gcgattacat ttttatggat caatggtgca tggctataaa gttttcctag gttcagatat  36360
atcagaaata catggtaaag tgatttccct gttctatgat aatgctggta attatctagg  36420
gccaactata ccagttgaat cagtacccga tccattgact caacagaatg ttgttaaagc  36480
gttaatgaat ggtaggactg ctgagaaaat gcaaaatggt gaacgtgtaa ctctagtagc  36540
ttatgatgac gtgggtgggc ctgtttcgat tgctcaactc gttgtaatga atactgaagt  36600
tatagcncaa gaggatacct cnaagaaata tgtaggtggt atcactattg aatcaccatt  36660
catctcncca gctgatccna aagttattga gttcccatta aacgtaccag ttgaatcatt  36720
accgatgatg ggtgctgttc attaccgtga tggtaagaag catgtgatga atattgatgg  36780
tacggcaatg gcaatttatg gtttacgtaa ctatattgcc actgaggaag gacaagagtt  36840
taaattaact ctatcttacc aattagcaca agatgagtta tcatacttat cgactccttc  36900
ggctaaccgt cgtattcagg agacatatac agcgcgtacc acgcctgtac agggtgctta  36960
cagttgtcgt atgtttgttt atccngcttg ggttaatgag gcagtnggtt acagattaga  37020
attctggtta gccaatattg atcgtcaaca aatttggaat attaccccat atgttgaatt  37080
aggtgcaaac tcagcaccct ttaacccacg tggttatggt actatccaaa cactaacata  37140
tgcggttaac ctaaaccaag ttgatggacg attcctacca gttcgatttg catctacttt  37200
ccaagtagca ctattgagcg ctggtaataa tcggaatgct aactgggana tctattcacg  37260
```

ccctgancaa ggtgaagcat atggtcgtga tcttaaagcc gatatngaat ttatcaatgg 37320
taatctttgg gatctccggt tagctaatgg ngcacagtca caagctgcct ggcttaagaa 37380
aatgtacttt gctgctgagc cattaactgg tccaatggaa gctactccnc cnacacctac 37440
gcatttccgg gtgcgtacag tgcataacga gtatgagtat acggtaagtc aatggaatac 37500
tgcnttncgn attaatgctc aagatatggc cgatggtgct ttactacaan tcacctggat 37560
tcgtcgtgag tatgatacng acctacagtt agccattacc gcattacctt gtttacaacg 37620
ttaaatatan ngccccctag gnnnnnccta gggggcttta taacgtcttt taacacatta 37680
tccatatgag actatacttt acaattgccg ttcaatacgg ctttattatg gcacattaaa 37740
ataagtacct taaagggcag tgtatggacg ttatactttt caatagtgat tgggataaat 37800
actacagcgc tagtgttgat cttactacta aaaataaatc ntttataaag ttagcnttna 37860
cttataaaaa gatgggtatt aaaaattaca aatttatact agctatattg gaccaaggtt 37920
taattggggt ggatccatat gaccctaatc ttagcgaaga aatgaagttn cgtattaaca 37980
tggaatgcaa atataatcct tggtattttt ttagggaagt ggcaagaatc cccccctaact 38040 cgggtaataa nccaattcca ttccaagcta accgtggtaa tattgcttta ttctggtgtt 38100
atttcaatca cgtagatttt ggtttattac agcctcgtca gacaggtaag tccgtatcaa 38160
ctgacgtgct caatacaggc atgatgtata tctggggnga gaacactaag attaanctta 38220
ttactaaaga taacaaacta cgnaatgcta acatcgagcg tctaaaagta atgcgtgatt 38280
tgttaccaga gtatatccac tatacngatc cattagatgc ggataactcc gaattgatga 38340
catgtattag attaggtaat aggtatntaa cagctgttgg tcgaaatgat gttaacgcag 38400
ctgataaatt aggtcgtggt cttactgtac caaatatgca ctttgacgaa cttgcctata 38460
ttaacttaat tggtgtttca ctacctgttg cacttgcntc aggttcagca gctcgtgatg 38520
aagctcgccg tgagaaccag ccttatggta acatctatac aactacagct ggtaacatca 38580
ctacccgtga tggtgaattt gcatatcact tcttaacagg tggntgccca tggtcagagg 38640
aattctttga tctaccagat cagaaaactc tacatcgtgt tgtagaaaaa ggcactactg 38700
gaaagaaacc tctagtttat ggtgcattta accaccgtca attaggacgt accgatgagt 38760
ggttatataa cacacttcgt gaatcaggtt cattcggtga aattgccgat agggacttct 38820
tcaatatctg gacagttggt ggtgaaggtt cacccttatc atcagatgag aaagataaac 38880
ttaaaaacaa tatgcgtgag ccaagctgga cagaaatcac ngatgatggt tanacacttc 38940
gttggtatat accaaaagan gaagtagcct cacggatgat gaagggtagg ttcgttatgg 39000
gtaccgaccc atctgaactt cttggtgaag ataatgacgc cactggcaca gttgtagttg 39060
acgtagaaac acatgaggtt atgtgtgttg gnagatacaa tgaatcatca gtnccatcaa 39120
tgggtaattt ctttgcaaca atgctattna natatcctaa tattctttgg ataccagaac 39180
gtaaatcaat aggtatatcg ttaattgacc atgttatctt gattctncat actaaaggan 39240
tagatccatt ccggcgtatc tttaacagaa ttgtcaatga atcatcagaa agagaaaatg 39300
atttcagaga cattcaaact ccgntatcag caagacaacc atcgttntat gataggttta 39360
aacgttattt tggctatgca acgtcaggta ctggcgagta ttctcgtgat aatctattta 39420
aggtggcatt accatcagca atgcattatg gggtaaggac catctatgat aaaccactta 39480
gcacggagtt attagcactt actatccgta atggtagaat tgaccatgct aaggggaacc 39540
atgangactt agtggtatca ttattattag cccantggtt attaatacaa ggtaagaatt 39600

-continued

```
tatcttatta tggtatcaat gttcccatct taggtaaatc aaaattacgt gataaagaac  39660
caagncaact tgaaaaatat catgaagaga aagaacagca aggtcgnaaa gaatttgaag  39720
agataattga ncagcttcgc ggtgaaaaga acccgatgat tgcagctaaa ttagaaatgc  39780
gnttgaaaca attgtctaaa cgtgttaata ttgatgatan cagtggtgta ggtattgatg  39840
ccatgttaaa tcaagctcgt gcagagcgta cacgtagagt gcgtattaac agatattcta  39900
gaaatagttg gtattaaaca aaaaaaataa taatacgtta ccctcttcgc aatgaagagg  39960
gtatttgaag ttaagnaact ctagcgaaca aaagattact ggagttagaa ttaatatgat  40020
agttagacga tccgtcaatc catttagcat cggaaatctt gtttacaagc tgaccattgc  40080
caatgtaacc taggaaagtt ttattatcat atacagcaat tttgattagc tcatttcgtc  40140
cgtagactag tggcttacca ttgaatgctg ttacttctaa accagacatg tatccataaa  40200
ttggatcagg tctggaactt gtttcaaaga ctttcattcg aagtctcatc tgcaagaaag  40260
cccattttgg gcaaaaaatg tcaagcttaa acttgacgac atatagccct cctggtgcga  40320
caggagggct aatcttttca gaacgtacgg tgttgttata atactgctag cgaaaatacc  40380
catgataggt aagtagctaa tccgcagttc tcttggatga tacctactga cagtgtagtt  40440
gcaaatgtgc tgtttggaac cccactggtt tagcggccag tgggaattcc ttttatgccg  40500
ctttttcttt ctttactgga tatttcttat atttacaaac ccacgttctt acgctggtag  40560
gtatcttcct tcttattata ttcgtagttc tcgatgaggc acttgttgct gaactcgacc  40620
atcgaacaca tcttgtccat gatgacttca gatatttacc atgttcataa attcggcgta  40680
gttgtagccg gtattcatgt cgagatagtc ttgttcgacc atatcgtcat tcaggtactt  40740
gacgtaagcc tcggcgtgag cagtggctac cgacttggtg aagaagtaac gagcgtgctg  40800
acggttctgt tcgaactgac gcagattagt agtggcctga ccgccgaaac cattgacctc  40860
cattaccccg taaacagtac gatcatccag agtagtgatc tgtgcaatca ctacacgaga  40920
agcattttcc gaatggtcga tgaacgtcat actgtaaatc tcgatttctt tgaagtcttc  40980
cattagaatt tcctgttaaa aaaatgaata gacaacccct accttcgggt aggggcttta  41040
tgccgtcaac cgacaataag gtcccgaatc gttacgatct aggtatcaga tgcaggttta  41100
gtcaaacgag ttacacgaat ataaaccatg tagtcactca gagatagaac tttttcactt  41160
atacatcttc cagcgtcatg attacgacat gataaggact atcagcattg tgacccatgc  41220
acgtctcgca tttgaagatc cgccacatgc catacgaagg cagctcgcgg tttttcacat  41280
aaacgtagtc gtgcgctgcc acgaggtatt tttgttgaat cgagaattca caagtgatgt  41340
aaccttttc acggatgaat tcttgagtca tctgatcaaa agtctgtttg agttcatcag  41400
taagagcgac ttgggtttcg aacattgaaa tattcctttt gatatattaa atagttttga  41460
ttatttcgga gttattgaat atttaggtta ccatctgctc tatatagact cggctgattt  41520
catttaagta agcgagtgcc aatagaatac cagcccaaat aacaattttt cgagtagtct  41580
gtttttctat tacacctggg tgtgattcac gaatactacg gtgacaaaat acataaaaca  41640
gacacagact cattgtaaca aagataatgg taaaccatcc tagatagatc attttcttca  41700
cctattttta taaatagagt ttatagttta gtcaggcgga tgatttcttc taaagctgca  41760
tcaacttgat aatacggcca tgaatcaaca cgaggttcgt tatcaaagta tgtccaaagt  41820
tgaatacctt ggagtttatt gtagaataca ttgattctga ttccttcatg gccaacaaga  41880
ccttcaatgt aagctgcacc atgcacatac gtaacatgta gtgcgtactc gctatcttca  41940
ccagcgtatt gcataggtct ggagtagatg aaggaataag gattaaatgg atcagcctga  42000
```

gtgatatgtt cgaagaattc tttcaaacta gattttttca tattggacat tatattttcc 42060
tcatgattta ttaagtctat cttctaggag gtagacttaa tactattcga tgttatttta 42120
agacgcctgc cttgtaacct ttaacaacag ttctagcttc taatgcactg atttcgccaa 42180
tgtgtttacg cagtgcttta atagcgttga tggtaggttc attatccgcg atatgtcgcc 42240
agtttccctt acccttaatg agttcaacat cctggacata tagaccatct ttaactagat 42300
ccattgtttc taccaacttt tcgacttctt tagttagatg cgtatgaaga ctggcgaggg 42360
acatgtcagt catttgatgc acatcataga gaaatcccta ttatcagaag acgataaaat 42420
ttctttggtg agtttattta cagtgtcaat gtttgctgca attgaaacta gcagtgcagc 42480
atatttctct gcattataat tcattaatac gtattcctat ttaaaattgg atttagtgta 42540
atgcggtaat actgcgaata tctaattcat gtaaatcata tttctttagg aactcattca 42600
ccgcttgctg aatggtgtac ccactcggag attcccactg agtaccatta aaagcaataa 42660
tacgataacc taccattttt tattcctcta atcacaaaat aaataccctc ccgaaggagg 42720
gtatttatat cgttaccaat tgattacagc gacaaactca aatacccgac acaattcttt 42780
atcacgatgg gcatgatgaa aagatttacc ttcaataccg caatacggat aaaacaattt 42840
tcggtgttcc gtgtcgccga accagaaggt ggtgttattg gaatcaacca caccatggat 42900
agccacatca cgaatgtact gaaatacatg aactgcctta tcagtgatca ctcgaagttc 42960
tacaccgtgt tccttcatca tagccaggat gtcttccttg gtgtaatctg cttgttcagc 43020
attggtcatg atcttgtgag tcagagaacg cttttccttg tcaccgaaac agatacagac 43080
caattgcacc aactgacctt ctaccttgag accactggtc ggttttagta gaacgaactc 43140
atcatatttg taatcattgg tgacaatcag tgccgactta ttgcgagtga caatgcctag 43200
gttatacgac ataattaatc ttcctcattt tagaatatgt tgaaccttgt ggatgtcttc 43260
caggctatga ccaagaccag tggctttgta agaatgttcc tgatcaacac gcttgtgata 43320
tgcaagcagt gcatctactg gatgttcagc gaagaagtat tcagtgttgt tgcagtccca 43380
agcgaactcc cattcaccat cacgaatctc tattttgtta gcactgaggt aagtgatatt 43440
gatggtattt acagtggcat taccaccaat gaggtagtac gatccttcat tgctacgaac 43500
atcgatcctg ccgccatcga tagtatcctg atagtagaaa ccacggtcga agaataactt 43560
cagcatcgaa gtgaagtagc tgttcaatac agcttgagca tctttctctt cgaccaccca 43620
ttttccatca acgatgttat tcaggtaatt acgatcatga ttgatcccga cattatccac 43680
gatgtcagcg tagttcttat ggaacttagc aatctcgtac aaacgttcca gagcagcaaa 43740
acggaaaggg ctggtgggat gcagagccag aatgatccga cctacgctcc acaaaccggt 43800
cccgttgacc tcgtaacttt cttcgaggta acctttgata ccacagttaa cttcaagttc 43860
atctgctggg aaaccggtgc ggagccgcct acggatagcc aatagtaccg attcggattc 43920
ttccggatcg aacaggtcta tgccgaaagt aatccagcta ccacgtactt tgtgctggta 43980
tgccaggcgt acagtatcac cgaatggaga aatgaaccag cgttcgtctt ccgatacgac 44040
caaatggcaa ccacattgcc acagggtact tagaggatcg ttagaggcga gaatgcgctt 44100
ggtgtcgttc atatccgacg aagtagcatc tggactgcca tgtaggtgtg tcagaataaa 44160
cagaagcgat gattctgtag tttgagcact caacattgcg cgagtgatgg ttgcattgat 44220
gatcatgaga tatcttcctt tttacagttt atgaatatat tgctaaataa aaaaatatta 44280
cgatgtagaa aataaaaggg agtccgaaga ctcccattat tgcgtgtaat ctatttgatg 44340

-continued

```
ataaccgctt tagaaagagt ttccatactt ccaataacta atttggattt ctcttcttca  44400
gggttcncca ttgcttcacg caggagttca ccaatagttt tgggttgaac atcatcactg  44460
atttcacgcg agcatgccga gtcgtcgtac atatcaaaca cattcagatc atcatcatcc  44520
aggggcgtgc tgtcattcca tgaatagctt gattcatccg aggtatcatc agactcacca  44580
tactgttcac tgaggtcacg gtccagttca gcctcataca tctcgctaat tgctttatcg  44640
tcttcttctt gcgccttacg acgagaagtc ttgtagaacg gaagcaggcg ttgcaggact  44700
ttatggaact tcttcttgct gatcaaccag ctaacagagt agcgagacag ctttacttca  44760
gctgctttga tagtcggatc ggagtacagc gccatgacta gcttgtccag tttgtgcaga  44820
tgatctttaa acgagtttgc ataagcagga tgttcccgaa gagtgaacat cacaaacgaa  44880
cgcatgtcag tgatatagta ctgactgtga tgtttgttga tttcgatgta taccggatct  44940
actgcgcggt tataatcgaa ttcctctgcc caggtaaggc tacgtacttt agtaggacga  45000
ggaccttctg cccaacgaac agtcggatgt ttctcacgga tgttccaacc atgattgcga  45060
tcatactcgg ttgactcttc tttgaaccag gtgaaattac cttcaccgcg cgatacaata  45120
ccacggcacc aactgacgtt gattgccttg ttacggcttt cagtaagatc acagggcatg  45180
tccagaatag cgacataact gttatgacca ttggccacaa cgccgagaac agtagcttcg  45240
aatgtctcgt agcgctgtcc aggatacaca cgttcattct catccaggta acgaagggag  45300
caggattcga agatagcacg agtaccggca gggaaatggg cacgaccgaa aggttgttcg  45360
gcctttcttt ctttacgacg gctgataacc cattccagtt tttctttggt cagacgggtt  45420
acgggttcac gatactgttt catggtaatt tcctttttac gattgattgg gttgagtaca  45480
tctcaatgca tccttttcaa gacgcattga gatggggtct ccgaagagac ccatctatta  45540
ttcttgggtc agttccccaa gacgaccttc ggctttcatg cgacggattt ccgagatgga  45600
tttaccgtac attttggcca gttctttcac agtaccttca ggcacaggtt tgttcatgtc  45660
gcggaagttc tgcttagcga tattgtaacg ctgatgttga agagtcttca gttccgaacg  45720
taccagagcg ttaccggcac attgggagat gaatgtaacc atgaaggtct tcagcttgcc  45780
acggtagacg ttgacccaag cacaggactc atccacgtgg atgttcttgt actcggaaac  45840
cttggcgtat tccagcaggc cgacggcatc gggaccgttg tcctgataaa ccatcttgtt  45900
gaacaggccc agggcgatat cggaggaacg ctcacctttt atgaaggcga tggcgtcttc  45960
gatgatcttg gtttccaggt ctttgtactt gaccgggtcg ttcttgatca acagtagcat  46020
ggcgtcgacc ttgacagtca aacccatgtc ggcaccgcgt cgatcgatca actcgttgtg  46080
ctgtttctgc gtgaacacgg gatctatgtt cttgaaagct ttcaggagac gctgttccat  46140
ttacttgtcc tctttgacgt tgaatgcata catggtacat ttcggcttag ccgggtgttg  46200
gcaccactct ttagatacct tgccctcagg tttagtgaga tcgtaataga actcaccacc  46260
tgcggcagcg atacccatca gtactgcaat gaatcccatt ccgatcttta ctttcatttg  46320
gcaatgatcc gttgtacgaa gtgttgaagg ttggctacca ggcgttcgaa ttcttcttcg  46380
gttacctggt cacgatgcga ttccagaagt acttctactt ccggcaggac gttcatggcg  46440
atatccaact ggatacggct gatgaactct tccgttgtga tatttcgatc acgacgaata  46500
cgacttacca gcttgcgatg ttgttcgctg ttgcggtagg tngagatctt atcgataaga  46560
atatcagaga tactgctttc gatctgttcg gctacagcct gaccgtcttc ctttacggta  46620
gctttgaccg cgaggatggc agcaacggct gttgcgccaa ctgccagtgc aataagacca  46680
agtgcgtttt ctttgatgaa gttcatattg attatccttt caaagttgca tcatcattga  46740
```

```
agatatcagg acccaccgag agacttccca gaagatccgg agcaatgtaa acagagttga  46800
gggtttcgta tacaccggta acagcatcta cgttaaccag gctagaactg cgcatgggta  46860
cccattcacc gttacggaag gcttcaccga ccagtacacg aacatcatct acgtcagtgc  46920
ggttcggcca tagatcctta ccttctacta tttttacatt acgagcatgg tagaccagtt  46980
taccattcat gcgagcaacg atattcggac ggcacatgtt gtcgattact ttaactgcta  47040
cggacttttc catttttatt tctctattta gttacgagca tttcttgacc attgggaccg  47100
atacgatgac cgaggataac agtttcatta gaaatagttt gctcttcaaa cttagcgttt  47160
acaaacagtc caccaaaagt caaaccaata accactagtg cgaatgcttt catttttaaa  47220
gtcccttttt acattaattg aaggttaaat atcaagttag taatatactg tttaaatatg  47280
gtttgaataa gggagtagta gttattacat atcgtgcagg taggtctcat caatgatggc  47340
acgggctagc tcaatgagac tatcttcatc aacaacaatg ttaccatctt tccaggtagc  47400
gctatgggat aaccagttac ggtaatcctt acctcgtaca ggattgatgc atacctgacg  47460
agtagctgca tcacggtcac cacggaaacc catgatagca cgtgcacgac ggattgcttc  47520
tttctccaag tcttcgtcag atttaaaagt caggaaagtt gtcatagttt gattcctttt  47580
tactgattta ataggtttaa ttacactgtt gtgatatact ggttaaaatg gtttgaatgt  47640
attatttcat ttccacagac gacaatagtc atctacatgt cgagtgattt ctgcaacagc  47700
cctgagtcgc cggcggccag ttaatttaga gcagtgttta ttaactaatg tatcaacagt  47760
tttacgtaac ctaacacagc gttcttcatt aggtatatct tgttcgataa acaggctagt  47820
taatttatgg atttccatat ggattttctt acatacatcg ttagccgatt ttcttcattt  47880
aatttgttgt atgattcgac taacttaaca atagttgtag caacagtagt tgcggcaaca  47940
aaaatttgaa taccattgat aaaattttta ttaaacattt ttaaactcca actaatgtat  48000
taaaaaaata tgtctatatt gaaaataaag ccctccccga agggagggtg tatgtcgcca  48060
ataagtgtta ctaatttatt tagttagttt gaccatacgt tctttcaaag ttgtttacat  48120
cataacctga gtggtgtgtt gcagaaccac ctgaagtagt atctataatc ttaactacca  48180
cttcatcatt ttcaatgtaa accgacagtt tatctcgcat aaaatccacg tggtcatttc  48240
gataacgtag atatttcatt acagcttcgc cactgatttt actgttagcc attattattt  48300
cctcgattga ttccagttaa aattatcttt tgcattttta gtgaagaacc cgttacccca  48360
accaaatgag tatctaaagt ccttgattac accaacatcc gaatcgataa ccttatattc  48420
aatgacttta tcactattct ccagaatgac taagatcgcg ataagatctt taggatcacc  48480
tacagtcaat tcatgtcttt cagactcgtc tctgtggata acgatgtaca tggtacttta  48540
tcctctaatt atacccattt agttactggg agttcgaagg tttcacacaa gtcgagtact  48600
ttacgatgtt ccaagttatt ttctggatag aaggtaatgg gtgtagtcgg actaccccaa  48660
ttaacacgac atccagtttc tttatggatt tcgccaagta cagtatatgc acctgcccca  48720
tctgcataac ccatttgatt agggttaacg cagatttgag taaaacgctc cgtcaatact  48780
cgattaatag tgatggtcaa gagacgaacg aactcacgag tcttctcgat gtcgtctacc  48840
cagaattcca gaaggatcca tttcccatga gggttatcat gcccaccttg gaagaataca  48900
cagaaacctt cttttgcctt ataaaactcg tgattggtaa tgttacattc aaccatttgt  48960
ttcactgcat gccatacacg ctcggtgaca taatcaccat aaagttcgat gcagtgacca  49020
cggccaggga attgttcttt tttagaaaat ttaatttcga acatggtata gattcctttt  49080
```

-continued

```
tacattaatt gaaggttaaa tatcaagtta gtaatatact gtttaaaatg gtttgaatgt  49140
attatcggta ggggagggtt accctttaa ctttttaata ctattggata agtacatgac  49200
actacggaaa attttgaatc ttgaaaagta ttcacgtact tctttttag tcaatacaag  49260
tcttccatct ttgtttacat tatcaccaaa gacaatttcc tgagtattct tccataaaga  49320
tctataaaga taacagccat gtggtgcatc acaccaatca tagatcttaa gttcaaattc  49380
aactttgtcg acaatatcat catcaaataa aatagtattt cctttactat ttaattccat  49440
taactcattt gcacaattta ttgcaaactc aaccgctgcc caggttctac caccgctgaa  49500
catatcttta cttaatttat ttagatcgat agcattataa gttgttttct tagtgttttt  49560
catggactgc acccctcaat aataaataga ataatctgta tttaattcac ctttgtaata  49620
tactttaaat acatttgaat acatgacata aagccttccc ctggggaagg ctattattat  49680
gttttaatcc aatgggtata tgtacatagg tcagtttctt taataatggt tgatttccat  49740
ttatcccatt taatgatttc tttagggaaa taaacacaac tactattatc natttccatc  49800
ttgacagtag taatgtacat ttcgtctaaa atatcctttt caatgacttc tttataaagt  49860
tgagaaccgc caatgatcca tacatccttt ccagtttctt tattgaaatg agtggcataa  49920
acaatagctg cacttagatt agggagtaca cctaatttat tatcataggc tactggataa  49980
ttaccgttac gatataaact tgatgataca acaatgttat tacgattagg taacggttta  50040
ctacctaagg ataagaaagt atttttaccc atgataacac agcaaccagt tgtcatttct  50100
ttaaagaaag ctaaatcctc aggtatatgc caaggtaata gattattata tccaatgaca  50160
ccatttaggt catgggcaac gattaattta atagccatta attttcctta ggccagaatt  50220
tacaagatac ttcattatct ttaaattcaa tagcccaact acagcaagtg aaattagttt  50280
taaacttaaa tgtagacgct aataggtaat taatttgagc catttgtaat agcgttaatt  50340
caccatatac tttctcatca atcaatacac caggtctttt atgtttaata actaattcat  50400
tcaacttaat atcttgttca atatagaggt attccacttc gcctttttct agtataggca  50460
tgtcccaaag aatcagacta atctgttgtg tgaattcctc aatactagtt gtaatatcta  50520
gtccttcata acctatcaat agatttataa gtacttgtag actaatcaga ttaacaggta  50580
agtcttttaa atcgtcttct ttaatagttg ttctaaaata aacagtgcca tctaagtttt  50640
taactaataa tctatttaat agatgattga cttctgattt aatctgataa tccagtttga  50700
tcattagcta actccttgag tctagtcatg ccattactaa cttcaataat gtaactaaag  50760
tcaaaactat atttcatcat tttgaattct tctttaaagt tagcgatatt tccagacaga  50820
gcaatttgtt caaatcgact aaaatcagta atagtttcat cgaacattag ttctcttgcg  50880
gtaatatctg gatcatagtt aggatgatca actacagtac cttcgtggtt taaagtacct  50940
tgaaaattca aagtcttttt aacatggtct acagttattt tccaactagt tgcaatatac  51000
cgagctttaa ctaaattagg agcatacctg taaatacacc attgtaatgg agtgccaaca  51060
gtttgcgtat catgcgtggc ttttataact ttaataaaat tctcaagttg atcaaatgta  51120
acattcctag ttacaccatc attagtggtt atattaagag atggtcgaag accagtacca  51180
agatcattgg tgatgattat atcctcaact aaagcttcat ataactttag tccttctttt  51240
ctggatccaa catcattacc cattgtttag cttcctcttt tgttaccagt tgataaagtt  51300
tattaaattc acgttgacgc attaatttgt aatctagtat acgcccatta tttttacgaa  51360
ttaaaataat aaaatcaccc ggacagacaa ttttatcttt atctgggcct acacgtaaaa  51420
taccatgact agattcagtt agattacata atgggcaaat cgcattacta agagtagact  51480
```

ctttagtagg tatagcataa ccaacaatag caccttggtt gatattattg ataacgccat 51540
caccaggtat atcaccgttc tttttccatt cgattgcttc aattggatcg gtgtatttcg 51600
gtagataaaa agacattctt aattaactcc gataaataat agtagtatag taaaaagcac 51660
ttaggtatat ttctatttta agctatattg ttgataaaat aaaacctaag ggtacatagt 51720
gggttattat ttaaagctct taaatagcat ggtagaacga tattggacta tatagctgta 51780
acccttaagg cactaaggct acagaggttt ttaagataaa gatatccaat gtaccataat 51840
atgcttttac aatagatcaa ctaaattcat ttaaaatggg tcgtaaaaat acttagttga 51900
tctaaagata tgttgaatac tttttcacat gaacttacga ctcacaattg gaaattaaca 51960
atgttaaaaa ctatcattaa actagacggt actgaagaag catactcacc tgctaagatt 52020
aatggttggg gtgaatgggc agcccaacat cttggcgata aggtggattg gagtagtgtt 52080
gtgatggatg ctgttcaagc tcttggtgat aaaacttcat cacaagaact acaattacaa 52140
cttattgaag aatgtttaaa tcgtaagaca tggtcttatt atctaatggc tggtagacta 52200
tatgcgattt atcttcgtaa gaagttctat ggtctaaatg gcatcccaac tgttaaagcg 52260
cttcaaacca ggatgcgtaa agatggtatc attgttaaat tagattatag tagtaaagaa 52320
tacgctcaga ttgaaaagat cattgatcac gatcttgacc tactttgtcc gcatttttca 52380
cttcatcaca ttcgtggaaa gtatgctcta cgtaatcgta aaactggtca agaatatgag 52440
actgcccagt ttgtatatat gcgaatggca atggctctag ctgaaaaaga gccagctgaa 52500
actcgcatga ctcatgtgga gaattactat aaactacttt ctaataaaat tcttagtgcg 52560
ccaacaccta actacgttaa cctaggtact aagcttcgtg gttttgcatc atgttgccta 52620
tttgcttctg gtgataatgg tgtatcactg gcaatgggcg attatattgc taacatcatg 52680
acccaatcat cagcaggcat aggtgttaac ttaatgacta ggtcaattgg tgatcctatc 52740
cgtaatggcc taatcattca ccaaggtaag aaaccataca tcgatgtaat tggtaaagca 52800
gtaagggcta acctacaaaa tggtcgaggt ggtgctgtta cgtgttacta cagtgctttc 52860
gatcctgaag cagatatgat tactcagcta cgtaatccac gttctactga ggataggaag 52920
aaccgtgatc ttcactatgc attcctaagt aataagttct ttgctaagaa agcagctcag 52980
aaagatggta tgatctttgt attcaatcca tttactgctc cagatctaca tgatgctttc 53040
tatagtggtg atattgataa gtttattaag ctttatgaaa aatatgaagc ggatcctaaa 53100
tttgagaaaa cttatgtaaa tgctcgggat cttctcaaat caatgctagt tgaagcatat 53160
gagactggaa ccatctattc agctcaaatt gatgaactca atcatcatac accatttaaa 53220
gaacctattt acagttctaa cctatgcctt gaaatcgcag aacccactaa gccttactat 53280
cgaatggaag atctttattc tagtgaggat cacgggcgcg gtgagattgc tacttgttca 53340
ctggctgcta ttgcagtgga taacgttcct gataagcaaa cttatgaaat ggcggcttac 53400
tacgcactta agatgattga ctattgtatc cttaatgcag agtatgcttt cccacacctt 53460
gcactaaccg ctaagaatcg aatgagtgct ggtgttggta tcatgggtct agccacacat 53520
atggcacgtg ctggccttaa atatagcagc gatgctggta aagctgaaat ccacttcatt 53580
gctgaacggc atatgtactt ccttatcaag gcgtcactta agatttctaa agaacgcggg 53640
aatgcgcctt ggattcataa gactaaatgg ccagagggat ggactccacg taagacttat 53700
aataagtcag tggatactat cattgaaggt ggctttgaag aactttatcc atgggatgag 53760
ctagagaaag aaattaagga gaatggtggt attgcacact ccgtactagc tgcatacatg 53820

-continued

```
cctggtgagg catcatctaa agcactaggg tcaactaatg gtccatatcc ggtacgtcgt  53880
ctaattctga ataagactga taatggcgca cgtgtgttat gggctgctcc atatggagat  53940
gatgattcct atgtgtatga atcagcttat gatatcccca ctaaagatct tattgactgc  54000
tatgccatta ttcaaaagtg gactgatcaa acaatcagtg cagacctcta tcgacgcatt  54060
gtaggttcgg aaaagatctc ttctaatgaa atgctaagta atcacttcta catggtgaaa  54120
cgtggaatga aaacccggta ttatgtaaat ctagaaacag cggcaggact tgacattaaa  54180
tcacttgaac gtgctgttga ggtaactaat actgaagttg ggtgtgcagg tggttcgtgc  54240
actctttaag tgtatacacc ctcccttaat tgggagggtg ttattcccaa tttatactaa  54300
cctctattat ttattgtaag aaatattttt aaattgtaaa ggaantaaca tgtctactaa  54360
atctcaacta ccaaagaaaa tcttcaatgt tgctaagagt gattatcatc taccggaaat  54420
tattcttgga gatgatccag gtctactaga ttcaatccac actcattatc ctaaaatgtg  54480
ggagctatat aagcgtctaa agatgcttga ttgggatgag ctagaatttg acttttccac  54540
ttgtctagta gaatttgaaa cgtgtgataa atcaacttat gacatgatga ttaagacact  54600
ggcctggcaa tgggaagctg actctgtagc cagtcgttcc attgttaata ttctatcacc  54660
tgtcatgaca gattcacgag tatgggcggg atatgtacgt attaatgata atgaagacgt  54720
acatgcttta acttattctg aaattgtacg taatagcttt aaagatccta aagttattct  54780
agacgaaatt cttagggtag aagaagcaca agaacgaatg gttgcagtag cccgcactat  54840
gggtgaagca catgacgcag ttcatgcgta tgctcttaat caggtaccca atgatcaaga  54900
actttacaat aaagtattca tgttcttcat cgctctatat ttcctagaac gtatccagtt  54960
catggcatcc tttgcagtaa cctttgctat tggtcgtact ggtgcattcc agcaaattgc  55020
aaccgctgtt aagaaaattg cccaagacga attcgaaatc catgcacaat atggacaaga  55080
agttattcgt gcactactgg caactgaacg cggtaaactc gcttacagtc aatgtaaaga  55140
taaaatcatt gaactactat gggaaattgt aaagactgaa gttacctgga ttaattatct  55200
attctctgaa ggtcgtgaac taactggtgt taatgcgact aaacttatta actgggtact  55260
tttcaatgct aatgccgcag caacattcct aagtattgaa aatgatgttg tagaacagta  55320
tcaagtggag tttaaagaat cagctggatt tgattttgtt tggccagaga agaacccact  55380
tctttatatg gaagactacc tagatatttc atcaacccaa gcatctcctc aggaagaaga  55440
gaagcctgat tacatggtca acgttgtaaa tgatgttggt gaagaagaag aatttgaggt  55500
tgacttctta tgattaagat tatcgcattc gtagttttaa tgtggtccac tgtcctattt  55560
gcagcaactg aagtaaaatc aactacagat ggtattattg cacattcaga atgtcagcta  55620
gttgctaaag atagtagtgt tgtcggcact actgttggag gtgcggttgg agccaccgca  55680
ggcgctgtat taggtcgagc aatctttggt aaatctggag gttgggtagg tggtttaatc  55740
ggtggtgccg caggcggcgc agtcggtaat aatgttagtg ctactgaaac atttcaatgt  55800
aaactgattg ttaatacaga tggcaagcag tacatggttc aaacagttac caatgaaaaa  55860
ccaaaggttg gtgataaagt cactgttgtt gaaatgaatg atggtacacg agatataatg  55920
tagacataat gaccctccct taattgggag ggtttatgct aacaattcta tagcactctt  55980
attaacagtc atcaacgaga gagtagacat gaataaaatg ctaaacttcc taaaccgtac  56040
gctatatagc ggtactgaaa aagtatcttc aaaagctaca ccaagtctag aacactttaa  56100
aacaaatgtt gaacaagtag ataaaaagat tctacaaccc tttagtacta aatttaaaac  56160
cattctaaaa gaatgttaca gtaatgagga gtgggttgaa gaacaatcat ttattgaaga  56220
```

-continued

```
acctattgat cttggttcag ctgcacgcgg tcttaccgag cgcggtatta tgcgtggtga  56280
ttggggacgc ttagcgcatt ccactattaa agaagcagaa ggtatgatgc gtacttatag  56340
tggtcgtcta aatgaagata tggaggcatc tgaaattaat gaagtaattc aagatatgcc  56400
ttataacttc acagctggct cagctaatac tagccgttta gaagaagatg actctatttt  56460
tgttgaagca gatacaactg tagttgaacc tctgtctaag cagactctgc caaaagtagc  56520
agagcttact aatcaattag tggaagtcta taaccgaatt actgaagaat ttacagaaac  56580
tggtattgct aaagttgaac aagttgaaca gccagcagtt cttgtagcac ttggtgagat  56640
cattagtagt tttaataaac taattgattt atcttgcggt gctctaccag tggaagaaac  56700
tgttattgta gaggaggatc cgttacctgc cattgttact ggtccaacta ctgaacccat  56760
tgatggtgaa attctaccgg ttgatgctat taataattct gcggcattag aagaattcat  56820
tgaagaagta ttaagtacta atccagaatt cattaaatat caaagtatga atgatagtaa  56880
tattgattca tatctaactg ggatgactgg gattatactg aaattcaaag atggttctta  56940
ttatttatac aatgcccaaa gtgccggtga aacgaatata gaaatcatga aagatatggc  57000
cgaaactggt agtggtctta atggttttat aaatcgggtt attcgtggcg ggtatgtaga  57060
gaagtccatc attaatactc ccggttttat acaagtctca aatgaaggtc ttatcgattc  57120
aatcaaaaaa gttcttggca tttctaatcg aggtgatcag aaacgtatct ggcgttcatc  57180
gtccagtgca agaggatttc tggaacaact agaatctaca tttggcaatc cacaatggct  57240
taataagcag gtattcgtta ctggcgatat caatagtaat ggtatagcta acgtactgag  57300
tattaatggt aaagtcagta tcgaggatgc cattcgtgca gtagaaccat tcttcaaact  57360
cgaagaaaag tctaatcgcg aaatggagtc ttacaggcag aagactaaac ctgcattgga  57420
tctactcatt aagaatgcac ataacctaga cgctaacgta tacaaagaag caaaggctat  57480
cgtagacaag gcacgtgctg gattcaagac tagtgttaaa tggcctgccg gtactattac  57540
aggtaagggt acctataatt cacctcgcac cgtggtcgcg aaatatccat ctactgatag  57600
taaactcaaa gctcttactg aagaagaagc agctaaggcc atgaacttaa ttatatcggc  57660
attggaacgt cagataactc ttagcttcaa gttccctgat ttaccagatc cactggaagg  57720
actaatctac gatatgttgg ataaccctag tccaatagct ggtatcgatt actatgattg  57780
gaatgatttg ttattcgcat gctttggccc tgggattgat gatgatgtga tggaagttaa  57840
taaaatgcgg caataccact cattcattga tatcatggag gccgccgcaa aatgggtaga  57900
tcggtctata aaaggtaggt tagcaatggg taatgaaaac taccagtaat gtatctaata  57960
ttatgtagaa ataatccctc cccctttgttt ctacattagt cataatagat cggagccagt  58020
ccccccttcca actggctccc agagagtaaa actctttgct gggcattaat gacgatatat  58080
cgcctccctt cggggaggct ttatattttg tttttacgta tgtatattaa aatatgtata  58140
aacaacatag agtaattata aaatgatcaa aaatgaactt ttaccagggc taatctatgc  58200
ccaaaaagaa tttgataaaa ttgcagctaa tgtaaaagac tatgataant ataaaagacg  58260
cgaagctggt agggcaagtg ccgttttaag aagtctagtg agcaatattg taaatcagaa  58320
taaaccatcc tcacttgaac atgaaggcaa agttagtact actaatacta atgaatattt  58380
agaagaagtt aataattact tctttaacat taataatatt aaattaattt ctcctaaact  58440
cataaaagag aaattaacaa ttgatctaat gaatatttat gttaaatgga atatgattgg  58500
agtggctggc cgaaatgatg ttccaattat tgaacacaga attaatgatt ggtgcgaagt  58560
```

-continued gaccgatgtc tacattaatg gtaataagat aacttcttta caatggccac gttgaattta 58620
aaataagttg taataaaata cctagcatta catgttatgt attgaagcac aatgcccgaa 58680
tggtgaaatt ggtaaacaca gaagacttaa aatcttccgg ctacggtctt gtcggttcga 58740
atccgacttc gggcaccaat ttaaatacgg agtgtagcgc agttggtagc gcgcctgctt 58800
tgggagcagg atgtcgggag ttcgagtctc cccactccga ccattttaat aataggtaaa 58860
taggatggat aataaatgga tatcatggga acatcaaatt ataggaacag ctctttacgc 58920
tattcttagt gaccctgaat taactaatat tcaattagct caaggcttac actatctaac 58980
agaagcaaag tcttctgtat tacatgtttg taataaccat attacattca ctgtaaccta 59040
tccacatggc acatttagaa ccaatgtaat tagagagtgc cctgctagtg atacaaatac 59100
attcaaatgg tcaggtgtat tagtccgtca aaaagatgga acattcttac cagaataaat 59160
aaaaagggcc tatagctcag ttggttagag caggcgactc ataatcgctt ggtcgcaggt 59220
tcaagtcctg ctgggcccac catatactag cctcccactt gggggaggtt ttatactgtc 59280
tcattgagga aaacatgaat acagtaataa tgttggtatt atctatcaaa gttggattat 59340
ttggtttcat ttcgactaat gaaagtaata tcctatttga aaatagggaa cagtgtattt 59400
ctcatctgga tattctggaa cataaataca agtctcttga agttattcga aatgagaata 59460
ctctaaagat aaccgaaaga gataaccatt ctatttatat ttttaaatgt ctctaggaaa 59520
atacatggaa catcaanaac aaaaagaact attgagacaa ccattacaaa cactttataa 59580
tcttactttt agtccccgtt tacgtaatgg agcgaaggct cccgattgga ttcacctgac 59640
cgatgaagta accctattcc caaacggatt agatattaca atcaacgctg ttacacgttg 59700
catcaaatgg gaacttatcg gcgaggatgt aagtaacatt acttatgttg aagctatgtt 59760
ctttaataaa ggtcttaaag cagttaaagc ctatctcaaa catacggagt aaatatggat 59820
catctaaccc caacgcagag cgctgtatat ttcacattta ttagccctga gtttataaag 59880
ctaactcttg ttgaatcttt tgtagcgatc cacaagaaac atccagaagt aaagcattgc 59940
gttaagaaaa agattagtgc taatgaaacg cagtttatct ttatcttcaa agatgggact 60000
gataatttaa tcattacacg taaaactgaa ccttgccctg aactggatag cccagtaggc 60060
gatagtatta agttgtccgg cgaagaactt aaaaatattc ttgctaagta cgatcgtccc 60120
aaggatggta actatttcaa gcactggact gatcgcccgt aataaaatat tactggttat 60180
gtaatactat gtaggaagtc atgtccatac gtttgcgctc atagttcagt tggttagaat 60240
acccgcctgt cacgcgggtg gtcaggggtt cgagtcccct tgggcgcgcc atttaattcc 60300
gtgatagctc agtcggtaga gcaagtgact gttaatcact gggtccctgg ttcgagtcca 60360
ggtcacggag ccatattcta aagagtagct tcggctactc ttttatgttg ccatgggtta 60420
tcttatgaat taaaatgatt tacttgagag cacactcatg tttgaattac tattatcncc 60480
agatataggc gaagagttac ccttggttgg atttaatgaa attattaaat taggtgatct 60540
acctgtagcg ttagctggta caatgtcata tgtggatgga aatacactgt atgttggatc 60600
tggtcatcat actgaaggac aaacagctgc aactgtgttc agacgtttta ccatatcgcc 60660
atttgccgat ataggtgcaa ctgcttctgg aacattctta ccaggggtat ctttaggatt 60720
tgggacatta cataagaata actttattgt ttatggcggt attactggat ggaactcggc 60780
tggtaatggt ggtacgggaa catctaactt tatacaacat tttgatatag ctacaggcaa 60840
tagggttgag cgatatagtg gtcccgtacc actttggggc acagcctccg catcagatgg 60900
taatgatctt attctatgcg ttaacccant tggngtaann gcaatgcgnt taaaaccatc 60960

```
nngtaagncn tggcttagng gncaaganta ttcaggtggt gctcgttcag gtcaacagtt  61020
attcttttat aatggttact tttaccattt tggtggttgg gataatacaa agaacatacc  61080
taatcttgaa gtttatcgat ataatgcaac taccttaata tgggagcaaa caccttggat  61140
gattatacct gctgataaag gaacaatctg gcaaggtaan ggttatgtag atggngacta  61200
ttttaattac cttaacgctg ttgatgtcgg cggtgtaact aaaatgtttg cacaacgttt  61260
taatattagg cgccggaaat gggctgaacc atttgaacta ggtatcggat tcctnaatat  61320
ttcatctata gctaaaggtc cggataatag catgatcatt gtaggtggat ctaaaatgcc  61380
agttggtggt ggagcanana tgttgaaaag ccaattgtta tcaggtntct atcaggtaaa  61440
actagcacca ttaatcattg attaaaataa taatatttat aactatttag ataattatac  61500
tggcacgatg atattatgta agagtactat antaaagtat tcttaaatct atccactaaa  61560
cacactcggt ggtagaactt attatagagt gtgtctaaat gccaggggtt tgccacccct  61620
ggntatattc attgttacta ttataaattc atttatagat gagaaaaggt tttatcacct  61680
tttcaaaatc ggcatttaat tccagttaaa aaaactgaat ctatgctaca ttgtaataaa  61740
ggagtctatt atgactaact ctaatccgtt tgtaagaact attgtaaagt accaagatat  61800
cctagatgct ttaattcaaa aaacgaatga gaactgggtt aattatcgat ctaattctat  61860
tggncatatt gttattcgtg aatacaggac tgttggatta tttgtaggtc ggcaatgtgg  61920
tagtacaact gcattgattg agtttgctaa tcgtcancct ggcgaatgtc tagctgtatt  61980
tgtagaagat aaaattaaac aggctgtact ggctaagttc cagaatgcta aagataatat  62040
tgtttcttgt ttaattacac accaactccg naaatatatt catcaacctg aagaatcatc  62100
tattcaaaaa gatattaaag aagaattaat atcgtctgta aaatatattc ttgttgacaa  62160
tgcctcattt aatctgaacc tacgcggtat cactgataaa gaatttaacc agtgggttgc  62220
agatactttt ggtacagagg taatggtggt tcgttttagt tagaattagt aactttgata  62280
gtttctaata agattaacta cacgttattt acataatgtc ataacaagaa ataaataata  62340
ctcagattgt aataatatgt agttattaca tatctatatt aggttgtcag taactcatct  62400
ctaatataaa atcgccataa ttcttccgtg atagctcagt cggtagagca agtgactgtt  62460
acgatttcat tggtaagtac ccgagtggca gcagggagcg gactgttaat ccgttggcga  62520
aagcccaccg taggttcgaa tcctacctta ccagccaaat tctaaagagt agccagctgg  62580
ctacttttat cttgttctat agatcgaact agctatctat tttttaaacc ctaggttcga  62640
tatgaaagaa aaaaataatt aatggttatc gggctctgta tttacctgaa catcggcagg  62700
caaaagctaa ccccaaaatg tttggatggg tatacgaaca ccgtgtagtc ggtgaagata  62760
caatcggaag atctctttac gatgacgaag aggttcatca tttggatgag aacaaactca  62820
ataaccatcc cgataatctt ttgatcctcc ctcaatcaca gcatctaaaa ctacatgcat  62880
ggatgaaacg actgggcatt gatccaaaga actatcctac aaaactttgt ggtgcttgtg  62940
gtagggtaat gaatcataaa ttgattaaat tctgtaaccc tgagtgttct gccaaaggtc  63000
gacgtaaggt tgatcgacca tctaaagaac aactcgtcct tgacgttaca ttgttatctc  63060
ttgtgaaaat aggagaaaag tatggggtat cggataatgc aattcgtaaa tggtgtcggt  63120
catacaaaat caatattcca gctaggttta ttagggtcag cactaatggg ggtattagca  63180
ccttggcccc cacacaataa aaatatactc gatgtagatt aatatacaaa aacataatca  63240
ctgggtccct ggttcnannc caggtcacgg agccaattca tagttttaga tttagttata  63300
```

```
tttcactact atgtaaacta taaaggcagc taatgctgcc tttatgtcgt cttgtaaaag  63360
tacccagtag ttgaatctta tagctgaata caaatagggt aaagacatgt cacttaaagc  63420
attgcaagat atagttagta gtgttcctac aaatgaacaa aaggaacgat tagttaaagt  63480
tcggaaaacg atggaagagc taaatgagtc tattaagaat cagattcgta ataaacgacc  63540
tagtcaagct cttctcgaca aaacgataaa ctggggtacc aagtatggct aagacattag  63600
ttcgtgcaaa gctgattact gaagctggtc aatggatgtc gtctgactgg gaatgtggtt  63660
tccgtgcatg tcgattcgtg aaacttggta atgatcatgt aaacataaaa gactttgagg  63720
ctatgatcac ggcattcgaa gttggtgaca tgttagtgat ttggccaaat gggcttagaa  63780
cttcgtatag tgtggataat ttcaataagt acttttccca tatcaaagat gaataccatg  63840
agactgatct ccgtccactc ttttacccca agtagttgag cttatgataa ctatattcgt  63900
gtataaatac attacattcg ttataccctt taattgattg aaatcaagct acataaaagt  63960
gatgaatact ttaacccaat gatgtataaa ttaaaaagta tgcacactaa aaatacagat  64020
ggtgtttatt tgatattttt accaacgcct actatcgatg atcaaattaa caccatgcaa  64080
gggtatatta tcaataaatc cggtaatctc attaggacta ctgtacagtc atggcgattt  64140
gagaaaattg aattcaaaga cttagccaaa catgatagac gttggttatt tattgaatat  64200
tacattaatg ttaaacaaac gaaaaataat ataatcaaag agcaacaaga tgaattaact  64260
aaatttattt attatagtac tctaagttaa aacaaataaa aaaataaata taagagctag  64320
cccctaatgg gctagcttta tgttatctta ctctgctaca tcttttacat caggtttatt  64380
attccaacgt actgctctcg caataccata cgtaagaata agagcaccca cggtgccaat  64440
agtggtgcta ataataatgc caagagtttt tggntcnata ttcatattta gtntcctatt  64500
tacaattaat agaaaatatt acttttagta atatcanntt nntnatatac nntttaaata  64560
ngtttgaata taactttatt tattataata aattaaaata atactttcat atacactata  64620
tgtagaagat tncgccgcta tagctcagct aggtagagca acgcacttgt aatgcgtagg  64680
tcctccgttc gattcggagt ggcggcacca aatttactga ggtttaaact attcttaaat  64740
atattagtta ggatgggatt gaacgngaaa gactcagtaa atcatattgc ccctccatat  64800
ggaggggctt atgtttgtca ttaatcagga aaatataaaa tgagncatct attatttatc  64860
atccaagaat acattactaa taaatttgag ataacacgaa ttgatatgaa gccaggtaat  64920
agaatgttac gtgtatgttt atacggtcaa cataagggaa aaggtttcgt ccgtatagat  64980
ttatggtcag ttggttatcg cattacaaag aaataatact ccagattatt taatatgtat  65040
taatcaaagg agtttataat gagtaatgaa actaactatc taggttatga atggaaaaca  65100
gatataacta cttcaaatct taatagagtg gttgatttat atacacttga attaacatgg  65160
ttaaaagaag attttaatga tactcttttt ataaagtctt ataaagtgct agagggtcta  65220
ttagaggaac cgtctagggc aatccatgat gatacagtan ccattcaaga tcaattagat  65280
gaattaaata ctgtttttaa attagtattt ggaaaagata ataacgtaga gttatcaatt  65340
aataatgatt caattattgt gatcggtgct acagatgcaa ctaaagaaaa gttagaagca  65400
gaggtgcgtg agtttgcata tagaaaatca ttaattgatg aacgttatcc aganattgta  65460
acggattaaa atacttacag ctatctagta tgtaactagg cggattgcca tttgtaaatt  65520
atctatttaa tcgaactgag gaaatactaa tgaaacaatt ctttcaacta cttctaagcc  65580
tacttttcaa actaccggtt ctatcatatt ttgctgagaa gaaacgatta gagaaagaga  65640
aaaaggaaga agaaaagcgt cagcaagaac aacgtcaaaa agaactactt gatgaacaac  65700
```

gtcgcgaact agaagatcat tatcgaaaga cggcttacga tcgcctagca aaacttattc 65760
atactcggtg gtatgatgag tttaatgcat acgaaaagaa actagttgat cttgctgtat 65820
cgagtggtaa agcagttagt gttaagtatg gtaaagttac taagatgcag caccctcatc 65880
aatttaaact acttaatgat tggctggatg atattccagt agaagattat tctaagtgag 65940
tttaaataaa agaaaataaa gacatagccc ctctccannt ggagaggggt ttatgccgta 66000
attatacact tactttgata agatttttaa tatcagtnaa atgggtatat gttgcctttt 66060
tatctttgtg aaccagtang caacaggtnc cttcatttac ngtattggtt tgttttaatg 66120
ggatatttaa agcatattca aanagatcat ccatccagtt aaatnccatg aacttattga 66180
taaggacatg atcgaaatca attaatncaa taaacgaatc gatctcanat tgataatact 66240
ctacaaccat tttagaccat tctttgttta tngcctcaat gacattagga ttatttattt 66300
tattaaataa ctcantncgt tcctnagtag gtaaactgag gtaataatta atattactcc 66360
taacgatatc tggattagtg atatcnattt tttctggtaa gttatattta ctatctacat 66420
aattcttagt ttctggtgtc attctccagc aaccataatc agcagtagta cttgatggat 66480
ctattttagt ctccactact ttagaaaata catctacata taaattaaca gattcgtata 66540
catcaggtct gattggatta aagtttaaac ttttaataag acccctaact ggccgagtac 66600
caattagaca atgcaattca agcttaacat tttcctcttt agccatctta aatanatcag 66660
caaaactgag cttttctgcc atttagaata taccttttat taattggaca aatagattag 66720
atacacatag caatagaata aaccataaac ctagtctttg taatttatct atacgcttag 66780
ctttttgttt cctctttaat ctaactaata atgtattttt aatatcattc attaaattat 66840
ctcagatttt tagacggtgt ataaaccctc agtattacat gttgttatga tattgtaaag 66900
acgatgccaa tagcgatcat acgtattttt acgtttgtag ctattggtnc ggatgactag 66960
attggcgacc cagtgattct gatcaatggt ctcatgtaga tgcccgaaat aagcccccag 67020
ttcaatttcg aatgggatct tacactcacg ccccttacac attgcttcac gcaataaacg 67080
cattgcagaa ttctctgcat tggtatcttt aaataaaaga ctaatgtatc cagggctacc 67140
accagtttct tcatcaacat ggcctgaaca gcaataaata gttgcaacat tgataaattg 67200
attaaaccat ttaattaatg gcctacatgc ttcatcaata agatcttcat attcaggttt 67260
atacattact ttaacagtat catctgcacg ttgtttcaca tgatgaaaat attgctccca 67320
atttacatta gtgtaatata gcatatccat attagaatta ctcatacaaa tcaaccccat 67380
atgttattgg catattcgcg gtcattgaaa atgcgggtaa gatccatccg cttttgaatg 67440
cgcgctagta tccattttag ttgtttagtt gatagttctt gattttgctt gtactcacct 67500
gtagcatgga tgtaataatc aaatttacga cttacagtag tagtatgtgc acatgcaata 67560
gcaaatgctt caagtgcagt tagtttggtt gatccattat cattacaatt agggataaac 67620
tcaagtacac tattaactgc atctacacca ctacccaaat gagcccaatc tttcttggtg 67680
atgttgatac ccatgtcttt aagaataact gtatatatgt caccattctc catagtgaac 67740
atcatagaag tattaccatt aaacaacctg cgttctatga ctggcaagat atttacttca 67800
actttaaacc aatcagctaa atcaacacct gcggtaaggg cattcaatag atcataaaca 67860
ttatctatag ttccagcaaa agccatagtt ttaacacgtt taccttgcca agtaactgtc 67920
ggatgaaaaa ttatcttgtg gcaatcattg taatatacat ctacaccttc agctttagca 67980
gttagatcaa tataaccgtt atctaatact ggaagtcgcc caatgctatc agttgcatta 68040

```
ttccgctcaa ttaataggca gtctgcaatc atgactttac catcatttac gatatatgtc  68100
attttcactc cttataataa aataaatagg cttaagcgaa ataaagccct ccccgaaggg  68160
agggcattat caataggtgg gatctcggcg gcaccttcat ttgcggacgg gaacgctgaa  68220
gggagatagt ccgggagatc ccgatttggg tattctttac atatggtatt actgcaagta  68280
tttgttcccc gcagtataat caccattgat ccaatttttg attacaacac tgatcccttc  68340
atttcttta acggtaaccc ccaactcaag atcgattgat tgataagcta cagccgccag  68400
tgttaaccga agataaacgg atccatcttt ttcgatatcg taggatacta cgaacccgtc  68460
ttgtagattt gtagctggaa tgtattagca tgttgtggat ggagacgatc catattgtac  68520
tcgacgacat ctagtagata ttgccgagca tcagcagcat tatcaaatcc gagancgcac  68580
agaccgatcg gatagcgagc ttgcgtgcat gtaactttca tagatactac acgatgttgt  68640
ttgcacatta tattttcctc ttagatgtca aaaccctccc gatcagggga gggtatctca  68700
ttggtacttc ttcagcaaaa ctgaaactaa gataaaagag caatcgtaaa ggaactacat  68760
agaatagtgt atttctttta ctatttttac acaacctctt tagatggggg ttctttatga  68820
atccagtcta aagttgttgg taaactatta tctgatctga aggtacacac cgtccggaac  68880
cgagagtgat caactacaga taattgcccg ttaatcgcag cctcatattg cctacacaac  68940
ttcacacacc ttttctctag atcagttggt tcgtaacctt cttctcttgg ttcagtgtat  69000
ggtccatccc aaaagaatat taatctaaga tcaatcccag atttatactc cgcttggtat  69060
gaatattgnt gaacatcaaa atcatctaat tcttcaacta gatgtgatgt tattgttcta  69120
ggntgttcat gagttaattc actgtatata tgtttatttc tagggttttg taaatcaact  69180
acgataagtt gactagtcat tttaactttt atccagatgt ctattacgag tgcgttccac  69240
tgctgtaggt tcgacagtgg ctcgcggtag ataagtaatc tccgggaaag tcttattaag  69300
agcatcttca attagctctt tagcaatctc tgcatcgatg taatggttta gaataatacc  69360
acgatgatac aggaagaagc tgtattcatc ataaccatgg cgaagactta ctttaccacg  69420
atacccacca taggttagag tatcttcgtt aattcattcc gataaatatc aagttggata  69480
ttattttgaa gatgcatttg aatgaagtca ttactatcac cgccgaatag ggttggtcgt  69540
ttccgaccag taacaacatc ttggatggaa tccattagtc ggttaatgtc tgtttctaat  69600
cgttggatat cacattgaga attcattgct tcatggaaac gagttacaac tgcattgaat  69660
tcttcttcag tccaaccact ggtacgtttt cataatcaac aatgataata ccgaaccagg  69720
cataaccgtt agaatgttta ctttaacaca tagatgaggt acattatcag cacctgactg  69780
atggttaaca gtgtaattat tattacggct gattactagt ttgataaaag gtagactaat  69840
gattgacgcc atggaaatat tccttttgta ttttttaaat taaagtagga gttattattg  69900
agtttcaact caatacatca ataactccag tatgttttca aaattaaata catgtattta  69960
cagttacatt gtaaccagtt agttttgcca acaatacaaa ttagcgaacc tgttcgattt  70020
tttcagaaac aatgaaaata tgtgcaatac gatcctcatc aanataccga tatcgaaatg  70080
aggtataact agatgacaca tccgtatcgt ttaaataggt gatattaaaa tcatctactt  70140
ccctaccatt agcagccgca acggtattta gaatgttgag tagactcatt ttacagattc  70200
ctttttagta tattaatatt tcaatagact attgataaaa gcattagggt cataacggtt  70260
atttgaaaaa gccgccatta catcacaccc tggctgatct ttaaatctga tatcttcagg  70320
aatatcgaag tcagggaaca ttagtttaat atactcccta acttcttgat ctcgtagata  70380
tggaatctcc accatgtaat caacgcgacc tttccttaga agtgctttat caatattctc  70440
```

aggatggttt gtagttagaa tggtcatagt ctcatctagt ggaacaatgc catctagccc 70500
atttaataga gctgacaaag ttaatccgct agctggttgt tcatacgtga ttccattctt 70560
catgcatttc tttaatttcc accatcggcg aattgtggta aataatggat ctttttcatc 70620
ggcccatttg aaacacccag ttcagccata gcataagcac ttatcccaaa accttgatca 70680
tcgctatttt catcaaagat atagatggtg tcattaaccc aactacagag tatccttcat 70740
agtcatcttt aagatcaacc catgcagacg gatatttttc aattaaatca ataaaagaat 70800
atttcctctc taattccttt atctctttat ctagttttac aggatcattt aaaacacgat 70860
ctttaactgc cggggtatca tcgaaatctt caattagaag aatattacct ttaggtagtg 70920
tagtaaatgc ccgcctaaga ctatcattgg tcatagaggc taatgacagt gcactaacat 70980
ttttattaaa atgtgaggca atcgctttac tgattgaggt ttaccagtac caggaggacc 71040
tgttagaaca caagtgaatt tatagggtag tccacgatca tcgtaccatt tccgatcaga 71100
atagaattct tcaatcttat taaggaattc ttctttgatc tctttacgca aaatcaccgt 71160
gttgatatcg cgtttagtaa cttcaatctc attgccccaa cggttaccat cccaatgtga 71220
aatagtcaga cccctttcat ttgggcgcca atggtaagca tctactaaat caataattag 71280
tttactactc ctagataatc cacggatagt aatatccatt tgatctcgac tggcattttg 71340
actatcccgg cgtgctttta caaaccagaa taacctacct ttaaacagaa agaaatgtaa 71400
gccaaaacca acaccaattt tctgtttagt tgcactataa ctttgctcat caacattagt 71460
tgaaaaacgt cgattaaatc cagctaatgg ctgcttaata taccattcca tgaaacaatc 71520
aaagttcttc tcgttcagcc cattacccat gttggtaata tgtagactaa ctgtaaactg 71580
atttaatgcg aacctagcta gtttacttgg taagcctctt agagtggtcc agaataaacc 71640
accaattgcc attccgatag ctccacccat aaccatattc ttctgagaga tatcgatgaa 71700
catggcgtaa tattgcaata aggtttctat aatcatacta gcatccctct ggatagctta 71760
ggaaatattg tccacagatc atgtattcac gttctagaaa tctagagtat gactttcaaa 71820
tatttcacct acatctttac catagatttc cgtataccca tttttgaata cggccattac 71880
ataaacatca gacatagtca tgccgtagtt ataaatttga ttgtctctgt attttggatg 71940
aaataggtca tataaaaaac gagtcattga actattggca acagttgtca cccctttctg 72000
ctttaaggca taacgtactt gtttaaccac atagttaact ttagagcgct cgccaaatac 72060
cgtcagttta tctacattgc aattacgata tcccataaca ccaggattag ctatcacggt 72120
gtgttttgga acacgtacat caaagataat gccattaggg gatagaataa tcttttcatg 72180
gttaaataga acatgaaata aatgtcgttc tggtttagtg attttgatac ttaacccaat 72240
caccccacta atctttcttt ctagatcttc tagtgactgc atcaccatgt gatattgatt 72300
gaagaaagca ttgttcttat attgatctaa ttcaaagtat ttccaacttc cacgaaatga 72360
atagcatggc tttggtataa cctttagtta atcgacactt gagtttgtca aaccagcttt 72420
caagataact ctcgactgta aaccaagtgg gttattatat aagtttattg gaatatgata 72480
agctaaatct gtacatagtt cgacgatgca tttatattcc tgccaaataa agaaaaataa 72540
agggctccga agagcccttt atgtattaga tttttacaga ccaactttgc tcgaattcct 72600
gatataggaa attgtctgac gcattatccc aattttctcg atcagttaca ccataataat 72660
ggaattctag ttcagtaggt ccaccaacaa aaccattctt agcatagcta taaacttgcc 72720
attggttagc ttaatcagtg tatccacata gaaactatta cggttccata tttcattgtg 72780
gatgtactta aataccacac tgtngatata cttaaattgc gcacttggtt ttccgagtac 72840
actccaatag aatttacgga tacctatttc ggtcttgaaa ttaaactctc cgttgcgaat 72900
gttgttagaa acaatacgtg ccagtttatt aacccgattt cttcaccgat tagatagatc 72960
ccggaaacac tacatccatc tcctattgat ccattattaa ctagtggatc aacaccatat 73020
tcatcagtga aaatggtttt gataacctct ttaccttctc gacgcactaa catattcagg 73080
tgaccatctt cgatatatga catatggcta ggctgaatat attcacttgt atcgacgata 73140
acatcattcg ccattacatt aaactgtaga tggtttacca gatcactaat acctttaaaa 73200
cgaatggctt ggttcgctgt atttagatcg acatacacca cgacatcaat aatgccttgt 73260
tttagtgatt tgtcatcttt gtcagtagtt gtatcaattt tacgtaattt tgatatagtt 73320
cactaaaaca agatatgatg tcatcatgta gtttaattac atcagatcca tttcgttcaa 73380
gcgctttaag cgatacgtta aaccaatacg aattttatta gaacgacgtg ccatggttat 73440
atcacctatg ttaaattaat gaattattta ttcaattacc gtactacatc tgtgattaga 73500
ataagttcac catcactatt gataacacta tagcttttac aatttcgatg cgcttactaa 73560
taatcttatt ctctagatct acttttacga tattaacacg aattacctta ttcgattgat 73620
catgcatttc tttaaaatgc attcgatatt ttaccaatga cagcttttaa ttttcaatgc 73680
tgtcaatgga tgaatattta aaactatatg cttctgccag ggttttgcat tacccacaac 73740
cgtagttagg gtaccccaat aatcataaac atacaacgca gtatcactat tgggattatc 73800
gataatttca attataaatc cacttgtatc actcctatta gtttattgat agtacacttg 73860
taatatagat cttaaataaa ttatgatcta accatttaaa atagataaag cctctatatg 73920
ccaatggtgt attagttctt ctttactaat aatattattg aagtagttta accgatgtga 73980
taccattaat ttagaatgca tatcgacttc actacttacc ttaatcaccc cagtctctaa 74040
taattgcaga gatccaacat acgcaaataa agttggtttt aaataccagt gttccctata 74100
ttgtttttga tcaggtacat ttcctataat gtagtcagta gaattacttc ggtatgcgta 74160
aatagttgat ttagaaccaa gtaaattaag atcgatatca taactcccgc ttttagctgc 74220
aatacattca ataactgatg gggccacaca tatacggttg gttacactgt cttcgccatc 74280
agctctatta cttggaatat atggccttaa taaacataat ccccaaggta tactgtcgat 74340
atgtgataca taattaacct atttaattaa aacagataac gctctgttac tgaacgatat 74400
tgtgacatga tgtttaatgg atcaacatcc actggtgctt tagtgacagt taagcgagca 74460
ccttttaaaa atcaccaata tctaatttcc ttacagtaac atcatggata gtgtttttcg 74520
taatccactc agtatcaatg ctattgtgag gatattattc ttaatccatt tgtcagagtc 74580
cctaaatgga atggtataaa catacacaac cattttaaaa tatcactttt atcgatatta 74640
tttgacaata gattgtaata tccctatcaa cagtagcata tctatcacta tcaaataact 74700
tttcgatagc gctaccaata cctaaataag atgcatcttt ttcagatgac gttgcatata 74760
ggtattggtt agactcaata ccatcccaca taacaagttc accagatctt ttaaatcctg 74820
gcattaattc atcttgttta taaagagaac catggtaagt aattctggtt tattcataat 74880
aaaatccact atgctttata agagttatgg ttatcaatta acttcaaggt agtagtgtgg 74940
cagtattgaa gtgattggtt actgcttcga tcagcatttg ctcgatgttg attttgtagt 75000
attctggttc ttcgttcaat tcccaataat agtcgcacgt aatagtgcag gtgctatgaa 75060
tctaactacc ttaccatgtg tgtcaaactc tacatgaaca ttgcatattg ttcagtagta 75120
tgattttata gaaatgaatt accagcgtaa ctgcgacctc tatttcacca tgaatactgg 75180
agtaggtttc ctggtggaat actttacctt taaggcgtgt attctcttca atgatattac 75240
caattctttc aatttgtctt atctagttgc atttgtaggt tcctattaat aaatgtatac 75300
gatggatatc ttttacgatt tccggtgctt atccatatct agttttatat cagtatatat 75360
cttgaatcta ttagataggc tatccatatc tacgtgcaat gcccgaatat gcatatcagt 75420
atcttttggt ttaccttcag actcccatac ggcctttgcg atatcaaatg ctacattgtt 75480
caaatagtat tcgacttcat gttcatcaag caaaagagca tcatggaaac caatacgtga 75540
tagaatggcg taatcacgct gattaacatc tctccaatct ttacgcacta agtaactttt 75600
accaattcca tcttttttac aacttttact aataatttct ataatgaact tatcatgcca 75660
tttataatcc ataatcatta ctcctttatt taatcagctt cattactaga ggaacagata 75720
gacttatgcc attagccatt ttagctagaa tatgatagac atcgtctgct tcttgattat 75780
tgtacaaggt atagaaatgg catcaccata gtaaggactg tagttaatac ggtcgccata 75840
cacaccactc acaaaactat aatctaatcc atccgtggta gtcataataa ctacaacatg 75900
atcatcccca actataccgg attctaaatc ctcacatagt tctagttttg ttgcacacct 75960
cgttgacaga tccatacttc acggtattga tgatgaggat atggattaca tgctacatca 76020
ttttcactaa cgaagtacat agtcccccag ttgtaagact ggaattgggt tgttgtttgt 76080
gggcttccca tacctcttcc atacaaaggt atgttgttaa cccatagacc atcgttatta 76140
agactatcaa cgatccatca cggacacgta ctacacggag tgtttttgcc atttttaatt 76200
atcctaaata cataaaggaa tcacttagta aacaccattg acaatagcat cgcggaaacg 76260
agaccattcc gtttgaccaa ctacgaatac tcgttcttta ggacgccata gatgatcacc 76320
gcagtcaaga cccaagtaaa gcatattggt tttccatgat tgcgatgaac acgtagttta 76380
gctgatacac tgaactcaca cattacttca tttacatcaa gatgtgtagt gtatcactat 76440
catacctgac atactgatac caattgattt acgaactcgg attagatcct cagtcatcac 76500
ccgccaagtt accagatgct cgtaatactc atctggtgtc atgttgtttt tataattcag 76560
tgcacctgga gtcattgaca tcagttagtg aactggaagt catgtaatac atccaatcac 76620
tattatgacg gagttcttta agcttctctg tattacgata ttagtagttg ctttagtcat 76680
ctacgtaccc tcatcagata cataagtacg ttcaggctga acacatattt gatgttatta 76740
attacagctg tgatataaac ctgatattct tttgaaatag attccatcag ttcaatagat 76800
acggaattga actctgaata agttatttac tttcttagtt catcaattct accgaccgta 76860
attacaccaa catctctgaa actgataact ggatagtgtt tccaatataa caattcagtt 76920
taccaagatg aattacttga attgtttcat cgcaccattg tttcttttct attgtagtat 76980
tcaacacgac gttcgatgaa gacgcgagta ccagaaacag aggtgtacgc attcagtcat 77040
aaccatactt atggtacgtt atttggatct tggcgccatt ttggatgaat gctttcattt 77100
gtattttcct tttacgaaat agaagccctc ccgaaggagg gcaattacca ttattaaatt 77160
acgagtctat tacttctttt aattttcacc aggggtagct agataatcta cattatattt 77220
aatagcaatt acaccacaag ttctttttca tagctgttct acctgatcgc atatttatca 77280
atagctccat cttctacatc ctcgtataat ggatattgac tataatatta tcaggtgtaa 77340
gtacagacag tttcaatccc atctttacca atgactgggt gatatgtctg tttaagacct 77400
ttacaatgat agtgataggt atgcgctgtg tttaggtggt catgtaaaga tacctcataa 77460
accgttgggt agtccgtctt taagacagtt agttgattaa catctttcaa tgattatctg 77520
caatattctt agccaataac agtagatcat tggtgatatg ttttaatgag aacttaagcc 77580
tctccctttg tttatatcgg aaccttatta tcacagtaac tccatccggt tatttttata 77640
attcagtaca gtgattggtg tattcggtac aaagacggct agttcgtcat cgaatacaat 77700
gtaaaccatc actttataat tattaaccga ttcttggaat tgttgtgtga ttacattata 77760
gtcttttgtg cgatggctaa gaaacagctc actattagct cggcagaaac tatgtcgcgc 77820
tttttatcag cactcataac agcgatacca cggataatga atttattatc taaggtatat 77880
tttctttgag acatcgcata gtcgactaca tcaacatcgc cgccaaatag cacggcattt 77940
tcaccgtatc cacaaataag agccatttat aattacctgt ttaaaaatta tattcaataa 78000
attgagagtg aatagttcac tacattccca tgtacgactt gctaatttat atttaccttt 78060
aacaggtaag tcaaataacg taatgctttt ctactgaacc agcctcatga ttaaccaata 78120
gaacattcct agccttcaga atatttgaac aatttacaag ttcataatca tctcgcttag 78180
gtgtcaatag ctacattagt gcctggtttc tagcatacca gagcacctca tgaccctctg 78240
gattaataat agagatatag ctgacgttca gcgggtaacc acaagttacg tggatcatan 78300
tctccattaa catcaaagaa tttaaatatc atagagttgg aaccggtttt gatggatcag 78360
caattantgc agattcntct acataaacca ttgcnaagtt ttcaccttct ttacgaatac 78420
cagtagaagg tgttttcgat ggatcataac gataattggc actgctgtcc agctgttaaa 78480
taagttgggc cagttaatgc attgggtttt ggatgaggaa tatcaatttt agtaatacaa 78540
tattgaccag tacgaaactc acgcattata ttaacctctt aatgaataac tgttgcagaa 78600
ggacgacatt tcatagtttt aaaaatgtca gtaggataga tattaccagc ttgtccgaaa 78660
ggtttatcgg ctagaagaaa ctgcggacaa actgtttgta gataaccact atcagtgggt 78720
aggaatcctt caatatcact gatgagaatt tgccagatgg gcaattggtt ataatagtca 78780
tccatattgt agtatgcgtg gagtttacca ccgaacccat atacaaactg atgagtatca 78840
attagacgaa taccaaattt aggttgtcgt cccatcctt 78879

<210> SEQ ID NO 2
<211> LENGTH: 1374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
ttaattgatg aacgttatcc agatattgta acggattaaa atacttacag ctatctagta 60
tgtaactagg cggattgcca tttgtaaatt atctatttaa tcgaactgag gaaatactaa 120
tgaaacaatt ctttcaacta cttctaagcc tacttttcaa actaccggtt ctatcatatt 180
ttgctgagaa gaaacgatta gagaaagaga aaaaggaaga agaaaagcgt cagcaagaac 240
aacgtcaaaa agaactactt gatgaacaac gtcgcgaaca agaagatcat tatcgaaaaa 300
ccgcttacga tcgcctagca aaacttattc atactcggtg gtatgatgag tttaatgcat 360
acgaaaagaa actagttgat cttgctgtat cgagtggtaa agcagttagt gttaagtatg 420
gtaaagttac taagatgcag caccctcatc aatttaaact acttaatgat tggctggatg 480
atattccagt agaagattat tctaagtgaa gaggagatat acaatggtct tcacactcga 540
agatttcgtt ggggactggc gacagacagc cggctacaac ctggaccaag tccttgaaca 600
gggaggtgtg tccagtttgt ttcagaatct cggggtgtcc gtaactccga tccaaaggat 660

-continued

```
tgtcctgagc ggtgaaaatg ggctgaagat cgacatccat gtcatcatcc cgtatgaagg    720

tctgagcggc gaccaaatgg gccagatcga aaaaattttt aaggtggtgt accctgtgga    780

tgatcatcac tttaaggtga tcctgcacta tggcacactg gtaatcgacg gggttacgcc    840

gaacatgatc gactatttcg gacggccgta tgaaggcatc gccgtgttcg acggcaaaaa    900

gatcactgta acagggaccc tgtggaacgg caacaaaatt atcgacgagc gcctgatcaa    960

ccccgacggc tccctgctgt tccgagtaac catcaacgga gtgaccggct ggcggctgtg   1020

cgaacgcatt ctggcgtaag tttaaataaa agaaaataaa gacgaagttt ttctttacat   1080

ggagaggggt ttatgccgta attatacact tactttgata agatttttaa tatcagtaaa   1140

atgggtatat gttgcctttt tatctttgtg aaccagtaag caacaggttc cttcatttac   1200

ggtattggtt tgttttaatg ggatatttaa agcatattca aacagatcat ccatccagtt   1260

aaatgccatg aacttattga taaggacatg atcgaaatca attaattcaa taaacgaatc   1320

gatctcagat tgataatact ctacaaccat tttagaccat tctttgttta tcgc         1374
```

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
ttctaagtga agaggagata tacaatggtc ttca 34

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
cgcattctgg cgtaagttta aataaaag 28

<210> SEQ ID NO 5
<211> LENGTH: 20
<212> TYPE: DNA
<213> ORGANISM: Pseudomonas phage B11

<400> SEQUENCE: 5
agaagatcat tatcgaaaga 20

<210> SEQ ID NO 6
<211> LENGTH: 20
<212> TYPE: DNA
<213> ORGANISM: Pseudomonas phage B11

<400> SEQUENCE: 6
agacatagcc cctctccaca 20

<210> SEQ ID NO 7
<211> LENGTH: 103
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 7
agaagaucau uaucgaaaga guuuuagagc uagaaauagc aaguuaaaau aaggcuaguc 60
cguuaucaac uugaaaaagu ggcaccgagu cggugcuuuu uuu 103

<210> SEQ ID NO 8
<211> LENGTH: 103
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 8
agacauagcc ccucuccaca guuuuagagc uagaaauagc aaguuaaaau aaggcuaguc 60
cguuaucaac uugaaaaagu ggcaccgagu cggugcuuuu uuu 103

<210> SEQ ID NO 9
<211> LENGTH: 23
<212> TYPE: DNA
<213> ORGANISM: Pseudomonas phage B11

<400> SEQUENCE: 9
agaagatcat tatcgaaaga cgg 23

<210> SEQ ID NO 10
<211> LENGTH: 23
<212> TYPE: DNA
<213> ORGANISM: Pseudomonas phage B11

<400> SEQUENCE: 10
agacatagcc cctctccaca tgg 23

<210> SEQ ID NO 11
<211> LENGTH: 272
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
agcagtggta aggtctctta acagaagatc attatcgaaa gagttttaga gctagaaata 60
gcaagttaaa ataaggctag tccgttatca acttgaaaaa gtggcaccga gtcggtgctt 120
tttttgctaa ctgataccga ctacgcctga acagtcgaat cttcacctcg tctggtaccg 180
acgcggtccc aaatattgac aacataaaaa actttgtgtt atacttgtaa cagacatagc 240
ccctctccac agttttgaga ccagctcgta gg 272

<210> SEQ ID NO 12
<211> LENGTH: 79409
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (203)..(203)
<223> OTHER INFORMATION: a, c, t, g, unknown or other
<220> FEATURE:
<221> NAME/KEY: modified_base
<222> LOCATION: (212)..(212)
<223> OTHER INFORMATION: a, c, t, g, unknown or other
<220> FEATURE:

<221> NAME/KEY: modified_base
<222> LOCATION: (223)..(224)
<223> OTHER INFORMATION: a, c, t, g, unknown or other
<220> FEATURE:
<221> NAME/KEY: modified_base
<222> LOCATION: (226)..(226)
<223> OTHER INFORMATION: a, c, t, g, unknown or other
<220> FEATURE:
<221> NAME/KEY: modified_base
<222> LOCATION: (236)..(238)
<223> OTHER INFORMATION: a, c, t, g, unknown or other
<220> FEATURE:
<221> NAME/KEY: modified_base
<222> LOCATION: (242)..(242)
<223> OTHER INFORMATION: a, c, t, g, unknown or other
<220> FEATURE:
<221> NAME/KEY: modified_base
<222> LOCATION: (244)..(244)
<223> OTHER INFORMATION: a, c, t, g, unknown or other
<220> FEATURE:
<221> NAME/KEY: modified_base
<222> LOCATION: (250)..(251)
<223> OTHER INFORMATION: a, c, t, g, unknown or other
<220> FEATURE:
<221> NAME/KEY: modified_base
<222> LOCATION: (256)..(256)
<223> OTHER INFORMATION: a, c, t, g, unknown or other
<220> FEATURE:
<221> NAME/KEY: modified_base
<222> LOCATION: (281)..(281)
<223> OTHER INFORMATION: a, c, t, g, unknown or other
<220> FEATURE:
<221> NAME/KEY: modified_base
<222> LOCATION: (285)..(285)
<223> OTHER INFORMATION: a, c, t, g, unknown or other
<220> FEATURE:
<221> NAME/KEY: modified_base
<222> LOCATION: (293)..(293)
<223> OTHER INFORMATION: a, c, t, g, unknown or other
<220> FEATURE:
<221> NAME/KEY: modified_base
<222> LOCATION: (311)..(311)
<223> OTHER INFORMATION: a, c, t, g, unknown or other
<220> FEATURE:
<221> NAME/KEY: modified_base
<222> LOCATION: (419)..(419)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (509)..(509)
<223> OTHER INFORMATION: a, c, t, g, unknown or other
<220> FEATURE:
<221> NAME/KEY: modified_base
<222> LOCATION: (513)..(513)
<223> OTHER INFORMATION: a, c, t, g, unknown or other
<220> FEATURE:
<221> NAME/KEY: modified_base
<222> LOCATION: (522)..(522)
<223> OTHER INFORMATION: a, c, t, g, unknown or other
<220> FEATURE:
<221> NAME/KEY: modified_base
<222> LOCATION: (531)..(531)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (564)..(564)
<223> OTHER INFORMATION: a, c, t, g, unknown or other
<220> FEATURE:
<221> NAME/KEY: modified_base
<222> LOCATION: (569)..(570)
<223> OTHER INFORMATION: a, c, t, g, unknown or other
<220> FEATURE:
<221> NAME/KEY: modified_base
<222> LOCATION: (579)..(579)
<223> OTHER INFORMATION: a, c, t, g, unknown or other
<220> FEATURE:
<221> NAME/KEY: modified_base
<222> LOCATION: (594)..(594)
<223> OTHER INFORMATION: a, c, t, g, unknown or other
<220> FEATURE:
<221> NAME/KEY: modified_base
<222> LOCATION: (621)..(621)
<223> OTHER INFORMATION: a, c, t, g, unknown or other
<220> FEATURE:
<221> NAME/KEY: modified_base
<222> LOCATION: (648)..(648)
<223> OTHER INFORMATION: a, c, t, g, unknown or other
<220> FEATURE:
<221> NAME/KEY: modified_base
<222> LOCATION: (3627)..(3627)
<223> OTHER INFORMATION: a, c, t, g, unknown or other
<220> FEATURE:
<221> NAME/KEY: modified_base
<222> LOCATION: (3636)..(3636)
<223> OTHER INFORMATION: a, c, t, g, unknown or other
<220> FEATURE:
<221> NAME/KEY: modified_base
<222> LOCATION: (3639)..(3639)
<223> OTHER INFORMATION: a, c, t, g, unknown or other
<220> FEATURE:
<221> NAME/KEY: modified_base
<222> LOCATION: (3642)..(3642)
<223> OTHER INFORMATION: a, c, t, g, unknown or other
<220> FEATURE:
<221> NAME/KEY: modified_base
<222> LOCATION: (3675)..(3675)
<223> OTHER INFORMATION: a, c, t, g, unknown or other
<220> FEATURE:
<221> NAME/KEY: modified_base
<222> LOCATION: (3681)..(3681)
<223> OTHER INFORMATION: a, c, t, g, unknown or other
<220> FEATURE:
<221> NAME/KEY: modified_base
<222> LOCATION: (3684)..(3684)
<223> OTHER INFORMATION: a, c, t, g, unknown or other
<220> FEATURE:
<221> NAME/KEY: modified_base
<222> LOCATION: (3692)..(3692)
<223> OTHER INFORMATION: a, c, t, g, unknown or other
<220> FEATURE:
<221> NAME/KEY: modified_base
<222> LOCATION: (4080)..(4080)
<223> OTHER INFORMATION: a, c, t, g, unknown or other
<220> FEATURE:
<221> NAME/KEY: modified_base
<222> LOCATION: (4182)..(4182)
<223> OTHER INFORMATION: a, c, t, g, unknown or other
<220> FEATURE:
<221> NAME/KEY: modified_base
<222> LOCATION: (4212)..(4212)
<223> OTHER INFORMATION: a, c, t, g, unknown or other
<220> FEATURE:
<221> NAME/KEY: modified_base
<222> LOCATION: (4314)..(4314)
<223> OTHER INFORMATION: a, c, t, g, unknown or other
<220> FEATURE:
<221> NAME/KEY: modified_base
<222> LOCATION: (4323)..(4323)
<223> OTHER INFORMATION: a, c, t, g, unknown or other
<220> FEATURE:
<221> NAME/KEY: modified_base
<222> LOCATION: (5079)..(5079)
<223> OTHER INFORMATION: a, c, t, g, unknown or other
<220> FEATURE:
<221> NAME/KEY: modified_base
<222> LOCATION: (5190)..(5190)

<223> OTHER INFORMATION: a, c, t, g, unknown or other
<220> FEATURE:
<221> NAME/KEY: modified_base
<222> LOCATION: (6180)..(6180)
<223> OTHER INFORMATION: a, c, t, g, unknown or other
<220> FEATURE:
<221> NAME/KEY: modified_base
<222> LOCATION: (6252)..(6252)
<223> OTHER INFORMATION: a, c, t, g, unknown or other
<220> FEATURE:
<221> NAME/KEY: modified_base
<222> LOCATION: (6273)..(6273)
<223> OTHER INFORMATION: a, c, t, g, unknown or other
<220> FEATURE:
<221> NAME/KEY: modified_base
<222> LOCATION: (6279)..(6279)
<223> OTHER INFORMATION: a, c, t, g, unknown or other
<220> FEATURE:
<221> NAME/KEY: modified_base
<222> LOCATION: (6612)..(6612)
<223> OTHER INFORMATION: a, c, t, g, unknown or other
<220> FEATURE:
<221> NAME/KEY: modified_base
<222> LOCATION: (6621)..(6621)
<223> OTHER INFORMATION: a, c, t, g, unknown or other
<220> FEATURE:
<221> NAME/KEY: modified_base
<222> LOCATION: (6627)..(6627)
<223> OTHER INFORMATION: a, c, t, g, unknown or other
<220> FEATURE:
<221> NAME/KEY: modified_base
<222> LOCATION: (6783)..(6783)
<223> OTHER INFORMATION: a, c, t, g, unknown or other
<220> FEATURE:
<221> NAME/KEY: modified_base
<222> LOCATION: (6792)..(6792)
<223> OTHER INFORMATION: a, c, t, g, unknown or other
<220> FEATURE:
<221> NAME/KEY: modified_base
<222> LOCATION: (6800)..(6801)
<223> OTHER INFORMATION: a, c, t, g, unknown or other
<220> FEATURE:
<221> NAME/KEY: modified_base
<222> LOCATION: (6819)..(6819)
<223> OTHER INFORMATION: a, c, t, g, unknown or other
<220> FEATURE:
<221> NAME/KEY: modified_base
<222> LOCATION: (6840)..(6840)
<223> OTHER INFORMATION: a, c, t, g, unknown or other
<220> FEATURE:
<221> NAME/KEY: modified_base
<222> LOCATION: (6846)..(6846)
<223> OTHER INFORMATION: a, c, t, g, unknown or other
<220> FEATURE:
<221> NAME/KEY: modified_base
<222> LOCATION: (6945)..(6945)
<223> OTHER INFORMATION: a, c, t, g, unknown or other
<220> FEATURE:
<221> NAME/KEY: modified_base
<222> LOCATION: (9573)..(9573)
<223> OTHER INFORMATION: a, c, t, g, unknown or other
<220> FEATURE:
<221> NAME/KEY: modified_base
<222> LOCATION: (9576)..(9576)
<223> OTHER INFORMATION: a, c, t, g, unknown or other
<220> FEATURE:
<221> NAME/KEY: modified_base
<222> LOCATION: (9578)..(9578)
<223> OTHER INFORMATION: a, c, t, g, unknown or other
<220> FEATURE:
<221> NAME/KEY: modified_base
<222> LOCATION: (9582)..(9583)
<223> OTHER INFORMATION: a, c, t, g, unknown or other
<220> FEATURE:
<221> NAME/KEY: modified_base
<222> LOCATION: (9603)..(9603)
<223> OTHER INFORMATION: a, c, t, g, unknown or other
<220> FEATURE:
<221> NAME/KEY: modified_base
<222> LOCATION: (9606)..(9606)
<223> OTHER INFORMATION: a, c, t, g, unknown or other
<220> FEATURE:
<221> NAME/KEY: modified_base
<222> LOCATION: (9609)..(9609)
<223> OTHER INFORMATION: a, c, t, g, unknown or other
<220> FEATURE:
<221> NAME/KEY: modified_base
<222> LOCATION: (9661)..(9661)
<223> OTHER INFORMATION: a, c, t, g, unknown or other
<220> FEATURE:
<221> NAME/KEY: modified_base
<222> LOCATION: (9854)..(9854)
<223> OTHER INFORMATION: a, c, t, g, unknown or other
<220> FEATURE:
<221> NAME/KEY: modified_base
<222> LOCATION: (10379)..(10379)
<223> OTHER INFORMATION: a, c, t, g, unknown or other
<220> FEATURE:
<221> NAME/KEY: modified_base
<222> LOCATION: (10382)..(10382)
<223> OTHER INFORMATION: a, c, t, g, unknown or other
<220> FEATURE:
<221> NAME/KEY: modified_base
<222> LOCATION: (10385)..(10385)
<223> OTHER INFORMATION: a, c, t, g, unknown or other
<220> FEATURE:
<221> NAME/KEY: modified_base
<222> LOCATION: (10388)..(10388)
<223> OTHER INFORMATION: a, c, t, g, unknown or other
<220> FEATURE:
<221> NAME/KEY: modified_base
<222> LOCATION: (10397)..(10397)
<223> OTHER INFORMATION: a, c, t, g, unknown or other
<220> FEATURE:
<221> NAME/KEY: modified_base
<222> LOCATION: (10400)..(10400)
<223> OTHER INFORMATION: a, c, t, g, unknown or other
<220> FEATURE:
<221> NAME/KEY: modified_base
<222> LOCATION: (10403)..(10403)
<223> OTHER INFORMATION: a, c, t, g, unknown or other
<220> FEATURE:
<221> NAME/KEY: modified_base
<222> LOCATION: (10415)..(10415)
<223> OTHER INFORMATION: a, c, t, g, unknown or other
<220> FEATURE:
<221> NAME/KEY: modified_base
<222> LOCATION: (10488)..(10488)
<223> OTHER INFORMATION: a, c, t, g, unknown or other
<220> FEATURE:
<221> NAME/KEY: modified_base
<222> LOCATION: (10556)..(10556)
<223> OTHER INFORMATION: a, c, t, g, unknown or other
<220> FEATURE:
<221> NAME/KEY: modified_base
<222> LOCATION: (10580)..(10580)
<223> OTHER INFORMATION: a, c, t, g, unknown or other
<220> FEATURE:
<221> NAME/KEY: modified_base
<222> LOCATION: (10598)..(10598)
<223> OTHER INFORMATION: a, c, t, g, unknown or other
<220> FEATURE:
<221> NAME/KEY: modified_base
<222> LOCATION: (10610)..(10610)
<223> OTHER INFORMATION: a, c, t, g, unknown or other
<220> FEATURE:
<221> NAME/KEY: modified_base
<222> LOCATION: (10835)..(10835)
<223> OTHER INFORMATION: a, c, t, g, unknown or other
<220> FEATURE:
<221> NAME/KEY: modified_base
<222> LOCATION: (10837)..(10837)
<223> OTHER INFORMATION: a, c, t, g, unknown or other
<220> FEATURE:
<221> NAME/KEY: modified_base
<222> LOCATION: (10850)..(10850)
<223> OTHER INFORMATION: a, c, t, g, unknown or other
<220> FEATURE:

<221> NAME/KEY: modified_base
<222> LOCATION: (10853)..(10853)
<223> OTHER INFORMATION: a, c, t, g, unknown or other
<220> FEATURE:
<221> NAME/KEY: modified_base
<222> LOCATION: (10913)..(10913)
<223> OTHER INFORMATION: a, c, t, g, unknown or other
<220> FEATURE:
<221> NAME/KEY: modified_base
<222> LOCATION: (11051)..(11051)
<223> OTHER INFORMATION: a, c, t, g, unknown or other
<220> FEATURE:
<221> NAME/KEY: modified_base
<222> LOCATION: (11108)..(11108)
<223> OTHER INFORMATION: a, c, t, g, unknown or other
<220> FEATURE:
<221> NAME/KEY: modified_base
<222> LOCATION: (11117)..(11117)
<223> OTHER INFORMATION: a, c, t, g, unknown or other
<220> FEATURE:
<221> NAME/KEY: modified_base
<222> LOCATION: (11244)..(11244)
<223> OTHER INFORMATION: a, c, t, g, unknown or other
<220> FEATURE:
<221> NAME/KEY: modified_base
<222> LOCATION: (11246)..(11246)
<223> OTHER INFORMATION: a, c, t, g, unknown or other
<220> FEATURE:
<221> NAME/KEY: modified_base
<222> LOCATION: (11450)..(11450)
<223> OTHER INFORMATION: a, c, t, g, unknown or other
<220> FEATURE:
<221> NAME/KEY: modified_base
<222> LOCATION: (11453)..(11453)
<223> OTHER INFORMATION: a, c, t, g, unknown or other
<220> FEATURE:
<221> NAME/KEY: modified_base
<222> LOCATION: (11549)..(11549)
<223> OTHER INFORMATION: a, c, t, g, unknown or other
<220> FEATURE:
<221> NAME/KEY: modified_base
<222> LOCATION: (11585)..(11585)
<223> OTHER INFORMATION: a, c, t, g, unknown or other
<220> FEATURE:
<221> NAME/KEY: modified_base
<222> LOCATION: (11606)..(11606)
<223> OTHER INFORMATION: a, c, t, g, unknown or other
<220> FEATURE:
<221> NAME/KEY: modified_base
<222> LOCATION: (12014)..(12014)
<223> OTHER INFORMATION: a, c, t, g, unknown or other
<220> FEATURE:
<221> NAME/KEY: modified_base
<222> LOCATION: (12058)..(12058)
<223> OTHER INFORMATION: a, c, t, g, unknown or other
<220> FEATURE:
<221> NAME/KEY: modified_base
<222> LOCATION: (12112)..(12112)
<223> OTHER INFORMATION: a, c, t, g, unknown or other
<220> FEATURE:
<221> NAME/KEY: modified_base
<222> LOCATION: (12125)..(12125)
<223> OTHER INFORMATION: a, c, t, g, unknown or other
<220> FEATURE:
<221> NAME/KEY: modified_base
<222> LOCATION: (12145)..(12145)
<223> OTHER INFORMATION: a, c, t, g, unknown or other
<220> FEATURE:
<221> NAME/KEY: modified_base
<222> LOCATION: (12200)..(12200)
<223> OTHER INFORMATION: a, c, t, g, unknown or other
<220> FEATURE:
<221> NAME/KEY: modified_base
<222> LOCATION: (12262)..(12262)
<223> OTHER INFORMATION: a, c, t, g, unknown or other
<220> FEATURE:
<221> NAME/KEY: modified_base
<222> LOCATION: (12266)..(12266)
<223> OTHER INFORMATION: a, c, t, g, unknown or other -continued
<220> FEATURE:
<221> NAME/KEY: modified_base
<222> LOCATION: (12308)..(12308)
<223> OTHER INFORMATION: a, c, t, g, unknown or other
<220> FEATURE:
<221> NAME/KEY: modified_base
<222> LOCATION: (12311)..(12311)
<223> OTHER INFORMATION: a, c, t, g, unknown or other
<220> FEATURE:
<221> NAME/KEY: modified_base
<222> LOCATION: (12356)..(12356)
<223> OTHER INFORMATION: a, c, t, g, unknown or other
<220> FEATURE:
<221> NAME/KEY: modified_base
<222> LOCATION: (12389)..(12389)
<223> OTHER INFORMATION: a, c, t, g, unknown or other
<220> FEATURE:
<221> NAME/KEY: modified_base
<222> LOCATION: (12422)..(12422)
<223> OTHER INFORMATION: a, c, t, g, unknown or other
<220> FEATURE:
<221> NAME/KEY: modified_base
<222> LOCATION: (12630)..(12630)
<223> OTHER INFORMATION: a, c, t, g, unknown or other
<220> FEATURE:
<221> NAME/KEY: modified_base
<222> LOCATION: (12663)..(12663)
<223> OTHER INFORMATION: a, c, t, g, unknown or other
<220> FEATURE:
<221> NAME/KEY: modified_base
<222> LOCATION: (12674)..(12674)
<223> OTHER INFORMATION: a, c, t, g, unknown or other
<220> FEATURE:
<221> NAME/KEY: modified_base
<222> LOCATION: (12686)..(12686)
<223> OTHER INFORMATION: a, c, t, g, unknown or other
<220> FEATURE:
<221> NAME/KEY: modified_base
<222> LOCATION: (12693)..(12693)
<223> OTHER INFORMATION: a, c, t, g, unknown or other
<220> FEATURE:
<221> NAME/KEY: modified_base
<222> LOCATION: (12723)..(12723)
<223> OTHER INFORMATION: a, c, t, g, unknown or other
<220> FEATURE:
<221> NAME/KEY: modified_base
<222> LOCATION: (12777)..(12777)
<223> OTHER INFORMATION: a, c, t, g, unknown or other
<220> FEATURE:
<221> NAME/KEY: modified_base
<222> LOCATION: (12822)..(12822)
<223> OTHER INFORMATION: a, c, t, g, unknown or other
<220> FEATURE:
<221> NAME/KEY: modified_base
<222> LOCATION: (14712)..(14712)
<223> OTHER INFORMATION: a, c, t, g, unknown or other
<220> FEATURE:
<221> NAME/KEY: modified_base
<222> LOCATION: (14904)..(14904)
<223> OTHER INFORMATION: a, c, t, g, unknown or other
<220> FEATURE:
<221> NAME/KEY: modified_base
<222> LOCATION: (14906)..(14906)
<223> OTHER INFORMATION: a, c, t, g, unknown or other
<220> FEATURE:
<221> NAME/KEY: modified_base
<222> LOCATION: (14910)..(14910)
<223> OTHER INFORMATION: a, c, t, g, unknown or other
<220> FEATURE:
<221> NAME/KEY: modified_base
<222> LOCATION: (14916)..(14916)
<223> OTHER INFORMATION: a, c, t, g, unknown or other
<220> FEATURE:
<221> NAME/KEY: modified_base
<222> LOCATION: (15003)..(15003)
<223> OTHER INFORMATION: a, c, t, g, unknown or other
<220> FEATURE:
<221> NAME/KEY: modified_base
<222> LOCATION: (15088)..(15088)

<223> OTHER INFORMATION: a, c, t, g, unknown or other
<220> FEATURE:
<221> NAME/KEY: modified_base
<222> LOCATION: (15091)..(15091)
<223> OTHER INFORMATION: a, c, t, g, unknown or other
<220> FEATURE:
<221> NAME/KEY: modified_base
<222> LOCATION: (15102)..(15102)
<223> OTHER INFORMATION: a, c, t, g, unknown or other
<220> FEATURE:
<221> NAME/KEY: modified_base
<222> LOCATION: (15105)..(15105)
<223> OTHER INFORMATION: a, c, t, g, unknown or other
<220> FEATURE:
<221> NAME/KEY: modified_base
<222> LOCATION: (15108)..(15108)
<223> OTHER INFORMATION: a, c, t, g, unknown or other
<220> FEATURE:
<221> NAME/KEY: modified_base
<222> LOCATION: (15180)..(15180)
<223> OTHER INFORMATION: a, c, t, g, unknown or other
<220> FEATURE:
<221> NAME/KEY: modified_base
<222> LOCATION: (16845)..(16845)
<223> OTHER INFORMATION: a, c, t, g, unknown or other
<220> FEATURE:
<221> NAME/KEY: modified_base
<222> LOCATION: (16852)..(16852)
<223> OTHER INFORMATION: a, c, t, g, unknown or other
<220> FEATURE:
<221> NAME/KEY: modified_base
<222> LOCATION: (17294)..(17294)
<223> OTHER INFORMATION: a, c, t, g, unknown or other
<220> FEATURE:
<221> NAME/KEY: modified_base
<222> LOCATION: (17399)..(17399)
<223> OTHER INFORMATION: a, c, t, g, unknown or other
<220> FEATURE:
<221> NAME/KEY: modified_base
<222> LOCATION: (17648)..(17648)
<223> OTHER INFORMATION: a, c, t, g, unknown or other
<220> FEATURE:
<221> NAME/KEY: modified_base
<222> LOCATION: (17673)..(17674)
<223> OTHER INFORMATION: a, c, t, g, unknown or other
<220> FEATURE:
<221> NAME/KEY: modified_base
<222> LOCATION: (17982)..(17983)
<223> OTHER INFORMATION: a, c, t, g, unknown or other
<220> FEATURE:
<221> NAME/KEY: modified_base
<222> LOCATION: (17993)..(17993)
<223> OTHER INFORMATION: a, c, t, g, unknown or other
<220> FEATURE:
<221> NAME/KEY: modified_base
<222> LOCATION: (18008)..(18008)
<223> OTHER INFORMATION: a, c, t, g, unknown or other
<220> FEATURE:
<221> NAME/KEY: modified_base
<222> LOCATION: (18020)..(18020)
<223> OTHER INFORMATION: a, c, t, g, unknown or other
<220> FEATURE:
<221> NAME/KEY: modified_base
<222> LOCATION: (18029)..(18029)
<223> OTHER INFORMATION: a, c, t, g, unknown or other
<220> FEATURE:
<221> NAME/KEY: modified_base
<222> LOCATION: (18041)..(18041)
<223> OTHER INFORMATION: a, c, t, g, unknown or other
<220> FEATURE:
<221> NAME/KEY: modified_base
<222> LOCATION: (18110)..(18111)
<223> OTHER INFORMATION: a, c, t, g, unknown or other
<220> FEATURE:
<221> NAME/KEY: modified_base
<222> LOCATION: (18309)..(18309)
<223> OTHER INFORMATION: a, c, t, g, unknown or other
<220> FEATURE:
<221> NAME/KEY: modified_base
<222> LOCATION: (18401)..(18401)
<223> OTHER INFORMATION: a, c, t, g, unknown or other
<220> FEATURE:
<221> NAME/KEY: modified_base
<222> LOCATION: (18405)..(18405)
<223> OTHER INFORMATION: a, c, t, g, unknown or other
<220> FEATURE:
<221> NAME/KEY: modified_base
<222> LOCATION: (18450)..(18450)
<223> OTHER INFORMATION: a, c, t, g, unknown or other
<220> FEATURE:
<221> NAME/KEY: modified_base
<222> LOCATION: (18458)..(18458)
<223> OTHER INFORMATION: a, c, t, g, unknown or other
<220> FEATURE:
<221> NAME/KEY: modified_base
<222> LOCATION: (18574)..(18574)
<223> OTHER INFORMATION: a, c, t, g, unknown or other
<220> FEATURE:
<221> NAME/KEY: modified_base
<222> LOCATION: (18641)..(18641)
<223> OTHER INFORMATION: a, c, t, g, unknown or other
<220> FEATURE:
<221> NAME/KEY: modified_base
<222> LOCATION: (18740)..(18740)
<223> OTHER INFORMATION: a, c, t, g, unknown or other
<220> FEATURE:
<221> NAME/KEY: modified_base
<222> LOCATION: (18779)..(18779)
<223> OTHER INFORMATION: a, c, t, g, unknown or other
<220> FEATURE:
<221> NAME/KEY: modified_base
<222> LOCATION: (18881)..(18881)
<223> OTHER INFORMATION: a, c, t, g, unknown or other
<220> FEATURE:
<221> NAME/KEY: modified_base
<222> LOCATION: (19177)..(19177)
<223> OTHER INFORMATION: a, c, t, g, unknown or other
<220> FEATURE:
<221> NAME/KEY: modified_base
<222> LOCATION: (19326)..(19326)
<223> OTHER INFORMATION: a, c, t, g, unknown or other
<220> FEATURE:
<221> NAME/KEY: modified_base
<222> LOCATION: (19349)..(19349)
<223> OTHER INFORMATION: a, c, t, g, unknown or other
<220> FEATURE:
<221> NAME/KEY: modified_base
<222> LOCATION: (19370)..(19370)
<223> OTHER INFORMATION: a, c, t, g, unknown or other
<220> FEATURE:
<221> NAME/KEY: modified_base
<222> LOCATION: (19616)..(19616)
<223> OTHER INFORMATION: a, c, t, g, unknown or other
<220> FEATURE:
<221> NAME/KEY: modified_base
<222> LOCATION: (19732)..(19732)
<223> OTHER INFORMATION: a, c, t, g, unknown or other
<220> FEATURE:
<221> NAME/KEY: modified_base
<222> LOCATION: (19749)..(19749)
<223> OTHER INFORMATION: a, c, t, g, unknown or other
<220> FEATURE:
<221> NAME/KEY: modified_base
<222> LOCATION: (19756)..(19756)
<223> OTHER INFORMATION: a, c, t, g, unknown or other
<220> FEATURE:
<221> NAME/KEY: modified_base
<222> LOCATION: (19758)..(19758)
<223> OTHER INFORMATION: a, c, t, g, unknown or other
<220> FEATURE:
<221> NAME/KEY: modified_base
<222> LOCATION: (19760)..(19760)
<223> OTHER INFORMATION: a, c, t, g, unknown or other
<220> FEATURE:
<221> NAME/KEY: modified_base
<222> LOCATION: (20043)..(20043)
<223> OTHER INFORMATION: a, c, t, g, unknown or other
<220> FEATURE:

<221> NAME/KEY: modified_base
<222> LOCATION: (20053)..(20053)
<223> OTHER INFORMATION: a, c, t, g, unknown or other
<220> FEATURE:
<221> NAME/KEY: modified_base
<222> LOCATION: (20085)..(20085)
<223> OTHER INFORMATION: a, c, t, g, unknown or other
<220> FEATURE:
<221> NAME/KEY: modified_base
<222> LOCATION: (20152)..(20152)
<223> OTHER INFORMATION: a, c, t, g, unknown or other
<220> FEATURE:
<221> NAME/KEY: modified_base
<222> LOCATION: (20170)..(20170)
<223> OTHER INFORMATION: a, c, t, g, unknown or other
<220> FEATURE:
<221> NAME/KEY: modified_base
<222> LOCATION: (20176)..(20176)
<223> OTHER INFORMATION: a, c, t, g, unknown or other
<220> FEATURE:
<221> NAME/KEY: modified_base
<222> LOCATION: (20251)..(20251)
<223> OTHER INFORMATION: a, c, t, g, unknown or other
<220> FEATURE:
<221> NAME/KEY: modified_base
<222> LOCATION: (20257)..(20257)
<223> OTHER INFORMATION: a, c, t, g, unknown or other
<220> FEATURE:
<221> NAME/KEY: modified_base
<222> LOCATION: (20269)..(20269)
<223> OTHER INFORMATION: a, c, t, g, unknown or other
<220> FEATURE:
<221> NAME/KEY: modified_base
<222> LOCATION: (20296)..(20296)
<223> OTHER INFORMATION: a, c, t, g, unknown or other
<220> FEATURE:
<221> NAME/KEY: modified_base
<222> LOCATION: (20299)..(20299)
<223> OTHER INFORMATION: a, c, t, g, unknown or other
<220> FEATURE:
<221> NAME/KEY: modified_base
<222> LOCATION: (20302)..(20302)
<223> OTHER INFORMATION: a, c, t, g, unknown or other
<220> FEATURE:
<221> NAME/KEY: modified_base
<222> LOCATION: (20305)..(20305)
<223> OTHER INFORMATION: a, c, t, g, unknown or other
<220> FEATURE:
<221> NAME/KEY: modified_base
<222> LOCATION: (20313)..(20313)
<223> OTHER INFORMATION: a, c, t, g, unknown or other
<220> FEATURE:
<221> NAME/KEY: modified_base
<222> LOCATION: (20416)..(20416)
<223> OTHER INFORMATION: a, c, t, g, unknown or other
<220> FEATURE:
<221> NAME/KEY: modified_base
<222> LOCATION: (20488)..(20488)
<223> OTHER INFORMATION: a, c, t, g, unknown or other
<220> FEATURE:
<221> NAME/KEY: modified_base
<222> LOCATION: (21006)..(21006)
<223> OTHER INFORMATION: a, c, t, g, unknown or other
<220> FEATURE:
<221> NAME/KEY: modified_base
<222> LOCATION: (21012)..(21012)
<223> OTHER INFORMATION: a, c, t, g, unknown or other
<220> FEATURE:
<221> NAME/KEY: modified_base
<222> LOCATION: (21019)..(21019)
<223> OTHER INFORMATION: a, c, t, g, unknown or other
<220> FEATURE:
<221> NAME/KEY: modified_base
<222> LOCATION: (21024)..(21024)
<223> OTHER INFORMATION: a, c, t, g, unknown or other
<220> FEATURE:
<221> NAME/KEY: modified_base
<222> LOCATION: (21173)..(21173)
<223> OTHER INFORMATION: a, c, t, g, unknown or other
<220> FEATURE:
<221> NAME/KEY: modified_base
<222> LOCATION: (21175)..(21175)
<223> OTHER INFORMATION: a, c, t, g, unknown or other
<220> FEATURE:
<221> NAME/KEY: modified_base
<222> LOCATION: (21182)..(21182)
<223> OTHER INFORMATION: a, c, t, g, unknown or other
<220> FEATURE:
<221> NAME/KEY: modified_base
<222> LOCATION: (21184)..(21184)
<223> OTHER INFORMATION: a, c, t, g, unknown or other
<220> FEATURE:
<221> NAME/KEY: modified_base
<222> LOCATION: (21423)..(21423)
<223> OTHER INFORMATION: a, c, t, g, unknown or other
<220> FEATURE:
<221> NAME/KEY: modified_base
<222> LOCATION: (21425)..(21429)
<223> OTHER INFORMATION: a, c, t, g, unknown or other
<220> FEATURE:
<221> NAME/KEY: modified_base
<222> LOCATION: (21432)..(21432)
<223> OTHER INFORMATION: a, c, t, g, unknown or other
<220> FEATURE:
<221> NAME/KEY: modified_base
<222> LOCATION: (21435)..(21435)
<223> OTHER INFORMATION: a, c, t, g, unknown or other
<220> FEATURE:
<221> NAME/KEY: modified_base
<222> LOCATION: (21440)..(21440)
<223> OTHER INFORMATION: a, c, t, g, unknown or other
<220> FEATURE:
<221> NAME/KEY: modified_base
<222> LOCATION: (21454)..(21454)
<223> OTHER INFORMATION: a, c, t, g, unknown or other
<220> FEATURE:
<221> NAME/KEY: modified_base
<222> LOCATION: (21456)..(21457)
<223> OTHER INFORMATION: a, c, t, g, unknown or other
<220> FEATURE:
<221> NAME/KEY: modified_base
<222> LOCATION: (21471)..(21472)
<223> OTHER INFORMATION: a, c, t, g, unknown or other
<220> FEATURE:
<221> NAME/KEY: modified_base
<222> LOCATION: (21474)..(21474)
<223> OTHER INFORMATION: a, c, t, g, unknown or other
<220> FEATURE:
<221> NAME/KEY: modified_base
<222> LOCATION: (21478)..(21478)
<223> OTHER INFORMATION: a, c, t, g, unknown or other
<220> FEATURE:
<221> NAME/KEY: modified_base
<222> LOCATION: (21496)..(21496)
<223> OTHER INFORMATION: a, c, t, g, unknown or other
<220> FEATURE:
<221> NAME/KEY: modified_base
<222> LOCATION: (21517)..(21517)
<223> OTHER INFORMATION: a, c, t, g, unknown or other
<220> FEATURE:
<221> NAME/KEY: modified_base
<222> LOCATION: (21533)..(21534)
<223> OTHER INFORMATION: a, c, t, g, unknown or other
<220> FEATURE:
<221> NAME/KEY: modified_base
<222> LOCATION: (21544)..(21544)
<223> OTHER INFORMATION: a, c, t, g, unknown or other
<220> FEATURE:
<221> NAME/KEY: modified_base
<222> LOCATION: (21559)..(21559)
<223> OTHER INFORMATION: a, c, t, g, unknown or other
<220> FEATURE:
<221> NAME/KEY: modified_base
<222> LOCATION: (21570)..(21570)
<223> OTHER INFORMATION: a, c, t, g, unknown or other
<220> FEATURE:
<221> NAME/KEY: modified_base
<222> LOCATION: (21574)..(21574)

<223> OTHER INFORMATION: a, c, t, g, unknown or other
<220> FEATURE:
<221> NAME/KEY: modified_base
<222> LOCATION: (21583)..(21583)
<223> OTHER INFORMATION: a, c, t, g, unknown or other
<220> FEATURE:
<221> NAME/KEY: modified_base
<222> LOCATION: (21660)..(21660)
<223> OTHER INFORMATION: a, c, t, g, unknown or other
<220> FEATURE:
<221> NAME/KEY: modified_base
<222> LOCATION: (21684)..(21684)
<223> OTHER INFORMATION: a, c, t, g, unknown or other
<220> FEATURE:
<221> NAME/KEY: modified_base
<222> LOCATION: (21710)..(21710)
<223> OTHER INFORMATION: a, c, t, g, unknown or other
<220> FEATURE:
<221> NAME/KEY: modified_base
<222> LOCATION: (21778)..(21778)
<223> OTHER INFORMATION: a, c, t, g, unknown or other
<220> FEATURE:
<221> NAME/KEY: modified_base
<222> LOCATION: (21789)..(21789)
<223> OTHER INFORMATION: a, c, t, g, unknown or other
<220> FEATURE:
<221> NAME/KEY: modified_base
<222> LOCATION: (21798)..(21798)
<223> OTHER INFORMATION: a, c, t, g, unknown or other
<220> FEATURE:
<221> NAME/KEY: modified_base
<222> LOCATION: (21823)..(21823)
<223> OTHER INFORMATION: a, c, t, g, unknown or other
<220> FEATURE:
<221> NAME/KEY: modified_base
<222> LOCATION: (21874)..(21874)
<223> OTHER INFORMATION: a, c, t, g, unknown or other
<220> FEATURE:
<221> NAME/KEY: modified_base
<222> LOCATION: (21876)..(21876)
<223> OTHER INFORMATION: a, c, t, g, unknown or other
<220> FEATURE:
<221> NAME/KEY: modified_base
<222> LOCATION: (21880)..(21880)
<223> OTHER INFORMATION: a, c, t, g, unknown or other
<220> FEATURE:
<221> NAME/KEY: modified_base
<222> LOCATION: (21889)..(21889)
<223> OTHER INFORMATION: a, c, t, g, unknown or other
<220> FEATURE:
<221> NAME/KEY: modified_base
<222> LOCATION: (21894)..(21894)
<223> OTHER INFORMATION: a, c, t, g, unknown or other
<220> FEATURE:
<221> NAME/KEY: modified_base
<222> LOCATION: (22844)..(22844)
<223> OTHER INFORMATION: a, c, t, g, unknown or other
<220> FEATURE:
<221> NAME/KEY: modified_base
<222> LOCATION: (22907)..(22907)
<223> OTHER INFORMATION: a, c, t, g, unknown or other
<220> FEATURE:
<221> NAME/KEY: modified_base
<222> LOCATION: (22914)..(22914)
<223> OTHER INFORMATION: a, c, t, g, unknown or other
<220> FEATURE:
<221> NAME/KEY: modified_base
<222> LOCATION: (23167)..(23167)
<223> OTHER INFORMATION: a, c, t, g, unknown or other
<220> FEATURE:
<221> NAME/KEY: modified_base
<222> LOCATION: (23348)..(23348)
<223> OTHER INFORMATION: a, c, t, g, unknown or other
<220> FEATURE:
<221> NAME/KEY: modified_base
<222> LOCATION: (23351)..(23351)
<223> OTHER INFORMATION: a, c, t, g, unknown or other
<220> FEATURE:
<221> NAME/KEY: modified_base
<222> LOCATION: (23406)..(23406)
<223> OTHER INFORMATION: a, c, t, g, unknown or other
<220> FEATURE:
<221> NAME/KEY: modified_base
<222> LOCATION: (23647)..(23647)
<223> OTHER INFORMATION: a, c, t, g, unknown or other
<220> FEATURE:
<221> NAME/KEY: modified_base
<222> LOCATION: (23806)..(23806)
<223> OTHER INFORMATION: a, c, t, g, unknown or other
<220> FEATURE:
<221> NAME/KEY: modified_base
<222> LOCATION: (24617)..(24617)
<223> OTHER INFORMATION: a, c, t, g, unknown or other
<220> FEATURE:
<221> NAME/KEY: modified_base
<222> LOCATION: (24853)..(24853)
<223> OTHER INFORMATION: a, c, t, g, unknown or other
<220> FEATURE:
<221> NAME/KEY: modified_base
<222> LOCATION: (25080)..(25080)
<223> OTHER INFORMATION: a, c, t, g, unknown or other
<220> FEATURE:
<221> NAME/KEY: modified_base
<222> LOCATION: (25108)..(25108)
<223> OTHER INFORMATION: a, c, t, g, unknown or other
<220> FEATURE:
<221> NAME/KEY: modified_base
<222> LOCATION: (25371)..(25371)
<223> OTHER INFORMATION: a, c, t, g, unknown or other
<220> FEATURE:
<221> NAME/KEY: modified_base
<222> LOCATION: (25397)..(25397)
<223> OTHER INFORMATION: a, c, t, g, unknown or other
<220> FEATURE:
<221> NAME/KEY: modified_base
<222> LOCATION: (25411)..(25411)
<223> OTHER INFORMATION: a, c, t, g, unknown or other
<220> FEATURE:
<221> NAME/KEY: modified_base
<222> LOCATION: (25507)..(25507)
<223> OTHER INFORMATION: a, c, t, g, unknown or other
<220> FEATURE:
<221> NAME/KEY: modified_base
<222> LOCATION: (25692)..(25692)
<223> OTHER INFORMATION: a, c, t, g, unknown or other
<220> FEATURE:
<221> NAME/KEY: modified_base
<222> LOCATION: (25712)..(25713)
<223> OTHER INFORMATION: a, c, t, g, unknown or other
<220> FEATURE:
<221> NAME/KEY: modified_base
<222> LOCATION: (25718)..(25718)
<223> OTHER INFORMATION: a, c, t, g, unknown or other
<220> FEATURE:
<221> NAME/KEY: modified_base
<222> LOCATION: (25728)..(25728)
<223> OTHER INFORMATION: a, c, t, g, unknown or other
<220> FEATURE:
<221> NAME/KEY: modified_base
<222> LOCATION: (25742)..(25742)
<223> OTHER INFORMATION: a, c, t, g, unknown or other
<220> FEATURE:
<221> NAME/KEY: modified_base
<222> LOCATION: (25774)..(25774)
<223> OTHER INFORMATION: a, c, t, g, unknown or other
<220> FEATURE:
<221> NAME/KEY: modified_base
<222> LOCATION: (27450)..(27450)
<223> OTHER INFORMATION: a, c, t, g, unknown or other
<220> FEATURE:
<221> NAME/KEY: modified_base
<222> LOCATION: (29480)..(29480)
<223> OTHER INFORMATION: a, c, t, g, unknown or other
<220> FEATURE:
<221> NAME/KEY: modified_base
<222> LOCATION: (29507)..(29507)
<223> OTHER INFORMATION: a, c, t, g, unknown or other
<220> FEATURE:

<221> NAME/KEY: modified_base
<222> LOCATION: (31101)..(31101)
<223> OTHER INFORMATION: a, c, t, g, unknown or other
<220> FEATURE:
<221> NAME/KEY: modified_base
<222> LOCATION: (32562)..(32562)
<223> OTHER INFORMATION: a, c, t, g, unknown or other
<220> FEATURE:
<221> NAME/KEY: modified_base
<222> LOCATION: (32840)..(32840)
<223> OTHER INFORMATION: a, c, t, g, unknown or other
<220> FEATURE:
<221> NAME/KEY: modified_base
<222> LOCATION: (32855)..(32855)
<223> OTHER INFORMATION: a, c, t, g, unknown or other
<220> FEATURE:
<221> NAME/KEY: modified_base
<222> LOCATION: (32865)..(32865)
<223> OTHER INFORMATION: a, c, t, g, unknown or other
<220> FEATURE:
<221> NAME/KEY: modified_base
<222> LOCATION: (32922)..(32922)
<223> OTHER INFORMATION: a, c, t, g, unknown or other
<220> FEATURE:
<221> NAME/KEY: modified_base
<222> LOCATION: (32988)..(32988)
<223> OTHER INFORMATION: a, c, t, g, unknown or other
<220> FEATURE:
<221> NAME/KEY: modified_base
<222> LOCATION: (32991)..(32991)
<223> OTHER INFORMATION: a, c, t, g, unknown or other
<220> FEATURE:
<221> NAME/KEY: modified_base
<222> LOCATION: (33295)..(33295)
<223> OTHER INFORMATION: a, c, t, g, unknown or other
<220> FEATURE:
<221> NAME/KEY: modified_base
<222> LOCATION: (33364)..(33364)
<223> OTHER INFORMATION: a, c, t, g, unknown or other
<220> FEATURE:
<221> NAME/KEY: modified_base
<222> LOCATION: (35517)..(35517)
<223> OTHER INFORMATION: a, c, t, g, unknown or other
<220> FEATURE:
<221> NAME/KEY: modified_base
<222> LOCATION: (35526)..(35526)
<223> OTHER INFORMATION: a, c, t, g, unknown or other
<220> FEATURE:
<221> NAME/KEY: modified_base
<222> LOCATION: (35718)..(35718)
<223> OTHER INFORMATION: a, c, t, g, unknown or other
<220> FEATURE:
<221> NAME/KEY: modified_base
<222> LOCATION: (36058)..(36058)
<223> OTHER INFORMATION: a, c, t, g, unknown or other
<220> FEATURE:
<221> NAME/KEY: modified_base
<222> LOCATION: (36064)..(36064)
<223> OTHER INFORMATION: a, c, t, g, unknown or other
<220> FEATURE:
<221> NAME/KEY: modified_base
<222> LOCATION: (36607)..(36607)
<223> OTHER INFORMATION: a, c, t, g, unknown or other
<220> FEATURE:
<221> NAME/KEY: modified_base
<222> LOCATION: (36622)..(36622)
<223> OTHER INFORMATION: a, c, t, g, unknown or other
<220> FEATURE:
<221> NAME/KEY: modified_base
<222> LOCATION: (36667)..(36667)
<223> OTHER INFORMATION: a, c, t, g, unknown or other
<220> FEATURE:
<221> NAME/KEY: modified_base
<222> LOCATION: (36679)..(36679)
<223> OTHER INFORMATION: a, c, t, g, unknown or other
<220> FEATURE:
<221> NAME/KEY: modified_base
<222> LOCATION: (36985)..(36985)
<223> OTHER INFORMATION: a, c, t, g, unknown or other
<220> FEATURE:
<221> NAME/KEY: modified_base
<222> LOCATION: (37006)..(37006)
<223> OTHER INFORMATION: a, c, t, g, unknown or other
<220> FEATURE:
<221> NAME/KEY: modified_base
<222> LOCATION: (37249)..(37249)
<223> OTHER INFORMATION: a, c, t, g, unknown or other
<220> FEATURE:
<221> NAME/KEY: modified_base
<222> LOCATION: (37267)..(37267)
<223> OTHER INFORMATION: a, c, t, g, unknown or other
<220> FEATURE:
<221> NAME/KEY: modified_base
<222> LOCATION: (37306)..(37306)
<223> OTHER INFORMATION: a, c, t, g, unknown or other
<220> FEATURE:
<221> NAME/KEY: modified_base
<222> LOCATION: (37351)..(37351)
<223> OTHER INFORMATION: a, c, t, g, unknown or other
<220> FEATURE:
<221> NAME/KEY: modified_base
<222> LOCATION: (37429)..(37429)
<223> OTHER INFORMATION: a, c, t, g, unknown or other
<220> FEATURE:
<221> NAME/KEY: modified_base
<222> LOCATION: (37432)..(37432)
<223> OTHER INFORMATION: a, c, t, g, unknown or other
<220> FEATURE:
<221> NAME/KEY: modified_base
<222> LOCATION: (37504)..(37504)
<223> OTHER INFORMATION: a, c, t, g, unknown or other
<220> FEATURE:
<221> NAME/KEY: modified_base
<222> LOCATION: (37507)..(37507)
<223> OTHER INFORMATION: a, c, t, g, unknown or other
<220> FEATURE:
<221> NAME/KEY: modified_base
<222> LOCATION: (37510)..(37510)
<223> OTHER INFORMATION: a, c, t, g, unknown or other
<220> FEATURE:
<221> NAME/KEY: modified_base
<222> LOCATION: (37550)..(37550)
<223> OTHER INFORMATION: a, c, t, g, unknown or other
<220> FEATURE:
<221> NAME/KEY: modified_base
<222> LOCATION: (37579)..(37579)
<223> OTHER INFORMATION: a, c, t, g, unknown or other
<220> FEATURE:
<221> NAME/KEY: modified_base
<222> LOCATION: (37630)..(37631)
<223> OTHER INFORMATION: a, c, t, g, unknown or other
<220> FEATURE:
<221> NAME/KEY: modified_base
<222> LOCATION: (37642)..(37646)
<223> OTHER INFORMATION: a, c, t, g, unknown or other
<220> FEATURE:
<221> NAME/KEY: modified_base
<222> LOCATION: (37841)..(37841)
<223> OTHER INFORMATION: a, c, t, g, unknown or other
<220> FEATURE:
<221> NAME/KEY: modified_base
<222> LOCATION: (37856)..(37856)
<223> OTHER INFORMATION: a, c, t, g, unknown or other
<220> FEATURE:
<221> NAME/KEY: modified_base
<222> LOCATION: (37859)..(37859)
<223> OTHER INFORMATION: a, c, t, g, unknown or other
<220> FEATURE:
<221> NAME/KEY: modified_base
<222> LOCATION: (37970)..(37970)
<223> OTHER INFORMATION: a, c, t, g, unknown or other
<220> FEATURE:
<221> NAME/KEY: modified_base
<222> LOCATION: (38051)..(38051)
<223> OTHER INFORMATION: a, c, t, g, unknown or other
<220> FEATURE:
<221> NAME/KEY: modified_base
<222> LOCATION: (38198)..(38198)

<223> OTHER INFORMATION: a, c, t, g, unknown or other
<220> FEATURE:
<221> NAME/KEY: modified_base
<222> LOCATION: (38216)..(38216)
<223> OTHER INFORMATION: a, c, t, g, unknown or other
<220> FEATURE:
<221> NAME/KEY: modified_base
<222> LOCATION: (38243)..(38243)
<223> OTHER INFORMATION: a, c, t, g, unknown or other
<220> FEATURE:
<221> NAME/KEY: modified_base
<222> LOCATION: (38306)..(38306)
<223> OTHER INFORMATION: a, c, t, g, unknown or other
<220> FEATURE:
<221> NAME/KEY: modified_base
<222> LOCATION: (38367)..(38367)
<223> OTHER INFORMATION: a, c, t, g, unknown or other
<220> FEATURE:
<221> NAME/KEY: modified_base
<222> LOCATION: (38498)..(38498)
<223> OTHER INFORMATION: a, c, t, g, unknown or other
<220> FEATURE:
<221> NAME/KEY: modified_base
<222> LOCATION: (38624)..(38624)
<223> OTHER INFORMATION: a, c, t, g, unknown or other
<220> FEATURE:
<221> NAME/KEY: modified_base
<222> LOCATION: (38921)..(38921)
<223> OTHER INFORMATION: a, c, t, g, unknown or other
<220> FEATURE:
<221> NAME/KEY: modified_base
<222> LOCATION: (38933)..(38933)
<223> OTHER INFORMATION: a, c, t, g, unknown or other
<220> FEATURE:
<221> NAME/KEY: modified_base
<222> LOCATION: (38960)..(38960)
<223> OTHER INFORMATION: a, c, t, g, unknown or other
<220> FEATURE:
<221> NAME/KEY: modified_base
<222> LOCATION: (39092)..(39092)
<223> OTHER INFORMATION: a, c, t, g, unknown or other
<220> FEATURE:
<221> NAME/KEY: modified_base
<222> LOCATION: (39113)..(39113)
<223> OTHER INFORMATION: a, c, t, g, unknown or other
<220> FEATURE:
<221> NAME/KEY: modified_base
<222> LOCATION: (39149)..(39149)
<223> OTHER INFORMATION: a, c, t, g, unknown or other
<220> FEATURE:
<221> NAME/KEY: modified_base
<222> LOCATION: (39151)..(39151)
<223> OTHER INFORMATION: a, c, t, g, unknown or other
<220> FEATURE:
<221> NAME/KEY: modified_base
<222> LOCATION: (39227)..(39227)
<223> OTHER INFORMATION: a, c, t, g, unknown or other
<220> FEATURE:
<221> NAME/KEY: modified_base
<222> LOCATION: (39240)..(39240)
<223> OTHER INFORMATION: a, c, t, g, unknown or other
<220> FEATURE:
<221> NAME/KEY: modified_base
<222> LOCATION: (39324)..(39324)
<223> OTHER INFORMATION: a, c, t, g, unknown or other
<220> FEATURE:
<221> NAME/KEY: modified_base
<222> LOCATION: (39347)..(39347)
<223> OTHER INFORMATION: a, c, t, g, unknown or other
<220> FEATURE:
<221> NAME/KEY: modified_base
<222> LOCATION: (39545)..(39545)
<223> OTHER INFORMATION: a, c, t, g, unknown or other
<220> FEATURE:
<221> NAME/KEY: modified_base
<222> LOCATION: (39575)..(39575)
<223> OTHER INFORMATION: a, c, t, g, unknown or other
<220> FEATURE:
<221> NAME/KEY: modified_base
<222> LOCATION: (39665)..(39665)
<223> OTHER INFORMATION: a, c, t, g, unknown or other
<220> FEATURE:
<221> NAME/KEY: modified_base
<222> LOCATION: (39707)..(39707)
<223> OTHER INFORMATION: a, c, t, g, unknown or other
<220> FEATURE:
<221> NAME/KEY: modified_base
<222> LOCATION: (39731)..(39731)
<223> OTHER INFORMATION: a, c, t, g, unknown or other
<220> FEATURE:
<221> NAME/KEY: modified_base
<222> LOCATION: (39782)..(39782)
<223> OTHER INFORMATION: a, c, t, g, unknown or other
<220> FEATURE:
<221> NAME/KEY: modified_base
<222> LOCATION: (39820)..(39820)
<223> OTHER INFORMATION: a, c, t, g, unknown or other
<220> FEATURE:
<221> NAME/KEY: modified_base
<222> LOCATION: (39976)..(39976)
<223> OTHER INFORMATION: a, c, t, g, unknown or other
<220> FEATURE:
<221> NAME/KEY: modified_base
<222> LOCATION: (44407)..(44407)
<223> OTHER INFORMATION: a, c, t, g, unknown or other
<220> FEATURE:
<221> NAME/KEY: modified_base
<222> LOCATION: (46542)..(46542)
<223> OTHER INFORMATION: a, c, t, g, unknown or other
<220> FEATURE:
<221> NAME/KEY: modified_base
<222> LOCATION: (49791)..(49791)
<223> OTHER INFORMATION: a, c, t, g, unknown or other
<220> FEATURE:
<221> NAME/KEY: modified_base
<222> LOCATION: (54345)..(54345)
<223> OTHER INFORMATION: a, c, t, g, unknown or other
<220> FEATURE:
<221> NAME/KEY: modified_base
<222> LOCATION: (58249)..(58249)
<223> OTHER INFORMATION: a, c, t, g, unknown or other
<220> FEATURE:
<221> NAME/KEY: modified_base
<222> LOCATION: (59537)..(59537)
<223> OTHER INFORMATION: a, c, t, g, unknown or other
<220> FEATURE:
<221> NAME/KEY: modified_base
<222> LOCATION: (60478)..(60478)
<223> OTHER INFORMATION: a, c, t, g, unknown or other
<220> FEATURE:
<221> NAME/KEY: modified_base
<222> LOCATION: (60929)..(60929)
<223> OTHER INFORMATION: a, c, t, g, unknown or other
<220> FEATURE:
<221> NAME/KEY: modified_base
<222> LOCATION: (60934)..(60934)
<223> OTHER INFORMATION: a, c, t, g, unknown or other
<220> FEATURE:
<221> NAME/KEY: modified_base
<222> LOCATION: (60939)..(60940)
<223> OTHER INFORMATION: a, c, t, g, unknown or other
<220> FEATURE:
<221> NAME/KEY: modified_base
<222> LOCATION: (60949)..(60949)
<223> OTHER INFORMATION: a, c, t, g, unknown or other
<220> FEATURE:
<221> NAME/KEY: modified_base
<222> LOCATION: (60961)..(60962)
<223> OTHER INFORMATION: a, c, t, g, unknown or other
<220> FEATURE:
<221> NAME/KEY: modified_base
<222> LOCATION: (60968)..(60968)
<223> OTHER INFORMATION: a, c, t, g, unknown or other
<220> FEATURE:
<221> NAME/KEY: modified_base
<222> LOCATION: (60970)..(60970)
<223> OTHER INFORMATION: a, c, t, g, unknown or other
<220> FEATURE:

<221> NAME/KEY: modified_base
<222> LOCATION: (60979)..(60979)
<223> OTHER INFORMATION: a, c, t, g, unknown or other
<220> FEATURE:
<221> NAME/KEY: modified_base
<222> LOCATION: (60982)..(60982)
<223> OTHER INFORMATION: a, c, t, g, unknown or other
<220> FEATURE:
<221> NAME/KEY: modified_base
<222> LOCATION: (60988)..(60988)
<223> OTHER INFORMATION: a, c, t, g, unknown or other
<220> FEATURE:
<221> NAME/KEY: modified_base
<222> LOCATION: (61180)..(61180)
<223> OTHER INFORMATION: a, c, t, g, unknown or other
<220> FEATURE:
<221> NAME/KEY: modified_base
<222> LOCATION: (61195)..(61195)
<223> OTHER INFORMATION: a, c, t, g, unknown or other
<220> FEATURE:
<221> NAME/KEY: modified_base
<222> LOCATION: (61315)..(61315)
<223> OTHER INFORMATION: a, c, t, g, unknown or other
<220> FEATURE:
<221> NAME/KEY: modified_base
<222> LOCATION: (61397)..(61397)
<223> OTHER INFORMATION: a, c, t, g, unknown or other
<220> FEATURE:
<221> NAME/KEY: modified_base
<222> LOCATION: (61399)..(61399)
<223> OTHER INFORMATION: a, c, t, g, unknown or other
<220> FEATURE:
<221> NAME/KEY: modified_base
<222> LOCATION: (61427)..(61427)
<223> OTHER INFORMATION: a, c, t, g, unknown or other
<220> FEATURE:
<221> NAME/KEY: modified_base
<222> LOCATION: (61532)..(61532)
<223> OTHER INFORMATION: a, c, t, g, unknown or other
<220> FEATURE:
<221> NAME/KEY: modified_base
<222> LOCATION: (61623)..(61623)
<223> OTHER INFORMATION: a, c, t, g, unknown or other
<220> FEATURE:
<221> NAME/KEY: modified_base
<222> LOCATION: (61864)..(61864)
<223> OTHER INFORMATION: a, c, t, g, unknown or other
<220> FEATURE:
<221> NAME/KEY: modified_base
<222> LOCATION: (61957)..(61957)
<223> OTHER INFORMATION: a, c, t, g, unknown or other
<220> FEATURE:
<221> NAME/KEY: modified_base
<222> LOCATION: (62071)..(62071)
<223> OTHER INFORMATION: a, c, t, g, unknown or other
<220> FEATURE:
<221> NAME/KEY: modified_base
<222> LOCATION: (63256)..(63256)
<223> OTHER INFORMATION: a, c, t, g, unknown or other
<220> FEATURE:
<221> NAME/KEY: modified_base
<222> LOCATION: (63258)..(63259)
<223> OTHER INFORMATION: a, c, t, g, unknown or other
<220> FEATURE:
<221> NAME/KEY: modified_base
<222> LOCATION: (64474)..(64474)
<223> OTHER INFORMATION: a, c, t, g, unknown or other
<220> FEATURE:
<221> NAME/KEY: modified_base
<222> LOCATION: (64477)..(64477)
<223> OTHER INFORMATION: a, c, t, g, unknown or other
<220> FEATURE:
<221> NAME/KEY: modified_base
<222> LOCATION: (64493)..(64493)
<223> OTHER INFORMATION: a, c, t, g, unknown or other
<220> FEATURE:
<221> NAME/KEY: modified_base
<222> LOCATION: (64537)..(64538)
<223> OTHER INFORMATION: a, c, t, g, unknown or other
<220> FEATURE:
<221> NAME/KEY: modified_base
<222> LOCATION: (64541)..(64542)
<223> OTHER INFORMATION: a, c, t, g, unknown or other
<220> FEATURE:
<221> NAME/KEY: modified_base
<222> LOCATION: (64544)..(64544)
<223> OTHER INFORMATION: a, c, t, g, unknown or other
<220> FEATURE:
<221> NAME/KEY: modified_base
<222> LOCATION: (64551)..(64552)
<223> OTHER INFORMATION: a, c, t, g, unknown or other
<220> FEATURE:
<221> NAME/KEY: modified_base
<222> LOCATION: (64561)..(64561)
<223> OTHER INFORMATION: a, c, t, g, unknown or other
<220> FEATURE:
<221> NAME/KEY: modified_base
<222> LOCATION: (64632)..(64632)
<223> OTHER INFORMATION: a, c, t, g, unknown or other
<220> FEATURE:
<221> NAME/KEY: modified_base
<222> LOCATION: (64766)..(64766)
<223> OTHER INFORMATION: a, c, t, g, unknown or other
<220> FEATURE:
<221> NAME/KEY: modified_base
<222> LOCATION: (64845)..(64845)
<223> OTHER INFORMATION: a, c, t, g, unknown or other
<220> FEATURE:
<221> NAME/KEY: modified_base
<222> LOCATION: (65260)..(65260)
<223> OTHER INFORMATION: a, c, t, g, unknown or other
<220> FEATURE:
<221> NAME/KEY: modified_base
<222> LOCATION: (66845)..(66845)
<223> OTHER INFORMATION: a, c, t, g, unknown or other
<220> FEATURE:
<221> NAME/KEY: modified_base
<222> LOCATION: (66847)..(66847)
<223> OTHER INFORMATION: a, c, t, g, unknown or other
<220> FEATURE:
<221> NAME/KEY: modified_base
<222> LOCATION: (66855)..(66855)
<223> OTHER INFORMATION: a, c, t, g, unknown or other
<220> FEATURE:
<221> NAME/KEY: modified_base
<222> LOCATION: (66916)..(66916)
<223> OTHER INFORMATION: a, c, t, g, unknown or other
<220> FEATURE:
<221> NAME/KEY: modified_base
<222> LOCATION: (67185)..(67185)
<223> OTHER INFORMATION: a, c, t, g, unknown or other
<220> FEATURE:
<221> NAME/KEY: modified_base
<222> LOCATION: (67479)..(67479)
<223> OTHER INFORMATION: a, c, t, g, unknown or other
<220> FEATURE:
<221> NAME/KEY: modified_base
<222> LOCATION: (69105)..(69105)
<223> OTHER INFORMATION: a, c, t, g, unknown or other
<220> FEATURE:
<221> NAME/KEY: modified_base
<222> LOCATION: (69599)..(69599)
<223> OTHER INFORMATION: a, c, t, g, unknown or other
<220> FEATURE:
<221> NAME/KEY: modified_base
<222> LOCATION: (69653)..(69653)
<223> OTHER INFORMATION: a, c, t, g, unknown or other
<220> FEATURE:
<221> NAME/KEY: modified_base
<222> LOCATION: (70593)..(70593)
<223> OTHER INFORMATION: a, c, t, g, unknown or other
<220> FEATURE:
<221> NAME/KEY: modified_base
<222> LOCATION: (73334)..(73334)
<223> OTHER INFORMATION: a, c, t, g, unknown or other
<220> FEATURE:
<221> NAME/KEY: modified_base
<222> LOCATION: (78830)..(78830)

<223> OTHER INFORMATION: a, c, t, g, unknown or other
<220> FEATURE:
<221> NAME/KEY: modified_base
<222> LOCATION: (78897)..(78897)
<223> OTHER INFORMATION: a, c, t, g, unknown or other
<220> FEATURE:
<221> NAME/KEY: modified_base
<222> LOCATION: (78907)..(78907)
<223> OTHER INFORMATION: a, c, t, g, unknown or other
<220> FEATURE:
<221> NAME/KEY: modified_base
<222> LOCATION: (78925)..(78925)
<223> OTHER INFORMATION: a, c, t, g, unknown or other

<400> SEQUENCE: 12
cgatttgctt agtacattca ttacatttac tattcatcct tatttacctt taataaattt 60
gcttatcaaa agagcaatta attgggatag tgataacttc attagtaact acatgtttgc 120
ctgtcttttt aaagaattgg gcaaattttg aagtagctgg aattacaaag gtatcatccc 180
gatcattatt tgacatattg tanaaagtaa anttaccgtc tanntnaaac ctaatnnncc 240
antnaatatn ncgtantttg aaatctatac caaatcttaa ntgancatca atnaattcag 300
aaccaccgta ntcataagct ccggtgaaat tccaattaat ttctgcgaat tggaaagtta 360
caggatgttc gccatgttca tcttgtatgt agtaaccatc atgagctttc caatagatna 420
ctaaatcatg catgctacca gcctcaaaga aataataggg gagtctagac tcccctatta 480
atttattttg cttttagcca ntcttctant ggnggtaaat anttctcatg ngcccantta 540
atnattgttt ctacaacagg accntgtann tcaaggttnc ctgagatttc atgnggttca 600
tcaatagata gaacccacgt ntgtggcgca atgcgttcag ttgctttngt tagatacaca 660
tcaggcatta acgtaagatt caattgatcg ccgtcaaaat cagccgtatt gttcagtatc 720
agtcgttaat tgatacccgc accattacgt gcagctctag ctttcactag aagaccagac 780
tatatcttca cccttccttt cggagtgggg tgtctcccat ttcgagtcac ttgaccctac 840
atcctatttc taggaccggt gcacctgata ccgtgatagt cgttgaacct tctcctattc 900
ctaaatggaa tgttacggag cttggctgct gattgaccct acctaatctt tttcaaacct 960
tggctttgtc tttcgactcg cagtggtaga ttagtttaac aggatatccc agcaattaga 1020
gagaactcaa cccaacgatt actcattggg ggaactagat ttgattaact taataaggta 1080
tttatcaagc accccattct tttcaaagat tgctcttcga acagtattcg gatgcttaat 1140
accgacatct cttgcaaagt gtggaatact cggatacact ttggtagtgt tcaagatggt 1200
gtcagttact tcaattggag taccttttcc attactaggt tttccaaatg aggcttcaat 1260
ttctttttga gtgtatttag ggaaatcttc aggattagcg gtatatgaga ataccaaacc 1320
atccatgatt tccttactac ctctaactag atggtaatag gctttattac gtttagtacc 1380
tagtgcaagt tccatttctg ctaagttatg aaacacatgt aatgtcttag tcttatagtc 1440
taaaacataa actgtcttgg tactatctcg atcagcaatc ttagtctcac cggtaataaa 1500
ttcaaatgtg aatctatttc tatacggctt agtcttatga tcacgtataa taacccaaac 1560
cgtattttta ttaactccta atgcccgagc aagttcattc atcgagtaat aagtagtctt 1620
ttcaccagtg gtaacgtcag ttgcaattac ccgtctattt tcttttctta atccattttt 1680
gtaagcatgc tcaatgtttt caccacgagt catccactcc aaattagatg gtaagttatt 1740
atgtttgttg ccgtctttat gattgacttc ataatctggt ccaggtgatg gaccatggaa 1800
agctaaacag attaatatat gaactccctt actcttagat gtttttttcat cattttttgc 1860 accaatattg agatatgtcc caatcgatgt tttagtaagg aagaaattac atattctatt 1920

-continued

```
taaccgctta tgacgaattg ttcctaagtt actagcttca tatgctgagt atccaggaat   1980
atcccgccat tcaattttaa atgaagccgg atcaaagacg gacactactc cgttttgttc   2040
cattgttttt acccttattt agttattcaa ttgtccatta ggcgctttaa ggcataaaac   2100
tgacatgctg atagaattat cattaatgtc atcttttact ttagtaataa agaactgctg   2160
cgtagatcca cgttgaagcg ttggcaatat cttcagatag ttcgttaggc tatcccgcac   2220
cattacgtgc agctctagtt ctcactagat gttgagacta tatcttcacc tttggcttta   2280
tccagtaagg tgcttcccac ttcgatttaa gggattctat acccacccac ttgggcccta   2340
ctctactccc tctaccttac ggcatggttt cgatagtcgt tgaggattcc tcatactcct   2400
tttaattaag aaggttagag gctttcctgc tgattgactc tattcaatac ttttcgaact   2460
tttccgtatt agctttcgct atccgtttca gtgtattgac ctagcgagtt atcccagcat   2520
ttcaagaagt tttgtcgagt atcatttctg atacaaggaa accattatta agttgatcca   2580
ctacactaag attacttagg tggtatgtag cttctcttta cgcgctttgt atcggttata   2640
ttcgtcaatg gatttattaa ccatctcttg agttaattta gaaacgtatt cgaatagccg   2700
ttccttatct tcaactctac agatgacata tccattaaat aatctcagtt ctggtttctt   2760
caagatgtct tgcactgacc ccttgattaa tccagtccta agttgcaatt gtgttaagtt   2820
ctcatacctg ccaaaggtgt tagttttgaa gtctatgcaa taaacttcaa tagcgttctt   2880
ccgcttctgt ggatgataat ccccagttac ttcaaacacg tacttaccat tgtaaggttt   2940
agttagatgc gccatgacta catgcagccc tttaccatga cctagctcta agaactctgc   3000
aacttctttc atcgagatga agttatacac ctcacccgtg gttacatcag tgcatttaac   3060
agctaatgcg tgtttgtttg caccggttat aaatgcatgt tttacattac cactgcgagt   3120
ttcccactct aggttaaggt aatggttatg atgcttattg gtgtctttat ggttaacgtc   3180
caaggataca taattctcag gtaatccatg gaaagccata catacgaaac gatgcacgta   3240
tcgtattttg cgaacacctt catcattgtg gatattaacc gtcaggtaag taccctttaga   3300
tgttttgttc tcatgttgag aaatcaactc acctttaagg ttccttactt gaccatggtc   3360
actgacttca tagttactga aaccaggtat acttcgccat cttatttctt cattcatatt   3420
tcctcattag agattcttgg ttaccacacc cagaatctgt agcgctacga cttaataaat   3480
taatttcggt gaaaagtaca acccatccct ttataagggg ctgcttctgc aattagctct   3540
ttaaatagat ctgcaatgat ttggttatat tgaagtacat tctcatatac aaatgagaat   3600
gcttcacgag ttgtcatgtt aaacttngct tttagnttnt tngttagatg atactttaat   3660
aattgacaac ctacnccccca nggnatatgt anttcatcat aatcatgcgg gtcactaata   3720
gaagtgatta ctgcacgtgc cgtagcgttg agacgagcac caaacatgtg acgccgagca   3780
agaccaggct tttgagcaat tcgtgatttt gcgtagatct cgtagaactg gccatatagt   3840
cttagtcctc gcatagtcct attctgagct ttaattggac taagtggtac agatgatgca   3900
tcaatactag cgaaggttaa ggtagcatca attgctgctt caattggttt atctaagtaa   3960
gtaccagatg tggttgattc tgctacgaaa cagagtttag aaggaactgg taaatattta   4020
gggaataact tatctttatt ctgagcaacg aattgagcga attcggattt attattagan   4080
ataatatttg catctagtag gaattggaag atctcattga aattatcaat gaagtgattt   4140
aatcctcttt caaatcctcg atgcagtagc ctatctactt tnctgcgtgt ttctttagaa   4200
ccaatagatt cnacatcgta tcgataagaa gtatcagtta gatatgctaa gaaatcgaat   4260
```

-continued

```
tctttagtta ctagatatcc ggttagcata atgattaaac gtgggttaat tagnctacgt   4320
acntgttttg gtgtacgaac ccacattgat ggttcgatag gacggctaga agtattgaca   4380
actggagtat tacaaatatc acagattact ccgagtttat gtgcgtcttc gattgctcga   4440
caatcacagc ttacactact ttcaattgct tctgaatctt ggaaatgaga atagaaatgc   4500
ctatcaaatt cttctttctc atctgagtta ctcgtattgt aatcattggc ataaattcgt   4560
ttacccgtaa attgatcatg aacttcatta tgatcaacaa ctttggcata aagacccata   4620
ccaaactcct atttatcgat taacaaaaaa ggagatataa gcggcccccg aaggagccgc   4680
tatatcagtt tttacaatgg accaccaacg gagcctggcc cgatcctagc gtcatctaca   4740
aagcttaacc tccgctcttc tctgtagcat accggcacta gtatcattta ccatccattg   4800
tagtttttga tcacacgtca ccttttgagt aactcctttc ggttaagtga tctatcatcc   4860
tcgtgtagtg ataggtcgac ctagactaag tccactagtc gattacttca cggaacctac   4920
tcctaaccgt tatcaccgaa gtgaaccagg gtcgcagtat tagaatcggg atgttactta   4980
tttaacatcc ctatctaccg aggtatttcc tattagtacc aggtacccgg tgcattatag   5040
gaaggagcgc cgtaagtttg acccatgctg ccagccatnc caacttgtgc actaccagaa   5100
acagccatgt tacccatacc ggtgtaacca gcgaagcgct gttgaccgaa gttggtaatt   5160
aggttttcca tggttacagt tacaccagcn gctgctgctg cggcatccat tgcggtgatg   5220
aatttcgggt taaaggttag acgacgagca cgaccagtat aggtaacgtt acctaggtac   5280
atcttgtcga agcctttact gttattcata cgacgcacaa tgtggtcatt acctacctga   5340
gtagcatacc aggtcttcca ctcttggtca ttaccttcag acatgttcat ggcacctaga   5400
acgtcgagat cacgacggtc gcttagttca ccatgctcat cagtgtagtg accgaggtct   5460
acttcatgat ggttgtcaaa gataatcgga ccagcttcag ctagattata gaactgacgg   5520
aaatcagtgc cgtataggtt agttagagct tggaagatca gactaactgc acgagcttgg   5580
tttacgccac cagctgcatc taggacgact tgctcaatag ctgagttgtc tcccattgga   5640
tcgacatcga tctggaatgc agggttctgg ttaaccatct tgttcattag cattacgaag   5700
ttgctgtcgt ctgccatgaa tgcttcggtg cgagtttcaa tcgctttacc tagctctgag   5760
taataaccaa gtgcaccaat atcacgcatc ttactagtag cgatcttcgg cattagagta   5820
cgagcccatg cctgagatgc agttgcacga tacgcgttac caagcgcgaa cagccacatt   5880
tctagagtcc atgcttggat ccaggacgcc ttacgaacgt cagtaataac gatgtaagga   5940
gtgaactgcg gaggtagaac tgcaccaggt agagttacgc caaacatgcc ttgttgctgg   6000
ccagtggtcg gagtccaatg tagatctacg aatagactaa cttggtttag ctggctatcg   6060
gtatcataga actcgttctc aggtacgttg gttttcttac cacggctagt ggagatgacc   6120
aggtcagaac ggatcggatt accacagcta tctttaaccg gaataccatt gtagtctagn   6180
ttgcaggtaa gctgttcgtt ttctgctttg atgtgggtcg caatagagaa cggagtctca   6240
ttgttacgac gngcaatagc atcttcacag atnttaacng attcaactag taggttctta   6300
acagctagtt catctttgaa gtcgaagtca gcatacactg cacgtggacc ggcagatagt   6360
acttctagac cagggatgtt gtaacggttc cgtaggaact cgccgatctt gctccagtat   6420
tgagcagtga atacatcacg cggtagtacc ttctcttcaa tgatgtcatc agttagacca   6480
ttgttgattt tgtgggtacg gggacggatg cgagtaccag gtaggttatc gagtactaga   6540
gtacgaacga atgccttcat ggaaccattg atatctttag ctagtttaac aatgagtaga   6600
ccagccatac cnacttgttg ngcatcncga tcgaaacgat ggatatcgaa gtcatcaggt   6660
```

```
aggtcctgat ggcggattgc ttcttctttt actttagtga atacttgtag ggcatctgct   6720
gaacgagcat cagagccatc tagccgacca gagcgacgca ttagatggtt aatgccagta   6780
gtngacccag gngcgccagn nggacgttga gcttgacgnt gtgcagtggg ttgcggagcn   6840
ggagcngtag cttgagtttg aacggtgccg atttcgtttt cgttaacagc cattttaaat   6900
acctttacga ttatggtttc ttgatcaaga agaacctaag tactnagtat actagattca   6960
atttagtaat ataaatctca aatttttttc attacaacat agacgctata atctgctatc   7020
agcagatcgt aacgaacact atgttcacta catattatta caatctgagt attatttatt   7080
tttcatctta caatttccat atcttctttt ttgagtttat gggtataaag tttgaatcca   7140
gaaactaatt tacgtcagtc ctgtattaaa taataactat cagtattttt ataaaatgca   7200
gttatcattt acttcgcata tacttacgaa ctgttccaaa aagagaatga tacagtttgt   7260
atagtttact aactggatca actttattat tatcagttgt atcaaattta gcaataaatg   7320
gtgaatgtgc cgaagcagat gtttcattta ctttaactac actaccaaat cgatatgcga   7380
ctaatacctt tattaattcc tcatggagtt tagtagcagt tgctaatgga ttgggatcat   7440
taggatctat cttaatccta cgctcgacat tgaaaaagtt tactacaatt tctttgctag   7500
tcatgtatac agtaagatct ttgttattac ctaaatatag tggcggatct tcaacattat   7560
ttttagccat tgtatattcc tatttgtaat tactactgtt gttaccaaac tatgatatag   7620
atctcaatta atttttaatc ggataataac catgtataat ttatttaaga atgctccgtc   7680
acgtaaattg gggcaggtgg ttgatcctaa catccattat atccgacgaa tctacgctga   7740
gcaaattagg gacgttaaaa gttattatag acgggcaccg aagtatgttg aatctaaaaa   7800
catattagca caaatgattc gacattttaa cgtagagtta ctaagtgatg atgctacttt   7860
tataaagaac gtggacgatc gttcacgtgc tattattcgt tcatttggta ttacatcatc   7920
tttaaataaa ggtaaggttc atgtaggtgg tgttacactt ggtcctcaaa ctgaagaagt   7980
tctagtatcc acatcagaga gctttgatct aaaagatcta aataaaacat ggtataaact   8040
ttcccctgtt acgtatctgt atcatacacg tactgatact aatttaccta tcatgaacaa   8100
taccacacag ggtagaggct atggtgtaac tctagtaaat ataccaatgc ttcttgtgat   8160
gtaccgttac tggtatcgat ggcaagttga gaagaatcct gatgaagtag aagacactta   8220
taggtttata ggatcatttg tattgccaaa tatggttgac tcttatttag atatttcttt   8280
ctttaatagg ttagcaagga atgctttaga tattaaaaat ccaacattcc ctataccgca   8340
tccattttac atcactgata tgaatccacg tattgataaa ctatgtacaa ctatcaatag   8400
agaatccata ttaaaaggtg tagacatgga aggtttatca tggataacac cagctatcgt   8460
acaatctaat ttgttcgata tgatgcggct cccacgagaa cctattaaca ggaataatga   8520
atgggcttat gtattggctc gcacaccctt cattaagtat cttgtagggc agcttttaaa   8580
gaatactggt tatgatcaat cttctgttaa cactgtatta attgatctta tagaagcatc   8640
taatgatcaa gcatttaagc aacaagcaaa tagtgagttt gtaaaagctc aacaggcaca   8700
agttgattgg atgatagatg cacttaaaag aaaagaaatg tgacataaac cccctcctaa   8760
attggagggg gttatatgcc gttttattag aaattacctt tcttcatttt agaaagtaat   8820
tttctacgtt cagctcggtt aattcctggg atagctggta atagcatttt attactaaac   8880
ttacctggct tgcggtcatg atttagtaat tgatcaacta cagcttggtc actgctttta   8940
actccattat ccatttcatc taatgggtcc ataatagctt tagcagtcaa tcttagatga   9000
```

-continued

```
gtaactagtt catcaaatga actatcggta ttaataagtt gtttatcaac accttcttta   9060
agagcttgtt taatagttac gtcttttacc aggatattat cacattccca aagagttgta   9120
tgatgggtat ttaacattaa ttcaagtgag acattattgt aatcgttgtc agcacttgag   9180
tgccaattga attcatcaat atagtcattt agactcatta actttggtgg ttcgttacta   9240
gaggtaatta aaccaattgg ttgaacatca tctagtgaac ttttatcact agtaattgca   9300
gttgtttcag tagtaacatc aacttctttt aattcgttgg tataagttac atatactaat   9360
tcttcactac cgtcatccaa aagaacatag gctgttgctt tggtggaatc atcaggtgct   9420
aatccatgga tcctaatacg attatcattt actaatttac tataatcatt ccagtgatta   9480
cacgaacttc attagtcttt tccattatca tctacctctt ttaatttatc tttaatatat   9540
ttcggataaa gctcgttttc ttcacgagtt aanccngntg gnncggttgg taatgtgata   9600
gtnccnctnt taattgcctt cttcatccga tctaagtcaa aattaaattc ggtatgattt   9660
ntcattatat tgaaccatat taagttagta attggcaatc agactatata aatcttaatt   9720
attttttagt atataagcct cccactaggg gaggctatat ttcttaatag aagtcagaga   9780
tgagtcgatc gttattttta tcaataagga aaatacctag ggactctaag gttagataga   9840
atacacccat agtntttcca atgatagttc taacgtcagc aacacgcgta ataacttctg   9900
gaatacgacc agtttctact actgtactcg ggatatggaa atcaccaata ctggttttat   9960
tttcttcagt aacccatgct tgaatacgag cagctaattt cttatcttcg ataccatcaa  10020
tccattcttt gatcgcagtt ttattattaa gagtaactga gatctttaca tgtgaataag  10080
gtggatcacc agcgtcacca aatgatggag caaatacagt cttccacact aatccctttt  10140
tatgggttga gttatcttca gatttataag actcaggtcg tttagtttga ccacttgtca  10200
gatactcagc tttaccactt ctaacagact caataatttc tctttcgata tcaccaactt  10260
cttttagaat tgaagccaag tcgattttct cttcagtctt tacagtttta atgatatctt  10320
ccatgagtgt tttagcacga ctattaatct tcttaggtac tttactatcc cttagtccna  10380
cnccnttnat ctccatncgn gantcattaa acatnacccc ttcttgggca tcctgtgatg  10440
caaagtaatg tttagaacga gtagttaagg ccagtactgc gaaataanat tcgttcttca  10500
ttgcaaatag acgaagctta tctttagata cacccatatt agcggattga atcgcnaaga  10560
tatgcataac tacttcagan actagaaaca ctagtgcnaa tactagtcgn ttagcttcat  10620
tgctaaaagt tactttacca aagaattcct caacccacca ttgtaatgta aacatagtgg  10680
agtcagtatc tgaaataaca gcagctcgtc tatacacagt tggaaaagca tgaatgcttg  10740
atggtacaca tttagtcaag aagaaagctt caatcaatag acgatattca ttaagagttt  10800
cagcgatatt tcgaccagtg gcataaactt ggttnantgt atctggatcn gantctttta  10860
gtttagcttt agatcgacct ttaacagtat caaagcaaat aaagctagcc aanagatcca  10920
tatcaccatc ataagttgaa tattcttctt cagtgatgat ttgttctttt gttccaacct  10980
ggcttaattt aattagaaag ctcttgatta attctttatt gtatttatat aagtgatata  11040
gatcacctac ntacataact gctgctcgtt cgactggtgt catcccagta gctagtttta  11100
aaatctgngc cgtgtantac ttattttgcc aatagtgttt agttgaataa agaaccatat  11160
caactacttc ttctggcgtt gggcaatgta gattaaaatt agttactgct ttttgaatta  11220
actccatatc agctacatta atantnttta ctaaattagc ttttgtgatt tctggagtat  11280
aataatgcct attacccata atgaattttt cattatttga gttagcataa gaggtaccag  11340
ttctacaggt agatgttaaa ctagagtgtg tggacttata ataaagaata gtggcagcag  11400
```

atacagtacc gcctgaatat gagttattgt taattttgaa gttttcttgn tcncctttac 11460
gtacttgtgc aagttctgtt ttaatttgtg aattctcttt atcgccggcc tgtaggaaag 11520
cagctgcttc acgttcagcc tgcatctgnt cacctttaac acgcttacgg tttttcacac 11580
cttcngcaat atagatggag tgcgtngact gtctaacaga ctctggtaaa tatgcggtca 11640
ttgatggaga taataataga ttctgtttct taacacggtt aagaaaagcc ataaatgaaa 11700
ccgtctttaa ttccctatca ccaaacttat ttttatctag aatagttgct aatggattac 11760
gaagtgcata ttcgccattt tgacgtaatt gttctttaac aaattcttta cattcttcta 11820
aactaatatt taattcatct tttgtcatta attgaagata tttggcatta tcatcaagac 11880
atgcattaat gatatcaata tcacgatggt aatcattgac atcttttaaa aacggatttg 11940
gttgggcaaa tgcggtcatt tcacatatct ctcagtatac ttattttttta attatagtga 12000
atgatttctc tctntttaac taaaaaagaa aaggaaagaa tgggtaccct atacgggnac 12060
cctaaattga gaggtagcac atcaacttac attcacatta gatgatgtaa gnaagtaaaa 12120
ataanacaac ataaaaggag ccatnatggc tcctttatag ttattcatat gtcactgaag 12180
ttggtggtgc attattttgn cgcactgcca atagaatgcg atcatacatt ttattatcga 12240
catcatccca tactaatgtc anacgnttac catctacacg ttctaatgta ttcgcaacaa 12300
tccaaggnat nccaataaac atcacacttt cattattggc cattcgtaca cgaatntaat 12360
tgtattgtgt tggatcaact ggagctganc ctgctggtaa acttggatat acttgctgcc 12420
cngcagcagc tacatcaaaa cccattgcag atgctacaga cgcagtaaca ataccttcga 12480
ctgtaacgtt cttaaaatta gtacctagga tagcatatgg atagacctcg aatgagatcc 12540
tatcacctgc ttgaatgtct cgaatattaa cagccatggt aataccctaa aatagttggt 12600
tacatagggt attactcatc tagtaatacn actacaccaa acagaccttt cgtatccatt 12660
ggnactgtaa tgantacatg tccatntgga tanttttctt taaagctatt gataaagtcg 12720
gtncaatatt caataacata tcctttagta gaataattct ctaactcaat atcttcntca 12780
ggatcatcaa atgagtcatg tccatacatc agcatatgga tntatatgtc attattaagc 12840
gtatccatat aacttaactt acgtgattct tcaaataaat caagtggtgt tggacaatct 12900
ggatatatca ttcgttttgt atattcacga agcaaatgtt gcgaatatac ttctgactct 12960
ttagatttaa atacgataaa tactcgtttt tccatatcgg ttcctagtag gaagcctatg 13020
tgaaccgata ggctttccta tttgcgtcaa ttgttaatat gtgtcactta atccacatca 13080
ttgtaacagt ccataccaaa gtcttcacct tctagaatat aaccctgatt atgttgatca 13140
actgctattg attggattct ttctacacca tatccattct gatagagatg tgctatttca 13200
gattgtagtt tgctagccaa tgttttacac acggtcgcaa accacatatt aagaatactc 13260
aatgcatatt tatcttgcat aatcacaggt gctaccgatg gaaagtattc ttgtaaataa 13320
tagtcaaccc ctataattgg ttgagtaggc tgttgcgcta gaaattcaat atatgaatta 13380
attgcctgat accataattg ttctatagac tggtgttcag tatatgggta agggtattgt 13440
aagacttatt gacaactaca tcagccattt tattaacaat gggccagata tcactgatgt 13500
taataactac gaaactcgtc attccttgtt gacctggagt tatgttatta gcatcattta 13560
tccgctgcat ttcttgttgt ctataaagaa gtggatgcat catgtttgag acctcataac 13620
taatttagtt accatcttat atttatctac ttctatacat ttaagactag taataagatt 13680
acctgcttga ataacttgtt tttggattat ctctaggaaa tcagttccaa ataaatccaa 13740

```
taccctttcg ataatctcag cagatcttaa gtgccaattg atggtattag gatttccctg  13800
atgatcaaat accatcatac tcgtcggtct atccggttct atataggtat cgcttaagta  13860
atcttctaac cattgctcta aaaaggtagg ccaatctaat ctctgccagt ggttaaaata  13920
ttcacatatg ctgctagaag tctattgata caccacagta caaagtcagt cggttcatct  13980
acacctagct cttccgtaaa agaacgcggt ttcaaaatta gcaacaattg catattgact  14040
ccactcttta ccagtgacta tagttaatag aacaactttg ttatctatta cactaatgaa  14100
cttatagtct attaaattct tcggtgttct atgtagtaat tggattccag ttgtatagaa  14160
caaattaatg aactcatccc aatctggacc atttcctagt tgtattgata tatccacaaa  14220
aggaataacc gtattatcct gttgtaattt agacatcatc ttaacaaccc attgagttaa  14280
taagacgatg actgtagctt catctttatt tgttaggtaa gtaaatttct ttatcaatgt  14340
gattaattgt gggaatacca cttcgattgg caatacatat accagacgtt gtacttcctc  14400
cgatgtacaa tccatctcgt gcttctgttt cataccacag ttccttagta tttgttggaa  14460
tgaggtgcat gatctgctca gcaccctcat cgagaagttc tattagttta tgcatgaaat  14520
gaatgtcttt agcatattca tagaacattt cttctttaac gaccatttgc ataagcttct  14580
gttctgccaa tgcaacaagc aaatgcattg cttcgatata actaatatct aaaaagtcca  14640
atacaaatct tagatagtta tcatctttaa taagtttact tttagtcgct cttagtaaaa  14700
aacgaggttg tngtgtgggt aatggtgacg tatagatctt ctggtttctc agtatcataa  14760
ataaccctat ttaactggat gttaccagct gatggtagaa ctacccggtt agaacaatta  14820
tacagataag ttgttaaatc aatatcacaa atatccctat aacccagcat ctgattaatt  14880
agttctatga catcattaga tgtncnaccn gatgcnctct cagacgctgc tgccaataca  14940
attgttaatg catattctgc accaatacta ttttttatag atttccaaat atcagaatgt  15000
tgntcttgta caaaagatct tacttccatt ctgatacaca ttgatgtgtc tttatcatta  15060
gatatgttca ttataaaaac cttataancg ntataaagcc cnccntangg agggctttat  15120
ttagtataga ttattttcta aaatgtatcg ctcagcttgc gctcgctgat catcaggtan  15180
ataatcacca cgttgatatt caaatactaa tttctcaata ggataagttg cattcttatt  15240
cttgtataca gaaattacat agctatgata ctctagttca tacttaacat catgctcaat  15300
tctggttgaa aaataagcca tgttaataga actaactaga gggctaatat atttctcttc  15360
aaatagtaat aaattatcaa gtcctaaact tgcaaagaaa tcatggttaa ccttaggtat  15420
taggtaagat actttaatat tactatattg tttaacaatt acgccaataa gtaatgcagt  15480
taactgttct tgaatatatt ctactgcgat gttgtatgca tggttagtgg tgatgtggtc  15540
tttatttaaa gtatagctac cgccattggt aatagatggc tgagttttac gtctagattc  15600
gtagatacta taacctagtg tttgtaaatt aattttgtca aagccatgga agaaagtccg  15660
tagaaattca ctaaataaat agtttaatgg gttcagtagg ttaagtgata ccactgcatg  15720
atcatcacca ttatcaatcc catggacacg atcatattct gcgattcgat aatctttacc  15780
actgattaaa gttataactg aaccagcttt aactacatcc cattggatcc atgtaccgct  15840
atcgatatat tttgctactt gcttatagat atctagatag atagtttcta gataaggtag  15900
tttcattaga ttttctaccc aagcaacttt attactatct acgtcagtta cagcacaatt  15960
aaaaatagct gcggccatct taagattggt gtactggtct ttggctgttt tatatgaaac  16020
taaactctct actatatttt caaccattag atgtaaaaac tgttgagcca catctttact  16080
caatttcacc ccaatcgctt catcaattga agctgaagct gtaagctgac ctagtaaatc  16140
```

```
gtatattgct ttttcttggt ggcgcgtatc aagtacaatg agcttattcg acattatatt  16200
tctccaatta attttttgga atagcgatcc aaactgtgtt ctttaaccga tagaatatta  16260
caaacttacc tgcatttact ctaggtataa tttttaatat atcccaaaga tcagatgcgg  16320
cctcatgatt atcatgaaac cattggattt cttgaggggt gttatttatt ggattatatc  16380
cagtagtata catgaattca aaagagtcaa tagagtattt aaagaagtca tcaattaagc  16440
tgtcctctac tgatttaaat atatgctcta atgtaccata gtcatctgga tgtattccaa  16500
agctttggca cctaatcgct aaacgcgtat ttattaactc ttttggcgat cttggtacta  16560
acttggctat caccctcgtt acatctatta catacaggtc agccacttgg ggagtagtca  16620
cagtacaatc tctcgttaaa tgttcaggaa catgatatag atctaaaaat atttttagtc  16680
aaatctgttc gtggtaagcc gatgtatatt ataccttagt tgggtattat ctccatcgaa  16740
aaaacgcgta cagcgcatta taggacgttt ttatgaatcc aattactaag gctttacgtg  16800
atatttcttt taagatccca aaacagatat taaatactgt tttcntatct ancgaaatgt  16860
caggctgtgg tgcagctatc tcactagaaa ccaggatacg cgaagctgtt attgaaccac  16920
gtgttatgtt agatattgat ttagtcggtg gttcaaaagt attcattcca ctagattttc  16980
cagtgcaagc agaatatgtt gacccttata cagtggttta ttacattcca gacgaataca  17040
ctcagcaacg cccaattatc caatgttaca gtatccattt tggagtatta ggattccata  17100
ctgctggcta tgctatgcac tataatgaat caagtatggg tgcattaaca cgacgtgtac  17160
tagattcagc tagacagtta ccagtcgccc aaacagcata tatcaactta attaacccac  17220
acactgtcat ggtcaggtat atcaatatcc ctaactactc atcattcctt gcctgtcgcg  17280
taggtaatga tgangagcta aataccatac gacctacagc catacctgca ttttcaaaac  17340
tcattgagta tgctgttaag tcatacatct acaatgagtt atttgtatct atgggtgang  17400
cacagttatc aggtggtgct gagttaggtg tattccgtga taaggtttat gaatatgccg  17460
atgctgaaga actatatcag gaacaattaa tgcgttggat gaaaatatcc aggcagttca  17520
atgatcctga aggtaagcga catcatattc ggacaatcac agccgctcaa taaaaaaata  17580
aaaaaaagac atattgccct cccattgcgg gagggcttat gccattaagg taatatctaa  17640
ataacacnat atttaaaaac atactggtat aanncatcat caattaacac tgttgagaat  17700
ctttttgatg agatcaccag gtgcgatacc aatgcctgaa caataccgtc taaagttatt  17760
acacggttga catgctttct tttcaacgat atttaattca aagcaaatat tgccacgtga  17820
atctagaatg gatataaatg ctttgttacc tgttacgcga tatgtcttac cgaatacaac  17880
agttgtttta tatgcaaggc tattcatgat tattccttta acatggatta ttatcatgtt  17940
tgtaatatag cctttaaatg tatttaaata tttattaaac cnnatagcga tgngctatat  18000
atgttttnaa tacctcatan gccttatcng ttgccatgga nctattgaca aaatcagaat  18060
gatcaatctt aataatctta ccgaatgaat cataatcgat agttgtaacn nctattcgat  18120
cactatcacg gatcaatagt ttattttatt taaaacaaaa atattccatt tctcgccatc  18180
ggctaaaata acatcctcat ctttaagatt aagacgaaca aactgtttta cataaatact  18240
taactgagca actgttgaca taatgatttc tcgatatctg ttaatgaact aatcatatct  18300
cggacattna tggtaataac atttttataa gttaaataag ttggatatga acccataaat  18360
gtaatagtcc cacagatatg atttttatat ctaatatcaa nacanccgtc atatctccag  18420
ataaaatcaa atgatccttt agtgtggtgn tcaagtgnaa gaatagaacc actaactaat  18480
```

-continued

```
ttaggatatt gttcaaattc agacattaca taatctgcca gttccttaac ctcaggataa  18540
tcaatcaata atagcatata cgtaaatctc aatnagttaa tataacaccc catccagggt  18600
ggactctttc gaaaaatggt aatgtattat ttcgtatact ntctgcatca atatttggaa  18660
tgtggatggt acaacagtgg gggttactgt caatcttgaa atagaaatta tcttttaaat  18720
cttcaacctt ggatgtttgn aatggatata aaataccatt cccccaaaca taccaacgnc  18780
tatacagctt atcgtttaac cgcttctcaa taaccgaatg cgatttgaaa cgaggaactc  18840
gcaaacgcat cccgtttact tcagcccatt tgtctacccg ntcatagcta ataattccat  18900
ccttaaccat tacaaagata aatccctcaa ctatgttggg gagacgaact acgtgtttca  18960
gaaccatagt aaacggagat aacgtcagat caagttcagc tgccatttgc tcgtcgagct  19020
ttttagcagt gttctttgcc atcggttatc tcctaatata cagattatta attatcgcta  19080
gttatttaat atctgcaaaa ttctgattta ctttacccat aaaaatacca tcggctctat  19140
cgtcataata aagcttccct gctttagcat tacatanaac tccataaatg tgaccattgt  19200
aaccatcaaa attaaataaa gatggattat gcggtacatg aatgaatccc attttatcgc  19260
acagaaactt agctacagca gccgatcggc taatacctgc ctcacagtgt acgaataggt  19320
gttgancctt accaagagct tcacagaang aaataatacg ttgtgcatgn cgatgatcaa  19380
atagatcata agaagaatca acataatcct caatgtcatc aacattgata cgtaaataat  19440
taagatgttt tgctgaataa agtgggactc tacctttctc cagtagacag atcatatttc  19500
taggggaata aaatgattca gccacatgca aaggaatata agtaactgta tttactggct  19560
tcatattaca cctcgttaca aaaaaataaa aggagccccg aagggctcca gtatangtta  19620
atcgaataca agaccactac tagttgcttg gtcatccaca tctagagtag actgacgctt  19680
acgcatatta gctttggctc gattcatcat ttcacgacgt tcttctaatc gnttacgaat  19740
atcttcaana gatagncnan tgatcacaaa atgcatttga tcgaaatcat atttctcggg  19800
atcagcataa ccagtggtac gagttaaaac agtgttaatg gatacttcgc gatcagggtc  19860
agtgtatagc gaagcaatag aaattgggtc cagaatagcc tgggcttctt gacgatcaaa  19920
acacacgtgt aattggacag tctgtacagg tacatcatgg tgtttatgga agtgtgccca  19980
gttagtgata tccattagat caagactttg gtgttcttga ttaaatagag ttactagtgc  20040
atntagtact tcnagaatgt tttggttcac cattgactgc ggtanacctt caacattctc  20100
atgatagtta ataatcatcg gaactttact aacagaggaa accccttcaa angtcttaag  20160
gctaccactn ctattncgaa gactaatatc actgtcgtaa gatccaatga ccacacttac  20220
aactacttca ccttgttgtt gtagatgact nacaagngaa ggaccaatng ttgaaccaga  20280
agcaccaccc attgantana cnacnatgtt agnatcccct gctgggaaat gatgggcaat  20340
ggcaggaata tgtgcagaga ttagttctgc ggctgcctta cgatctttac ccataccgat  20400
agcacgttta cgtgcngtct ggtcagctag cttagtatcc gcttcaataa tgatcgtatt  20460
atcgtcagta ttgtgtttgt gtttattntg tacactggta tcaatgtagc aaacatcctc  20520
atgataacca tggaatagtt caccaatacg gaaaccagca ccaccacaaa agtaaattcg  20580
agttttactt tagacatcat tacacctcat tgtgattaat ataattcata taccaacttg  20640
taaatggtat cagtgcttaa aagtaacgat ctcttcatga gttcgttctt gatgaacatt  20700
aattcattaa ccactttacc agtatcagat ttaaattcga ttaccatctt atctcgacac  20760
atgtatgttt gccaagtacc accagactta acacaatcaa taatcatgtt aagtacattc  20820
ttaacttcaa tcttactaac tttataacga taaacgttta gaagttcagt aagccatttc  20880
```

gtttttggga ttttggcatt tttacgttct tttgaaatat caaaaggaat tagtgcaatg 20940
atctcaccat ctttgttggt gaattcaaat accattcctt ttgagttagc taaaggacga 21000
atgttntaat tncctttanc actncatact tcttcagata acttaactaa cctatctagt 21060
tgaacatcag atgcatgaat gttatcttct ttaaatgctt tctttagttc atcatgagtt 21120
agtggagtac gtactagagt gtaatctttc tgttcagtca tttttcattt ttncnatttt 21180
cnanttcaaa ttaaacggta ttggctttta tagccaatcc cttattacta aaagtaatag 21240
attctcgaac taaggatggt tataccctt ctctaataat aaggaatatt atatgggacc 21300
ccccaaaggg tccccccaca taatatacta tttatataat ttcttttaga agaaaagaga 21360
taaataagag aaatacagtc tattaaagta atgaatttct caaaaattaa atagtacacc 21420
gcncnnnnnt tncgncggan ggtcctgccg gacnanngtc cggatgtgcg nnantagngg 21480
gtttttcaaa aatacntgca tcgcggttga attgagnggt tgattataac gtnngatctt 21540
aatngtaaat agaacttcnt caacatctgn atgncatcct tcnaaactaa aatatacttc 21600
agtccgatca ataaactgat acatttctac agctggttca gctggatctt taaaggccan 21660
cttattagcg aaataatcag tatngcctag aattaattct tttacattan ttgcattctt 21720
cttatcaaca aggaattcaa actcttcaag gttatctgtt ttgaaaatac cttgatanga 21780
tgacgactng attagttnat cactgatatc atcaacatga acncctggca taaattcaat 21840
gactggtaga ataagcttgt tacctcctac gccntnagcn atatgaatnc caancacatt 21900
accatcacta atgtattcgt cattaccgca aataacggca ccagccgcta gatataaatt 21960
atcaacatat ttcagattat cggcaataat gcgagatagt acatattctc gcaccatggc 22020
atcatctgga cttgactgcg gtttaaaagt atagtgggtg ttatgactac tcatggtcgc 22080
acatgtaaca aaaactgaaa tatctactgg attaaatacc caatgaacgg agatatcctc 22140
taatttatgt ggatgatgta aaccatctag cttagatagg gcttggagtt gttcttccca 22200
ggtgatgtta aattgagtca tttttctaac ctcttcattt attaaaaata atacacttat 22260
tttactttag cagttgatac ttcacataca ttaactaatt gttcaaataa cggttcatta 22320
tctggatcat taactaattt gatgtattaa taataatacc agaatacagc atatcagctg 22380
catctcgatc acttgtttta attctggtta caccttccca cttccatcca tagtaaatta 22440
aatcaaatga tgaaccaatg ttaaaggttg attgaataaa tttgcatgta ccattttctt 22500
ttaaccaatc aggcctatat ggttcatttt tataaaattc atgcatgagt actttaaaat 22560
cagttttaat gttttcatga ataatgcaat caatagaatt aagagcttca tcaagagctg 22620
atttagactc aataatgatt tctaatacat tggcagattt tagtgtaatc atacctagtt 22680
catctgagtg tgctcttccg atttgaaata cattgagctt accaattggt aaggtggctt 22740
ttaatggcag attagtatag tgagatacat cgcttttata actgtcttca tatgactcaa 22800
ttaaattaag ccatgctctt tcaatacgtg tattctcaaa atgntgttct tcttctagta 22860
gtctagaaat tagatgatta atgtattgaa cattatggcc agtaccngta attnaattat 22920
atttcgtatt accggtaatt ccccatttat tattttcttt atttatccaa ccgtagatta 22980
cactgttttt aggatattta tttttaaaat tatcgtatat ttcttttaga tgtggattag 23040
gggtaaaact aaaagtagtt gattcagtca ttatagatac ctatttgaat attgtttatt 23100
attgcaaatt agtaatatag atcttaaact tttttaactc agcataaagc ctcccctagg 23160
ggaggcnata tgttcattta tctatttcag cgtttggatc ataccaaggt aataaactta 23220

-continued

```
gtagtgccgg ttgttgtttc ttcatatcct ctaagattgt tgcttcactt gcaccttcta  23280
acatagtggt gaaagtaatc atgttcttag agttatatat cggacgtaga ccattaccaa  23340
agaatttnac ntgttgaacc attattttga aatcagggtt atcgactaca tctgggatat  23400
agatancagg tggcgcactg aaataacgtt taattaactc aatagcccaa tacgttggta  23460
aatcaccaaa ctgtgatttc actgtagcta ggtttaattg gaatgcttta ggttcttcag  23520
gcggcggttc caccggatca attggatcag tgggttcttc agggccagta ggttcagtag  23580
gctcttcagg atcctctgga tcgccttctg ttggcttttc ttcagatgtg ccaccatcag  23640
ggtcacntga accatcatca tcttcaacgg gctcctcagg cgtttctata ggctccttcg  23700
gatcttcctg attctccgat agatcgggct cttctgattc cccatctcca tttgcttcag  23760
tagaagacgt gtcttctgat tcttcatctg ttgtcgagtc agttgnggct gtgttttctg  23820
aatcggcagt ggtatttcat tttcacttga ttcagtagaa acaatttcag taggagtggt  23880
ttcaagttca ttgacactat cctctgcatt agttacttca ttagggattt cactaatttc  23940
tgataatgtt actggtgcac ttactgcgcg agcttttcgt ttagccatgg ttgtacctta  24000
gatagaatag tattatggta agtgactaat tcaggatcag ttaaattgat actttgaata  24060
gtcatattca gaattacata ggagtccatt gttctccggg tatatccagt taattccatc  24120
ttgttatatt tctgtacatg atctggaacc caatcaccaa agataacacc cagtttatga  24180
aaacgataca ccaatctgga taatgcacgt tgggtttcag ttgggaatat atcgggaaca  24240
ttttcgggaa cagtacattt atcactaaat ggagtaataa taggaccacg atgaatggtg  24300
tagctaagct taaagataac agcaccaagt tcgtcattaa tacgcctaag tatacgataa  24360
ccataatcgg tacgctcaag tttatataca ttactaggat cagcatctgc taaccttcta  24420
gcatgtcgtc tagtgcacgt ttgataccac ggttatagat gagttcacgt tctatgtaat  24480
ctctctcaaa agcggcctga gggctttctt tctcaaattc cttagttact gaccaagaaa  24540
ttgtttcacc agttaattca tcagttaaaa catacagata tgtcatagag tcaacgtatg  24600
aatactggat agagtancgt gataaatcac atggcttagc atttaatcgt tcttctttta  24660
aatagaaaaa catatcttgt aaatgattat aagtttggca gccaccacca agatgatcaa  24720
tatcaataga cgtatctggc ttgactggag ctttgcagca actcattaca cacctctaca  24780
attatatttg agttattgta ctacagatga taaagagaaa atacatcata agccctctcc  24840
ttatggagag ggnattatat ttacatagtg ttaaaacacg cattaaattt agataatgag  24900
cagccagtat aaattaatga ttgctctagt tgtatgatga catcgccatt actatcaaaa  24960
tcagcagcaa taaaagtaga ttcagttatc ttaaaagtag atggcagcat ttctaaataa  25020
ttaaatattg cttgattatc gatgtcatga ggatttaaat ccatatgtta cctatacatn  25080
gatagttatg gaccaaatat taacaggnct gcataagaca attgtgatta aatctccatg  25140
agttctctga taatggttga aacacataac tttgattaac tttaattttt tagtttcttt  25200
attttgaatt tctttgataa gtgattcaat aagatcagta gtaataagtg aatgaccatc  25260
aataaatggt tttatactta ctagcgaatc tttgttaaat agaattgcat catcatattc  25320
acatgtagat gcggtcttgt atatggatgc aactttatta actttgtcat nagtgactat  25380
agaaaaatta aattcantct tagttttact naacgatgtt tcaaataatt tatatttatc  25440
aataatagtt ttattatcaa taaatgattt cattccaata tttaaatcta tgtccagggt  25500
ataagantta tgtattaatc caactgatag ttgagtttca ttaccactat tgttaaactt  25560
aatattatta actgaacata tctgattatt aataaacgat aataatagtt tagaaatagt  25620
```

```
tttaataaca ttaacttcat aatcattatt agtacaagca agtgcagttg tcatgtatcg  25680
actaacttga cnaacatcta gtttctgata gnnactanca ctatctancc atgggtcaat  25740
anttaaaaaa atccttagac tagctagaat atcngaagat gtttcagaat aaatgaaaaa  25800
cacattatta ttaagatcat cttttagcca accactagtt ctaagatttt ctagatcttt  25860
ttcattagat accgattgac ttaattgctg aattaaacta gggttagcta ggtttaataa  25920
actaatcatt ttataaacca ttttattatc ctctaattta tgtaattaca tggaataaat  25980
aacataagta cttttatgac ttatgatttg attctccagg aggttttccc aatggcaact  26040
attaaagaag tccttgatag aaattttaag gatgttcaat ttgatcgcga tttatgtaaa  26100
agaattattg actttactat cagttttatg aataggaatg ctgatcactc tgctttcttt  26160
ggtggtgtat tactaggtgt acaacaagtt aaattcttcg atacggatcg tgagatttgg  26220
tatgatgatg ttttacgaat tgatgaagcg ctgttagtcc aagattttaa gtcagttgaa  26280
ttcattgacc ctaaccatcg tgtaatgtca gatgtattca atcatcttcc tgcctatatt  26340
tgttctaggc ttttaaaaac aactaatgtt cctttgaata ttagacatga agcaatggtt  26400
agttgtttca tggtgttgca ttttaaatat ctaacatctt tacttgtacc acgctttaaa  26460
tatcctgcac gtaaagaagt agccgaagct gcattcgccg cactcaatta tcgatttgac  26520
attaagacaa ttgggtcatg ggagaaacta tttaggcaac gggctgaagg tatcattgca  26580
cctgattcta tttatgcacc tttcttaact ggtaaaacac aagaactgga ttattggtct  26640
ggtcgtgtgg tatctgatac tcaaacacgt ctacgtgaat taatcaacaa gtactatgat  26700
gtttatatca gaacactgca atcaggtggt aaattagtta tttcatcgga tatggctgtt  26760
aattctgatg gtgagcagat tctacgcgat aagtctactg ggtatcgctc atatcttact  26820
tatatccatc aagttgcgca acaagaacaa aatttcatta gacctgagtt agtcggtatt  26880
attgaaaaga taatgcccac aatgccacca gaaatgttca tggcgacact tagacacctt  26940
tcccgtaaca tcggtcaacc tagggcacaa aagcttgaga aactcgtaga tgagtgctta  27000
ttgtatgctt tcgattatat gcaatcactc cgtacaatgg ttgctagaaa taatgatcta  27060
caaacattgc ttgtaaaaat acgagcaaag ataatggcat ctaaaacaga aaatgctcaa  27120
gttattttca tgcgtgaaga aggtgagaag ttagttaggg atgcgactaa ttctagggta  27180
cctgcatata tcgcagcaac taggactggg ttgatgttgt atttaattct acgtgctatg  27240
actaagaatt actatacaaa acaaaataaa cataatgccc tcccgcaatg ggagggctta  27300
tgctgttaag taacattagc tagattgatc attacataaa tttttcagag catcgtaaat  27360
agccacataa gtaaaatagt taaactatct ttaatttcct tacgtggggt gccactgaat  27420
ccaccccatg atacatttgt attactaacn catacagtgc taatagctgg ctcatgatag  27480
ccaccatcta ctttacgctt tgcataaacc ttagccgtaa tttctccacg taactttttg  27540
aagaaaacta gagcacccgg aacgactata cgtttattac caatcttcgt aataaattct  27600
ttacgattag taaagtgctc ttttaataaa tcattaataa ttttagttaa actatcaatt  27660
tcattcttca tcgacacgtt gttagttcct tacaaataaa cttgataacg tgatcactta  27720
caaatttcaa tggaccagaa caattagatt tctcaatagc ggtttcagtg tatgaaatta  27780
tttgatttcc acttaaggat aatgaatcaa ataattcata agagttatta ttttattctt  27840
aaaggatact gcatattgac tatttcacta ttgatgcaaa ataggttaat agctgggata  27900
gatacagagt tatctgaagt atggctattt tccgtaatat tccaattact gtatacagtg  27960
```

-continued

```
aaaatatttg cagctagtaa aaggttggca ttaaccgttt ctaaactaac atactccaca  28020
gaagtacctt tatgccaata tagttcaatt ggattaaccc aagtataccc aatggtttta  28080
tagaaggcat gcattacata ttctcgccaa cgtgtgggtt tcttattatc agttaaaaca  28140
cacgtaatat tgcctgacgg ataaatgtgg tggatgctac atgcattaat ttcatctcta  28200
acattagttg tttcagtaat attagaatga tcctgtttga atagccattt taaatgacta  28260
ttagttgtgt catcaccttc cccatttgca atgtcatttt ctaaccactt ttcaaatgta  28320
gcttgtctat caggtgttgg cattccccaa taggtagcta aatgaaacga taatagtatc  28380
gaataatatc atcatcgtta agaatatttt atccagtttc cagtgatgtt gatactcgta  28440
tacttcgctt ggaatattat ttacttgata ccatgtatta attaatactt gaattgttaa  28500
ttgccgaata ctctcacttg ttagagtgta atattccctg ctatgcggct cttcaattgt  28560
cacttcttga tcagtataac caatgtattt aggtttacca tcgatgagtg caaaattaac  28620
attccatgat gtatcattac taaaagtgat attaataaaa ccttgttcaa agctaggctt  28680
cactacgaaa ctgacatcat ccttctgata tgtcatttgc gttagaatac caaaattaat  28740
tttagatgta aattctttat cgaagttatg tttataaagt aatcctagta aacaatcaat  28800
tttattaata gtgtggtttt ctaataataa atcagtattt gtaagttcat taattttcat  28860
tttaacctct ctaaaattta caatctagtt ttacttattg aataagcaaa catgtaatat  28920
atatcttaat tatttttagc atagttttta acaacataaa gcctccccga agggaggcga  28980
tatgctttag ctttttggtt agtaccgaca gtctgctcat tcttttcagt ttgagcattt  29040
cgccgaagtt gactaaccag accattgcca gccgcaacta catcgggaga aaagaatgca  29100
ttgatatcaa agttctgatc ttggttgcga gtcttcccag gtgggaccat cggatatact  29160
tttgccatta gcttaatcct acaccgtcgt aagttacccg attaccaact gcacgttcaa  29220
tctggtcttg aataccatta cgtgcacgta gtacgtcagc agataaacca ccccagtcta  29280
atttctggtt attggggttc ataccgcgaa tgtttagttt acggaacatt tgacgagcgt  29340
attcttgtac accttcagaa acatcagtca gtgcagagaa ctcaacgttt agatcaaggt  29400
tctgaccaat ctgtgatgca tctttacggt tttcccaagg accagtagtt aatgggaaca  29460
tgttggtgca aagataagcn ttaacgcaat cctggaaggt aggatcnggt tctacgaata  29520
gaacagtcat accgtagaag gtagcgtcgt atttctcaac cggtacaatg ccatctgata  29580
caatacgcgg tactttggta ttctcatctg caataccata gttgatccac cattgtaaga  29640
aacgttggat agcgcggttt tgtaattccc agcaaccaaa gtttgggtta gaccgggcac  29700
gggttacgtt agtagccgtt tggataactt caccagaacc accccagggt gcttcagcgt  29760
tatctacagt aagcgtacgt tgtaaaccat cgatggtacg agtatgcgtt tcaacgaaag  29820
ccttaagaca tgcaactaac cagttagtat tactagcata cttaaagaat cgtggagcat  29880
ctagtaggaa cggcactaag ttacgtgcca catatggcgt gttagtagcc aggttagcta  29940
agtcaggccg aaatacgtta gtaccagcct gagcaaggtt tacagtgtta cgggcaccac  30000
cagcaccata accagtctcg ggtgccatcg gatcattata gcgagccatt taacttttcc  30060
tcattctgaa agccacccac tcattgctga gcaggtgggg tttcaatacg aacagtttcc  30120
agattgaagt tcaacgtggt ccgcgggtta ttagcctcaa cagttacgtt gcaagtccag  30180
ctggtgccgt tatttgcgtc aatcggagtg atctctgtac gcgggataat gttgacacga  30240
gtaccgaaca tatcacgtac tagatcgaga atatactcgt cacaacgctc aactaattgt  30300
tcaggtgtta gtgtagcatt accgctaaat tgagcgtgta ctttatggat cagtcggatt  30360
```

aatacacagc aaatattaac agtaatcggt gatagaagta cagatgtatc atctagcatt 30420
actgaacgta ggcacggata ataggagcta cgatggtcat atgactgact ccaagtagca 30480
ccattcgccc aagcttgtgc ccgtacacga tcatcaaaga atttaacatt tagatcttta 30540
acaaaagtaa cacggttatt aggacttaca tccatttcca tacctggaac tagattacca 30600
gttccagcac ctgcatagcg tgcccatgac atagctacgt ctaaaagctg cggtacatat 30660
ttacgatagg taccatccat tagtttgcca gattgcatta caatcatagc gcgacaaaca 30720
ccagttccgt atagagtgga ttctgggaaa gcttttaggc gagtgataat ctgttgaaca 30780
cgacttagct cagtagcttc atcaggtaga cgactatcag tttctacgaa tgtagtgaag 30840
aaatattgta gatcacgccg cgcacttagt acgcgcattg cccgatattt tgattccatc 30900
ggaaggccag tgtcataaag aacaccgaac tgatattctg caatgttatt atagcgatca 30960
tttaatttgc caaagttaat attttcaata tcaactaatt tggcatattc ttctagatca 31020
gttgtaccgt cagtaccacc actagcatag atgttaccat ctttacctaa cgtaatgccg 31080
ccatctagtg gaccgagtac ntgaataccc tggtaaggat caccatcaac agctaagaag 31140
gttaggaagt caatttcacc aggtgcagta gtatgcgcag cagcggctgg gttaactcgc 31200
atctcagtgt cataaatcat ctgacgaaca agatcaatgt tctcatgata gacgtagaac 31260
tgagagaacg gtgaataaag tggacttagg ccagagacta caccatcatc tgagtaagaa 31320
tcaactaata catcaccaac ataaaggtca gcgttataca tatcgctgta aacaccttta 31380
tcaaatgtaa tgtttagata atcttgctgg tcagcagttt tgacaataac tggactagtg 31440
cctacttcag gcttctcaat taactgaata cggaattgac gagttttaaa cttcgccata 31500
gctgcttcat cgaactcttc gatatcagca gttgtagtac tccatacacg cataccgtta 31560
gaatcaccta atttaccaaa gaaggaaacc ggtgcttcaa ataacggata tactagtgat 31620
tgagatccat ctttatctga tactaaagta cctggtagta cacgttgtgt acctacttca 31680
gaggtattat cttcaataag aataatacgt gcctttagac catcaacttt atcagcagtc 31740
gggactggtg cattaccaat gtcacgaaca ctgtttggat agttgaaacc actaagacga 31800
cgaatcgtaa gtgggatttc atcttccaca atttcaatag caacaattaa ccgagatgga 31860
ttagctgcat cttcaggacg tagacgttta acataaaacc attaccacgg ccaagaaggt 31920
taagtgctaa tagtgattgt gtattgaaaa acttactacg tggatcaagc gatgcttgac 31980
catagatgga tgcaaaacca tcatcagaat caccgacata agtggtttca gtcggtcctg 32040
tctcagtgaa gagacgtaat agcggacagt gttgtgcgaa cgtgatgtcc ggacggatca 32100
ggggccggcg gctacgatcc cggataccat taaacacaac cctagggaca gcgttgtaat 32160
atgccatctt tttgattctc ccaagttgga gctttgaact cgatgttatg agtgttaact 32220
aacagtcaat catagatatt aatcatagtt gaccatacta gttatttttt actatccatt 32280
taaggagtag cggtaatgtt tttgctaccg tatgaaacta cagtttgtaa aactctatac 32340
aatcccaccg gcggtggaaa attatatcct aaacaatatg ttgatcaaat tgaaaatgcg 32400
atcaagaaag ccaatgtgta tctacccatt ccacctgttg atgcacgtaa tggtgaaacg 32460
ctagagcata gtggacagat taccccagtt gatgattttg aggatattaa gaaatttact 32520
caaattgtca atatcggtga tcgtgataat cctaagctag tngttgatgc tcgtctatat 32580
aaaaagattg aacagcgtac tggtattcct aggattattc agcagaatga gtggcaattc 32640
caatatattc ggatggcact taatatcaaa ctattacgtg aaggcccgga cttcctccat 32700

-continued cgcttaggtg atatcccagt taaagttttc tataattgga tctcaggcat cctaacacaa 32760
aaatacagcc taccacctga atcaacccaa gctatttggg taatctgtgc tgtttattac 32820
tttgctatgc aagatgatgn tctaacagaa ccagntcagg aacgngatcg gttaatacca 32880
attatttccc gtcttacata tattccagct ggttttattg cngatgttat tgatacatta 32940
ggtccacttc ataatgccgg tgatctagct tatgagattt caactaangg ncgttcgatc 33000
aggatgggta aactaaaatt cagtgatcta caattattag tatcaccgag ttggtttggt 33060
accgcttccc gtgaaaacgt aggtgtggca ctagaacaca tgccaactta catcacactg 33120
atctacatgg cattagctga tcgctcatac cgtaaaacag ttttaagtca gaaagttgaa 33180
atgatttcac gttctgatga tgcaagtcgt tttattaatc tagtgaatga agctgtaagt 33240
agccaattcg ttaagtaaat ataggggtga atcaatgaac gcatatctat tgcgncatgc 33300
gattgataac gtttggtgta acccagccca ggaccgacag tttgtttatg aactgaaaca 33360
gctnacccca cgctacggcg tgagggtaaa ctgggtggtt gattacaccc ggtataagct 33420
accagtccaa agtacacgtg attattggca tctttatcaa attggtaaaa tgattcctaa 33480
acacctgggc ttgcctaagg tttacaataa gtggatgagc ctaaatgagt tggctcaaaa 33540
ccatttaaat ttagcagacg tttatgtaaa tagtggtatt aattattcac gtaatgatac 33600
atacgtttta ataaccagtt cgcaaaatct tttaattgct gttaagatag atccattatt 33660
ccctgatctc gatgaaaatc aaccctatct tcatgtttat aacaatgctt actttcaatc 33720
aaatagatcg gatgtagctg gacatagatg gttagtttct gaatcgtatc gagttaaaac 33780
aatatctgaa ttaactcaat ttcagattaa gataatggat accatagcat ctaaaggtgg 33840
tgttcctaaa tactttgtaa atggtagata tgttaatgag atatctcctg ttacagcaac 33900
agtcggtgat gtttgtgatt tcattctaga tccatccatt aaaaggatgg tagattttga 33960
tctacgtaca ttacctgttt tcatgtcaga aatagatagt gaaagaaata tattttacac 34020
tacactgata agactgtgca aacaattgag ttctttgatg atgttgaagc atatatctat 34080
cagccattag gtaataatcg ttatactggt gttaattacc atcataacga gagccgttgg 34140
atgcggatgc ttacacataa agattattct ataccaactg cacgaattga tcagtttaaa 34200
gcacttcatc cagaagatcc tcgacgtggt gctgatccta ctcgttggcc aagtcaaaac 34260
tggaaagcat tagataatct agtatttaga atctacatac atcattctgg ttatgatcgc 34320
ccattagttg ctgattcaca tcgtattcaa attctgtatc gtttaaaatc agaagatatc 34380
ataagggcta tgactggtgc agattctggt aatcctttat ggcgagctga aaatctagag 34440
caatcaccat attgctggtt catgtcagca ccatctagtt tcgtataccc attaacattc 34500
aatctacctg aagaaacatc gcctagtaag gtagaagcgc agaatatggc tggtgatgtt 34560
tttggttatt atgaagcagc taatattcaa ggttataatc cagcttgggt ttataatgat 34620
gctggtctaa agaccgctga tttacgatac aactactggc tagatgcaac tgtatttgag 34680
tatgatgaga aaggtatctt attaggttat aattatcata cagcaggtcg caaatatttc 34740
cctaaagata gtcgttgtgc atatgttgaa tgcattaatg gtaaaggaag tgtagatcta 34800
catgaagcat atgggaatga tcccgtgcct ttacgtgatg gtgacaactg gcgagtttat 34860
gttagtcctg tttgggctgg cgtaccaact ggcgaatggc aagatataac agaccatcca 34920
gatcgaaaca actggggttt ttatgatgat accactgatg ataaacgttg ggtttggata 34980
gctaagtcaa atgagtggta tggcctagta agaaccgatg agtacttcta tctaaaagaa 35040
ttaaagttta ataaaactga tggtatcatt aaatggagta tacgtaatac tgaaactcat 35100
aatggtgtaa aagtcgataa attgatggag ataccatttg gtcagtatga tgtgtttgta 35160
aatggtcggc ctatcattga aggtcttgat tacacgcgtg aatggcctca aactgtatta 35220
tgtaatctgg aatatttaaa tgcagatcca aatgcagtta atacgattct tctacgtgga 35280
acaggtttcc caacaccaga tttaaaacca tacgaacctg gcgagattgg tttcattgag 35340
tatggcgtat tgtctaatga tggtatttat aaagtacatt caaataaaca atcacgcata 35400
atcattgatg gtcattatcg tgaccctgct gatcttgaat tccaagaaga tcaaggcact 35460
actgttatca ctgatgaacg caatggtgca ccattccaaa tacaaacacc acaggcncgc 35520
ttccgngatg tttataatga tgattaccaa gctaggatta aggatgatgc acgggataaa 35580
caagtcactg attttatgac tgaatatttc ccaatgaaac ctcaacctaa tccggacaag 35640
atcgattata gataccaggt gctttcagcg ttttcatgta agatcattca tgatatcgta 35700
aaagaatata tcaaaccncc atatcaaaat ggacggtata gtgacgatga tattgttaag 35760
cagctaaaag attacgagtg gttagcagct tatgacatta tcaataaagg ctacaacaaa 35820
aataaagttg tagtttatcc acattggtat actgaacctg tagaactaga tatttccaat 35880
gggaatattt aaatcgtatt ctatcgatat atctacgtga agtaccgcca ctatccttgt 35940
tcgttaagat taaaaggaat caaccatgac aacgtcatat gaaagtagcc agtaccaacc 36000
accacagcat aaaaaccatt tctggtttag aggtgatatt gtctcatatg ctggtganac 36060
tggnaaagca atccctgcta aaggagattt agtatttgac gcagcacaag gttggtttat 36120
tgttcgtgaa gttgatgaaa caactggggt atctatctta gatccatggt acatgcccca 36180
aaaaccaggc aatgaaaatg aacaaaacct actagttgct gtaggtccag gatatagctc 36240
agaatcttat cggttattcc tagatcagtc tgtaacacca tttaatattt gcccagaccg 36300
gcgattacat ttttatggat caatggtgca tggctataaa gttttcctag gttcagatat 36360
atcagaaata catggtaaag tgatttccct gttctatgat aatgctggta attatctagg 36420
gccaactata ccagttgaat cagtacccga tccattgact caacagaatg ttgttaaagc 36480
gttaatgaat ggtaggactg ctgagaaaat gcaaaatggt gaacgtgtaa ctctagtagc 36540
ttatgatgac gtgggtgggc ctgtttcgat tgctcaactc gttgtaatga atactgaagt 36600
tatagcncaa gaggatacct cnaagaaata tgtaggtggt atcactattg aatcaccatt 36660
catctcncca gctgatccna aagttattga gttcccatta aacgtaccag ttgaatcatt 36720
accgatgatg ggtgctgttc attaccgtga tggtaagaag catgtgatga atattgatgg 36780
tacggcaatg gcaatttatg gtttacgtaa ctatattgcc actgaggaag gacaagagtt 36840
taaattaact ctatcttacc aattagcaca agatgagtta tcatacttat cgactccttc 36900
ggctaaccgt cgtattcagg agacatatac agcgcgtacc acgcctgtac agggtgctta 36960
cagttgtcgt atgtttgttt atccngcttg ggttaatgag gcagtnggtt acagattaga 37020
attctggtta gccaatattg atcgtcaaca aatttggaat attaccccat atgttgaatt 37080
aggtgcaaac tcagcaccct ttaacccacg tggttatggt actatccaaa cactaacata 37140
tgcggttaac ctaaaccaag ttgatggacg attcctacca gttcgatttg catctacttt 37200
ccaagtagca ctattgagcg ctggtaataa tcggaatgct aactgggana tctattcacg 37260
ccctgancaa ggtgaagcat atggtcgtga tcttaaagcc gatatngaat ttatcaatgg 37320
taatctttgg gatctccggt tagctaatgg ngcacagtca caagctgcct ggcttaagaa 37380
aatgtacttt gctgctgagc cattaactgg tccaatggaa gctactccnc cnacacctac 37440

-continued

```
gcatttccgg gtgcgtacag tgcataacga gtatgagtat acggtaagtc aatggaatac  37500
tgcnttncgn attaatgctc aagatatggc cgatggtgct ttactacaan tcacctggat  37560
tcgtcgtgag tatgatacng acctacagtt agccattacc gcattacctt gtttacaacg  37620
ttaaatatan ngccccctag gnnnnnccta gggggcttta taacgtcttt taacacatta  37680
tccatatgag actatacttt acaattgccg ttcaatacgg ctttattatg gcacattaaa  37740
ataagtacct taaagggcag tgtatggacg ttatactttt caatagtgat tgggataaat  37800
actacagcgc tagtgttgat cttactacta aaaataaatc ntttataaag ttagcnttna  37860
cttataaaaa gatgggtatt aaaaattaca aatttatact agctatattg gaccaaggtt  37920
taattggggt ggatccatat gaccctaatc ttagcgaaga aatgaagttn cgtattaaca  37980
tggaatgcaa atataatcct tggtattttt ttagggaagt ggcaagaatc ccccctaact  38040
cgggtaataa nccaattcca ttccaagcta accgtggtaa tattgcttta ttctggtgtt  38100
atttcaatca cgtagatttt ggtttattac agcctcgtca gacaggtaag tccgtatcaa  38160
ctgacgtgct caatacaggc atgatgtata tctggggnga gaacactaag attaanctta  38220
ttactaaaga taacaaacta cgnaatgcta acatcgagcg tctaaaagta atgcgtgatt  38280
tgttaccaga gtatatccac tatacngatc cattagatgc ggataactcc gaattgatga  38340
catgtattag attaggtaat aggtatntaa cagctgttgg tcgaaatgat gttaacgcag  38400
ctgataaatt aggtcgtggt cttactgtac caaatatgca ctttgacgaa cttgcctata  38460
ttaacttaat tggtgtttca ctacctgttg cacttgcntc aggttcagca gctcgtgatg  38520
aagctcgccg tgagaaccag ccttatggta acatctatac aactacagct ggtaacatca  38580
ctacccgtga tggtgaattt gcatatcact tcttaacagg tggntgccca tggtcagagg  38640
aattctttga tctaccagat cagaaaactc tacatcgtgt tgtagaaaaa ggcactactg  38700
gaaagaaacc tctagtttat ggtgcattta accaccgtca attaggacgt accgatgagt  38760
ggttatataa cacacttcgt gaatcaggtt cattcggtga aattgccgat agggacttct  38820
tcaatatctg gacagttggt ggtgaaggtt caccccttatc atcagatgag aaagataaac  38880
ttaaaaacaa tatgcgtgag ccaagctgga cagaaatcac ngatgatggt tanacacttc  38940
gttggtatat accaaaagan gaagtagcct cacggatgat gaagggtagg ttcgttatgg  39000
gtaccgaccc atctgaactt cttggtgaag ataatgacgc cactggcaca gttgtagttg  39060
acgtagaaac acatgaggtt atgtgtgttg gnagatacaa tgaatcatca gtnccatcaa  39120
tgggtaattt ctttgcaaca atgctattna natatcctaa tattctttgg ataccagaac  39180
gtaaatcaat aggtatatcg ttaattgacc atgttatctt gattctncat actaaaggan  39240
tagatccatt ccggcgtatc tttaacagaa ttgtcaatga atcatcagaa agagaaaatg  39300
atttcagaga cattcaaact ccgntatcag caagacaacc atcgttntat gataggttta  39360
aacgttattt tggctatgca acgtcaggta ctggcgagta ttctcgtgat aatctattta  39420
aggtggcatt accatcagca atgcattatg gggtaaggac catctatgat aaaccactta  39480
gcacggagtt attagcactt actatccgta atggtagaat tgaccatgct aaggggaacc  39540
atgangactt agtggtatca ttattattag cccantggtt attaatacaa ggtaagaatt  39600
tatcttatta tggtatcaat gttcccatct taggtaaatc aaaattacgt gataaagaac  39660
caagncaact tgaaaaatat catgaagaga aagaacagca aggtcgnaaa gaatttgaag  39720
agataattga ncagcttcgc ggtgaaaaga acccgatgat tgcagctaaa ttagaaatgc  39780
gnttgaaaca attgtctaaa cgtgttaata ttgatgatan cagtggtgta ggtattgatg  39840
```

```
ccatgttaaa tcaagctcgt gcagagcgta cacgtagagt gcgtattaac agatattcta  39900
gaaatagttg gtattaaaca aaaaaaataa taatacgtta ccctcttcgc aatgaagagg  39960
gtatttgaag ttaagnaact ctagcgaaca aaagattact ggagttagaa ttaatatgat  40020
agttagacga tccgtcaatc catttagcat cggaaatctt gtttacaagc tgaccattgc  40080
caatgtaacc taggaaagtt ttattatcat atacagcaat tttgattagc tcatttcgtc  40140
cgtagactag tggcttacca ttgaatgctg ttacttctaa accagacatg tatccataaa  40200
ttggatcagg tctggaactt gtttcaaaga ctttcattcg aagtctcatc tgcaagaaag  40260
cccattttgg gcaaaaaatg tcaagcttaa acttgacgac atatagccct cctggtgcga  40320
caggagggct aatcttttca gaacgtacgg tgttgttata atactgctag cgaaaatacc  40380
catgataggt aagtagctaa tccgcagttc tcttggatga tacctactga cagtgtagtt  40440
gcaaatgtgc tgtttggaac cccactggtt tagcggccag tgggaattcc ttttatgccg  40500
ctttttcttt ctttactgga tatttcttat atttacaaac ccacgttctt acgctggtag  40560
gtatcttcct tcttattata ttcgtagttc tcgatgaggc acttgttgct gaactcgacc  40620
atcgaacaca tcttgtccat gatgacttca gatatttacc atgttcataa attcggcgta  40680
gttgtagccg gtattcatgt cgagatagtc ttgttcgacc atatcgtcat tcaggtactt  40740
gacgtaagcc tcggcgtgag cagtggctac cgacttggtg aagaagtaac gagcgtgctg  40800
acggttctgt tcgaactgac gcagattagt agtggcctga ccgccgaaac cattgacctc  40860
cattaccccg taaacagtac gatcatccag agtagtgatc tgtgcaatca ctacacgaga  40920
agcattttcc gaatggtcga tgaacgtcat actgtaaatc tcgatttctt tgaagtcttc  40980
cattagaatt tcctgttaaa aaaatgaata gacaacccct accttcgggt aggggcttta  41040
tgccgtcaac cgacaataag gtcccgaatc gttacgatct aggtatcaga tgcaggttta  41100
gtcaaacgag ttacacgaat ataaaccatg tagtcactca gagatagaac tttttcactt  41160
atacatcttc cagcgtcatg attacgacat gataaggact atcagcattg tgacccatgc  41220
acgtctcgca tttgaagatc cgccacatgc catacgaagg cagctcgcgg tttttcacat  41280
aaacgtagtc gtgcgctgcc acgaggtatt tttgttgaat cgagaattca caagtgatgt  41340
aacctttttc acggatgaat tcttgagtca tctgatcaaa agtctgtttg agttcatcag  41400
taagagcgac ttgggtttcg aacattgaaa tattcctttt gatatattaa atagttttga  41460
ttatttcgga gttattgaat atttaggtta ccatctgctc tatatagact cggctgattt  41520
catttaagta agcgagtgcc aatagaatac cagcccaaat aacaattttt cgagtagtct  41580
gtttttctat tacacctggg tgtgattcac gaatactacg gtgacaaaat acataaaaca  41640
gacacagact cattgtaaca aagataatgg taaaccatcc tagatagatc attttcttca  41700
cctattttta taaatagagt ttatagttta gtcaggcgga tgatttcttc taaagctgca  41760
tcaacttgat aatacggcca tgaatcaaca cgaggttcgt tatcaaagta tgtccaaagt  41820
tgaatacctt ggagtttatt gtagaataca ttgattctga ttccttcatg gccaacaaga  41880
ccttcaatgt aagctgcacc atgcacatac gtaacatgta gtgcgtactc gctatcttca  41940
ccagcgtatt gcataggtct ggagtagatg aaggaataag gattaaatgg atcagcctga  42000
gtgatatgtt cgaagaattc tttcaaacta gattttttca tattggacat tatattttcc  42060
tcatgattta ttaagtctat cttctaggag gtagacttaa tactattcga tgttatttta  42120
agacgcctgc cttgtaacct ttaacaacag ttctagcttc taatgcactg atttcgccaa  42180
```

-continued tgtgtttacg cagtgcttta atagcgttga tggtaggttc attatccgcg atatgtcgcc 42240
agtttccctt acccttaatg agttcaacat cctggacata tagaccatct ttaactagat 42300
ccattgtttc taccaacttt tcgacttctt tagttagatg cgtatgaaga ctggcgaggg 42360
acatgtcagt catttgatgc acatcataga gaaatcccta ttatcagaag acgataaaat 42420
ttctttggtg agtttattta cagtgtcaat gtttgctgca attgaaacta gcagtgcagc 42480
atatttctct gcattataat tcattaatac gtattcctat ttaaaattgg atttagtgta 42540
atgcggtaat actgcgaata tctaattcat gtaaatcata tttctttagg aactcattca 42600
ccgcttgctg aatggtgtac ccactcggag attcccactg agtaccatta aaagcaataa 42660
tacgataacc taccattttt tattcctcta atcacaaaat aaataccctc ccgaaggagg 42720
gtatttatat cgttaccaat tgattacagc gacaaactca aatacccgac acaattcttt 42780
atcacgatgg gcatgatgaa aagatttacc ttcaataccg caatacggat aaaacaattt 42840
tcggtgttcc gtgtcgccga accagaaggt ggtgttattg gaatcaacca caccatggat 42900
agccacatca cgaatgtact gaaatacatg aactgcctta tcagtgatca ctcgaagttc 42960
tacaccgtgt tccttcatca tagccaggat gtcttccttg gtgtaatctg cttgttcagc 43020
attggtcatg atcttgtgag tcagagaacg cttttccttg tcaccgaaac agatacagac 43080
caattgcacc aactgacctt ctaccttgag accactggtc ggttttagta gaacgaactc 43140
atcatatttg taatcattgg tgacaatcag tgccgactta ttgcgagtga caatgcctag 43200
gttatacgac ataattaatc ttcctcattt tagaatatgt tgaaccttgt ggatgtcttc 43260
caggctatga ccaagaccag tggctttgta agaatgttcc tgatcaacac gcttgtgata 43320
tgcaagcagt gcatctactg gatgttcagc gaagaagtat tcagtgttgt tgcagtccca 43380
agcgaactcc cattcaccat cacgaatctc tattttgtta gcactgaggt aagtgatatt 43440
gatggtattt acagtggcat taccaccaat gaggtagtac gatccttcat tgctacgaac 43500
atcgatcctg ccgccatcga tagtatcctg atagtagaaa ccacggtcga agaataactt 43560
cagcatcgaa gtgaagtagc tgttcaatac agcttgagca tctttctctt cgaccaccca 43620
ttttccatca acgatgttat tcaggtaatt acgatcatga ttgatcccga cattatccac 43680
gatgtcagcg tagttcttat ggaacttagc aatctcgtac aaacgttcca gagcagcaaa 43740
acggaaaggg ctggtgggat gcagagccag aatgatccga cctacgctcc acaaaccggt 43800
cccgttgacc tcgtaacttt cttcgaggta acctttgata ccacagttaa cttcaagttc 43860
atctgctggg aaaccggtgc ggagccgcct acggatagcc aatagtaccg attcggattc 43920
ttccggatcg aacaggtcta tgccgaaagt aatccagcta ccacgtactt tgtgctggta 43980
tgccaggcgt acagtatcac cgaatggaga aatgaaccag cgttcgtctt ccgatacgac 44040
caaatggcaa ccacattgcc acagggtact tagaggatcg ttagaggcga gaatgcgctt 44100
ggtgtcgttc atatccgacg aagtagcatc tggactgcca tgtaggtgtg tcagaataaa 44160
cagaagcgat gattctgtag tttgagcact caacattgcg cgagtgatgg ttgcattgat 44220
gatcatgaga tatcttcctt tttacagttt atgaatatat tgctaaataa aaaaatatta 44280
cgatgtagaa aataaaaggg agtccgaaga ctcccattat tgcgtgtaat ctatttgatg 44340
ataaccgctt tagaaagagt ttccatactt ccaataacta atttggattt ctcttcttca 44400
gggttcncca ttgcttcacg caggagttca ccaatagttt tgggttgaac atcatcactg 44460
atttcacgcg agcatgccga gtcgtcgtac atatcaaaca cattcagatc atcatcatcc 44520
aggggcgtgc tgtcattcca tgaatagctt gattcatccg aggtatcatc agactcacca 44580

-continued tactgttcac tgaggtcacg gtccagttca gcctcataca tctcgctaat tgctttatcg 44640
tcttcttctt gcgccttacg acgagaagtc ttgtagaacg gaagcaggcg ttgcaggact 44700
ttatggaact tcttcttgct gatcaaccag ctaacagagt agcgagacag ctttacttca 44760
gctgctttga tagtcggatc ggagtacagc gccatgacta gcttgtccag tttgtgcaga 44820
tgatctttaa acgagtttgc ataagcagga tgttcccgaa gagtgaacat cacaaacgaa 44880
cgcatgtcag tgatatagta ctgactgtga tgtttgttga tttcgatgta taccggatct 44940
actgcgcggt tataatcgaa ttcctctgcc caggtaaggc tacgtacttt agtaggacga 45000
ggaccttctg cccaacgaac agtcggatgt ttctcacgga tgttccaacc atgattgcga 45060
tcatactcgg ttgactcttc tttgaaccag gtgaaattac cttcaccgcg cgatacaata 45120
ccacggcacc aactgacgtt gattgccttg ttacggcttt cagtaagatc acagggcatg 45180
tccagaatag cgacataact gttatgacca ttggccacaa cgccgagaac agtagcttcg 45240
aatgtctcgt agcgctgtcc aggatacaca cgttcattct catccaggta acgaagggag 45300
caggattcga agatagcacg agtaccggca gggaaatggg cacgaccgaa aggttgttcg 45360
gcctttcttt ctttacgacg gctgataacc cattccagtt tttctttggt cagacgggtt 45420
acgggttcac gatactgttt catggtaatt tcctttttac gattgattgg gttgagtaca 45480
tctcaatgca tccttttcaa gacgcattga gatggggtct ccgaagagac ccatctatta 45540
ttcttgggtc agttccccaa gacgaccttc ggctttcatg cgacggattt ccgagatgga 45600
tttaccgtac attttggcca gttctttcac agtaccttca ggcacaggtt tgttcatgtc 45660
gcggaagttc tgcttagcga tattgtaacg ctgatgttga agagtcttca gttccgaacg 45720
taccagagcg ttaccggcac attgggagat gaatgtaacc atgaaggtct tcagcttgcc 45780
acggtagacg ttgacccaag cacaggactc atccacgtgg atgttcttgt actcggaaac 45840
cttggcgtat tccagcaggc cgacggcatc gggaccgttg tcctgataaa ccatcttgtt 45900
gaacaggccc agggcgatat cggaggaacg ctcacctttt atgaaggcga tggcgtcttc 45960
gatgatcttg gtttccaggt ctttgtactt gaccgggtcg ttcttgatca acagtagcat 46020
ggcgtcgacc ttgacagtca aacccatgtc ggcaccgcgt cgatcgatca actcgttgtg 46080
ctgtttctgc gtgaacacgg gatctatgtt cttgaaagct ttcaggagac gctgttccat 46140
ttacttgtcc tctttgacgt tgaatgcata catggtacat ttcggcttag ccgggtgttg 46200
gcaccactct ttagatacct tgccctcagg tttagtgaga tcgtaataga actcaccacc 46260
tgcggcagcg atacccatca gtactgcaat gaatcccatt ccgatcttta ctttcatttg 46320
gcaatgatcc gttgtacgaa gtgttgaagg ttggctacca ggcgttcgaa ttcttcttcg 46380
gttacctggt cacgatgcga ttccagaagt acttctactt ccggcaggac gttcatggcg 46440
atatccaact ggatacggct gatgaactct tccgttgtga tatttcgatc acgacgaata 46500
cgacttacca gcttgcgatg ttgttcgctg ttgcggtagg tngagatctt atcgataaga 46560
atatcagaga tactgctttc gatctgttcg gctacagcct gaccgtcttc ctttacggta 46620
gctttgaccg cgaggatggc agcaacggct gttgcgccaa ctgccagtgc aataagacca 46680
agtgcgtttt ctttgatgaa gttcatattg attatccttt caaagttgca tcatcattga 46740
agatatcagg acccaccgag agacttccca gaagatccgg agcaatgtaa acagagttga 46800
gggtttcgta tacaccggta acagcatcta cgttaaccag gctagaactg cgcatgggta 46860
cccattcacc gttacggaag gcttcaccga ccagtacacg aacatcatct acgtcagtgc 46920

-continued

```
ggttcggcca tagatcctta ccttctacta tttttacatt acgagcatgg tagaccagtt  46980
taccattcat gcgagcaacg atattcggac ggcacatgtt gtcgattact ttaactgcta  47040
cggacttttc catttttatt tctctattta gttacgagca tttcttgacc attgggaccg  47100
atacgatgac cgaggataac agtttcatta gaaatagttt gctcttcaaa cttagcgttt  47160
acaaacagtc caccaaaagt caaaccaata accactagtg cgaatgcttt catttttaaa  47220
gtcccttttt acattaattg aaggttaaat atcaagttag taatatactg tttaaatatg  47280
gtttgaataa gggagtagta gttattacat atcgtgcagg taggtctcat caatgatggc  47340
acgggctagc tcaatgagac tatcttcatc aacaacaatg ttaccatctt tccaggtagc  47400
gctatgggat aaccagttac ggtaatcctt acctcgtaca ggattgatgc atacctgacg  47460
agtagctgca tcacggtcac cacggaaacc catgatagca cgtgcacgac ggattgcttc  47520
tttctccaag tcttcgtcag atttaaaagt caggaaagtt gtcatagttt gattcctttt  47580
tactgattta ataggtttaa ttacactgtt gtgatatact ggttaaaatg gtttgaatgt  47640
attatttcat ttccacagac gacaatagtc atctacatgt cgagtgattt ctgcaacagc  47700
cctgagtcgc cggcggccag ttaatttaga gcagtgttta ttaactaatg tatcaacagt  47760
tttacgtaac ctaacacagc gttcttcatt aggtatatct tgttcgataa acaggctagt  47820
taatttatgg atttccatat ggattttctt acatacatcg ttagccgatt ttcttcattt  47880
aatttgttgt atgattcgac taacttaaca atagttgtag caacagtagt tgcggcaaca  47940
aaaatttgaa taccattgat aaaattttta ttaaacattt ttaaactcca actaatgtat  48000
taaaaaaata tgtctatatt gaaaataaag ccctccccga agggagggtg tatgtcgcca  48060
ataagtgtta ctaatttatt tagttagttt gaccatacgt tctttcaaag ttgtttacat  48120
cataacctga gtggtgtgtt gcagaaccac ctgaagtagt atctataatc ttaactacca  48180
cttcatcatt ttcaatgtaa accgacagtt tatctcgcat aaaatccacg tggtcatttc  48240
gataacgtag atatttcatt acagcttcgc cactgatttt actgttagcc attattattt  48300
cctcgattga ttccagttaa aattatcttt tgcattttta gtgaagaacc cgttacccca  48360
accaaatgag tatctaaagt ccttgattac accaacatcc gaatcgataa ccttatattc  48420
aatgacttta tcactattct ccagaatgac taagatcgcg ataagatctt taggatcacc  48480
tacagtcaat tcatgtcttt cagactcgtc tctgtggata acgatgtaca tggtacttta  48540
tcctctaatt atacccattt agttactggg agttcgaagg tttcacacaa gtcgagtact  48600
ttacgatgtt ccaagttatt ttctggatag aaggtaatgg gtgtagtcgg actaccccaa  48660
ttaacacgac atccagtttc tttatggatt tcgccaagta cagtatatgc acctgcccca  48720
tctgcataac ccatttgatt agggttaacg cagatttgag taaaacgctc cgtcaatact  48780
cgattaatag tgatggtcaa gagacgaacg aactcacgag tcttctcgat gtcgtctacc  48840
cagaattcca gaaggatcca tttcccatga gggttatcat gcccaccttg gaagaataca  48900
cagaaacctt cttttgcctt ataaaactcg tgattggtaa tgttacattc aaccatttgt  48960
ttcactgcat gccatacacg ctcggtgaca taatcaccat aaagttcgat gcagtgacca  49020
cggccaggga attgttcttt tttagaaaat ttaatttcga acatggtata gattcctttt  49080
tacattaatt gaaggttaaa tatcaagtta gtaatatact gtttaaaatg gtttgaatgt  49140
attatcggta ggggagggtt acccttttaa ctttttaata ctattggata agtacatgac  49200
actacggaaa attttgaatc ttgaaaagta ttcacgtact tcttttttag tcaatacaag  49260
tcttccatct ttgtttacat tatcaccaaa gacaatttcc tgagtattct tccataaaga  49320
```

-continued tctataaaga taacagccat gtggtgcatc acaccaatca tagatcttaa gttcaaattc 49380
aactttgtcg acaatatcat catcaaataa aatagtattt cctttactat ttaattccat 49440
taactcattt gcacaattta ttgcaaactc aaccgctgcc caggttctac caccgctgaa 49500
catatcttta cttaatttat ttagatcgat agcattataa gttgttttct tagtgttttt 49560
catggactgc acccctcaat aataaataga ataatctgta tttaattcac ctttgtaata 49620
tactttaaat acatttgaat acatgacata aagccttccc ctggggaagg ctattattat 49680
gttttaatcc aatgggtata tgtacatagg tcagtttctt taataatggt tgatttccat 49740
ttatcccatt taatgatttc tttagggaaa taaacacaac tactattatc natttccatc 49800
ttgacagtag taatgtacat ttcgtctaaa atatcctttt caatgacttc tttataaagt 49860
tgagaaccgc caatgatcca tacatccttt ccagtttctt tattgaaatg agtggcataa 49920
acaatagctg cacttagatt agggagtaca cctaatttat tatcataggc tactggataa 49980
ttaccgttac gatataaact tgatgataca acaatgttat tacgattagg taacggttta 50040
ctacctaagg ataagaaagt atttttaccc atgataacac agcaaccagt tgtcatttct 50100
ttaaagaaag ctaaatcctc aggtatatgc caaggtaata gattattata tccaatgaca 50160
ccatttaggt catgggcaac gattaattta atagccatta attttcctta ggccagaatt 50220
tacaagatac ttcattatct ttaaattcaa tagcccaact acagcaagtg aaattagttt 50280
taaacttaaa tgtagacgct aataggtaat taatttgagc catttgtaat agcgttaatt 50340
caccatatac tttctcatca atcaatacac caggtctttt atgtttaata actaattcat 50400
tcaacttaat atcttgttca atatagaggt attccacttc gccttttttct agtataggca 50460 tgtcccaaag aatcagacta atctgttgtg tgaattcctc aatactagtt gtaatatcta 50520
gtccttcata acctatcaat agatttataa gtacttgtag actaatcaga ttaacaggta 50580
agtcttttaa atcgtcttct ttaatagttg ttctaaaata aacagtgcca tctaagtttt 50640
taactaataa tctatttaat agatgattga cttctgattt aatctgataa tccagtttga 50700
tcattagcta actccttgag tctagtcatg ccattactaa cttcaataat gtaactaaag 50760
tcaaaactat atttcatcat tttgaattct tctttaaagt tagcgatatt tccagacaga 50820
gcaatttgtt caaatcgact aaaatcagta atagtttcat cgaacattag ttctcttgcg 50880
gtaatatctg gatcatagtt aggatgatca actacagtac cttcgtggtt taaagtacct 50940
tgaaaattca aagtcttttt aacatggtct acagttattt tccaactagt tgcaatatac 51000
cgagctttaa ctaaattagg agcatacctg taaatacacc attgtaatgg agtgccaaca 51060
gtttgcgtat catgcgtggc ttttataact ttaataaaat tctcaagttg atcaaatgta 51120
acattcctag ttacaccatc attagtggtt atattaagag atggtcgaag accagtacca 51180
agatcattgg tgatgattat atcctcaact aaagcttcat ataactttag tccttctttt 51240
ctggatccaa catcattacc cattgtttag cttcctcttt tgttaccagt tgataaagtt 51300
tattaaattc acgttgacgc attaatttgt aatctagtat acgcccatta tttttacgaa 51360
ttaaaataat aaaatcaccc ggacagacaa ttttatcttt atctgggcct acacgtaaaa 51420
taccatgact agattcagtt agattacata atgggcaaat cgcattacta agagtagact 51480
ctttagtagg tatagcataa ccaacaatag caccttggtt gatattattg ataacgccat 51540
caccaggtat atcaccgttc tttttccatt cgattgcttc aattggatcg gtgtatttcg 51600
gtagataaaa agacattctt aattaactcc gataaataat agtagtatag taaaaagcac 51660

```
ttaggtatat ttctatttta agctatattg ttgataaaat aaaacctaag ggtacatagt  51720
gggttattat ttaaagctct taaatagcat ggtagaacga tattggacta tatagctgta  51780
acccttaagg cactaaggct acagaggttt ttaagataaa gatatccaat gtaccataat  51840
atgcttttac aatagatcaa ctaaattcat ttaaaatggg tcgtaaaaat acttagttga  51900
tctaaagata tgttgaatac tttttcacat gaacttacga ctcacaattg gaaattaaca  51960
atgttaaaaa ctatcattaa actagacggt actgaagaag catactcacc tgctaagatt  52020
aatggttggg gtgaatgggc agcccaacat cttggcgata aggtggattg gagtagtgtt  52080
gtgatggatg ctgttcaagc tcttggtgat aaaacttcat cacaagaact acaattacaa  52140
cttattgaag aatgtttaaa tcgtaagaca tggtcttatt atctaatggc tggtagacta  52200
tatgcgattt atcttcgtaa gaagttctat ggtctaaatg gcatcccaac tgttaaagcg  52260
cttcaaacca ggatgcgtaa agatggtatc attgttaaat tagattatag tagtaaagaa  52320
tacgctcaga ttgaaaagat cattgatcac gatcttgacc tactttgtcc gcatttttca  52380
cttcatcaca ttcgtggaaa gtatgctcta cgtaatcgta aaactggtca agaatatgag  52440
actgcccagt ttgtatatat gcgaatggca atggctctag ctgaaaaaga gccagctgaa  52500
actcgcatga ctcatgtgga gaattactat aaactacttt ctaataaaat tcttagtgcg  52560
ccaacaccta actacgttaa cctaggtact aagcttcgtg gttttgcatc atgttgccta  52620
tttgcttctg gtgataatgg tgtatcactg gcaatgggcg attatattgc taacatcatg  52680
acccaatcat cagcaggcat aggtgttaac ttaatgacta ggtcaattgg tgatcctatc  52740
cgtaatggcc taatcattca ccaaggtaag aaaccataca tcgatgtaat tggtaaagca  52800
gtaagggcta acctacaaaa tggtcgaggt ggtgctgtta cgtgttacta cagtgctttc  52860
gatcctgaag cagatatgat tactcagcta cgtaatccac gttctactga ggataggaag  52920
aaccgtgatc ttcactatgc attcctaagt aataagttct ttgctaagaa agcagctcag  52980
aaagatggta tgatctttgt attcaatcca tttactgctc cagatctaca tgatgctttc  53040
tatagtggtg atattgataa gtttattaag ctttatgaaa aatatgaagc ggatcctaaa  53100
tttgagaaaa cttatgtaaa tgctcgggat cttctcaaat caatgctagt tgaagcatat  53160
gagactggaa ccatctattc agctcaaatt gatgaactca atcatcatac accatttaaa  53220
gaacctattt acagttctaa cctatgcctt gaaatcgcag aacccactaa gccttactat  53280
cgaatggaag atctttattc tagtgaggat cacgggcgcg gtgagattgc tacttgttca  53340
ctggctgcta ttgcagtgga taacgttcct gataagcaaa cttatgaaat ggcggcttac  53400
tacgcactta agatgattga ctattgtatc cttaatgcag agtatgcttt cccacacctt  53460
gcactaaccg ctaagaatcg aatgagtgct ggtgttggta tcatgggtct agccacacat  53520
atggcacgtg ctggccttaa atatagcagc gatgctggta aagctgaaat ccacttcatt  53580
gctgaacggc atatgtactt ccttatcaag gcgtcactta agatttctaa agaacgcggg  53640
aatgcgcctt ggattcataa gactaaatgg ccagagggat ggactccacg taagacttat  53700
aataagtcag tggatactat cattgaaggt ggctttgaag aactttatcc atgggatgag  53760
ctagagaaag aaattaagga gaatggtggt attgcacact ccgtactagc tgcatacatg  53820
cctggtgagg catcatctaa agcactaggg tcaactaatg gtccatatcc ggtacgtcgt  53880
ctaattctga ataagactga taatggcgca cgtgtgttat gggctgctcc atatggagat  53940
gatgattcct atgtgtatga atcagcttat gatatcccca ctaaagatct tattgactgc  54000
tatgccatta ttcaaaagtg gactgatcaa acaatcagtg cagacctcta tcgacgcatt  54060
```

```
gtaggttcgg aaaagatctc ttctaatgaa atgctaagta atcacttcta catggtgaaa  54120
cgtggaatga aaacccggta ttatgtaaat ctagaaacag cggcaggact tgacattaaa  54180
tcacttgaac gtgctgttga ggtaactaat actgaagttg ggtgtgcagg tggttcgtgc  54240
actctttaag tgtatacacc ctcccttaat tgggagggtg ttattcccaa tttatactaa  54300
cctctattat ttattgtaag aaatattttt aaattgtaaa ggaantaaca tgtctactaa  54360
atctcaacta ccaaagaaaa tcttcaatgt tgctaagagt gattatcatc taccggaaat  54420
tattcttgga gatgatccag gtctactaga ttcaatccac actcattatc ctaaaatgtg  54480
ggagctatat aagcgtctaa agatgcttga ttgggatgag ctagaatttg acttttccac  54540
ttgtctagta gaatttgaaa cgtgtgataa atcaacttat gacatgatga ttaagacact  54600
ggcctggcaa tgggaagctg actctgtagc cagtcgttcc attgttaata ttctatcacc  54660
tgtcatgaca gattcacgag tatgggcggg atatgtacgt attaatgata atgaagacgt  54720
acatgcttta acttattctg aaattgtacg taatagcttt aaagatccta aagttattct  54780
agacgaaatt cttagggtag aagaagcaca agaacgaatg gttgcagtag cccgcactat  54840
gggtgaagca catgacgcag ttcatgcgta tgctcttaat caggtaccca atgatcaaga  54900
actttacaat aaagtattca tgttcttcat cgctctatat ttcctagaac gtatccagtt  54960
catggcatcc tttgcagtaa cctttgctat tggtcgtact ggtgcattcc agcaaattgc  55020
aaccgctgtt aagaaaattg cccaagacga attcgaaatc catgcacaat atggacaaga  55080
agttattcgt gcactactgg caactgaacg cggtaaactc gcttacagtc aatgtaaaga  55140
taaaatcatt gaactactat gggaaattgt aaagactgaa gttacctgga ttaattatct  55200
attctctgaa ggtcgtgaac taactggtgt taatgcgact aaacttatta actgggtact  55260
tttcaatgct aatgccgcag caacattcct aagtattgaa aatgatgttg tagaacagta  55320
tcaagtggag tttaaagaat cagctggatt tgattttgtt tggccagaga agaacccact  55380
tctttatatg gaagactacc tagatatttc atcaacccaa gcatctcctc aggaagaaga  55440
gaagcctgat tacatggtca acgttgtaaa tgatgttggt gaagaagaag aatttgaggt  55500
tgacttctta tgattaagat tatcgcattc gtagttttaa tgtggtccac tgtcctattt  55560
gcagcaactg aagtaaaatc aactacagat ggtattattg cacattcaga atgtcagcta  55620
gttgctaaag atagtagtgt tgtcggcact actgttggag gtgcggttgg agccaccgca  55680
ggcgctgtat taggtcgagc aatctttggt aaatctggag gttgggtagg tggtttaatc  55740
ggtggtgccg caggcggcgc agtcggtaat aatgttagtg ctactgaaac atttcaatgt  55800
aaactgattg ttaatacaga tggcaagcag tacatggttc aaacagttac caatgaaaaa  55860
ccaaaggttg gtgataaagt cactgttgtt gaaatgaatg atggtacacg agatataatg  55920
tagacataat gaccctccct taattgggag ggtttatgct aacaattcta tagcactctt  55980
attaacagtc atcaacgaga gagtagacat gaataaaatg ctaaacttcc taaaccgtac  56040
gctatatagc ggtactgaaa aagtatcttc aaaagctaca ccaagtctag aacactttaa  56100
aacaaatgtt gaacaagtag ataaaaagat tctacaaccc tttagtacta aatttaaaac  56160
cattctaaaa gaatgttaca gtaatgagga gtgggttgaa gaacaatcat ttattgaaga  56220
acctattgat cttggttcag ctgcacgcgg tcttaccgag cgcggtatta tgcgtggtga  56280
ttggggacgc ttagcgcatt ccactattaa agaagcagaa ggtatgatgc gtacttatag  56340
tggtcgtcta aatgaagata tggaggcatc tgaaattaat gaagtaattc aagatatgcc  56400
```

ttataacttc acagctggct cagctaatac tagccgttta gaagaagatg actctatttt 56460
tgttgaagca gatacaactg tagttgaacc tctgtctaag cagactctgc caaaagtagc 56520
agagcttact aatcaattag tggaagtcta taaccgaatt actgaagaat ttacagaaac 56580
tggtattgct aaagttgaac aagttgaaca gccagcagtt cttgtagcac ttggtgagat 56640
cattagtagt tttaataaac taattgattt atcttgcggt gctctaccag tggaagaaac 56700
tgttattgta gaggaggatc cgttacctgc cattgttact ggtccaacta ctgaacccat 56760
tgatggtgaa attctaccgg ttgatgctat taataattct gcggcattag aagaattcat 56820
tgaagaagta ttaagtacta atccagaatt cattaaatat caaagtatga atgatagtaa 56880
tattgattca tatctaactg ggatgactg gattatactg aaattcaaag atggttctta 56940
ttatttatac aatgcccaaa gtgccggtga aacgaatata gaaatcatga aagatatggc 57000
cgaaactggt agtggtctta atggttttat aaatcgggtt attcgtggcg ggtatgtaga 57060
gaagtccatc attaatactc ccggttttat acaagtctca aatgaaggtc ttatcgattc 57120
aatcaaaaaa gttcttggca tttctaatcg aggtgatcag aaacgtatct ggcgttcatc 57180
gtccagtgca agaggatttc tggaacaact agaatctaca tttggcaatc cacaatggct 57240
taataagcag gtattcgtta ctggcgatat caatagtaat ggtatagcta acgtactgag 57300
tattaatggt aaagtcagta tcgaggatgc cattcgtgca gtagaaccat tcttcaaact 57360
cgaagaaaag tctaatcgcg aaatggagtc ttacaggcag aagactaaac ctgcattgga 57420
tctactcatt aagaatgcac ataacctaga cgctaacgta tacaaagaag caaaggctat 57480
cgtagacaag gcacgtgctg gattcaagac tagtgttaaa tggcctgccg gtactattac 57540
aggtaagggt acctataatt cacctcgcac cgtggtcgcg aaatatccat ctactgatag 57600
taaactcaaa gctcttactg aagaagaagc agctaaggcc atgaacttaa ttatatcggc 57660
attggaacgt cagataactc ttagcttcaa gttccctgat ttaccagatc cactggaagg 57720
actaatctac gatatgttgg ataaccctag tccaatagct ggtatcgatt actatgattg 57780
gaatgatttg ttattcgcat gctttggccc tgggattgat gatgatgtga tggaagttaa 57840
taaaatgcgg caataccact cattcattga tatcatggag gccgccgcaa aatgggtaga 57900
tcggtctata aaaggtaggt tagcaatggg taatgaaaac taccagtaat gtatctaata 57960
ttatgtagaa ataatccctc cccttgttt ctacattagt cataatagat cggagccagt 58020
ccccttcca actggctccc agagagtaaa actctttgct gggcattaat gacgatatat 58080
cgcctccctt cggggaggct ttatattttg tttttacgta tgtatattaa aatatgtata 58140
aacaacatag agtaattata aaatgatcaa aaatgaactt ttaccagggc taatctatgc 58200
ccaaaaagaa tttgataaaa ttgcagctaa tgtaaaagac tatgataant ataaaagacg 58260
cgaagctggt agggcaagtg ccgttttaag aagtctagtg agcaatattg taaatcagaa 58320
taaaccatcc tcacttgaac atgaaggcaa agttagtact actaatacta atgaatattt 58380
agaagaagtt aataattact tctttaacat taataatatt aaattaattt ctcctaaact 58440
cataaaagag aaattaacaa ttgatctaat gaatatttat gttaaatgga atatgattgg 58500
agtggctggc cgaaatgatg ttccaattat tgaacacaga attaatgatt ggtgcgaagt 58560
gaccgatgtc tacattaatg gtaataagat aacttcttta caatggccac gttgaattta 58620
aaataagttg taataaaata cctagcatta catgttatgt attgaagcac aatgcccgaa 58680
tggtgaaatt ggtaaacaca gaagacttaa aatcttccgg ctacggtctt gtcggttcga 58740
atccgacttc gggcaccaat ttaaatacgg agtgtagcgc agttggtagc gcgcctgctt 58800

-continued

```
tgggagcagg atgtcgggag ttcgagtctc cccactccga ccattttaat aataggtaaa  58860
taggatggat aataaatgga tatcatggga acatcaaatt ataggaacag ctctttacgc  58920
tattcttagt gaccctgaat taactaatat tcaattagct caaggcttac actatctaac  58980
agaagcaaag tcttctgtat tacatgtttg taataaccat attacattca ctgtaaccta  59040
tccacatggc acatttagaa ccaatgtaat tagagagtgc cctgctagtg atacaaatac  59100
attcaaatgg tcaggtgtat tagtccgtca aaaagatgga acattcttac cagaataaat  59160
aaaaagggcc tatagctcag ttggttagag caggcgactc ataatcgctt ggtcgcaggt  59220
tcaagtcctg ctgggcccac catatactag cctcccactt gggggaggtt ttatactgtc  59280
tcattgagga aaacatgaat acagtaataa tgttggtatt atctatcaaa gttggattat  59340
ttggtttcat ttcgactaat gaaagtaata tcctatttga aaatagggaa cagtgtattt  59400
ctcatctgga tattctggaa cataaataca agtctcttga agttattcga aatgagaata  59460
ctctaaagat aaccgaaaga gataaccatt ctatttatat ttttaaatgt ctctaggaaa  59520
atacatggaa catcaanaac aaaaagaact attgagacaa ccattacaaa cactttataa  59580
tcttactttt agtccccgtt tacgtaatgg agcgaaggct cccgattgga ttcacctgac  59640
cgatgaagta accctattcc caaacggatt agatattaca atcaacgctg ttacacgttg  59700
catcaaatgg gaacttatcg gcgaggatgt aagtaacatt acttatgttg aagctatgtt  59760
ctttaataaa ggtcttaaag cagttaaagc ctatctcaaa catacggagt aaatatggat  59820
catctaaccc caacgcagag cgctgtatat ttcacattta ttagccctga gtttataaag  59880
ctaactcttg ttgaatcttt tgtagcgatc cacaagaaac atccagaagt aaagcattgc  59940
gttaagaaaa agattagtgc taatgaaacg cagtttatct ttatcttcaa agatgggact  60000
gataatttaa tcattacacg taaaactgaa ccttgccctg aactggatag cccagtaggc  60060
gatagtatta agttgtccgg cgaagaactt aaaaatattc ttgctaagta cgatcgtccc  60120
aaggatggta actatttcaa gcactggact gatcgcccgt aataaaatat tactggttat  60180
gtaatactat gtaggaagtc atgtccatac gtttgcgctc atagttcagt tggttagaat  60240
acccgcctgt cacgcgggtg gtcaggggtt cgagtcccct tgggcgcgcc atttaattcc  60300
gtgatagctc agtcggtaga gcaagtgact gttaatcact gggtccctgg ttcgagtcca  60360
ggtcacggag ccatattcta aagagtagct tcggctactc ttttatgttg ccatgggtta  60420
tcttatgaat taaaatgatt tacttgagag cacactcatg tttgaattac tattatcncc  60480
agatataggc gaagagttac ccttggttgg atttaatgaa attattaaat taggtgatct  60540
acctgtagcg ttagctggta caatgtcata tgtggatgga aatacactgt atgttggatc  60600
tggtcatcat actgaaggac aaacagctgc aactgtgttc agacgtttta ccatatcgcc  60660
atttgccgat ataggtgcaa ctgcttctgg aacattctta ccaggggtat ctttaggatt  60720
tgggacatta cataagaata actttattgt ttatggcggt attactggat ggaactcggc  60780
tggtaatggt ggtacgggaa catctaactt tatacaacat tttgatatag ctacaggcaa  60840
tagggttgag cgatatagtg gtcccgtacc actttggggc acagcctccg catcagatgg  60900
taatgatctt attctatgcg ttaacccant tggngtaann gcaatgcgnt taaaaccatc  60960
nngtaagncn tggcttagng gncaaganta ttcaggtggt gctcgttcag gtcaacagtt  61020
attcttttat aatggttact tttaccattt tggtggttgg gataatacaa agaacatacc  61080
taatcttgaa gtttatcgat ataatgcaac taccttaata tgggagcaaa caccttggat  61140
```

-continued

```
gattatacct gctgataaag gaacaatctg gcaaggtaan ggttatgtag atggngacta  61200
ttttaattac cttaacgctg ttgatgtcgg cggtgtaact aaaatgtttg cacaacgttt  61260
taatattagg cgccggaaat gggctgaacc atttgaacta ggtatcggat tcctnaatat  61320
ttcatctata gctaaaggtc cggataatag catgatcatt gtaggtggat ctaaaatgcc  61380
agttggtggt ggagcanana tgttgaaaag ccaattgtta tcaggtntct atcaggtaaa  61440
actagcacca ttaatcattg attaaaataa taatatttat aactatttag ataattatac  61500
tggcacgatg atattatgta agagtactat antaaagtat tcttaaatct atccactaaa  61560
cacactcggt ggtagaactt attatagagt gtgtctaaat gccaggggtt tgccacccct  61620
ggntatattc attgttacta ttataaattc atttatagat gagaaaaggt tttatcacct  61680
tttcaaaatc ggcatttaat tccagttaaa aaaactgaat ctatgctaca ttgtaataaa  61740
ggagtctatt atgactaact ctaatccgtt tgtaagaact attgtaaagt accaagatat  61800
cctagatgct ttaattcaaa aaacgaatga gaactgggtt aattatcgat ctaattctat  61860
tggncatatt gttattcgtg aatacaggac tgttggatta tttgtaggtc ggcaatgtgg  61920
tagtacaact gcattgattg agtttgctaa tcgtcancct ggcgaatgtc tagctgtatt  61980
tgtagaagat aaaattaaac aggctgtact ggctaagttc cagaatgcta aagataatat  62040
tgtttcttgt ttaattacac accaactccg naaatatatt catcaacctg aagaatcatc  62100
tattcaaaaa gatattaaag aagaattaat atcgtctgta aaatatattc ttgttgacaa  62160
tgcctcattt aatctgaacc tacgcggtat cactgataaa gaatttaacc agtgggttgc  62220
agatactttt ggtacagagg taatggtggt tcgttttagt tagaattagt aactttgata  62280
gtttctaata agattaacta cacgttattt acataatgtc ataacaagaa ataaataata  62340
ctcagattgt aataatatgt agttattaca tatctatatt aggttgtcag taactcatct  62400
ctaatataaa atcgccataa ttcttccgtg atagctcagt cggtagagca agtgactgtt  62460
acgatttcat tggtaagtac ccgagtggca gcagggagcg gactgttaat ccgttggcga  62520
aagcccaccg taggttcgaa tcctacctta ccagccaaat tctaaagagt agccagctgg  62580
ctacttttat cttgttctat agatcgaact agctatctat tttttaaacc ctaggttcga  62640
tatgaaagaa aaaaataatt aatggttatc gggctctgta tttacctgaa catcggcagg  62700
caaaagctaa ccccaaaatg tttggatggg tatacgaaca ccgtgtagtc ggtgaagata  62760
caatcggaag atctctttac gatgacgaag aggttcatca tttggatgag aacaaactca  62820
ataaccatcc cgataatctt ttgatcctcc ctcaatcaca gcatctaaaa ctacatgcat  62880
ggatgaaacg actgggcatt gatccaaaga actatcctac aaaactttgt ggtgcttgtg  62940
gtagggtaat gaatcataaa ttgattaaat tctgtaaccc tgagtgttct gccaaaggtc  63000
gacgtaaggt tgatcgacca tctaaagaac aactcgtcct tgacgttaca ttgttatctc  63060
ttgtgaaaat aggagaaaag tatggggtat cggataatgc aattcgtaaa tggtgtcggt  63120
catacaaaat caatattcca gctaggttta ttagggtcag cactaatggg ggtattagca  63180
ccttggcccc cacacaataa aaatatactc gatgtagatt aatatacaaa aacataatca  63240
ctgggtccct ggttcnannc caggtcacgg agccaattca tagttttaga tttagttata  63300
tttcactact atgtaaacta taaaggcagc taatgctgcc tttatgtcgt cttgtaaaag  63360
tacccagtag ttgaatctta tagctgaata caaatagggt aaagacatgt cacttaaagc  63420
attgcaagat atagttagta gtgttcctac aaatgaacaa aaggaacgat tagttaaagt  63480
tcggaaaacg atggaagagc taaatgagtc tattaagaat cagattcgta ataaacgacc  63540
```

tagtcaagct cttctcgaca aaacgataaa ctggggtacc aagtatggct aagacattag 63600
ttcgtgcaaa gctgattact gaagctggtc aatggatgtc gtctgactgg gaatgtggtt 63660
tccgtgcatg tcgattcgtg aaacttggta atgatcatgt aaacataaaa gactttgagg 63720
ctatgatcac ggcattcgaa gttggtgaca tgttagtgat ttggccaaat gggcttagaa 63780
cttcgtatag tgtggataat ttcaataagt acttttccca tatcaaagat gaataccatg 63840
agactgatct ccgtccactc ttttacccca agtagttgag cttatgataa ctatattcgt 63900
gtataaatac attacattcg ttataccctt taattgattg aaatcaagct acataaaagt 63960
gatgaatact ttaacccaat gatgtataaa ttaaaaagta tgcacactaa aaatacagat 64020
ggtgtttatt tgatattttt accaacgcct actatcgatg atcaaattaa caccatgcaa 64080
gggtatatta tcaataaatc cggtaatctc attaggacta ctgtacagtc atggcgattt 64140
gagaaaattg aattcaaaga cttagccaaa catgatagac gttggttatt tattgaatat 64200
tacattaatg ttaaacaaac gaaaaataat ataatcaaag agcaacaaga tgaattaact 64260
aaatttattt attatagtac tctaagttaa aacaaataaa aaaataaata taagagctag 64320
cccctaatgg gctagcttta tgttatctta ctctgctaca tcttttacat caggtttatt 64380
attccaacgt actgctctcg caataccata cgtaagaata agagcaccca cggtgccaat 64440
agtggtgcta ataataatgc caagagtttt tggntcnata ttcatattta gtntcctatt 64500
tacaattaat agaaaatatt acttttagta atatcanntt nntnatatac nntttaaata 64560
ngtttgaata taactttatt tattataata aattaaaata atactttcat atacactata 64620
tgtagaagat tncgccgcta tagctcagct aggtagagca acgcacttgt aatgcgtagg 64680
tcctccgttc gattcggagt ggcggcacca aatttactga ggtttaaact attcttaaat 64740
atattagtta ggatgggatt gaacgngaaa gactcagtaa atcatattgc ccctccatat 64800
ggaggggctt atgtttgtca ttaatcagga aaatataaaa tgagncatct attatttatc 64860
atccaagaat acattactaa taaatttgag ataacacgaa ttgatatgaa gccaggtaat 64920
agaatgttac gtgtatgttt atacggtcaa cataagggaa aaggtttcgt ccgtatagat 64980
ttatggtcag ttggttatcg cattacaaag aaataatact ccagattatt taatatgtat 65040
taatcaaagg agtttataat gagtaatgaa actaactatc taggttatga atggaaaaca 65100
gatataacta cttcaaatct taatagagtg gttgatttat atacacttga attaacatgg 65160
ttaaaagaag attttaatga tactcttttt ataaagtctt ataaagtgct agagggtcta 65220
ttagaggaac cgtctagggc aatccatgat gatacagtan ccattcaaga tcaattagat 65280
gaattaaata ctgtttttaa attagtattt ggaaaagata ataacgtaga gttatcaatt 65340
aataatgatt caattattgt gatcggtgct acagatgcaa ctaaagaaaa gttagaagca 65400
gaggtgcgtg agtttgcata tagaaaatca ttaattgatg aacgttatcc agatattgta 65460
acggattaaa atacttacag ctatctagta tgtaactagg cggattgcca tttgtaaatt 65520
atctatttaa tcgaactgag gaaatactaa tgaaacaatt ctttcaacta cttctaagcc 65580
tacttttcaa actaccggtt ctatcatatt ttgctgagaa gaaacgatta gagaaagaga 65640
aaaaggaaga agaaaagcgt cagcaagaac aacgtcaaaa agaactactt gatgaacaac 65700
gtcgcgaaca agaagatcat tatcgaaaaa ccgcttacga tcgcctagca aaacttattc 65760
atactcggtg gtatgatgag tttaatgcat acgaaaagaa actagttgat cttgctgtat 65820
cgagtggtaa agcagttagt gttaagtatg gtaaagttac taagatgcag caccctcatc 65880
aatttaaact acttaatgat tggctggatg atattccagt agaagattat tctaagtgaa 65940
gaggagatat acaatggtct tcacactcga agatttcgtt ggggactggc gacagacagc 66000
cggctacaac ctggaccaag tccttgaaca gggaggtgtg tccagtttgt ttcagaatct 66060
cggggtgtcc gtaactccga tccaaaggat tgtcctgagc ggtgaaaatg ggctgaagat 66120
cgacatccat gtcatcatcc cgtatgaagg tctgagcggc gaccaaatgg gccagatcga 66180
aaaaattttt aaggtggtgt accctgtgga tgatcatcac tttaaggtga tcctgcacta 66240
tggcacactg gtaatcgacg gggttacgcc gaacatgatc gactatttcg gacggccgta 66300
tgaaggcatc gccgtgttcg acggcaaaaa gatcactgta acagggaccc tgtggaacgg 66360
caacaaaatt atcgacgagc gcctgatcaa ccccgacggc tccctgctgt tccgagtaac 66420
catcaacgga gtgaccggct ggcggctgtg cgaacgcatt ctggcgtaag tttaaataaa 66480
agaaaataaa gacgaagttt ttctttacat ggagaggggt ttatgccgta attatacact 66540
tactttgata agatttttaa tatcagtaaa atgggtatat gttgcctttt tatctttgtg 66600
aaccagtaag caacaggtac cttcatttac tgtattggtt tgttttaatg ggatatttaa 66660
agcatattca aacagatcat ccatccagtt aaataccatg aacttattga taaggacatg 66720
atcgaaatca attaatccaa taaacgaatc gatctcagat tgataatact ctacaaccat 66780
tttagaccat tctttgttta tcgcctcaat gacattagga ttatttattt tattaaataa 66840
ctcantncgt tcctnagtag gtaaactgag gtaataatta atattactcc taacgatatc 66900
tggattagtg atatcnattt tttctggtaa gttatattta ctatctacat aattcttagt 66960
ttctggtgtc attctccagc aaccataatc agcagtagta cttgatggat ctattttagt 67020
ctccactact ttagaaaata catctacata taaattaaca gattcgtata catcaggtct 67080
gattggatta aagtttaaac ttttaataag accccctaact ggccgagtac caattagaca 67140
atgcaattca agcttaacat tttcctcttt agccatctta aatanatcag caaaactgag 67200
cttttctgcc atttagaata taccttttat taattggaca aatagattag atacacatag 67260
caatagaata aaccataaac ctagtctttg taatttatct atacgcttag ctttttgttt 67320
cctctttaat ctaactaata atgtattttt aatatcattc attaaattat ctcagatttt 67380
tagacggtgt ataaaccctc agtattacat gttgttatga tattgtaaag acgatgccaa 67440
tagcgatcat acgtattttt acgtttgtag ctattggtnc ggatgactag attggcgacc 67500
cagtgattct gatcaatggt ctcatgtaga tgcccgaaat aagcccccag ttcaatttcg 67560
aatgggatct tacactcacg ccccttacac attgcttcac gcaataaacg cattgcagaa 67620
ttctctgcat tggtatcttt aaataaaaga ctaatgtatc cagggctacc accagtttct 67680
tcatcaacat ggcctgaaca gcaataaata gttgcaacat tgataaattg attaaaccat 67740
ttaattaatg gcctacatgc ttcatcaata agatcttcat attcaggttt atacattact 67800
ttaacagtat catctgcacg ttgtttcaca tgatgaaaat attgctccca atttacatta 67860
gtgtaatata gcatatccat attagaatta ctcatacaaa tcaaccccat atgttattgg 67920
catattcgcg gtcattgaaa atgcgggtaa gatccatccg cttttgaatg cgcgctagta 67980
tccattttag ttgtttagtt gatagttctt gattttgctt gtactcacct gtagcatgga 68040
tgtaataatc aaatttacga cttacagtag tagtatgtgc acatgcaata gcaaatgctt 68100
caagtgcagt tagtttggtt gatccattat cattacaatt agggataaac tcaagtacac 68160
tattaactgc atctacacca ctacccaaat gagcccaatc tttcttggtg atgttgatac 68220
ccatgtcttt aagaataact gtatatatgt caccattctc catagtgaac atcatagaag 68280
tattaccatt aaacaacctg cgttctatga ctggcaagat atttacttca actttaaacc 68340
aatcagctaa atcaacacct gcggtaaggg cattcaatag atcataaaca ttatctatag 68400
ttccagcaaa agccatagtt ttaacacgtt taccttgcca agtaactgtc ggatgaaaaa 68460
ttatcttgtg gcaatcattg taatatacat ctacaccttc agctttagca gttagatcaa 68520
tataaccgtt atctaatact ggaagtcgcc caatgctatc agttgcatta ttccgctcaa 68580
ttaataggca gtctgcaatc atgactttac catcatttac gatatatgtc attttcactc 68640
cttataataa aataaatagg cttaagcgaa ataaagccct ccccgaaggg agggcattat 68700
caataggtgg gatctcggcg gcaccttcat ttgcggacgg gaacgctgaa gggagatagt 68760
ccgggagatc ccgatttggg tattctttac atatggtatt actgcaagta tttgttcccc 68820
gcagtataat caccattgat ccaatttttg attacaacac tgatcccttc attttcttta 68880
acggtaaccc ccaactcaag atcgattgat tgataagcta cagccgccag tgttaaccga 68940
agataaacgg atccatcttt ttcgatatcg taggatacta cgaacccgtc ttgtagattt 69000
gtagctggaa tgtattagca tgttgtggat ggagacgatc catattgtac tcgacgacat 69060
ctagtagata ttgccgagca tcagcagcat tatcaaatcc gagancgcac agaccgatcg 69120
gatagcgagc ttgcgtgcat gtaactttca tagatactac acgatgttgt ttgcacatta 69180
tattttcctc ttagatgtca aaaccctccc gatcagggga gggtatctca ttggtacttc 69240
ttcagcaaaa ctgaaactaa gataaaagag caatcgtaaa ggaactacat agaatagtgt 69300
atttctttta ctatttttac acaacctctt tagatggggg ttctttatga atccagtcta 69360
aagttgttgg taaactatta tctgatctga aggtacacac cgtccggaac cgagagtgat 69420
caactacaga taattgcccg ttaatcgcag cctcatattg cctacacaac ttcacacacc 69480
ttttctctag atcagttggt tcgtaacctt cttctcttgg ttcagtgtat ggtccatccc 69540
aaaagaatat taatctaaga tcaatcccag atttatactc cgcttggtat gaatattgnt 69600
gaacatcaaa atcatctaat tcttcaacta gatgtgatgt tattgttcta ggntgttcat 69660
gagttaattc actgtatata tgtttatttc tagggttttg taaatcaact acgataagtt 69720
gactagtcat tttaactttt atccagatgt ctattacgag tgcgttccac tgctgtaggt 69780
tcgacagtgg ctcgcggtag ataagtaatc tccgggaaag tcttattaag agcatcttca 69840
attagctctt tagcaatctc tgcatcgatg taatggttta gaataatacc acgatgatac 69900
aggaagaagc tgtattcatc ataaccatgg cgaagactta ctttaccacg atacccacca 69960
taggttagag tatcttcgtt aattcattcc gataaatatc aagttggata ttattttgaa 70020
gatgcatttg aatgaagtca ttactatcac cgccgaatag ggttggtcgt ttccgaccag 70080
taacaacatc ttggatggaa tccattagtc ggttaatgtc tgtttctaat cgttggatat 70140
cacattgaga attcattgct tcatggaaac gagttacaac tgcattgaat tcttcttcag 70200
tccaaccact ggtacgtttt cataatcaac aatgataata ccgaaccagg cataaccgtt 70260
agaatgttta ctttaacaca tagatgaggt acattatcag cacctgactg atggttaaca 70320
gtgtaattat tattacggct gattactagt ttgataaaag gtagactaat gattgacgcc 70380
atggaaatat tccttttgta ttttttaaat taaagtagga gttattattg agtttcaact 70440
caatacatca ataactccag tatgttttca aaattaaata catgtattta cagttacatt 70500
gtaaccagtt agttttgcca acaatacaaa ttagcgaacc tgttcgattt tttcagaaac 70560
aatgaaaata tgtgcaatac gatcctcatc aanataccga tatcgaaatg aggtataact 70620

```
agatgacaca tccgtatcgt ttaaataggt gatattaaaa tcatctactt ccctaccatt  70680
agcagccgca acggtattta gaatgttgag tagactcatt ttacagattc ctttttagta  70740
tattaatatt tcaatagact attgataaaa gcattagggt cataacggtt atttgaaaaa  70800
gccgccatta catcacaccc tggctgatct ttaaatctga tatcttcagg aatatcgaag  70860
tcagggaaca ttagtttaat atactcccta acttcttgat ctcgtagata tggaatctcc  70920
accatgtaat caacgcgacc tttccttaga agtgctttat caatattctc aggatggttt  70980
gtagttagaa tggtcatagt ctcatctagt ggaacaatgc catctagccc atttaataga  71040
gctgacaaag ttaatccgct agctggttgt tcatacgtga ttccattctt catgcatttc  71100
tttaatttcc accatcggcg aattgtggta aataatggat ctttttcatc ggcccatttg  71160
aaacacccag ttcagccata gcataagcac ttatcccaaa accttgatca tcgctatttt  71220
catcaaagat atagatggtg tcattaaccc aactacagag tatccttcat agtcatcttt  71280
aagatcaacc catgcagacg gatatttttc aattaaatca ataaaagaat atttcctctc  71340
taattccttt atctctttat ctagttttac aggatcattt aaaacacgat ctttaactgc  71400
cggggtatca tcgaaatctt caattagaag aatattacct ttaggtagtg tagtaaatgc  71460
ccgcctaaga ctatcattgg tcatagaggc taatgacagt gcactaacat ttttattaaa  71520
atgtgaggca atcgctttac tgattgaggt ttaccagtac caggaggacc tgttagaaca  71580
caagtgaatt tatagggtag tccacgatca tcgtaccatt tccgatcaga atagaattct  71640
tcaatcttat taaggaattc ttctttgatc tctttacgca aaatcaccgt gttgatatcg  71700
cgtttagtaa cttcaatctc attgccccaa cggttaccat cccaatgtga aatagtcaga  71760
ccccttcat ttgggcgcca atggtaagca tctactaaat caataattag tttactactc  71820
ctagataatc cacggatagt aatatccatt tgatctcgac tggcattttg actatcccgg  71880
cgtgctttta caaaccagaa taacctacct ttaaacagaa agaaatgtaa gccaaaacca  71940
acaccaattt tctgtttagt tgcactataa ctttgctcat caacattagt tgaaaaacgt  72000
cgattaaatc cagctaatgg ctgcttaata taccattcca tgaaacaatc aaagttcttc  72060
tcgttcagcc cattacccat gttggtaata tgtagactaa ctgtaaactg atttaatgcg  72120
aacctagcta gtttacttgg taagcctctt agagtggtcc agaataaacc accaattgcc  72180
attccgatag ctccacccat aaccatattc ttctgagaga tatcgatgaa catggcgtaa  72240
tattgcaata aggtttctat aatcatacta gcatccctct ggatagctta ggaaatattg  72300
tccacagatc atgtattcac gttctagaaa tctagagtat gactttcaaa tatttcacct  72360
acatctttac catagatttc cgtataccca tttttgaata cggccattac ataaacatca  72420
gacatagtca tgccgtagtt ataaatttga ttgtctctgt attttggatg aaataggtca  72480
tataaaaaac gagtcattga actattggca acagttgtca ccccttctg ctttaaggca  72540
taacgtactt gtttaaccac atagttaact ttagagcgct cgccaaatac cgtcagttta  72600
tctacattgc aattacgata tcccataaca ccaggattag ctatcacggt gtgttttgga  72660
acacgtacat caaagataat gccattaggg gatagaataa tcttttcatg gttaaataga  72720
acatgaaata aatgtcgttc tggtttagtg attttgatac ttaacccaat caccccacta  72780
atctttcttt ctagatcttc tagtgactgc atcaccatgt gatattgatt gaagaaagca  72840
ttgttcttat attgatctaa ttcaaagtat ttccaacttc cacgaaatga atagcatggc  72900
tttggtataa cctttagtta atcgacactt gagtttgtca aaccagcttt caagataact  72960
ctcgactgta aaccaagtgg gttattatat aagtttattg gaatatgata agctaaatct  73020
```

gtacatagtt cgacgatgca tttatattcc tgccaaataa agaaaaataa agggctccga 73080
agagcccttt atgtattaga tttttacaga ccaactttgc tcgaattcct gatataggaa 73140
attgtctgac gcattatccc aattttctcg atcagttaca ccataataat ggaattctag 73200
ttcagtaggt ccaccaacaa aaccattctt agcatagcta taaacttgcc attggttagc 73260
ttaatcagtg tatccacata gaaactatta cggttccata tttcattgtg gatgtactta 73320
aataccacac tgtngatata cttaaattgc gcacttggtt ttccgagtac actccaatag 73380
aatttacgga tacctatttc ggtcttgaaa ttaaactctc cgttgcgaat gttgttagaa 73440
acaatacgtg ccagtttatt aacccgattt cttcaccgat tagatagatc ccggaaacac 73500
tacatccatc tcctattgat ccattattaa ctagtggatc aacaccatat tcatcagtga 73560
aaatggtttt gataacctct ttaccttctc gacgcactaa catattcagg tgaccatctt 73620
cgatatatga catatggcta ggctgaatat attcacttgt atcgacgata acatcattcg 73680
ccattacatt aaactgtaga tggtttacca gatcactaat acctttaaaa cgaatggctt 73740
ggttcgctgt atttagatcg acatacacca cgacatcaat aatgccttgt tttagtgatt 73800
tgtcatcttt gtcagtagtt gtatcaattt tacgtaattt tgatatagtt cactaaaaca 73860
agatatgatg tcatcatgta gtttaattac atcagatcca tttcgttcaa gcgctttaag 73920
cgatacgtta aaccaatacg aattttatta gaacgacgtg ccatggttat atcacctatg 73980
ttaaattaat gaattattta ttcaattacc gtactacatc tgtgattaga ataagttcac 74040
catcactatt gataacacta tagcttttac aatttcgatg cgcttactaa taatcttatt 74100
ctctagatct acttttacga tattaacacg aattacctta ttcgattgat catgcatttc 74160
tttaaaatgc attcgatatt ttaccaatga cagcttttaa ttttcaatgc tgtcaatgga 74220
tgaatattta aaactatatg cttctgccag ggttttgcat tacccacaac cgtagttagg 74280
gtaccccaat aatcataaac atacaacgca gtatcactat tgggattatc gataatttca 74340
attataaatc cacttgtatc actcctatta gtttattgat agtacacttg taatatagat 74400
cttaaataaa ttatgatcta accatttaaa atagataaag cctctatatg ccaatggtgt 74460
attagttctt ctttactaat aatattattg aagtagttta accgatgtga taccattaat 74520
ttagaatgca tatcgacttc actacttacc ttaatcaccc cagtctctaa taattgcaga 74580
gatccaacat acgcaaataa agttggtttt aaataccagt gttccctata ttgtttttga 74640
tcaggtacat ttcctataat gtagtcagta gaattacttc ggtatgcgta aatagttgat 74700
ttagaaccaa gtaaattaag atcgatatca taactcccgc ttttagctgc aatacattca 74760
ataactgatg gggccacaca tatacggttg gttacactgt cttcgccatc agctctatta 74820
cttggaatat atggccttaa taaacataat ccccaaggta tactgtcgat atgtgataca 74880
taattaacct atttaattaa aacagataac gctctgttac tgaacgatat tgtgacatga 74940
tgtttaatgg atcaacatcc actggtgctt tagtgacagt taagcgagca ccttttaaaa 75000
atcaccaata tctaatttcc ttacagtaac atcatggata gtgtttttcg taatccactc 75060
agtatcaatg ctattgtgag gatattattc ttaatccatt tgtcagagtc cctaaatgga 75120
atggtataaa catacacaac cattttaaaa tatcactttt atcgatatta tttgacaata 75180
gattgtaata tccctatcaa cagtagcata tctatcacta tcaaataact tttcgatagc 75240
gctaccaata cctaaataag atgcatcttt ttcagatgac gttgcatata ggtattggtt 75300
agactcaata ccatcccaca taacaagttc accagatctt ttaaatcctg gcattaattc 75360

```
atcttgttta taaagagaac catggtaagt aattctggtt tattcataat aaaatccact  75420
atgctttata agagttatgg ttatcaatta acttcaaggt agtagtgtgg cagtattgaa  75480
gtgattggtt actgcttcga tcagcatttg ctcgatgttg attttgtagt attctggttc  75540
ttcgttcaat tcccaataat agtcgcacgt aatagtgcag gtgctatgaa tctaactacc  75600
ttaccatgtg tgtcaaactc tacatgaaca ttgcatattg ttcagtagta tgattttata  75660
gaaatgaatt accagcgtaa ctgcgacctc tatttcacca tgaatactgg agtaggtttc  75720
ctggtggaat actttacctt taaggcgtgt attctcttca atgatattac caattctttc  75780
aatttgtctt atctagttgc atttgtaggt tcctattaat aaatgtatac gatggatatc  75840
ttttacgatt tccggtgctt atccatatct agttttatat cagtatatat cttgaatcta  75900
ttagataggc tatccatatc tacgtgcaat gcccgaatat gcatatcagt atcttttggt  75960
ttaccttcag actcccatac ggcctttgcg atatcaaatg ctacattgtt caaatagtat  76020
tcgacttcat gttcatcaag caaaagagca tcatggaaac caatacgtga tagaatggcg  76080
taatcacgct gattaacatc tctccaatct ttacgcacta agtaactttt accaattcca  76140
tctttttttac aacttttact aataatttct ataatgaact tatcatgcca tttataatcc  76200
ataatcatta ctcctttatt taatcagctt cattactaga ggaacagata gacttatgcc  76260
attagccatt ttagctagaa tatgatagac atcgtctgct tcttgattat tgtacaaggt  76320
atagaaatgg catcaccata gtaaggactg tagttaatac ggtcgccata cacaccactc  76380
acaaaactat aatctaatcc atccgtggta gtcataataa ctacaacatg atcatcccca  76440
actataccgg attctaaatc ctcacatagt tctagttttg ttgcacacct cgttgacaga  76500
tccatacttc acggtattga tgatgaggat atggattaca tgctacatca ttttcactaa  76560
cgaagtacat agtcccccag ttgtaagact ggaattgggt tgttgtttgt gggcttccca  76620
tacctcttcc atacaaaggt atgttgttaa cccatagacc atcgttatta agactatcaa  76680
cgatccatca cggacacgta ctacacggag tgtttttgcc atttttaatt atcctaaata  76740
cataaaggaa tcacttagta aacaccattg acaatagcat cgcggaaacg agaccattcc  76800
gtttgaccaa ctacgaatac tcgttcttta ggacgccata gatgatcacc gcagtcaaga  76860
cccaagtaaa gcatattggt tttccatgat tgcgatgaac acgtagttta gctgatacac  76920
tgaactcaca cattacttca tttacatcaa gatgtgtagt gtatcactat catacctgac  76980
atactgatac caattgattt acgaactcgg attagatcct cagtcatcac ccgccaagtt  77040
accagatgct cgtaatactc atctggtgtc atgttgtttt tataattcag tgcacctgga  77100
gtcattgaca tcagttagtg aactggaagt catgtaatac atccaatcac tattatgacg  77160
gagttcttta agcttctctg tattacgata ttagtagttg ctttagtcat ctacgtaccc  77220
tcatcagata cataagtacg ttcaggctga acacatattt gatgttatta attacagctg  77280
tgatataaac ctgatattct tttgaaatag attccatcag ttcaatagat acggaattga  77340
actctgaata agttatttac tttcttagtt catcaattct accgaccgta attacaccaa  77400
catctctgaa actgataact ggatagtgtt tccaatataa caattcagtt taccaagatg  77460
aattacttga attgtttcat cgcaccattg tttcttttct attgtagtat tcaacacgac  77520
gttcgatgaa gacgcgagta ccagaaacag aggtgtacgc attcagtcat aaccatactt  77580
atggtacgtt atttggatct tggcgccatt ttggatgaat gctttcattt gtattttcct  77640
tttacgaaat agaagccctc ccgaaggagg gcaattacca ttattaaatt acgagtctat  77700
tacttctttt aattttcacc aggggtagct agataatcta cattatattt aatagcaatt  77760
```

acaccacaag ttctttttca tagctgttct acctgatcgc atatttatca atagctccat 77820
cttctacatc ctcgtataat ggatattgac tataatatta tcaggtgtaa gtacagacag 77880
tttcaatccc atctttacca atgactgggt gatatgtctg tttaagacct ttacaatgat 77940
agtgataggt atgcgctgtg tttaggtggt catgtaaaga tacctcataa accgttgggt 78000
agtccgtctt taagacagtt agttgattaa catctttcaa tgattatctg caatattctt 78060
agccaataac agtagatcat tggtgatatg ttttaatgag aacttaagcc tctccctttg 78120
tttatatcgg aaccttatta tcacagtaac tccatccggt tatttttata attcagtaca 78180
gtgattggtg tattcggtac aaagacggct agttcgtcat cgaatacaat gtaaaccatc 78240
actttataat tattaaccga ttcttggaat tgttgtgtga ttacattata gtcttttgtg 78300
cgatggctaa gaaacagctc actattagct cggcagaaac tatgtcgcgc tttttatcag 78360
cactcataac agcgatacca cggataatga atttattatc taaggtatat tttctttgag 78420
acatcgcata gtcgactaca tcaacatcgc cgccaaatag cacggcattt tcaccgtatc 78480
cacaaataag agccatttat aattacctgt ttaaaaatta tattcaataa attgagagtg 78540
aatagttcac tacattccca tgtacgactt gctaatttat atttaccttt aacaggtaag 78600
tcaaataacg taatgctttt ctactgaacc agcctcatga ttaaccaata gaacattcct 78660
agccttcaga atatttgaac aatttacaag ttcataatca tctcgcttag gtgtcaatag 78720
ctacattagt gcctggtttc tagcatacca gagcacctca tgaccctctg gattaataat 78780
agagatatag ctgacgttca gcgggtaacc acaagttacg tggatcatan tctccattaa 78840
catcaaagaa tttaaatatc atagagttgg aaccggtttt gatggatcag caattantgc 78900
agattcntct acataaacca ttgcnaagtt ttcaccttct ttacgaatac cagtagaagg 78960
tgttttcgat ggatcataac gataattggc actgctgtcc agctgttaaa taagttgggc 79020
cagttaatgc attgggtttt ggatgaggaa tatcaatttt agtaatacaa tattgaccag 79080
tacgaaactc acgcattata ttaacctctt aatgaataac tgttgcagaa ggacgacatt 79140
tcatagtttt aaaaatgtca gtaggataga tattaccagc ttgtccgaaa ggtttatcgg 79200
ctagaagaaa ctgcggacaa actgtttgta gataaccact atcagtgggt aggaatcctt 79260
caatatcact gatgagaatt tgccagatgg gcaattggtt ataatagtca tccatattgt 79320
agtatgcgtg gagtttacca ccgaacccat atacaaactg atgagtatca attagacgaa 79380
taccaaattt aggttgtcgt cccatcctt 79409

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
caggttcatc atgccgtttg tg 22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tatttgccca tggacgcaca c 21

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
atatagaaaa tcattaattg atgaacg 27

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

His Ile Glu Asn His
1 5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Tyr Arg Lys Ser Leu Ile Asp Glu Arg
1 5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Arg Ile Leu Ala
1

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
ctttgtttat cgcctcaatg acatta 26

<210> SEQ ID NO 20
<211> LENGTH: 5
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 20

Arg Gln Lys Asp Gly
1               5
```